US012486328B2

(12) United States Patent
Malecova et al.

(10) Patent No.: US 12,486,328 B2
(45) Date of Patent: Dec. 2, 2025

(54) COMPOSITIONS AND METHODS OF TREATING FACIOSCAPULOHUMERAL MUSCULAR DYSTROPHY

(71) Applicant: Avidity Biosciences, Inc., San Diego, CA (US)

(72) Inventors: Barbora Malecova, San Diego, CA (US); Rob Burke, Carlsbad, CA (US); Beatrice Diana Darimont, San Diego, CA (US); David Sala Cano, San Diego, CA (US)

(73) Assignee: AVIDITY BIOSCIENCES, INC., San Diego, CA (US)

(*) Notice: Subject to any disclaimer, the term of this patent is extended or adjusted under 35 U.S.C. 154(b) by 0 days.

(21) Appl. No.: 19/267,411

(22) Filed: Jul. 11, 2025

(65) Prior Publication Data

US 2025/0333529 A1 Oct. 30, 2025

Related U.S. Application Data

(60) Continuation of application No. 18/809,215, filed on Aug. 19, 2024, which is a continuation of application No. 18/402,604, filed on Jan. 2, 2024, now Pat. No. 12,157,774, which is a division of application No. 17/932,653, filed on Sep. 15, 2022, now Pat. No. 11,912,779.

(60) Provisional application No. 63/245,123, filed on Sep. 16, 2021.

(51) Int. Cl.

| | |
|---|---|
| ***C07K 16/28*** | (2006.01) |
| ***A61K 39/00*** | (2006.01) |
| ***A61P 21/00*** | (2006.01) |
| ***C12N 15/113*** | (2010.01) |

(52) U.S. Cl.

CPC .......... *C07K 16/2881* (2013.01); *A61P 21/00* (2018.01); *C12N 15/113* (2013.01); *A61K 2039/505* (2013.01); *C12N 2310/141* (2013.01); *C12N 2310/315* (2013.01); *C12N 2310/321* (2013.01)

(58) Field of Classification Search

None

See application file for complete search history.

(56) References Cited

U.S. PATENT DOCUMENTS

| | | | |
|---|---|---|---|
| 5,627,053 | A | 5/1997 | Usman et al. |
| 5,716,824 | A | 2/1998 | Beigelman et al. |
| 5,889,136 | A | 3/1999 | Scaringe et al. |
| 6,008,400 | A | 12/1999 | Scaringe et al. |
| 6,111,086 | A | 8/2000 | Scaringe |
| 6,716,821 | B2 | 4/2004 | Zhao et al. |
| 6,821,783 | B1 | 11/2004 | Comely et al. |
| 6,884,869 | B2 | 4/2005 | Senter et al. |
| 6,942,972 | B2 | 9/2005 | Farooqui et al. |
| 7,049,311 | B1 | 5/2006 | Thurston et al. |
| 7,132,519 | B2 | 11/2006 | Monforte et al. |
| 7,595,387 | B2 | 9/2009 | Leake et al. |
| 7,709,226 | B2 | 5/2010 | Foote |
| 7,750,116 | B1 | 7/2010 | Doronina et al. |
| 7,834,171 | B2 | 11/2010 | Khvorova et al. |
| 7,850,975 | B2 | 12/2010 | Mullis |
| 7,943,762 | B2 | 5/2011 | Weller et al. |
| 7,964,566 | B2 | 6/2011 | Doronina et al. |
| 8,137,695 | B2 | 3/2012 | Rozema et al. |
| 8,389,710 | B2 | 3/2013 | Bruno et al. |
| 8,404,678 | B2 | 3/2013 | Bouchard et al. |
| 8,481,698 | B2 | 7/2013 | Lieberman et al. |
| 8,501,930 | B2 | 8/2013 | Rozema et al. |
| 8,580,820 | B2 | 11/2013 | Zanda et al. |
| 8,609,105 | B2 | 12/2013 | Senter et al. |
| 8,703,714 | B2 | 4/2014 | Doronina et al. |
| 8,846,875 | B2 | 9/2014 | Schwartz et al. |
| 8,906,847 | B2 | 12/2014 | Cleemann et al. |
| 8,936,910 | B2 | 1/2015 | Mitsch et al. |
| 9,089,614 | B2 | 7/2015 | Lin et al. |
| 9,242,013 | B2 | 1/2016 | Howard et al. |
| 9,243,252 | B2 | 1/2016 | Popplewell et al. |
| 9,328,345 | B2 | 5/2016 | Li et al. |
| 9,364,553 | B2 | 6/2016 | Lee |
| 9,499,818 | B2 | 11/2016 | Van Deutekom |
| 9,605,019 | B2 | 3/2017 | Verdine et al. |
| 9,695,211 | B2 | 7/2017 | Wada et al. |
| 9,708,406 | B2 | 7/2017 | Zhang et al. |
| 9,982,257 | B2 | 5/2018 | Butler et al. |
| 10,087,210 | B2 | 10/2018 | Prakash et al. |
| 10,301,649 | B2 | 5/2019 | Harper et al. |
| 10,538,763 | B2 | 1/2020 | Rigo et al. |
| 10,612,027 | B2 | 4/2020 | Maier et al. |
| 10,865,445 | B2 | 12/2020 | Van Der Maarel et al. |

(Continued)

FOREIGN PATENT DOCUMENTS

| | | | |
|---|---|---|---|
| EP | 1579015 | A2 | 9/2005 |
| EP | 2119783 | A1 | 11/2009 |

(Continued)

OTHER PUBLICATIONS

Aartsma-Rus et al. Guidelines for antisense oligonucleotide design and insight into splice-modulating mechanisms. Mol Ther 17(3):548-53 (2009).

Aartsma-Rus et al. Targeted exon skipping as a potential gene correction therapy for Duchenne muscular dystrophy. Neuromuscul Disord. 12 Suppl 1:S71-7 (2002).

Abramova, T. et al., Novel oligonucleotide analogues based on morpholino nucleoside subunits antisense technologies: New chemical possibilities. Indian Journal of Chemistry 48B:1721-1726 (2009).

(Continued)

*Primary Examiner* — Ruixiang Li

(74) *Attorney, Agent, or Firm* — WILSON SONSINI GOODRICH & ROSATI

(57) ABSTRACT

Disclosed herein are polynucleic acid molecules, pharmaceutical compositions, and methods for treating facioscapulohumeral muscular dystrophy (FSHD).

19 Claims, 14 Drawing Sheets

Specification includes a Sequence Listing.

(56) References Cited

U.S. PATENT DOCUMENTS

| | | | |
|---|---|---|---|
| 10,881,743 | B2 | 1/2021 | Geall et al. |
| 10,913,800 | B2 | 2/2021 | Darimont et al. |
| 10,994,020 | B2 | 5/2021 | Levin et al. |
| 11,028,179 | B2 | 6/2021 | Darimont et al. |
| 11,111,309 | B2 | 9/2021 | Subramanian et al. |
| 11,286,305 | B2 | 3/2022 | Subramanian et al. |
| 11,339,224 | B2 | 5/2022 | Takemori et al. |
| 11,504,391 | B1 | 11/2022 | Schlegel et al. |
| 11,525,137 | B2 | 12/2022 | Malecova et al. |
| 11,555,190 | B2 | 1/2023 | Malecova et al. |
| 11,638,761 | B2 | 5/2023 | Subramanian et al. |
| 11,834,510 | B2 | 12/2023 | Darimont et al. |
| 11,912,779 | B2 | 2/2024 | Malecova et al. |
| 11,999,955 | B2 | 6/2024 | Malecova et al. |
| 12,049,629 | B2 | 7/2024 | Malecova et al. |
| 12,071,485 | B2 | 8/2024 | Malecova et al. |
| 12,104,156 | B2 | 10/2024 | Malecova et al. |
| 12,157,774 | B2 | 12/2024 | Malecova et al. |
| 2002/0142980 | A1 | 10/2002 | Thompson et al. |
| 2011/0293512 | A1 | 12/2011 | Violette et al. |
| 2011/0294753 | A1 | 12/2011 | De Kimpe et al. |
| 2011/0301218 | A1 | 12/2011 | Bozzoni et al. |
| 2012/0065169 | A1 | 3/2012 | Hanson et al. |
| 2012/0094299 | A1 | 4/2012 | Ranum et al. |
| 2012/0122800 | A1 | 5/2012 | Kadushin et al. |
| 2012/0225034 | A1 | 9/2012 | Belayew et al. |
| 2012/0270925 | A1 | 10/2012 | Wilton et al. |
| 2013/0029900 | A1 | 1/2013 | Widdison |
| 2013/0172238 | A1 | 7/2013 | Mitsch et al. |
| 2013/0217638 | A1 | 8/2013 | Wessjohann et al. |
| 2013/0224228 | A1 | 8/2013 | Jackson et al. |
| 2013/0288976 | A1 | 10/2013 | Van Der Maarel et al. |
| 2013/0309256 | A1 | 11/2013 | Lyon et al. |
| 2013/0323268 | A1 | 12/2013 | Chari et al. |
| 2014/0127239 | A1 | 5/2014 | Howard |
| 2014/0194610 | A1 | 7/2014 | Verdine et al. |
| 2014/0286970 | A1 | 9/2014 | Jeffrey et al. |
| 2014/0294851 | A1 | 10/2014 | Nguyen |
| 2014/0294868 | A1 | 10/2014 | Howard et al. |
| 2014/0296321 | A1 | 10/2014 | Iversen |
| 2014/0315862 | A1 | 10/2014 | Kaye |
| 2014/0363454 | A1 | 12/2014 | Jackson et al. |
| 2015/0018540 | A1 | 1/2015 | Prakash et al. |
| 2015/0037360 | A1 | 2/2015 | Smith |
| 2015/0056220 | A1 | 2/2015 | Chennamsetty et al. |
| 2015/0105539 | A1 | 4/2015 | Miao et al. |
| 2015/0105540 | A1 | 4/2015 | Miao et al. |
| 2015/0111954 | A1 | 4/2015 | Sliz et al. |
| 2015/0211006 | A1 | 7/2015 | Butler et al. |
| 2015/0238516 | A1 | 8/2015 | Dowdy et al. |
| 2015/0275212 | A1 | 10/2015 | Albaek et al. |
| 2016/0002637 | A1 | 1/2016 | Sazani et al. |
| 2016/0053262 | A1 | 2/2016 | Platenburg et al. |
| 2016/0102148 | A1 | 4/2016 | Park et al. |
| 2016/0193354 | A1 | 7/2016 | Noe et al. |
| 2016/0193355 | A1 | 7/2016 | Qin et al. |
| 2016/0304864 | A1 | 10/2016 | De Kimpe et al. |
| 2016/0304874 | A1 | 10/2016 | Krauss |
| 2016/0367687 | A1 | 12/2016 | Manoharan et al. |
| 2017/0009230 | A1 | 1/2017 | Agrawal et al. |
| 2017/0204410 | A1 | 7/2017 | Watanabe et al. |
| 2017/0281795 | A1 | 10/2017 | Geall et al. |
| 2018/0273942 | A1 | 9/2018 | Rigo et al. |
| 2018/0369400 | A1 | 12/2018 | Levin et al. |
| 2019/0192681 | A1 | 6/2019 | Geall et al. |
| 2019/0300903 | A1 | 10/2019 | Harper et al. |
| 2020/0190523 | A1 | 6/2020 | Mardinoglu et al. |
| 2021/0206868 | A1 | 7/2021 | Subramanian et al. |
| 2023/0279395 | A1 | 9/2023 | Malecova et al. |
| 2023/0287420 | A1 | 9/2023 | Malecova et al. |
| 2023/0340474 | A1 | 10/2023 | Malecova et al. |
| 2024/0124600 | A1 | 4/2024 | Malecova et al. |
| 2024/0132610 | A1 | 4/2024 | Malecova et al. |
| 2024/0132611 | A1 | 4/2024 | Darimont et al. |
| 2024/0287522 | A1 | 8/2024 | Malecova et al. |
| 2024/0309382 | A1 | 9/2024 | Malecova et al. |
| 2024/0400707 | A1 | 12/2024 | Malecova et al. |

FOREIGN PATENT DOCUMENTS

| | | | |
|---|---|---|---|
| EP | 1608733 | B1 | 12/2011 |
| EP | 2580326 | A1 | 4/2013 |
| EP | 4208548 | A1 | 7/2023 |
| WO | WO-9104753 | A1 | 4/1991 |
| WO | WO-9207065 | A1 | 4/1992 |
| WO | WO-9315187 | A1 | 8/1993 |
| WO | WO-9726270 | A2 | 7/1997 |
| WO | WO-9734631 | A1 | 9/1997 |
| WO | WO-9813526 | A1 | 4/1998 |
| WO | WO-2004009851 | A2 | 1/2004 |
| WO | WO-2008036127 | A2 | 3/2008 |
| WO | WO-2009099942 | A2 | 8/2009 |
| WO | WO-2009126933 | A2 | 10/2009 |
| WO | WO-2009144481 | A2 | 12/2009 |
| WO | WO-2011003557 | A1 | 1/2011 |
| WO | WO-2011009624 | A1 | 1/2011 |
| WO | WO-2011150408 | A2 | 12/2011 |
| WO | WO-2012012443 | A2 | 1/2012 |
| WO | WO-2012092373 | A2 | 7/2012 |
| WO | WO-2012125850 | A1 | 9/2012 |
| WO | WO-2013016352 | A1 | 1/2013 |
| WO | WO-2014080251 | A1 | 5/2014 |
| WO | WO-2014140317 | A2 | 9/2014 |
| WO | WO-2014145090 | A1 | 9/2014 |
| WO | WO-2014154835 | A2 | 10/2014 |
| WO | WO-2014177042 | A1 | 11/2014 |
| WO | WO-2014189973 | A2 | 11/2014 |
| WO | WO-2014197854 | A1 | 12/2014 |
| WO | WO-2015021457 | A2 | 2/2015 |
| WO | WO-2015038426 | A1 | 3/2015 |
| WO | WO-2015057699 | A2 | 4/2015 |
| WO | WO-2015069587 | A2 | 5/2015 |
| WO | WO-2015107425 | A2 | 7/2015 |
| WO | WO-2015113922 | A1 | 8/2015 |
| WO | WO-2016115490 | A1 | 7/2016 |
| WO | WO-2016187425 | A1 | 11/2016 |
| WO | WO-2016207240 | A1 | 12/2016 |
| WO | WO-2017007886 | A2 | 1/2017 |
| WO | WO-2017173408 | A1 | 10/2017 |
| WO | WO-2017192679 | A1 | 11/2017 |
| WO | WO-2017221883 | A1 | 12/2017 |
| WO | WO-2018129384 | A1 | 7/2018 |
| WO | WO-2019060775 | A1 | 3/2019 |
| WO | WO-2019071028 | A1 | 4/2019 |
| WO | WO-2019071147 | A1 | 4/2019 |
| WO | WO-2019113393 | A1 | 6/2019 |
| WO | WO-2020028832 | A1 | 2/2020 |
| WO | WO-2020028836 | A1 | 2/2020 |
| WO | WO-2020028864 | A1 | 2/2020 |
| WO | WO-2020132584 | A1 | 6/2020 |
| WO | WO-2020142479 | A1 | 7/2020 |
| WO | WO-2020203880 | A1 | 10/2020 |
| WO | WO-2020247818 | A1 | 12/2020 |
| WO | WO-2021142275 | A1 | 7/2021 |
| WO | WO-2021188390 | A1 | 9/2021 |
| WO | WO-2022051332 | A1 | 3/2022 |
| WO | WO-2023288289 | A2 | 1/2023 |
| WO | WO-2023043953 | A1 | 3/2023 |

OTHER PUBLICATIONS

Agarwal, Paresh et al. A Pictet-Spengler Ligation for Protein Chemical Modification. PNAS USA 110(1):46-51 (2013).

Albarran, Brian et al. Efficient intracellular delivery of a pro-apoptotic peptide with a pH-responsive carrier. Reactive and Functional Polymers 71(3):261-265 (2011).

Alegre, Maria-Luisa et al. Effect of a Single Amino Acid Mutation on the Activating and Immunosuppressive Properties of a “Humanized” OKT3 Monoclonal Antibody. Journal of Immunology 148(11):3461-3468 (1992).

(56) References Cited

OTHER PUBLICATIONS

Al-Lazikani, Bissan et al. Standard Conformations for the Canonical Structures of Immunoglobulins. Journal of Molecular Biology 273(4):927-948 (1997).
Axup, Jun Y. et al. Synthesis of Site-specific Antibody-drug Conjugates Using Unnatural Amino Acids. PNAS USA 109(40):16101-16106 (2012).
Ballangrud et al. Response of LNCaP Spheroids After Treatment With an Alpha-Particle Emitter (213Bi)-labeled Anti-Prostate-Specific Membrane Antigen Antibody (J591) Cancer Res. 61:2008-2014 (2001).
Beigelman, Leonid et al. Chemical Modification of Hammerhead Ribozymes: Catalytic Activity and Nuclease Resistance. Journal of Biological Chemistry 270(43):25702-25708 (1995).
Bird, Robert E. et al. Single-chain Antigen-binding Proteins. Science 242(4877):423-426 (1988).
Blaney, Paul et al. Traceless Solid-phase Organic Synthesis. Chemical Reviews 102(7):2607-2624 (2002).
Borchardt et al. Targeted actinium-225 in Vivo Generators for Therapy of Ovarian Cancer Cancer Res. 63:5084-50 (2003).
Brinkmann, Ulrich et al. The making of bispecific antibodies. MAbs 9(2):182-212 (2017).
Burke et al. siRNA-mediated knockdown of P450 oxidoreductase in rats: a tool to reduce metabolism by CYPs and increase exposure of high clearance compounds. Pharm. Res. 31(12):3445-3460 (2014).
Burlina, Fabienne et al. Chemical Engineering of RNase Resistant and Catalytically Active Hammerhead Ribozymes. Bioorganic and Medicinal Chemistry 5(11):1999-2010 (1997).
Carter et al. Antibody-drug conjugates for cancer therapy. Cancer J 14(3):154-69 (2008).
Casi, Giulio et al. Antibody-drug conjugates: basic concepts, examples and future perspectives. Journal of Controlled Release 161(2):422-428 (2012).
Casi, Giulio et al. Site-specific Traceless Coupling of Potent Cytotoxic Drugs to Recombinant Antibodies for Pharmacodelivery. Journal of the American Chemical Society 134(13):5887-5892 (2012).
JP2016-122187, filed on Jun. 20, 2016 (English counterpart U.S. Pat. No. 2019240346).
U.S. Appl. No. 62/316,919, filed Apr. 1, 2016.
Chen et al. Real-time quantification of microRNAs by stem-loop RT-PCR. Nucleic Acids Res. 33:e179 (2005).
Chen, Yvonne et al. Selection and Analysis of an Optimized Anti-VEGF Antibody: Crystal Structure of an Affinity-matured Fab in Complex With Antigen. Journal of Molecular Biology 293(4):865-881 (1999).
Chothia, Cyrus et al. Canonical Structures for the Hypervariable Regions of Immunoglobulins. Journal of Molecular Biology 196(4):901-917 (1987).
Chothia, Cyrus et al. Structural Repertoire of the Human VH Segments. Journal of Molecular Biology 227(3):799-817 (1992).
Clackson, Tim et al. Making Antibody Fragments using Phage Display Libraries. Nature 352(6336):624-628 (1991).
Colbere-Garapin, Florence et al. A New Dominant Hybrid Selective Marker for Higher Eukaryotic Cells. Journal of Molecular Biology 150(1):1-14 (1981).
Cole, S.P.C. et al. The EBV-Hybridoma Technique and its Application to Human Lung Cancer. Monoclonal Antibodies and Cancer Therapy 27:77-96 (1985).
Co-pending U.S. Appl. No. 19/267,387, inventors Malecova; Barbora et al., filed on Jul. 11, 2025.
Crouse, Gray F. et al. Expression and Amplification of Engineered Mouse Dihydrofolate Reductase Minigenes. Molecular Cell Biology 3(2):257-266 (1983).
Dawson, Philip E. et al. Modulation of Reactivity in Native Chemical Ligation through the Use of Thiol Additives. Journal of American Chemical Society 119(19):4325-4329 (1997).
Dawson, Philip E. et al. Synthesis of Proteins by Native Chemical Ligation. Science 266(5186):776-779 (1994).
De Angelis et al. Chimeric snRNA molecules carrying antisense sequences against the splice junctions of exon 51 of the dystrophin pre-mRNA induce exon skipping and restoration of a dystrophin synthesis in Delta 48-50 DMD cells. PNAS USA 99:9456-9461 (2002).
De Pascalis, Roberto et al. Grafting of "Abbreviated" Complementarity-Determining Regions Containing Specificity-Determining Residues Essential for Ligand Contact to Engineer a Less Immunogenic Humanized Monoclonal Antibody. The Journal of Immunology 169(6):3076-3084 (2002).
Dietel et al. A 2015 update on predictive molecular pathology and its role in targeted cancer therapy: a review focussing on clinical relevance. Cancer Gene Ther 22(9):417-430 (2015).
Dimasi, Nazzareno et al. Development of a Trispecific Antibody Designed to Simultaneously and Efficiently Target Three Different Antigens on Tumor Cells. Molecular Pharmaceutics 12(9):3490-3501 (2015).
Dracopoli, Nicholas et al. Unit 2.7: Restriction Fragment Length Polymorphism Analysis. Current Protocols in Human Genetics (Supplemental 1 CPHG) (pp. 2.7.1-2.7.5) (1994).
Earnshaw, David J. et al. Modified Oligoribonucleotides as Site-Specific Probes of RNA Structure and Function. Biopolymers (Nucleic Acid Sciences) 48(1):39-55 (1998).
Ferreboeuf et al. DUX4 and DUX4 downstream target genes are expressed in fetal FSHD muscles. Human Molecular Genetics 23(1):171-181 (2014).
Flanary et al. Antigen delivery with poly(propylacrylic acid) conjugation enhanced MHC-1 presentation and T-cell activation. Bioconjugate Chem. 20:241-248 (2009).
Genbank HQ266760.1 A "*Homo sapiens* clone 34-15 double homeodomain protein DUX4-fl (DUX4) mRNA, complete cds" accessed from ncbi.nlm.nih.gov on Dec. 16, 2021 (2010).
Giorgetti et al. Rescue of Metabolic Alterations in AR113Q Skeletal Muscle by Peripheral Androgen Receptor Gene Silencing. Cell Rep 17(1):125-136 (2016).
Goldmacher et al. Antibody-drug conjugates: using monoclonal antibodies for delivery of cytotoxic payloads to cancer cells. Therapeutic Delivery 2:397-416 (2011).
Goldspiel, Barry R. et al. Human Gene Therapy. Clinical Pharmacy 12(7):488-505 (1993).
Griffey, Richard H. et al. 2'-O-aminopropyl Ribonucleotides: A Zwitterionic Modification that Enhances the Exonuclease Resistance and Biological Activity of Antisense Oligonucleotides. Journal of Medicinal Chemistry 39(26):5100-5109 (1997).
Hackeng, Tilman M. et al. Protein Synthesis by Native Chemical Ligation: Expanded Scope by Using Straightforward Methodology. PNAS USA 96(18):10068-10073 (1999).
Hanes, Jozef et al. In Vitro Selection and Evolution of Functional Proteins by Using Ribosome Display. PNAS USA 94(10):4937-4942 (1997).
Hejesen, Christian et al. A Traceless Aryl-triazene Linker for DNA-directed Chemistry. Organic and Biomolecular Chemistry 11(15):2493-2497 (2013).
Huse, William D. et al. Generation of a Large Combinatorial Library of the Immunoglobulin Repertoire in Phage Lambda. Science 246(4935):1275-1281 (1989).
Huston, James S. et al. Protein Engineering of Antibody Binding Sites: Recovery of Specific Activity in an Anti-digoxin Single-chain Fv Analogue Produced in *Escherichia Coli*. PNAS USA 85(16):5879-5883 (1988).
Idusogie, Eshoe E. et al. Mapping of the C1q Binding Site on Rituxan, a Chimeric Antibody with a Human IgG1 Fc. The Journal of Immunology 164(8):4178-4184 (2000).
Idusogie, Esohe E. et al. Engineered Antibodies with Increased Activity to Recruit Complement. Journal of Immunology 166(4):2571-2575 (2001).
Invivogen "RNA Interference" accessed from invivogen.com on Dec. 17, 2021 (2006).
Jagannathan et al. Model systems of DUX4 expression recapitulate the transcriptional profile of FSHD cells. Hum Mol Genet 25(20):4419-4431 (2016).
Jearawiriyapaisarn, N. et al., Sustained Dystrophin Expression Induced by Peptide-conjugated Morpholino Oligomers in the Muscles of mdx Mice. Molecular Therapy 16(9):1624-1629 (2008).

(56) References Cited

OTHER PUBLICATIONS

Jones et al. A cre-inducible DUX4 transgenic mouse model for investigating facioscapulohumeral muscular dystrophy. PLoS One 13(2):e0192657 (2018).

Jones et al. Transgenic mice expressing tunable levels of DUX4 develop characteristic facioscapulohumeral muscular dystrophy-like pathophysiology ranging in severity. Skelet Muscle. 10(1):8 (2020).

Kabat, Elvin A. et al. Attempts to Locate Complementarity-Determining Residues in the Variable Positions of Light and Heavy Chains. Annals of the New York Academy of Sciences 190:382-393 (1971).

Kabat, Elvin A. et al. Sequences of Proteins of Immunological Interest, 5th Edition. U.S. Department of Health and Human Services NIH Publication No. 91-3242 (1991).

Kaneko, Etsuji et al. Optimizing Therapeutic Antibody Function: Progress with Fc Domain Engineering. Bio Drugs 25(1):1-11 (2011).

Karpeisky, Alexander et al. Highly Efficient Synthesis of 2-O-amino Nucleosides and their Incorporation in Hammerhead Ribozymes. Tetrahedron Letters 39(10):1131-1134 (1998).

Köhler, G. et al. Continuous Cultures of Fused Cells Secreting Antibody of Predefined Specificity. Nature 256(5517):495-497 (1975).

Koizumi, M. ENA Oligonucleotides as Therapeutics. Current Opinion in Molecular Therapeutics 8(2):144-149 (2006).

Kozbor, Danuta et al. The Production of Monoclonal Antibodies From Human Lymphocytes. Immunology Today 4(3):72-79 (1983).

Kutmeier, G. et al. Assembly of Humanized Antibody Genes from Synthetic Oligonucleotides Using a Single-round PCR. Biotechniques 17(2):242-246 (1994).

Lazar, Greg A. et al. Engineered Antibody Fc Variants with Enhanced Effector Function. PNAS USA 103(11):4005-4010 (2006).

Lefranc, Marie-Paule et al. IMGT, The International ImMunoGeneTics Database. Nucleic Acids Research 27(1):209-212 (1999).

Lefranc, Marie-Paule et al. The IMGT Unique Numbering for Immunoglobulins, T-Cell Receptors and Ig-Like Domains. The Immunologist 7(4):132-136 (1999).

Leroy et al. Epidermal growth factor receptor down-regulation triggers human myoblast differentiation. PLOS One 8(8):e71770 (2013).

Livak et al. Analysis of Relative Gene Expression Data Using RealTime Quantitative PCR and the 2-delta delta Ct Method. Methods 25:402-408 (2001).

Loakes, David. Survey and Summary: The applications of universal DNA base analogues. Nucleic Acids Research 29(12):2437-2447 (2001).

Lowy, Israel et al. Isolation of Transforming DNA: Cloning the Hamster aprt Gene. Cell 22(3):817-823 (1980).

Lyon, Robert P. et al. Self-Hydrolyzing Maleimides improve the Stability and Pharmacological Properties of Antibody-drug Conjugates. Nature Biotechnology 32(10):1059-1062 (2014).

Malecova et al. DUX4 siRNA Optimization for the Development of an Antibody-Oligonucleotide Conjugate (AOC) for the Treatment of FSHD (P17-13.009). Neurology 98:(18 Supplement) (2022).

Martin, Andrew C. et al., Chapter 3: Protein Sequence and Structure Analysis of Antibody Variable Domains. In: Antibody Engineering Lab Manual (Ed: Duebel, S. and Kontermann, R., Springer-Verlag, Heidelberg) 2:33-51 (2010).

Martinez, Javier et al. Single-Stranded Antisense siRNAs Guide Target RNA Cleavage in RNAi. Cell 110(5):563-574 (2002).

McDevitt et al. Tumor Therapy With Targeted Atomic Nanogenerators. Science 294:1537-1540 (2001).

McEnaney, Patrick J. et al. Antibody-Recruiting Molecules: An Emerging Paradigm for Engaging Immune Function in Treating Human Disease. ACS Chemical Biology 7(7):1139-1151 (2012).

Moore, Gregory L. et al. Engineered Fc Variant Antibodies with Enhanced Ability to Recruit Complement and Mediate Effector Functions. mAbs 2(2):181-189 (2010).

Morgan, Richard A. et al. Human Gene Therapy. Annual Review of Biochemistry 62:191-217 (1993).

Morrison, Sherie L. et al. Chimeric human antibody molecules: mouse antigen-binding domains with human constant region domains. PNAS USA 81(21):6851-6855 (1984).

Mulders et al. Molecular therapy in myotonic dystrophy: focus on RNA gain-of-function. Hum Mol Gen 19(R1):R90-R97 (2010).

Mulders et al. Supporting Information for Triplet-repeat oligonucleotide-mediated reversal of RNA toxicity in myotonic dystrophy. PNAS 106(33):13915-13920 (2009) (13 pgs).

Mulders et al. Triplet-repeat oligonucleotide-mediated reversal of RNA toxicity in myotonic dystrophy. PNAS 106(33):13915-13920 (2009).

Mullard. Antibody-oligonucleotide conjugates enter the clinic. Nat Rev Drug Discov 21(1):6-8 (2022).

Mulligan, R. C. et al. Selection for Animal Cells That Express the *Escherichia coli* Gene Coding for Xanthine-guanine Phosphoribosyltransferase. PNAS USA 78(4):2072-2076 (1981).

Mulligan, Richard C. The Basic Science of Gene Therapy. Science 260(5110):926-932 (1993).

Muratovska et al. Conjugate for efficient delivery of short interfering RNA (siRNA) into mammalian cells. FEBS Lett. 558(1-3):63-8 (2004).

Naisbitt, D. J. et al. Disposition of Amodiaquine and Related Antimalarial Agents in Human Neutrophils: Implications for Drug Design. The Journal of Pharmacology and Experimental Therapeutics 280(2):884-893 (1997).

Natsume, Akito et al. Engineered Antibodies of IgG1/IgG3 Mixed Isotype with Enhanced Cytotoxic Activities. Cancer Research 68(10):3863-3872 (2008).

Neuberger, Michael S. et al. Recombinant Antibodies Possessing Novel Effector Functions. Nature 312(5995):604-608 (1984).

Nielsen et al. Advances in targeted delivery of small interfering RNA using simple bioconjugates. Expert Opinion on Drug Delivery 11(5):791-822 (2014).

Obika, Satosh et al. Synthesis of 2'-0,4'-C-methyleneuridine and -cytidine. Novel bicyclic nucleosides having a fixed C3'-endo sugar puckering. Tetrahedron Letters 38(50):8735-8738 (1997).

O'Hare, K. et al. Transformation of Mouse Fibroblasts to Methotrexate Resistance by a Recombinant Plasmid Expressing a Prokaryotic Dihydrofolate Reductase. PNAS USA 78(3):1527-1531 (1981).

PCT/US2019/068078 International Search Report and Written Opinion dated Apr. 24, 2020.

PCT/US2021/022214 International Search Report and Written Opinion dated Jun. 28, 2021.

PCT/US2022/043705 International Search Report and Written Opinion dated Dec. 13, 2022.

Pei et al. Quantitative evaluation of siRNA delivery in vivo. RNA 16:2553-2563 (2010).

Perrault, Jean-Pierre et al. Mixed Deoxyribo- and Ribo-Oligonucleotides with Catalytic Activity. Nature 344(6266):565-568 (1990).

Pieken, Wolfgang A. et al. Kinetic Characterization of Ribonuclease-Resistant 2'-Modified Hammerhead Ribozymes. Science 253(5017):314-317 (1991).

Pizzamiglio et al. Expression of iron-related proteins differentiate non-cancerous and cancerous breast tumors. Int J Mol Sci. 18(2):410 (2017).

Rangasamy et al. New mechanism for release of endosomal contents: osmotic lysis via nigeri-cin-mediated K+/H+ exchange. Bioconjugate Chem. 29:1047-1059 (2018).

Rosager et al., Transferrin receptor-1 and ferritin heavy and light chains in astrocytic brain tu-mors: Expression and prognostic value. PLoS One 12:e0182954 (2017).

Rozema et al. Dynamic PolyConjugates for targeted in vivo delivery of siRNA to hepatocytes. PNAS USA 104(32):12982-12987 (2007).

Rychtarcikova et al. Tumor-initiating cells of breast and prostate origin show alterations in the expression of genes related to iron metabolism. Oncotarget. 8:6376-6398 (2017).

Sacheck et al. Rapid disuse and denervation atrophy involve transcriptional changes similar to those of muscle wasting during systemic diseases. FASEB J. 21(1):140-155 (2007).

Sartori et al. Smad2 and 3 transcription factors control muscle mass in adulthood. Am J Physiol Cell Physiol 296:C1248-C1257 (2009).

(56) References Cited

OTHER PUBLICATIONS

Shields, Robert L. et al. High Resolution Mapping of the Binding Site on Human IgG1 for Fc Gamma RI, Fc Gamma RII, Fc Gamma RIII, and FcRn and design of IgG1 Variants with Improved Binding to the Fc Gamma R. Journal of Biological Chemistry 276(9):6591-6604 (2001).
Singh et al. Recent developments in oligonucleotide conjugation. Chem Soc Rev 39(6):2054-2070 (2010).
Skerra, Arne et al. Assembly of a Functional Immunoglobulin Fv Fragment in *Escherichia coli*. Science 240(4855):1038-1041 (1988).
Stavenhagen, Jeffrey B. et al. Enhancing the Potency of Therapeutic Monoclonal Antibodies via Fc Optimization. Advances in Enzyme Regulation 48(1):152-164 (2008).
Stavenhagen, Jeffrey B. et al. Fc Optimization of Therapeutic Antibodies Enhances their Ability to Kill Tumor Cells in vitro and Controls Tumor Expansion in vivo via Low-Affinity Activating Fcgamma Receptors. Cancer Research 67(18):8882-8890 (2007).
Strop, Pavel et al. Location Matters: Site of Conjugation Modulates Stability and Pharmacokinetics of Antibody Drug Conjugates. Chemistry and Biology 20(2):161-167 (2013).
Summerton, James et al. Morpholino Antisense Oligomers: Design, Preparation, and Properties. Antisense Nucleic Acid Drug Development 7(3):187-195 (1997).
Szybalska, Elizabeth Hunter et al. Genetics of Human Cell Lines, IV. DNA-mediated Heritable Transformation of a Biochemical Trait. PNAS USA 48(12):2026-2034 (1962).
Takeda, Shun-Ichi et al. Construction of Chimaeric Processed Immunoglobulin Genes Containing Mouse Variable and Human Constant Region Sequences. Nature 314(6010):452-454 (1985).
Tolstoshev, Paul. Gene Therapy, Concepts, Current Trials and Future Directions. Annual Review Pharmacology and Toxicology 32:573-596 (1993).
Tramontano, Anna et al. Framework Residue 71 Is a Major Determinant of the Position and Conformation of the Second Hypervariable Region in the VH Domains of Immunoglobulins. Journal of Molecular Biology 215(1):175-182 (1990).
Turner et al. The myotonic dystrophies: diagnosis and management. J Neurol Neurosurg Psychiatry 81:358-367 (2010).
U.S. Appl. No. 17/200,612 Office Action dated Apr. 20, 2022.
U.S. Appl. No. 17/200,612 Office Action dated Dec. 21, 2021.
U.S. Appl. No. 17/200,661 Office Action dated Jan. 31, 2022.
U.S. Appl. No. 17/200,661 Office Action dated May 23, 2022.
U.S. Appl. No. 17/932,653 Office Action dated Jul. 7, 2023.
U.S. Appl. No. 18/052,898 Office Action dated Oct. 13, 2023.
U.S. Appl. No. 18/052,899 Office Action dated Feb. 15, 2024.
U.S. Appl. No. 18/052,899 Office Action dated Jul. 5, 2023.
U.S. Appl. No. 18/052,899 Office Action dated Oct. 24, 2023.
U.S. Appl. No. 18/052,900 Office Action dated Dec. 14, 2023.
U.S. Appl. No. 18/052,900 Office Action dated Sep. 6, 2023.
U.S. Appl. No. 18/402,604 Office Action dated Jun. 14, 2024.
U.S. Appl. No. 18/660,147 Office Action dated Feb. 18, 2025.
U.S. Appl. No. 18/660,147 Office Action dated Jun. 3, 2025.
U.S. Appl. No. 18/660,147 Office Action dated Oct. 29, 2024.
Usman, Nassim et al. Exploiting the Chemical Synthesis of RNA. Trends in Biochemical Sciences 17:334-339 (1992).
Verma, Sandeep et al. Modified Oligonucleotides: Synthesis and Strategy for Users. Annual Review of Biochemistry 67(1):99-134 (1998).
Walker et al. Improved cellular delivery of antisense oligonucleotides using transferrin receptor antibody-oligonucleotide conjugates. Pharmaceutical research 12(10):1548-1553 (1995).
Wallace et al. RNA interference inhibits DUX4-induced muscle toxicity in vivo: implications for a targeted FSHD therapy. Molecular Therapy 20.7 (2012): 1417-1423.
Ward, E Sally. et al. Binding Activities of a Repertoire of Single Immunoglobulin Variable Domains Secreted from *Escherichia coli*. Nature 341(6242):544-546 (1989).
Watts, Jonathan K. et al., Chemically Modified siRNA: Tools and Applications. Drug Discovery Today 13(19-20):842-855 (2008).
Whiddon et al. Conservation and innovation in the DUX4-family gene network. Nat Genet. 49(6):935-940 (2017).
Wigler, M. et al. Transformation of Mammalian Cells With an Amplifiable Dominant-acting Gene. PNAS USA 77(6):3567-3570 (1980).
Wigler, Michael et al. Transfer of Purified Herpes Virus Thymidine Kinase Gene to Cultured Mouse Cells. Cell 11(1):223-232 (1977).
Winkler, Johannes. Oligonucleotide conjugates for therapeutic applications. Therapeutic Delivery 4(7):791-809 (2013).
Wong et al. Co-injection of a targeted, reversibly masked endosomolytic polymer dramatically improves the efficacy of cholesterol-conjugated small interfering RNAs in vivo. Nucleic Acid Ther 22(6):380-390 (2012).
Wu, Bin et al. Building Complex Glycopeptides: Development of a Cysteine-free Native Chemical Ligation Protocol. Angewandte Chemie 45(25):4116-4125 (2006).
Wu et al. Cell-penetrating peptides as transporters for morpholino oligomers: effects of amino acid composition on intracellular delivery and cytotoxicity. Nucleic Acids Res 35(15):5182-5191 (2007).
Wu, George Y. et al. Delivery systems for Gene Therapy. Biotherapy 3(1):87-95 (1991).
Wu, Peng et al. Site-specific Chemical Modification of Recombinant Proteins Produced in Mammalian Cells by Using the Genetically Encoded Aldehyde Tag. PNAS USA 106(9):3000-3005 (2009).
Xia et al. Intravenous siRNA of brain cancer with receptor targeting and avidin-biotin technology. Pharm Res 24(12):2309-16 (2007).
Xu et al. Delivery systems for siRNA drug development in cancer therapy. Asian Journal of Pharmaceutical Sciences 10(1):1-12 (2015).
Yao et al. DUX4-induced gene expression is the major molecular signature in FSHD skeletal muscle. Human molecular genetics 23(20):5342-5352 (2014).
Yazdi et al. Influence of cellular trafficking on protein synthesis inhibition of immunotoxins directed against the transferrin receptor. Cancer Res 55:3763-3771 (1995).
Zapata, Gerardo et al. Engineering Linear F(ab')2 Fragments for Efficient Production in *Escherichia coli* and Enhanced Antiproliferative Activity. Protein Engineering 8(10):1057-1062 (1995).
Zeng, W et al. GenBank Accession No. NM_001306068. Version No. NM_001306068.1 *Homo sapiens* double homeobox 4 (DUX4), transcript variant 1, mRNA: Record Apr. 14, 2015. Retrieved Nov. 7, 2024. Retrieved from: https://www.ncbi.nlm.nih.gov/nuccore/807045794?sat=21&satkey=10089314.
Zhang, Andrew X. et al. A Remote Arene-Binding Site on Prostate Specific Membrane Antigen Revealed by Antibody-Recruiting Small Molecules. Journal of the American Chemical Society 132(36):12711-12716 (2010).
Zhang, Yuanfan. Therapeutic Development for Facioscapulohumeral Muscular Dystrophy Utilizing a Novel Human Skeletal Muscle Xenograft Model. Johns Hopkins University (2016).

X = O or S

3' end

5' end

X = O or S

X = O or S

3' end

5' end

X = O or S

X = O or S

X = O or S

R = Ethyl or PEG 0.5 kDa to 10 kDa

5' end

3' end

X = O or S

X = O or S

R = Ethyl or PEG 0.5 kDa to 10 kDa

5' end

3' end

SEQUENCE LISTING

```
Sequence total quantity: 438
SEQ ID NO: 1             moltype = DNA  length = 19
FEATURE                  Location/Qualifiers
source                   1..19
                         mol_type = other DNA
                         organism = synthetic construct
SEQUENCE: 1
cgacaccctc ggacagcac                                               19

SEQ ID NO: 2             moltype = DNA  length = 19
FEATURE                  Location/Qualifiers
source                   1..19
                         mol_type = other DNA
                         organism = synthetic construct
SEQUENCE: 2
acggcgacgg agactcgtt                                               19

SEQ ID NO: 3             moltype = DNA  length = 19
FEATURE                  Location/Qualifiers
source                   1..19
                         mol_type = other DNA
                         organism = synthetic construct
SEQUENCE: 3
cggcgacgga gactcgttt                                               19

SEQ ID NO: 4             moltype = DNA  length = 19
FEATURE                  Location/Qualifiers
source                   1..19
                         mol_type = other DNA
                         organism = synthetic construct
SEQUENCE: 4
ggcgacggag actcgtttg                                               19

SEQ ID NO: 5             moltype = DNA  length = 19
FEATURE                  Location/Qualifiers
source                   1..19
                         mol_type = other DNA
                         organism = synthetic construct
SEQUENCE: 5
gcgacggaga ctcgtttgg                                               19

SEQ ID NO: 6             moltype = DNA  length = 19
FEATURE                  Location/Qualifiers
source                   1..19
                         mol_type = other DNA
                         organism = synthetic construct
SEQUENCE: 6
cgacggagac tcgtttgga                                               19

SEQ ID NO: 7             moltype = DNA  length = 19
FEATURE                  Location/Qualifiers
source                   1..19
                         mol_type = other DNA
                         organism = synthetic construct
SEQUENCE: 7
gacggagact cgtttggac                                               19

SEQ ID NO: 8             moltype = DNA  length = 19
FEATURE                  Location/Qualifiers
source                   1..19
                         mol_type = other DNA
                         organism = synthetic construct
SEQUENCE: 8
acggagactc gtttggacc                                               19
```

-continued

```
SEQ ID NO: 9            moltype = DNA  length = 19
FEATURE                 Location/Qualifiers
source                  1..19
                        mol_type = other DNA
                        organism = synthetic construct
SEQUENCE: 9
ggaccccgag ccaaagcga                                              19

SEQ ID NO: 10           moltype = DNA  length = 19
FEATURE                 Location/Qualifiers
source                  1..19
                        mol_type = other DNA
                        organism = synthetic construct
SEQUENCE: 10
gaccccgagc caaagcgag                                              19

SEQ ID NO: 11           moltype = DNA  length = 19
FEATURE                 Location/Qualifiers
source                  1..19
                        mol_type = other DNA
                        organism = synthetic construct
SEQUENCE: 11
accccgagcc aaagcgagg                                              19

SEQ ID NO: 12           moltype = DNA  length = 19
FEATURE                 Location/Qualifiers
source                  1..19
                        mol_type = other DNA
                        organism = synthetic construct
SEQUENCE: 12
cctgcgagcc tgctttgag                                              19

SEQ ID NO: 13           moltype = DNA  length = 19
FEATURE                 Location/Qualifiers
source                  1..19
                        mol_type = other DNA
                        organism = synthetic construct
SEQUENCE: 13
gcgagcctgc tttgagcgg                                              19

SEQ ID NO: 14           moltype = DNA  length = 19
FEATURE                 Location/Qualifiers
source                  1..19
                        mol_type = other DNA
                        organism = synthetic construct
SEQUENCE: 14
tcgccaccag agaacggct                                              19

SEQ ID NO: 15           moltype = DNA  length = 19
FEATURE                 Location/Qualifiers
source                  1..19
                        mol_type = other DNA
                        organism = synthetic construct
SEQUENCE: 15
caggccatcg gcattccgg                                              19

SEQ ID NO: 16           moltype = DNA  length = 19
FEATURE                 Location/Qualifiers
source                  1..19
                        mol_type = other DNA
                        organism = synthetic construct
SEQUENCE: 16
ggccatcggc attccggag                                              19

SEQ ID NO: 17           moltype = DNA  length = 19
FEATURE                 Location/Qualifiers
source                  1..19
                        mol_type = other DNA
                        organism = synthetic construct
SEQUENCE: 17
gccatcggca ttccggagc                                              19

SEQ ID NO: 18           moltype = DNA  length = 19
FEATURE                 Location/Qualifiers
source                  1..19
                        mol_type = other DNA
                        organism = synthetic construct
SEQUENCE: 18
gcaccggcgg gaatctcgg                                              19
```

```
SEQ ID NO: 19          moltype = DNA  length = 19
FEATURE                Location/Qualifiers
source                 1..19
                       mol_type = other DNA
                       organism = synthetic construct
SEQUENCE: 19
caccggcggg aatctcggc                                               19

SEQ ID NO: 20          moltype = DNA  length = 19
FEATURE                Location/Qualifiers
source                 1..19
                       mol_type = other DNA
                       organism = synthetic construct
SEQUENCE: 20
ccagaaggcc ggcgaaagc                                               19

SEQ ID NO: 21          moltype = DNA  length = 19
FEATURE                Location/Qualifiers
source                 1..19
                       mol_type = other DNA
                       organism = synthetic construct
SEQUENCE: 21
agaaggccgg cgaaagcgg                                               19

SEQ ID NO: 22          moltype = DNA  length = 19
FEATURE                Location/Qualifiers
source                 1..19
                       mol_type = other DNA
                       organism = synthetic construct
SEQUENCE: 22
gaaggccggc gaaagcgga                                               19

SEQ ID NO: 23          moltype = DNA  length = 19
FEATURE                Location/Qualifiers
source                 1..19
                       mol_type = other DNA
                       organism = synthetic construct
SEQUENCE: 23
gcgaaagcgg accgccgtc                                               19

SEQ ID NO: 24          moltype = DNA  length = 19
FEATURE                Location/Qualifiers
source                 1..19
                       mol_type = other DNA
                       organism = synthetic construct
SEQUENCE: 24
gaaagcggac cgccgtcac                                               19

SEQ ID NO: 25          moltype = DNA  length = 19
FEATURE                Location/Qualifiers
source                 1..19
                       mol_type = other DNA
                       organism = synthetic construct
SEQUENCE: 25
cggaccgccg tcaccggat                                               19

SEQ ID NO: 26          moltype = DNA  length = 19
FEATURE                Location/Qualifiers
source                 1..19
                       mol_type = other DNA
                       organism = synthetic construct
SEQUENCE: 26
ggaccgccgt caccggatc                                               19

SEQ ID NO: 27          moltype = DNA  length = 19
FEATURE                Location/Qualifiers
source                 1..19
                       mol_type = other DNA
                       organism = synthetic construct
SEQUENCE: 27
gaccgccgtc accggatcc                                               19

SEQ ID NO: 28          moltype = DNA  length = 19
FEATURE                Location/Qualifiers
source                 1..19
                       mol_type = other DNA
                       organism = synthetic construct
SEQUENCE: 28
```

```
agacgggcct cccggagtc                                             19

SEQ ID NO: 29          moltype = DNA  length = 19
FEATURE                Location/Qualifiers
source                 1..19
                       mol_type = other DNA
                       organism = synthetic construct
SEQUENCE: 29
cctcgtgggt cgccttcgc                                             19

SEQ ID NO: 30          moltype = DNA  length = 19
FEATURE                Location/Qualifiers
source                 1..19
                       mol_type = other DNA
                       organism = synthetic construct
SEQUENCE: 30
ctcgtgggtc gccttcgcc                                             19

SEQ ID NO: 31          moltype = DNA  length = 19
FEATURE                Location/Qualifiers
source                 1..19
                       mol_type = other DNA
                       organism = synthetic construct
SEQUENCE: 31
gaggggatct cccaacctg                                             19

SEQ ID NO: 32          moltype = DNA  length = 19
FEATURE                Location/Qualifiers
source                 1..19
                       mol_type = other DNA
                       organism = synthetic construct
SEQUENCE: 32
cgcgcgggga tttcgccta                                             19

SEQ ID NO: 33          moltype = DNA  length = 19
FEATURE                Location/Qualifiers
source                 1..19
                       mol_type = other DNA
                       organism = synthetic construct
SEQUENCE: 33
gcgcggggat ttcgcctac                                             19

SEQ ID NO: 34          moltype = DNA  length = 19
FEATURE                Location/Qualifiers
source                 1..19
                       mol_type = other DNA
                       organism = synthetic construct
SEQUENCE: 34
cggggatttc gcctacgcc                                             19

SEQ ID NO: 35          moltype = DNA  length = 19
FEATURE                Location/Qualifiers
source                 1..19
                       mol_type = other DNA
                       organism = synthetic construct
SEQUENCE: 35
tgcttgcgcc acccacgtc                                             19

SEQ ID NO: 36          moltype = DNA  length = 19
FEATURE                Location/Qualifiers
source                 1..19
                       mol_type = other DNA
                       organism = synthetic construct
SEQUENCE: 36
ctggcgagcc cggagtttc                                             19

SEQ ID NO: 37          moltype = DNA  length = 19
FEATURE                Location/Qualifiers
source                 1..19
                       mol_type = other DNA
                       organism = synthetic construct
SEQUENCE: 37
ggcgagcccg gagtttctg                                             19

SEQ ID NO: 38          moltype = DNA  length = 19
FEATURE                Location/Qualifiers
source                 1..19
                       mol_type = other DNA
                       organism = synthetic construct
```

```
SEQUENCE: 38
ggcgcaacct ctcctagaa                                              19

SEQ ID NO: 39           moltype = DNA  length = 19
FEATURE                 Location/Qualifiers
source                  1..19
                        mol_type = other DNA
                        organism = synthetic construct
SEQUENCE: 39
gcgcaacctc tcctagaaa                                              19

SEQ ID NO: 40           moltype = DNA  length = 19
FEATURE                 Location/Qualifiers
source                  1..19
                        mol_type = other DNA
                        organism = synthetic construct
SEQUENCE: 40
aacctctcct agaaacgga                                              19

SEQ ID NO: 41           moltype = DNA  length = 19
FEATURE                 Location/Qualifiers
source                  1..19
                        mol_type = other DNA
                        organism = synthetic construct
SEQUENCE: 41
cagcgaggaa gaataccgg                                              19

SEQ ID NO: 42           moltype = DNA  length = 19
FEATURE                 Location/Qualifiers
source                  1..19
                        mol_type = other DNA
                        organism = synthetic construct
SEQUENCE: 42
agcgaggaag aataccggg                                              19

SEQ ID NO: 43           moltype = DNA  length = 19
FEATURE                 Location/Qualifiers
source                  1..19
                        mol_type = other DNA
                        organism = synthetic construct
SEQUENCE: 43
gcgaggaaga ataccgggc                                              19

SEQ ID NO: 44           moltype = DNA  length = 19
FEATURE                 Location/Qualifiers
source                  1..19
                        mol_type = other DNA
                        organism = synthetic construct
SEQUENCE: 44
gttgggacgg ggtcgggtg                                              19

SEQ ID NO: 45           moltype = DNA  length = 19
FEATURE                 Location/Qualifiers
source                  1..19
                        mol_type = other DNA
                        organism = synthetic construct
SEQUENCE: 45
acggggtcgg gtggttcgg                                              19

SEQ ID NO: 46           moltype = DNA  length = 19
FEATURE                 Location/Qualifiers
source                  1..19
                        mol_type = other DNA
                        organism = synthetic construct
SEQUENCE: 46
ggtcgggtgg ttcggggca                                              19

SEQ ID NO: 47           moltype = DNA  length = 19
FEATURE                 Location/Qualifiers
source                  1..19
                        mol_type = other DNA
                        organism = synthetic construct
SEQUENCE: 47
gtcgggtggt tcggggcag                                              19

SEQ ID NO: 48           moltype = DNA  length = 19
FEATURE                 Location/Qualifiers
source                  1..19
                        mol_type = other DNA
```

```
                        organism = synthetic construct
SEQUENCE: 48
gcggtggcct ctctttcgc                                                19

SEQ ID NO: 49           moltype = DNA  length = 19
FEATURE                 Location/Qualifiers
source                  1..19
                        mol_type = other DNA
                        organism = synthetic construct
SEQUENCE: 49
cggtggcctc tctttcgcg                                                19

SEQ ID NO: 50           moltype = DNA  length = 19
FEATURE                 Location/Qualifiers
source                  1..19
                        mol_type = other DNA
                        organism = synthetic construct
SEQUENCE: 50
ggtggcctct ctttcgcgg                                                19

SEQ ID NO: 51           moltype = DNA  length = 19
FEATURE                 Location/Qualifiers
source                  1..19
                        mol_type = other DNA
                        organism = synthetic construct
SEQUENCE: 51
gcctctcttt cgcggggaa                                                19

SEQ ID NO: 52           moltype = DNA  length = 19
FEATURE                 Location/Qualifiers
source                  1..19
                        mol_type = other DNA
                        organism = synthetic construct
SEQUENCE: 52
cacctggctg gctacggag                                                19

SEQ ID NO: 53           moltype = DNA  length = 19
FEATURE                 Location/Qualifiers
source                  1..19
                        mol_type = other DNA
                        organism = synthetic construct
SEQUENCE: 53
gctacggagg ggcgtgtct                                                19

SEQ ID NO: 54           moltype = DNA  length = 19
FEATURE                 Location/Qualifiers
source                  1..19
                        mol_type = other DNA
                        organism = synthetic construct
SEQUENCE: 54
ctacggaggg gcgtgtctc                                                19

SEQ ID NO: 55           moltype = DNA  length = 19
FEATURE                 Location/Qualifiers
source                  1..19
                        mol_type = other DNA
                        organism = synthetic construct
SEQUENCE: 55
acgtgcaagg gagctcgct                                                19

SEQ ID NO: 56           moltype = DNA  length = 19
FEATURE                 Location/Qualifiers
source                  1..19
                        mol_type = other DNA
                        organism = synthetic construct
SEQUENCE: 56
cgtgcaaggg agctcgctg                                                19

SEQ ID NO: 57           moltype = DNA  length = 19
FEATURE                 Location/Qualifiers
source                  1..19
                        mol_type = other DNA
                        organism = synthetic construct
SEQUENCE: 57
gtgcaaggga gctcgctgg                                                19

SEQ ID NO: 58           moltype = DNA  length = 19
FEATURE                 Location/Qualifiers
source                  1..19
```

-continued

```
                        mol_type = other DNA
                        organism = synthetic construct
SEQUENCE: 58
caccttccga cgctgtcta                                              19

SEQ ID NO: 59           moltype = DNA  length = 19
FEATURE                 Location/Qualifiers
source                  1..19
                        mol_type = other DNA
                        organism = synthetic construct
SEQUENCE: 59
accttccgac gctgtctag                                              19

SEQ ID NO: 60           moltype = DNA  length = 19
FEATURE                 Location/Qualifiers
source                  1..19
                        mol_type = other DNA
                        organism = synthetic construct
SEQUENCE: 60
ccttccgacg ctgtctagg                                              19

SEQ ID NO: 61           moltype = DNA  length = 19
FEATURE                 Location/Qualifiers
source                  1..19
                        mol_type = other DNA
                        organism = synthetic construct
SEQUENCE: 61
cttccgacgc tgtctaggc                                              19

SEQ ID NO: 62           moltype = DNA  length = 19
FEATURE                 Location/Qualifiers
source                  1..19
                        mol_type = other DNA
                        organism = synthetic construct
SEQUENCE: 62
tccgacgctg tctaggcaa                                              19

SEQ ID NO: 63           moltype = DNA  length = 19
FEATURE                 Location/Qualifiers
source                  1..19
                        mol_type = other DNA
                        organism = synthetic construct
SEQUENCE: 63
ccgacgctgt ctaggcaaa                                              19

SEQ ID NO: 64           moltype = DNA  length = 19
FEATURE                 Location/Qualifiers
source                  1..19
                        mol_type = other DNA
                        organism = synthetic construct
SEQUENCE: 64
acgctgtcta ggcaaacct                                              19

SEQ ID NO: 65           moltype = DNA  length = 19
FEATURE                 Location/Qualifiers
source                  1..19
                        mol_type = other DNA
                        organism = synthetic construct
SEQUENCE: 65
aaacctggat tagagttac                                              19

SEQ ID NO: 66           moltype = DNA  length = 19
FEATURE                 Location/Qualifiers
source                  1..19
                        mol_type = other DNA
                        organism = synthetic construct
SEQUENCE: 66
ctttgagaag gatcgcttt                                              19

SEQ ID NO: 67           moltype = DNA  length = 19
FEATURE                 Location/Qualifiers
source                  1..19
                        mol_type = other DNA
                        organism = synthetic construct
SEQUENCE: 67
gccggcagag ggatctcc                                               19

SEQ ID NO: 68           moltype = DNA  length = 19
FEATURE                 Location/Qualifiers
```

```
source                  1..19
                        mol_type = other DNA
                        organism = synthetic construct
SEQUENCE: 68
gggccaaggg gtgcttgcg                                              19

SEQ ID NO: 69           moltype = DNA  length = 19
FEATURE                 Location/Qualifiers
source                  1..19
                        mol_type = other DNA
                        organism = synthetic construct
SEQUENCE: 69
gccaaggggt gcttgcgcc                                              19

SEQ ID NO: 70           moltype = DNA  length = 19
FEATURE                 Location/Qualifiers
source                  1..19
                        mol_type = other DNA
                        organism = synthetic construct
SEQUENCE: 70
atgcaaggca tcccggcgc                                              19

SEQ ID NO: 71           moltype = DNA  length = 19
FEATURE                 Location/Qualifiers
source                  1..19
                        mol_type = other DNA
                        organism = synthetic construct
SEQUENCE: 71
gtgctgtccg agggtgtcg                                              19

SEQ ID NO: 72           moltype = DNA  length = 19
FEATURE                 Location/Qualifiers
source                  1..19
                        mol_type = other DNA
                        organism = synthetic construct
SEQUENCE: 72
aacgagtctc cgtcgccgt                                              19

SEQ ID NO: 73           moltype = DNA  length = 19
FEATURE                 Location/Qualifiers
source                  1..19
                        mol_type = other DNA
                        organism = synthetic construct
SEQUENCE: 73
aaacgagtct ccgtcgccg                                              19

SEQ ID NO: 74           moltype = DNA  length = 19
FEATURE                 Location/Qualifiers
source                  1..19
                        mol_type = other DNA
                        organism = synthetic construct
SEQUENCE: 74
caaacgagtc tccgtcgcc                                              19

SEQ ID NO: 75           moltype = DNA  length = 19
FEATURE                 Location/Qualifiers
source                  1..19
                        mol_type = other DNA
                        organism = synthetic construct
SEQUENCE: 75
ccaaacgagt ctccgtcgc                                              19

SEQ ID NO: 76           moltype = DNA  length = 19
FEATURE                 Location/Qualifiers
source                  1..19
                        mol_type = other DNA
                        organism = synthetic construct
SEQUENCE: 76
tccaaacgag tctccgtcg                                              19

SEQ ID NO: 77           moltype = DNA  length = 19
FEATURE                 Location/Qualifiers
source                  1..19
                        mol_type = other DNA
                        organism = synthetic construct
SEQUENCE: 77
gtccaaacga gtctccgtc                                              19

SEQ ID NO: 78           moltype = DNA  length = 19
```

-continued

```
FEATURE                Location/Qualifiers
source                 1..19
                       mol_type = other DNA
                       organism = synthetic construct
SEQUENCE: 78
ggtccaaacg agtctccgt                                                19

SEQ ID NO: 79          moltype = DNA  length = 19
FEATURE                Location/Qualifiers
source                 1..19
                       mol_type = other DNA
                       organism = synthetic construct
SEQUENCE: 79
tcgctttggc tcggggtcc                                                19

SEQ ID NO: 80          moltype = DNA  length = 19
FEATURE                Location/Qualifiers
source                 1..19
                       mol_type = other DNA
                       organism = synthetic construct
SEQUENCE: 80
ctcgctttgg ctcggggtc                                                19

SEQ ID NO: 81          moltype = DNA  length = 19
FEATURE                Location/Qualifiers
source                 1..19
                       mol_type = other DNA
                       organism = synthetic construct
SEQUENCE: 81
cctcgctttg gctcggggt                                                19

SEQ ID NO: 82          moltype = DNA  length = 19
FEATURE                Location/Qualifiers
source                 1..19
                       mol_type = other DNA
                       organism = synthetic construct
SEQUENCE: 82
ctcaaagcag gctcgcagg                                                19

SEQ ID NO: 83          moltype = DNA  length = 19
FEATURE                Location/Qualifiers
source                 1..19
                       mol_type = other DNA
                       organism = synthetic construct
SEQUENCE: 83
ccgctcaaag caggctcgc                                                19

SEQ ID NO: 84          moltype = DNA  length = 19
FEATURE                Location/Qualifiers
source                 1..19
                       mol_type = other DNA
                       organism = synthetic construct
SEQUENCE: 84
agccgttctc tggtggcga                                                19

SEQ ID NO: 85          moltype = DNA  length = 19
FEATURE                Location/Qualifiers
source                 1..19
                       mol_type = other DNA
                       organism = synthetic construct
SEQUENCE: 85
ccggaatgcc gatggcctg                                                19

SEQ ID NO: 86          moltype = DNA  length = 19
FEATURE                Location/Qualifiers
source                 1..19
                       mol_type = other DNA
                       organism = synthetic construct
SEQUENCE: 86
ctccggaatg ccgatggcc                                                19

SEQ ID NO: 87          moltype = DNA  length = 19
FEATURE                Location/Qualifiers
source                 1..19
                       mol_type = other DNA
                       organism = synthetic construct
SEQUENCE: 87
gctccggaat gccgatggc                                                19
```

```
SEQ ID NO: 88           moltype = DNA  length = 19
FEATURE                 Location/Qualifiers
source                  1..19
                        mol_type = other DNA
                        organism = synthetic construct
SEQUENCE: 88
ccgagattcc cgccggtgc                                               19

SEQ ID NO: 89           moltype = DNA  length = 19
FEATURE                 Location/Qualifiers
source                  1..19
                        mol_type = other DNA
                        organism = synthetic construct
SEQUENCE: 89
gccgagattc ccgccggtg                                               19

SEQ ID NO: 90           moltype = DNA  length = 19
FEATURE                 Location/Qualifiers
source                  1..19
                        mol_type = other DNA
                        organism = synthetic construct
SEQUENCE: 90
gctttcgccg gccttctgg                                               19

SEQ ID NO: 91           moltype = DNA  length = 19
FEATURE                 Location/Qualifiers
source                  1..19
                        mol_type = other DNA
                        organism = synthetic construct
SEQUENCE: 91
ccgctttcgc cggccttct                                               19

SEQ ID NO: 92           moltype = DNA  length = 19
FEATURE                 Location/Qualifiers
source                  1..19
                        mol_type = other DNA
                        organism = synthetic construct
SEQUENCE: 92
tccgctttcg ccggccttc                                               19

SEQ ID NO: 93           moltype = DNA  length = 19
FEATURE                 Location/Qualifiers
source                  1..19
                        mol_type = other DNA
                        organism = synthetic construct
SEQUENCE: 93
gacggcggtc cgctttcgc                                               19

SEQ ID NO: 94           moltype = DNA  length = 19
FEATURE                 Location/Qualifiers
source                  1..19
                        mol_type = other DNA
                        organism = synthetic construct
SEQUENCE: 94
gtgacggcgg tccgctttc                                               19

SEQ ID NO: 95           moltype = DNA  length = 19
FEATURE                 Location/Qualifiers
source                  1..19
                        mol_type = other DNA
                        organism = synthetic construct
SEQUENCE: 95
atccggtgac ggcggtccg                                               19

SEQ ID NO: 96           moltype = DNA  length = 19
FEATURE                 Location/Qualifiers
source                  1..19
                        mol_type = other DNA
                        organism = synthetic construct
SEQUENCE: 96
gatccggtga cggcggtcc                                               19

SEQ ID NO: 97           moltype = DNA  length = 19
FEATURE                 Location/Qualifiers
source                  1..19
                        mol_type = other DNA
                        organism = synthetic construct
SEQUENCE: 97
ggatccggtg acggcggtc                                               19
```

```
SEQ ID NO: 98           moltype = DNA  length = 19
FEATURE                 Location/Qualifiers
source                  1..19
                        mol_type = other DNA
                        organism = synthetic construct
SEQUENCE: 98
gactccggga ggcccgtct                                                  19

SEQ ID NO: 99           moltype = DNA  length = 19
FEATURE                 Location/Qualifiers
source                  1..19
                        mol_type = other DNA
                        organism = synthetic construct
SEQUENCE: 99
gcgaaggcga cccacgagg                                                  19

SEQ ID NO: 100          moltype = DNA  length = 19
FEATURE                 Location/Qualifiers
source                  1..19
                        mol_type = other DNA
                        organism = synthetic construct
SEQUENCE: 100
ggcgaaggcg acccacgag                                                  19

SEQ ID NO: 101          moltype = DNA  length = 19
FEATURE                 Location/Qualifiers
source                  1..19
                        mol_type = other DNA
                        organism = synthetic construct
SEQUENCE: 101
caggttggga gatcccctc                                                  19

SEQ ID NO: 102          moltype = DNA  length = 19
FEATURE                 Location/Qualifiers
source                  1..19
                        mol_type = other DNA
                        organism = synthetic construct
SEQUENCE: 102
taggcgaaat ccccgcgcg                                                  19

SEQ ID NO: 103          moltype = DNA  length = 19
FEATURE                 Location/Qualifiers
source                  1..19
                        mol_type = other DNA
                        organism = synthetic construct
SEQUENCE: 103
gtaggcgaaa tccccgcgc                                                  19

SEQ ID NO: 104          moltype = DNA  length = 19
FEATURE                 Location/Qualifiers
source                  1..19
                        mol_type = other DNA
                        organism = synthetic construct
SEQUENCE: 104
ggcgtaggcg aaatccccg                                                  19

SEQ ID NO: 105          moltype = DNA  length = 19
FEATURE                 Location/Qualifiers
source                  1..19
                        mol_type = other DNA
                        organism = synthetic construct
SEQUENCE: 105
gacgtgggtg gcgcaagca                                                  19

SEQ ID NO: 106          moltype = DNA  length = 19
FEATURE                 Location/Qualifiers
source                  1..19
                        mol_type = other DNA
                        organism = synthetic construct
SEQUENCE: 106
gaaactccgg gctcgccag                                                  19

SEQ ID NO: 107          moltype = DNA  length = 19
FEATURE                 Location/Qualifiers
source                  1..19
                        mol_type = other DNA
                        organism = synthetic construct
SEQUENCE: 107
```

```
cagaaactcc gggctcgcc                                                     19

SEQ ID NO: 108          moltype = DNA  length = 19
FEATURE                 Location/Qualifiers
source                  1..19
                        mol_type = other DNA
                        organism = synthetic construct
SEQUENCE: 108
ttctaggaga ggttgcgcc                                                     19

SEQ ID NO: 109          moltype = DNA  length = 19
FEATURE                 Location/Qualifiers
source                  1..19
                        mol_type = other DNA
                        organism = synthetic construct
SEQUENCE: 109
tttctaggag aggttgcgc                                                     19

SEQ ID NO: 110          moltype = DNA  length = 19
FEATURE                 Location/Qualifiers
source                  1..19
                        mol_type = other DNA
                        organism = synthetic construct
SEQUENCE: 110
tccgtttcta ggagaggtt                                                     19

SEQ ID NO: 111          moltype = DNA  length = 19
FEATURE                 Location/Qualifiers
source                  1..19
                        mol_type = other DNA
                        organism = synthetic construct
SEQUENCE: 111
ccggtattct tcctcgctg                                                     19

SEQ ID NO: 112          moltype = DNA  length = 19
FEATURE                 Location/Qualifiers
source                  1..19
                        mol_type = other DNA
                        organism = synthetic construct
SEQUENCE: 112
cccggtattc ttcctcgct                                                     19

SEQ ID NO: 113          moltype = DNA  length = 19
FEATURE                 Location/Qualifiers
source                  1..19
                        mol_type = other DNA
                        organism = synthetic construct
SEQUENCE: 113
gcccggtatt cttcctcgc                                                     19

SEQ ID NO: 114          moltype = DNA  length = 19
FEATURE                 Location/Qualifiers
source                  1..19
                        mol_type = other DNA
                        organism = synthetic construct
SEQUENCE: 114
cacccgaccc cgtcccaac                                                     19

SEQ ID NO: 115          moltype = DNA  length = 19
FEATURE                 Location/Qualifiers
source                  1..19
                        mol_type = other DNA
                        organism = synthetic construct
SEQUENCE: 115
ccgaaccacc cgaccccgt                                                     19

SEQ ID NO: 116          moltype = DNA  length = 19
FEATURE                 Location/Qualifiers
source                  1..19
                        mol_type = other DNA
                        organism = synthetic construct
SEQUENCE: 116
tgccccgaac cacccgacc                                                     19

SEQ ID NO: 117          moltype = DNA  length = 19
FEATURE                 Location/Qualifiers
source                  1..19
                        mol_type = other DNA
                        organism = synthetic construct
```

```
SEQUENCE: 117
ctgccccgaa ccacccgac                                              19

SEQ ID NO: 118          moltype = DNA  length = 19
FEATURE                 Location/Qualifiers
source                  1..19
                        mol_type = other DNA
                        organism = synthetic construct
SEQUENCE: 118
gcgaaagaga ggccaccgc                                              19

SEQ ID NO: 119          moltype = DNA  length = 19
FEATURE                 Location/Qualifiers
source                  1..19
                        mol_type = other DNA
                        organism = synthetic construct
SEQUENCE: 119
cgcgaaagag aggccaccg                                              19

SEQ ID NO: 120          moltype = DNA  length = 19
FEATURE                 Location/Qualifiers
source                  1..19
                        mol_type = other DNA
                        organism = synthetic construct
SEQUENCE: 120
ccgcgaaaga gaggccacc                                              19

SEQ ID NO: 121          moltype = DNA  length = 19
FEATURE                 Location/Qualifiers
source                  1..19
                        mol_type = other DNA
                        organism = synthetic construct
SEQUENCE: 121
ttccccgcga aagagaggc                                              19

SEQ ID NO: 122          moltype = DNA  length = 19
FEATURE                 Location/Qualifiers
source                  1..19
                        mol_type = other DNA
                        organism = synthetic construct
SEQUENCE: 122
ctccgtagcc agccaggtg                                              19

SEQ ID NO: 123          moltype = DNA  length = 19
FEATURE                 Location/Qualifiers
source                  1..19
                        mol_type = other DNA
                        organism = synthetic construct
SEQUENCE: 123
agacacgccc ctccgtagc                                              19

SEQ ID NO: 124          moltype = DNA  length = 19
FEATURE                 Location/Qualifiers
source                  1..19
                        mol_type = other DNA
                        organism = synthetic construct
SEQUENCE: 124
gagacacgcc cctccgtag                                              19

SEQ ID NO: 125          moltype = DNA  length = 19
FEATURE                 Location/Qualifiers
source                  1..19
                        mol_type = other DNA
                        organism = synthetic construct
SEQUENCE: 125
agcgagctcc cttgcacgt                                              19

SEQ ID NO: 126          moltype = DNA  length = 19
FEATURE                 Location/Qualifiers
source                  1..19
                        mol_type = other DNA
                        organism = synthetic construct
SEQUENCE: 126
cagcgagctc ccttgcacg                                              19

SEQ ID NO: 127          moltype = DNA  length = 19
FEATURE                 Location/Qualifiers
source                  1..19
                        mol_type = other DNA
```

```
                        organism = synthetic construct
SEQUENCE: 127
ccagcgagct cccttgcac                                           19

SEQ ID NO: 128          moltype = DNA  length = 19
FEATURE                 Location/Qualifiers
source                  1..19
                        mol_type = other DNA
                        organism = synthetic construct
SEQUENCE: 128
tagacagcgt cggaaggtg                                           19

SEQ ID NO: 129          moltype = DNA  length = 19
FEATURE                 Location/Qualifiers
source                  1..19
                        mol_type = other DNA
                        organism = synthetic construct
SEQUENCE: 129
ctagacagcg tcggaaggt                                           19

SEQ ID NO: 130          moltype = DNA  length = 19
FEATURE                 Location/Qualifiers
source                  1..19
                        mol_type = other DNA
                        organism = synthetic construct
SEQUENCE: 130
cctagacagc gtcggaagg                                           19

SEQ ID NO: 131          moltype = DNA  length = 19
FEATURE                 Location/Qualifiers
source                  1..19
                        mol_type = other DNA
                        organism = synthetic construct
SEQUENCE: 131
gcctagacag cgtcggaag                                           19

SEQ ID NO: 132          moltype = DNA  length = 19
FEATURE                 Location/Qualifiers
source                  1..19
                        mol_type = other DNA
                        organism = synthetic construct
SEQUENCE: 132
ttgcctagac agcgtcgga                                           19

SEQ ID NO: 133          moltype = DNA  length = 19
FEATURE                 Location/Qualifiers
source                  1..19
                        mol_type = other DNA
                        organism = synthetic construct
SEQUENCE: 133
tttgcctaga cagcgtcgg                                           19

SEQ ID NO: 134          moltype = DNA  length = 19
FEATURE                 Location/Qualifiers
source                  1..19
                        mol_type = other DNA
                        organism = synthetic construct
SEQUENCE: 134
aggtttgcct agacagcgt                                           19

SEQ ID NO: 135          moltype = DNA  length = 19
FEATURE                 Location/Qualifiers
source                  1..19
                        mol_type = other DNA
                        organism = synthetic construct
SEQUENCE: 135
gtaactctaa tccaggttt                                           19

SEQ ID NO: 136          moltype = DNA  length = 19
FEATURE                 Location/Qualifiers
source                  1..19
                        mol_type = other DNA
                        organism = synthetic construct
SEQUENCE: 136
aaagcgatcc ttctcaaag                                           19

SEQ ID NO: 137          moltype = DNA  length = 19
FEATURE                 Location/Qualifiers
source                  1..19
```

```
                         mol_type = other DNA
                         organism = synthetic construct
SEQUENCE: 137
ggagatcccc tctgccggc                                                  19

SEQ ID NO: 138           moltype = DNA  length = 19
FEATURE                  Location/Qualifiers
source                   1..19
                         mol_type = other DNA
                         organism = synthetic construct
SEQUENCE: 138
cgcaagcacc ccttggccc                                                  19

SEQ ID NO: 139           moltype = DNA  length = 19
FEATURE                  Location/Qualifiers
source                   1..19
                         mol_type = other DNA
                         organism = synthetic construct
SEQUENCE: 139
ggcgcaagca ccccttggc                                                  19

SEQ ID NO: 140           moltype = DNA  length = 19
FEATURE                  Location/Qualifiers
source                   1..19
                         mol_type = other DNA
                         organism = synthetic construct
SEQUENCE: 140
gcgccgggat gccttgcat                                                  19

SEQ ID NO: 141           moltype = RNA  length = 19
FEATURE                  Location/Qualifiers
modified_base            19
                         mod_base = OTHER
                         note = 2'-O-methyladenosine
modified_base            2
                         mod_base = OTHER
                         note = 2'-O-methylguanosine phosphorothioate
modified_base            6
                         mod_base = OTHER
                         note = 2'-O-methylcytidine
modified_base            9
                         mod_base = OTHER
                         note = 2'-fluorouridine
modified_base            17
                         mod_base = OTHER
                         note = 2'-O-methylcytidine phosphorothioate
modified_base            11
                         mod_base = OTHER
                         note = 2'-O-methylguanosine
modified_base            16
                         mod_base = OTHER
                         note = 2'-O-methylguanosine
modified_base            8
                         mod_base = OTHER
                         note = 2'-fluorocytidine
modified_base            1
                         mod_base = OTHER
                         note = 2'-O-methylcytidine phosphorothioate
modified_base            4
                         mod_base = OTHER
                         note = 2'-O-methylcytidine
modified_base            5
                         mod_base = OTHER
                         note = 2'-O-methyladenosine
modified_base            18
                         mod_base = OTHER
                         note = 2'-O-methyladenosine phosphorothioate
modified_base            12
                         mod_base = OTHER
                         note = 2'-O-methylguanosine
modified_base            10
                         mod_base = OTHER
                         note = 2'-O-methylcytidine
source                   1..19
                         mol_type = other RNA
                         organism = synthetic construct
modified_base            7
                         mod_base = OTHER
                         note = 2'-fluorocytidine
```

-continued

```
modified_base          15
                       mod_base = OTHER
                       note = 2'-O-methyladenosine
modified_base          13
                       mod_base = OTHER
                       note = 2'-O-methyladenosine
modified_base          3
                       mod_base = OTHER
                       note = 2'-O-methyladenosine
modified_base          14
                       mod_base = OTHER
                       note = 2'-O-methylcytidine
SEQUENCE: 141
cgacaccctc ggacagcaa                                              19

SEQ ID NO: 142         moltype = RNA  length = 19
FEATURE                Location/Qualifiers
modified_base          1
                       mod_base = OTHER
                       note = 2'-O-methyladenosine phosphorothioate
modified_base          11
                       mod_base = OTHER
                       note = 2'-O-methyladenosine
modified_base          19
                       mod_base = OTHER
                       note = 2'-O-methyladenosine
modified_base          4
                       mod_base = OTHER
                       note = 2'-O-methylguanosine
modified_base          18
                       mod_base = OTHER
                       note = 2'-O-methyluridine phosphorothioate
modified_base          8
                       mod_base = OTHER
                       note = 2'-fluorocytidine
modified_base          2
                       mod_base = OTHER
                       note = 2'-O-methylcytidine phosphorothioate
modified_base          17
                       mod_base = OTHER
                       note = 2'-O-methylguanosine phosphorothioate
source                 1..19
                       mol_type = other RNA
                       organism = synthetic construct
modified_base          6
                       mod_base = OTHER
                       note = 2'-O-methylguanosine
modified_base          16
                       mod_base = OTHER
                       note = 2'-O-methylcytidine
modified_base          7
                       mod_base = OTHER
                       note = 2'-fluoroadenosine
modified_base          12
                       mod_base = OTHER
                       note = 2'-O-methylguanosine
modified_base          13
                       mod_base = OTHER
                       note = 2'-O-methyladenosine
modified_base          3
                       mod_base = OTHER
                       note = 2'-O-methylguanosine
modified_base          5
                       mod_base = OTHER
                       note = 2'-O-methylcytidine
modified_base          10
                       mod_base = OTHER
                       note = 2'-O-methylguanosine
modified_base          15
                       mod_base = OTHER
                       note = 2'-O-methyluridine
modified_base          14
                       mod_base = OTHER
                       note = 2'-O-methylcytidine
modified_base          9
                       mod_base = OTHER
                       note = 2'-fluoroguanosine
SEQUENCE: 142
acggcgacgg agactcgta                                              19
```

```
SEQ ID NO: 143          moltype = RNA  length = 19
FEATURE                 Location/Qualifiers
modified_base           19
                        mod_base = OTHER
                        note = 2'-O-methyladenosine
modified_base           17
                        mod_base = OTHER
                        note = 2'-O-methyluridine phosphorothioate
modified_base           1
                        mod_base = OTHER
                        note = 2'-O-methylcytidine phosphorothioate
modified_base           16
                        mod_base = OTHER
                        note = 2'-O-methylguanosine
modified_base           3
                        mod_base = OTHER
                        note = 2'-O-methylguanosine
modified_base           11
                        mod_base = OTHER
                        note = 2'-O-methylguanosine
modified_base           8
                        mod_base = OTHER
                        note = 2'-fluoroguanosine
modified_base           13
                        mod_base = OTHER
                        note = 2'-O-methylcytidine
modified_base           6
                        mod_base = OTHER
                        note = 2'-O-methyladenosine
modified_base           7
                        mod_base = OTHER
                        note = 2'-fluorocytidine
modified_base           4
                        mod_base = OTHER
                        note = 2'-O-methylcytidine
modified_base           5
                        mod_base = OTHER
                        note = 2'-O-methylguanosine
modified_base           14
                        mod_base = OTHER
                        note = 2'-O-methyluridine
modified_base           15
                        mod_base = OTHER
                        note = 2'-O-methylcytidine
modified_base           18
                        mod_base = OTHER
                        note = 2'-O-methyluridine phosphorothioate
modified_base           2
                        mod_base = OTHER
                        note = 2'-O-methylguanosine phosphorothioate
modified_base           12
                        mod_base = OTHER
                        note = 2'-O-methyladenosine
source                  1..19
                        mol_type = other RNA
                        organism = synthetic construct
modified_base           10
                        mod_base = OTHER
                        note = 2'-O-methyladenosine
modified_base           9
                        mod_base = OTHER
                        note = 2'-fluoroguanosine
SEQUENCE: 143
cggcgacgga gactcgtta                                                19

SEQ ID NO: 144          moltype = RNA  length = 19
FEATURE                 Location/Qualifiers
modified_base           7
                        mod_base = OTHER
                        note = 2'-fluoroguanosine
modified_base           8
                        mod_base = OTHER
                        note = 2'-fluoroguanosine
modified_base           1
                        mod_base = OTHER
                        note = 2'-O-methylguanosine phosphorothioate
modified_base           9
                        mod_base = OTHER
```

-continued

| | |
|---|---|
| | note = 2'-fluoroadenosine |
| modified_base | 14 |
| | mod_base = OTHER |
| | note = 2'-O-methylcytidine |
| modified_base | 11 |
| | mod_base = OTHER |
| | note = 2'-O-methyladenosine |
| modified_base | 15 |
| | mod_base = OTHER |
| | note = 2'-O-methylguanosine |
| modified_base | 19 |
| | mod_base = OTHER |
| | note = 2'-O-methyladenosine |
| modified_base | 4 |
| | mod_base = OTHER |
| | note = 2'-O-methylguanosine |
| modified_base | 18 |
| | mod_base = OTHER |
| | note = 2'-O-methyluridine phosphorothioate |
| modified_base | 17 |
| | mod_base = OTHER |
| | note = 2'-O-methyluridine phosphorothioate |
| modified_base | 10 |
| | mod_base = OTHER |
| | note = 2'-O-methylguanosine |
| modified_base | 13 |
| | mod_base = OTHER |
| | note = 2'-O-methyluridine |
| modified_base | 6 |
| | mod_base = OTHER |
| | note = 2'-O-methylcytidine |
| modified_base | 2 |
| | mod_base = OTHER |
| | note = 2'-O-methylguanosine phosphorothioate |
| modified_base | 16 |
| | mod_base = OTHER |
| | note = 2'-O-methyluridine |
| source | 1..19 |
| | mol_type = other RNA |
| | organism = synthetic construct |
| modified_base | 12 |
| | mod_base = OTHER |
| | note = 2'-O-methylcytidine |
| modified_base | 3 |
| | mod_base = OTHER |
| | note = 2'-O-methylcytidine |
| modified_base | 5 |
| | mod_base = OTHER |
| | note = 2'-O-methyladenosine |

SEQUENCE: 144
ggcgacggag actcgttta 19

| | |
|---|---|
| SEQ ID NO: 145 | moltype = RNA length = 19 |
| FEATURE | Location/Qualifiers |
| modified_base | 1 |
| | mod_base = OTHER |
| | note = 2'-O-methylguanosine phosphorothioate |
| modified_base | 2 |
| | mod_base = OTHER |
| | note = 2'-O-methylcytidine phosphorothioate |
| modified_base | 9 |
| | mod_base = OTHER |
| | note = 2'-fluoroguanosine |
| modified_base | 6 |
| | mod_base = OTHER |
| | note = 2'-O-methylguanosine |
| modified_base | 11 |
| | mod_base = OTHER |
| | note = 2'-O-methylcytidine |
| modified_base | 4 |
| | mod_base = OTHER |
| | note = 2'-O-methyladenosine |
| modified_base | 18 |
| | mod_base = OTHER |
| | note = 2'-O-methylguanosine phosphorothioate |
| modified_base | 7 |
| | mod_base = OTHER |
| | note = 2'-fluoroguanosine |
| modified_base | 19 |

-continued

```
                        mod_base = OTHER
                        note = 2'-O-methyladenosine
modified_base           8
                        mod_base = OTHER
                        note = 2'-fluoroadenosine
source                  1..19
                        mol_type = other RNA
                        organism = synthetic construct
modified_base           12
                        mod_base = OTHER
                        note = 2'-O-methyluridine
modified_base           15
                        mod_base = OTHER
                        note = 2'-O-methyluridine
modified_base           3
                        mod_base = OTHER
                        note = 2'-O-methylguanosine
modified_base           5
                        mod_base = OTHER
                        note = 2'-O-methylcytidine
modified_base           13
                        mod_base = OTHER
                        note = 2'-O-methylcytidine
modified_base           16
                        mod_base = OTHER
                        note = 2'-O-methyluridine
modified_base           17
                        mod_base = OTHER
                        note = 2'-O-methyluridine phosphorothioate
modified_base           10
                        mod_base = OTHER
                        note = 2'-O-methyladenosine
modified_base           14
                        mod_base = OTHER
                        note = 2'-O-methylguanosine
SEQUENCE: 145
gcgacggaga ctcgtttga                                                  19

SEQ ID NO: 146          moltype = RNA  length = 19
FEATURE                 Location/Qualifiers
modified_base           14
                        mod_base = OTHER
                        note = 2'-O-methyluridine
modified_base           5
                        mod_base = OTHER
                        note = 2'-O-methylguanosine
modified_base           1
                        mod_base = OTHER
                        note = 2'-O-methylcytidine phosphorothioate
modified_base           6
                        mod_base = OTHER
                        note = 2'-O-methylguanosine
modified_base           12
                        mod_base = OTHER
                        note = 2'-O-methylcytidine
modified_base           11
                        mod_base = OTHER
                        note = 2'-O-methyluridine
modified_base           10
                        mod_base = OTHER
                        note = 2'-O-methylcytidine
modified_base           19
                        mod_base = OTHER
                        note = 2'-O-methyladenosine
modified_base           2
                        mod_base = OTHER
                        note = 2'-O-methylguanosine phosphorothioate
modified_base           15
                        mod_base = OTHER
                        note = 2'-O-methyluridine
source                  1..19
                        mol_type = other RNA
                        organism = synthetic construct
modified_base           3
                        mod_base = OTHER
                        note = 2'-O-methyladenosine
modified_base           9
                        mod_base = OTHER
                        note = 2'-fluoroadenosine
```

```
modified_base          17
                       mod_base = OTHER
                       note = 2'-O-methylguanosine phosphorothioate
modified_base          4
                       mod_base = OTHER
                       note = 2'-O-methylcytidine
modified_base          8
                       mod_base = OTHER
                       note = 2'-fluoroguanosine
modified_base          18
                       mod_base = OTHER
                       note = 2'-O-methylguanosine phosphorothioate
modified_base          16
                       mod_base = OTHER
                       note = 2'-O-methyluridine
modified_base          7
                       mod_base = OTHER
                       note = 2'-fluoroadenosine
modified_base          13
                       mod_base = OTHER
                       note = 2'-O-methylguanosine
SEQUENCE: 146
cgacggagac tcgtttgga                                              19

SEQ ID NO: 147         moltype = RNA  length = 19
FEATURE                Location/Qualifiers
modified_base          11
                       mod_base = OTHER
                       note = 2'-O-methylcytidine
modified_base          6
                       mod_base = OTHER
                       note = 2'-O-methyladenosine
modified_base          3
                       mod_base = OTHER
                       note = 2'-O-methylcytidine
modified_base          10
                       mod_base = OTHER
                       note = 2'-O-methyluridine
modified_base          12
                       mod_base = OTHER
                       note = 2'-O-methylguanosine
modified_base          17
                       mod_base = OTHER
                       note = 2'-O-methylguanosine phosphorothioate
modified_base          8
                       mod_base = OTHER
                       note = 2'-fluoroadenosine
modified_base          5
                       mod_base = OTHER
                       note = 2'-O-methylguanosine
modified_base          16
                       mod_base = OTHER
                       note = 2'-O-methylguanosine
modified_base          9
                       mod_base = OTHER
                       note = 2'-fluorocytidine
source                 1..19
                       mol_type = other RNA
                       organism = synthetic construct
modified_base          7
                       mod_base = OTHER
                       note = 2'-fluoroguanosine
modified_base          19
                       mod_base = OTHER
                       note = 2'-O-methyladenosine
modified_base          13
                       mod_base = OTHER
                       note = 2'-O-methyluridine
modified_base          4
                       mod_base = OTHER
                       note = 2'-O-methylguanosine
modified_base          2
                       mod_base = OTHER
                       note = 2'-O-methyladenosine phosphorothioate
modified_base          14
                       mod_base = OTHER
                       note = 2'-O-methyluridine
modified_base          15
                       mod_base = OTHER
```

```
                        note = 2'-O-methyluridine
modified_base           18
                        mod_base = OTHER
                        note = 2'-O-methyladenosine phosphorothioate
modified_base           1
                        mod_base = OTHER
                        note = 2'-O-methylguanosine phosphorothioate
SEQUENCE: 147
gacggagact cgtttggaa                                               19

SEQ ID NO: 148          moltype = RNA  length = 19
FEATURE                 Location/Qualifiers
modified_base           1
                        mod_base = OTHER
                        note = 2'-O-methyladenosine phosphorothioate
modified_base           14
                        mod_base = OTHER
                        note = 2'-O-methyluridine
source                  1..19
                        mol_type = other RNA
                        organism = synthetic construct
modified_base           12
                        mod_base = OTHER
                        note = 2'-O-methyluridine
modified_base           11
                        mod_base = OTHER
                        note = 2'-O-methylguanosine
modified_base           8
                        mod_base = OTHER
                        note = 2'-fluorocytidine
modified_base           6
                        mod_base = OTHER
                        note = 2'-O-methylguanosine
modified_base           15
                        mod_base = OTHER
                        note = 2'-O-methylguanosine
modified_base           16
                        mod_base = OTHER
                        note = 2'-O-methylguanosine
modified_base           19
                        mod_base = OTHER
                        note = 2'-O-methyladenosine
modified_base           9
                        mod_base = OTHER
                        note = 2'-fluorouridine
modified_base           5
                        mod_base = OTHER
                        note = 2'-O-methyladenosine
modified_base           18
                        mod_base = OTHER
                        note = 2'-O-methylcytidine phosphorothioate
modified_base           3
                        mod_base = OTHER
                        note = 2'-O-methylguanosine
modified_base           7
                        mod_base = OTHER
                        note = 2'-fluoroadenosine
modified_base           10
                        mod_base = OTHER
                        note = 2'-O-methylcytidine
modified_base           4
                        mod_base = OTHER
                        note = 2'-O-methylguanosine
modified_base           2
                        mod_base = OTHER
                        note = 2'-O-methylcytidine phosphorothioate
modified_base           13
                        mod_base = OTHER
                        note = 2'-O-methyluridine
modified_base           17
                        mod_base = OTHER
                        note = 2'-O-methyladenosine phosphorothioate
SEQUENCE: 148
acggagactc gtttggaca                                               19

SEQ ID NO: 149          moltype = RNA  length = 19
FEATURE                 Location/Qualifiers
modified_base           12
                        mod_base = OTHER
```

```
                        note = 2'-O-methylcytidine
modified_base           1
                        mod_base = OTHER
                        note = 2'-O-methylguanosine phosphorothioate
modified_base           16
                        mod_base = OTHER
                        note = 2'-O-methylguanosine
modified_base           19
                        mod_base = OTHER
                        note = 2'-O-methyladenosine
modified_base           14
                        mod_base = OTHER
                        note = 2'-O-methyladenosine
source                  1..19
                        mol_type = other RNA
                        organism = synthetic construct
modified_base           15
                        mod_base = OTHER
                        note = 2'-O-methyladenosine
modified_base           11
                        mod_base = OTHER
                        note = 2'-O-methylcytidine
modified_base           17
                        mod_base = OTHER
                        note = 2'-O-methylcytidine phosphorothioate
modified_base           8
                        mod_base = OTHER
                        note = 2'-fluoroguanosine
modified_base           6
                        mod_base = OTHER
                        note = 2'-O-methylcytidine
modified_base           10
                        mod_base = OTHER
                        note = 2'-O-methylguanosine
modified_base           13
                        mod_base = OTHER
                        note = 2'-O-methyladenosine
modified_base           5
                        mod_base = OTHER
                        note = 2'-O-methylcytidine
modified_base           18
                        mod_base = OTHER
                        note = 2'-O-methylguanosine phosphorothioate
modified_base           7
                        mod_base = OTHER
                        note = 2'-fluorocytidine
modified_base           2
                        mod_base = OTHER
                        note = 2'-O-methylguanosine phosphorothioate
modified_base           9
                        mod_base = OTHER
                        note = 2'-fluoroadenosine
modified_base           3
                        mod_base = OTHER
                        note = 2'-O-methyladenosine
modified_base           4
                        mod_base = OTHER
                        note = 2'-O-methylcytidine
SEQUENCE: 149
ggaccccgag ccaaagcga                                                19

SEQ ID NO: 150          moltype = RNA  length = 19
FEATURE                 Location/Qualifiers
modified_base           1
                        mod_base = OTHER
                        note = 2'-O-methylguanosine phosphorothioate
source                  1..19
                        mol_type = other RNA
                        organism = synthetic construct
modified_base           3
                        mod_base = OTHER
                        note = 2'-O-methylcytidine
modified_base           17
                        mod_base = OTHER
                        note = 2'-O-methylguanosine phosphorothioate
modified_base           9
                        mod_base = OTHER
                        note = 2'-fluoroguanosine
modified_base           18
```

```
                        mod_base = OTHER
                        note = 2'-O-methyladenosine phosphorothioate
modified_base           4
                        mod_base = OTHER
                        note = 2'-O-methylcytidine
modified_base           2
                        mod_base = OTHER
                        note = 2'-O-methyladenosine phosphorothioate
modified_base           7
                        mod_base = OTHER
                        note = 2'-fluoroguanosine
modified_base           13
                        mod_base = OTHER
                        note = 2'-O-methyladenosine
modified_base           12
                        mod_base = OTHER
                        note = 2'-O-methyladenosine
modified_base           19
                        mod_base = OTHER
                        note = 2'-O-methyladenosine
modified_base           16
                        mod_base = OTHER
                        note = 2'-O-methylcytidine
modified_base           6
                        mod_base = OTHER
                        note = 2'-O-methylcytidine
modified_base           5
                        mod_base = OTHER
                        note = 2'-O-methylcytidine
modified_base           14
                        mod_base = OTHER
                        note = 2'-O-methyladenosine
modified_base           11
                        mod_base = OTHER
                        note = 2'-O-methylcytidine
modified_base           15
                        mod_base = OTHER
                        note = 2'-O-methylguanosine
modified_base           8
                        mod_base = OTHER
                        note = 2'-fluoroadenosine
modified_base           10
                        mod_base = OTHER
                        note = 2'-O-methylcytidine
SEQUENCE: 150
gaccccgagc caaagcgaa                                              19

SEQ ID NO: 151          moltype = RNA  length = 19
FEATURE                 Location/Qualifiers
modified_base           10
                        mod_base = OTHER
                        note = 2'-O-methylcytidine
modified_base           19
                        mod_base = OTHER
                        note = 2'-O-methyladenosine
modified_base           7
                        mod_base = OTHER
                        note = 2'-fluoroadenosine
modified_base           15
                        mod_base = OTHER
                        note = 2'-O-methylcytidine
modified_base           14
                        mod_base = OTHER
                        note = 2'-O-methylguanosine
modified_base           1
                        mod_base = OTHER
                        note = 2'-O-methyladenosine phosphorothioate
modified_base           2
                        mod_base = OTHER
                        note = 2'-O-methylcytidine phosphorothioate
modified_base           13
                        mod_base = OTHER
                        note = 2'-O-methyladenosine
modified_base           9
                        mod_base = OTHER
                        note = 2'-fluorocytidine
modified_base           17
                        mod_base = OTHER
                        note = 2'-O-methyladenosine phosphorothioate
```

```
modified_base          18
                       mod_base = OTHER
                       note = 2'-O-methylguanosine phosphorothioate
modified_base          12
                       mod_base = OTHER
                       note = 2'-O-methyladenosine
modified_base          11
                       mod_base = OTHER
                       note = 2'-O-methyladenosine
modified_base          3
                       mod_base = OTHER
                       note = 2'-O-methylcytidine
modified_base          6
                       mod_base = OTHER
                       note = 2'-O-methylguanosine
modified_base          8
                       mod_base = OTHER
                       note = 2'-fluoroguanosine
source                 1..19
                       mol_type = other RNA
                       organism = synthetic construct
modified_base          5
                       mod_base = OTHER
                       note = 2'-O-methylcytidine
modified_base          4
                       mod_base = OTHER
                       note = 2'-O-methylcytidine
modified_base          16
                       mod_base = OTHER
                       note = 2'-O-methylguanosine
SEQUENCE: 151
accccgagcc aaagcgaga                                               19

SEQ ID NO: 152         moltype = RNA  length = 19
FEATURE                Location/Qualifiers
modified_base          1
                       mod_base = OTHER
                       note = 2'-O-methylcytidine phosphorothioate
modified_base          15
                       mod_base = OTHER
                       note = 2'-O-methyluridine
modified_base          7
                       mod_base = OTHER
                       note = 2'-fluoroadenosine
modified_base          2
                       mod_base = OTHER
                       note = 2'-O-methylcytidine phosphorothioate
modified_base          8
                       mod_base = OTHER
                       note = 2'-fluoroguanosine
modified_base          5
                       mod_base = OTHER
                       note = 2'-O-methylcytidine
modified_base          6
                       mod_base = OTHER
                       note = 2'-O-methylguanosine
modified_base          19
                       mod_base = OTHER
                       note = 2'-O-methyladenosine
modified_base          11
                       mod_base = OTHER
                       note = 2'-O-methyluridine
modified_base          4
                       mod_base = OTHER
                       note = 2'-O-methylguanosine
modified_base          17
                       mod_base = OTHER
                       note = 2'-O-methylguanosine phosphorothioate
modified_base          13
                       mod_base = OTHER
                       note = 2'-O-methylcytidine
modified_base          18
                       mod_base = OTHER
                       note = 2'-O-methyladenosine phosphorothioate
modified_base          16
                       mod_base = OTHER
                       note = 2'-O-methyluridine
modified_base          3
                       mod_base = OTHER
```

-continued

```
                        note = 2'-O-methyluridine
modified_base           14
                        mod_base = OTHER
                        note = 2'-O-methyluridine
modified_base           10
                        mod_base = OTHER
                        note = 2'-O-methylcytidine
modified_base           9
                        mod_base = OTHER
                        note = 2'-fluorocytidine
modified_base           12
                        mod_base = OTHER
                        note = 2'-O-methylguanosine
source                  1..19
                        mol_type = other RNA
                        organism = synthetic construct
SEQUENCE: 152
cctgcgagcc tgctttgaa                                               19

SEQ ID NO: 153          moltype = RNA  length = 19
FEATURE                 Location/Qualifiers
modified_base           16
                        mod_base = OTHER
                        note = 2'-O-methylguanosine
modified_base           9
                        mod_base = OTHER
                        note = 2'-fluoroguanosine
modified_base           4
                        mod_base = OTHER
                        note = 2'-O-methyladenosine
modified_base           13
                        mod_base = OTHER
                        note = 2'-O-methyluridine
modified_base           19
                        mod_base = OTHER
                        note = 2'-O-methyladenosine
modified_base           8
                        mod_base = OTHER
                        note = 2'-fluorouridine
modified_base           18
                        mod_base = OTHER
                        note = 2'-O-methylguanosine phosphorothioate
modified_base           3
                        mod_base = OTHER
                        note = 2'-O-methylguanosine
modified_base           11
                        mod_base = OTHER
                        note = 2'-O-methyluridine
modified_base           7
                        mod_base = OTHER
                        note = 2'-fluorocytidine
modified_base           17
                        mod_base = OTHER
                        note = 2'-O-methylcytidine phosphorothioate
modified_base           5
                        mod_base = OTHER
                        note = 2'-O-methylguanosine
modified_base           15
                        mod_base = OTHER
                        note = 2'-O-methyladenosine
modified_base           14
                        mod_base = OTHER
                        note = 2'-O-methylguanosine
modified_base           2
                        mod_base = OTHER
                        note = 2'-O-methylcytidine phosphorothioate
modified_base           12
                        mod_base = OTHER
                        note = 2'-O-methyluridine
modified_base           1
                        mod_base = OTHER
                        note = 2'-O-methylguanosine phosphorothioate
modified_base           6
                        mod_base = OTHER
                        note = 2'-O-methylcytidine
source                  1..19
                        mol_type = other RNA
                        organism = synthetic construct
modified_base           10
```

```
                         mod_base = OTHER
                         note = 2'-O-methylcytidine
SEQUENCE: 153
gcgagcctgc tttgagcga                                              19

SEQ ID NO: 154           moltype = RNA  length = 19
FEATURE                  Location/Qualifiers
modified_base            13
                         mod_base = OTHER
                         note = 2'-O-methyladenosine
modified_base            1
                         mod_base = OTHER
                         note = 2'-O-methyluridine phosphorothioate
modified_base            12
                         mod_base = OTHER
                         note = 2'-O-methylguanosine
modified_base            3
                         mod_base = OTHER
                         note = 2'-O-methylguanosine
modified_base            9
                         mod_base = OTHER
                         note = 2'-fluoroadenosine
modified_base            5
                         mod_base = OTHER
                         note = 2'-O-methylcytidine
modified_base            19
                         mod_base = OTHER
                         note = 2'-O-methyladenosine
modified_base            7
                         mod_base = OTHER
                         note = 2'-fluorocytidine
modified_base            2
                         mod_base = OTHER
                         note = 2'-O-methylcytidine phosphorothioate
source                   1..19
                         mol_type = other RNA
                         organism = synthetic construct
modified_base            14
                         mod_base = OTHER
                         note = 2'-O-methyladenosine
modified_base            17
                         mod_base = OTHER
                         note = 2'-O-methylguanosine phosphorothioate
modified_base            10
                         mod_base = OTHER
                         note = 2'-O-methylguanosine
modified_base            6
                         mod_base = OTHER
                         note = 2'-O-methyladenosine
modified_base            8
                         mod_base = OTHER
                         note = 2'-fluorocytidine
modified_base            11
                         mod_base = OTHER
                         note = 2'-O-methyladenosine
modified_base            16
                         mod_base = OTHER
                         note = 2'-O-methylguanosine
modified_base            15
                         mod_base = OTHER
                         note = 2'-O-methylcytidine
modified_base            18
                         mod_base = OTHER
                         note = 2'-O-methylcytidine phosphorothioate
modified_base            4
                         mod_base = OTHER
                         note = 2'-O-methylcytidine
SEQUENCE: 154
tcgccaccag agaacggca                                              19

SEQ ID NO: 155           moltype = RNA  length = 19
FEATURE                  Location/Qualifiers
modified_base            4
                         mod_base = OTHER
                         note = 2'-O-methylguanosine
modified_base            6
                         mod_base = OTHER
                         note = 2'-O-methylcytidine
modified_base            2
```

```
                        mod_base = OTHER
                        note = 2'-O-methyladenosine phosphorothioate
modified_base           9
                        mod_base = OTHER
                        note = 2'-fluorocytidine
modified_base           18
                        mod_base = OTHER
                        note = 2'-O-methylguanosine phosphorothioate
modified_base           13
                        mod_base = OTHER
                        note = 2'-O-methyladenosine
modified_base           12
                        mod_base = OTHER
                        note = 2'-O-methylcytidine
modified_base           17
                        mod_base = OTHER
                        note = 2'-O-methylcytidine phosphorothioate
modified_base           19
                        mod_base = OTHER
                        note = 2'-O-methyladenosine
source                  1..19
                        mol_type = other RNA
                        organism = synthetic construct
modified_base           7
                        mod_base = OTHER
                        note = 2'-fluoroadenosine
modified_base           15
                        mod_base = OTHER
                        note = 2'-O-methyluridine
modified_base           1
                        mod_base = OTHER
                        note = 2'-O-methylcytidine phosphorothioate
modified_base           14
                        mod_base = OTHER
                        note = 2'-O-methyluridine
modified_base           3
                        mod_base = OTHER
                        note = 2'-O-methylguanosine
modified_base           11
                        mod_base = OTHER
                        note = 2'-O-methylguanosine
modified_base           5
                        mod_base = OTHER
                        note = 2'-O-methylcytidine
modified_base           10
                        mod_base = OTHER
                        note = 2'-O-methylguanosine
modified_base           16
                        mod_base = OTHER
                        note = 2'-O-methylcytidine
modified_base           8
                        mod_base = OTHER
                        note = 2'-fluorouridine
SEQUENCE: 155
caggccatcg gcattccga                                            19

SEQ ID NO: 156          moltype = RNA  length = 19
FEATURE                 Location/Qualifiers
modified_base           5
                        mod_base = OTHER
                        note = 2'-O-methyladenosine
modified_base           13
                        mod_base = OTHER
                        note = 2'-O-methyluridine
modified_base           3
                        mod_base = OTHER
                        note = 2'-O-methylcytidine
modified_base           16
                        mod_base = OTHER
                        note = 2'-O-methylguanosine
modified_base           18
                        mod_base = OTHER
                        note = 2'-O-methyladenosine phosphorothioate
source                  1..19
                        mol_type = other RNA
                        organism = synthetic construct
modified_base           8
                        mod_base = OTHER
                        note = 2'-fluoroguanosine
```

```
modified_base          10
                       mod_base = OTHER
                       note = 2'-O-methylcytidine
modified_base          4
                       mod_base = OTHER
                       note = 2'-O-methylcytidine
modified_base          7
                       mod_base = OTHER
                       note = 2'-fluorocytidine
modified_base          6
                       mod_base = OTHER
                       note = 2'-O-methyluridine
modified_base          9
                       mod_base = OTHER
                       note = 2'-fluoroguanosine
modified_base          19
                       mod_base = OTHER
                       note = 2'-O-methyladenosine
modified_base          1
                       mod_base = OTHER
                       note = 2'-O-methylguanosine phosphorothioate
modified_base          12
                       mod_base = OTHER
                       note = 2'-O-methyluridine
modified_base          11
                       mod_base = OTHER
                       note = 2'-O-methyladenosine
modified_base          2
                       mod_base = OTHER
                       note = 2'-O-methylguanosine phosphorothioate
modified_base          14
                       mod_base = OTHER
                       note = 2'-O-methylcytidine
modified_base          15
                       mod_base = OTHER
                       note = 2'-O-methylcytidine
modified_base          17
                       mod_base = OTHER
                       note = 2'-O-methylguanosine phosphorothioate
SEQUENCE: 156
ggccatcggc attccggaa                                              19

SEQ ID NO: 157         moltype = RNA  length = 19
FEATURE                Location/Qualifiers
modified_base          12
                       mod_base = OTHER
                       note = 2'-O-methyluridine
modified_base          15
                       mod_base = OTHER
                       note = 2'-O-methylguanosine
modified_base          6
                       mod_base = OTHER
                       note = 2'-O-methylcytidine
modified_base          4
                       mod_base = OTHER
                       note = 2'-O-methyladenosine
modified_base          11
                       mod_base = OTHER
                       note = 2'-O-methyluridine
modified_base          10
                       mod_base = OTHER
                       note = 2'-O-methyladenosine
modified_base          8
                       mod_base = OTHER
                       note = 2'-fluoroguanosine
modified_base          19
                       mod_base = OTHER
                       note = 2'-O-methyladenosine
modified_base          9
                       mod_base = OTHER
                       note = 2'-fluorocytidine
modified_base          2
                       mod_base = OTHER
                       note = 2'-O-methylcytidine phosphorothioate
modified_base          1
                       mod_base = OTHER
                       note = 2'-O-methylguanosine phosphorothioate
modified_base          13
                       mod_base = OTHER
```

-continued

```
                        note = 2'-O-methylcytidine
source                  1..19
                        mol_type = other RNA
                        organism = synthetic construct
modified_base           7
                        mod_base = OTHER
                        note = 2'-fluoroguanosine
modified_base           14
                        mod_base = OTHER
                        note = 2'-O-methylcytidine
modified_base           18
                        mod_base = OTHER
                        note = 2'-O-methylguanosine phosphorothioate
modified_base           3
                        mod_base = OTHER
                        note = 2'-O-methylcytidine
modified_base           17
                        mod_base = OTHER
                        note = 2'-O-methyladenosine phosphorothioate
modified_base           16
                        mod_base = OTHER
                        note = 2'-O-methylguanosine
modified_base           5
                        mod_base = OTHER
                        note = 2'-O-methyluridine
SEQUENCE: 157
gccatcggca ttccggaga                                               19

SEQ ID NO: 158          moltype = RNA  length = 19
FEATURE                 Location/Qualifiers
modified_base           1
                        mod_base = OTHER
                        note = 2'-O-methylguanosine phosphorothioate
modified_base           6
                        mod_base = OTHER
                        note = 2'-O-methylguanosine
modified_base           18
                        mod_base = OTHER
                        note = 2'-O-methylguanosine phosphorothioate
modified_base           16
                        mod_base = OTHER
                        note = 2'-O-methyluridine
modified_base           3
                        mod_base = OTHER
                        note = 2'-O-methyladenosine
modified_base           2
                        mod_base = OTHER
                        note = 2'-O-methylcytidine phosphorothioate
modified_base           19
                        mod_base = OTHER
                        note = 2'-O-methyladenosine
modified_base           10
                        mod_base = OTHER
                        note = 2'-O-methylguanosine
modified_base           15
                        mod_base = OTHER
                        note = 2'-O-methylcytidine
modified_base           4
                        mod_base = OTHER
                        note = 2'-O-methylcytidine
modified_base           5
                        mod_base = OTHER
                        note = 2'-O-methylcytidine
modified_base           13
                        mod_base = OTHER
                        note = 2'-O-methyladenosine
modified_base           12
                        mod_base = OTHER
                        note = 2'-O-methyladenosine
modified_base           14
                        mod_base = OTHER
                        note = 2'-O-methyluridine
modified_base           11
                        mod_base = OTHER
                        note = 2'-O-methylguanosine
modified_base           7
                        mod_base = OTHER
                        note = 2'-fluoroguanosine
modified_base           17
```

-continued

```
                        mod_base = OTHER
                        note = 2'-O-methylcytidine phosphorothioate
source                  1..19
                        mol_type = other RNA
                        organism = synthetic construct
modified_base           9
                        mod_base = OTHER
                        note = 2'-fluoroguanosine
modified_base           8
                        mod_base = OTHER
                        note = 2'-fluorocytidine
SEQUENCE: 158
gcaccggcgg gaatctcga                                        19

SEQ ID NO: 159          moltype = RNA  length = 19
FEATURE                 Location/Qualifiers
modified_base           1
                        mod_base = OTHER
                        note = 2'-O-methylcytidine phosphorothioate
modified_base           8
                        mod_base = OTHER
                        note = 2'-fluoroguanosine
modified_base           4
                        mod_base = OTHER
                        note = 2'-O-methylcytidine
modified_base           3
                        mod_base = OTHER
                        note = 2'-O-methylcytidine
modified_base           15
                        mod_base = OTHER
                        note = 2'-O-methyluridine
modified_base           18
                        mod_base = OTHER
                        note = 2'-O-methylguanosine phosphorothioate
modified_base           17
                        mod_base = OTHER
                        note = 2'-O-methylguanosine phosphorothioate
modified_base           7
                        mod_base = OTHER
                        note = 2'-fluorocytidine
modified_base           12
                        mod_base = OTHER
                        note = 2'-O-methyladenosine
source                  1..19
                        mol_type = other RNA
                        organism = synthetic construct
modified_base           10
                        mod_base = OTHER
                        note = 2'-O-methylguanosine
modified_base           6
                        mod_base = OTHER
                        note = 2'-O-methylguanosine
modified_base           14
                        mod_base = OTHER
                        note = 2'-O-methylcytidine
modified_base           2
                        mod_base = OTHER
                        note = 2'-O-methyladenosine phosphorothioate
modified_base           16
                        mod_base = OTHER
                        note = 2'-O-methylcytidine
modified_base           5
                        mod_base = OTHER
                        note = 2'-O-methylguanosine
modified_base           11
                        mod_base = OTHER
                        note = 2'-O-methyladenosine
modified_base           13
                        mod_base = OTHER
                        note = 2'-O-methyluridine
modified_base           19
                        mod_base = OTHER
                        note = 2'-O-methyladenosine
modified_base           9
                        mod_base = OTHER
                        note = 2'-fluoroguanosine
SEQUENCE: 159
caccggcggg aatctcgga                                        19
```

-continued

```
SEQ ID NO: 160          moltype = RNA  length = 19
FEATURE                 Location/Qualifiers
modified_base           14
                        mod_base = OTHER
                        note = 2'-O-methylguanosine
modified_base           9
                        mod_base = OTHER
                        note = 2'-fluorocytidine
modified_base           17
                        mod_base = OTHER
                        note = 2'-O-methyladenosine phosphorothioate
modified_base           8
                        mod_base = OTHER
                        note = 2'-fluoroguanosine
modified_base           1
                        mod_base = OTHER
                        note = 2'-O-methylcytidine phosphorothioate
modified_base           19
                        mod_base = OTHER
                        note = 2'-O-methyladenosine
modified_base           6
                        mod_base = OTHER
                        note = 2'-O-methyladenosine
modified_base           15
                        mod_base = OTHER
                        note = 2'-O-methyladenosine
modified_base           18
                        mod_base = OTHER
                        note = 2'-O-methylguanosine phosphorothioate
modified_base           4
                        mod_base = OTHER
                        note = 2'-O-methylguanosine
modified_base           13
                        mod_base = OTHER
                        note = 2'-O-methylcytidine
modified_base           3
                        mod_base = OTHER
                        note = 2'-O-methyladenosine
modified_base           10
                        mod_base = OTHER
                        note = 2'-O-methylcytidine
modified_base           16
                        mod_base = OTHER
                        note = 2'-O-methyladenosine
modified_base           12
                        mod_base = OTHER
                        note = 2'-O-methylguanosine
source                  1..19
                        mol_type = other RNA
                        organism = synthetic construct
modified_base           5
                        mod_base = OTHER
                        note = 2'-O-methyladenosine
modified_base           2
                        mod_base = OTHER
                        note = 2'-O-methylcytidine phosphorothioate
modified_base           11
                        mod_base = OTHER
                        note = 2'-O-methylguanosine
modified_base           7
                        mod_base = OTHER
                        note = 2'-fluoroguanosine
SEQUENCE: 160
ccagaaggcc ggcgaaaga                                                19

SEQ ID NO: 161          moltype = RNA  length = 19
FEATURE                 Location/Qualifiers
modified_base           7
                        mod_base = OTHER
                        note = 2'-fluorocytidine
modified_base           17
                        mod_base = OTHER
                        note = 2'-O-methylcytidine phosphorothioate
modified_base           14
                        mod_base = OTHER
                        note = 2'-O-methyladenosine
modified_base           3
                        mod_base = OTHER
                        note = 2'-O-methyladenosine
```

```
modified_base          10
                       mod_base = OTHER
                       note = 2'-O-methylguanosine
modified_base          6
                       mod_base = OTHER
                       note = 2'-O-methylguanosine
modified_base          11
                       mod_base = OTHER
                       note = 2'-O-methylcytidine
modified_base          9
                       mod_base = OTHER
                       note = 2'-fluoroguanosine
modified_base          18
                       mod_base = OTHER
                       note = 2'-O-methylguanosine phosphorothioate
modified_base          15
                       mod_base = OTHER
                       note = 2'-O-methyladenosine
modified_base          16
                       mod_base = OTHER
                       note = 2'-O-methylguanosine
modified_base          2
                       mod_base = OTHER
                       note = 2'-O-methylguanosine phosphorothioate
modified_base          8
                       mod_base = OTHER
                       note = 2'-fluorocytidine
modified_base          12
                       mod_base = OTHER
                       note = 2'-O-methylguanosine
source                 1..19
                       mol_type = other RNA
                       organism = synthetic construct
modified_base          5
                       mod_base = OTHER
                       note = 2'-O-methylguanosine
modified_base          13
                       mod_base = OTHER
                       note = 2'-O-methyladenosine
modified_base          19
                       mod_base = OTHER
                       note = 2'-O-methyladenosine
modified_base          4
                       mod_base = OTHER
                       note = 2'-O-methyladenosine
modified_base          1
                       mod_base = OTHER
                       note = 2'-O-methyladenosine phosphorothioate
SEQUENCE: 161
agaaggccgg cgaaagcga                                            19

SEQ ID NO: 162         moltype = RNA  length = 19
FEATURE                Location/Qualifiers
modified_base          3
                       mod_base = OTHER
                       note = 2'-O-methyladenosine
modified_base          19
                       mod_base = OTHER
                       note = 2'-O-methyladenosine
modified_base          15
                       mod_base = OTHER
                       note = 2'-O-methylguanosine
modified_base          5
                       mod_base = OTHER
                       note = 2'-O-methylguanosine
modified_base          12
                       mod_base = OTHER
                       note = 2'-O-methyladenosine
modified_base          13
                       mod_base = OTHER
                       note = 2'-O-methyladenosine
modified_base          14
                       mod_base = OTHER
                       note = 2'-O-methyladenosine
source                 1..19
                       mol_type = other RNA
                       organism = synthetic construct
modified_base          10
                       mod_base = OTHER
```

```
                        note = 2'-O-methylcytidine
modified_base           1
                        mod_base = OTHER
                        note = 2'-O-methylguanosine phosphorothioate
modified_base           16
                        mod_base = OTHER
                        note = 2'-O-methylcytidine
modified_base           6
                        mod_base = OTHER
                        note = 2'-O-methylcytidine
modified_base           18
                        mod_base = OTHER
                        note = 2'-O-methylguanosine phosphorothioate
modified_base           4
                        mod_base = OTHER
                        note = 2'-O-methylguanosine
modified_base           7
                        mod_base = OTHER
                        note = 2'-fluorocytidine
modified_base           2
                        mod_base = OTHER
                        note = 2'-O-methyladenosine phosphorothioate
modified_base           17
                        mod_base = OTHER
                        note = 2'-O-methylguanosine phosphorothioate
modified_base           9
                        mod_base = OTHER
                        note = 2'-fluoroguanosine
modified_base           8
                        mod_base = OTHER
                        note = 2'-fluoroguanosine
modified_base           11
                        mod_base = OTHER
                        note = 2'-O-methylguanosine
SEQUENCE: 162
gaaggccggc gaaagcgga                                                19

SEQ ID NO: 163          moltype = RNA  length = 19
FEATURE                 Location/Qualifiers
modified_base           16
                        mod_base = OTHER
                        note = 2'-O-methylcytidine
modified_base           8
                        mod_base = OTHER
                        note = 2'-fluorocytidine
modified_base           2
                        mod_base = OTHER
                        note = 2'-O-methylcytidine phosphorothioate
modified_base           7
                        mod_base = OTHER
                        note = 2'-fluoroguanosine
modified_base           14
                        mod_base = OTHER
                        note = 2'-O-methylguanosine
modified_base           4
                        mod_base = OTHER
                        note = 2'-O-methyladenosine
modified_base           19
                        mod_base = OTHER
                        note = 2'-O-methyladenosine
modified_base           13
                        mod_base = OTHER
                        note = 2'-O-methylcytidine
modified_base           5
                        mod_base = OTHER
                        note = 2'-O-methyladenosine
modified_base           18
                        mod_base = OTHER
                        note = 2'-O-methyluridine phosphorothioate
modified_base           1
                        mod_base = OTHER
                        note = 2'-O-methylguanosine phosphorothioate
modified_base           3
                        mod_base = OTHER
                        note = 2'-O-methylguanosine
modified_base           10
                        mod_base = OTHER
                        note = 2'-O-methylguanosine
modified_base           9
```

```
                         mod_base = OTHER
                         note = 2'-fluoroguanosine
modified_base            12
                         mod_base = OTHER
                         note = 2'-O-methylcytidine
modified_base            17
                         mod_base = OTHER
                         note = 2'-O-methylguanosine phosphorothioate
source                   1..19
                         mol_type = other RNA
                         organism = synthetic construct
modified_base            11
                         mod_base = OTHER
                         note = 2'-O-methyladenosine
modified_base            15
                         mod_base = OTHER
                         note = 2'-O-methylcytidine
modified_base            6
                         mod_base = OTHER
                         note = 2'-O-methyladenosine
SEQUENCE: 163
gcgaaagcgg accgccgta                                                19

SEQ ID NO: 164           moltype = RNA  length = 19
FEATURE                  Location/Qualifiers
modified_base            4
                         mod_base = OTHER
                         note = 2'-O-methyladenosine
modified_base            12
                         mod_base = OTHER
                         note = 2'-O-methylguanosine
modified_base            16
                         mod_base = OTHER
                         note = 2'-O-methyluridine
modified_base            15
                         mod_base = OTHER
                         note = 2'-O-methylguanosine
modified_base            9
                         mod_base = OTHER
                         note = 2'-fluoroadenosine
modified_base            8
                         mod_base = OTHER
                         note = 2'-fluoroguanosine
modified_base            7
                         mod_base = OTHER
                         note = 2'-fluoroguanosine
modified_base            1
                         mod_base = OTHER
                         note = 2'-O-methylguanosine phosphorothioate
modified_base            6
                         mod_base = OTHER
                         note = 2'-O-methylcytidine
modified_base            3
                         mod_base = OTHER
                         note = 2'-O-methyladenosine
modified_base            5
                         mod_base = OTHER
                         note = 2'-O-methylguanosine
modified_base            17
                         mod_base = OTHER
                         note = 2'-O-methylcytidine phosphorothioate
modified_base            14
                         mod_base = OTHER
                         note = 2'-O-methylcytidine
modified_base            11
                         mod_base = OTHER
                         note = 2'-O-methylcytidine
modified_base            18
                         mod_base = OTHER
                         note = 2'-O-methyladenosine phosphorothioate
modified_base            2
                         mod_base = OTHER
                         note = 2'-O-methyladenosine phosphorothioate
modified_base            13
                         mod_base = OTHER
                         note = 2'-O-methylcytidine
modified_base            10
                         mod_base = OTHER
                         note = 2'-O-methylcytidine
```

```
modified_base         19
                      mod_base = OTHER
                      note = 2'-O-methyladenosine
source                1..19
                      mol_type = other RNA
                      organism = synthetic construct
SEQUENCE: 164
gaaagcggac cgccgtcaa                                              19

SEQ ID NO: 165        moltype = RNA  length = 19
FEATURE               Location/Qualifiers
modified_base         16
                      mod_base = OTHER
                      note = 2'-O-methylguanosine
modified_base         8
                      mod_base = OTHER
                      note = 2'-fluorocytidine
modified_base         10
                      mod_base = OTHER
                      note = 2'-O-methylguanosine
modified_base         13
                      mod_base = OTHER
                      note = 2'-O-methyladenosine
modified_base         3
                      mod_base = OTHER
                      note = 2'-O-methylguanosine
modified_base         11
                      mod_base = OTHER
                      note = 2'-O-methyluridine
source                1..19
                      mol_type = other RNA
                      organism = synthetic construct
modified_base         17
                      mod_base = OTHER
                      note = 2'-O-methylguanosine phosphorothioate
modified_base         4
                      mod_base = OTHER
                      note = 2'-O-methyladenosine
modified_base         18
                      mod_base = OTHER
                      note = 2'-O-methyladenosine phosphorothioate
modified_base         6
                      mod_base = OTHER
                      note = 2'-O-methylcytidine
modified_base         19
                      mod_base = OTHER
                      note = 2'-O-methyladenosine
modified_base         5
                      mod_base = OTHER
                      note = 2'-O-methylcytidine
modified_base         2
                      mod_base = OTHER
                      note = 2'-O-methylguanosine phosphorothioate
modified_base         14
                      mod_base = OTHER
                      note = 2'-O-methylcytidine
modified_base         12
                      mod_base = OTHER
                      note = 2'-O-methylcytidine
modified_base         15
                      mod_base = OTHER
                      note = 2'-O-methylcytidine
modified_base         9
                      mod_base = OTHER
                      note = 2'-fluorocytidine
modified_base         7
                      mod_base = OTHER
                      note = 2'-fluoroguanosine
modified_base         1
                      mod_base = OTHER
                      note = 2'-O-methylcytidine phosphorothioate
SEQUENCE: 165
cggaccgccg tcaccggaa                                              19

SEQ ID NO: 166        moltype = RNA  length = 19
FEATURE               Location/Qualifiers
modified_base         2
                      mod_base = OTHER
                      note = 2'-O-methylguanosine phosphorothioate
```

```
modified_base          19
                       mod_base = OTHER
                       note = 2'-O-methyladenosine
modified_base          7
                       mod_base = OTHER
                       note = 2'-fluorocytidine
modified_base          4
                       mod_base = OTHER
                       note = 2'-O-methylcytidine
modified_base          14
                       mod_base = OTHER
                       note = 2'-O-methylcytidine
modified_base          15
                       mod_base = OTHER
                       note = 2'-O-methylguanosine
modified_base          1
                       mod_base = OTHER
                       note = 2'-O-methylguanosine phosphorothioate
modified_base          18
                       mod_base = OTHER
                       note = 2'-O-methyluridine phosphorothioate
modified_base          17
                       mod_base = OTHER
                       note = 2'-O-methyladenosine phosphorothioate
modified_base          3
                       mod_base = OTHER
                       note = 2'-O-methyladenosine
source                 1..19
                       mol_type = other RNA
                       organism = synthetic construct
modified_base          9
                       mod_base = OTHER
                       note = 2'-fluoroguanosine
modified_base          5
                       mod_base = OTHER
                       note = 2'-O-methylcytidine
modified_base          13
                       mod_base = OTHER
                       note = 2'-O-methylcytidine
modified_base          11
                       mod_base = OTHER
                       note = 2'-O-methylcytidine
modified_base          10
                       mod_base = OTHER
                       note = 2'-O-methyluridine
modified_base          16
                       mod_base = OTHER
                       note = 2'-O-methylguanosine
modified_base          6
                       mod_base = OTHER
                       note = 2'-O-methylguanosine
modified_base          8
                       mod_base = OTHER
                       note = 2'-fluorocytidine
modified_base          12
                       mod_base = OTHER
                       note = 2'-O-methyladenosine
SEQUENCE: 166
ggaccgccgt caccggata                                                19

SEQ ID NO: 167         moltype = RNA  length = 19
FEATURE                Location/Qualifiers
modified_base          8
                       mod_base = OTHER
                       note = 2'-fluoroguanosine
source                 1..19
                       mol_type = other RNA
                       organism = synthetic construct
modified_base          15
                       mod_base = OTHER
                       note = 2'-O-methylguanosine
modified_base          9
                       mod_base = OTHER
                       note = 2'-fluorouridine
modified_base          13
                       mod_base = OTHER
                       note = 2'-O-methylcytidine
modified_base          3
                       mod_base = OTHER
```

```
                        note = 2'-O-methylcytidine
modified_base           18
                        mod_base = OTHER
                        note = 2'-O-methylcytidine phosphorothioate
modified_base           7
                        mod_base = OTHER
                        note = 2'-fluorocytidine
modified_base           17
                        mod_base = OTHER
                        note = 2'-O-methyluridine phosphorothioate
modified_base           5
                        mod_base = OTHER
                        note = 2'-O-methylguanosine
modified_base           4
                        mod_base = OTHER
                        note = 2'-O-methylcytidine
modified_base           2
                        mod_base = OTHER
                        note = 2'-O-methyladenosine phosphorothioate
modified_base           10
                        mod_base = OTHER
                        note = 2'-O-methylcytidine
modified_base           6
                        mod_base = OTHER
                        note = 2'-O-methylcytidine
modified_base           16
                        mod_base = OTHER
                        note = 2'-O-methyladenosine
modified_base           19
                        mod_base = OTHER
                        note = 2'-O-methyladenosine
modified_base           14
                        mod_base = OTHER
                        note = 2'-O-methylguanosine
modified_base           1
                        mod_base = OTHER
                        note = 2'-O-methylguanosine phosphorothioate
modified_base           11
                        mod_base = OTHER
                        note = 2'-O-methyladenosine
modified_base           12
                        mod_base = OTHER
                        note = 2'-O-methylcytidine
SEQUENCE: 167
gaccgccgtc accggatca                                            19

SEQ ID NO: 168          moltype = RNA  length = 19
FEATURE                 Location/Qualifiers
source                  1..19
                        mol_type = other RNA
                        organism = synthetic construct
modified_base           13
                        mod_base = OTHER
                        note = 2'-O-methylcytidine
modified_base           10
                        mod_base = OTHER
                        note = 2'-O-methyluridine
modified_base           8
                        mod_base = OTHER
                        note = 2'-fluorocytidine
modified_base           12
                        mod_base = OTHER
                        note = 2'-O-methylcytidine
modified_base           4
                        mod_base = OTHER
                        note = 2'-O-methylcytidine
modified_base           17
                        mod_base = OTHER
                        note = 2'-O-methylguanosine phosphorothioate
modified_base           1
                        mod_base = OTHER
                        note = 2'-O-methyladenosine phosphorothioate
modified_base           19
                        mod_base = OTHER
                        note = 2'-O-methyladenosine
modified_base           5
                        mod_base = OTHER
                        note = 2'-O-methylguanosine
modified_base           7
```

```
                        mod_base = OTHER
                        note = 2'-fluoroguanosine
modified_base           11
                        mod_base = OTHER
                        note = 2'-O-methylcytidine
modified_base           15
                        mod_base = OTHER
                        note = 2'-O-methylguanosine
modified_base           3
                        mod_base = OTHER
                        note = 2'-O-methyladenosine
modified_base           18
                        mod_base = OTHER
                        note = 2'-O-methyluridine phosphorothioate
modified_base           6
                        mod_base = OTHER
                        note = 2'-O-methylguanosine
modified_base           14
                        mod_base = OTHER
                        note = 2'-O-methylguanosine
modified_base           9
                        mod_base = OTHER
                        note = 2'-fluorocytidine
modified_base           2
                        mod_base = OTHER
                        note = 2'-O-methylguanosine phosphorothioate
modified_base           16
                        mod_base = OTHER
                        note = 2'-O-methyladenosine
SEQUENCE: 168
agacgggcct cccggagta                                                19

SEQ ID NO: 169          moltype = RNA  length = 19
FEATURE                 Location/Qualifiers
modified_base           7
                        mod_base = OTHER
                        note = 2'-fluoroguanosine
modified_base           13
                        mod_base = OTHER
                        note = 2'-O-methylcytidine
modified_base           5
                        mod_base = OTHER
                        note = 2'-O-methylguanosine
modified_base           1
                        mod_base = OTHER
                        note = 2'-O-methylcytidine phosphorothioate
modified_base           8
                        mod_base = OTHER
                        note = 2'-fluoroguanosine
modified_base           17
                        mod_base = OTHER
                        note = 2'-O-methylcytidine phosphorothioate
modified_base           14
                        mod_base = OTHER
                        note = 2'-O-methylcytidine
source                  1..19
                        mol_type = other RNA
                        organism = synthetic construct
modified_base           15
                        mod_base = OTHER
                        note = 2'-O-methyluridine
modified_base           11
                        mod_base = OTHER
                        note = 2'-O-methylcytidine
modified_base           2
                        mod_base = OTHER
                        note = 2'-O-methylcytidine phosphorothioate
modified_base           10
                        mod_base = OTHER
                        note = 2'-O-methyluridine
modified_base           4
                        mod_base = OTHER
                        note = 2'-O-methylcytidine
modified_base           6
                        mod_base = OTHER
                        note = 2'-O-methyluridine
modified_base           16
                        mod_base = OTHER
                        note = 2'-O-methyluridine
```

-continued

```
modified_base          18
                       mod_base = OTHER
                       note = 2'-O-methylguanosine phosphorothioate
modified_base          9
                       mod_base = OTHER
                       note = 2'-fluoroguanosine
modified_base          3
                       mod_base = OTHER
                       note = 2'-O-methyluridine
modified_base          19
                       mod_base = OTHER
                       note = 2'-O-methyladenosine
modified_base          12
                       mod_base = OTHER
                       note = 2'-O-methylguanosine
SEQUENCE: 169
cctcgtgggt cgccttcga                                            19

SEQ ID NO: 170         moltype = RNA  length = 19
FEATURE                Location/Qualifiers
modified_base          13
                       mod_base = OTHER
                       note = 2'-O-methylcytidine
modified_base          18
                       mod_base = OTHER
                       note = 2'-O-methylcytidine phosphorothioate
modified_base          6
                       mod_base = OTHER
                       note = 2'-O-methylguanosine
modified_base          2
                       mod_base = OTHER
                       note = 2'-O-methyluridine phosphorothioate
modified_base          10
                       mod_base = OTHER
                       note = 2'-O-methylcytidine
modified_base          16
                       mod_base = OTHER
                       note = 2'-O-methylcytidine
modified_base          19
                       mod_base = OTHER
                       note = 2'-O-methyladenosine
modified_base          11
                       mod_base = OTHER
                       note = 2'-O-methylguanosine
modified_base          14
                       mod_base = OTHER
                       note = 2'-O-methyluridine
modified_base          5
                       mod_base = OTHER
                       note = 2'-O-methyluridine
modified_base          12
                       mod_base = OTHER
                       note = 2'-O-methylcytidine
source                 1..19
                       mol_type = other RNA
                       organism = synthetic construct
modified_base          15
                       mod_base = OTHER
                       note = 2'-O-methyluridine
modified_base          9
                       mod_base = OTHER
                       note = 2'-fluorouridine
modified_base          3
                       mod_base = OTHER
                       note = 2'-O-methylcytidine
modified_base          7
                       mod_base = OTHER
                       note = 2'-fluoroguanosine
modified_base          1
                       mod_base = OTHER
                       note = 2'-O-methylcytidine phosphorothioate
modified_base          17
                       mod_base = OTHER
                       note = 2'-O-methylguanosine phosphorothioate
modified_base          8
                       mod_base = OTHER
                       note = 2'-fluoroguanosine
modified_base          4
                       mod_base = OTHER
```

-continued

```
                        note = 2'-O-methylguanosine
SEQUENCE: 170
ctcgtgggtc gccttcgca                                            19

SEQ ID NO: 171          moltype = RNA  length = 19
FEATURE                 Location/Qualifiers
modified_base           12
                        mod_base = OTHER
                        note = 2'-O-methylcytidine
modified_base           8
                        mod_base = OTHER
                        note = 2'-fluorouridine
modified_base           3
                        mod_base = OTHER
                        note = 2'-O-methylguanosine
modified_base           15
                        mod_base = OTHER
                        note = 2'-O-methyladenosine
modified_base           2
                        mod_base = OTHER
                        note = 2'-O-methyladenosine phosphorothioate
modified_base           6
                        mod_base = OTHER
                        note = 2'-O-methylguanosine
modified_base           16
                        mod_base = OTHER
                        note = 2'-O-methylcytidine
modified_base           1
                        mod_base = OTHER
                        note = 2'-O-methylguanosine phosphorothioate
source                  1..19
                        mol_type = other RNA
                        organism = synthetic construct
modified_base           17
                        mod_base = OTHER
                        note = 2'-O-methylcytidine phosphorothioate
modified_base           7
                        mod_base = OTHER
                        note = 2'-fluoroadenosine
modified_base           10
                        mod_base = OTHER
                        note = 2'-O-methyluridine
modified_base           11
                        mod_base = OTHER
                        note = 2'-O-methylcytidine
modified_base           18
                        mod_base = OTHER
                        note = 2'-O-methyluridine phosphorothioate
modified_base           13
                        mod_base = OTHER
                        note = 2'-O-methylcytidine
modified_base           14
                        mod_base = OTHER
                        note = 2'-O-methyladenosine
modified_base           19
                        mod_base = OTHER
                        note = 2'-O-methyladenosine
modified_base           9
                        mod_base = OTHER
                        note = 2'-fluorocytidine
modified_base           5
                        mod_base = OTHER
                        note = 2'-O-methylguanosine
modified_base           4
                        mod_base = OTHER
                        note = 2'-O-methylguanosine
SEQUENCE: 171
gaggggatct cccaaccta                                            19

SEQ ID NO: 172          moltype = RNA  length = 19
FEATURE                 Location/Qualifiers
modified_base           17
                        mod_base = OTHER
                        note = 2'-O-methylcytidine phosphorothioate
modified_base           2
                        mod_base = OTHER
                        note = 2'-O-methylguanosine phosphorothioate
modified_base           5
                        mod_base = OTHER
```

```
                         note = 2'-O-methylcytidine
modified_base            7
                         mod_base = OTHER
                         note = 2'-fluoroguanosine
modified_base            10
                         mod_base = OTHER
                         note = 2'-O-methyladenosine
modified_base            13
                         mod_base = OTHER
                         note = 2'-O-methyluridine
modified_base            6
                         mod_base = OTHER
                         note = 2'-O-methylguanosine
source                   1..19
                         mol_type = other RNA
                         organism = synthetic construct
modified_base            1
                         mod_base = OTHER
                         note = 2'-O-methylcytidine phosphorothioate
modified_base            18
                         mod_base = OTHER
                         note = 2'-O-methyluridine phosphorothioate
modified_base            19
                         mod_base = OTHER
                         note = 2'-O-methyladenosine
modified_base            14
                         mod_base = OTHER
                         note = 2'-O-methylcytidine
modified_base            15
                         mod_base = OTHER
                         note = 2'-O-methylguanosine
modified_base            4
                         mod_base = OTHER
                         note = 2'-O-methylguanosine
modified_base            11
                         mod_base = OTHER
                         note = 2'-O-methyluridine
modified_base            12
                         mod_base = OTHER
                         note = 2'-O-methyluridine
modified_base            16
                         mod_base = OTHER
                         note = 2'-O-methylcytidine
modified_base            8
                         mod_base = OTHER
                         note = 2'-fluoroguanosine
modified_base            3
                         mod_base = OTHER
                         note = 2'-O-methylcytidine
modified_base            9
                         mod_base = OTHER
                         note = 2'-fluoroguanosine
SEQUENCE: 172
cgcgcgggga tttcgccta                                              19

SEQ ID NO: 173           moltype = RNA  length = 19
FEATURE                  Location/Qualifiers
modified_base            8
                         mod_base = OTHER
                         note = 2'-fluoroguanosine
modified_base            11
                         mod_base = OTHER
                         note = 2'-O-methyluridine
modified_base            9
                         mod_base = OTHER
                         note = 2'-fluoroadenosine
modified_base            18
                         mod_base = OTHER
                         note = 2'-O-methyladenosine phosphorothioate
source                   1..19
                         mol_type = other RNA
                         organism = synthetic construct
modified_base            14
                         mod_base = OTHER
                         note = 2'-O-methylguanosine
modified_base            4
                         mod_base = OTHER
                         note = 2'-O-methylcytidine
modified_base            12
```

-continued

| | |
|---|---|
| | mod_base = OTHER |
| | note = 2'-O-methyluridine |
| modified_base | 2 |
| | mod_base = OTHER |
| | note = 2'-O-methylcytidine phosphorothioate |
| modified_base | 5 |
| | mod_base = OTHER |
| | note = 2'-O-methylguanosine |
| modified_base | 10 |
| | mod_base = OTHER |
| | note = 2'-O-methyluridine |
| modified_base | 16 |
| | mod_base = OTHER |
| | note = 2'-O-methylcytidine |
| modified_base | 7 |
| | mod_base = OTHER |
| | note = 2'-fluoroguanosine |
| modified_base | 13 |
| | mod_base = OTHER |
| | note = 2'-O-methylcytidine |
| modified_base | 19 |
| | mod_base = OTHER |
| | note = 2'-O-methyladenosine |
| modified_base | 6 |
| | mod_base = OTHER |
| | note = 2'-O-methylguanosine |
| modified_base | 1 |
| | mod_base = OTHER |
| | note = 2'-O-methylguanosine phosphorothioate |
| modified_base | 17 |
| | mod_base = OTHER |
| | note = 2'-O-methyluridine phosphorothioate |
| modified_base | 15 |
| | mod_base = OTHER |
| | note = 2'-O-methylcytidine |
| modified_base | 3 |
| | mod_base = OTHER |
| | note = 2'-O-methylguanosine |

SEQUENCE: 173
gcgcggggat ttcgcctaa 19

| | |
|---|---|
| SEQ ID NO: 174 | moltype = RNA length = 19 |
| FEATURE | Location/Qualifiers |
| modified_base | 19 |
| | mod_base = OTHER |
| | note = 2'-O-methyladenosine |
| modified_base | 10 |
| | mod_base = OTHER |
| | note = 2'-O-methylcytidine |
| modified_base | 12 |
| | mod_base = OTHER |
| | note = 2'-O-methylcytidine |
| modified_base | 11 |
| | mod_base = OTHER |
| | note = 2'-O-methylguanosine |
| modified_base | 2 |
| | mod_base = OTHER |
| | note = 2'-O-methylguanosine phosphorothioate |
| modified_base | 7 |
| | mod_base = OTHER |
| | note = 2'-fluorouridine |
| modified_base | 18 |
| | mod_base = OTHER |
| | note = 2'-O-methylcytidine phosphorothioate |
| modified_base | 5 |
| | mod_base = OTHER |
| | note = 2'-O-methylguanosine |
| modified_base | 16 |
| | mod_base = OTHER |
| | note = 2'-O-methylcytidine |
| modified_base | 9 |
| | mod_base = OTHER |
| | note = 2'-fluorouridine |
| modified_base | 15 |
| | mod_base = OTHER |
| | note = 2'-O-methyladenosine |
| modified_base | 4 |
| | mod_base = OTHER |
| | note = 2'-O-methylguanosine |

```
modified_base         3
                      mod_base = OTHER
                      note = 2'-O-methylguanosine
source                1..19
                      mol_type = other RNA
                      organism = synthetic construct
modified_base         17
                      mod_base = OTHER
                      note = 2'-O-methylguanosine phosphorothioate
modified_base         13
                      mod_base = OTHER
                      note = 2'-O-methylcytidine
modified_base         8
                      mod_base = OTHER
                      note = 2'-fluorouridine
modified_base         6
                      mod_base = OTHER
                      note = 2'-O-methyladenosine
modified_base         14
                      mod_base = OTHER
                      note = 2'-O-methyluridine
modified_base         1
                      mod_base = OTHER
                      note = 2'-O-methylcytidine phosphorothioate
SEQUENCE: 174
cggggatttc gcctacgca                                            19

SEQ ID NO: 175        moltype = RNA  length = 19
FEATURE               Location/Qualifiers
modified_base         13
                      mod_base = OTHER
                      note = 2'-O-methylcytidine
modified_base         3
                      mod_base = OTHER
                      note = 2'-O-methylcytidine
modified_base         8
                      mod_base = OTHER
                      note = 2'-fluoroguanosine
modified_base         4
                      mod_base = OTHER
                      note = 2'-O-methyluridine
modified_base         1
                      mod_base = OTHER
                      note = 2'-O-methyluridine phosphorothioate
modified_base         15
                      mod_base = OTHER
                      note = 2'-O-methyladenosine
modified_base         9
                      mod_base = OTHER
                      note = 2'-fluorocytidine
modified_base         12
                      mod_base = OTHER
                      note = 2'-O-methylcytidine
modified_base         6
                      mod_base = OTHER
                      note = 2'-O-methylguanosine
modified_base         7
                      mod_base = OTHER
                      note = 2'-fluorocytidine
modified_base         14
                      mod_base = OTHER
                      note = 2'-O-methylcytidine
source                1..19
                      mol_type = other RNA
                      organism = synthetic construct
modified_base         17
                      mod_base = OTHER
                      note = 2'-O-methylguanosine phosphorothioate
modified_base         5
                      mod_base = OTHER
                      note = 2'-O-methyluridine
modified_base         18
                      mod_base = OTHER
                      note = 2'-O-methyluridine phosphorothioate
modified_base         10
                      mod_base = OTHER
                      note = 2'-O-methylcytidine
modified_base         16
                      mod_base = OTHER
```

-continued

```
                      note = 2'-O-methylcytidine
modified_base         2
                      mod_base = OTHER
                      note = 2'-O-methylguanosine phosphorothioate
modified_base         19
                      mod_base = OTHER
                      note = 2'-O-methyladenosine
modified_base         11
                      mod_base = OTHER
                      note = 2'-O-methyladenosine
SEQUENCE: 175
tgcttgcgcc acccacgta                                              19

SEQ ID NO: 176        moltype = RNA  length = 19
FEATURE               Location/Qualifiers
modified_base         16
                      mod_base = OTHER
                      note = 2'-O-methyluridine
source                1..19
                      mol_type = other RNA
                      organism = synthetic construct
modified_base         5
                      mod_base = OTHER
                      note = 2'-O-methylcytidine
modified_base         10
                      mod_base = OTHER
                      note = 2'-O-methylcytidine
modified_base         9
                      mod_base = OTHER
                      note = 2'-fluorocytidine
modified_base         1
                      mod_base = OTHER
                      note = 2'-O-methylcytidine phosphorothioate
modified_base         2
                      mod_base = OTHER
                      note = 2'-O-methyluridine phosphorothioate
modified_base         3
                      mod_base = OTHER
                      note = 2'-O-methylguanosine
modified_base         19
                      mod_base = OTHER
                      note = 2'-O-methyladenosine
modified_base         13
                      mod_base = OTHER
                      note = 2'-O-methylguanosine
modified_base         4
                      mod_base = OTHER
                      note = 2'-O-methylguanosine
modified_base         14
                      mod_base = OTHER
                      note = 2'-O-methyladenosine
modified_base         8
                      mod_base = OTHER
                      note = 2'-fluoroguanosine
modified_base         7
                      mod_base = OTHER
                      note = 2'-fluoroadenosine
modified_base         18
                      mod_base = OTHER
                      note = 2'-O-methyluridine phosphorothioate
modified_base         12
                      mod_base = OTHER
                      note = 2'-O-methylguanosine
modified_base         11
                      mod_base = OTHER
                      note = 2'-O-methylcytidine
modified_base         6
                      mod_base = OTHER
                      note = 2'-O-methylguanosine
modified_base         15
                      mod_base = OTHER
                      note = 2'-O-methylguanosine
modified_base         17
                      mod_base = OTHER
                      note = 2'-O-methyluridine phosphorothioate
SEQUENCE: 176
ctggcgagcc cggagttta                                              19

SEQ ID NO: 177        moltype = RNA  length = 19
```

-continued

```
FEATURE                Location/Qualifiers
modified_base          1
                       mod_base = OTHER
                       note = 2'-O-methylguanosine phosphorothioate
modified_base          2
                       mod_base = OTHER
                       note = 2'-O-methylguanosine phosphorothioate
modified_base          17
                       mod_base = OTHER
                       note = 2'-O-methylcytidine phosphorothioate
modified_base          5
                       mod_base = OTHER
                       note = 2'-O-methyladenosine
source                 1..19
                       mol_type = other RNA
                       organism = synthetic construct
modified_base          6
                       mod_base = OTHER
                       note = 2'-O-methylguanosine
modified_base          16
                       mod_base = OTHER
                       note = 2'-O-methyluridine
modified_base          4
                       mod_base = OTHER
                       note = 2'-O-methylguanosine
modified_base          18
                       mod_base = OTHER
                       note = 2'-O-methyluridine phosphorothioate
modified_base          19
                       mod_base = OTHER
                       note = 2'-O-methyladenosine
modified_base          3
                       mod_base = OTHER
                       note = 2'-O-methylcytidine
modified_base          7
                       mod_base = OTHER
                       note = 2'-fluorocytidine
modified_base          14
                       mod_base = OTHER
                       note = 2'-O-methyluridine
modified_base          8
                       mod_base = OTHER
                       note = 2'-fluorocytidine
modified_base          12
                       mod_base = OTHER
                       note = 2'-O-methyladenosine
modified_base          11
                       mod_base = OTHER
                       note = 2'-O-methylguanosine
modified_base          10
                       mod_base = OTHER
                       note = 2'-O-methylguanosine
modified_base          15
                       mod_base = OTHER
                       note = 2'-O-methyluridine
modified_base          13
                       mod_base = OTHER
                       note = 2'-O-methylguanosine
modified_base          9
                       mod_base = OTHER
                       note = 2'-fluorocytidine
SEQUENCE: 177
ggcgagcccg gagtttcta                                            19

SEQ ID NO: 178         moltype = RNA  length = 19
FEATURE                Location/Qualifiers
modified_base          17
                       mod_base = OTHER
                       note = 2'-O-methylguanosine phosphorothioate
modified_base          4
                       mod_base = OTHER
                       note = 2'-O-methylguanosine
modified_base          12
                       mod_base = OTHER
                       note = 2'-O-methyluridine
modified_base          9
                       mod_base = OTHER
                       note = 2'-fluorocytidine
modified_base          13
```

```
                        mod_base = OTHER
                        note = 2'-O-methylcytidine
modified_base           8
                        mod_base = OTHER
                        note = 2'-fluorocytidine
modified_base           14
                        mod_base = OTHER
                        note = 2'-O-methylcytidine
modified_base           15
                        mod_base = OTHER
                        note = 2'-O-methyluridine
modified_base           7
                        mod_base = OTHER
                        note = 2'-fluoroadenosine
modified_base           3
                        mod_base = OTHER
                        note = 2'-O-methylcytidine
modified_base           18
                        mod_base = OTHER
                        note = 2'-O-methyladenosine phosphorothioate
modified_base           19
                        mod_base = OTHER
                        note = 2'-O-methyladenosine
modified_base           1
                        mod_base = OTHER
                        note = 2'-O-methylguanosine phosphorothioate
modified_base           6
                        mod_base = OTHER
                        note = 2'-O-methyladenosine
source                  1..19
                        mol_type = other RNA
                        organism = synthetic construct
modified_base           2
                        mod_base = OTHER
                        note = 2'-O-methylguanosine phosphorothioate
modified_base           10
                        mod_base = OTHER
                        note = 2'-O-methyluridine
modified_base           11
                        mod_base = OTHER
                        note = 2'-O-methylcytidine
modified_base           16
                        mod_base = OTHER
                        note = 2'-O-methyladenosine
modified_base           5
                        mod_base = OTHER
                        note = 2'-O-methylcytidine
SEQUENCE: 178
ggcgcaacct ctcctagaa                                              19

SEQ ID NO: 179          moltype = RNA  length = 19
FEATURE                 Location/Qualifiers
modified_base           9
                        mod_base = OTHER
                        note = 2'-fluorouridine
modified_base           8
                        mod_base = OTHER
                        note = 2'-fluorocytidine
modified_base           14
                        mod_base = OTHER
                        note = 2'-O-methyluridine
modified_base           17
                        mod_base = OTHER
                        note = 2'-O-methyladenosine phosphorothioate
modified_base           11
                        mod_base = OTHER
                        note = 2'-O-methyluridine
modified_base           16
                        mod_base = OTHER
                        note = 2'-O-methylguanosine
modified_base           13
                        mod_base = OTHER
                        note = 2'-O-methylcytidine
modified_base           4
                        mod_base = OTHER
                        note = 2'-O-methylcytidine
modified_base           12
                        mod_base = OTHER
                        note = 2'-O-methylcytidine
```

```
modified_base          6
                       mod_base = OTHER
                       note = 2'-O-methyladenosine
modified_base          1
                       mod_base = OTHER
                       note = 2'-O-methylguanosine phosphorothioate
modified_base          19
                       mod_base = OTHER
                       note = 2'-O-methyladenosine
modified_base          5
                       mod_base = OTHER
                       note = 2'-O-methyladenosine
modified_base          18
                       mod_base = OTHER
                       note = 2'-O-methyladenosine phosphorothioate
modified_base          10
                       mod_base = OTHER
                       note = 2'-O-methylcytidine
modified_base          7
                       mod_base = OTHER
                       note = 2'-fluorocytidine
source                 1..19
                       mol_type = other RNA
                       organism = synthetic construct
modified_base          3
                       mod_base = OTHER
                       note = 2'-O-methylguanosine
modified_base          15
                       mod_base = OTHER
                       note = 2'-O-methyladenosine
modified_base          2
                       mod_base = OTHER
                       note = 2'-O-methylcytidine phosphorothioate
SEQUENCE: 179
gcgcaacctc tcctagaaa                                              19

SEQ ID NO: 180         moltype = RNA  length = 19
FEATURE                Location/Qualifiers
modified_base          18
                       mod_base = OTHER
                       note = 2'-O-methylguanosine phosphorothioate
modified_base          12
                       mod_base = OTHER
                       note = 2'-O-methylguanosine
modified_base          14
                       mod_base = OTHER
                       note = 2'-O-methyladenosine
modified_base          1
                       mod_base = OTHER
                       note = 2'-O-methyladenosine phosphorothioate
modified_base          7
                       mod_base = OTHER
                       note = 2'-fluorouridine
source                 1..19
                       mol_type = other RNA
                       organism = synthetic construct
modified_base          10
                       mod_base = OTHER
                       note = 2'-O-methyluridine
modified_base          11
                       mod_base = OTHER
                       note = 2'-O-methyladenosine
modified_base          13
                       mod_base = OTHER
                       note = 2'-O-methyladenosine
modified_base          16
                       mod_base = OTHER
                       note = 2'-O-methylcytidine
modified_base          3
                       mod_base = OTHER
                       note = 2'-O-methylcytidine
modified_base          5
                       mod_base = OTHER
                       note = 2'-O-methyluridine
modified_base          8
                       mod_base = OTHER
                       note = 2'-fluorocytidine
modified_base          19
                       mod_base = OTHER
```

```
                        note = 2'-O-methyladenosine
modified_base           17
                        mod_base = OTHER
                        note = 2'-O-methylguanosine phosphorothioate
modified_base           15
                        mod_base = OTHER
                        note = 2'-O-methyladenosine
modified_base           2
                        mod_base = OTHER
                        note = 2'-O-methyladenosine phosphorothioate
modified_base           6
                        mod_base = OTHER
                        note = 2'-O-methylcytidine
modified_base           4
                        mod_base = OTHER
                        note = 2'-O-methylcytidine
modified_base           9
                        mod_base = OTHER
                        note = 2'-fluorocytidine
SEQUENCE: 180
aacctctcct agaaacgga                                              19

SEQ ID NO: 181          moltype = RNA  length = 19
FEATURE                 Location/Qualifiers
modified_base           12
                        mod_base = OTHER
                        note = 2'-O-methyladenosine
modified_base           3
                        mod_base = OTHER
                        note = 2'-O-methylguanosine
modified_base           10
                        mod_base = OTHER
                        note = 2'-O-methyladenosine
modified_base           1
                        mod_base = OTHER
                        note = 2'-O-methylcytidine phosphorothioate
modified_base           19
                        mod_base = OTHER
                        note = 2'-O-methyladenosine
modified_base           14
                        mod_base = OTHER
                        note = 2'-O-methyluridine
modified_base           6
                        mod_base = OTHER
                        note = 2'-O-methyladenosine
modified_base           4
                        mod_base = OTHER
                        note = 2'-O-methylcytidine
modified_base           17
                        mod_base = OTHER
                        note = 2'-O-methylcytidine phosphorothioate
modified_base           7
                        mod_base = OTHER
                        note = 2'-fluoroguanosine
source                  1..19
                        mol_type = other RNA
                        organism = synthetic construct
modified_base           9
                        mod_base = OTHER
                        note = 2'-fluoroadenosine
modified_base           11
                        mod_base = OTHER
                        note = 2'-O-methylguanosine
modified_base           18
                        mod_base = OTHER
                        note = 2'-O-methylguanosine phosphorothioate
modified_base           16
                        mod_base = OTHER
                        note = 2'-O-methylcytidine
modified_base           8
                        mod_base = OTHER
                        note = 2'-fluoroguanosine
modified_base           5
                        mod_base = OTHER
                        note = 2'-O-methylguanosine
modified_base           15
                        mod_base = OTHER
                        note = 2'-O-methyladenosine
modified_base           13
```

```
                        mod_base = OTHER
                        note = 2'-O-methyladenosine
modified_base           2
                        mod_base = OTHER
                        note = 2'-O-methyladenosine phosphorothioate
SEQUENCE: 181
cagcgaggaa gaataccga                                            19

SEQ ID NO: 182          moltype = RNA  length = 19
FEATURE                 Location/Qualifiers
modified_base           5
                        mod_base = OTHER
                        note = 2'-O-methyladenosine
modified_base           7
                        mod_base = OTHER
                        note = 2'-fluoroguanosine
modified_base           9
                        mod_base = OTHER
                        note = 2'-fluoroadenosine
modified_base           18
                        mod_base = OTHER
                        note = 2'-O-methylguanosine phosphorothioate
modified_base           10
                        mod_base = OTHER
                        note = 2'-O-methylguanosine
modified_base           15
                        mod_base = OTHER
                        note = 2'-O-methylcytidine
source                  1..19
                        mol_type = other RNA
                        organism = synthetic construct
modified_base           6
                        mod_base = OTHER
                        note = 2'-O-methylguanosine
modified_base           4
                        mod_base = OTHER
                        note = 2'-O-methylguanosine
modified_base           8
                        mod_base = OTHER
                        note = 2'-fluoroadenosine
modified_base           3
                        mod_base = OTHER
                        note = 2'-O-methylcytidine
modified_base           16
                        mod_base = OTHER
                        note = 2'-O-methylcytidine
modified_base           19
                        mod_base = OTHER
                        note = 2'-O-methyladenosine
modified_base           17
                        mod_base = OTHER
                        note = 2'-O-methylguanosine phosphorothioate
modified_base           1
                        mod_base = OTHER
                        note = 2'-O-methyladenosine phosphorothioate
modified_base           11
                        mod_base = OTHER
                        note = 2'-O-methyladenosine
modified_base           13
                        mod_base = OTHER
                        note = 2'-O-methyluridine
modified_base           14
                        mod_base = OTHER
                        note = 2'-O-methyladenosine
modified_base           12
                        mod_base = OTHER
                        note = 2'-O-methyladenosine
modified_base           2
                        mod_base = OTHER
                        note = 2'-O-methylguanosine phosphorothioate
SEQUENCE: 182
agcgaggaag aataccgga                                            19

SEQ ID NO: 183          moltype = RNA  length = 19
FEATURE                 Location/Qualifiers
modified_base           7
                        mod_base = OTHER
                        note = 2'-fluoroadenosine
modified_base           9
```

```
                          mod_base = OTHER
                          note = 2'-fluoroguanosine
modified_base             4
                          mod_base = OTHER
                          note = 2'-O-methyladenosine
modified_base             18
                          mod_base = OTHER
                          note = 2'-O-methylguanosine phosphorothioate
source                    1..19
                          mol_type = other RNA
                          organism = synthetic construct
modified_base             2
                          mod_base = OTHER
                          note = 2'-O-methylcytidine phosphorothioate
modified_base             17
                          mod_base = OTHER
                          note = 2'-O-methylguanosine phosphorothioate
modified_base             14
                          mod_base = OTHER
                          note = 2'-O-methylcytidine
modified_base             19
                          mod_base = OTHER
                          note = 2'-O-methyladenosine
modified_base             11
                          mod_base = OTHER
                          note = 2'-O-methyladenosine
modified_base             5
                          mod_base = OTHER
                          note = 2'-O-methylguanosine
modified_base             10
                          mod_base = OTHER
                          note = 2'-O-methyladenosine
modified_base             8
                          mod_base = OTHER
                          note = 2'-fluoroadenosine
modified_base             15
                          mod_base = OTHER
                          note = 2'-O-methylcytidine
modified_base             12
                          mod_base = OTHER
                          note = 2'-O-methyluridine
modified_base             3
                          mod_base = OTHER
                          note = 2'-O-methylguanosine
modified_base             6
                          mod_base = OTHER
                          note = 2'-O-methylguanosine
modified_base             13
                          mod_base = OTHER
                          note = 2'-O-methyladenosine
modified_base             1
                          mod_base = OTHER
                          note = 2'-O-methylguanosine phosphorothioate
modified_base             16
                          mod_base = OTHER
                          note = 2'-O-methylguanosine
SEQUENCE: 183
gcgaggaaga ataccggga                                              19

SEQ ID NO: 184            moltype = RNA  length = 19
FEATURE                   Location/Qualifiers
source                    1..19
                          mol_type = other RNA
                          organism = synthetic construct
modified_base             19
                          mod_base = OTHER
                          note = 2'-O-methyladenosine
modified_base             4
                          mod_base = OTHER
                          note = 2'-O-methylguanosine
modified_base             15
                          mod_base = OTHER
                          note = 2'-O-methylguanosine
modified_base             8
                          mod_base = OTHER
                          note = 2'-fluorocytidine
modified_base             5
                          mod_base = OTHER
                          note = 2'-O-methylguanosine
```

-continued

```
modified_base        12
                     mod_base = OTHER
                     note = 2'-O-methylguanosine
modified_base        3
                     mod_base = OTHER
                     note = 2'-O-methyluridine
modified_base        7
                     mod_base = OTHER
                     note = 2'-fluoroadenosine
modified_base        18
                     mod_base = OTHER
                     note = 2'-O-methyluridine phosphorothioate
modified_base        2
                     mod_base = OTHER
                     note = 2'-O-methyluridine phosphorothioate
modified_base        6
                     mod_base = OTHER
                     note = 2'-O-methylguanosine
modified_base        14
                     mod_base = OTHER
                     note = 2'-O-methylcytidine
modified_base        17
                     mod_base = OTHER
                     note = 2'-O-methylguanosine phosphorothioate
modified_base        11
                     mod_base = OTHER
                     note = 2'-O-methylguanosine
modified_base        1
                     mod_base = OTHER
                     note = 2'-O-methylguanosine phosphorothioate
modified_base        9
                     mod_base = OTHER
                     note = 2'-fluoroguanosine
modified_base        10
                     mod_base = OTHER
                     note = 2'-O-methylguanosine
modified_base        13
                     mod_base = OTHER
                     note = 2'-O-methyluridine
modified_base        16
                     mod_base = OTHER
                     note = 2'-O-methylguanosine
SEQUENCE: 184
gttgggacgg ggtcgggta                                             19

SEQ ID NO: 185       moltype = RNA  length = 19
FEATURE              Location/Qualifiers
modified_base        17
                     mod_base = OTHER
                     note = 2'-O-methylcytidine phosphorothioate
modified_base        4
                     mod_base = OTHER
                     note = 2'-O-methylguanosine
source               1..19
                     mol_type = other RNA
                     organism = synthetic construct
modified_base        19
                     mod_base = OTHER
                     note = 2'-O-methyladenosine
modified_base        5
                     mod_base = OTHER
                     note = 2'-O-methylguanosine
modified_base        11
                     mod_base = OTHER
                     note = 2'-O-methylguanosine
modified_base        8
                     mod_base = OTHER
                     note = 2'-fluorocytidine
modified_base        16
                     mod_base = OTHER
                     note = 2'-O-methyluridine
modified_base        14
                     mod_base = OTHER
                     note = 2'-O-methylguanosine
modified_base        1
                     mod_base = OTHER
                     note = 2'-O-methyladenosine phosphorothioate
modified_base        2
                     mod_base = OTHER
```

```
                        note = 2'-O-methylcytidine phosphorothioate
modified_base           15
                        mod_base = OTHER
                        note = 2'-O-methyluridine
modified_base           12
                        mod_base = OTHER
                        note = 2'-O-methyluridine
modified_base           7
                        mod_base = OTHER
                        note = 2'-fluorouridine
modified_base           18
                        mod_base = OTHER
                        note = 2'-O-methylguanosine phosphorothioate
modified_base           13
                        mod_base = OTHER
                        note = 2'-O-methylguanosine
modified_base           10
                        mod_base = OTHER
                        note = 2'-O-methylguanosine
modified_base           6
                        mod_base = OTHER
                        note = 2'-O-methylguanosine
modified_base           3
                        mod_base = OTHER
                        note = 2'-O-methylguanosine
modified_base           9
                        mod_base = OTHER
                        note = 2'-fluoroguanosine
SEQUENCE: 185
acggggtcgg gtggttcga                                           19

SEQ ID NO: 186          moltype = RNA  length = 19
FEATURE                 Location/Qualifiers
modified_base           4
                        mod_base = OTHER
                        note = 2'-O-methylcytidine
modified_base           17
                        mod_base = OTHER
                        note = 2'-O-methylguanosine phosphorothioate
modified_base           2
                        mod_base = OTHER
                        note = 2'-O-methylguanosine phosphorothioate
modified_base           11
                        mod_base = OTHER
                        note = 2'-O-methyluridine
modified_base           18
                        mod_base = OTHER
                        note = 2'-O-methylcytidine phosphorothioate
modified_base           16
                        mod_base = OTHER
                        note = 2'-O-methylguanosine
modified_base           10
                        mod_base = OTHER
                        note = 2'-O-methylguanosine
modified_base           14
                        mod_base = OTHER
                        note = 2'-O-methylguanosine
modified_base           8
                        mod_base = OTHER
                        note = 2'-fluorouridine
modified_base           12
                        mod_base = OTHER
                        note = 2'-O-methyluridine
source                  1..19
                        mol_type = other RNA
                        organism = synthetic construct
modified_base           5
                        mod_base = OTHER
                        note = 2'-O-methylguanosine
modified_base           6
                        mod_base = OTHER
                        note = 2'-O-methylguanosine
modified_base           19
                        mod_base = OTHER
                        note = 2'-O-methyladenosine
modified_base           15
                        mod_base = OTHER
                        note = 2'-O-methylguanosine
modified_base           7
```

-continued

```
                        mod_base = OTHER
                        note = 2'-fluoroguanosine
modified_base           13
                        mod_base = OTHER
                        note = 2'-O-methylcytidine
modified_base           3
                        mod_base = OTHER
                        note = 2'-O-methyluridine
modified_base           1
                        mod_base = OTHER
                        note = 2'-O-methylguanosine phosphorothioate
modified_base           9
                        mod_base = OTHER
                        note = 2'-fluoroguanosine
SEQUENCE: 186
ggtcgggtgg ttcggggca                                             19

SEQ ID NO: 187          moltype = RNA  length = 19
FEATURE                 Location/Qualifiers
modified_base           18
                        mod_base = OTHER
                        note = 2'-O-methyladenosine phosphorothioate
modified_base           15
                        mod_base = OTHER
                        note = 2'-O-methylguanosine
modified_base           1
                        mod_base = OTHER
                        note = 2'-O-methylguanosine phosphorothioate
modified_base           12
                        mod_base = OTHER
                        note = 2'-O-methylcytidine
source                  1..19
                        mol_type = other RNA
                        organism = synthetic construct
modified_base           8
                        mod_base = OTHER
                        note = 2'-fluoroguanosine
modified_base           16
                        mod_base = OTHER
                        note = 2'-O-methylguanosine
modified_base           3
                        mod_base = OTHER
                        note = 2'-O-methylcytidine
modified_base           6
                        mod_base = OTHER
                        note = 2'-O-methylguanosine
modified_base           2
                        mod_base = OTHER
                        note = 2'-O-methyluridine phosphorothioate
modified_base           5
                        mod_base = OTHER
                        note = 2'-O-methylguanosine
modified_base           13
                        mod_base = OTHER
                        note = 2'-O-methylguanosine
modified_base           14
                        mod_base = OTHER
                        note = 2'-O-methylguanosine
modified_base           11
                        mod_base = OTHER
                        note = 2'-O-methyluridine
modified_base           4
                        mod_base = OTHER
                        note = 2'-O-methylguanosine
modified_base           9
                        mod_base = OTHER
                        note = 2'-fluoroguanosine
modified_base           7
                        mod_base = OTHER
                        note = 2'-fluorouridine
modified_base           19
                        mod_base = OTHER
                        note = 2'-O-methyladenosine
modified_base           17
                        mod_base = OTHER
                        note = 2'-O-methylcytidine phosphorothioate
modified_base           10
                        mod_base = OTHER
                        note = 2'-O-methyluridine
```

```
SEQUENCE: 187
gtcgggtggt tcggggcaa                                              19

SEQ ID NO: 188          moltype = RNA  length = 19
FEATURE                 Location/Qualifiers
modified_base           9
                        mod_base = OTHER
                        note = 2'-fluorocytidine
modified_base           7
                        mod_base = OTHER
                        note = 2'-fluoroguanosine
modified_base           1
                        mod_base = OTHER
                        note = 2'-O-methylguanosine phosphorothioate
modified_base           10
                        mod_base = OTHER
                        note = 2'-O-methyluridine
modified_base           16
                        mod_base = OTHER
                        note = 2'-O-methyluridine
modified_base           13
                        mod_base = OTHER
                        note = 2'-O-methylcytidine
modified_base           8
                        mod_base = OTHER
                        note = 2'-fluorocytidine
modified_base           6
                        mod_base = OTHER
                        note = 2'-O-methylguanosine
modified_base           11
                        mod_base = OTHER
                        note = 2'-O-methylcytidine
modified_base           19
                        mod_base = OTHER
                        note = 2'-O-methyladenosine
modified_base           15
                        mod_base = OTHER
                        note = 2'-O-methyluridine
modified_base           4
                        mod_base = OTHER
                        note = 2'-O-methylguanosine
modified_base           12
                        mod_base = OTHER
                        note = 2'-O-methyluridine
modified_base           17
                        mod_base = OTHER
                        note = 2'-O-methylcytidine phosphorothioate
modified_base           18
                        mod_base = OTHER
                        note = 2'-O-methylguanosine phosphorothioate
modified_base           5
                        mod_base = OTHER
                        note = 2'-O-methyluridine
modified_base           3
                        mod_base = OTHER
                        note = 2'-O-methylguanosine
source                  1..19
                        mol_type = other RNA
                        organism = synthetic construct
modified_base           14
                        mod_base = OTHER
                        note = 2'-O-methyluridine
modified_base           2
                        mod_base = OTHER
                        note = 2'-O-methylcytidine phosphorothioate
SEQUENCE: 188
gcggtggcct ctctttcga                                              19

SEQ ID NO: 189          moltype = RNA  length = 19
FEATURE                 Location/Qualifiers
modified_base           14
                        mod_base = OTHER
                        note = 2'-O-methyluridine
modified_base           6
                        mod_base = OTHER
                        note = 2'-O-methylguanosine
modified_base           12
                        mod_base = OTHER
                        note = 2'-O-methylcytidine
```

-continued

```
source                1..19
                      mol_type = other RNA
                      organism = synthetic construct
modified_base         3
                      mod_base = OTHER
                      note = 2'-O-methylguanosine
modified_base         15
                      mod_base = OTHER
                      note = 2'-O-methyluridine
modified_base         18
                      mod_base = OTHER
                      note = 2'-O-methylcytidine phosphorothioate
modified_base         2
                      mod_base = OTHER
                      note = 2'-O-methylguanosine phosphorothioate
modified_base         4
                      mod_base = OTHER
                      note = 2'-O-methyluridine
modified_base         11
                      mod_base = OTHER
                      note = 2'-O-methyluridine
modified_base         9
                      mod_base = OTHER
                      note = 2'-fluorouridine
modified_base         7
                      mod_base = OTHER
                      note = 2'-fluorocytidine
modified_base         10
                      mod_base = OTHER
                      note = 2'-O-methylcytidine
modified_base         16
                      mod_base = OTHER
                      note = 2'-O-methylcytidine
modified_base         17
                      mod_base = OTHER
                      note = 2'-O-methylguanosine phosphorothioate
modified_base         5
                      mod_base = OTHER
                      note = 2'-O-methylguanosine
modified_base         1
                      mod_base = OTHER
                      note = 2'-O-methylcytidine phosphorothioate
modified_base         13
                      mod_base = OTHER
                      note = 2'-O-methyluridine
modified_base         8
                      mod_base = OTHER
                      note = 2'-fluorocytidine
modified_base         19
                      mod_base = OTHER
                      note = 2'-O-methyladenosine
SEQUENCE: 189
cggtggcctc tctttcgca                                                  19

SEQ ID NO: 190        moltype = RNA  length = 19
FEATURE               Location/Qualifiers
modified_base         11
                      mod_base = OTHER
                      note = 2'-O-methylcytidine
modified_base         15
                      mod_base = OTHER
                      note = 2'-O-methylcytidine
modified_base         14
                      mod_base = OTHER
                      note = 2'-O-methyluridine
modified_base         10
                      mod_base = OTHER
                      note = 2'-O-methyluridine
modified_base         16
                      mod_base = OTHER
                      note = 2'-O-methylguanosine
modified_base         6
                      mod_base = OTHER
                      note = 2'-O-methylcytidine
modified_base         13
                      mod_base = OTHER
                      note = 2'-O-methyluridine
modified_base         9
                      mod_base = OTHER
```

-continued

```
                         note = 2'-fluorocytidine
source                   1..19
                         mol_type = other RNA
                         organism = synthetic construct
modified_base            17
                         mod_base = OTHER
                         note = 2'-O-methylcytidine phosphorothioate
modified_base            3
                         mod_base = OTHER
                         note = 2'-O-methyluridine
modified_base            1
                         mod_base = OTHER
                         note = 2'-O-methylguanosine phosphorothioate
modified_base            12
                         mod_base = OTHER
                         note = 2'-O-methyluridine
modified_base            5
                         mod_base = OTHER
                         note = 2'-O-methylguanosine
modified_base            4
                         mod_base = OTHER
                         note = 2'-O-methylguanosine
modified_base            2
                         mod_base = OTHER
                         note = 2'-O-methylguanosine phosphorothioate
modified_base            18
                         mod_base = OTHER
                         note = 2'-O-methylguanosine phosphorothioate
modified_base            8
                         mod_base = OTHER
                         note = 2'-fluorouridine
modified_base            7
                         mod_base = OTHER
                         note = 2'-fluorocytidine
modified_base            19
                         mod_base = OTHER
                         note = 2'-O-methyladenosine
SEQUENCE: 190
ggtggcctct ctttcgcga                                              19

SEQ ID NO: 191           moltype = RNA  length = 19
FEATURE                  Location/Qualifiers
modified_base            5
                         mod_base = OTHER
                         note = 2'-O-methylcytidine
modified_base            10
                         mod_base = OTHER
                         note = 2'-O-methyluridine
modified_base            19
                         mod_base = OTHER
                         note = 2'-O-methyladenosine
modified_base            17
                         mod_base = OTHER
                         note = 2'-O-methylguanosine phosphorothioate
modified_base            9
                         mod_base = OTHER
                         note = 2'-fluorouridine
source                   1..19
                         mol_type = other RNA
                         organism = synthetic construct
modified_base            4
                         mod_base = OTHER
                         note = 2'-O-methyluridine
modified_base            14
                         mod_base = OTHER
                         note = 2'-O-methylguanosine
modified_base            15
                         mod_base = OTHER
                         note = 2'-O-methylguanosine
modified_base            3
                         mod_base = OTHER
                         note = 2'-O-methylcytidine
modified_base            6
                         mod_base = OTHER
                         note = 2'-O-methyluridine
modified_base            18
                         mod_base = OTHER
                         note = 2'-O-methyladenosine phosphorothioate
modified_base            16
```

-continued

```
                        mod_base = OTHER
                        note = 2'-O-methylguanosine
modified_base           11
                        mod_base = OTHER
                        note = 2'-O-methylcytidine
modified_base           8
                        mod_base = OTHER
                        note = 2'-fluorouridine
modified_base           7
                        mod_base = OTHER
                        note = 2'-fluorocytidine
modified_base           13
                        mod_base = OTHER
                        note = 2'-O-methylcytidine
modified_base           2
                        mod_base = OTHER
                        note = 2'-O-methylcytidine phosphorothioate
modified_base           1
                        mod_base = OTHER
                        note = 2'-O-methylguanosine phosphorothioate
modified_base           12
                        mod_base = OTHER
                        note = 2'-O-methylguanosine
SEQUENCE: 191
gcctctcttt cgcggggaa                                            19

SEQ ID NO: 192          moltype = RNA  length = 19
FEATURE                 Location/Qualifiers
modified_base           4
                        mod_base = OTHER
                        note = 2'-O-methylcytidine
modified_base           17
                        mod_base = OTHER
                        note = 2'-O-methylguanosine phosphorothioate
modified_base           1
                        mod_base = OTHER
                        note = 2'-O-methylcytidine phosphorothioate
modified_base           13
                        mod_base = OTHER
                        note = 2'-O-methyluridine
modified_base           16
                        mod_base = OTHER
                        note = 2'-O-methylguanosine
modified_base           19
                        mod_base = OTHER
                        note = 2'-O-methyladenosine
modified_base           14
                        mod_base = OTHER
                        note = 2'-O-methyladenosine
modified_base           2
                        mod_base = OTHER
                        note = 2'-O-methyladenosine phosphorothioate
modified_base           8
                        mod_base = OTHER
                        note = 2'-fluorocytidine
modified_base           9
                        mod_base = OTHER
                        note = 2'-fluorouridine
modified_base           5
                        mod_base = OTHER
                        note = 2'-O-methyluridine
modified_base           12
                        mod_base = OTHER
                        note = 2'-O-methylcytidine
modified_base           3
                        mod_base = OTHER
                        note = 2'-O-methylcytidine
modified_base           15
                        mod_base = OTHER
                        note = 2'-O-methylcytidine
modified_base           10
                        mod_base = OTHER
                        note = 2'-O-methylguanosine
modified_base           7
                        mod_base = OTHER
                        note = 2'-fluoroguanosine
source                  1..19
                        mol_type = other RNA
                        organism = synthetic construct
```

```
modified_base          11
                       mod_base = OTHER
                       note = 2'-O-methylguanosine
modified_base          6
                       mod_base = OTHER
                       note = 2'-O-methylguanosine
modified_base          18
                       mod_base = OTHER
                       note = 2'-O-methyladenosine phosphorothioate
SEQUENCE: 192
cacctggctg gctacggaa                                              19

SEQ ID NO: 193         moltype = RNA  length = 19
FEATURE                Location/Qualifiers
modified_base          4
                       mod_base = OTHER
                       note = 2'-O-methyladenosine
modified_base          1
                       mod_base = OTHER
                       note = 2'-O-methylguanosine phosphorothioate
modified_base          13
                       mod_base = OTHER
                       note = 2'-O-methylcytidine
modified_base          7
                       mod_base = OTHER
                       note = 2'-fluoroguanosine
modified_base          6
                       mod_base = OTHER
                       note = 2'-O-methylguanosine
modified_base          17
                       mod_base = OTHER
                       note = 2'-O-methyluridine phosphorothioate
modified_base          16
                       mod_base = OTHER
                       note = 2'-O-methylguanosine
modified_base          11
                       mod_base = OTHER
                       note = 2'-O-methylguanosine
modified_base          14
                       mod_base = OTHER
                       note = 2'-O-methylguanosine
modified_base          5
                       mod_base = OTHER
                       note = 2'-O-methylcytidine
modified_base          12
                       mod_base = OTHER
                       note = 2'-O-methylguanosine
modified_base          19
                       mod_base = OTHER
                       note = 2'-O-methyladenosine
modified_base          18
                       mod_base = OTHER
                       note = 2'-O-methylcytidine phosphorothioate
modified_base          15
                       mod_base = OTHER
                       note = 2'-O-methyluridine
modified_base          2
                       mod_base = OTHER
                       note = 2'-O-methylcytidine phosphorothioate
source                 1..19
                       mol_type = other RNA
                       organism = synthetic construct
modified_base          3
                       mod_base = OTHER
                       note = 2'-O-methyluridine
modified_base          10
                       mod_base = OTHER
                       note = 2'-O-methylguanosine
modified_base          8
                       mod_base = OTHER
                       note = 2'-fluoroadenosine
modified_base          9
                       mod_base = OTHER
                       note = 2'-fluoroguanosine
SEQUENCE: 193
gctacggagg ggcgtgtca                                              19

SEQ ID NO: 194         moltype = RNA  length = 19
FEATURE                Location/Qualifiers
```

```
modified_base         15
                      mod_base = OTHER
                      note = 2'-O-methylguanosine
modified_base         16
                      mod_base = OTHER
                      note = 2'-O-methyluridine
modified_base         9
                      mod_base = OTHER
                      note = 2'-fluoroguanosine
modified_base         11
                      mod_base = OTHER
                      note = 2'-O-methylguanosine
modified_base         4
                      mod_base = OTHER
                      note = 2'-O-methylcytidine
modified_base         19
                      mod_base = OTHER
                      note = 2'-O-methyladenosine
modified_base         8
                      mod_base = OTHER
                      note = 2'-fluoroguanosine
modified_base         3
                      mod_base = OTHER
                      note = 2'-O-methyladenosine
modified_base         1
                      mod_base = OTHER
                      note = 2'-O-methylcytidine phosphorothioate
modified_base         5
                      mod_base = OTHER
                      note = 2'-O-methylguanosine
modified_base         13
                      mod_base = OTHER
                      note = 2'-O-methylguanosine
modified_base         2
                      mod_base = OTHER
                      note = 2'-O-methyluridine phosphorothioate
source                1..19
                      mol_type = other RNA
                      organism = synthetic construct
modified_base         14
                      mod_base = OTHER
                      note = 2'-O-methyluridine
modified_base         18
                      mod_base = OTHER
                      note = 2'-O-methyluridine phosphorothioate
modified_base         6
                      mod_base = OTHER
                      note = 2'-O-methylguanosine
modified_base         12
                      mod_base = OTHER
                      note = 2'-O-methylcytidine
modified_base         7
                      mod_base = OTHER
                      note = 2'-fluoroadenosine
modified_base         10
                      mod_base = OTHER
                      note = 2'-O-methylguanosine
modified_base         17
                      mod_base = OTHER
                      note = 2'-O-methylcytidine phosphorothioate
SEQUENCE: 194
ctacggaggg gcgtgtcta                                           19

SEQ ID NO: 195        moltype = RNA  length = 19
FEATURE               Location/Qualifiers
modified_base         5
                      mod_base = OTHER
                      note = 2'-O-methylguanosine
modified_base         3
                      mod_base = OTHER
                      note = 2'-O-methylguanosine
modified_base         12
                      mod_base = OTHER
                      note = 2'-O-methyladenosine
modified_base         7
                      mod_base = OTHER
                      note = 2'-fluoroadenosine
modified_base         14
                      mod_base = OTHER
```

```
                        note = 2'-O-methylcytidine
modified_base           1
                        mod_base = OTHER
                        note = 2'-O-methyladenosine phosphorothioate
modified_base           6
                        mod_base = OTHER
                        note = 2'-O-methylcytidine
modified_base           15
                        mod_base = OTHER
                        note = 2'-O-methyluridine
modified_base           16
                        mod_base = OTHER
                        note = 2'-O-methylcytidine
source                  1..19
                        mol_type = other RNA
                        organism = synthetic construct
modified_base           17
                        mod_base = OTHER
                        note = 2'-O-methylguanosine phosphorothioate
modified_base           13
                        mod_base = OTHER
                        note = 2'-O-methylguanosine
modified_base           4
                        mod_base = OTHER
                        note = 2'-O-methyluridine
modified_base           9
                        mod_base = OTHER
                        note = 2'-fluoroguanosine
modified_base           2
                        mod_base = OTHER
                        note = 2'-O-methylcytidine phosphorothioate
modified_base           11
                        mod_base = OTHER
                        note = 2'-O-methylguanosine
modified_base           8
                        mod_base = OTHER
                        note = 2'-fluoroadenosine
modified_base           19
                        mod_base = OTHER
                        note = 2'-O-methyladenosine
modified_base           10
                        mod_base = OTHER
                        note = 2'-O-methylguanosine
modified_base           18
                        mod_base = OTHER
                        note = 2'-O-methylcytidine phosphorothioate
SEQUENCE: 195
acgtgcaagg gagctcgca                                              19

SEQ ID NO: 196          moltype = RNA  length = 19
FEATURE                 Location/Qualifiers
modified_base           18
                        mod_base = OTHER
                        note = 2'-O-methyluridine phosphorothioate
modified_base           4
                        mod_base = OTHER
                        note = 2'-O-methylguanosine
source                  1..19
                        mol_type = other RNA
                        organism = synthetic construct
modified_base           19
                        mod_base = OTHER
                        note = 2'-O-methyladenosine
modified_base           14
                        mod_base = OTHER
                        note = 2'-O-methyluridine
modified_base           11
                        mod_base = OTHER
                        note = 2'-O-methyladenosine
modified_base           1
                        mod_base = OTHER
                        note = 2'-O-methylcytidine phosphorothioate
modified_base           6
                        mod_base = OTHER
                        note = 2'-O-methyladenosine
modified_base           3
                        mod_base = OTHER
                        note = 2'-O-methyluridine
modified_base           2
```

```
                         mod_base = OTHER
                         note = 2'-O-methylguanosine phosphorothioate
modified_base            13
                         mod_base = OTHER
                         note = 2'-O-methylcytidine
modified_base            16
                         mod_base = OTHER
                         note = 2'-O-methylguanosine
modified_base            10
                         mod_base = OTHER
                         note = 2'-O-methylguanosine
modified_base            15
                         mod_base = OTHER
                         note = 2'-O-methylcytidine
modified_base            7
                         mod_base = OTHER
                         note = 2'-fluoroadenosine
modified_base            17
                         mod_base = OTHER
                         note = 2'-O-methylcytidine phosphorothioate
modified_base            8
                         mod_base = OTHER
                         note = 2'-fluoroguanosine
modified_base            5
                         mod_base = OTHER
                         note = 2'-O-methylcytidine
modified_base            12
                         mod_base = OTHER
                         note = 2'-O-methylguanosine
modified_base            9
                         mod_base = OTHER
                         note = 2'-fluoroguanosine
SEQUENCE: 196
cgtgcaaggg agctcgcta                                                   19

SEQ ID NO: 197           moltype = RNA  length = 19
FEATURE                  Location/Qualifiers
modified_base            16
                         mod_base = OTHER
                         note = 2'-O-methylcytidine
modified_base            5
                         mod_base = OTHER
                         note = 2'-O-methyladenosine
modified_base            17
                         mod_base = OTHER
                         note = 2'-O-methyluridine phosphorothioate
modified_base            9
                         mod_base = OTHER
                         note = 2'-fluoroguanosine
modified_base            11
                         mod_base = OTHER
                         note = 2'-O-methylguanosine
modified_base            12
                         mod_base = OTHER
                         note = 2'-O-methylcytidine
modified_base            7
                         mod_base = OTHER
                         note = 2'-fluoroguanosine
modified_base            13
                         mod_base = OTHER
                         note = 2'-O-methyluridine
modified_base            3
                         mod_base = OTHER
                         note = 2'-O-methylguanosine
modified_base            4
                         mod_base = OTHER
                         note = 2'-O-methylcytidine
modified_base            15
                         mod_base = OTHER
                         note = 2'-O-methylguanosine
modified_base            1
                         mod_base = OTHER
                         note = 2'-O-methylguanosine phosphorothioate
modified_base            2
                         mod_base = OTHER
                         note = 2'-O-methyluridine phosphorothioate
modified_base            19
                         mod_base = OTHER
                         note = 2'-O-methyladenosine
```

```
source                  1..19
                        mol_type = other RNA
                        organism = synthetic construct
modified_base           14
                        mod_base = OTHER
                        note = 2'-O-methylcytidine
modified_base           10
                        mod_base = OTHER
                        note = 2'-O-methyladenosine
modified_base           18
                        mod_base = OTHER
                        note = 2'-O-methylguanosine phosphorothioate
modified_base           8
                        mod_base = OTHER
                        note = 2'-fluoroguanosine
modified_base           6
                        mod_base = OTHER
                        note = 2'-O-methyladenosine
SEQUENCE: 197
gtgcaaggga gctcgctga                                             19

SEQ ID NO: 198          moltype = RNA  length = 19
FEATURE                 Location/Qualifiers
modified_base           6
                        mod_base = OTHER
                        note = 2'-O-methyluridine
modified_base           5
                        mod_base = OTHER
                        note = 2'-O-methyluridine
modified_base           8
                        mod_base = OTHER
                        note = 2'-fluorocytidine
modified_base           2
                        mod_base = OTHER
                        note = 2'-O-methyladenosine phosphorothioate
modified_base           14
                        mod_base = OTHER
                        note = 2'-O-methyluridine
modified_base           12
                        mod_base = OTHER
                        note = 2'-O-methylguanosine
modified_base           1
                        mod_base = OTHER
                        note = 2'-O-methylcytidine phosphorothioate
modified_base           9
                        mod_base = OTHER
                        note = 2'-fluoroguanosine
modified_base           16
                        mod_base = OTHER
                        note = 2'-O-methyluridine
modified_base           13
                        mod_base = OTHER
                        note = 2'-O-methylcytidine
modified_base           15
                        mod_base = OTHER
                        note = 2'-O-methylguanosine
modified_base           11
                        mod_base = OTHER
                        note = 2'-O-methylcytidine
modified_base           10
                        mod_base = OTHER
                        note = 2'-O-methyladenosine
modified_base           4
                        mod_base = OTHER
                        note = 2'-O-methylcytidine
modified_base           3
                        mod_base = OTHER
                        note = 2'-O-methylcytidine
modified_base           19
                        mod_base = OTHER
                        note = 2'-O-methyladenosine
modified_base           18
                        mod_base = OTHER
                        note = 2'-O-methyluridine phosphorothioate
modified_base           7
                        mod_base = OTHER
                        note = 2'-fluorocytidine
source                  1..19
                        mol_type = other RNA
```

```
                        organism = synthetic construct
modified_base           17
                        mod_base = OTHER
                        note = 2'-O-methylcytidine phosphorothioate
SEQUENCE: 198
caccttccga cgctgtcta                                              19

SEQ ID NO: 199          moltype = RNA  length = 19
FEATURE                 Location/Qualifiers
modified_base           14
                        mod_base = OTHER
                        note = 2'-O-methylguanosine
source                  1..19
                        mol_type = other RNA
                        organism = synthetic construct
modified_base           5
                        mod_base = OTHER
                        note = 2'-O-methyluridine
modified_base           15
                        mod_base = OTHER
                        note = 2'-O-methyluridine
modified_base           19
                        mod_base = OTHER
                        note = 2'-O-methyladenosine
modified_base           1
                        mod_base = OTHER
                        note = 2'-O-methyladenosine phosphorothioate
modified_base           12
                        mod_base = OTHER
                        note = 2'-O-methylcytidine
modified_base           9
                        mod_base = OTHER
                        note = 2'-fluoroadenosine
modified_base           13
                        mod_base = OTHER
                        note = 2'-O-methyluridine
modified_base           7
                        mod_base = OTHER
                        note = 2'-fluorocytidine
modified_base           4
                        mod_base = OTHER
                        note = 2'-O-methyluridine
modified_base           16
                        mod_base = OTHER
                        note = 2'-O-methylcytidine
modified_base           10
                        mod_base = OTHER
                        note = 2'-O-methylcytidine
modified_base           6
                        mod_base = OTHER
                        note = 2'-O-methylcytidine
modified_base           8
                        mod_base = OTHER
                        note = 2'-fluoroguanosine
modified_base           11
                        mod_base = OTHER
                        note = 2'-O-methylguanosine
modified_base           18
                        mod_base = OTHER
                        note = 2'-O-methyladenosine phosphorothioate
modified_base           17
                        mod_base = OTHER
                        note = 2'-O-methyluridine phosphorothioate
modified_base           2
                        mod_base = OTHER
                        note = 2'-O-methylcytidine phosphorothioate
modified_base           3
                        mod_base = OTHER
                        note = 2'-O-methylcytidine
SEQUENCE: 199
accttccgac gctgtctaa                                              19

SEQ ID NO: 200          moltype = RNA  length = 19
FEATURE                 Location/Qualifiers
modified_base           18
                        mod_base = OTHER
                        note = 2'-O-methylguanosine phosphorothioate
modified_base           17
                        mod_base = OTHER
```

```
                        note = 2'-O-methyladenosine phosphorothioate
modified_base           13
                        mod_base = OTHER
                        note = 2'-O-methylguanosine
modified_base           16
                        mod_base = OTHER
                        note = 2'-O-methyluridine
modified_base           8
                        mod_base = OTHER
                        note = 2'-fluoroadenosine
modified_base           1
                        mod_base = OTHER
                        note = 2'-O-methylcytidine phosphorothioate
modified_base           5
                        mod_base = OTHER
                        note = 2'-O-methylcytidine
modified_base           7
                        mod_base = OTHER
                        note = 2'-fluoroguanosine
modified_base           15
                        mod_base = OTHER
                        note = 2'-O-methylcytidine
modified_base           10
                        mod_base = OTHER
                        note = 2'-O-methylguanosine
modified_base           12
                        mod_base = OTHER
                        note = 2'-O-methyluridine
modified_base           6
                        mod_base = OTHER
                        note = 2'-O-methylcytidine
modified_base           9
                        mod_base = OTHER
                        note = 2'-fluorocytidine
source                  1..19
                        mol_type = other RNA
                        organism = synthetic construct
modified_base           19
                        mod_base = OTHER
                        note = 2'-O-methyladenosine
modified_base           2
                        mod_base = OTHER
                        note = 2'-O-methylcytidine phosphorothioate
modified_base           14
                        mod_base = OTHER
                        note = 2'-O-methyluridine
modified_base           11
                        mod_base = OTHER
                        note = 2'-O-methylcytidine
modified_base           4
                        mod_base = OTHER
                        note = 2'-O-methyluridine
modified_base           3
                        mod_base = OTHER
                        note = 2'-O-methyluridine
SEQUENCE: 200
ccttccgacg ctgtctaga                                                   19

SEQ ID NO: 201          moltype = RNA  length = 19
FEATURE                 Location/Qualifiers
modified_base           7
                        mod_base = OTHER
                        note = 2'-fluoroadenosine
modified_base           17
                        mod_base = OTHER
                        note = 2'-O-methylguanosine phosphorothioate
modified_base           18
                        mod_base = OTHER
                        note = 2'-O-methylguanosine phosphorothioate
modified_base           15
                        mod_base = OTHER
                        note = 2'-O-methyluridine
modified_base           8
                        mod_base = OTHER
                        note = 2'-fluorocytidine
modified_base           14
                        mod_base = OTHER
                        note = 2'-O-methylcytidine
source                  1..19
```

-continued

```
                        mol_type = other RNA
                        organism = synthetic construct
modified_base           16
                        mod_base = OTHER
                        note = 2'-O-methyladenosine
modified_base           10
                        mod_base = OTHER
                        note = 2'-O-methylcytidine
modified_base           1
                        mod_base = OTHER
                        note = 2'-O-methylcytidine phosphorothioate
modified_base           19
                        mod_base = OTHER
                        note = 2'-O-methyladenosine
modified_base           9
                        mod_base = OTHER
                        note = 2'-fluoroguanosine
modified_base           5
                        mod_base = OTHER
                        note = 2'-O-methylcytidine
modified_base           11
                        mod_base = OTHER
                        note = 2'-O-methyluridine
modified_base           13
                        mod_base = OTHER
                        note = 2'-O-methyluridine
modified_base           4
                        mod_base = OTHER
                        note = 2'-O-methylcytidine
modified_base           3
                        mod_base = OTHER
                        note = 2'-O-methyluridine
modified_base           2
                        mod_base = OTHER
                        note = 2'-O-methyluridine phosphorothioate
modified_base           6
                        mod_base = OTHER
                        note = 2'-O-methylguanosine
modified_base           12
                        mod_base = OTHER
                        note = 2'-O-methylguanosine
SEQUENCE: 201
cttccgacgc tgtctagga                                                  19

SEQ ID NO: 202          moltype = RNA  length = 19
FEATURE                 Location/Qualifiers
modified_base           19
                        mod_base = OTHER
                        note = 2'-O-methyladenosine
modified_base           1
                        mod_base = OTHER
                        note = 2'-O-methyluridine phosphorothioate
modified_base           8
                        mod_base = OTHER
                        note = 2'-fluorocytidine
modified_base           9
                        mod_base = OTHER
                        note = 2'-fluorouridine
modified_base           10
                        mod_base = OTHER
                        note = 2'-O-methylguanosine
modified_base           11
                        mod_base = OTHER
                        note = 2'-O-methyluridine
modified_base           5
                        mod_base = OTHER
                        note = 2'-O-methyladenosine
modified_base           7
                        mod_base = OTHER
                        note = 2'-fluoroguanosine
modified_base           18
                        mod_base = OTHER
                        note = 2'-O-methyladenosine phosphorothioate
modified_base           14
                        mod_base = OTHER
                        note = 2'-O-methyladenosine
modified_base           4
                        mod_base = OTHER
                        note = 2'-O-methylguanosine
```

-continued

```
modified_base           12
                        mod_base = OTHER
                        note = 2'-O-methylcytidine
modified_base           13
                        mod_base = OTHER
                        note = 2'-O-methyluridine
modified_base           17
                        mod_base = OTHER
                        note = 2'-O-methylcytidine phosphorothioate
modified_base           3
                        mod_base = OTHER
                        note = 2'-O-methylcytidine
modified_base           15
                        mod_base = OTHER
                        note = 2'-O-methylguanosine
modified_base           2
                        mod_base = OTHER
                        note = 2'-O-methylcytidine phosphorothioate
modified_base           16
                        mod_base = OTHER
                        note = 2'-O-methylguanosine
modified_base           6
                        mod_base = OTHER
                        note = 2'-O-methylcytidine
source                  1..19
                        mol_type = other RNA
                        organism = synthetic construct
SEQUENCE: 202
tccgacgctg tctaggcaa                                             19

SEQ ID NO: 203          moltype = RNA  length = 19
FEATURE                 Location/Qualifiers
modified_base           12
                        mod_base = OTHER
                        note = 2'-O-methyluridine
modified_base           4
                        mod_base = OTHER
                        note = 2'-O-methyladenosine
modified_base           17
                        mod_base = OTHER
                        note = 2'-O-methyladenosine phosphorothioate
modified_base           9
                        mod_base = OTHER
                        note = 2'-fluoroguanosine
modified_base           14
                        mod_base = OTHER
                        note = 2'-O-methylguanosine
modified_base           1
                        mod_base = OTHER
                        note = 2'-O-methylcytidine phosphorothioate
modified_base           10
                        mod_base = OTHER
                        note = 2'-O-methyluridine
modified_base           5
                        mod_base = OTHER
                        note = 2'-O-methylcytidine
modified_base           18
                        mod_base = OTHER
                        note = 2'-O-methyladenosine phosphorothioate
source                  1..19
                        mol_type = other RNA
                        organism = synthetic construct
modified_base           8
                        mod_base = OTHER
                        note = 2'-fluorouridine
modified_base           6
                        mod_base = OTHER
                        note = 2'-O-methylguanosine
modified_base           13
                        mod_base = OTHER
                        note = 2'-O-methyladenosine
modified_base           2
                        mod_base = OTHER
                        note = 2'-O-methylcytidine phosphorothioate
modified_base           16
                        mod_base = OTHER
                        note = 2'-O-methylcytidine
modified_base           19
                        mod_base = OTHER
```

```
                      note = 2'-O-methyladenosine
modified_base         7
                      mod_base = OTHER
                      note = 2'-fluorocytidine
modified_base         3
                      mod_base = OTHER
                      note = 2'-O-methylguanosine
modified_base         11
                      mod_base = OTHER
                      note = 2'-O-methylcytidine
modified_base         15
                      mod_base = OTHER
                      note = 2'-O-methylguanosine
SEQUENCE: 203
ccgacgctgt ctaggcaaa                                          19

SEQ ID NO: 204        moltype = RNA  length = 19
FEATURE               Location/Qualifiers
modified_base         17
                      mod_base = OTHER
                      note = 2'-O-methylcytidine phosphorothioate
modified_base         15
                      mod_base = OTHER
                      note = 2'-O-methyladenosine
modified_base         4
                      mod_base = OTHER
                      note = 2'-O-methylcytidine
modified_base         13
                      mod_base = OTHER
                      note = 2'-O-methylcytidine
modified_base         8
                      mod_base = OTHER
                      note = 2'-fluorocytidine
modified_base         9
                      mod_base = OTHER
                      note = 2'-fluorouridine
modified_base         6
                      mod_base = OTHER
                      note = 2'-O-methylguanosine
modified_base         10
                      mod_base = OTHER
                      note = 2'-O-methyladenosine
modified_base         14
                      mod_base = OTHER
                      note = 2'-O-methyladenosine
modified_base         1
                      mod_base = OTHER
                      note = 2'-O-methyladenosine phosphorothioate
modified_base         12
                      mod_base = OTHER
                      note = 2'-O-methylguanosine
modified_base         19
                      mod_base = OTHER
                      note = 2'-O-methyladenosine
modified_base         18
                      mod_base = OTHER
                      note = 2'-O-methylcytidine phosphorothioate
modified_base         2
                      mod_base = OTHER
                      note = 2'-O-methylcytidine phosphorothioate
source                1..19
                      mol_type = other RNA
                      organism = synthetic construct
modified_base         3
                      mod_base = OTHER
                      note = 2'-O-methylguanosine
modified_base         5
                      mod_base = OTHER
                      note = 2'-O-methyluridine
modified_base         7
                      mod_base = OTHER
                      note = 2'-fluorouridine
modified_base         16
                      mod_base = OTHER
                      note = 2'-O-methyladenosine
modified_base         11
                      mod_base = OTHER
                      note = 2'-O-methylguanosine
SEQUENCE: 204
```

```
acgctgtcta ggcaaacca                                       19

SEQ ID NO: 205          moltype = RNA  length = 19
FEATURE                 Location/Qualifiers
modified_base           12
                        mod_base = OTHER
                        note = 2'-O-methyladenosine
source                  1..19
                        mol_type = other RNA
                        organism = synthetic construct
modified_base           6
                        mod_base = OTHER
                        note = 2'-O-methyluridine
modified_base           13
                        mod_base = OTHER
                        note = 2'-O-methylguanosine
modified_base           1
                        mod_base = OTHER
                        note = 2'-O-methyladenosine phosphorothioate
modified_base           3
                        mod_base = OTHER
                        note = 2'-O-methyladenosine
modified_base           16
                        mod_base = OTHER
                        note = 2'-O-methyluridine
modified_base           14
                        mod_base = OTHER
                        note = 2'-O-methyladenosine
modified_base           11
                        mod_base = OTHER
                        note = 2'-O-methyluridine
modified_base           5
                        mod_base = OTHER
                        note = 2'-O-methylcytidine
modified_base           8
                        mod_base = OTHER
                        note = 2'-fluoroguanosine
modified_base           9
                        mod_base = OTHER
                        note = 2'-fluoroadenosine
modified_base           15
                        mod_base = OTHER
                        note = 2'-O-methylguanosine
modified_base           10
                        mod_base = OTHER
                        note = 2'-O-methyluridine
modified_base           2
                        mod_base = OTHER
                        note = 2'-O-methyladenosine phosphorothioate
modified_base           7
                        mod_base = OTHER
                        note = 2'-fluoroguanosine
modified_base           17
                        mod_base = OTHER
                        note = 2'-O-methyluridine phosphorothioate
modified_base           18
                        mod_base = OTHER
                        note = 2'-O-methyladenosine phosphorothioate
modified_base           19
                        mod_base = OTHER
                        note = 2'-O-methyladenosine
modified_base           4
                        mod_base = OTHER
                        note = 2'-O-methylcytidine
SEQUENCE: 205
aaacctggat tagagttaa                                       19

SEQ ID NO: 206          moltype = RNA  length = 19
FEATURE                 Location/Qualifiers
modified_base           15
                        mod_base = OTHER
                        note = 2'-O-methylguanosine
modified_base           7
                        mod_base = OTHER
                        note = 2'-fluoroguanosine
modified_base           4
                        mod_base = OTHER
                        note = 2'-O-methyluridine
modified_base           9
```

-continued

```
                            mod_base = OTHER
                            note = 2'-fluoroadenosine
modified_base               3
                            mod_base = OTHER
                            note = 2'-O-methyluridine
source                      1..19
                            mol_type = other RNA
                            organism = synthetic construct
modified_base               1
                            mod_base = OTHER
                            note = 2'-O-methylcytidine phosphorothioate
modified_base               17
                            mod_base = OTHER
                            note = 2'-O-methyluridine phosphorothioate
modified_base               10
                            mod_base = OTHER
                            note = 2'-O-methylguanosine
modified_base               13
                            mod_base = OTHER
                            note = 2'-O-methyluridine
modified_base               5
                            mod_base = OTHER
                            note = 2'-O-methylguanosine
modified_base               11
                            mod_base = OTHER
                            note = 2'-O-methylguanosine
modified_base               8
                            mod_base = OTHER
                            note = 2'-fluoroadenosine
modified_base               14
                            mod_base = OTHER
                            note = 2'-O-methylcytidine
modified_base               16
                            mod_base = OTHER
                            note = 2'-O-methylcytidine
modified_base               6
                            mod_base = OTHER
                            note = 2'-O-methyladenosine
modified_base               19
                            mod_base = OTHER
                            note = 2'-O-methyladenosine
modified_base               18
                            mod_base = OTHER
                            note = 2'-O-methyluridine phosphorothioate
modified_base               2
                            mod_base = OTHER
                            note = 2'-O-methyluridine phosphorothioate
modified_base               12
                            mod_base = OTHER
                            note = 2'-O-methyladenosine
SEQUENCE: 206
ctttgagaag gatcgctta                                                19

SEQ ID NO: 207              moltype = RNA  length = 19
FEATURE                     Location/Qualifiers
modified_base               2
                            mod_base = OTHER
                            note = 2'-O-methylcytidine phosphorothioate
modified_base               19
                            mod_base = OTHER
                            note = 2'-O-methyladenosine
modified_base               10
                            mod_base = OTHER
                            note = 2'-O-methylguanosine
modified_base               8
                            mod_base = OTHER
                            note = 2'-fluoroguanosine
modified_base               13
                            mod_base = OTHER
                            note = 2'-O-methylguanosine
modified_base               17
                            mod_base = OTHER
                            note = 2'-O-methyluridine phosphorothioate
modified_base               11
                            mod_base = OTHER
                            note = 2'-O-methylguanosine
modified_base               12
                            mod_base = OTHER
                            note = 2'-O-methylguanosine
```

modified_base 5
mod_base = OTHER
note = 2'-O-methylguanosine
modified_base 16
mod_base = OTHER
note = 2'-O-methylcytidine
modified_base 14
mod_base = OTHER
note = 2'-O-methyladenosine
modified_base 15
mod_base = OTHER
note = 2'-O-methyluridine
source 1..19
mol_type = other RNA
organism = synthetic construct
modified_base 9
mod_base = OTHER
note = 2'-fluoroadenosine
modified_base 7
mod_base = OTHER
note = 2'-fluoroadenosine
modified_base 3
mod_base = OTHER
note = 2'-O-methylcytidine
modified_base 6
mod_base = OTHER
note = 2'-O-methylcytidine
modified_base 18
mod_base = OTHER
note = 2'-O-methylcytidine phosphorothioate
modified_base 4
mod_base = OTHER
note = 2'-O-methylguanosine
modified_base 1
mod_base = OTHER
note = 2'-O-methylguanosine phosphorothioate
SEQUENCE: 207
gccggcagag ggatctca 19

SEQ ID NO: 208 moltype = RNA length = 19
FEATURE Location/Qualifiers
modified_base 8
mod_base = OTHER
note = 2'-fluoroguanosine
modified_base 14
mod_base = OTHER
note = 2'-O-methylcytidine
modified_base 7
mod_base = OTHER
note = 2'-fluoroadenosine
modified_base 2
mod_base = OTHER
note = 2'-O-methylguanosine phosphorothioate
modified_base 1
mod_base = OTHER
note = 2'-O-methylguanosine phosphorothioate
modified_base 18
mod_base = OTHER
note = 2'-O-methylcytidine phosphorothioate
modified_base 17
mod_base = OTHER
note = 2'-O-methylguanosine phosphorothioate
modified_base 19
mod_base = OTHER
note = 2'-O-methyladenosine
modified_base 3
mod_base = OTHER
note = 2'-O-methylguanosine
modified_base 11
mod_base = OTHER
note = 2'-O-methylguanosine
source 1..19
mol_type = other RNA
organism = synthetic construct
modified_base 6
mod_base = OTHER
note = 2'-O-methyladenosine
modified_base 13
mod_base = OTHER

```
                         note = 2'-O-methylguanosine
modified_base            5
                         mod_base = OTHER
                         note = 2'-O-methylcytidine
modified_base            15
                         mod_base = OTHER
                         note = 2'-O-methyluridine
modified_base            10
                         mod_base = OTHER
                         note = 2'-O-methylguanosine
modified_base            16
                         mod_base = OTHER
                         note = 2'-O-methyluridine
modified_base            12
                         mod_base = OTHER
                         note = 2'-O-methyluridine
modified_base            4
                         mod_base = OTHER
                         note = 2'-O-methylcytidine
modified_base            9
                         mod_base = OTHER
                         note = 2'-fluoroguanosine
SEQUENCE: 208
gggccaaggg gtgcttgca                                                19

SEQ ID NO: 209           moltype = RNA  length = 19
FEATURE                  Location/Qualifiers
modified_base            17
                         mod_base = OTHER
                         note = 2'-O-methylguanosine phosphorothioate
modified_base            16
                         mod_base = OTHER
                         note = 2'-O-methylcytidine
modified_base            2
                         mod_base = OTHER
                         note = 2'-O-methylcytidine phosphorothioate
modified_base            6
                         mod_base = OTHER
                         note = 2'-O-methylguanosine
modified_base            4
                         mod_base = OTHER
                         note = 2'-O-methyladenosine
modified_base            18
                         mod_base = OTHER
                         note = 2'-O-methylcytidine phosphorothioate
modified_base            1
                         mod_base = OTHER
                         note = 2'-O-methylguanosine phosphorothioate
modified_base            11
                         mod_base = OTHER
                         note = 2'-O-methylguanosine
modified_base            5
                         mod_base = OTHER
                         note = 2'-O-methyladenosine
source                   1..19
                         mol_type = other RNA
                         organism = synthetic construct
modified_base            12
                         mod_base = OTHER
                         note = 2'-O-methylcytidine
modified_base            13
                         mod_base = OTHER
                         note = 2'-O-methyluridine
modified_base            15
                         mod_base = OTHER
                         note = 2'-O-methylguanosine
modified_base            19
                         mod_base = OTHER
                         note = 2'-O-methyladenosine
modified_base            3
                         mod_base = OTHER
                         note = 2'-O-methylcytidine
modified_base            9
                         mod_base = OTHER
                         note = 2'-fluoroguanosine
modified_base            10
                         mod_base = OTHER
                         note = 2'-O-methyluridine
modified_base            14
```

```
                        mod_base = OTHER
                        note = 2'-O-methyluridine
modified_base           7
                        mod_base = OTHER
                        note = 2'-fluoroguanosine
modified_base           8
                        mod_base = OTHER
                        note = 2'-fluoroguanosine
SEQUENCE: 209
gccaaggggt gcttgcgca                                            19

SEQ ID NO: 210          moltype = RNA  length = 19
FEATURE                 Location/Qualifiers
modified_base           8
                        mod_base = OTHER
                        note = 2'-fluoroguanosine
modified_base           1
                        mod_base = OTHER
                        note = 2'-O-methyladenosine phosphorothioate
modified_base           15
                        mod_base = OTHER
                        note = 2'-O-methylguanosine
modified_base           4
                        mod_base = OTHER
                        note = 2'-O-methylcytidine
source                  1..19
                        mol_type = other RNA
                        organism = synthetic construct
modified_base           13
                        mod_base = OTHER
                        note = 2'-O-methylcytidine
modified_base           9
                        mod_base = OTHER
                        note = 2'-fluorocytidine
modified_base           2
                        mod_base = OTHER
                        note = 2'-O-methyluridine phosphorothioate
modified_base           3
                        mod_base = OTHER
                        note = 2'-O-methylguanosine
modified_base           16
                        mod_base = OTHER
                        note = 2'-O-methylguanosine
modified_base           10
                        mod_base = OTHER
                        note = 2'-O-methyladenosine
modified_base           19
                        mod_base = OTHER
                        note = 2'-O-methyladenosine
modified_base           18
                        mod_base = OTHER
                        note = 2'-O-methylguanosine phosphorothioate
modified_base           14
                        mod_base = OTHER
                        note = 2'-O-methylcytidine
modified_base           7
                        mod_base = OTHER
                        note = 2'-fluoroguanosine
modified_base           17
                        mod_base = OTHER
                        note = 2'-O-methylcytidine phosphorothioate
modified_base           6
                        mod_base = OTHER
                        note = 2'-O-methyladenosine
modified_base           11
                        mod_base = OTHER
                        note = 2'-O-methyluridine
modified_base           5
                        mod_base = OTHER
                        note = 2'-O-methyladenosine
modified_base           12
                        mod_base = OTHER
                        note = 2'-O-methylcytidine
SEQUENCE: 210
atgcaaggca tcccggcga                                            19

SEQ ID NO: 211          moltype = RNA  length = 21
FEATURE                 Location/Qualifiers
modified_base           6
```

```
                         mod_base = OTHER
                         note = 2'-fluoroguanosine
modified_base            14
                         mod_base = OTHER
                         note = 2'-fluoroguanosine
modified_base            9
                         mod_base = OTHER
                         note = 2'-O-methylcytidine
modified_base            11
                         mod_base = OTHER
                         note = 2'-O-methyladenosine
modified_base            13
                         mod_base = OTHER
                         note = 2'-O-methylguanosine
modified_base            4
                         mod_base = OTHER
                         note = 2'-O-methylcytidine
modified_base            19
                         mod_base = OTHER
                         note = 2'-O-methylguanosine phosphorothioate
modified_base            2
                         mod_base = OTHER
                         note = 2'-fluorouridine phosphorothioate
modified_base            8
                         mod_base = OTHER
                         note = 2'-O-methylcytidine
modified_base            5
                         mod_base = OTHER
                         note = 2'-O-methyluridine
modified_base            1
                         mod_base = OTHER
                         note = 2'-fluorouridine phosphorothioate
modified_base            21
                         mod_base = OTHER
                         note = 2'-O-methyluridine
modified_base            15
                         mod_base = OTHER
                         note = 2'-O-methyluridine
modified_base            7
                         mod_base = OTHER
                         note = 2'-O-methyluridine
modified_base            18
                         mod_base = OTHER
                         note = 2'-O-methylcytidine
modified_base            20
                         mod_base = OTHER
                         note = 2'-O-methyluridine phosphorothioate
modified_base            17
                         mod_base = OTHER
                         note = 2'-O-methyluridine
source                   1..21
                         mol_type = other RNA
                         organism = synthetic construct
modified_base            12
                         mod_base = OTHER
                         note = 2'-O-methylguanosine
modified_base            3
                         mod_base = OTHER
                         note = 2'-O-methylguanosine
modified_base            16
                         mod_base = OTHER
                         note = 2'-fluoroguanosine
modified_base            10
                         mod_base = OTHER
                         note = 2'-O-methylguanosine
SEQUENCE: 211
ttgctgtccg agggtgtcgt t                                            21

SEQ ID NO: 212           moltype = RNA  length = 21
FEATURE                  Location/Qualifiers
modified_base            11
                         mod_base = OTHER
                         note = 2'-O-methylcytidine
modified_base            19
                         mod_base = OTHER
                         note = 2'-O-methyluridine phosphorothioate
modified_base            18
                         mod_base = OTHER
                         note = 2'-O-methylguanosine
```

```
modified_base          5
                       mod_base = OTHER
                       note = 2'-O-methyladenosine
modified_base          21
                       mod_base = OTHER
                       note = 2'-O-methyluridine
modified_base          9
                       mod_base = OTHER
                       note = 2'-O-methyluridine
modified_base          7
                       mod_base = OTHER
                       note = 2'-O-methyluridine
modified_base          8
                       mod_base = OTHER
                       note = 2'-O-methylcytidine
modified_base          20
                       mod_base = OTHER
                       note = 2'-O-methyluridine phosphorothioate
modified_base          12
                       mod_base = OTHER
                       note = 2'-O-methylguanosine
modified_base          16
                       mod_base = OTHER
                       note = 2'-fluorocytidine
modified_base          4
                       mod_base = OTHER
                       note = 2'-O-methylguanosine
modified_base          15
                       mod_base = OTHER
                       note = 2'-O-methylguanosine
modified_base          13
                       mod_base = OTHER
                       note = 2'-O-methyluridine
source                 1..21
                       mol_type = other RNA
                       organism = synthetic construct
modified_base          17
                       mod_base = OTHER
                       note = 2'-O-methylcytidine
modified_base          14
                       mod_base = OTHER
                       note = 2'-fluorocytidine
modified_base          10
                       mod_base = OTHER
                       note = 2'-O-methylcytidine
modified_base          1
                       mod_base = OTHER
                       note = 2'-fluorouridine phosphorothioate
modified_base          6
                       mod_base = OTHER
                       note = 2'-fluoroguanosine
modified_base          3
                       mod_base = OTHER
                       note = 2'-O-methylcytidine
modified_base          2
                       mod_base = OTHER
                       note = 2'-fluoroadenosine phosphorothioate
SEQUENCE: 212
tacgagtctc cgtcgccgtt t                                            21

SEQ ID NO: 213         moltype = RNA  length = 21
FEATURE                Location/Qualifiers
modified_base          20
                       mod_base = OTHER
                       note = 2'-O-methyluridine phosphorothioate
modified_base          12
                       mod_base = OTHER
                       note = 2'-O-methylcytidine
modified_base          8
                       mod_base = OTHER
                       note = 2'-O-methyluridine
modified_base          21
                       mod_base = OTHER
                       note = 2'-O-methyluridine
modified_base          5
                       mod_base = OTHER
                       note = 2'-O-methylguanosine
modified_base          13
                       mod_base = OTHER
```

-continued

```
                        note = 2'-O-methylguanosine
modified_base           3
                        mod_base = OTHER
                        note = 2'-O-methyladenosine
modified_base           14
                        mod_base = OTHER
                        note = 2'-fluorouridine
modified_base           11
                        mod_base = OTHER
                        note = 2'-O-methylcytidine
modified_base           16
                        mod_base = OTHER
                        note = 2'-fluoroguanosine
modified_base           10
                        mod_base = OTHER
                        note = 2'-O-methyluridine
modified_base           19
                        mod_base = OTHER
                        note = 2'-O-methylguanosine phosphorothioate
modified_base           9
                        mod_base = OTHER
                        note = 2'-O-methylcytidine
modified_base           17
                        mod_base = OTHER
                        note = 2'-O-methylcytidine
modified_base           15
                        mod_base = OTHER
                        note = 2'-O-methylcytidine
modified_base           7
                        mod_base = OTHER
                        note = 2'-O-methylguanosine
modified_base           1
                        mod_base = OTHER
                        note = 2'-fluorouridine phosphorothioate
modified_base           4
                        mod_base = OTHER
                        note = 2'-O-methylcytidine
modified_base           2
                        mod_base = OTHER
                        note = 2'-fluoroadenosine phosphorothioate
modified_base           6
                        mod_base = OTHER
                        note = 2'-fluoroadenosine
modified_base           18
                        mod_base = OTHER
                        note = 2'-O-methylcytidine
source                  1..21
                        mol_type = other RNA
                        organism = synthetic construct
SEQUENCE: 213
taacgagtct ccgtcgccgt t                                              21

SEQ ID NO: 214          moltype = RNA  length = 21
FEATURE                 Location/Qualifiers
modified_base           11
                        mod_base = OTHER
                        note = 2'-O-methyluridine
modified_base           5
                        mod_base = OTHER
                        note = 2'-O-methylcytidine
modified_base           9
                        mod_base = OTHER
                        note = 2'-O-methyluridine
modified_base           16
                        mod_base = OTHER
                        note = 2'-fluorocytidine
modified_base           12
                        mod_base = OTHER
                        note = 2'-O-methylcytidine
modified_base           15
                        mod_base = OTHER
                        note = 2'-O-methyluridine
modified_base           6
                        mod_base = OTHER
                        note = 2'-fluoroguanosine
modified_base           19
                        mod_base = OTHER
                        note = 2'-O-methylcytidine phosphorothioate
modified_base           2
```

```
                         mod_base = OTHER
                         note = 2'-fluoroadenosine phosphorothioate
modified_base            3
                         mod_base = OTHER
                         note = 2'-O-methyladenosine
modified_base            10
                         mod_base = OTHER
                         note = 2'-O-methylcytidine
modified_base            13
                         mod_base = OTHER
                         note = 2'-O-methylcytidine
modified_base            21
                         mod_base = OTHER
                         note = 2'-O-methyluridine
modified_base            4
                         mod_base = OTHER
                         note = 2'-O-methyladenosine
modified_base            18
                         mod_base = OTHER
                         note = 2'-O-methylcytidine
modified_base            17
                         mod_base = OTHER
                         note = 2'-O-methylguanosine
modified_base            1
                         mod_base = OTHER
                         note = 2'-fluorouridine phosphorothioate
modified_base            14
                         mod_base = OTHER
                         note = 2'-fluoroguanosine
modified_base            20
                         mod_base = OTHER
                         note = 2'-O-methyluridine phosphorothioate
source                   1..21
                         mol_type = other RNA
                         organism = synthetic construct
modified_base            7
                         mod_base = OTHER
                         note = 2'-O-methyladenosine
modified_base            8
                         mod_base = OTHER
                         note = 2'-O-methylguanosine
SEQUENCE: 214
taaacgagtc tccgtcgcct t                                              21

SEQ ID NO: 215           moltype = RNA  length = 21
FEATURE                  Location/Qualifiers
modified_base            4
                         mod_base = OTHER
                         note = 2'-O-methyladenosine
modified_base            12
                         mod_base = OTHER
                         note = 2'-O-methyluridine
modified_base            5
                         mod_base = OTHER
                         note = 2'-O-methyladenosine
modified_base            7
                         mod_base = OTHER
                         note = 2'-O-methylguanosine
modified_base            11
                         mod_base = OTHER
                         note = 2'-O-methylcytidine
modified_base            20
                         mod_base = OTHER
                         note = 2'-O-methyluridine phosphorothioate
modified_base            9
                         mod_base = OTHER
                         note = 2'-O-methylguanosine
modified_base            1
                         mod_base = OTHER
                         note = 2'-fluorouridine phosphorothioate
modified_base            19
                         mod_base = OTHER
                         note = 2'-O-methylcytidine phosphorothioate
modified_base            13
                         mod_base = OTHER
                         note = 2'-O-methylcytidine
modified_base            3
                         mod_base = OTHER
                         note = 2'-O-methyladenosine
```

modified_base 21
mod_base = OTHER
note = 2'-O-methyluridine
modified_base 16
mod_base = OTHER
note = 2'-fluorouridine
modified_base 10
mod_base = OTHER
note = 2'-O-methyluridine
modified_base 8
mod_base = OTHER
note = 2'-O-methyladenosine
source 1..21
mol_type = other RNA
organism = synthetic construct
modified_base 15
mod_base = OTHER
note = 2'-O-methylguanosine
modified_base 17
mod_base = OTHER
note = 2'-O-methylcytidine
modified_base 6
mod_base = OTHER
note = 2'-fluorocytidine
modified_base 2
mod_base = OTHER
note = 2'-fluorocytidine phosphorothioate
modified_base 14
mod_base = OTHER
note = 2'-fluorocytidine
modified_base 18
mod_base = OTHER
note = 2'-O-methylguanosine
SEQUENCE: 215
tcaaacgagt ctccgtcgct t 21

SEQ ID NO: 216 moltype = RNA length = 21
FEATURE Location/Qualifiers
modified_base 3
mod_base = OTHER
note = 2'-O-methylcytidine
modified_base 19
mod_base = OTHER
note = 2'-O-methylguanosine phosphorothioate
modified_base 17
mod_base = OTHER
note = 2'-O-methyluridine
modified_base 10
mod_base = OTHER
note = 2'-O-methylguanosine
modified_base 2
mod_base = OTHER
note = 2'-fluorocytidine phosphorothioate
modified_base 4
mod_base = OTHER
note = 2'-O-methyladenosine
modified_base 13
mod_base = OTHER
note = 2'-O-methyluridine
modified_base 6
mod_base = OTHER
note = 2'-fluoroadenosine
modified_base 21
mod_base = OTHER
note = 2'-O-methyluridine
modified_base 15
mod_base = OTHER
note = 2'-O-methylcytidine
modified_base 8
mod_base = OTHER
note = 2'-O-methylguanosine
source 1..21
mol_type = other RNA
organism = synthetic construct
modified_base 11
mod_base = OTHER
note = 2'-O-methyluridine
modified_base 5
mod_base = OTHER

```
                        note = 2'-O-methyladenosine
modified_base           20
                        mod_base = OTHER
                        note = 2'-O-methyluridine phosphorothioate
modified_base           9
                        mod_base = OTHER
                        note = 2'-O-methyladenosine
modified_base           7
                        mod_base = OTHER
                        note = 2'-O-methylcytidine
modified_base           18
                        mod_base = OTHER
                        note = 2'-O-methylcytidine
modified_base           14
                        mod_base = OTHER
                        note = 2'-fluorocytidine
modified_base           16
                        mod_base = OTHER
                        note = 2'-fluoroguanosine
modified_base           1
                        mod_base = OTHER
                        note = 2'-fluorouridine phosphorothioate
modified_base           12
                        mod_base = OTHER
                        note = 2'-O-methylcytidine
SEQUENCE: 216
tccaaacgag tctccgtcgt t                                              21

SEQ ID NO: 217          moltype = RNA  length = 21
FEATURE                 Location/Qualifiers
modified_base           2
                        mod_base = OTHER
                        note = 2'-fluorouridine phosphorothioate
modified_base           8
                        mod_base = OTHER
                        note = 2'-O-methylcytidine
modified_base           4
                        mod_base = OTHER
                        note = 2'-O-methylcytidine
modified_base           17
                        mod_base = OTHER
                        note = 2'-O-methylguanosine
modified_base           11
                        mod_base = OTHER
                        note = 2'-O-methylguanosine
modified_base           16
                        mod_base = OTHER
                        note = 2'-fluorocytidine
modified_base           12
                        mod_base = OTHER
                        note = 2'-O-methyluridine
source                  1..21
                        mol_type = other RNA
                        organism = synthetic construct
modified_base           9
                        mod_base = OTHER
                        note = 2'-O-methylguanosine
modified_base           19
                        mod_base = OTHER
                        note = 2'-O-methylcytidine phosphorothioate
modified_base           6
                        mod_base = OTHER
                        note = 2'-fluoroadenosine
modified_base           3
                        mod_base = OTHER
                        note = 2'-O-methylcytidine
modified_base           5
                        mod_base = OTHER
                        note = 2'-O-methyladenosine
modified_base           1
                        mod_base = OTHER
                        note = 2'-fluorouridine phosphorothioate
modified_base           21
                        mod_base = OTHER
                        note = 2'-O-methyluridine
modified_base           13
                        mod_base = OTHER
                        note = 2'-O-methylcytidine
modified_base           7
```

```
                        mod_base = OTHER
                        note = 2'-O-methyladenosine
modified_base           14
                        mod_base = OTHER
                        note = 2'-fluorouridine
modified_base           10
                        mod_base = OTHER
                        note = 2'-O-methyladenosine
modified_base           18
                        mod_base = OTHER
                        note = 2'-O-methyluridine
modified_base           20
                        mod_base = OTHER
                        note = 2'-O-methyluridine phosphorothioate
modified_base           15
                        mod_base = OTHER
                        note = 2'-O-methylcytidine
SEQUENCE: 217
ttccaaacga gtctccgtct t                                                21

SEQ ID NO: 218          moltype = RNA  length = 21
FEATURE                 Location/Qualifiers
modified_base           5
                        mod_base = OTHER
                        note = 2'-O-methylcytidine
modified_base           10
                        mod_base = OTHER
                        note = 2'-O-methylguanosine
modified_base           4
                        mod_base = OTHER
                        note = 2'-O-methylcytidine
modified_base           9
                        mod_base = OTHER
                        note = 2'-O-methylcytidine
modified_base           12
                        mod_base = OTHER
                        note = 2'-O-methylguanosine
modified_base           19
                        mod_base = OTHER
                        note = 2'-O-methyluridine phosphorothioate
modified_base           15
                        mod_base = OTHER
                        note = 2'-O-methyluridine
modified_base           11
                        mod_base = OTHER
                        note = 2'-O-methyladenosine
modified_base           6
                        mod_base = OTHER
                        note = 2'-fluoroadenosine
modified_base           17
                        mod_base = OTHER
                        note = 2'-O-methylcytidine
modified_base           18
                        mod_base = OTHER
                        note = 2'-O-methylguanosine
modified_base           7
                        mod_base = OTHER
                        note = 2'-O-methyladenosine
modified_base           14
                        mod_base = OTHER
                        note = 2'-fluorocytidine
modified_base           21
                        mod_base = OTHER
                        note = 2'-O-methyluridine
modified_base           2
                        mod_base = OTHER
                        note = 2'-fluoroguanosine phosphorothioate
modified_base           8
                        mod_base = OTHER
                        note = 2'-O-methyladenosine
modified_base           3
                        mod_base = OTHER
                        note = 2'-O-methyluridine
modified_base           16
                        mod_base = OTHER
                        note = 2'-fluorocytidine
modified_base           13
                        mod_base = OTHER
                        note = 2'-O-methyluridine
```

```
source                  1..21
                        mol_type = other RNA
                        organism = synthetic construct
modified_base           1
                        mod_base = OTHER
                        note = 2'-fluorouridine phosphorothioate
modified_base           20
                        mod_base = OTHER
                        note = 2'-O-methyluridine phosphorothioate
SEQUENCE: 218
tgtccaaacg agtctccgtt t                                            21

SEQ ID NO: 219          moltype = RNA  length = 21
FEATURE                 Location/Qualifiers
modified_base           21
                        mod_base = OTHER
                        note = 2'-O-methyluridine
modified_base           8
                        mod_base = OTHER
                        note = 2'-O-methylguanosine
modified_base           18
                        mod_base = OTHER
                        note = 2'-O-methylcytidine
modified_base           4
                        mod_base = OTHER
                        note = 2'-O-methylcytidine
modified_base           13
                        mod_base = OTHER
                        note = 2'-O-methylguanosine
modified_base           17
                        mod_base = OTHER
                        note = 2'-O-methyluridine
modified_base           10
                        mod_base = OTHER
                        note = 2'-O-methylcytidine
modified_base           11
                        mod_base = OTHER
                        note = 2'-O-methyluridine
modified_base           5
                        mod_base = OTHER
                        note = 2'-O-methyluridine
modified_base           9
                        mod_base = OTHER
                        note = 2'-O-methylguanosine
modified_base           12
                        mod_base = OTHER
                        note = 2'-O-methylcytidine
source                  1..21
                        mol_type = other RNA
                        organism = synthetic construct
modified_base           14
                        mod_base = OTHER
                        note = 2'-fluoroguanosine
modified_base           7
                        mod_base = OTHER
                        note = 2'-O-methyluridine
modified_base           19
                        mod_base = OTHER
                        note = 2'-O-methylcytidine phosphorothioate
modified_base           15
                        mod_base = OTHER
                        note = 2'-O-methylguanosine
modified_base           1
                        mod_base = OTHER
                        note = 2'-fluorouridine phosphorothioate
modified_base           3
                        mod_base = OTHER
                        note = 2'-O-methylguanosine
modified_base           16
                        mod_base = OTHER
                        note = 2'-fluoroguanosine
modified_base           6
                        mod_base = OTHER
                        note = 2'-fluorouridine
modified_base           20
                        mod_base = OTHER
                        note = 2'-O-methyluridine phosphorothioate
modified_base           2
                        mod_base = OTHER
```

-continued

```
                         note = 2'-fluorocytidine phosphorothioate
SEQUENCE: 219
tcgctttggc tcggggtcct t                                          21

SEQ ID NO: 220           moltype = RNA  length = 21
FEATURE                  Location/Qualifiers
modified_base            14
                         mod_base = OTHER
                         note = 2'-fluoroguanosine
modified_base            12
                         mod_base = OTHER
                         note = 2'-O-methyluridine
modified_base            21
                         mod_base = OTHER
                         note = 2'-O-methyluridine
modified_base            2
                         mod_base = OTHER
                         note = 2'-fluorouridine phosphorothioate
modified_base            4
                         mod_base = OTHER
                         note = 2'-O-methylguanosine
modified_base            1
                         mod_base = OTHER
                         note = 2'-fluorouridine phosphorothioate
modified_base            3
                         mod_base = OTHER
                         note = 2'-O-methylcytidine
modified_base            18
                         mod_base = OTHER
                         note = 2'-O-methyluridine
modified_base            20
                         mod_base = OTHER
                         note = 2'-O-methyluridine phosphorothioate
modified_base            16
                         mod_base = OTHER
                         note = 2'-fluoroguanosine
modified_base            15
                         mod_base = OTHER
                         note = 2'-O-methylguanosine
modified_base            19
                         mod_base = OTHER
                         note = 2'-O-methylcytidine phosphorothioate
modified_base            10
                         mod_base = OTHER
                         note = 2'-O-methylguanosine
modified_base            13
                         mod_base = OTHER
                         note = 2'-O-methylcytidine
modified_base            6
                         mod_base = OTHER
                         note = 2'-fluorouridine
modified_base            9
                         mod_base = OTHER
                         note = 2'-O-methylguanosine
source                   1..21
                         mol_type = other RNA
                         organism = synthetic construct
modified_base            11
                         mod_base = OTHER
                         note = 2'-O-methylcytidine
modified_base            7
                         mod_base = OTHER
                         note = 2'-O-methyluridine
modified_base            17
                         mod_base = OTHER
                         note = 2'-O-methylguanosine
modified_base            8
                         mod_base = OTHER
                         note = 2'-O-methyluridine
modified_base            5
                         mod_base = OTHER
                         note = 2'-O-methylcytidine
SEQUENCE: 220
ttcgctttgg ctcggggtct t                                          21

SEQ ID NO: 221           moltype = RNA  length = 21
FEATURE                  Location/Qualifiers
modified_base            19
                         mod_base = OTHER
```

```
                        note = 2'-O-methyluridine phosphorothioate
modified_base           7
                        mod_base = OTHER
                        note = 2'-O-methyluridine
modified_base           2
                        mod_base = OTHER
                        note = 2'-fluorocytidine phosphorothioate
modified_base           4
                        mod_base = OTHER
                        note = 2'-O-methylcytidine
modified_base           15
                        mod_base = OTHER
                        note = 2'-O-methylguanosine
modified_base           5
                        mod_base = OTHER
                        note = 2'-O-methylguanosine
modified_base           1
                        mod_base = OTHER
                        note = 2'-fluorouridine phosphorothioate
modified_base           3
                        mod_base = OTHER
                        note = 2'-O-methyluridine
modified_base           18
                        mod_base = OTHER
                        note = 2'-O-methylguanosine
modified_base           20
                        mod_base = OTHER
                        note = 2'-O-methyluridine phosphorothioate
modified_base           13
                        mod_base = OTHER
                        note = 2'-O-methyluridine
modified_base           9
                        mod_base = OTHER
                        note = 2'-O-methyluridine
modified_base           10
                        mod_base = OTHER
                        note = 2'-O-methylguanosine
modified_base           6
                        mod_base = OTHER
                        note = 2'-fluorocytidine
modified_base           14
                        mod_base = OTHER
                        note = 2'-fluorocytidine
source                  1..21
                        mol_type = other RNA
                        organism = synthetic construct
modified_base           12
                        mod_base = OTHER
                        note = 2'-O-methylcytidine
modified_base           21
                        mod_base = OTHER
                        note = 2'-O-methyluridine
modified_base           17
                        mod_base = OTHER
                        note = 2'-O-methylguanosine
modified_base           16
                        mod_base = OTHER
                        note = 2'-fluoroguanosine
modified_base           8
                        mod_base = OTHER
                        note = 2'-O-methyluridine
modified_base           11
                        mod_base = OTHER
                        note = 2'-O-methylguanosine
SEQUENCE: 221
tctcgctttg gctcggggtt t                                          21

SEQ ID NO: 222          moltype = RNA  length = 21
FEATURE                 Location/Qualifiers
modified_base           21
                        mod_base = OTHER
                        note = 2'-O-methyluridine
modified_base           2
                        mod_base = OTHER
                        note = 2'-fluorouridine phosphorothioate
modified_base           6
                        mod_base = OTHER
                        note = 2'-fluoroadenosine
modified_base           1
```

```
                          mod_base = OTHER
                          note = 2'-fluorouridine phosphorothioate
modified_base             5
                          mod_base = OTHER
                          note = 2'-O-methyladenosine
modified_base             20
                          mod_base = OTHER
                          note = 2'-O-methyluridine phosphorothioate
modified_base             14
                          mod_base = OTHER
                          note = 2'-fluorocytidine
modified_base             17
                          mod_base = OTHER
                          note = 2'-O-methyladenosine
modified_base             15
                          mod_base = OTHER
                          note = 2'-O-methylguanosine
modified_base             8
                          mod_base = OTHER
                          note = 2'-O-methylcytidine
modified_base             16
                          mod_base = OTHER
                          note = 2'-fluorocytidine
modified_base             12
                          mod_base = OTHER
                          note = 2'-O-methylcytidine
modified_base             7
                          mod_base = OTHER
                          note = 2'-O-methylguanosine
modified_base             3
                          mod_base = OTHER
                          note = 2'-O-methylcytidine
modified_base             10
                          mod_base = OTHER
                          note = 2'-O-methylguanosine
modified_base             4
                          mod_base = OTHER
                          note = 2'-O-methyladenosine
source                    1..21
                          mol_type = other RNA
                          organism = synthetic construct
modified_base             13
                          mod_base = OTHER
                          note = 2'-O-methyluridine
modified_base             18
                          mod_base = OTHER
                          note = 2'-O-methylguanosine
modified_base             9
                          mod_base = OTHER
                          note = 2'-O-methyladenosine
modified_base             19
                          mod_base = OTHER
                          note = 2'-O-methylguanosine phosphorothioate
modified_base             11
                          mod_base = OTHER
                          note = 2'-O-methylguanosine
SEQUENCE: 222
ttcaaagcag gctcgcaggt t                                              21

SEQ ID NO: 223            moltype = RNA  length = 21
FEATURE                   Location/Qualifiers
modified_base             2
                          mod_base = OTHER
                          note = 2'-fluorocytidine phosphorothioate
modified_base             19
                          mod_base = OTHER
                          note = 2'-O-methylcytidine phosphorothioate
modified_base             16
                          mod_base = OTHER
                          note = 2'-fluorouridine
modified_base             6
                          mod_base = OTHER
                          note = 2'-fluorocytidine
modified_base             8
                          mod_base = OTHER
                          note = 2'-O-methyladenosine
modified_base             3
                          mod_base = OTHER
                          note = 2'-O-methylguanosine
```

```
modified_base          5
                       mod_base = OTHER
                       note = 2'-O-methyluridine
modified_base          18
                       mod_base = OTHER
                       note = 2'-O-methylguanosine
modified_base          11
                       mod_base = OTHER
                       note = 2'-O-methylcytidine
modified_base          14
                       mod_base = OTHER
                       note = 2'-fluoroguanosine
modified_base          7
                       mod_base = OTHER
                       note = 2'-O-methyladenosine
modified_base          1
                       mod_base = OTHER
                       note = 2'-fluorouridine phosphorothioate
modified_base          9
                       mod_base = OTHER
                       note = 2'-O-methyladenosine
source                 1..21
                       mol_type = other RNA
                       organism = synthetic construct
modified_base          12
                       mod_base = OTHER
                       note = 2'-O-methyladenosine
modified_base          20
                       mod_base = OTHER
                       note = 2'-O-methyluridine phosphorothioate
modified_base          13
                       mod_base = OTHER
                       note = 2'-O-methylguanosine
modified_base          17
                       mod_base = OTHER
                       note = 2'-O-methylcytidine
modified_base          21
                       mod_base = OTHER
                       note = 2'-O-methyluridine
modified_base          10
                       mod_base = OTHER
                       note = 2'-O-methylguanosine
modified_base          4
                       mod_base = OTHER
                       note = 2'-O-methylcytidine
modified_base          15
                       mod_base = OTHER
                       note = 2'-O-methylcytidine
SEQUENCE: 223
tcgctcaaag caggctcgct t                                               21

SEQ ID NO: 224         moltype = RNA  length = 21
FEATURE                Location/Qualifiers
modified_base          2
                       mod_base = OTHER
                       note = 2'-fluoroguanosine phosphorothioate
modified_base          20
                       mod_base = OTHER
                       note = 2'-O-methyluridine phosphorothioate
modified_base          11
                       mod_base = OTHER
                       note = 2'-O-methyluridine
modified_base          21
                       mod_base = OTHER
                       note = 2'-O-methyluridine
modified_base          5
                       mod_base = OTHER
                       note = 2'-O-methylguanosine
modified_base          4
                       mod_base = OTHER
                       note = 2'-O-methylcytidine
modified_base          12
                       mod_base = OTHER
                       note = 2'-O-methylguanosine
modified_base          8
                       mod_base = OTHER
                       note = 2'-O-methylcytidine
modified_base          6
                       mod_base = OTHER
```

```
                        note = 2'-fluorouridine
modified_base           7
                        mod_base = OTHER
                        note = 2'-O-methyluridine
modified_base           1
                        mod_base = OTHER
                        note = 2'-fluorouridine phosphorothioate
modified_base           16
                        mod_base = OTHER
                        note = 2'-fluoroguanosine
modified_base           9
                        mod_base = OTHER
                        note = 2'-O-methyluridine
modified_base           13
                        mod_base = OTHER
                        note = 2'-O-methylguanosine
modified_base           10
                        mod_base = OTHER
                        note = 2'-O-methylcytidine
modified_base           14
                        mod_base = OTHER
                        note = 2'-fluorouridine
modified_base           17
                        mod_base = OTHER
                        note = 2'-O-methylcytidine
modified_base           19
                        mod_base = OTHER
                        note = 2'-O-methyladenosine phosphorothioate
modified_base           15
                        mod_base = OTHER
                        note = 2'-O-methylguanosine
modified_base           3
                        mod_base = OTHER
                        note = 2'-O-methylcytidine
source                  1..21
                        mol_type = other RNA
                        organism = synthetic construct
modified_base           18
                        mod_base = OTHER
                        note = 2'-O-methylguanosine
SEQUENCE: 224
tgccgttctc tggtggcgat t                                              21

SEQ ID NO: 225          moltype = RNA  length = 21
FEATURE                 Location/Qualifiers
modified_base           18
                        mod_base = OTHER
                        note = 2'-O-methyluridine
modified_base           10
                        mod_base = OTHER
                        note = 2'-O-methylcytidine
modified_base           8
                        mod_base = OTHER
                        note = 2'-O-methylguanosine
modified_base           4
                        mod_base = OTHER
                        note = 2'-O-methylguanosine
modified_base           1
                        mod_base = OTHER
                        note = 2'-fluorouridine phosphorothioate
modified_base           14
                        mod_base = OTHER
                        note = 2'-fluoroguanosine
modified_base           3
                        mod_base = OTHER
                        note = 2'-O-methylguanosine
source                  1..21
                        mol_type = other RNA
                        organism = synthetic construct
modified_base           7
                        mod_base = OTHER
                        note = 2'-O-methyluridine
modified_base           19
                        mod_base = OTHER
                        note = 2'-O-methylguanosine phosphorothioate
modified_base           5
                        mod_base = OTHER
                        note = 2'-O-methyladenosine
modified_base           12
```

-continued

```
                          mod_base = OTHER
                          note = 2'-O-methyladenosine
modified_base             16
                          mod_base = OTHER
                          note = 2'-fluorocytidine
modified_base             6
                          mod_base = OTHER
                          note = 2'-fluoroadenosine
modified_base             11
                          mod_base = OTHER
                          note = 2'-O-methylguanosine
modified_base             13
                          mod_base = OTHER
                          note = 2'-O-methyluridine
modified_base             9
                          mod_base = OTHER
                          note = 2'-O-methylcytidine
modified_base             15
                          mod_base = OTHER
                          note = 2'-O-methylguanosine
modified_base             20
                          mod_base = OTHER
                          note = 2'-O-methyluridine phosphorothioate
modified_base             2
                          mod_base = OTHER
                          note = 2'-fluorocytidine phosphorothioate
modified_base             21
                          mod_base = OTHER
                          note = 2'-O-methyluridine
modified_base             17
                          mod_base = OTHER
                          note = 2'-O-methylcytidine
SEQUENCE: 225
tcggaatgcc gatggcctgt t                                        21

SEQ ID NO: 226            moltype = RNA  length = 21
FEATURE                   Location/Qualifiers
modified_base             6
                          mod_base = OTHER
                          note = 2'-fluoroguanosine
modified_base             12
                          mod_base = OTHER
                          note = 2'-O-methylcytidine
modified_base             9
                          mod_base = OTHER
                          note = 2'-O-methyluridine
modified_base             2
                          mod_base = OTHER
                          note = 2'-fluorouridine phosphorothioate
modified_base             17
                          mod_base = OTHER
                          note = 2'-O-methylguanosine
modified_base             7
                          mod_base = OTHER
                          note = 2'-O-methyladenosine
modified_base             16
                          mod_base = OTHER
                          note = 2'-fluoroguanosine
modified_base             10
                          mod_base = OTHER
                          note = 2'-O-methylguanosine
modified_base             5
                          mod_base = OTHER
                          note = 2'-O-methylguanosine
modified_base             8
                          mod_base = OTHER
                          note = 2'-O-methyladenosine
modified_base             4
                          mod_base = OTHER
                          note = 2'-O-methylcytidine
modified_base             1
                          mod_base = OTHER
                          note = 2'-fluorouridine phosphorothioate
modified_base             18
                          mod_base = OTHER
                          note = 2'-O-methylcytidine
modified_base             13
                          mod_base = OTHER
                          note = 2'-O-methylguanosine
```

```
source                  1..21
                        mol_type = other RNA
                        organism = synthetic construct
modified_base           11
                        mod_base = OTHER
                        note = 2'-O-methylcytidine
modified_base           20
                        mod_base = OTHER
                        note = 2'-O-methyluridine phosphorothioate
modified_base           19
                        mod_base = OTHER
                        note = 2'-O-methylcytidine phosphorothioate
modified_base           3
                        mod_base = OTHER
                        note = 2'-O-methylcytidine
modified_base           15
                        mod_base = OTHER
                        note = 2'-O-methyluridine
modified_base           21
                        mod_base = OTHER
                        note = 2'-O-methyluridine
modified_base           14
                        mod_base = OTHER
                        note = 2'-fluoroadenosine
SEQUENCE: 226
ttccggaatg ccgatggcct t                                              21

SEQ ID NO: 227          moltype = RNA  length = 21
FEATURE                 Location/Qualifiers
modified_base           3
                        mod_base = OTHER
                        note = 2'-O-methyluridine
modified_base           19
                        mod_base = OTHER
                        note = 2'-O-methylcytidine phosphorothioate
modified_base           13
                        mod_base = OTHER
                        note = 2'-O-methylcytidine
modified_base           16
                        mod_base = OTHER
                        note = 2'-fluorouridine
modified_base           18
                        mod_base = OTHER
                        note = 2'-O-methylguanosine
modified_base           5
                        mod_base = OTHER
                        note = 2'-O-methylcytidine
modified_base           14
                        mod_base = OTHER
                        note = 2'-fluoroguanosine
modified_base           7
                        mod_base = OTHER
                        note = 2'-O-methylguanosine
modified_base           2
                        mod_base = OTHER
                        note = 2'-fluorocytidine phosphorothioate
modified_base           12
                        mod_base = OTHER
                        note = 2'-O-methylcytidine
modified_base           8
                        mod_base = OTHER
                        note = 2'-O-methyladenosine
modified_base           15
                        mod_base = OTHER
                        note = 2'-O-methyladenosine
modified_base           1
                        mod_base = OTHER
                        note = 2'-fluorouridine phosphorothioate
source                  1..21
                        mol_type = other RNA
                        organism = synthetic construct
modified_base           10
                        mod_base = OTHER
                        note = 2'-O-methyluridine
modified_base           17
                        mod_base = OTHER
                        note = 2'-O-methylguanosine
modified_base           9
                        mod_base = OTHER
```

```
                        note = 2'-O-methyladenosine
modified_base           6
                        mod_base = OTHER
                        note = 2'-fluoroguanosine
modified_base           11
                        mod_base = OTHER
                        note = 2'-O-methylguanosine
modified_base           20
                        mod_base = OTHER
                        note = 2'-O-methyluridine phosphorothioate
modified_base           21
                        mod_base = OTHER
                        note = 2'-O-methyluridine
modified_base           4
                        mod_base = OTHER
                        note = 2'-O-methylcytidine
SEQUENCE: 227
tctccggaat gccgatggct t                                              21

SEQ ID NO: 228          moltype = RNA  length = 21
FEATURE                 Location/Qualifiers
modified_base           15
                        mod_base = OTHER
                        note = 2'-O-methylguanosine
modified_base           10
                        mod_base = OTHER
                        note = 2'-O-methylcytidine
modified_base           21
                        mod_base = OTHER
                        note = 2'-O-methyluridine
modified_base           9
                        mod_base = OTHER
                        note = 2'-O-methylcytidine
modified_base           1
                        mod_base = OTHER
                        note = 2'-fluorouridine phosphorothioate
modified_base           6
                        mod_base = OTHER
                        note = 2'-fluoroadenosine
modified_base           3
                        mod_base = OTHER
                        note = 2'-O-methylguanosine
modified_base           19
                        mod_base = OTHER
                        note = 2'-O-methylcytidine phosphorothioate
modified_base           16
                        mod_base = OTHER
                        note = 2'-fluoroguanosine
modified_base           13
                        mod_base = OTHER
                        note = 2'-O-methylcytidine
modified_base           5
                        mod_base = OTHER
                        note = 2'-O-methylguanosine
modified_base           7
                        mod_base = OTHER
                        note = 2'-O-methyluridine
modified_base           4
                        mod_base = OTHER
                        note = 2'-O-methyladenosine
modified_base           20
                        mod_base = OTHER
                        note = 2'-O-methyluridine phosphorothioate
source                  1..21
                        mol_type = other RNA
                        organism = synthetic construct
modified_base           14
                        mod_base = OTHER
                        note = 2'-fluorocytidine
modified_base           17
                        mod_base = OTHER
                        note = 2'-O-methyluridine
modified_base           11
                        mod_base = OTHER
                        note = 2'-O-methylcytidine
modified_base           8
                        mod_base = OTHER
                        note = 2'-O-methyluridine
modified_base           12
```

```
                        mod_base = OTHER
                        note = 2'-O-methylguanosine
modified_base           2
                        mod_base = OTHER
                        note = 2'-fluorocytidine phosphorothioate
modified_base           18
                        mod_base = OTHER
                        note = 2'-O-methylguanosine
SEQUENCE: 228
tcgagattcc cgccggtgct t                                              21

SEQ ID NO: 229          moltype = RNA  length = 21
FEATURE                 Location/Qualifiers
modified_base           21
                        mod_base = OTHER
                        note = 2'-O-methyluridine
modified_base           1
                        mod_base = OTHER
                        note = 2'-fluorouridine phosphorothioate
modified_base           13
                        mod_base = OTHER
                        note = 2'-O-methylguanosine
modified_base           5
                        mod_base = OTHER
                        note = 2'-O-methyladenosine
modified_base           18
                        mod_base = OTHER
                        note = 2'-O-methyluridine
modified_base           15
                        mod_base = OTHER
                        note = 2'-O-methylcytidine
modified_base           20
                        mod_base = OTHER
                        note = 2'-O-methyluridine phosphorothioate
source                  1..21
                        mol_type = other RNA
                        organism = synthetic construct
modified_base           2
                        mod_base = OTHER
                        note = 2'-fluorocytidine phosphorothioate
modified_base           3
                        mod_base = OTHER
                        note = 2'-O-methylcytidine
modified_base           7
                        mod_base = OTHER
                        note = 2'-O-methyladenosine
modified_base           14
                        mod_base = OTHER
                        note = 2'-fluorocytidine
modified_base           19
                        mod_base = OTHER
                        note = 2'-O-methylguanosine phosphorothioate
modified_base           11
                        mod_base = OTHER
                        note = 2'-O-methylcytidine
modified_base           17
                        mod_base = OTHER
                        note = 2'-O-methylguanosine
modified_base           4
                        mod_base = OTHER
                        note = 2'-O-methylguanosine
modified_base           6
                        mod_base = OTHER
                        note = 2'-fluoroguanosine
modified_base           8
                        mod_base = OTHER
                        note = 2'-O-methyluridine
modified_base           10
                        mod_base = OTHER
                        note = 2'-O-methylcytidine
modified_base           9
                        mod_base = OTHER
                        note = 2'-O-methyluridine
modified_base           12
                        mod_base = OTHER
                        note = 2'-O-methylcytidine
modified_base           16
                        mod_base = OTHER
                        note = 2'-fluoroguanosine
```

```
SEQUENCE: 229
tccgagattc ccgccggtgt t                                        21

SEQ ID NO: 230          moltype = RNA  length = 21
FEATURE                 Location/Qualifiers
modified_base           2
                        mod_base = OTHER
                        note = 2'-fluorocytidine phosphorothioate
modified_base           3
                        mod_base = OTHER
                        note = 2'-O-methyluridine
modified_base           20
                        mod_base = OTHER
                        note = 2'-O-methyluridine phosphorothioate
modified_base           18
                        mod_base = OTHER
                        note = 2'-O-methylguanosine
modified_base           11
                        mod_base = OTHER
                        note = 2'-O-methylguanosine
modified_base           4
                        mod_base = OTHER
                        note = 2'-O-methyluridine
modified_base           6
                        mod_base = OTHER
                        note = 2'-fluorocytidine
modified_base           9
                        mod_base = OTHER
                        note = 2'-O-methylcytidine
modified_base           8
                        mod_base = OTHER
                        note = 2'-O-methylcytidine
modified_base           19
                        mod_base = OTHER
                        note = 2'-O-methylguanosine phosphorothioate
modified_base           13
                        mod_base = OTHER
                        note = 2'-O-methylcytidine
modified_base           5
                        mod_base = OTHER
                        note = 2'-O-methyluridine
modified_base           15
                        mod_base = OTHER
                        note = 2'-O-methyluridine
modified_base           14
                        mod_base = OTHER
                        note = 2'-fluorouridine
modified_base           7
                        mod_base = OTHER
                        note = 2'-O-methylguanosine
source                  1..21
                        mol_type = other RNA
                        organism = synthetic construct
modified_base           21
                        mod_base = OTHER
                        note = 2'-O-methyluridine
modified_base           17
                        mod_base = OTHER
                        note = 2'-O-methyluridine
modified_base           16
                        mod_base = OTHER
                        note = 2'-fluorocytidine
modified_base           1
                        mod_base = OTHER
                        note = 2'-fluorouridine phosphorothioate
modified_base           10
                        mod_base = OTHER
                        note = 2'-O-methylguanosine
modified_base           12
                        mod_base = OTHER
                        note = 2'-O-methylcytidine
SEQUENCE: 230
tctttcgccg gccttctggt t                                        21

SEQ ID NO: 231          moltype = RNA  length = 21
FEATURE                 Location/Qualifiers
modified_base           20
                        mod_base = OTHER
                        note = 2'-O-methyluridine phosphorothioate
```

```
modified_base          6
                       mod_base = OTHER
                       note = 2'-fluorouridine
modified_base          17
                       mod_base = OTHER
                       note = 2'-O-methyluridine
modified_base          11
                       mod_base = OTHER
                       note = 2'-O-methylcytidine
modified_base          12
                       mod_base = OTHER
                       note = 2'-O-methylguanosine
modified_base          9
                       mod_base = OTHER
                       note = 2'-O-methylguanosine
modified_base          7
                       mod_base = OTHER
                       note = 2'-O-methyluridine
modified_base          8
                       mod_base = OTHER
                       note = 2'-O-methylcytidine
modified_base          18
                       mod_base = OTHER
                       note = 2'-O-methylcytidine
modified_base          4
                       mod_base = OTHER
                       note = 2'-O-methylcytidine
modified_base          14
                       mod_base = OTHER
                       note = 2'-fluorocytidine
modified_base          2
                       mod_base = OTHER
                       note = 2'-fluorocytidine phosphorothioate
modified_base          3
                       mod_base = OTHER
                       note = 2'-O-methylguanosine
modified_base          5
                       mod_base = OTHER
                       note = 2'-O-methyluridine
modified_base          15
                       mod_base = OTHER
                       note = 2'-O-methylcytidine
modified_base          10
                       mod_base = OTHER
                       note = 2'-O-methylcytidine
modified_base          19
                       mod_base = OTHER
                       note = 2'-O-methyluridine phosphorothioate
modified_base          21
                       mod_base = OTHER
                       note = 2'-O-methyluridine
source                 1..21
                       mol_type = other RNA
                       organism = synthetic construct
modified_base          13
                       mod_base = OTHER
                       note = 2'-O-methylguanosine
modified_base          1
                       mod_base = OTHER
                       note = 2'-fluorouridine phosphorothioate
modified_base          16
                       mod_base = OTHER
                       note = 2'-fluorouridine
SEQUENCE: 231
tcgctttcgc cggccttctt t                                            21

SEQ ID NO: 232         moltype = RNA  length = 21
FEATURE                Location/Qualifiers
modified_base          8
                       mod_base = OTHER
                       note = 2'-O-methyluridine
modified_base          11
                       mod_base = OTHER
                       note = 2'-O-methylcytidine
modified_base          10
                       mod_base = OTHER
                       note = 2'-O-methylguanosine
modified_base          16
                       mod_base = OTHER
```

```
                        note = 2'-fluorocytidine
modified_base           14
                        mod_base = OTHER
                        note = 2'-fluoroguanosine
modified_base           7
                        mod_base = OTHER
                        note = 2'-O-methyluridine
modified_base           2
                        mod_base = OTHER
                        note = 2'-fluorocytidine phosphorothioate
modified_base           13
                        mod_base = OTHER
                        note = 2'-O-methylguanosine
modified_base           5
                        mod_base = OTHER
                        note = 2'-O-methylcytidine
modified_base           20
                        mod_base = OTHER
                        note = 2'-O-methyluridine phosphorothioate
modified_base           21
                        mod_base = OTHER
                        note = 2'-O-methyluridine
modified_base           4
                        mod_base = OTHER
                        note = 2'-O-methylguanosine
modified_base           18
                        mod_base = OTHER
                        note = 2'-O-methyluridine
modified_base           12
                        mod_base = OTHER
                        note = 2'-O-methylcytidine
modified_base           3
                        mod_base = OTHER
                        note = 2'-O-methylcytidine
source                  1..21
                        mol_type = other RNA
                        organism = synthetic construct
modified_base           17
                        mod_base = OTHER
                        note = 2'-O-methyluridine
modified_base           15
                        mod_base = OTHER
                        note = 2'-O-methylcytidine
modified_base           1
                        mod_base = OTHER
                        note = 2'-fluorouridine phosphorothioate
modified_base           19
                        mod_base = OTHER
                        note = 2'-O-methylcytidine phosphorothioate
modified_base           6
                        mod_base = OTHER
                        note = 2'-fluorouridine
modified_base           9
                        mod_base = OTHER
                        note = 2'-O-methylcytidine
SEQUENCE: 232
tccgctttcg ccggccttct t                                              21

SEQ ID NO: 233          moltype = RNA  length = 21
FEATURE                 Location/Qualifiers
modified_base           12
                        mod_base = OTHER
                        note = 2'-O-methylguanosine
modified_base           8
                        mod_base = OTHER
                        note = 2'-O-methylguanosine
modified_base           16
                        mod_base = OTHER
                        note = 2'-fluorouridine
modified_base           5
                        mod_base = OTHER
                        note = 2'-O-methylguanosine
modified_base           2
                        mod_base = OTHER
                        note = 2'-fluoroadenosine phosphorothioate
modified_base           10
                        mod_base = OTHER
                        note = 2'-O-methylcytidine
modified_base           1
```

-continued

```
                        mod_base = OTHER
                        note = 2'-fluorouridine phosphorothioate
modified_base           3
                        mod_base = OTHER
                        note = 2'-O-methylcytidine
modified_base           15
                        mod_base = OTHER
                        note = 2'-O-methyluridine
modified_base           4
                        mod_base = OTHER
                        note = 2'-O-methylguanosine
modified_base           20
                        mod_base = OTHER
                        note = 2'-O-methyluridine phosphorothioate
modified_base           11
                        mod_base = OTHER
                        note = 2'-O-methylcytidine
modified_base           18
                        mod_base = OTHER
                        note = 2'-O-methylguanosine
modified_base           19
                        mod_base = OTHER
                        note = 2'-O-methylcytidine phosphorothioate
modified_base           13
                        mod_base = OTHER
                        note = 2'-O-methylcytidine
modified_base           7
                        mod_base = OTHER
                        note = 2'-O-methylguanosine
modified_base           21
                        mod_base = OTHER
                        note = 2'-O-methyluridine
source                  1..21
                        mol_type = other RNA
                        organism = synthetic construct
modified_base           14
                        mod_base = OTHER
                        note = 2'-fluorouridine
modified_base           6
                        mod_base = OTHER
                        note = 2'-fluorocytidine
modified_base           17
                        mod_base = OTHER
                        note = 2'-O-methylcytidine
modified_base           9
                        mod_base = OTHER
                        note = 2'-O-methyluridine
SEQUENCE: 233
tacggcggtc cgctttcgct t                                                 21

SEQ ID NO: 234          moltype = RNA  length = 21
FEATURE                 Location/Qualifiers
modified_base           6
                        mod_base = OTHER
                        note = 2'-fluoroguanosine
modified_base           16
                        mod_base = OTHER
                        note = 2'-fluorouridine
source                  1..21
                        mol_type = other RNA
                        organism = synthetic construct
modified_base           3
                        mod_base = OTHER
                        note = 2'-O-methylguanosine
modified_base           2
                        mod_base = OTHER
                        note = 2'-fluorouridine phosphorothioate
modified_base           18
                        mod_base = OTHER
                        note = 2'-O-methyluridine
modified_base           15
                        mod_base = OTHER
                        note = 2'-O-methylcytidine
modified_base           8
                        mod_base = OTHER
                        note = 2'-O-methylcytidine
modified_base           5
                        mod_base = OTHER
                        note = 2'-O-methylcytidine
```

```
modified_base          19
                       mod_base = OTHER
                       note = 2'-O-methylcytidine phosphorothioate
modified_base          9
                       mod_base = OTHER
                       note = 2'-O-methylguanosine
modified_base          13
                       mod_base = OTHER
                       note = 2'-O-methylcytidine
modified_base          10
                       mod_base = OTHER
                       note = 2'-O-methylguanosine
modified_base          7
                       mod_base = OTHER
                       note = 2'-O-methylguanosine
modified_base          12
                       mod_base = OTHER
                       note = 2'-O-methylcytidine
modified_base          4
                       mod_base = OTHER
                       note = 2'-O-methyladenosine
modified_base          20
                       mod_base = OTHER
                       note = 2'-O-methyluridine phosphorothioate
modified_base          17
                       mod_base = OTHER
                       note = 2'-O-methyluridine
modified_base          14
                       mod_base = OTHER
                       note = 2'-fluoroguanosine
modified_base          21
                       mod_base = OTHER
                       note = 2'-O-methyluridine
modified_base          11
                       mod_base = OTHER
                       note = 2'-O-methyluridine
modified_base          1
                       mod_base = OTHER
                       note = 2'-fluorouridine phosphorothioate
SEQUENCE: 234
ttgacggcgg tccgctttct t                                    21

SEQ ID NO: 235         moltype = RNA  length = 21
FEATURE                Location/Qualifiers
source                 1..21
                       mol_type = other RNA
                       organism = synthetic construct
modified_base          10
                       mod_base = OTHER
                       note = 2'-O-methylcytidine
modified_base          9
                       mod_base = OTHER
                       note = 2'-O-methyladenosine
modified_base          16
                       mod_base = OTHER
                       note = 2'-fluorouridine
modified_base          6
                       mod_base = OTHER
                       note = 2'-fluoroguanosine
modified_base          4
                       mod_base = OTHER
                       note = 2'-O-methylcytidine
modified_base          20
                       mod_base = OTHER
                       note = 2'-O-methyluridine phosphorothioate
modified_base          17
                       mod_base = OTHER
                       note = 2'-O-methylcytidine
modified_base          19
                       mod_base = OTHER
                       note = 2'-O-methylguanosine phosphorothioate
modified_base          15
                       mod_base = OTHER
                       note = 2'-O-methylguanosine
modified_base          2
                       mod_base = OTHER
                       note = 2'-fluorouridine phosphorothioate
modified_base          8
                       mod_base = OTHER
```

```
                          note = 2'-O-methylguanosine
modified_base             12
                          mod_base = OTHER
                          note = 2'-O-methylguanosine
modified_base             1
                          mod_base = OTHER
                          note = 2'-fluorouridine phosphorothioate
modified_base             13
                          mod_base = OTHER
                          note = 2'-O-methylcytidine
modified_base             7
                          mod_base = OTHER
                          note = 2'-O-methyluridine
modified_base             3
                          mod_base = OTHER
                          note = 2'-O-methylcytidine
modified_base             11
                          mod_base = OTHER
                          note = 2'-O-methylguanosine
modified_base             5
                          mod_base = OTHER
                          note = 2'-O-methylguanosine
modified_base             14
                          mod_base = OTHER
                          note = 2'-fluoroguanosine
modified_base             21
                          mod_base = OTHER
                          note = 2'-O-methyluridine
modified_base             18
                          mod_base = OTHER
                          note = 2'-O-methylcytidine
SEQUENCE: 235
ttccggtgac ggcggtccgt t                                            21

SEQ ID NO: 236            moltype = RNA  length = 21
FEATURE                   Location/Qualifiers
modified_base             12
                          mod_base = OTHER
                          note = 2'-O-methylguanosine
modified_base             13
                          mod_base = OTHER
                          note = 2'-O-methylguanosine
modified_base             14
                          mod_base = OTHER
                          note = 2'-fluorocytidine
modified_base             4
                          mod_base = OTHER
                          note = 2'-O-methylcytidine
modified_base             3
                          mod_base = OTHER
                          note = 2'-O-methyluridine
modified_base             8
                          mod_base = OTHER
                          note = 2'-O-methyluridine
modified_base             9
                          mod_base = OTHER
                          note = 2'-O-methylguanosine
modified_base             11
                          mod_base = OTHER
                          note = 2'-O-methylcytidine
modified_base             16
                          mod_base = OTHER
                          note = 2'-fluoroguanosine
modified_base             7
                          mod_base = OTHER
                          note = 2'-O-methylguanosine
modified_base             1
                          mod_base = OTHER
                          note = 2'-fluorouridine phosphorothioate
modified_base             20
                          mod_base = OTHER
                          note = 2'-O-methyluridine phosphorothioate
modified_base             18
                          mod_base = OTHER
                          note = 2'-O-methylcytidine
modified_base             6
                          mod_base = OTHER
                          note = 2'-fluoroguanosine
modified_base             17
```

```
                         mod_base = OTHER
                         note = 2'-O-methyluridine
modified_base            2
                         mod_base = OTHER
                         note = 2'-fluoroadenosine phosphorothioate
modified_base            15
                         mod_base = OTHER
                         note = 2'-O-methylguanosine
modified_base            10
                         mod_base = OTHER
                         note = 2'-O-methyladenosine
modified_base            19
                         mod_base = OTHER
                         note = 2'-O-methylcytidine phosphorothioate
source                   1..21
                         mol_type = other RNA
                         organism = synthetic construct
modified_base            5
                         mod_base = OTHER
                         note = 2'-O-methylcytidine
modified_base            21
                         mod_base = OTHER
                         note = 2'-O-methyluridine
SEQUENCE: 236
tatccggtga cggcggtcct t                                              21

SEQ ID NO: 237           moltype = RNA  length = 21
FEATURE                  Location/Qualifiers
modified_base            10
                         mod_base = OTHER
                         note = 2'-O-methylguanosine
source                   1..21
                         mol_type = other RNA
                         organism = synthetic construct
modified_base            5
                         mod_base = OTHER
                         note = 2'-O-methylcytidine
modified_base            20
                         mod_base = OTHER
                         note = 2'-O-methyluridine phosphorothioate
modified_base            2
                         mod_base = OTHER
                         note = 2'-fluoroguanosine phosphorothioate
modified_base            17
                         mod_base = OTHER
                         note = 2'-O-methylguanosine
modified_base            11
                         mod_base = OTHER
                         note = 2'-O-methyladenosine
modified_base            4
                         mod_base = OTHER
                         note = 2'-O-methyluridine
modified_base            8
                         mod_base = OTHER
                         note = 2'-O-methylguanosine
modified_base            12
                         mod_base = OTHER
                         note = 2'-O-methylcytidine
modified_base            16
                         mod_base = OTHER
                         note = 2'-fluoroguanosine
modified_base            3
                         mod_base = OTHER
                         note = 2'-O-methyladenosine
modified_base            14
                         mod_base = OTHER
                         note = 2'-fluoroguanosine
modified_base            18
                         mod_base = OTHER
                         note = 2'-O-methyluridine
modified_base            1
                         mod_base = OTHER
                         note = 2'-fluorouridine phosphorothioate
modified_base            21
                         mod_base = OTHER
                         note = 2'-O-methyluridine
modified_base            13
                         mod_base = OTHER
                         note = 2'-O-methylguanosine
```

```
modified_base          7
                       mod_base = OTHER
                       note = 2'-O-methylguanosine
modified_base          9
                       mod_base = OTHER
                       note = 2'-O-methyluridine
modified_base          15
                       mod_base = OTHER
                       note = 2'-O-methylcytidine
modified_base          6
                       mod_base = OTHER
                       note = 2'-fluorocytidine
modified_base          19
                       mod_base = OTHER
                       note = 2'-O-methylcytidine phosphorothioate
SEQUENCE: 237
tgatccggtg acggcggtct t                                              21

SEQ ID NO: 238         moltype = RNA  length = 21
FEATURE                Location/Qualifiers
modified_base          9
                       mod_base = OTHER
                       note = 2'-O-methylguanosine
modified_base          4
                       mod_base = OTHER
                       note = 2'-O-methyluridine
modified_base          13
                       mod_base = OTHER
                       note = 2'-O-methylcytidine
modified_base          7
                       mod_base = OTHER
                       note = 2'-O-methylguanosine
modified_base          14
                       mod_base = OTHER
                       note = 2'-fluorocytidine
modified_base          18
                       mod_base = OTHER
                       note = 2'-O-methylcytidine
modified_base          5
                       mod_base = OTHER
                       note = 2'-O-methylcytidine
modified_base          16
                       mod_base = OTHER
                       note = 2'-fluoroguanosine
modified_base          20
                       mod_base = OTHER
                       note = 2'-O-methyluridine phosphorothioate
modified_base          11
                       mod_base = OTHER
                       note = 2'-O-methylguanosine
modified_base          1
                       mod_base = OTHER
                       note = 2'-fluorouridine phosphorothioate
modified_base          3
                       mod_base = OTHER
                       note = 2'-O-methylcytidine
modified_base          2
                       mod_base = OTHER
                       note = 2'-fluoroadenosine phosphorothioate
modified_base          17
                       mod_base = OTHER
                       note = 2'-O-methyluridine
modified_base          12
                       mod_base = OTHER
                       note = 2'-O-methylguanosine
modified_base          10
                       mod_base = OTHER
                       note = 2'-O-methyladenosine
modified_base          6
                       mod_base = OTHER
                       note = 2'-fluorocytidine
modified_base          21
                       mod_base = OTHER
                       note = 2'-O-methyluridine
modified_base          8
                       mod_base = OTHER
                       note = 2'-O-methylguanosine
source                 1..21
                       mol_type = other RNA
```

```
                         organism = synthetic construct
modified_base            15
                         mod_base = OTHER
                         note = 2'-O-methylcytidine
modified_base            19
                         mod_base = OTHER
                         note = 2'-O-methyluridine phosphorothioate
SEQUENCE: 238
tactccggga ggcccgtctt t                                              21

SEQ ID NO: 239           moltype = RNA  length = 21
FEATURE                  Location/Qualifiers
modified_base            21
                         mod_base = OTHER
                         note = 2'-O-methyluridine
modified_base            17
                         mod_base = OTHER
                         note = 2'-O-methyladenosine
source                   1..21
                         mol_type = other RNA
                         organism = synthetic construct
modified_base            8
                         mod_base = OTHER
                         note = 2'-O-methylcytidine
modified_base            19
                         mod_base = OTHER
                         note = 2'-O-methylguanosine phosphorothioate
modified_base            1
                         mod_base = OTHER
                         note = 2'-fluorouridine phosphorothioate
modified_base            18
                         mod_base = OTHER
                         note = 2'-O-methylguanosine
modified_base            3
                         mod_base = OTHER
                         note = 2'-O-methylguanosine
modified_base            10
                         mod_base = OTHER
                         note = 2'-O-methyladenosine
modified_base            5
                         mod_base = OTHER
                         note = 2'-O-methyladenosine
modified_base            4
                         mod_base = OTHER
                         note = 2'-O-methyladenosine
modified_base            11
                         mod_base = OTHER
                         note = 2'-O-methylcytidine
modified_base            2
                         mod_base = OTHER
                         note = 2'-fluorocytidine phosphorothioate
modified_base            13
                         mod_base = OTHER
                         note = 2'-O-methylcytidine
modified_base            6
                         mod_base = OTHER
                         note = 2'-fluoroguanosine
modified_base            7
                         mod_base = OTHER
                         note = 2'-O-methylguanosine
modified_base            20
                         mod_base = OTHER
                         note = 2'-O-methyluridine phosphorothioate
modified_base            12
                         mod_base = OTHER
                         note = 2'-O-methylcytidine
modified_base            15
                         mod_base = OTHER
                         note = 2'-O-methylcytidine
modified_base            16
                         mod_base = OTHER
                         note = 2'-fluoroguanosine
modified_base            14
                         mod_base = OTHER
                         note = 2'-fluoroadenosine
modified_base            9
                         mod_base = OTHER
                         note = 2'-O-methylguanosine
SEQUENCE: 239
```

```
tcgaaggcga cccacgaggt t                                              21

SEQ ID NO: 240          moltype = RNA  length = 21
FEATURE                 Location/Qualifiers
modified_base           18
                        mod_base = OTHER
                        note = 2'-O-methyladenosine
modified_base           4
                        mod_base = OTHER
                        note = 2'-O-methylguanosine
modified_base           16
                        mod_base = OTHER
                        note = 2'-fluorocytidine
modified_base           9
                        mod_base = OTHER
                        note = 2'-O-methylcytidine
modified_base           1
                        mod_base = OTHER
                        note = 2'-fluorouridine phosphorothioate
modified_base           2
                        mod_base = OTHER
                        note = 2'-fluoroguanosine phosphorothioate
modified_base           15
                        mod_base = OTHER
                        note = 2'-O-methyladenosine
modified_base           3
                        mod_base = OTHER
                        note = 2'-O-methylcytidine
modified_base           20
                        mod_base = OTHER
                        note = 2'-O-methyluridine phosphorothioate
modified_base           11
                        mod_base = OTHER
                        note = 2'-O-methyladenosine
modified_base           17
                        mod_base = OTHER
                        note = 2'-O-methylguanosine
modified_base           19
                        mod_base = OTHER
                        note = 2'-O-methylguanosine phosphorothioate
modified_base           21
                        mod_base = OTHER
                        note = 2'-O-methyluridine
modified_base           12
                        mod_base = OTHER
                        note = 2'-O-methylcytidine
modified_base           10
                        mod_base = OTHER
                        note = 2'-O-methylguanosine
modified_base           6
                        mod_base = OTHER
                        note = 2'-fluoroadenosine
modified_base           8
                        mod_base = OTHER
                        note = 2'-O-methylguanosine
modified_base           14
                        mod_base = OTHER
                        note = 2'-fluorocytidine
modified_base           7
                        mod_base = OTHER
                        note = 2'-O-methylguanosine
source                  1..21
                        mol_type = other RNA
                        organism = synthetic construct
modified_base           5
                        mod_base = OTHER
                        note = 2'-O-methyladenosine
modified_base           13
                        mod_base = OTHER
                        note = 2'-O-methylcytidine
SEQUENCE: 240
tgcgaaggcg acccacgagt t                                              21

SEQ ID NO: 241          moltype = RNA  length = 21
FEATURE                 Location/Qualifiers
modified_base           9
                        mod_base = OTHER
                        note = 2'-O-methylguanosine
modified_base           4
```

-continued

```
                         mod_base = OTHER
                         note = 2'-O-methylguanosine
modified_base            17
                         mod_base = OTHER
                         note = 2'-O-methylcytidine
source                   1..21
                         mol_type = other RNA
                         organism = synthetic construct
modified_base            6
                         mod_base = OTHER
                         note = 2'-fluorouridine
modified_base            3
                         mod_base = OTHER
                         note = 2'-O-methylguanosine
modified_base            21
                         mod_base = OTHER
                         note = 2'-O-methyluridine
modified_base            13
                         mod_base = OTHER
                         note = 2'-O-methyluridine
modified_base            11
                         mod_base = OTHER
                         note = 2'-O-methylguanosine
modified_base            15
                         mod_base = OTHER
                         note = 2'-O-methylcytidine
modified_base            8
                         mod_base = OTHER
                         note = 2'-O-methylguanosine
modified_base            12
                         mod_base = OTHER
                         note = 2'-O-methyladenosine
modified_base            2
                         mod_base = OTHER
                         note = 2'-fluoroadenosine phosphorothioate
modified_base            20
                         mod_base = OTHER
                         note = 2'-O-methyluridine phosphorothioate
modified_base            19
                         mod_base = OTHER
                         note = 2'-O-methylcytidine phosphorothioate
modified_base            18
                         mod_base = OTHER
                         note = 2'-O-methyluridine
modified_base            1
                         mod_base = OTHER
                         note = 2'-fluorouridine phosphorothioate
modified_base            16
                         mod_base = OTHER
                         note = 2'-fluorocytidine
modified_base            10
                         mod_base = OTHER
                         note = 2'-O-methyladenosine
modified_base            14
                         mod_base = OTHER
                         note = 2'-fluorocytidine
modified_base            5
                         mod_base = OTHER
                         note = 2'-O-methyluridine
modified_base            7
                         mod_base = OTHER
                         note = 2'-O-methylguanosine
SEQUENCE: 241
taggttggga gatcccctct t                                              21

SEQ ID NO: 242           moltype = RNA  length = 21
FEATURE                  Location/Qualifiers
modified_base            1
                         mod_base = OTHER
                         note = 2'-fluorouridine phosphorothioate
modified_base            20
                         mod_base = OTHER
                         note = 2'-O-methyluridine phosphorothioate
modified_base            17
                         mod_base = OTHER
                         note = 2'-O-methylguanosine
modified_base            4
                         mod_base = OTHER
                         note = 2'-O-methylguanosine
```

```
modified_base          2
                       mod_base = OTHER
                       note = 2'-fluoroadenosine phosphorothioate
modified_base          5
                       mod_base = OTHER
                       note = 2'-O-methylcytidine
modified_base          13
                       mod_base = OTHER
                       note = 2'-O-methylcytidine
modified_base          21
                       mod_base = OTHER
                       note = 2'-O-methyluridine
modified_base          8
                       mod_base = OTHER
                       note = 2'-O-methyladenosine
modified_base          9
                       mod_base = OTHER
                       note = 2'-O-methyladenosine
modified_base          6
                       mod_base = OTHER
                       note = 2'-fluoroguanosine
modified_base          3
                       mod_base = OTHER
                       note = 2'-O-methylguanosine
modified_base          7
                       mod_base = OTHER
                       note = 2'-O-methyladenosine
modified_base          19
                       mod_base = OTHER
                       note = 2'-O-methylguanosine phosphorothioate
modified_base          11
                       mod_base = OTHER
                       note = 2'-O-methylcytidine
modified_base          18
                       mod_base = OTHER
                       note = 2'-O-methylcytidine
modified_base          12
                       mod_base = OTHER
                       note = 2'-O-methylcytidine
source                 1..21
                       mol_type = other RNA
                       organism = synthetic construct
modified_base          15
                       mod_base = OTHER
                       note = 2'-O-methylguanosine
modified_base          16
                       mod_base = OTHER
                       note = 2'-fluorocytidine
modified_base          14
                       mod_base = OTHER
                       note = 2'-fluorocytidine
modified_base          10
                       mod_base = OTHER
                       note = 2'-O-methyluridine
SEQUENCE: 242
taggcgaaat ccccgcgcgt t                                            21

SEQ ID NO: 243         moltype = RNA  length = 21
FEATURE                Location/Qualifiers
modified_base          12
                       mod_base = OTHER
                       note = 2'-O-methylcytidine
modified_base          1
                       mod_base = OTHER
                       note = 2'-fluorouridine phosphorothioate
modified_base          16
                       mod_base = OTHER
                       note = 2'-fluoroguanosine
modified_base          20
                       mod_base = OTHER
                       note = 2'-O-methyluridine phosphorothioate
modified_base          17
                       mod_base = OTHER
                       note = 2'-O-methylcytidine
modified_base          14
                       mod_base = OTHER
                       note = 2'-fluorocytidine
modified_base          21
                       mod_base = OTHER
```

```
                        note = 2'-O-methyluridine
modified_base           10
                        mod_base = OTHER
                        note = 2'-O-methyladenosine
modified_base           9
                        mod_base = OTHER
                        note = 2'-O-methyladenosine
modified_base           2
                        mod_base = OTHER
                        note = 2'-fluorouridine phosphorothioate
modified_base           4
                        mod_base = OTHER
                        note = 2'-O-methylguanosine
modified_base           6
                        mod_base = OTHER
                        note = 2'-fluorocytidine
modified_base           3
                        mod_base = OTHER
                        note = 2'-O-methyladenosine
modified_base           18
                        mod_base = OTHER
                        note = 2'-O-methylguanosine
modified_base           5
                        mod_base = OTHER
                        note = 2'-O-methylguanosine
modified_base           11
                        mod_base = OTHER
                        note = 2'-O-methyluridine
modified_base           19
                        mod_base = OTHER
                        note = 2'-O-methylcytidine phosphorothioate
modified_base           7
                        mod_base = OTHER
                        note = 2'-O-methylguanosine
modified_base           8
                        mod_base = OTHER
                        note = 2'-O-methyladenosine
source                  1..21
                        mol_type = other RNA
                        organism = synthetic construct
modified_base           13
                        mod_base = OTHER
                        note = 2'-O-methylcytidine
modified_base           15
                        mod_base = OTHER
                        note = 2'-O-methylcytidine
SEQUENCE: 243
ttaggcgaaa tccccgcgct t                                              21

SEQ ID NO: 244          moltype = RNA  length = 21
FEATURE                 Location/Qualifiers
modified_base           3
                        mod_base = OTHER
                        note = 2'-O-methylcytidine
modified_base           15
                        mod_base = OTHER
                        note = 2'-O-methylcytidine
modified_base           13
                        mod_base = OTHER
                        note = 2'-O-methyladenosine
modified_base           16
                        mod_base = OTHER
                        note = 2'-fluorocytidine
modified_base           5
                        mod_base = OTHER
                        note = 2'-O-methyluridine
modified_base           4
                        mod_base = OTHER
                        note = 2'-O-methylguanosine
modified_base           14
                        mod_base = OTHER
                        note = 2'-fluorouridine
modified_base           6
                        mod_base = OTHER
                        note = 2'-fluoroadenosine
modified_base           17
                        mod_base = OTHER
                        note = 2'-O-methylcytidine
modified_base           21
```

```
                        mod_base = OTHER
                        note = 2'-O-methyluridine
modified_base           19
                        mod_base = OTHER
                        note = 2'-O-methylguanosine phosphorothioate
source                  1..21
                        mol_type = other RNA
                        organism = synthetic construct
modified_base           20
                        mod_base = OTHER
                        note = 2'-O-methyluridine phosphorothioate
modified_base           7
                        mod_base = OTHER
                        note = 2'-O-methylguanosine
modified_base           2
                        mod_base = OTHER
                        note = 2'-fluoroguanosine phosphorothioate
modified_base           8
                        mod_base = OTHER
                        note = 2'-O-methylguanosine
modified_base           18
                        mod_base = OTHER
                        note = 2'-O-methylcytidine
modified_base           9
                        mod_base = OTHER
                        note = 2'-O-methylcytidine
modified_base           1
                        mod_base = OTHER
                        note = 2'-fluorouridine phosphorothioate
modified_base           11
                        mod_base = OTHER
                        note = 2'-O-methyladenosine
modified_base           12
                        mod_base = OTHER
                        note = 2'-O-methyladenosine
modified_base           10
                        mod_base = OTHER
                        note = 2'-O-methylguanosine
SEQUENCE: 244
tgcgtaggcg aaatccccgt t                                                 21

SEQ ID NO: 245          moltype = RNA  length = 21
FEATURE                 Location/Qualifiers
modified_base           2
                        mod_base = OTHER
                        note = 2'-fluoroadenosine phosphorothioate
modified_base           5
                        mod_base = OTHER
                        note = 2'-O-methyluridine
modified_base           15
                        mod_base = OTHER
                        note = 2'-O-methyladenosine
modified_base           18
                        mod_base = OTHER
                        note = 2'-O-methylcytidine
modified_base           1
                        mod_base = OTHER
                        note = 2'-fluorouridine phosphorothioate
source                  1..21
                        mol_type = other RNA
                        organism = synthetic construct
modified_base           8
                        mod_base = OTHER
                        note = 2'-O-methylguanosine
modified_base           7
                        mod_base = OTHER
                        note = 2'-O-methylguanosine
modified_base           3
                        mod_base = OTHER
                        note = 2'-O-methylcytidine
modified_base           9
                        mod_base = OTHER
                        note = 2'-O-methyluridine
modified_base           11
                        mod_base = OTHER
                        note = 2'-O-methylguanosine
modified_base           14
                        mod_base = OTHER
                        note = 2'-fluorocytidine
```

-continued

```
modified_base         12
                      mod_base = OTHER
                      note = 2'-O-methylcytidine
modified_base         20
                      mod_base = OTHER
                      note = 2'-O-methyluridine phosphorothioate
modified_base         10
                      mod_base = OTHER
                      note = 2'-O-methylguanosine
modified_base         17
                      mod_base = OTHER
                      note = 2'-O-methylguanosine
modified_base         19
                      mod_base = OTHER
                      note = 2'-O-methyladenosine phosphorothioate
modified_base         21
                      mod_base = OTHER
                      note = 2'-O-methyluridine
modified_base         13
                      mod_base = OTHER
                      note = 2'-O-methylguanosine
modified_base         16
                      mod_base = OTHER
                      note = 2'-fluoroadenosine
modified_base         6
                      mod_base = OTHER
                      note = 2'-fluoroguanosine
modified_base         4
                      mod_base = OTHER
                      note = 2'-O-methylguanosine
SEQUENCE: 245
tacgtgggtg gcgcaagcat t                                            21

SEQ ID NO: 246        moltype = RNA  length = 21
FEATURE               Location/Qualifiers
modified_base         9
                      mod_base = OTHER
                      note = 2'-O-methylguanosine
modified_base         20
                      mod_base = OTHER
                      note = 2'-O-methyluridine phosphorothioate
modified_base         12
                      mod_base = OTHER
                      note = 2'-O-methylcytidine
modified_base         5
                      mod_base = OTHER
                      note = 2'-O-methylcytidine
modified_base         16
                      mod_base = OTHER
                      note = 2'-fluorocytidine
modified_base         8
                      mod_base = OTHER
                      note = 2'-O-methylcytidine
modified_base         11
                      mod_base = OTHER
                      note = 2'-O-methylguanosine
source                1..21
                      mol_type = other RNA
                      organism = synthetic construct
modified_base         19
                      mod_base = OTHER
                      note = 2'-O-methylguanosine phosphorothioate
modified_base         3
                      mod_base = OTHER
                      note = 2'-O-methyladenosine
modified_base         13
                      mod_base = OTHER
                      note = 2'-O-methyluridine
modified_base         15
                      mod_base = OTHER
                      note = 2'-O-methylguanosine
modified_base         2
                      mod_base = OTHER
                      note = 2'-fluoroadenosine phosphorothioate
modified_base         6
                      mod_base = OTHER
                      note = 2'-fluorouridine
modified_base         14
                      mod_base = OTHER
```

```
                        note = 2'-fluorocytidine
modified_base           7
                        mod_base = OTHER
                        note = 2'-O-methylcytidine
modified_base           21
                        mod_base = OTHER
                        note = 2'-O-methyluridine
modified_base           4
                        mod_base = OTHER
                        note = 2'-O-methyladenosine
modified_base           1
                        mod_base = OTHER
                        note = 2'-fluorouridine phosphorothioate
modified_base           17
                        mod_base = OTHER
                        note = 2'-O-methylcytidine
modified_base           18
                        mod_base = OTHER
                        note = 2'-O-methyladenosine
modified_base           10
                        mod_base = OTHER
                        note = 2'-O-methylguanosine
SEQUENCE: 246
taaactccgg gctcgccagt t                                              21

SEQ ID NO: 247          moltype = RNA  length = 21
FEATURE                 Location/Qualifiers
modified_base           5
                        mod_base = OTHER
                        note = 2'-O-methyladenosine
modified_base           12
                        mod_base = OTHER
                        note = 2'-O-methylguanosine
modified_base           1
                        mod_base = OTHER
                        note = 2'-fluorouridine phosphorothioate
modified_base           6
                        mod_base = OTHER
                        note = 2'-fluoroadenosine
modified_base           14
                        mod_base = OTHER
                        note = 2'-fluorocytidine
modified_base           7
                        mod_base = OTHER
                        note = 2'-O-methylcytidine
modified_base           4
                        mod_base = OTHER
                        note = 2'-O-methyladenosine
modified_base           9
                        mod_base = OTHER
                        note = 2'-O-methylcytidine
modified_base           13
                        mod_base = OTHER
                        note = 2'-O-methylguanosine
modified_base           8
                        mod_base = OTHER
                        note = 2'-O-methyluridine
modified_base           2
                        mod_base = OTHER
                        note = 2'-fluoroadenosine phosphorothioate
modified_base           3
                        mod_base = OTHER
                        note = 2'-O-methylguanosine
modified_base           11
                        mod_base = OTHER
                        note = 2'-O-methylguanosine
source                  1..21
                        mol_type = other RNA
                        organism = synthetic construct
modified_base           20
                        mod_base = OTHER
                        note = 2'-O-methyluridine phosphorothioate
modified_base           18
                        mod_base = OTHER
                        note = 2'-O-methylcytidine
modified_base           10
                        mod_base = OTHER
                        note = 2'-O-methylcytidine
modified_base           19
```

```
                         mod_base = OTHER
                         note = 2'-O-methylcytidine phosphorothioate
modified_base            15
                         mod_base = OTHER
                         note = 2'-O-methyluridine
modified_base            16
                         mod_base = OTHER
                         note = 2'-fluorocytidine
modified_base            17
                         mod_base = OTHER
                         note = 2'-O-methylguanosine
modified_base            21
                         mod_base = OTHER
                         note = 2'-O-methyluridine
SEQUENCE: 247
tagaaactcc gggctcgcct t                                            21

SEQ ID NO: 248           moltype = RNA  length = 21
FEATURE                  Location/Qualifiers
modified_base            19
                         mod_base = OTHER
                         note = 2'-O-methylcytidine phosphorothioate
modified_base            6
                         mod_base = OTHER
                         note = 2'-fluoroguanosine
modified_base            10
                         mod_base = OTHER
                         note = 2'-O-methyladenosine
source                   1..21
                         mol_type = other RNA
                         organism = synthetic construct
modified_base            18
                         mod_base = OTHER
                         note = 2'-O-methylcytidine
modified_base            4
                         mod_base = OTHER
                         note = 2'-O-methyluridine
modified_base            5
                         mod_base = OTHER
                         note = 2'-O-methyladenosine
modified_base            3
                         mod_base = OTHER
                         note = 2'-O-methylcytidine
modified_base            11
                         mod_base = OTHER
                         note = 2'-O-methylguanosine
modified_base            13
                         mod_base = OTHER
                         note = 2'-O-methyluridine
modified_base            21
                         mod_base = OTHER
                         note = 2'-O-methyluridine
modified_base            2
                         mod_base = OTHER
                         note = 2'-fluorouridine phosphorothioate
modified_base            12
                         mod_base = OTHER
                         note = 2'-O-methylguanosine
modified_base            7
                         mod_base = OTHER
                         note = 2'-O-methylguanosine
modified_base            1
                         mod_base = OTHER
                         note = 2'-fluorouridine phosphorothioate
modified_base            14
                         mod_base = OTHER
                         note = 2'-fluorouridine
modified_base            16
                         mod_base = OTHER
                         note = 2'-fluorocytidine
modified_base            20
                         mod_base = OTHER
                         note = 2'-O-methyluridine phosphorothioate
modified_base            17
                         mod_base = OTHER
                         note = 2'-O-methylguanosine
modified_base            8
                         mod_base = OTHER
                         note = 2'-O-methyladenosine
```

```
modified_base          15
                       mod_base = OTHER
                       note = 2'-O-methylguanosine
modified_base          9
                       mod_base = OTHER
                       note = 2'-O-methylguanosine
SEQUENCE: 248
ttctaggaga ggttgcgcct t                                      21

SEQ ID NO: 249         moltype = RNA  length = 21
FEATURE                Location/Qualifiers
modified_base          4
                       mod_base = OTHER
                       note = 2'-O-methylcytidine
modified_base          7
                       mod_base = OTHER
                       note = 2'-O-methylguanosine
modified_base          1
                       mod_base = OTHER
                       note = 2'-fluorouridine phosphorothioate
modified_base          15
                       mod_base = OTHER
                       note = 2'-O-methyluridine
modified_base          17
                       mod_base = OTHER
                       note = 2'-O-methylcytidine
source                 1..21
                       mol_type = other RNA
                       organism = synthetic construct
modified_base          6
                       mod_base = OTHER
                       note = 2'-fluoroadenosine
modified_base          18
                       mod_base = OTHER
                       note = 2'-O-methylguanosine
modified_base          11
                       mod_base = OTHER
                       note = 2'-O-methyladenosine
modified_base          20
                       mod_base = OTHER
                       note = 2'-O-methyluridine phosphorothioate
modified_base          10
                       mod_base = OTHER
                       note = 2'-O-methylguanosine
modified_base          8
                       mod_base = OTHER
                       note = 2'-O-methylguanosine
modified_base          12
                       mod_base = OTHER
                       note = 2'-O-methylguanosine
modified_base          9
                       mod_base = OTHER
                       note = 2'-O-methyladenosine
modified_base          5
                       mod_base = OTHER
                       note = 2'-O-methyluridine
modified_base          14
                       mod_base = OTHER
                       note = 2'-fluorouridine
modified_base          21
                       mod_base = OTHER
                       note = 2'-O-methyluridine
modified_base          13
                       mod_base = OTHER
                       note = 2'-O-methylguanosine
modified_base          3
                       mod_base = OTHER
                       note = 2'-O-methyluridine
modified_base          16
                       mod_base = OTHER
                       note = 2'-fluoroguanosine
modified_base          2
                       mod_base = OTHER
                       note = 2'-fluorouridine phosphorothioate
modified_base          19
                       mod_base = OTHER
                       note = 2'-O-methylcytidine phosphorothioate
SEQUENCE: 249
tttctaggag aggttgcgct t                                      21
```

```
SEQ ID NO: 250          moltype = RNA  length = 21
FEATURE                 Location/Qualifiers
modified_base           19
                        mod_base = OTHER
                        note = 2'-O-methyluridine phosphorothioate
modified_base           2
                        mod_base = OTHER
                        note = 2'-fluorocytidine phosphorothioate
modified_base           4
                        mod_base = OTHER
                        note = 2'-O-methylguanosine
modified_base           18
                        mod_base = OTHER
                        note = 2'-O-methyluridine
modified_base           6
                        mod_base = OTHER
                        note = 2'-fluorouridine
modified_base           7
                        mod_base = OTHER
                        note = 2'-O-methyluridine
modified_base           11
                        mod_base = OTHER
                        note = 2'-O-methylguanosine
modified_base           12
                        mod_base = OTHER
                        note = 2'-O-methylguanosine
modified_base           8
                        mod_base = OTHER
                        note = 2'-O-methylcytidine
modified_base           15
                        mod_base = OTHER
                        note = 2'-O-methyladenosine
modified_base           3
                        mod_base = OTHER
                        note = 2'-O-methylcytidine
modified_base           1
                        mod_base = OTHER
                        note = 2'-fluorouridine phosphorothioate
modified_base           16
                        mod_base = OTHER
                        note = 2'-fluoroguanosine
modified_base           9
                        mod_base = OTHER
                        note = 2'-O-methyluridine
modified_base           20
                        mod_base = OTHER
                        note = 2'-O-methyluridine phosphorothioate
source                  1..21
                        mol_type = other RNA
                        organism = synthetic construct
modified_base           10
                        mod_base = OTHER
                        note = 2'-O-methyladenosine
modified_base           13
                        mod_base = OTHER
                        note = 2'-O-methyladenosine
modified_base           17
                        mod_base = OTHER
                        note = 2'-O-methylguanosine
modified_base           14
                        mod_base = OTHER
                        note = 2'-fluoroguanosine
modified_base           5
                        mod_base = OTHER
                        note = 2'-O-methyluridine
modified_base           21
                        mod_base = OTHER
                        note = 2'-O-methyluridine
SEQUENCE: 250
tccgtttcta ggagaggttt t                                                 21

SEQ ID NO: 251          moltype = RNA  length = 21
FEATURE                 Location/Qualifiers
modified_base           17
                        mod_base = OTHER
                        note = 2'-O-methylcytidine
modified_base           16
                        mod_base = OTHER
```

```
                        note = 2'-fluoroguanosine
modified_base           20
                        mod_base = OTHER
                        note = 2'-O-methyluridine phosphorothioate
modified_base           10
                        mod_base = OTHER
                        note = 2'-O-methyluridine
modified_base           5
                        mod_base = OTHER
                        note = 2'-O-methyluridine
modified_base           12
                        mod_base = OTHER
                        note = 2'-O-methylcytidine
modified_base           7
                        mod_base = OTHER
                        note = 2'-O-methyluridine
source                  1..21
                        mol_type = other RNA
                        organism = synthetic construct
modified_base           21
                        mod_base = OTHER
                        note = 2'-O-methyluridine
modified_base           14
                        mod_base = OTHER
                        note = 2'-fluorouridine
modified_base           15
                        mod_base = OTHER
                        note = 2'-O-methylcytidine
modified_base           6
                        mod_base = OTHER
                        note = 2'-fluoroadenosine
modified_base           18
                        mod_base = OTHER
                        note = 2'-O-methyluridine
modified_base           9
                        mod_base = OTHER
                        note = 2'-O-methylcytidine
modified_base           2
                        mod_base = OTHER
                        note = 2'-fluorocytidine phosphorothioate
modified_base           8
                        mod_base = OTHER
                        note = 2'-O-methyluridine
modified_base           4
                        mod_base = OTHER
                        note = 2'-O-methylguanosine
modified_base           1
                        mod_base = OTHER
                        note = 2'-fluorouridine phosphorothioate
modified_base           11
                        mod_base = OTHER
                        note = 2'-O-methyluridine
modified_base           3
                        mod_base = OTHER
                        note = 2'-O-methylguanosine
modified_base           19
                        mod_base = OTHER
                        note = 2'-O-methylguanosine phosphorothioate
modified_base           13
                        mod_base = OTHER
                        note = 2'-O-methylcytidine
SEQUENCE: 251
tcggtattct tcctcgctgt t                                               21

SEQ ID NO: 252          moltype = RNA  length = 21
FEATURE                 Location/Qualifiers
modified_base           3
                        mod_base = OTHER
                        note = 2'-O-methylcytidine
modified_base           13
                        mod_base = OTHER
                        note = 2'-O-methylcytidine
modified_base           18
                        mod_base = OTHER
                        note = 2'-O-methylcytidine
modified_base           12
                        mod_base = OTHER
                        note = 2'-O-methyluridine
modified_base           5
```

```
                        mod_base = OTHER
                        note = 2'-O-methylguanosine
modified_base           1
                        mod_base = OTHER
                        note = 2'-fluorouridine phosphorothioate
source                  1..21
                        mol_type = other RNA
                        organism = synthetic construct
modified_base           14
                        mod_base = OTHER
                        note = 2'-fluorocytidine
modified_base           15
                        mod_base = OTHER
                        note = 2'-O-methyluridine
modified_base           21
                        mod_base = OTHER
                        note = 2'-O-methyluridine
modified_base           4
                        mod_base = OTHER
                        note = 2'-O-methylguanosine
modified_base           6
                        mod_base = OTHER
                        note = 2'-fluorouridine
modified_base           11
                        mod_base = OTHER
                        note = 2'-O-methyluridine
modified_base           16
                        mod_base = OTHER
                        note = 2'-fluorocytidine
modified_base           19
                        mod_base = OTHER
                        note = 2'-O-methyluridine phosphorothioate
modified_base           7
                        mod_base = OTHER
                        note = 2'-O-methyladenosine
modified_base           17
                        mod_base = OTHER
                        note = 2'-O-methylguanosine
modified_base           10
                        mod_base = OTHER
                        note = 2'-O-methylcytidine
modified_base           2
                        mod_base = OTHER
                        note = 2'-fluorocytidine phosphorothioate
modified_base           9
                        mod_base = OTHER
                        note = 2'-O-methyluridine
modified_base           8
                        mod_base = OTHER
                        note = 2'-O-methyluridine
modified_base           20
                        mod_base = OTHER
                        note = 2'-O-methyluridine phosphorothioate
SEQUENCE: 252
tccggtattc ttcctcgctt t                                            21

SEQ ID NO: 253          moltype = RNA  length = 21
FEATURE                 Location/Qualifiers
modified_base           13
                        mod_base = OTHER
                        note = 2'-O-methyluridine
modified_base           17
                        mod_base = OTHER
                        note = 2'-O-methylcytidine
modified_base           14
                        mod_base = OTHER
                        note = 2'-fluorocytidine
modified_base           11
                        mod_base = OTHER
                        note = 2'-O-methylcytidine
modified_base           20
                        mod_base = OTHER
                        note = 2'-O-methyluridine phosphorothioate
modified_base           16
                        mod_base = OTHER
                        note = 2'-fluorouridine
modified_base           2
                        mod_base = OTHER
                        note = 2'-fluorocytidine phosphorothioate
```

```
modified_base           7
                        mod_base = OTHER
                        note = 2'-O-methyluridine
source                  1..21
                        mol_type = other RNA
                        organism = synthetic construct
modified_base           6
                        mod_base = OTHER
                        note = 2'-fluoroguanosine
modified_base           3
                        mod_base = OTHER
                        note = 2'-O-methylcytidine
modified_base           18
                        mod_base = OTHER
                        note = 2'-O-methylguanosine
modified_base           1
                        mod_base = OTHER
                        note = 2'-fluorouridine phosphorothioate
modified_base           4
                        mod_base = OTHER
                        note = 2'-O-methylcytidine
modified_base           21
                        mod_base = OTHER
                        note = 2'-O-methyluridine
modified_base           19
                        mod_base = OTHER
                        note = 2'-O-methylcytidine phosphorothioate
modified_base           10
                        mod_base = OTHER
                        note = 2'-O-methyluridine
modified_base           5
                        mod_base = OTHER
                        note = 2'-O-methylguanosine
modified_base           15
                        mod_base = OTHER
                        note = 2'-O-methylcytidine
modified_base           9
                        mod_base = OTHER
                        note = 2'-O-methyluridine
modified_base           8
                        mod_base = OTHER
                        note = 2'-O-methyladenosine
modified_base           12
                        mod_base = OTHER
                        note = 2'-O-methyluridine
SEQUENCE: 253
tcccggtatt cttcctcgct t                                             21

SEQ ID NO: 254          moltype = RNA  length = 21
FEATURE                 Location/Qualifiers
source                  1..21
                        mol_type = other RNA
                        organism = synthetic construct
modified_base           5
                        mod_base = OTHER
                        note = 2'-O-methylcytidine
modified_base           10
                        mod_base = OTHER
                        note = 2'-O-methylcytidine
modified_base           2
                        mod_base = OTHER
                        note = 2'-fluoroadenosine phosphorothioate
modified_base           19
                        mod_base = OTHER
                        note = 2'-O-methylcytidine phosphorothioate
modified_base           20
                        mod_base = OTHER
                        note = 2'-O-methyluridine phosphorothioate
modified_base           15
                        mod_base = OTHER
                        note = 2'-O-methylcytidine
modified_base           7
                        mod_base = OTHER
                        note = 2'-O-methyladenosine
modified_base           9
                        mod_base = OTHER
                        note = 2'-O-methylcytidine
modified_base           13
                        mod_base = OTHER
```

```
                        note = 2'-O-methyluridine
modified_base           18
                        mod_base = OTHER
                        note = 2'-O-methyladenosine
modified_base           17
                        mod_base = OTHER
                        note = 2'-O-methyladenosine
modified_base           11
                        mod_base = OTHER
                        note = 2'-O-methylcytidine
modified_base           21
                        mod_base = OTHER
                        note = 2'-O-methyluridine
modified_base           14
                        mod_base = OTHER
                        note = 2'-fluorocytidine
modified_base           3
                        mod_base = OTHER
                        note = 2'-O-methylcytidine
modified_base           8
                        mod_base = OTHER
                        note = 2'-O-methylcytidine
modified_base           6
                        mod_base = OTHER
                        note = 2'-fluoroguanosine
modified_base           4
                        mod_base = OTHER
                        note = 2'-O-methylcytidine
modified_base           12
                        mod_base = OTHER
                        note = 2'-O-methylguanosine
modified_base           16
                        mod_base = OTHER
                        note = 2'-fluorocytidine
modified_base           1
                        mod_base = OTHER
                        note = 2'-fluorouridine phosphorothioate
SEQUENCE: 254
tacccgaccc cgtcccaact t                                            21

SEQ ID NO: 255          moltype = RNA  length = 21
FEATURE                 Location/Qualifiers
modified_base           6
                        mod_base = OTHER
                        note = 2'-fluorocytidine
modified_base           3
                        mod_base = OTHER
                        note = 2'-O-methylguanosine
modified_base           1
                        mod_base = OTHER
                        note = 2'-fluorouridine phosphorothioate
modified_base           16
                        mod_base = OTHER
                        note = 2'-fluorocytidine
source                  1..21
                        mol_type = other RNA
                        organism = synthetic construct
modified_base           10
                        mod_base = OTHER
                        note = 2'-O-methylcytidine
modified_base           9
                        mod_base = OTHER
                        note = 2'-O-methylcytidine
modified_base           21
                        mod_base = OTHER
                        note = 2'-O-methyluridine
modified_base           11
                        mod_base = OTHER
                        note = 2'-O-methylcytidine
modified_base           4
                        mod_base = OTHER
                        note = 2'-O-methyladenosine
modified_base           13
                        mod_base = OTHER
                        note = 2'-O-methyladenosine
modified_base           12
                        mod_base = OTHER
                        note = 2'-O-methylguanosine
modified_base           14
```

```
                         mod_base = OTHER
                         note = 2'-fluorocytidine
modified_base            15
                         mod_base = OTHER
                         note = 2'-O-methylcytidine
modified_base            8
                         mod_base = OTHER
                         note = 2'-O-methyladenosine
modified_base            7
                         mod_base = OTHER
                         note = 2'-O-methylcytidine
modified_base            5
                         mod_base = OTHER
                         note = 2'-O-methyladenosine
modified_base            18
                         mod_base = OTHER
                         note = 2'-O-methylguanosine
modified_base            20
                         mod_base = OTHER
                         note = 2'-O-methyluridine phosphorothioate
modified_base            19
                         mod_base = OTHER
                         note = 2'-O-methyluridine phosphorothioate
modified_base            17
                         mod_base = OTHER
                         note = 2'-O-methylcytidine
modified_base            2
                         mod_base = OTHER
                         note = 2'-fluorocytidine phosphorothioate
SEQUENCE: 255
tcgaaccacc cgaccccgtt t                                      21

SEQ ID NO: 256           moltype = RNA  length = 21
FEATURE                  Location/Qualifiers
modified_base            6
                         mod_base = OTHER
                         note = 2'-fluorocytidine
modified_base            13
                         mod_base = OTHER
                         note = 2'-O-methylcytidine
modified_base            1
                         mod_base = OTHER
                         note = 2'-fluorouridine phosphorothioate
modified_base            4
                         mod_base = OTHER
                         note = 2'-O-methylcytidine
modified_base            7
                         mod_base = OTHER
                         note = 2'-O-methylguanosine
source                   1..21
                         mol_type = other RNA
                         organism = synthetic construct
modified_base            18
                         mod_base = OTHER
                         note = 2'-O-methylcytidine
modified_base            17
                         mod_base = OTHER
                         note = 2'-O-methyladenosine
modified_base            2
                         mod_base = OTHER
                         note = 2'-fluoroguanosine phosphorothioate
modified_base            21
                         mod_base = OTHER
                         note = 2'-O-methyluridine
modified_base            19
                         mod_base = OTHER
                         note = 2'-O-methylcytidine phosphorothioate
modified_base            16
                         mod_base = OTHER
                         note = 2'-fluoroguanosine
modified_base            20
                         mod_base = OTHER
                         note = 2'-O-methyluridine phosphorothioate
modified_base            12
                         mod_base = OTHER
                         note = 2'-O-methyladenosine
modified_base            11
                         mod_base = OTHER
                         note = 2'-O-methylcytidine
```

```
modified_base          9
                       mod_base = OTHER
                       note = 2'-O-methyladenosine
modified_base          8
                       mod_base = OTHER
                       note = 2'-O-methyladenosine
modified_base          10
                       mod_base = OTHER
                       note = 2'-O-methylcytidine
modified_base          14
                       mod_base = OTHER
                       note = 2'-fluorocytidine
modified_base          15
                       mod_base = OTHER
                       note = 2'-O-methylcytidine
modified_base          3
                       mod_base = OTHER
                       note = 2'-O-methylcytidine
modified_base          5
                       mod_base = OTHER
                       note = 2'-O-methylcytidine
SEQUENCE: 256
tgccccgaac cacccgacct t                                             21

SEQ ID NO: 257         moltype = RNA  length = 21
FEATURE                Location/Qualifiers
modified_base          13
                       mod_base = OTHER
                       note = 2'-O-methyladenosine
modified_base          10
                       mod_base = OTHER
                       note = 2'-O-methyladenosine
modified_base          19
                       mod_base = OTHER
                       note = 2'-O-methylcytidine phosphorothioate
modified_base          4
                       mod_base = OTHER
                       note = 2'-O-methylcytidine
modified_base          18
                       mod_base = OTHER
                       note = 2'-O-methyladenosine
source                 1..21
                       mol_type = other RNA
                       organism = synthetic construct
modified_base          1
                       mod_base = OTHER
                       note = 2'-fluorouridine phosphorothioate
modified_base          3
                       mod_base = OTHER
                       note = 2'-O-methylguanosine
modified_base          12
                       mod_base = OTHER
                       note = 2'-O-methylcytidine
modified_base          5
                       mod_base = OTHER
                       note = 2'-O-methylcytidine
modified_base          8
                       mod_base = OTHER
                       note = 2'-O-methylguanosine
modified_base          6
                       mod_base = OTHER
                       note = 2'-fluorocytidine
modified_base          7
                       mod_base = OTHER
                       note = 2'-O-methylcytidine
modified_base          20
                       mod_base = OTHER
                       note = 2'-O-methyluridine phosphorothioate
modified_base          16
                       mod_base = OTHER
                       note = 2'-fluorocytidine
modified_base          11
                       mod_base = OTHER
                       note = 2'-O-methylcytidine
modified_base          17
                       mod_base = OTHER
                       note = 2'-O-methylguanosine
modified_base          2
                       mod_base = OTHER
```

```
                      note = 2'-fluorouridine phosphorothioate
modified_base         21
                      mod_base = OTHER
                      note = 2'-O-methyluridine
modified_base         9
                      mod_base = OTHER
                      note = 2'-O-methyladenosine
modified_base         15
                      mod_base = OTHER
                      note = 2'-O-methylcytidine
modified_base         14
                      mod_base = OTHER
                      note = 2'-fluorocytidine
SEQUENCE: 257
ttgccccgaa ccacccgact t                                           21

SEQ ID NO: 258        moltype = RNA  length = 21
FEATURE               Location/Qualifiers
modified_base         15
                      mod_base = OTHER
                      note = 2'-O-methyladenosine
modified_base         4
                      mod_base = OTHER
                      note = 2'-O-methyladenosine
modified_base         16
                      mod_base = OTHER
                      note = 2'-fluorocytidine
modified_base         3
                      mod_base = OTHER
                      note = 2'-O-methylguanosine
modified_base         17
                      mod_base = OTHER
                      note = 2'-O-methylcytidine
modified_base         14
                      mod_base = OTHER
                      note = 2'-fluorocytidine
modified_base         5
                      mod_base = OTHER
                      note = 2'-O-methyladenosine
modified_base         8
                      mod_base = OTHER
                      note = 2'-O-methyladenosine
modified_base         13
                      mod_base = OTHER
                      note = 2'-O-methylcytidine
modified_base         20
                      mod_base = OTHER
                      note = 2'-O-methyluridine phosphorothioate
modified_base         19
                      mod_base = OTHER
                      note = 2'-O-methylcytidine phosphorothioate
modified_base         2
                      mod_base = OTHER
                      note = 2'-fluorocytidine phosphorothioate
modified_base         9
                      mod_base = OTHER
                      note = 2'-O-methylguanosine
modified_base         10
                      mod_base = OTHER
                      note = 2'-O-methyladenosine
source                1..21
                      mol_type = other RNA
                      organism = synthetic construct
modified_base         21
                      mod_base = OTHER
                      note = 2'-O-methyluridine
modified_base         6
                      mod_base = OTHER
                      note = 2'-fluoroadenosine
modified_base         11
                      mod_base = OTHER
                      note = 2'-O-methylguanosine
modified_base         12
                      mod_base = OTHER
                      note = 2'-O-methylguanosine
modified_base         7
                      mod_base = OTHER
                      note = 2'-O-methylguanosine
modified_base         18
```

```
                        mod_base = OTHER
                        note = 2'-O-methylguanosine
modified_base           1
                        mod_base = OTHER
                        note = 2'-fluorouridine phosphorothioate
SEQUENCE: 258
tcgaaagaga ggccaccgct t                                             21

SEQ ID NO: 259          moltype = RNA  length = 21
FEATURE                 Location/Qualifiers
modified_base           8
                        mod_base = OTHER
                        note = 2'-O-methylguanosine
modified_base           6
                        mod_base = OTHER
                        note = 2'-fluoroadenosine
modified_base           1
                        mod_base = OTHER
                        note = 2'-fluorouridine phosphorothioate
modified_base           2
                        mod_base = OTHER
                        note = 2'-fluoroguanosine phosphorothioate
modified_base           17
                        mod_base = OTHER
                        note = 2'-O-methylcytidine
modified_base           21
                        mod_base = OTHER
                        note = 2'-O-methyluridine
modified_base           15
                        mod_base = OTHER
                        note = 2'-O-methylcytidine
modified_base           18
                        mod_base = OTHER
                        note = 2'-O-methylcytidine
modified_base           3
                        mod_base = OTHER
                        note = 2'-O-methylcytidine
modified_base           11
                        mod_base = OTHER
                        note = 2'-O-methyladenosine
modified_base           12
                        mod_base = OTHER
                        note = 2'-O-methylguanosine
modified_base           16
                        mod_base = OTHER
                        note = 2'-fluoroadenosine
modified_base           19
                        mod_base = OTHER
                        note = 2'-O-methylguanosine phosphorothioate
modified_base           14
                        mod_base = OTHER
                        note = 2'-fluorocytidine
modified_base           9
                        mod_base = OTHER
                        note = 2'-O-methyladenosine
modified_base           7
                        mod_base = OTHER
                        note = 2'-O-methyladenosine
modified_base           10
                        mod_base = OTHER
                        note = 2'-O-methylguanosine
modified_base           20
                        mod_base = OTHER
                        note = 2'-O-methyluridine phosphorothioate
modified_base           13
                        mod_base = OTHER
                        note = 2'-O-methylguanosine
source                  1..21
                        mol_type = other RNA
                        organism = synthetic construct
modified_base           4
                        mod_base = OTHER
                        note = 2'-O-methylguanosine
modified_base           5
                        mod_base = OTHER
                        note = 2'-O-methyladenosine
SEQUENCE: 259
tgcgaaagag aggccaccgt t                                             21
```

```
SEQ ID NO: 260          moltype = RNA  length = 21
FEATURE                 Location/Qualifiers
modified_base           9
                        mod_base = OTHER
                        note = 2'-O-methylguanosine
modified_base           6
                        mod_base = OTHER
                        note = 2'-fluoroadenosine
modified_base           17
                        mod_base = OTHER
                        note = 2'-O-methyladenosine
modified_base           15
                        mod_base = OTHER
                        note = 2'-O-methylcytidine
modified_base           3
                        mod_base = OTHER
                        note = 2'-O-methylguanosine
modified_base           5
                        mod_base = OTHER
                        note = 2'-O-methylguanosine
modified_base           13
                        mod_base = OTHER
                        note = 2'-O-methylguanosine
modified_base           18
                        mod_base = OTHER
                        note = 2'-O-methylcytidine
modified_base           20
                        mod_base = OTHER
                        note = 2'-O-methyluridine phosphorothioate
modified_base           4
                        mod_base = OTHER
                        note = 2'-O-methylcytidine
modified_base           16
                        mod_base = OTHER
                        note = 2'-fluorocytidine
modified_base           10
                        mod_base = OTHER
                        note = 2'-O-methyladenosine
modified_base           1
                        mod_base = OTHER
                        note = 2'-fluorouridine phosphorothioate
modified_base           7
                        mod_base = OTHER
                        note = 2'-O-methyladenosine
modified_base           19
                        mod_base = OTHER
                        note = 2'-O-methylcytidine phosphorothioate
modified_base           2
                        mod_base = OTHER
                        note = 2'-fluorocytidine phosphorothioate
modified_base           21
                        mod_base = OTHER
                        note = 2'-O-methyluridine
modified_base           14
                        mod_base = OTHER
                        note = 2'-fluoroguanosine
source                  1..21
                        mol_type = other RNA
                        organism = synthetic construct
modified_base           11
                        mod_base = OTHER
                        note = 2'-O-methylguanosine
modified_base           8
                        mod_base = OTHER
                        note = 2'-O-methyladenosine
modified_base           12
                        mod_base = OTHER
                        note = 2'-O-methyladenosine
SEQUENCE: 260
tcgcgaaaga gaggccacct t                                              21

SEQ ID NO: 261          moltype = RNA  length = 21
FEATURE                 Location/Qualifiers
source                  1..21
                        mol_type = other RNA
                        organism = synthetic construct
modified_base           21
                        mod_base = OTHER
                        note = 2'-O-methyluridine
```

-continued

| | |
|---|---|
| modified_base | 19<br>mod_base = OTHER<br>note = 2'-O-methylcytidine phosphorothioate |
| modified_base | 11<br>mod_base = OTHER<br>note = 2'-O-methyladenosine |
| modified_base | 3<br>mod_base = OTHER<br>note = 2'-O-methylcytidine |
| modified_base | 12<br>mod_base = OTHER<br>note = 2'-O-methyladenosine |
| modified_base | 6<br>mod_base = OTHER<br>note = 2'-fluorocytidine |
| modified_base | 9<br>mod_base = OTHER<br>note = 2'-O-methylguanosine |
| modified_base | 8<br>mod_base = OTHER<br>note = 2'-O-methylcytidine |
| modified_base | 18<br>mod_base = OTHER<br>note = 2'-O-methylguanosine |
| modified_base | 2<br>mod_base = OTHER<br>note = 2'-fluorouridine phosphorothioate |
| modified_base | 4<br>mod_base = OTHER<br>note = 2'-O-methylcytidine |
| modified_base | 7<br>mod_base = OTHER<br>note = 2'-O-methylguanosine |
| modified_base | 14<br>mod_base = OTHER<br>note = 2'-fluoroadenosine |
| modified_base | 1<br>mod_base = OTHER<br>note = 2'-fluorouridine phosphorothioate |
| modified_base | 15<br>mod_base = OTHER<br>note = 2'-O-methylguanosine |
| modified_base | 10<br>mod_base = OTHER<br>note = 2'-O-methyladenosine |
| modified_base | 20<br>mod_base = OTHER<br>note = 2'-O-methyluridine phosphorothioate |
| modified_base | 13<br>mod_base = OTHER<br>note = 2'-O-methylguanosine |
| modified_base | 5<br>mod_base = OTHER<br>note = 2'-O-methylcytidine |
| modified_base | 17<br>mod_base = OTHER<br>note = 2'-O-methylguanosine |
| modified_base | 16<br>mod_base = OTHER<br>note = 2'-fluoroadenosine |
| SEQUENCE: 261 | |
| ttccccgcga aagagaggct t | 21 |

| | |
|---|---|
| SEQ ID NO: 262 | moltype = RNA length = 21 |
| FEATURE | Location/Qualifiers |
| modified_base | 16<br>mod_base = OTHER<br>note = 2'-fluoroguanosine |
| modified_base | 18<br>mod_base = OTHER<br>note = 2'-O-methyluridine |
| modified_base | 15<br>mod_base = OTHER<br>note = 2'-O-methyladenosine |
| modified_base | 20<br>mod_base = OTHER<br>note = 2'-O-methyluridine phosphorothioate |
| modified_base | 2<br>mod_base = OTHER |

```
                        note = 2'-fluorouridine phosphorothioate
modified_base           10
                        mod_base = OTHER
                        note = 2'-O-methylcytidine
modified_base           13
                        mod_base = OTHER
                        note = 2'-O-methylcytidine
modified_base           19
                        mod_base = OTHER
                        note = 2'-O-methylguanosine phosphorothioate
source                  1..21
                        mol_type = other RNA
                        organism = synthetic construct
modified_base           11
                        mod_base = OTHER
                        note = 2'-O-methyladenosine
modified_base           17
                        mod_base = OTHER
                        note = 2'-O-methylguanosine
modified_base           3
                        mod_base = OTHER
                        note = 2'-O-methylcytidine
modified_base           5
                        mod_base = OTHER
                        note = 2'-O-methylguanosine
modified_base           1
                        mod_base = OTHER
                        note = 2'-fluorouridine phosphorothioate
modified_base           12
                        mod_base = OTHER
                        note = 2'-O-methylguanosine
modified_base           6
                        mod_base = OTHER
                        note = 2'-fluorouridine
modified_base           21
                        mod_base = OTHER
                        note = 2'-O-methyluridine
modified_base           8
                        mod_base = OTHER
                        note = 2'-O-methylguanosine
modified_base           4
                        mod_base = OTHER
                        note = 2'-O-methylcytidine
modified_base           9
                        mod_base = OTHER
                        note = 2'-O-methylcytidine
modified_base           7
                        mod_base = OTHER
                        note = 2'-O-methyladenosine
modified_base           14
                        mod_base = OTHER
                        note = 2'-fluorocytidine
SEQUENCE: 262
ttccgtagcc agccaggtgt t                                               21

SEQ ID NO: 263          moltype = RNA  length = 21
FEATURE                 Location/Qualifiers
modified_base           7
                        mod_base = OTHER
                        note = 2'-O-methylguanosine
modified_base           18
                        mod_base = OTHER
                        note = 2'-O-methylguanosine
modified_base           14
                        mod_base = OTHER
                        note = 2'-fluorocytidine
modified_base           6
                        mod_base = OTHER
                        note = 2'-fluorocytidine
modified_base           19
                        mod_base = OTHER
                        note = 2'-O-methylcytidine phosphorothioate
modified_base           10
                        mod_base = OTHER
                        note = 2'-O-methylcytidine
modified_base           3
                        mod_base = OTHER
                        note = 2'-O-methyladenosine
modified_base           1
```

```
                         mod_base = OTHER
                         note = 2'-fluorouridine phosphorothioate
source                   1..21
                         mol_type = other RNA
                         organism = synthetic construct
modified_base            13
                         mod_base = OTHER
                         note = 2'-O-methylcytidine
modified_base            9
                         mod_base = OTHER
                         note = 2'-O-methylcytidine
modified_base            2
                         mod_base = OTHER
                         note = 2'-fluoroguanosine phosphorothioate
modified_base            5
                         mod_base = OTHER
                         note = 2'-O-methyladenosine
modified_base            20
                         mod_base = OTHER
                         note = 2'-O-methyluridine phosphorothioate
modified_base            12
                         mod_base = OTHER
                         note = 2'-O-methyluridine
modified_base            4
                         mod_base = OTHER
                         note = 2'-O-methylcytidine
modified_base            11
                         mod_base = OTHER
                         note = 2'-O-methylcytidine
modified_base            16
                         mod_base = OTHER
                         note = 2'-fluorouridine
modified_base            15
                         mod_base = OTHER
                         note = 2'-O-methylguanosine
modified_base            21
                         mod_base = OTHER
                         note = 2'-O-methyluridine
modified_base            17
                         mod_base = OTHER
                         note = 2'-O-methyladenosine
modified_base            8
                         mod_base = OTHER
                         note = 2'-O-methylcytidine
SEQUENCE: 263
tgacacgccc ctccgtagct t                                               21

SEQ ID NO: 264           moltype = RNA  length = 21
FEATURE                  Location/Qualifiers
modified_base            18
                         mod_base = OTHER
                         note = 2'-O-methyladenosine
modified_base            16
                         mod_base = OTHER
                         note = 2'-fluoroguanosine
modified_base            17
                         mod_base = OTHER
                         note = 2'-O-methyluridine
modified_base            6
                         mod_base = OTHER
                         note = 2'-fluoroadenosine
modified_base            2
                         mod_base = OTHER
                         note = 2'-fluoroadenosine phosphorothioate
modified_base            19
                         mod_base = OTHER
                         note = 2'-O-methylguanosine phosphorothioate
modified_base            12
                         mod_base = OTHER
                         note = 2'-O-methylcytidine
modified_base            15
                         mod_base = OTHER
                         note = 2'-O-methylcytidine
modified_base            1
                         mod_base = OTHER
                         note = 2'-fluorouridine phosphorothioate
modified_base            20
                         mod_base = OTHER
                         note = 2'-O-methyluridine phosphorothioate
```

```
modified_base          8
                       mod_base = OTHER
                       note = 2'-O-methylguanosine
modified_base          11
                       mod_base = OTHER
                       note = 2'-O-methylcytidine
modified_base          9
                       mod_base = OTHER
                       note = 2'-O-methylcytidine
modified_base          10
                       mod_base = OTHER
                       note = 2'-O-methylcytidine
modified_base          14
                       mod_base = OTHER
                       note = 2'-fluorocytidine
modified_base          3
                       mod_base = OTHER
                       note = 2'-O-methylguanosine
modified_base          21
                       mod_base = OTHER
                       note = 2'-O-methyluridine
modified_base          4
                       mod_base = OTHER
                       note = 2'-O-methyladenosine
modified_base          7
                       mod_base = OTHER
                       note = 2'-O-methylcytidine
modified_base          5
                       mod_base = OTHER
                       note = 2'-O-methylcytidine
modified_base          13
                       mod_base = OTHER
                       note = 2'-O-methyluridine
source                 1..21
                       mol_type = other RNA
                       organism = synthetic construct
SEQUENCE: 264
tagacacgcc cctccgtagt t                                              21

SEQ ID NO: 265         moltype = RNA  length = 21
FEATURE                Location/Qualifiers
modified_base          15
                       mod_base = OTHER
                       note = 2'-O-methylcytidine
modified_base          17
                       mod_base = OTHER
                       note = 2'-O-methylcytidine
source                 1..21
                       mol_type = other RNA
                       organism = synthetic construct
modified_base          2
                       mod_base = OTHER
                       note = 2'-fluoroguanosine phosphorothioate
modified_base          8
                       mod_base = OTHER
                       note = 2'-O-methyluridine
modified_base          14
                       mod_base = OTHER
                       note = 2'-fluoroguanosine
modified_base          11
                       mod_base = OTHER
                       note = 2'-O-methylcytidine
modified_base          13
                       mod_base = OTHER
                       note = 2'-O-methyluridine
modified_base          10
                       mod_base = OTHER
                       note = 2'-O-methylcytidine
modified_base          9
                       mod_base = OTHER
                       note = 2'-O-methylcytidine
modified_base          5
                       mod_base = OTHER
                       note = 2'-O-methyladenosine
modified_base          7
                       mod_base = OTHER
                       note = 2'-O-methylcytidine
modified_base          20
                       mod_base = OTHER
```

```
                        note = 2'-O-methyluridine phosphorothioate
modified_base           4
                        mod_base = OTHER
                        note = 2'-O-methylguanosine
modified_base           16
                        mod_base = OTHER
                        note = 2'-fluoroadenosine
modified_base           1
                        mod_base = OTHER
                        note = 2'-fluorouridine phosphorothioate
modified_base           21
                        mod_base = OTHER
                        note = 2'-O-methyluridine
modified_base           6
                        mod_base = OTHER
                        note = 2'-fluoroguanosine
modified_base           18
                        mod_base = OTHER
                        note = 2'-O-methylguanosine
modified_base           12
                        mod_base = OTHER
                        note = 2'-O-methyluridine
modified_base           19
                        mod_base = OTHER
                        note = 2'-O-methyluridine phosphorothioate
modified_base           3
                        mod_base = OTHER
                        note = 2'-O-methylcytidine
SEQUENCE: 265
tgcgagctcc cttgcacgtt t                                     21

SEQ ID NO: 266          moltype = RNA  length = 21
FEATURE                 Location/Qualifiers
modified_base           12
                        mod_base = OTHER
                        note = 2'-O-methylcytidine
modified_base           3
                        mod_base = OTHER
                        note = 2'-O-methylguanosine
modified_base           20
                        mod_base = OTHER
                        note = 2'-O-methyluridine phosphorothioate
modified_base           11
                        mod_base = OTHER
                        note = 2'-O-methylcytidine
modified_base           2
                        mod_base = OTHER
                        note = 2'-fluoroadenosine phosphorothioate
modified_base           18
                        mod_base = OTHER
                        note = 2'-O-methylcytidine
modified_base           13
                        mod_base = OTHER
                        note = 2'-O-methyluridine
modified_base           21
                        mod_base = OTHER
                        note = 2'-O-methyluridine
modified_base           5
                        mod_base = OTHER
                        note = 2'-O-methylguanosine
modified_base           1
                        mod_base = OTHER
                        note = 2'-fluorouridine phosphorothioate
source                  1..21
                        mol_type = other RNA
                        organism = synthetic construct
modified_base           10
                        mod_base = OTHER
                        note = 2'-O-methylcytidine
modified_base           7
                        mod_base = OTHER
                        note = 2'-O-methylguanosine
modified_base           9
                        mod_base = OTHER
                        note = 2'-O-methyluridine
modified_base           17
                        mod_base = OTHER
                        note = 2'-O-methyladenosine
modified_base           16
```

```
                        mod_base = OTHER
                        note = 2'-fluorocytidine
modified_base           4
                        mod_base = OTHER
                        note = 2'-O-methylcytidine
modified_base           8
                        mod_base = OTHER
                        note = 2'-O-methylcytidine
modified_base           15
                        mod_base = OTHER
                        note = 2'-O-methylguanosine
modified_base           14
                        mod_base = OTHER
                        note = 2'-fluorouridine
modified_base           19
                        mod_base = OTHER
                        note = 2'-O-methylguanosine phosphorothioate
modified_base           6
                        mod_base = OTHER
                        note = 2'-fluoroadenosine
SEQUENCE: 266
tagcgagctc ccttgcacgt t                                              21

SEQ ID NO: 267          moltype = RNA  length = 21
FEATURE                 Location/Qualifiers
modified_base           4
                        mod_base = OTHER
                        note = 2'-O-methylguanosine
modified_base           21
                        mod_base = OTHER
                        note = 2'-O-methyluridine
modified_base           3
                        mod_base = OTHER
                        note = 2'-O-methyladenosine
modified_base           10
                        mod_base = OTHER
                        note = 2'-O-methyluridine
modified_base           15
                        mod_base = OTHER
                        note = 2'-O-methyluridine
modified_base           7
                        mod_base = OTHER
                        note = 2'-O-methyladenosine
modified_base           6
                        mod_base = OTHER
                        note = 2'-fluoroguanosine
modified_base           14
                        mod_base = OTHER
                        note = 2'-fluorouridine
modified_base           8
                        mod_base = OTHER
                        note = 2'-O-methylguanosine
modified_base           20
                        mod_base = OTHER
                        note = 2'-O-methyluridine phosphorothioate
modified_base           1
                        mod_base = OTHER
                        note = 2'-fluorouridine phosphorothioate
modified_base           13
                        mod_base = OTHER
                        note = 2'-O-methylcytidine
modified_base           16
                        mod_base = OTHER
                        note = 2'-fluoroguanosine
modified_base           18
                        mod_base = OTHER
                        note = 2'-O-methyladenosine
source                  1..21
                        mol_type = other RNA
                        organism = synthetic construct
modified_base           12
                        mod_base = OTHER
                        note = 2'-O-methylcytidine
modified_base           19
                        mod_base = OTHER
                        note = 2'-O-methylcytidine phosphorothioate
modified_base           2
                        mod_base = OTHER
                        note = 2'-fluorocytidine phosphorothioate
```

```
modified_base          11
                       mod_base = OTHER
                       note = 2'-O-methylcytidine
modified_base          9
                       mod_base = OTHER
                       note = 2'-O-methylcytidine
modified_base          17
                       mod_base = OTHER
                       note = 2'-O-methylcytidine
modified_base          5
                       mod_base = OTHER
                       note = 2'-O-methylcytidine
SEQUENCE: 267
tcagcgagct cccttgcact t                                             21

SEQ ID NO: 268         moltype = RNA  length = 21
FEATURE                Location/Qualifiers
source                 1..21
                       mol_type = other RNA
                       organism = synthetic construct
modified_base          17
                       mod_base = OTHER
                       note = 2'-O-methylguanosine
modified_base          3
                       mod_base = OTHER
                       note = 2'-O-methylguanosine
modified_base          19
                       mod_base = OTHER
                       note = 2'-O-methylguanosine phosphorothioate
modified_base          20
                       mod_base = OTHER
                       note = 2'-O-methyluridine phosphorothioate
modified_base          18
                       mod_base = OTHER
                       note = 2'-O-methyluridine
modified_base          7
                       mod_base = OTHER
                       note = 2'-O-methylguanosine
modified_base          6
                       mod_base = OTHER
                       note = 2'-fluoroadenosine
modified_base          13
                       mod_base = OTHER
                       note = 2'-O-methylguanosine
modified_base          14
                       mod_base = OTHER
                       note = 2'-fluoroadenosine
modified_base          15
                       mod_base = OTHER
                       note = 2'-O-methyladenosine
modified_base          16
                       mod_base = OTHER
                       note = 2'-fluoroguanosine
modified_base          2
                       mod_base = OTHER
                       note = 2'-fluoroadenosine phosphorothioate
modified_base          1
                       mod_base = OTHER
                       note = 2'-fluorouridine phosphorothioate
modified_base          4
                       mod_base = OTHER
                       note = 2'-O-methyladenosine
modified_base          11
                       mod_base = OTHER
                       note = 2'-O-methylcytidine
modified_base          8
                       mod_base = OTHER
                       note = 2'-O-methylcytidine
modified_base          10
                       mod_base = OTHER
                       note = 2'-O-methyluridine
modified_base          5
                       mod_base = OTHER
                       note = 2'-O-methylcytidine
modified_base          21
                       mod_base = OTHER
                       note = 2'-O-methyluridine
modified_base          9
                       mod_base = OTHER
```

```
                        note = 2'-O-methylguanosine
modified_base           12
                        mod_base = OTHER
                        note = 2'-O-methylguanosine
SEQUENCE: 268
tagacagcgt cggaaggtgt t                                      21

SEQ ID NO: 269          moltype = RNA  length = 21
FEATURE                 Location/Qualifiers
modified_base           17
                        mod_base = OTHER
                        note = 2'-O-methylguanosine
modified_base           14
                        mod_base = OTHER
                        note = 2'-fluoroguanosine
modified_base           10
                        mod_base = OTHER
                        note = 2'-O-methylguanosine
modified_base           20
                        mod_base = OTHER
                        note = 2'-O-methyluridine phosphorothioate
modified_base           19
                        mod_base = OTHER
                        note = 2'-O-methyluridine phosphorothioate
modified_base           11
                        mod_base = OTHER
                        note = 2'-O-methyluridine
modified_base           7
                        mod_base = OTHER
                        note = 2'-O-methyladenosine
modified_base           9
                        mod_base = OTHER
                        note = 2'-O-methylcytidine
modified_base           6
                        mod_base = OTHER
                        note = 2'-fluorocytidine
modified_base           8
                        mod_base = OTHER
                        note = 2'-O-methylguanosine
modified_base           21
                        mod_base = OTHER
                        note = 2'-O-methyluridine
modified_base           2
                        mod_base = OTHER
                        note = 2'-fluorouridine phosphorothioate
modified_base           16
                        mod_base = OTHER
                        note = 2'-fluoroadenosine
modified_base           5
                        mod_base = OTHER
                        note = 2'-O-methyladenosine
modified_base           12
                        mod_base = OTHER
                        note = 2'-O-methylcytidine
modified_base           3
                        mod_base = OTHER
                        note = 2'-O-methyladenosine
source                  1..21
                        mol_type = other RNA
                        organism = synthetic construct
modified_base           1
                        mod_base = OTHER
                        note = 2'-fluorouridine phosphorothioate
modified_base           4
                        mod_base = OTHER
                        note = 2'-O-methylguanosine
modified_base           13
                        mod_base = OTHER
                        note = 2'-O-methylguanosine
modified_base           18
                        mod_base = OTHER
                        note = 2'-O-methylguanosine
modified_base           15
                        mod_base = OTHER
                        note = 2'-O-methyladenosine
SEQUENCE: 269
ttagacagcg tcggaaggtt t                                      21

SEQ ID NO: 270          moltype = RNA  length = 21
```

-continued

FEATURE Location/Qualifiers
modified_base 10
mod_base = OTHER
note = 2'-O-methylcytidine
modified_base 3
mod_base = OTHER
note = 2'-O-methyluridine
modified_base 21
mod_base = OTHER
note = 2'-O-methyluridine
modified_base 4
mod_base = OTHER
note = 2'-O-methyladenosine
modified_base 19
mod_base = OTHER
note = 2'-O-methylguanosine phosphorothioate
source 1..21
mol_type = other RNA
organism = synthetic construct
modified_base 15
mod_base = OTHER
note = 2'-O-methylguanosine
modified_base 16
mod_base = OTHER
note = 2'-fluoroadenosine
modified_base 2
mod_base = OTHER
note = 2'-fluorocytidine phosphorothioate
modified_base 1
mod_base = OTHER
note = 2'-fluorouridine phosphorothioate
modified_base 9
mod_base = OTHER
note = 2'-O-methylguanosine
modified_base 20
mod_base = OTHER
note = 2'-O-methyluridine phosphorothioate
modified_base 17
mod_base = OTHER
note = 2'-O-methyladenosine
modified_base 14
mod_base = OTHER
note = 2'-fluoroguanosine
modified_base 18
mod_base = OTHER
note = 2'-O-methylguanosine
modified_base 12
mod_base = OTHER
note = 2'-O-methyluridine
modified_base 8
mod_base = OTHER
note = 2'-O-methyladenosine
modified_base 7
mod_base = OTHER
note = 2'-O-methylcytidine
modified_base 6
mod_base = OTHER
note = 2'-fluoroadenosine
modified_base 5
mod_base = OTHER
note = 2'-O-methylguanosine
modified_base 13
mod_base = OTHER
note = 2'-O-methylcytidine
modified_base 11
mod_base = OTHER
note = 2'-O-methylguanosine
SEQUENCE: 270
tctagacagc gtcggaaggt t 21

SEQ ID NO: 271 moltype = RNA length = 21
FEATURE Location/Qualifiers
modified_base 13
mod_base = OTHER
note = 2'-O-methyluridine
source 1..21
mol_type = other RNA
organism = synthetic construct
modified_base 17

```
                        mod_base = OTHER
                        note = 2'-O-methyladenosine
modified_base           18
                        mod_base = OTHER
                        note = 2'-O-methyladenosine
modified_base           12
                        mod_base = OTHER
                        note = 2'-O-methylguanosine
modified_base           21
                        mod_base = OTHER
                        note = 2'-O-methyluridine
modified_base           14
                        mod_base = OTHER
                        note = 2'-fluorocytidine
modified_base           1
                        mod_base = OTHER
                        note = 2'-fluorouridine phosphorothioate
modified_base           11
                        mod_base = OTHER
                        note = 2'-O-methylcytidine
modified_base           8
                        mod_base = OTHER
                        note = 2'-O-methylcytidine
modified_base           4
                        mod_base = OTHER
                        note = 2'-O-methyluridine
modified_base           15
                        mod_base = OTHER
                        note = 2'-O-methylguanosine
modified_base           6
                        mod_base = OTHER
                        note = 2'-fluoroguanosine
modified_base           16
                        mod_base = OTHER
                        note = 2'-fluoroguanosine
modified_base           3
                        mod_base = OTHER
                        note = 2'-O-methylcytidine
modified_base           2
                        mod_base = OTHER
                        note = 2'-fluorocytidine phosphorothioate
modified_base           19
                        mod_base = OTHER
                        note = 2'-O-methylguanosine phosphorothioate
modified_base           7
                        mod_base = OTHER
                        note = 2'-O-methyladenosine
modified_base           9
                        mod_base = OTHER
                        note = 2'-O-methyladenosine
modified_base           5
                        mod_base = OTHER
                        note = 2'-O-methyladenosine
modified_base           20
                        mod_base = OTHER
                        note = 2'-O-methyluridine phosphorothioate
modified_base           10
                        mod_base = OTHER
                        note = 2'-O-methylguanosine
SEQUENCE: 271
tcctagacag cgtcggaagt t                                              21

SEQ ID NO: 272          moltype = RNA  length = 21
FEATURE                 Location/Qualifiers
modified_base           9
                        mod_base = OTHER
                        note = 2'-O-methyladenosine
modified_base           5
                        mod_base = OTHER
                        note = 2'-O-methylcytidine
modified_base           13
                        mod_base = OTHER
                        note = 2'-O-methylcytidine
modified_base           18
                        mod_base = OTHER
                        note = 2'-O-methylguanosine
modified_base           2
                        mod_base = OTHER
                        note = 2'-fluorouridine phosphorothioate
```

```
modified_base          14
                       mod_base = OTHER
                       note = 2'-fluoroguanosine
modified_base          19
                       mod_base = OTHER
                       note = 2'-O-methyladenosine phosphorothioate
modified_base          4
                       mod_base = OTHER
                       note = 2'-O-methylcytidine
modified_base          10
                       mod_base = OTHER
                       note = 2'-O-methylcytidine
modified_base          21
                       mod_base = OTHER
                       note = 2'-O-methyluridine
modified_base          3
                       mod_base = OTHER
                       note = 2'-O-methylguanosine
modified_base          1
                       mod_base = OTHER
                       note = 2'-fluorouridine phosphorothioate
modified_base          6
                       mod_base = OTHER
                       note = 2'-fluorouridine
modified_base          16
                       mod_base = OTHER
                       note = 2'-fluorocytidine
modified_base          15
                       mod_base = OTHER
                       note = 2'-O-methyluridine
modified_base          8
                       mod_base = OTHER
                       note = 2'-O-methylguanosine
modified_base          7
                       mod_base = OTHER
                       note = 2'-O-methyladenosine
modified_base          11
                       mod_base = OTHER
                       note = 2'-O-methyladenosine
source                 1..21
                       mol_type = other RNA
                       organism = synthetic construct
modified_base          17
                       mod_base = OTHER
                       note = 2'-O-methylguanosine
modified_base          20
                       mod_base = OTHER
                       note = 2'-O-methyluridine phosphorothioate
modified_base          12
                       mod_base = OTHER
                       note = 2'-O-methylguanosine
SEQUENCE: 272
ttgcctagac agcgtcggat t                                          21

SEQ ID NO: 273         moltype = RNA  length = 21
FEATURE                Location/Qualifiers
modified_base          20
                       mod_base = OTHER
                       note = 2'-O-methyluridine phosphorothioate
source                 1..21
                       mol_type = other RNA
                       organism = synthetic construct
modified_base          16
                       mod_base = OTHER
                       note = 2'-fluorouridine
modified_base          13
                       mod_base = OTHER
                       note = 2'-O-methylguanosine
modified_base          14
                       mod_base = OTHER
                       note = 2'-fluorocytidine
modified_base          15
                       mod_base = OTHER
                       note = 2'-O-methylguanosine
modified_base          6
                       mod_base = OTHER
                       note = 2'-fluorocytidine
modified_base          5
                       mod_base = OTHER
```

```
                         note = 2'-O-methylcytidine
modified_base            9
                         mod_base = OTHER
                         note = 2'-O-methylguanosine
modified_base            11
                         mod_base = OTHER
                         note = 2'-O-methylcytidine
modified_base            19
                         mod_base = OTHER
                         note = 2'-O-methylguanosine phosphorothioate
modified_base            4
                         mod_base = OTHER
                         note = 2'-O-methylguanosine
modified_base            12
                         mod_base = OTHER
                         note = 2'-O-methyladenosine
modified_base            10
                         mod_base = OTHER
                         note = 2'-O-methyladenosine
modified_base            2
                         mod_base = OTHER
                         note = 2'-fluorouridine phosphorothioate
modified_base            21
                         mod_base = OTHER
                         note = 2'-O-methyluridine
modified_base            18
                         mod_base = OTHER
                         note = 2'-O-methylguanosine
modified_base            8
                         mod_base = OTHER
                         note = 2'-O-methyladenosine
modified_base            1
                         mod_base = OTHER
                         note = 2'-fluorouridine phosphorothioate
modified_base            17
                         mod_base = OTHER
                         note = 2'-O-methylcytidine
modified_base            7
                         mod_base = OTHER
                         note = 2'-O-methyluridine
modified_base            3
                         mod_base = OTHER
                         note = 2'-O-methyluridine
SEQUENCE: 273
tttgcctaga cagcgtcggt t                                       21

SEQ ID NO: 274           moltype = RNA  length = 21
FEATURE                  Location/Qualifiers
modified_base            16
                         mod_base = OTHER
                         note = 2'-fluoroguanosine
modified_base            7
                         mod_base = OTHER
                         note = 2'-O-methylguanosine
modified_base            19
                         mod_base = OTHER
                         note = 2'-O-methyluridine phosphorothioate
source                   1..21
                         mol_type = other RNA
                         organism = synthetic construct
modified_base            20
                         mod_base = OTHER
                         note = 2'-O-methyluridine phosphorothioate
modified_base            4
                         mod_base = OTHER
                         note = 2'-O-methyluridine
modified_base            14
                         mod_base = OTHER
                         note = 2'-fluorocytidine
modified_base            15
                         mod_base = OTHER
                         note = 2'-O-methyladenosine
modified_base            12
                         mod_base = OTHER
                         note = 2'-O-methylguanosine
modified_base            5
                         mod_base = OTHER
                         note = 2'-O-methyluridine
modified_base            17
```

```
                        mod_base = OTHER
                        note = 2'-O-methylcytidine
modified_base           11
                        mod_base = OTHER
                        note = 2'-O-methyladenosine
modified_base           2
                        mod_base = OTHER
                        note = 2'-fluoroguanosine phosphorothioate
modified_base           9
                        mod_base = OTHER
                        note = 2'-O-methylcytidine
modified_base           3
                        mod_base = OTHER
                        note = 2'-O-methylguanosine
modified_base           1
                        mod_base = OTHER
                        note = 2'-fluorouridine phosphorothioate
modified_base           8
                        mod_base = OTHER
                        note = 2'-O-methylcytidine
modified_base           6
                        mod_base = OTHER
                        note = 2'-fluorouridine
modified_base           13
                        mod_base = OTHER
                        note = 2'-O-methyladenosine
modified_base           10
                        mod_base = OTHER
                        note = 2'-O-methyluridine
modified_base           21
                        mod_base = OTHER
                        note = 2'-O-methyluridine
modified_base           18
                        mod_base = OTHER
                        note = 2'-O-methylguanosine
SEQUENCE: 274
tggtttgcct agacagcgtt t                                                21

SEQ ID NO: 275          moltype = RNA  length = 21
FEATURE                 Location/Qualifiers
modified_base           21
                        mod_base = OTHER
                        note = 2'-O-methyluridine
modified_base           3
                        mod_base = OTHER
                        note = 2'-O-methyladenosine
modified_base           18
                        mod_base = OTHER
                        note = 2'-O-methyluridine
modified_base           13
                        mod_base = OTHER
                        note = 2'-O-methylcytidine
modified_base           4
                        mod_base = OTHER
                        note = 2'-O-methyladenosine
modified_base           9
                        mod_base = OTHER
                        note = 2'-O-methyladenosine
modified_base           11
                        mod_base = OTHER
                        note = 2'-O-methyluridine
modified_base           7
                        mod_base = OTHER
                        note = 2'-O-methylcytidine
modified_base           16
                        mod_base = OTHER
                        note = 2'-fluoroguanosine
modified_base           10
                        mod_base = OTHER
                        note = 2'-O-methyladenosine
modified_base           8
                        mod_base = OTHER
                        note = 2'-O-methyluridine
modified_base           1
                        mod_base = OTHER
                        note = 2'-fluorouridine phosphorothioate
modified_base           2
                        mod_base = OTHER
                        note = 2'-fluorouridine phosphorothioate
```

```
modified_base          12
                       mod_base = OTHER
                       note = 2'-O-methylcytidine
modified_base          15
                       mod_base = OTHER
                       note = 2'-O-methylguanosine
modified_base          6
                       mod_base = OTHER
                       note = 2'-fluorouridine
modified_base          19
                       mod_base = OTHER
                       note = 2'-O-methyluridine phosphorothioate
modified_base          14
                       mod_base = OTHER
                       note = 2'-fluoroadenosine
source                 1..21
                       mol_type = other RNA
                       organism = synthetic construct
modified_base          17
                       mod_base = OTHER
                       note = 2'-O-methyluridine
modified_base          20
                       mod_base = OTHER
                       note = 2'-O-methyluridine phosphorothioate
modified_base          5
                       mod_base = OTHER
                       note = 2'-O-methylcytidine
SEQUENCE: 275
ttaactctaa tccaggtttt t                                              21

SEQ ID NO: 276         moltype = RNA  length = 21
FEATURE                Location/Qualifiers
modified_base          8
                       mod_base = OTHER
                       note = 2'-O-methyluridine
modified_base          9
                       mod_base = OTHER
                       note = 2'-O-methylcytidine
modified_base          20
                       mod_base = OTHER
                       note = 2'-O-methyluridine phosphorothioate
modified_base          7
                       mod_base = OTHER
                       note = 2'-O-methyladenosine
modified_base          12
                       mod_base = OTHER
                       note = 2'-O-methyluridine
modified_base          5
                       mod_base = OTHER
                       note = 2'-O-methylcytidine
source                 1..21
                       mol_type = other RNA
                       organism = synthetic construct
modified_base          1
                       mod_base = OTHER
                       note = 2'-fluorouridine phosphorothioate
modified_base          3
                       mod_base = OTHER
                       note = 2'-O-methyladenosine
modified_base          6
                       mod_base = OTHER
                       note = 2'-fluoroguanosine
modified_base          19
                       mod_base = OTHER
                       note = 2'-O-methylguanosine phosphorothioate
modified_base          15
                       mod_base = OTHER
                       note = 2'-O-methylcytidine
modified_base          21
                       mod_base = OTHER
                       note = 2'-O-methyluridine
modified_base          13
                       mod_base = OTHER
                       note = 2'-O-methylcytidine
modified_base          2
                       mod_base = OTHER
                       note = 2'-fluoroadenosine phosphorothioate
modified_base          4
                       mod_base = OTHER
```

-continued

```
                          note = 2'-O-methylguanosine
modified_base             14
                          mod_base = OTHER
                          note = 2'-fluorouridine
modified_base             16
                          mod_base = OTHER
                          note = 2'-fluoroadenosine
modified_base             18
                          mod_base = OTHER
                          note = 2'-O-methyladenosine
modified_base             11
                          mod_base = OTHER
                          note = 2'-O-methyluridine
modified_base             17
                          mod_base = OTHER
                          note = 2'-O-methyladenosine
modified_base             10
                          mod_base = OTHER
                          note = 2'-O-methylcytidine
SEQUENCE: 276
taagcgatcc ttctcaaagt t                                       21

SEQ ID NO: 277            moltype = RNA  length = 21
FEATURE                   Location/Qualifiers
modified_base             16
                          mod_base = OTHER
                          note = 2'-fluorocytidine
modified_base             1
                          mod_base = OTHER
                          note = 2'-fluorouridine phosphorothioate
modified_base             13
                          mod_base = OTHER
                          note = 2'-O-methyluridine
modified_base             14
                          mod_base = OTHER
                          note = 2'-fluoroguanosine
modified_base             9
                          mod_base = OTHER
                          note = 2'-O-methylcytidine
modified_base             5
                          mod_base = OTHER
                          note = 2'-O-methyladenosine
modified_base             6
                          mod_base = OTHER
                          note = 2'-fluorouridine
modified_base             10
                          mod_base = OTHER
                          note = 2'-O-methylcytidine
modified_base             21
                          mod_base = OTHER
                          note = 2'-O-methyluridine
modified_base             18
                          mod_base = OTHER
                          note = 2'-O-methylguanosine
modified_base             4
                          mod_base = OTHER
                          note = 2'-O-methylguanosine
modified_base             20
                          mod_base = OTHER
                          note = 2'-O-methyluridine phosphorothioate
modified_base             17
                          mod_base = OTHER
                          note = 2'-O-methylguanosine
modified_base             2
                          mod_base = OTHER
                          note = 2'-fluoroguanosine phosphorothioate
modified_base             15
                          mod_base = OTHER
                          note = 2'-O-methylcytidine
source                    1..21
                          mol_type = other RNA
                          organism = synthetic construct
modified_base             8
                          mod_base = OTHER
                          note = 2'-O-methylcytidine
modified_base             11
                          mod_base = OTHER
                          note = 2'-O-methyluridine
modified_base             12
```

```
                         mod_base = OTHER
                         note = 2'-O-methylcytidine
modified_base            19
                         mod_base = OTHER
                         note = 2'-O-methylcytidine phosphorothioate
modified_base            3
                         mod_base = OTHER
                         note = 2'-O-methyladenosine
modified_base            7
                         mod_base = OTHER
                         note = 2'-O-methylcytidine
SEQUENCE: 277
tgagatcccc tctgccggct t                                            21

SEQ ID NO: 278           moltype = RNA  length = 21
FEATURE                  Location/Qualifiers
modified_base            12
                         mod_base = OTHER
                         note = 2'-O-methylcytidine
modified_base            3
                         mod_base = OTHER
                         note = 2'-O-methylcytidine
modified_base            1
                         mod_base = OTHER
                         note = 2'-fluorouridine phosphorothioate
modified_base            16
                         mod_base = OTHER
                         note = 2'-fluoroguanosine
modified_base            18
                         mod_base = OTHER
                         note = 2'-O-methylcytidine
modified_base            7
                         mod_base = OTHER
                         note = 2'-O-methylcytidine
modified_base            10
                         mod_base = OTHER
                         note = 2'-O-methylcytidine
modified_base            14
                         mod_base = OTHER
                         note = 2'-fluorouridine
modified_base            17
                         mod_base = OTHER
                         note = 2'-O-methylcytidine
modified_base            8
                         mod_base = OTHER
                         note = 2'-O-methyladenosine
modified_base            2
                         mod_base = OTHER
                         note = 2'-fluoroguanosine phosphorothioate
source                   1..21
                         mol_type = other RNA
                         organism = synthetic construct
modified_base            19
                         mod_base = OTHER
                         note = 2'-O-methylcytidine phosphorothioate
modified_base            20
                         mod_base = OTHER
                         note = 2'-O-methyluridine phosphorothioate
modified_base            21
                         mod_base = OTHER
                         note = 2'-O-methyluridine
modified_base            6
                         mod_base = OTHER
                         note = 2'-fluoroguanosine
modified_base            13
                         mod_base = OTHER
                         note = 2'-O-methyluridine
modified_base            5
                         mod_base = OTHER
                         note = 2'-O-methyladenosine
modified_base            9
                         mod_base = OTHER
                         note = 2'-O-methylcytidine
modified_base            11
                         mod_base = OTHER
                         note = 2'-O-methylcytidine
modified_base            4
                         mod_base = OTHER
                         note = 2'-O-methyladenosine
```

```
modified_base          15
                       mod_base = OTHER
                       note = 2'-O-methylguanosine
SEQUENCE: 278
tgcaagcacc ccttggccct t                                            21

SEQ ID NO: 279         moltype = RNA  length = 21
FEATURE                Location/Qualifiers
modified_base          3
                       mod_base = OTHER
                       note = 2'-O-methylcytidine
modified_base          20
                       mod_base = OTHER
                       note = 2'-O-methyluridine phosphorothioate
modified_base          2
                       mod_base = OTHER
                       note = 2'-fluoroguanosine phosphorothioate
modified_base          1
                       mod_base = OTHER
                       note = 2'-fluorouridine phosphorothioate
modified_base          21
                       mod_base = OTHER
                       note = 2'-O-methyluridine
modified_base          16
                       mod_base = OTHER
                       note = 2'-fluorouridine
modified_base          19
                       mod_base = OTHER
                       note = 2'-O-methylcytidine phosphorothioate
modified_base          15
                       mod_base = OTHER
                       note = 2'-O-methyluridine
modified_base          6
                       mod_base = OTHER
                       note = 2'-fluoroadenosine
modified_base          7
                       mod_base = OTHER
                       note = 2'-O-methyladenosine
modified_base          18
                       mod_base = OTHER
                       note = 2'-O-methylguanosine
modified_base          14
                       mod_base = OTHER
                       note = 2'-fluorocytidine
modified_base          9
                       mod_base = OTHER
                       note = 2'-O-methylcytidine
modified_base          17
                       mod_base = OTHER
                       note = 2'-O-methylguanosine
modified_base          10
                       mod_base = OTHER
                       note = 2'-O-methyladenosine
modified_base          4
                       mod_base = OTHER
                       note = 2'-O-methylguanosine
modified_base          5
                       mod_base = OTHER
                       note = 2'-O-methylcytidine
modified_base          12
                       mod_base = OTHER
                       note = 2'-O-methylcytidine
source                 1..21
                       mol_type = other RNA
                       organism = synthetic construct
modified_base          13
                       mod_base = OTHER
                       note = 2'-O-methylcytidine
modified_base          11
                       mod_base = OTHER
                       note = 2'-O-methylcytidine
modified_base          8
                       mod_base = OTHER
                       note = 2'-O-methylguanosine
SEQUENCE: 279
tgcgcaagca cccccttggct t                                           21

SEQ ID NO: 280         moltype = RNA  length = 21
FEATURE                Location/Qualifiers
```

```
source               1..21
                     mol_type = other RNA
                     organism = synthetic construct
modified_base        13
                     mod_base = OTHER
                     note = 2'-O-methylcytidine
modified_base        8
                     mod_base = OTHER
                     note = 2'-O-methylguanosine
modified_base        9
                     mod_base = OTHER
                     note = 2'-O-methyladenosine
modified_base        17
                     mod_base = OTHER
                     note = 2'-O-methylcytidine
modified_base        18
                     mod_base = OTHER
                     note = 2'-O-methyladenosine
modified_base        11
                     mod_base = OTHER
                     note = 2'-O-methylguanosine
modified_base        7
                     mod_base = OTHER
                     note = 2'-O-methylguanosine
modified_base        4
                     mod_base = OTHER
                     note = 2'-O-methylcytidine
modified_base        1
                     mod_base = OTHER
                     note = 2'-fluorouridine phosphorothioate
modified_base        19
                     mod_base = OTHER
                     note = 2'-O-methyluridine phosphorothioate
modified_base        20
                     mod_base = OTHER
                     note = 2'-O-methyluridine phosphorothioate
modified_base        15
                     mod_base = OTHER
                     note = 2'-O-methyluridine
modified_base        12
                     mod_base = OTHER
                     note = 2'-O-methylcytidine
modified_base        3
                     mod_base = OTHER
                     note = 2'-O-methylguanosine
modified_base        21
                     mod_base = OTHER
                     note = 2'-O-methyluridine
modified_base        2
                     mod_base = OTHER
                     note = 2'-fluorocytidine phosphorothioate
modified_base        16
                     mod_base = OTHER
                     note = 2'-fluoroguanosine
modified_base        14
                     mod_base = OTHER
                     note = 2'-fluorouridine
modified_base        6
                     mod_base = OTHER
                     note = 2'-fluoroguanosine
modified_base        10
                     mod_base = OTHER
                     note = 2'-O-methyluridine
modified_base        5
                     mod_base = OTHER
                     note = 2'-O-methylcytidine
SEQUENCE: 280
tcgccgggat gccttgcatt t                                     21

SEQ ID NO: 281       moltype = AA  length = 9
FEATURE              Location/Qualifiers
source               1..9
                     mol_type = protein
                     organism = synthetic construct
SEQUENCE: 281
YTFTNYWMH                                                   9

SEQ ID NO: 282       moltype = AA  length = 17
FEATURE              Location/Qualifiers
```

```
source                  1..17
                        mol_type = protein
                        organism = synthetic construct
SEQUENCE: 282
EINPINGRSN YAQKFQG                                              17

SEQ ID NO: 283          moltype = AA  length = 7
FEATURE                 Location/Qualifiers
source                  1..7
                        mol_type = protein
                        organism = synthetic construct
SEQUENCE: 283
GTRAMHY                                                         7

SEQ ID NO: 284          moltype = AA  length = 17
FEATURE                 Location/Qualifiers
source                  1..17
                        mol_type = protein
                        organism = synthetic construct
SEQUENCE: 284
EINPINGRSN YAEKFQG                                              17

SEQ ID NO: 285          moltype = AA  length = 17
FEATURE                 Location/Qualifiers
source                  1..17
                        mol_type = protein
                        organism = synthetic construct
SEQUENCE: 285
EINPIQGRSN YAEKFQG                                              17

SEQ ID NO: 286          moltype = AA  length = 11
FEATURE                 Location/Qualifiers
source                  1..11
                        mol_type = protein
                        organism = synthetic construct
SEQUENCE: 286
RTSENIYNNL A                                                    11

SEQ ID NO: 287          moltype = AA  length = 7
FEATURE                 Location/Qualifiers
source                  1..7
                        mol_type = protein
                        organism = synthetic construct
SEQUENCE: 287
AATNLAD                                                         7

SEQ ID NO: 288          moltype = AA  length = 9
FEATURE                 Location/Qualifiers
source                  1..9
                        mol_type = protein
                        organism = synthetic construct
SEQUENCE: 288
QHFWGTPLT                                                       9

SEQ ID NO: 289          moltype = AA  length = 7
FEATURE                 Location/Qualifiers
source                  1..7
                        mol_type = protein
                        organism = synthetic construct
SEQUENCE: 289
AATNLAE                                                         7

SEQ ID NO: 290          moltype = AA  length = 10
FEATURE                 Location/Qualifiers
source                  1..10
                        mol_type = protein
                        organism = synthetic construct
SEQUENCE: 290
QHFWGTPLTF                                                      10

SEQ ID NO: 291          moltype = AA  length = 11
FEATURE                 Location/Qualifiers
source                  1..11
                        mol_type = protein
                        organism = synthetic construct
SEQUENCE: 291
RTSENIYSNL A                                                    11

SEQ ID NO: 292          moltype = AA  length = 7
```

```
FEATURE                Location/Qualifiers
source                 1..7
                       mol_type = protein
                       organism = synthetic construct
SEQUENCE: 292
AGTNLAD                                                           7

SEQ ID NO: 293         moltype = AA  length = 116
FEATURE                Location/Qualifiers
source                 1..116
                       mol_type = protein
                       organism = synthetic construct
SEQUENCE: 293
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSS      116

SEQ ID NO: 294         moltype = AA  length = 116
FEATURE                Location/Qualifiers
source                 1..116
                       mol_type = protein
                       organism = synthetic construct
SEQUENCE: 294
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSS      116

SEQ ID NO: 295         moltype = AA  length = 116
FEATURE                Location/Qualifiers
source                 1..116
                       mol_type = protein
                       organism = synthetic construct
SEQUENCE: 295
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSS      116

SEQ ID NO: 296         moltype = AA  length = 116
FEATURE                Location/Qualifiers
source                 1..116
                       mol_type = protein
                       organism = synthetic construct
SEQUENCE: 296
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSS      116

SEQ ID NO: 297         moltype = AA  length = 116
FEATURE                Location/Qualifiers
source                 1..116
                       mol_type = protein
                       organism = synthetic construct
SEQUENCE: 297
QVQLQQPGAE LVKPGASVKL SCKASGYTFT NYWMHWVKQR PGQGLEWIGE INPINGRSNY  60
GERFKTKATL TVDKSSSTAY MQLSSLTSED SAVYYCARGT RAMHYWGQGT SVTVSS      116

SEQ ID NO: 298         moltype = AA  length = 107
FEATURE                Location/Qualifiers
source                 1..107
                       mol_type = protein
                       organism = synthetic construct
SEQUENCE: 298
DIQMTQSPSS LSASVGDRVT ITCRTSENIY NNLAWYQQKP GKSPKLLIYA ATNLADGVPS  60
RFSGSGSGTD YTLTISSLQP EDFATYYCQH FWGTPLTFGG GTKVEIK                107

SEQ ID NO: 299         moltype = AA  length = 107
FEATURE                Location/Qualifiers
source                 1..107
                       mol_type = protein
                       organism = synthetic construct
SEQUENCE: 299
DIQMTQSPSS LSASVGDRVT ITCRTSENIY NNLAWYQQKP GKAPKLLIYA ATNLADGVPS  60
RFSGSGSGTD YTLTISSLQP EDFATYYCQH FWGTPLTFGG GTKVEIK                107

SEQ ID NO: 300         moltype = AA  length = 107
FEATURE                Location/Qualifiers
source                 1..107
                       mol_type = protein
                       organism = synthetic construct
SEQUENCE: 300
DIQMTQSPSS LSASVGDRVT ITCRTSENIY NNLAWYQQKP GKAPKLLIYA ATNLAEGVPS  60
RFSGSGSGTD YTLTISSLQP EDFATYYCQH FWGTPLTFGG GTKVEIK                107
```

-continued

```
SEQ ID NO: 301          moltype = AA  length = 107
FEATURE                 Location/Qualifiers
source                  1..107
                        mol_type = protein
                        organism = synthetic construct
SEQUENCE: 301
DIQMTQSPSS LSASVGDRVT ITCRTSENIY SNLAWYQQKP GKAPKLLIYA GTNLADGVPS  60
RFSGSGSGTD YTLTISSLQP EDFANYYCQH FWGTPLTFGG GTKVEIK                107

SEQ ID NO: 302          moltype = AA  length = 107
FEATURE                 Location/Qualifiers
source                  1..107
                        mol_type = protein
                        organism = synthetic construct
SEQUENCE: 302
DIQMTQSPAS LSVSVGETVT ITCRTSENIY NNLAWYQQKQ GKSPQLLVYA ATNLADGVPS  60
RFSGSGSGTQ YSLKINSLQS EDFGNYYCQH FWGTPLTFGA GTKLELK                107

SEQ ID NO: 303          moltype = AA  length = 445
FEATURE                 Location/Qualifiers
source                  1..445
                        mol_type = protein
                        organism = synthetic construct
SEQUENCE: 303
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 304          moltype = AA  length = 445
FEATURE                 Location/Qualifiers
source                  1..445
                        mol_type = protein
                        organism = synthetic construct
SEQUENCE: 304
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 305          moltype = AA  length = 445
FEATURE                 Location/Qualifiers
source                  1..445
                        mol_type = protein
                        organism = synthetic construct
SEQUENCE: 305
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC GVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 306          moltype = AA  length = 445
FEATURE                 Location/Qualifiers
source                  1..445
                        mol_type = protein
                        organism = synthetic construct
SEQUENCE: 306
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKARPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 307          moltype = AA  length = 445
```

```
FEATURE                 Location/Qualifiers
source                  1..445
                        mol_type = protein
                        organism = synthetic construct
SEQUENCE: 307
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 308          moltype = AA  length = 445
FEATURE                 Location/Qualifiers
source                  1..445
                        mol_type = protein
                        organism = synthetic construct
SEQUENCE: 308
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVAVSHEDP EVKFNWYVDG VEVHNAKTKP REEQYGSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 309          moltype = AA  length = 445
FEATURE                 Location/Qualifiers
source                  1..445
                        mol_type = protein
                        organism = synthetic construct
SEQUENCE: 309
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 310          moltype = AA  length = 445
FEATURE                 Location/Qualifiers
source                  1..445
                        mol_type = protein
                        organism = synthetic construct
SEQUENCE: 310
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 311          moltype = AA  length = 445
FEATURE                 Location/Qualifiers
source                  1..445
                        mol_type = protein
                        organism = synthetic construct
SEQUENCE: 311
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC GVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 312          moltype = AA  length = 445
FEATURE                 Location/Qualifiers
source                  1..445
                        mol_type = protein
                        organism = synthetic construct
```

```
SEQUENCE: 312
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKARPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 313          moltype = AA  length = 445
FEATURE                 Location/Qualifiers
source                  1..445
                        mol_type = protein
                        organism = synthetic construct
SEQUENCE: 313
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 314          moltype = AA  length = 445
FEATURE                 Location/Qualifiers
source                  1..445
                        mol_type = protein
                        organism = synthetic construct
SEQUENCE: 314
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVAVSHEDP EVKFNWYVDG VEVHNAKTKP REEQYGSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 315          moltype = AA  length = 445
FEATURE                 Location/Qualifiers
source                  1..445
                        mol_type = protein
                        organism = synthetic construct
SEQUENCE: 315
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 316          moltype = AA  length = 445
FEATURE                 Location/Qualifiers
source                  1..445
                        mol_type = protein
                        organism = synthetic construct
SEQUENCE: 316
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 317          moltype = AA  length = 445
FEATURE                 Location/Qualifiers
source                  1..445
                        mol_type = protein
                        organism = synthetic construct
SEQUENCE: 317
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
```

```
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC GVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 318          moltype = AA  length = 445
FEATURE                 Location/Qualifiers
source                  1..445
                        mol_type = protein
                        organism = synthetic construct
SEQUENCE: 318
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKARPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 319          moltype = AA  length = 445
FEATURE                 Location/Qualifiers
source                  1..445
                        mol_type = protein
                        organism = synthetic construct
SEQUENCE: 319
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 320          moltype = AA  length = 445
FEATURE                 Location/Qualifiers
source                  1..445
                        mol_type = protein
                        organism = synthetic construct
SEQUENCE: 320
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVAVSHEDP EVKFNWYVDG VEVHNAKTKP REEQYGSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 321          moltype = AA  length = 445
FEATURE                 Location/Qualifiers
source                  1..445
                        mol_type = protein
                        organism = synthetic construct
SEQUENCE: 321
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 322          moltype = AA  length = 445
FEATURE                 Location/Qualifiers
source                  1..445
                        mol_type = protein
                        organism = synthetic construct
SEQUENCE: 322
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
```

```
VFSCSVMHEA LHNHYTQKSL SLSPG                                   445

SEQ ID NO: 323          moltype = AA  length = 445
FEATURE                 Location/Qualifiers
source                  1..445
                        mol_type = protein
                        organism = synthetic construct
SEQUENCE: 323
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC GVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                   445

SEQ ID NO: 324          moltype = AA  length = 445
FEATURE                 Location/Qualifiers
source                  1..445
                        mol_type = protein
                        organism = synthetic construct
SEQUENCE: 324
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKARPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                   445

SEQ ID NO: 325          moltype = AA  length = 445
FEATURE                 Location/Qualifiers
source                  1..445
                        mol_type = protein
                        organism = synthetic construct
SEQUENCE: 325
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                   445

SEQ ID NO: 326          moltype = AA  length = 445
FEATURE                 Location/Qualifiers
source                  1..445
                        mol_type = protein
                        organism = synthetic construct
SEQUENCE: 326
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVAVSHEDP EVKFNWYVDG VEVHNAKTKP REEQYGSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                   445

SEQ ID NO: 327          moltype = AA  length = 214
FEATURE                 Location/Qualifiers
source                  1..214
                        mol_type = protein
                        organism = synthetic construct
SEQUENCE: 327
DIQMTQSPSS LSASVGDRVT ITCRTSENIY NNLAWYQQKP GKSPKLLIYA ATNLADGVPS  60
RFSGSGSGTD YTLTISSLQP EDFATYYCQH FWGTPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                         214

SEQ ID NO: 328          moltype = AA  length = 214
FEATURE                 Location/Qualifiers
source                  1..214
                        mol_type = protein
                        organism = synthetic construct
SEQUENCE: 328
```

```
DIQMTQSPSS LSASVGDRVT ITCRTSENIY NNLAWYQQKP GKAPKLLIYA ATNLADGVPS  60
RFSGSGSGTD YTLTISSLQP EDFATYYCQH FWGTPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 329          moltype = AA  length = 214
FEATURE                 Location/Qualifiers
source                  1..214
                        mol_type = protein
                        organism = synthetic construct
SEQUENCE: 329
DIQMTQSPSS LSASVGDRVT ITCRTSENIY NNLAWYQQKP GKAPKLLIYA ATNLAEGVPS  60
RFSGSGSGTD YTLTISSLQP EDFATYYCQH FWGTPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 330          moltype = AA  length = 214
FEATURE                 Location/Qualifiers
source                  1..214
                        mol_type = protein
                        organism = synthetic construct
SEQUENCE: 330
DIQMTQSPSS LSASVGDRVT ITCRTSENIY SNLAWYQQKP GKAPKLLIYA GTNLADGVPS  60
RFSGSGSGTD YTLTISSLQP EDFANYYCQH FWGTPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 331          moltype = AA  length = 24
FEATURE                 Location/Qualifiers
source                  1..24
                        mol_type = protein
                        organism = synthetic construct
SEQUENCE: 331
CGIFGEIEEL IEEGLENLID WGNA                                         24

SEQ ID NO: 332          moltype = AA  length = 24
FEATURE                 Location/Qualifiers
source                  1..24
                        mol_type = protein
                        organism = synthetic construct
SEQUENCE: 332
GLFEAIEGFI ENGWEGMIDG WYGC                                         24

SEQ ID NO: 333          moltype = AA  length = 27
FEATURE                 Location/Qualifiers
source                  1..27
                        mol_type = protein
                        organism = synthetic construct
SEQUENCE: 333
GLFEAIEGFI ENGWEGMIWD YGSGSCG                                      27

SEQ ID NO: 334          moltype = AA  length = 23
FEATURE                 Location/Qualifiers
SITE                    23
                        note = Glycine hexaethylene glycol amide
source                  1..23
                        mol_type = protein
                        organism = synthetic construct
SEQUENCE: 334
GLFEAIEGFI ENGWEGMIDG WYG                                          23

SEQ ID NO: 335          moltype = AA  length = 27
FEATURE                 Location/Qualifiers
source                  1..27
                        mol_type = protein
                        organism = synthetic construct
CARBOHYD                27
                        note = Lysine N-linked
                         N-acetylgalactosaminyl-(1-3)-N-acetylgalactosamine
SEQUENCE: 335
GLFEAIEGFI ENGWEGMIWD YGSGSCK                                      27

SEQ ID NO: 336          moltype = AA  length = 27
FEATURE                 Location/Qualifiers
source                  1..27
                        mol_type = protein
                        organism = synthetic construct
SEQUENCE: 336
CLIGAILKVL ATGLPTLISW IKNKRKQ                                      27
```

```
SEQ ID NO: 337          moltype = AA  length = 26
FEATURE                 Location/Qualifiers
source                  1..26
                        mol_type = protein
                        organism = synthetic construct
SEQUENCE: 337
GIGAVLKVLT TGLPALISWI KRKRQQ                                            26

SEQ ID NO: 338          moltype = AA  length = 13
FEATURE                 Location/Qualifiers
SITE                    13
                        note = Phenylalanine amide
source                  1..13
                        mol_type = protein
                        organism = synthetic construct
SEQUENCE: 338
IFGAIAGLLK NIF                                                          13

SEQ ID NO: 339          moltype = AA  length = 18
FEATURE                 Location/Qualifiers
source                  1..18
                        mol_type = protein
                        organism = synthetic construct
SEQUENCE: 339
FFGHLFKLAT KIIPSLFQ                                                     18

SEQ ID NO: 340          moltype = AA  length = 21
FEATURE                 Location/Qualifiers
source                  1..21
                        mol_type = protein
                        organism = synthetic construct
SEQUENCE: 340
KETWWETWWT EWSQPKKKRK V                                                 21

SEQ ID NO: 341          moltype = AA  length = 19
FEATURE                 Location/Qualifiers
source                  1..19
                        mol_type = protein
                        organism = synthetic construct
SEQUENCE: 341
LLIILRRRRI RKQAHAHSK                                                    19

SEQ ID NO: 342          moltype = AA  length = 26
FEATURE                 Location/Qualifiers
source                  1..26
                        mol_type = protein
                        organism = synthetic construct
SEQUENCE: 342
DPKGDPKGVT VTVTVTVTGK GDPKPD                                            26

SEQ ID NO: 343          moltype = AA  length = 17
FEATURE                 Location/Qualifiers
source                  1..17
                        mol_type = protein
                        organism = synthetic construct
SEQUENCE: 343
CSIPPEVKFN KPFVYLI                                                      17

SEQ ID NO: 344          moltype = AA  length = 27
FEATURE                 Location/Qualifiers
source                  1..27
                        mol_type = protein
                        organism = synthetic construct
SEQUENCE: 344
GWTLNSAGYL LGKINLKALA ALAKKIL                                           27

SEQ ID NO: 345          moltype = AA  length = 21
FEATURE                 Location/Qualifiers
source                  1..21
                        mol_type = protein
                        organism = synthetic construct
SEQUENCE: 345
AGYLLGKINL KALAALAKKI L                                                 21

SEQ ID NO: 346          moltype = AA  length = 17
FEATURE                 Location/Qualifiers
source                  1..17
                        mol_type = protein
```

```
                      organism = synthetic construct
SEQUENCE: 346
GALFLGFLGA AGSTMGA                                             17

SEQ ID NO: 347        moltype = AA  length = 20
FEATURE               Location/Qualifiers
source                1..20
                      mol_type = protein
                      organism = synthetic construct
SEQUENCE: 347
HGLASTLTRW AHYNALIRAF                                          20

SEQ ID NO: 348        moltype = AA  length = 20
FEATURE               Location/Qualifiers
source                1..20
                      mol_type = protein
                      organism = synthetic construct
SEQUENCE: 348
GLWRALWRLL RSLWRLLWRA                                          20

SEQ ID NO: 349        moltype = AA  length = 30
FEATURE               Location/Qualifiers
source                1..30
                      mol_type = protein
                      organism = synthetic construct
SEQUENCE: 349
WEAALAEALA EALAEHLAEA LAEALEALAA                               30

SEQ ID NO: 350        moltype = AA  length = 24
FEATURE               Location/Qualifiers
source                1..24
                      mol_type = protein
                      organism = synthetic construct
SEQUENCE: 350
GLFEAIEGFI ENGWEGMIDG WYGC                                     24

SEQ ID NO: 351        moltype = AA  length = 23
FEATURE               Location/Qualifiers
source                1..23
                      mol_type = protein
                      organism = synthetic construct
SEQUENCE: 351
GLFGAIAGFI ENGWEGMIDG WYG                                      23

SEQ ID NO: 352        moltype = AA  length = 36
FEATURE               Location/Qualifiers
source                1..36
                      mol_type = protein
                      organism = synthetic construct
SITE                  36
                      note = Lysine amide
SEQUENCE: 352
GLFGAIAGFI ENGWEGMIDG RQIKIWFQNR RMKWKK                        36

SEQ ID NO: 353        moltype = AA  length = 26
FEATURE               Location/Qualifiers
source                1..26
                      mol_type = protein
                      organism = synthetic construct
SEQUENCE: 353
GLFGAIAGFI ENGWEGMIDG SSKKKK                                   26

SEQ ID NO: 354        moltype = AA  length = 24
FEATURE               Location/Qualifiers
source                1..24
                      mol_type = protein
                      organism = synthetic construct
SEQUENCE: 354
GLFEAIAGFI ENGWEGMIDG GGYC                                     24

SEQ ID NO: 355        moltype = AA  length = 23
FEATURE               Location/Qualifiers
source                1..23
                      mol_type = protein
                      organism = synthetic construct
SEQUENCE: 355
GLFHAIAHFI HGGWHGLIHG WYG                                      23

SEQ ID NO: 356        moltype = AA  length = 30
```

```
FEATURE                Location/Qualifiers
SITE                   30
                       note = Alanine hexaethylene glycol amide
source                 1..30
                       mol_type = protein
                       organism = synthetic construct
SEQUENCE: 356
GLFEAIEGFI ENGWEGLAEA LAEALEALAA                                   30

SEQ ID NO: 357         moltype = AA  length = 29
FEATURE                Location/Qualifiers
source                 1..29
                       mol_type = protein
                       organism = synthetic construct
SEQUENCE: 357
KWKLFKKIGA VLKVLTTGYG RKKRRQRRR                                    29

SEQ ID NO: 358         moltype = AA  length = 16
FEATURE                Location/Qualifiers
source                 1..16
                       mol_type = protein
                       organism = synthetic construct
SEQUENCE: 358
RQIKIWFQNR RMKWKK                                                  16

SEQ ID NO: 359         moltype = AA  length = 13
FEATURE                Location/Qualifiers
source                 1..13
                       mol_type = protein
                       organism = synthetic construct
SEQUENCE: 359
GRKKRRQRRR PPQ                                                     13

SEQ ID NO: 360         moltype = AA  length = 18
FEATURE                Location/Qualifiers
source                 1..18
                       mol_type = protein
                       organism = synthetic construct
SEQUENCE: 360
LLIILRRRIR KQAHAHSK                                                18

SEQ ID NO: 361         moltype = AA  length = 27
FEATURE                Location/Qualifiers
source                 1..27
                       mol_type = protein
                       organism = synthetic construct
SEQUENCE: 361
GWTLNSAGYL LGKINLKALA ALAKKIL                                      27

SEQ ID NO: 362         moltype = AA  length = 27
FEATURE                Location/Qualifiers
source                 1..27
                       mol_type = protein
                       organism = synthetic construct
SEQUENCE: 362
GALFLGFLGA AGSTMGAWSQ PKKKRKV                                      27

SEQ ID NO: 363         moltype = AA  length = 21
FEATURE                Location/Qualifiers
source                 1..21
                       mol_type = protein
                       organism = synthetic construct
SEQUENCE: 363
KETWWETWWT EWSQPKKKRK V                                            21

SEQ ID NO: 364         moltype = AA  length = 12
FEATURE                Location/Qualifiers
VARIANT                1..12
                       note = This sequence may encompass 6-12 residues
source                 1..12
                       mol_type = protein
                       organism = synthetic construct
SEQUENCE: 364
RRRRRRRRRR RR                                                      12

SEQ ID NO: 365         moltype = AA  length = 18
FEATURE                Location/Qualifiers
source                 1..18
                       mol_type = protein
```

```
                       organism = synthetic construct
SEQUENCE: 365
KLALKLALKA LKAALKLA                                             18

SEQ ID NO: 366         moltype = AA  length = 9
FEATURE                Location/Qualifiers
source                 1..9
                       mol_type = protein
                       organism = synthetic construct
SEQUENCE: 366
RRWWRRWRR                                                       9

SEQ ID NO: 367         moltype = AA  length = 13
FEATURE                Location/Qualifiers
source                 1..13
                       mol_type = protein
                       organism = synthetic construct
SEQUENCE: 367
CGYGPKKKRK VGG                                                  13

SEQ ID NO: 368         moltype = AA  length = 8
FEATURE                Location/Qualifiers
source                 1..8
                       mol_type = protein
                       organism = synthetic construct
SEQUENCE: 368
KKKKKKKK                                                        8

SEQ ID NO: 369         moltype = AA  length = 22
FEATURE                Location/Qualifiers
source                 1..22
                       mol_type = protein
                       organism = synthetic construct
SEQUENCE: 369
MVRRFLVTLR IRRACGPPRV RV                                        22

SEQ ID NO: 370         moltype = AA  length = 28
FEATURE                Location/Qualifiers
source                 1..28
                       mol_type = protein
                       organism = synthetic construct
SEQUENCE: 370
LSTAADMQGV VTDGMASGLD KDYLKPDD                                  28

SEQ ID NO: 371         moltype = DNA  length = 19
FEATURE                Location/Qualifiers
source                 1..19
                       mol_type = other DNA
                       organism = synthetic construct
SEQUENCE: 371
ctgcctctcc accagccca                                            19

SEQ ID NO: 372         moltype = DNA  length = 19
FEATURE                Location/Qualifiers
source                 1..19
                       mol_type = other DNA
                       organism = synthetic construct
SEQUENCE: 372
tgggctggtg gagaggcag                                            19

SEQ ID NO: 373         moltype = DNA  length = 19
FEATURE                Location/Qualifiers
source                 1..19
                       mol_type = other DNA
                       organism = synthetic construct
SEQUENCE: 373
gcagagatgg agagaggaa                                            19

SEQ ID NO: 374         moltype = DNA  length = 19
FEATURE                Location/Qualifiers
source                 1..19
                       mol_type = other DNA
                       organism = synthetic construct
SEQUENCE: 374
ttcctctctc catctctgc                                            19

SEQ ID NO: 375         moltype = DNA  length = 19
FEATURE                Location/Qualifiers
source                 1..19
```

```
                        mol_type = other DNA
                        organism = synthetic construct
SEQUENCE: 375
gcggtttcct ccgggacaa                                                19

SEQ ID NO: 376          moltype = DNA  length = 19
FEATURE                 Location/Qualifiers
source                  1..19
                        mol_type = other DNA
                        organism = synthetic construct
SEQUENCE: 376
ttgtcccgga ggaaaccgc                                                19

SEQ ID NO: 377          moltype = DNA  length = 19
FEATURE                 Location/Qualifiers
source                  1..19
                        mol_type = other DNA
                        organism = synthetic construct
SEQUENCE: 377
ggacgacgga ggcgtgatt                                                19

SEQ ID NO: 378          moltype = DNA  length = 19
FEATURE                 Location/Qualifiers
source                  1..19
                        mol_type = other DNA
                        organism = synthetic construct
SEQUENCE: 378
aatcacgcct ccgtcgtcc                                                19

SEQ ID NO: 379          moltype = DNA  length = 25
FEATURE                 Location/Qualifiers
source                  1..25
                        mol_type = other DNA
                        organism = synthetic construct
SEQUENCE: 379
cgggcacccg gaaacatgca gggaa                                         25

SEQ ID NO: 380          moltype = DNA  length = 25
FEATURE                 Location/Qualifiers
source                  1..25
                        mol_type = other DNA
                        organism = synthetic construct
SEQUENCE: 380
ttccctgcat gtttccgggt gcccg                                         25

SEQ ID NO: 381          moltype = DNA  length = 19
FEATURE                 Location/Qualifiers
source                  1..19
                        mol_type = other DNA
                        organism = synthetic construct
SEQUENCE: 381
ccggaaacat gcagggaag                                                19

SEQ ID NO: 382          moltype = DNA  length = 19
FEATURE                 Location/Qualifiers
source                  1..19
                        mol_type = other DNA
                        organism = synthetic construct
SEQUENCE: 382
cttccctgca tgtttccgg                                                19

SEQ ID NO: 383          moltype = DNA  length = 19
FEATURE                 Location/Qualifiers
source                  1..19
                        mol_type = other DNA
                        organism = synthetic construct
SEQUENCE: 383
gaaatgaacg agagccaca                                                19

SEQ ID NO: 384          moltype = DNA  length = 19
FEATURE                 Location/Qualifiers
source                  1..19
                        mol_type = other DNA
                        organism = synthetic construct
SEQUENCE: 384
tgtggctctc gttcatttc                                                19

SEQ ID NO: 385          moltype = DNA  length = 25
FEATURE                 Location/Qualifiers
```

```
source                  1..25
                        mol_type = other DNA
                        organism = synthetic construct
SEQUENCE: 385
tggcacactc aagactccca cggag                                         25

SEQ ID NO: 386          moltype = DNA  length = 25
FEATURE                 Location/Qualifiers
source                  1..25
                        mol_type = other DNA
                        organism = synthetic construct
SEQUENCE: 386
ctccgtggga gtcttgagtg tgcca                                         25

SEQ ID NO: 387          moltype = DNA  length = 19
FEATURE                 Location/Qualifiers
source                  1..19
                        mol_type = other DNA
                        organism = synthetic construct
SEQUENCE: 387
ccacggaggt tcagttcca                                                19

SEQ ID NO: 388          moltype = DNA  length = 19
FEATURE                 Location/Qualifiers
source                  1..19
                        mol_type = other DNA
                        organism = synthetic construct
SEQUENCE: 388
tggaactgaa cctccgtgg                                                19

SEQ ID NO: 389          moltype = DNA  length = 19
FEATURE                 Location/Qualifiers
source                  1..19
                        mol_type = other DNA
                        organism = synthetic construct
SEQUENCE: 389
accaccacca ccaccacca                                                19

SEQ ID NO: 390          moltype = DNA  length = 19
FEATURE                 Location/Qualifiers
source                  1..19
                        mol_type = other DNA
                        organism = synthetic construct
SEQUENCE: 390
tggtggtggt ggtggtggt                                                19

SEQ ID NO: 391          moltype = DNA  length = 19
FEATURE                 Location/Qualifiers
source                  1..19
                        mol_type = other DNA
                        organism = synthetic construct
SEQUENCE: 391
cgccattcat gaaggggtg                                                19

SEQ ID NO: 392          moltype = DNA  length = 19
FEATURE                 Location/Qualifiers
source                  1..19
                        mol_type = other DNA
                        organism = synthetic construct
SEQUENCE: 392
cacccettca tgaatggcg                                                19

SEQ ID NO: 393          moltype = DNA  length = 19
FEATURE                 Location/Qualifiers
source                  1..19
                        mol_type = other DNA
                        organism = synthetic construct
SEQUENCE: 393
catgaagggg tggagcctg                                                19

SEQ ID NO: 394          moltype = DNA  length = 19
FEATURE                 Location/Qualifiers
source                  1..19
                        mol_type = other DNA
                        organism = synthetic construct
SEQUENCE: 394
caggctccac cccttcatg                                                19

SEQ ID NO: 395          moltype = DNA  length = 19
```

```
FEATURE                Location/Qualifiers
source                 1..19
                       mol_type = other DNA
                       organism = synthetic construct
SEQUENCE: 395
gagcctgctt tgagcggaa                                            19

SEQ ID NO: 396         moltype = DNA  length = 19
FEATURE                Location/Qualifiers
source                 1..19
                       mol_type = other DNA
                       organism = synthetic construct
SEQUENCE: 396
ttccgctcaa agcaggctc                                            19

SEQ ID NO: 397         moltype = DNA  length = 25
FEATURE                Location/Qualifiers
source                 1..25
                       mol_type = other DNA
                       organism = synthetic construct
SEQUENCE: 397
ccgagccttt gagaaggatc gcttt                                     25

SEQ ID NO: 398         moltype = DNA  length = 25
FEATURE                Location/Qualifiers
source                 1..25
                       mol_type = other DNA
                       organism = synthetic construct
SEQUENCE: 398
aaagcgatcc ttctcaaagg ctcgg                                     25

SEQ ID NO: 399         moltype = DNA  length = 19
FEATURE                Location/Qualifiers
source                 1..19
                       mol_type = other DNA
                       organism = synthetic construct
SEQUENCE: 399
ggcagggcgc ccgcgcagg                                            19

SEQ ID NO: 400         moltype = DNA  length = 19
FEATURE                Location/Qualifiers
source                 1..19
                       mol_type = other DNA
                       organism = synthetic construct
SEQUENCE: 400
cctgcgcggg cgccctgcc                                            19

SEQ ID NO: 401         moltype = DNA  length = 19
FEATURE                Location/Qualifiers
source                 1..19
                       mol_type = other DNA
                       organism = synthetic construct
SEQUENCE: 401
gatgattagt tcagagata                                            19

SEQ ID NO: 402         moltype = DNA  length = 19
FEATURE                Location/Qualifiers
source                 1..19
                       mol_type = other DNA
                       organism = synthetic construct
SEQUENCE: 402
tatctctgaa ctaatcatc                                            19

SEQ ID NO: 403         moltype = AA  length = 4
FEATURE                Location/Qualifiers
source                 1..4
                       mol_type = protein
                       organism = synthetic construct
SEQUENCE: 403
GGFG                                                            4

SEQ ID NO: 404         moltype = AA  length = 4
FEATURE                Location/Qualifiers
source                 1..4
                       mol_type = protein
                       organism = synthetic construct
SEQUENCE: 404
ALAL                                                            4
```

-continued

```
SEQ ID NO: 405          moltype = AA  length = 4
FEATURE                 Location/Qualifiers
source                  1..4
                        mol_type = protein
                        organism = synthetic construct
SEQUENCE: 405
GFLG                                                                      4

SEQ ID NO: 406          moltype = AA  length = 17
FEATURE                 Location/Qualifiers
source                  1..17
                        mol_type = protein
                        organism = synthetic construct
VARIANT                 13
                        note = Q or E
VARIANT                 6
                        note = N or Q
SEQUENCE: 406
EINPIXGRSN YAXKFQG                                                        17

SEQ ID NO: 407          moltype = AA  length = 11
FEATURE                 Location/Qualifiers
source                  1..11
                        mol_type = protein
                        organism = synthetic construct
VARIANT                 8
                        note = N or S
SEQUENCE: 407
RTSENIYXNL A                                                              11

SEQ ID NO: 408          moltype = AA  length = 7
FEATURE                 Location/Qualifiers
source                  1..7
                        mol_type = protein
                        organism = synthetic construct
VARIANT                 2
                        note = A or G
VARIANT                 7
                        note = D or E
SEQUENCE: 408
AXTNLAX                                                                   7

SEQ ID NO: 409          moltype = AA  length = 10
FEATURE                 Location/Qualifiers
source                  1..10
                        mol_type = protein
                        organism = synthetic construct
VARIANT                 10
                        note = F or absent
SEQUENCE: 409
QHFWGTPLTX                                                                10

SEQ ID NO: 410          moltype = AA  length = 7
FEATURE                 Location/Qualifiers
source                  1..7
                        mol_type = protein
                        organism = synthetic construct
VARIANT                 7
                        note = D or E
SEQUENCE: 410
AATNLAX                                                                   7

SEQ ID NO: 411          moltype =   length =
SEQUENCE: 411
000

SEQ ID NO: 412          moltype = RNA  length = 21
FEATURE                 Location/Qualifiers
source                  1..21
                        mol_type = other RNA
                        organism = synthetic construct
modified_base           9
                        mod_base = OTHER
                        note = 2'-O-methyluridine
modified_base           2
                        mod_base = OTHER
                        note = 2'-fluoroadenosine phosphorothioate
modified_base           5
                        mod_base = OTHER
```

```
                        note = 2'-O-methyladenosine
modified_base           11
                        mod_base = OTHER
                        note = 2'-O-methylcytidine
modified_base           1
                        mod_base = OTHER
                        note = 2'-O-methyluridine phosphorothioate
modified_base           3
                        mod_base = OTHER
                        note = 2'-O-methylcytidine
modified_base           7
                        mod_base = OTHER
                        note = 2'-O-methyluridine
modified_base           4
                        mod_base = OTHER
                        note = 2'-O-methylguanosine
modified_base           10
                        mod_base = OTHER
                        note = 2'-O-methylcytidine
modified_base           12
                        mod_base = OTHER
                        note = 2'-O-methylguanosine
modified_base           14
                        mod_base = OTHER
                        note = 2'-fluorocytidine
modified_base           18
                        mod_base = OTHER
                        note = 2'-O-methylguanosine
modified_base           8
                        mod_base = OTHER
                        note = 2'-O-methylcytidine
modified_base           15
                        mod_base = OTHER
                        note = 2'-O-methylguanosine
modified_base           16
                        mod_base = OTHER
                        note = 2'-fluorocytidine
modified_base           20
                        mod_base = OTHER
                        note = 2'-O-methyluridine phosphorothioate
modified_base           13
                        mod_base = OTHER
                        note = 2'-O-methyluridine
modified_base           19
                        mod_base = OTHER
                        note = 2'-O-methyluridine phosphorothioate
modified_base           6
                        mod_base = OTHER
                        note = 2'-fluoroguanosine
modified_base           21
                        mod_base = OTHER
                        note = 2'-O-methyluridine
modified_base           17
                        mod_base = OTHER
                        note = 2'-O-methylcytidine
SEQUENCE: 412
tacgagtctc cgtcgccgtt t                                              21

SEQ ID NO: 413          moltype = RNA  length = 21
FEATURE                 Location/Qualifiers
modified_base           5
                        mod_base = OTHER
                        note = 2'-O-methyladenosine
modified_base           21
                        mod_base = OTHER
                        note = 2'-O-methyluridine
modified_base           15
                        mod_base = OTHER
                        note = 2'-O-methylcytidine
modified_base           13
                        mod_base = OTHER
                        note = 2'-O-methyluridine
modified_base           17
                        mod_base = OTHER
                        note = 2'-O-methyluridine
modified_base           7
                        mod_base = OTHER
                        note = 2'-O-methylcytidine
modified_base           10
```

```
                         mod_base = OTHER
                         note = 2'-O-methylguanosine
modified_base            11
                         mod_base = OTHER
                         note = 2'-O-methyluridine
modified_base            18
                         mod_base = OTHER
                         note = 2'-O-methylcytidine
modified_base            6
                         mod_base = OTHER
                         note = 2'-fluoroadenosine
modified_base            3
                         mod_base = OTHER
                         note = 2'-O-methylcytidine
modified_base            8
                         mod_base = OTHER
                         note = 2'-O-methylguanosine
source                   1..21
                         mol_type = other RNA
                         organism = synthetic construct
modified_base            16
                         mod_base = OTHER
                         note = 2'-fluoroguanosine
modified_base            20
                         mod_base = OTHER
                         note = 2'-O-methyluridine phosphorothioate
modified_base            12
                         mod_base = OTHER
                         note = 2'-O-methylcytidine
modified_base            9
                         mod_base = OTHER
                         note = 2'-O-methyladenosine
modified_base            4
                         mod_base = OTHER
                         note = 2'-O-methyladenosine
modified_base            14
                         mod_base = OTHER
                         note = 2'-fluorocytidine
modified_base            1
                         mod_base = OTHER
                         note = 2'-O-methyluridine phosphorothioate
modified_base            2
                         mod_base = OTHER
                         note = 2'-fluorocytidine phosphorothioate
modified_base            19
                         mod_base = OTHER
                         note = 2'-O-methylguanosine phosphorothioate
SEQUENCE: 413
tccaaacgag tctccgtcgt t                                                21

SEQ ID NO: 414           moltype = RNA  length = 21
FEATURE                  Location/Qualifiers
modified_base            12
                         mod_base = OTHER
                         note = 2'-O-methyluridine
modified_base            3
                         mod_base = OTHER
                         note = 2'-O-methyladenosine
modified_base            8
                         mod_base = OTHER
                         note = 2'-O-methyluridine
modified_base            15
                         mod_base = OTHER
                         note = 2'-O-methylcytidine
modified_base            7
                         mod_base = OTHER
                         note = 2'-O-methyladenosine
modified_base            14
                         mod_base = OTHER
                         note = 2'-fluorouridine
modified_base            20
                         mod_base = OTHER
                         note = 2'-O-methyluridine phosphorothioate
modified_base            2
                         mod_base = OTHER
                         note = 2'-fluoroadenosine phosphorothioate
source                   1..21
                         mol_type = other RNA
                         organism = synthetic construct
```

```
modified_base          9
                       mod_base = OTHER
                       note = 2'-O-methylcytidine
modified_base          4
                       mod_base = OTHER
                       note = 2'-O-methylguanosine
modified_base          5
                       mod_base = OTHER
                       note = 2'-O-methylcytidine
modified_base          10
                       mod_base = OTHER
                       note = 2'-O-methylcytidine
modified_base          17
                       mod_base = OTHER
                       note = 2'-O-methyladenosine
modified_base          6
                       mod_base = OTHER
                       note = 2'-fluoroguanosine
modified_base          11
                       mod_base = OTHER
                       note = 2'-O-methyluridine
modified_base          21
                       mod_base = OTHER
                       note = 2'-O-methyluridine
modified_base          13
                       mod_base = OTHER
                       note = 2'-O-methylcytidine
modified_base          1
                       mod_base = OTHER
                       note = 2'-O-methyluridine phosphorothioate
modified_base          18
                       mod_base = OTHER
                       note = 2'-O-methyladenosine
modified_base          19
                       mod_base = OTHER
                       note = 2'-O-methylguanosine phosphorothioate
modified_base          16
                       mod_base = OTHER
                       note = 2'-fluoroadenosine
SEQUENCE: 414
taagcgatcc ttctcaaagt t                                     21

SEQ ID NO: 415         moltype = RNA  length = 21
FEATURE                Location/Qualifiers
modified_base          5
                       mod_base = OTHER
                       note = 2'-O-methylguanosine
modified_base          6
                       mod_base = OTHER
                       note = 2'-fluoroadenosine
modified_base          13
                       mod_base = OTHER
                       note = 2'-O-methyluridine
modified_base          2
                       mod_base = OTHER
                       note = 2'-fluoroadenosine phosphorothioate
modified_base          16
                       mod_base = OTHER
                       note = 2'-fluorocytidine
modified_base          9
                       mod_base = OTHER
                       note = 2'-O-methyluridine
modified_base          20
                       mod_base = OTHER
                       note = 2'-O-methyluridine phosphorothioate
modified_base          18
                       mod_base = OTHER
                       note = 2'-O-methylcytidine
modified_base          11
                       mod_base = OTHER
                       note = 2'-O-methylcytidine
source                 1..21
                       mol_type = other RNA
                       organism = synthetic construct
modified_base          3
                       mod_base = OTHER
                       note = 2'-O-methylguanosine
modified_base          12
                       mod_base = OTHER
```

```
                        note = 2'-O-methylcytidine
modified_base           8
                        mod_base = OTHER
                        note = 2'-O-methylcytidine
modified_base           10
                        mod_base = OTHER
                        note = 2'-O-methylcytidine
modified_base           7
                        mod_base = OTHER
                        note = 2'-O-methylguanosine
modified_base           14
                        mod_base = OTHER
                        note = 2'-fluorouridine
modified_base           19
                        mod_base = OTHER
                        note = 2'-O-methylguanosine phosphorothioate
modified_base           1
                        mod_base = OTHER
                        note = 2'-O-methyluridine phosphorothioate
modified_base           21
                        mod_base = OTHER
                        note = 2'-O-methyluridine
modified_base           4
                        mod_base = OTHER
                        note = 2'-O-methylcytidine
modified_base           15
                        mod_base = OTHER
                        note = 2'-O-methylguanosine
modified_base           17
                        mod_base = OTHER
                        note = 2'-O-methyladenosine
SEQUENCE: 415
tagcgagctc ccttgcacgt t                                              21

SEQ ID NO: 416          moltype = RNA  length = 21
FEATURE                 Location/Qualifiers
modified_base           11
                        mod_base = OTHER
                        note = 2'-O-methylcytidine
modified_base           18
                        mod_base = OTHER
                        note = 2'-O-methyladenosine
modified_base           4
                        mod_base = OTHER
                        note = 2'-O-methyluridine
modified_base           7
                        mod_base = OTHER
                        note = 2'-O-methyladenosine
modified_base           20
                        mod_base = OTHER
                        note = 2'-O-methyluridine phosphorothioate
modified_base           12
                        mod_base = OTHER
                        note = 2'-O-methylguanosine
modified_base           8
                        mod_base = OTHER
                        note = 2'-O-methylcytidine
source                  1..21
                        mol_type = other RNA
                        organism = synthetic construct
modified_base           13
                        mod_base = OTHER
                        note = 2'-O-methyluridine
modified_base           21
                        mod_base = OTHER
                        note = 2'-O-methyluridine
modified_base           16
                        mod_base = OTHER
                        note = 2'-fluoroguanosine
modified_base           14
                        mod_base = OTHER
                        note = 2'-fluorocytidine
modified_base           10
                        mod_base = OTHER
                        note = 2'-O-methylguanosine
modified_base           1
                        mod_base = OTHER
                        note = 2'-O-methyluridine phosphorothioate
modified_base           17
```

```
                        mod_base = OTHER
                        note = 2'-O-methyladenosine
modified_base           9
                        mod_base = OTHER
                        note = 2'-O-methyladenosine
modified_base           5
                        mod_base = OTHER
                        note = 2'-O-methyladenosine
modified_base           3
                        mod_base = OTHER
                        note = 2'-O-methylcytidine
modified_base           6
                        mod_base = OTHER
                        note = 2'-fluoroguanosine
modified_base           19
                        mod_base = OTHER
                        note = 2'-O-methylguanosine phosphorothioate
modified_base           2
                        mod_base = OTHER
                        note = 2'-fluorocytidine phosphorothioate
modified_base           15
                        mod_base = OTHER
                        note = 2'-O-methylguanosine
SEQUENCE: 416
tcctagacag cgtcggaagt t                                             21

SEQ ID NO: 417          moltype = RNA  length = 21
FEATURE                 Location/Qualifiers
modified_base           16
                        mod_base = OTHER
                        note = 2'-fluorocytidine
modified_base           1
                        mod_base = OTHER
                        note = 2'-O-methyluridine phosphorothioate
modified_base           15
                        mod_base = OTHER
                        note = 2'-O-methyluridine
modified_base           21
                        mod_base = OTHER
                        note = 2'-O-methyluridine
modified_base           14
                        mod_base = OTHER
                        note = 2'-fluoroguanosine
modified_base           6
                        mod_base = OTHER
                        note = 2'-fluorouridine
modified_base           18
                        mod_base = OTHER
                        note = 2'-O-methylguanosine
modified_base           8
                        mod_base = OTHER
                        note = 2'-O-methylguanosine
modified_base           9
                        mod_base = OTHER
                        note = 2'-O-methyladenosine
modified_base           4
                        mod_base = OTHER
                        note = 2'-O-methylcytidine
modified_base           11
                        mod_base = OTHER
                        note = 2'-O-methyladenosine
modified_base           19
                        mod_base = OTHER
                        note = 2'-O-methyladenosine phosphorothioate
source                  1..21
                        mol_type = other RNA
                        organism = synthetic construct
modified_base           20
                        mod_base = OTHER
                        note = 2'-O-methyluridine phosphorothioate
modified_base           5
                        mod_base = OTHER
                        note = 2'-O-methylcytidine
modified_base           7
                        mod_base = OTHER
                        note = 2'-O-methyladenosine
modified_base           17
                        mod_base = OTHER
                        note = 2'-O-methylguanosine
```

```
modified_base           3
                        mod_base = OTHER
                        note = 2'-O-methylguanosine
modified_base           2
                        mod_base = OTHER
                        note = 2'-fluorouridine phosphorothioate
modified_base           13
                        mod_base = OTHER
                        note = 2'-O-methylcytidine
modified_base           10
                        mod_base = OTHER
                        note = 2'-O-methylcytidine
modified_base           12
                        mod_base = OTHER
                        note = 2'-O-methylguanosine
SEQUENCE: 417
ttgcctagac agcgtcggat t                                             21

SEQ ID NO: 418          moltype = RNA  length = 21
FEATURE                 Location/Qualifiers
modified_base           19
                        mod_base = OTHER
                        note = 2'-O-methylguanosine phosphorothioate
modified_base           16
                        mod_base = OTHER
                        note = 2'-fluorouridine
modified_base           13
                        mod_base = OTHER
                        note = 2'-O-methylguanosine
modified_base           4
                        mod_base = OTHER
                        note = 2'-O-methylguanosine
modified_base           8
                        mod_base = OTHER
                        note = 2'-O-methyladenosine
modified_base           9
                        mod_base = OTHER
                        note = 2'-O-methylguanosine
modified_base           17
                        mod_base = OTHER
                        note = 2'-O-methylcytidine
modified_base           6
                        mod_base = OTHER
                        note = 2'-fluorocytidine
modified_base           15
                        mod_base = OTHER
                        note = 2'-O-methylguanosine
modified_base           21
                        mod_base = OTHER
                        note = 2'-O-methyluridine
modified_base           5
                        mod_base = OTHER
                        note = 2'-O-methylcytidine
modified_base           1
                        mod_base = OTHER
                        note = 2'-O-methyluridine phosphorothioate
modified_base           7
                        mod_base = OTHER
                        note = 2'-O-methyluridine
modified_base           20
                        mod_base = OTHER
                        note = 2'-O-methyluridine phosphorothioate
source                  1..21
                        mol_type = other RNA
                        organism = synthetic construct
modified_base           18
                        mod_base = OTHER
                        note = 2'-O-methylguanosine
modified_base           12
                        mod_base = OTHER
                        note = 2'-O-methyladenosine
modified_base           11
                        mod_base = OTHER
                        note = 2'-O-methylcytidine
modified_base           3
                        mod_base = OTHER
                        note = 2'-O-methyluridine
modified_base           14
                        mod_base = OTHER
```

```
                         note = 2'-fluorocytidine
modified_base            2
                         mod_base = OTHER
                         note = 2'-fluorouridine phosphorothioate
modified_base            10
                         mod_base = OTHER
                         note = 2'-O-methyladenosine
SEQUENCE: 418
tttgcctaga cagcgtcggt t                                            21

SEQ ID NO: 419           moltype = RNA  length = 21
FEATURE                  Location/Qualifiers
modified_base            7
                         mod_base = OTHER
                         note = 2'-O-methylguanosine
modified_base            1
                         mod_base = OTHER
                         note = 2'-O-methyluridine phosphorothioate
modified_base            15
                         mod_base = OTHER
                         note = 2'-O-methyladenosine
modified_base            9
                         mod_base = OTHER
                         note = 2'-O-methylcytidine
modified_base            17
                         mod_base = OTHER
                         note = 2'-O-methylcytidine
modified_base            8
                         mod_base = OTHER
                         note = 2'-O-methylcytidine
modified_base            11
                         mod_base = OTHER
                         note = 2'-O-methyladenosine
modified_base            14
                         mod_base = OTHER
                         note = 2'-fluorocytidine
modified_base            21
                         mod_base = OTHER
                         note = 2'-O-methyluridine
modified_base            6
                         mod_base = OTHER
                         note = 2'-fluorouridine
source                   1..21
                         mol_type = other RNA
                         organism = synthetic construct
modified_base            10
                         mod_base = OTHER
                         note = 2'-O-methyluridine
modified_base            5
                         mod_base = OTHER
                         note = 2'-O-methyluridine
modified_base            16
                         mod_base = OTHER
                         note = 2'-fluoroguanosine
modified_base            19
                         mod_base = OTHER
                         note = 2'-O-methyluridine phosphorothioate
modified_base            12
                         mod_base = OTHER
                         note = 2'-O-methylguanosine
modified_base            13
                         mod_base = OTHER
                         note = 2'-O-methyladenosine
modified_base            3
                         mod_base = OTHER
                         note = 2'-O-methylguanosine
modified_base            20
                         mod_base = OTHER
                         note = 2'-O-methyluridine phosphorothioate
modified_base            18
                         mod_base = OTHER
                         note = 2'-O-methylguanosine
modified_base            4
                         mod_base = OTHER
                         note = 2'-O-methyluridine
modified_base            2
                         mod_base = OTHER
                         note = 2'-fluoroguanosine phosphorothioate
SEQUENCE: 419
```

-continued

```
tggtttgcct agacagcgtt t                                              21

SEQ ID NO: 420          moltype = RNA  length = 21
FEATURE                 Location/Qualifiers
modified_base           18
                        mod_base = OTHER
                        note = 2'-O-methyluridine
modified_base           11
                        mod_base = OTHER
                        note = 2'-O-methyluridine
modified_base           7
                        mod_base = OTHER
                        note = 2'-O-methylcytidine
modified_base           3
                        mod_base = OTHER
                        note = 2'-O-methyladenosine
modified_base           5
                        mod_base = OTHER
                        note = 2'-O-methylcytidine
modified_base           12
                        mod_base = OTHER
                        note = 2'-O-methylcytidine
modified_base           6
                        mod_base = OTHER
                        note = 2'-fluorouridine
source                  1..21
                        mol_type = other RNA
                        organism = synthetic construct
modified_base           8
                        mod_base = OTHER
                        note = 2'-O-methyluridine
modified_base           9
                        mod_base = OTHER
                        note = 2'-O-methyladenosine
modified_base           21
                        mod_base = OTHER
                        note = 2'-O-methyluridine
modified_base           2
                        mod_base = OTHER
                        note = 2'-fluorouridine phosphorothioate
modified_base           13
                        mod_base = OTHER
                        note = 2'-O-methylcytidine
modified_base           14
                        mod_base = OTHER
                        note = 2'-fluoroadenosine
modified_base           17
                        mod_base = OTHER
                        note = 2'-O-methyluridine
modified_base           10
                        mod_base = OTHER
                        note = 2'-O-methyladenosine
modified_base           16
                        mod_base = OTHER
                        note = 2'-fluoroguanosine
modified_base           15
                        mod_base = OTHER
                        note = 2'-O-methylguanosine
modified_base           4
                        mod_base = OTHER
                        note = 2'-O-methyladenosine
modified_base           1
                        mod_base = OTHER
                        note = 2'-O-methyluridine phosphorothioate
modified_base           19
                        mod_base = OTHER
                        note = 2'-O-methyluridine phosphorothioate
modified_base           20
                        mod_base = OTHER
                        note = 2'-O-methyluridine phosphorothioate
SEQUENCE: 420
ttaactctaa tccaggtttt t                                              21

SEQ ID NO: 421          moltype =   length =
SEQUENCE: 421
000

SEQ ID NO: 422          moltype =   length =
SEQUENCE: 422
```

```
000

SEQ ID NO: 423          moltype =   length =
SEQUENCE: 423
000

SEQ ID NO: 424          moltype =   length =
SEQUENCE: 424
000

SEQ ID NO: 425          moltype =   length =
SEQUENCE: 425
000

SEQ ID NO: 426          moltype =   length =
SEQUENCE: 426
000

SEQ ID NO: 427          moltype =   length =
SEQUENCE: 427
000

SEQ ID NO: 428          moltype =   length =
SEQUENCE: 428
000

SEQ ID NO: 429          moltype =   length =
SEQUENCE: 429
000

SEQ ID NO: 430          moltype = RNA  length = 21
FEATURE                 Location/Qualifiers
modified_base           15
                        mod_base = OTHER
                        note = 2'-O-methylguanosine
modified_base           10
                        mod_base = OTHER
                        note = 2'-O-methylcytidine
modified_base           20
                        mod_base = OTHER
                        note = 2'-O-methyluridine phosphorothioate
source                  1..21
                        mol_type = other RNA
                        organism = synthetic construct
modified_base           13
                        mod_base = OTHER
                        note = 2'-O-methyluridine
modified_base           2
                        mod_base = OTHER
                        note = 2'-fluoroadenosine phosphorothioate
modified_base           12
                        mod_base = OTHER
                        note = 2'-O-methylguanosine
modified_base           19
                        mod_base = OTHER
                        note = 2'-O-methyluridine phosphorothioate
modified_base           17
                        mod_base = OTHER
                        note = 2'-O-methylcytidine
modified_base           18
                        mod_base = OTHER
                        note = 2'-O-methylguanosine
modified_base           14
                        mod_base = OTHER
                        note = 2'-fluorocytidine
modified_base           8
                        mod_base = OTHER
                        note = 2'-O-methylcytidine
modified_base           5
                        mod_base = OTHER
                        note = 2'-O-methyladenosine
modified_base           3
                        mod_base = OTHER
                        note = 2'-O-methylcytidine
modified_base           16
                        mod_base = OTHER
                        note = 2'-fluorocytidine
modified_base           7
                        mod_base = OTHER
```

```
                        note = 2'-O-methyluridine
modified_base           1
                        mod_base = OTHER
                        note = vinyl phosphonate vpUq uracil phosphorothioate
modified_base           21
                        mod_base = OTHER
                        note = 2'-O-methyluridine
modified_base           4
                        mod_base = OTHER
                        note = 2'-O-methylguanosine
modified_base           9
                        mod_base = OTHER
                        note = 2'-O-methyluridine
modified_base           6
                        mod_base = OTHER
                        note = 2'-fluoroguanosine
modified_base           11
                        mod_base = OTHER
                        note = 2'-O-methylcytidine
SEQUENCE: 430
tacgagtctc cgtcgccgtt t                                              21

SEQ ID NO: 431          moltype = RNA  length = 21
FEATURE                 Location/Qualifiers
modified_base           3
                        mod_base = OTHER
                        note = 2'-O-methylcytidine
modified_base           13
                        mod_base = OTHER
                        note = 2'-O-methyluridine
modified_base           9
                        mod_base = OTHER
                        note = 2'-O-methyladenosine
modified_base           20
                        mod_base = OTHER
                        note = 2'-O-methyluridine phosphorothioate
modified_base           8
                        mod_base = OTHER
                        note = 2'-O-methylguanosine
modified_base           12
                        mod_base = OTHER
                        note = 2'-O-methylcytidine
source                  1..21
                        mol_type = other RNA
                        organism = synthetic construct
modified_base           11
                        mod_base = OTHER
                        note = 2'-O-methyluridine
modified_base           6
                        mod_base = OTHER
                        note = 2'-fluoroadenosine
modified_base           2
                        mod_base = OTHER
                        note = 2'-fluorocytidine phosphorothioate
modified_base           7
                        mod_base = OTHER
                        note = 2'-O-methylcytidine
modified_base           18
                        mod_base = OTHER
                        note = 2'-O-methylcytidine
modified_base           5
                        mod_base = OTHER
                        note = 2'-O-methyladenosine
modified_base           19
                        mod_base = OTHER
                        note = 2'-O-methylguanosine phosphorothioate
modified_base           10
                        mod_base = OTHER
                        note = 2'-O-methylguanosine
modified_base           17
                        mod_base = OTHER
                        note = 2'-O-methyluridine
modified_base           14
                        mod_base = OTHER
                        note = 2'-fluorocytidine
modified_base           16
                        mod_base = OTHER
                        note = 2'-fluoroguanosine
modified_base           1
```

```
                         mod_base = OTHER
                         note = vinyl phosphonate vpUq uracil phosphorothioate
modified_base            21
                         mod_base = OTHER
                         note = 2'-O-methyluridine
modified_base            4
                         mod_base = OTHER
                         note = 2'-O-methyladenosine
modified_base            15
                         mod_base = OTHER
                         note = 2'-O-methylcytidine
SEQUENCE: 431
tccaaacgag tctccgtcgt t                                                21

SEQ ID NO: 432           moltype = RNA  length = 21
FEATURE                  Location/Qualifiers
modified_base            2
                         mod_base = OTHER
                         note = 2'-fluoroadenosine phosphorothioate
modified_base            14
                         mod_base = OTHER
                         note = 2'-fluorouridine
modified_base            3
                         mod_base = OTHER
                         note = 2'-O-methyladenosine
modified_base            1
                         mod_base = OTHER
                         note = vinyl phosphonate vpUq uracil phosphorothioate
modified_base            13
                         mod_base = OTHER
                         note = 2'-O-methylcytidine
modified_base            4
                         mod_base = OTHER
                         note = 2'-O-methylguanosine
modified_base            10
                         mod_base = OTHER
                         note = 2'-O-methylcytidine
modified_base            15
                         mod_base = OTHER
                         note = 2'-O-methylcytidine
modified_base            5
                         mod_base = OTHER
                         note = 2'-O-methylcytidine
modified_base            21
                         mod_base = OTHER
                         note = 2'-O-methyluridine
modified_base            20
                         mod_base = OTHER
                         note = 2'-O-methyluridine phosphorothioate
modified_base            7
                         mod_base = OTHER
                         note = 2'-O-methyladenosine
modified_base            6
                         mod_base = OTHER
                         note = 2'-fluoroguanosine
source                   1..21
                         mol_type = other RNA
                         organism = synthetic construct
modified_base            11
                         mod_base = OTHER
                         note = 2'-O-methyluridine
modified_base            16
                         mod_base = OTHER
                         note = 2'-fluoroadenosine
modified_base            18
                         mod_base = OTHER
                         note = 2'-O-methyladenosine
modified_base            17
                         mod_base = OTHER
                         note = 2'-O-methyladenosine
modified_base            12
                         mod_base = OTHER
                         note = 2'-O-methyluridine
modified_base            8
                         mod_base = OTHER
                         note = 2'-O-methyluridine
modified_base            19
                         mod_base = OTHER
                         note = 2'-O-methylguanosine phosphorothioate
```

```
modified_base          9
                       mod_base = OTHER
                       note = 2'-O-methylcytidine
SEQUENCE: 432
taagcgatcc ttctcaaagt t                                           21

SEQ ID NO: 433         moltype = RNA  length = 21
FEATURE                Location/Qualifiers
modified_base          10
                       mod_base = OTHER
                       note = 2'-O-methylcytidine
modified_base          17
                       mod_base = OTHER
                       note = 2'-O-methyladenosine
modified_base          21
                       mod_base = OTHER
                       note = 2'-O-methyluridine
modified_base          19
                       mod_base = OTHER
                       note = 2'-O-methylguanosine phosphorothioate
source                 1..21
                       mol_type = other RNA
                       organism = synthetic construct
modified_base          5
                       mod_base = OTHER
                       note = 2'-O-methylguanosine
modified_base          20
                       mod_base = OTHER
                       note = 2'-O-methyluridine phosphorothioate
modified_base          18
                       mod_base = OTHER
                       note = 2'-O-methylcytidine
modified_base          14
                       mod_base = OTHER
                       note = 2'-fluorouridine
modified_base          1
                       mod_base = OTHER
                       note = vinyl phosphonate vpUq uracil phosphorothioate
modified_base          11
                       mod_base = OTHER
                       note = 2'-O-methylcytidine
modified_base          2
                       mod_base = OTHER
                       note = 2'-fluoroadenosine phosphorothioate
modified_base          7
                       mod_base = OTHER
                       note = 2'-O-methylguanosine
modified_base          3
                       mod_base = OTHER
                       note = 2'-O-methylguanosine
modified_base          9
                       mod_base = OTHER
                       note = 2'-O-methyluridine
modified_base          4
                       mod_base = OTHER
                       note = 2'-O-methylcytidine
modified_base          12
                       mod_base = OTHER
                       note = 2'-O-methylcytidine
modified_base          15
                       mod_base = OTHER
                       note = 2'-O-methylguanosine
modified_base          13
                       mod_base = OTHER
                       note = 2'-O-methyluridine
modified_base          8
                       mod_base = OTHER
                       note = 2'-O-methylcytidine
modified_base          16
                       mod_base = OTHER
                       note = 2'-fluorocytidine
modified_base          6
                       mod_base = OTHER
                       note = 2'-fluoroadenosine
SEQUENCE: 433
tagcgagctc ccttgcacgt t                                           21

SEQ ID NO: 434         moltype = RNA  length = 21
FEATURE                Location/Qualifiers
```

-continued

```
modified_base          4
                       mod_base = OTHER
                       note = 2'-O-methyluridine
modified_base          6
                       mod_base = OTHER
                       note = 2'-fluoroguanosine
modified_base          3
                       mod_base = OTHER
                       note = 2'-O-methylcytidine
modified_base          21
                       mod_base = OTHER
                       note = 2'-O-methyluridine
modified_base          7
                       mod_base = OTHER
                       note = 2'-O-methyladenosine
modified_base          20
                       mod_base = OTHER
                       note = 2'-O-methyluridine phosphorothioate
modified_base          14
                       mod_base = OTHER
                       note = 2'-fluorocytidine
modified_base          9
                       mod_base = OTHER
                       note = 2'-O-methyladenosine
modified_base          10
                       mod_base = OTHER
                       note = 2'-O-methylguanosine
modified_base          5
                       mod_base = OTHER
                       note = 2'-O-methyladenosine
modified_base          17
                       mod_base = OTHER
                       note = 2'-O-methyladenosine
modified_base          11
                       mod_base = OTHER
                       note = 2'-O-methylcytidine
modified_base          2
                       mod_base = OTHER
                       note = 2'-fluorocytidine phosphorothioate
modified_base          18
                       mod_base = OTHER
                       note = 2'-O-methyladenosine
source                 1..21
                       mol_type = other RNA
                       organism = synthetic construct
modified_base          16
                       mod_base = OTHER
                       note = 2'-fluoroguanosine
modified_base          8
                       mod_base = OTHER
                       note = 2'-O-methylcytidine
modified_base          12
                       mod_base = OTHER
                       note = 2'-O-methylguanosine
modified_base          19
                       mod_base = OTHER
                       note = 2'-O-methylguanosine phosphorothioate
modified_base          13
                       mod_base = OTHER
                       note = 2'-O-methyluridine
modified_base          15
                       mod_base = OTHER
                       note = 2'-O-methylguanosine
modified_base          1
                       mod_base = OTHER
                       note = vinyl phosphonate vpUq uracil phosphorothioate
SEQUENCE: 434
tcctagacag cgtcggaagt t                                            21

SEQ ID NO: 435         moltype = RNA  length = 21
FEATURE                Location/Qualifiers
modified_base          12
                       mod_base = OTHER
                       note = 2'-O-methylguanosine
modified_base          2
                       mod_base = OTHER
                       note = 2'-fluorouridine phosphorothioate
modified_base          20
                       mod_base = OTHER
```

```
                        note = 2'-O-methyluridine phosphorothioate
modified_base           10
                        mod_base = OTHER
                        note = 2'-O-methylcytidine
modified_base           19
                        mod_base = OTHER
                        note = 2'-O-methyladenosine phosphorothioate
modified_base           7
                        mod_base = OTHER
                        note = 2'-O-methyladenosine
modified_base           8
                        mod_base = OTHER
                        note = 2'-O-methylguanosine
modified_base           14
                        mod_base = OTHER
                        note = 2'-fluoroguanosine
modified_base           17
                        mod_base = OTHER
                        note = 2'-O-methylguanosine
modified_base           3
                        mod_base = OTHER
                        note = 2'-O-methylguanosine
modified_base           6
                        mod_base = OTHER
                        note = 2'-fluorouridine
modified_base           9
                        mod_base = OTHER
                        note = 2'-O-methyladenosine
modified_base           5
                        mod_base = OTHER
                        note = 2'-O-methylcytidine
modified_base           13
                        mod_base = OTHER
                        note = 2'-O-methylcytidine
modified_base           4
                        mod_base = OTHER
                        note = 2'-O-methylcytidine
modified_base           11
                        mod_base = OTHER
                        note = 2'-O-methyladenosine
modified_base           16
                        mod_base = OTHER
                        note = 2'-fluorocytidine
modified_base           1
                        mod_base = OTHER
                        note = vinyl phosphonate vpUq uracil phosphorothioate
modified_base           18
                        mod_base = OTHER
                        note = 2'-O-methylguanosine
modified_base           15
                        mod_base = OTHER
                        note = 2'-O-methyluridine
modified_base           21
                        mod_base = OTHER
                        note = 2'-O-methyluridine
source                  1..21
                        mol_type = other RNA
                        organism = synthetic construct
SEQUENCE: 435
ttgcctagac agcgtcggat t                                     21

SEQ ID NO: 436          moltype = RNA  length = 21
FEATURE                 Location/Qualifiers
modified_base           3
                        mod_base = OTHER
                        note = 2'-O-methyluridine
modified_base           2
                        mod_base = OTHER
                        note = 2'-fluorouridine phosphorothioate
source                  1..21
                        mol_type = other RNA
                        organism = synthetic construct
modified_base           17
                        mod_base = OTHER
                        note = 2'-O-methylcytidine
modified_base           8
                        mod_base = OTHER
                        note = 2'-O-methyladenosine
modified_base           11
```

```
                        mod_base = OTHER
                        note = 2'-O-methylcytidine
modified_base           16
                        mod_base = OTHER
                        note = 2'-fluorouridine
modified_base           21
                        mod_base = OTHER
                        note = 2'-O-methyluridine
modified_base           1
                        mod_base = OTHER
                        note = vinyl phosphonate vpUq uracil phosphorothioate
modified_base           9
                        mod_base = OTHER
                        note = 2'-O-methylguanosine
modified_base           4
                        mod_base = OTHER
                        note = 2'-O-methylguanosine
modified_base           19
                        mod_base = OTHER
                        note = 2'-O-methylguanosine phosphorothioate
modified_base           13
                        mod_base = OTHER
                        note = 2'-O-methylguanosine
modified_base           12
                        mod_base = OTHER
                        note = 2'-O-methyladenosine
modified_base           20
                        mod_base = OTHER
                        note = 2'-O-methyluridine phosphorothioate
modified_base           14
                        mod_base = OTHER
                        note = 2'-fluorocytidine
modified_base           7
                        mod_base = OTHER
                        note = 2'-O-methyluridine
modified_base           15
                        mod_base = OTHER
                        note = 2'-O-methylguanosine
modified_base           5
                        mod_base = OTHER
                        note = 2'-O-methylcytidine
modified_base           18
                        mod_base = OTHER
                        note = 2'-O-methylguanosine
modified_base           6
                        mod_base = OTHER
                        note = 2'-fluorocytidine
modified_base           10
                        mod_base = OTHER
                        note = 2'-O-methyladenosine
SEQUENCE: 436
tttgcctaga cagcgtcggt t                                       21

SEQ ID NO: 437          moltype = RNA  length = 21
FEATURE                 Location/Qualifiers
modified_base           6
                        mod_base = OTHER
                        note = 2'-fluorouridine
modified_base           7
                        mod_base = OTHER
                        note = 2'-O-methylguanosine
modified_base           5
                        mod_base = OTHER
                        note = 2'-O-methyluridine
modified_base           17
                        mod_base = OTHER
                        note = 2'-O-methylcytidine
modified_base           16
                        mod_base = OTHER
                        note = 2'-fluoroguanosine
modified_base           10
                        mod_base = OTHER
                        note = 2'-O-methyluridine
modified_base           12
                        mod_base = OTHER
                        note = 2'-O-methylguanosine
source                  1..21
                        mol_type = other RNA
                        organism = synthetic construct
```

-continued

```
modified_base         4
                      mod_base = OTHER
                      note = 2'-O-methyluridine
modified_base         13
                      mod_base = OTHER
                      note = 2'-O-methyladenosine
modified_base         21
                      mod_base = OTHER
                      note = 2'-O-methyluridine
modified_base         2
                      mod_base = OTHER
                      note = 2'-fluoroguanosine phosphorothioate
modified_base         11
                      mod_base = OTHER
                      note = 2'-O-methyladenosine
modified_base         20
                      mod_base = OTHER
                      note = 2'-O-methyluridine phosphorothioate
modified_base         8
                      mod_base = OTHER
                      note = 2'-O-methylcytidine
modified_base         14
                      mod_base = OTHER
                      note = 2'-fluorocytidine
modified_base         19
                      mod_base = OTHER
                      note = 2'-O-methyluridine phosphorothioate
modified_base         1
                      mod_base = OTHER
                      note = vinyl phosphonate vpUq uracil phosphorothioate
modified_base         18
                      mod_base = OTHER
                      note = 2'-O-methylguanosine
modified_base         15
                      mod_base = OTHER
                      note = 2'-O-methyladenosine
modified_base         9
                      mod_base = OTHER
                      note = 2'-O-methylcytidine
modified_base         3
                      mod_base = OTHER
                      note = 2'-O-methylguanosine
SEQUENCE: 437
tggtttgcct agacagcgtt t                                             21

SEQ ID NO: 438        moltype = RNA  length = 21
FEATURE               Location/Qualifiers
modified_base         1
                      mod_base = OTHER
                      note = vinyl phosphonate vpUq uracil phosphorothioate
modified_base         16
                      mod_base = OTHER
                      note = 2'-fluoroguanosine
modified_base         2
                      mod_base = OTHER
                      note = 2'-fluorouridine phosphorothioate
modified_base         20
                      mod_base = OTHER
                      note = 2'-O-methyluridine phosphorothioate
modified_base         18
                      mod_base = OTHER
                      note = 2'-O-methyluridine
modified_base         7
                      mod_base = OTHER
                      note = 2'-O-methylcytidine
modified_base         17
                      mod_base = OTHER
                      note = 2'-O-methyluridine
modified_base         21
                      mod_base = OTHER
                      note = 2'-O-methyluridine
modified_base         8
                      mod_base = OTHER
                      note = 2'-O-methyluridine
modified_base         5
                      mod_base = OTHER
                      note = 2'-O-methylcytidine
source                1..21
                      mol_type = other RNA
```

-continued

```
                        organism = synthetic construct
modified_base           12
                        mod_base = OTHER
                        note = 2'-O-methylcytidine
modified_base           3
                        mod_base = OTHER
                        note = 2'-O-methyladenosine
modified_base           11
                        mod_base = OTHER
                        note = 2'-O-methyluridine
modified_base           15
                        mod_base = OTHER
                        note = 2'-O-methylguanosine
modified_base           9
                        mod_base = OTHER
                        note = 2'-O-methyladenosine
modified_base           19
                        mod_base = OTHER
                        note = 2'-O-methyluridine phosphorothioate
modified_base           4
                        mod_base = OTHER
                        note = 2'-O-methyladenosine
modified_base           13
                        mod_base = OTHER
                        note = 2'-O-methylcytidine
modified_base           14
                        mod_base = OTHER
                        note = 2'-fluoroadenosine
modified_base           6
                        mod_base = OTHER
                        note = 2'-fluorouridine
modified_base           10
                        mod_base = OTHER
                        note = 2'-O-methyladenosine
SEQUENCE: 438
ttaactctaa tccaggtttt t                                21
```

COMPOSITIONS AND METHODS OF TREATING FACIOSCAPULOHUMERAL MUSCULAR DYSTROPHY

CROSS-REFERENCE

This application is a continuation of U.S. Non-provisional application Ser. No. 18/809,215, filed Aug. 19, 2024, which is a continuation of U.S. Non-provisional application Ser. No. 18/402,604, filed Jan. 2, 2024, issued as U.S. Pat. No. 12,157,774 on Dec. 3, 2024, which is a divisional of U.S. Non-Provisional application Ser. No. 17/932,653, filed Sep. 15, 2022, issued as U.S. Pat. No. 11,912,779, on Feb. 27, 2024, which claims the benefit of U.S. Provisional Application No. 63/245,123, filed Sep. 16, 2021, each of which is incorporated herein by reference in its entirety.

SEQUENCE LISTING

The instant application contains a Sequence Listing which has been submitted electronically in XML file format and is hereby incorporated by reference in its entirety. Said XML copy, created on Jul. 11, 2025, is named 45532-756_302_SL.xml and is 2,155,549 bytes in size.

BACKGROUND OF THE DISCLOSURE

Muscle atrophy is the loss of muscle mass or the progressive weakening and degeneration of muscles, such as skeletal or voluntary muscles that controls movement, cardiac muscles, and smooth muscles. Various pathophysiological conditions including disuse, starvation, cancer, diabetes, and renal failure, or treatment with glucocorticoids result in muscle atrophy and loss of strength. The phenotypical effects of muscle atrophy are induced by various molecular events, including inhibition of muscle protein synthesis, enhanced turnover of muscle proteins, abnormal regulation of satellite cells differentiation, and abnormal conversion of muscle fibers types.

FSHD is a rare, progressive and disabling disease for which there are no approved treatments. FSHD is one of the most common forms of muscular dystrophy and affects both sexes equally, with onset typically in teens and young adults. FSHD is characterized by progressive skeletal muscle loss that initially causes weakness in muscles in the face, shoulders, arms and trunk and progresses to weakness in muscles in lower extremities and the pelvic girdle. Skeletal muscle weakness results in significant physical limitations, including progressive loss of facial muscles that can cause an inability to smile or communicate, difficulty using arms for activities of daily living and difficulty getting out of bed, with many patients ultimately becoming dependent upon the use of a wheelchair for daily mobility activities. The majority of patients with FSHD also report experiencing chronic pain, anxiety and depression.

FSHD is caused by aberrant expression of a gene, DUX4, in skeletal muscle resulting in the inappropriate presence of DUX4 protein. Gene suppression by RNA-induced gene silencing provides several levels of control: transcription inactivation, small interfering RNA (siRNA)-induced mRNA degradation, and siRNA-induced transcriptional attenuation. In some instances, RNA interference (RNAi) provides long lasting effect over multiple cell divisions. As such, RNAi represents a viable method useful for drug target validation, gene function analysis, pathway analysis, and disease therapeutics.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE DISCLOSURE

Described herein, in some aspects, is a polynucleic acid molecule conjugate comprising: an antibody or antigen binding fragment thereof conjugated to a polynucleic acid molecule that hybridizes to a target sequence of DUX4; wherein the polynucleic acid molecule comprises a nucleic acid sequence that is at least 80%, at least 85%, at least 90%, at least 95%, or 100% identical to a sequence selected from SEQ ID NOs: 72, 76, 126, or 131-136; wherein the polynucleic acid molecule comprises 2'-F modified nucleotides at positions 2, 6, 14, and 16; and wherein the polynucleic acid molecule conjugate mediates RNA interference against the DUX4. In some embodiments, the antibody or antigen binding fragment thereof comprises a non-human antibody or antigen binding fragment thereof, a human antibody or antigen binding fragment thereof, a humanized antibody or antigen binding fragment thereof, chimeric antibody or antigen binding fragment thereof, monoclonal antibody or antigen binding fragment thereof, monovalent Fab', divalent Fab2, single-chain variable fragment (scFv), diabody, minibody, nanobody, single-domain antibody (sdAb), or camelid antibody or antigen binding fragment thereof. In some embodiments, the antibody or antigen binding fragment thereof is an anti-transferrin receptor antibody or antigen binding fragment thereof. In some embodiments, the polynucleic acid molecule is from about 16 to about 30 nucleotides in length. In some embodiments, the polynucleic acid molecule comprises a sense strand and an antisense strand, and the antisense strand comprises a nucleic acid sequence of at least one of UfsNfsnnnNfnnnnnnnNfnNfnnnsusu, usNfsnnnNfnnnnnnnNfnNfnnnsusu, or vpNsNfsnnnNfnnnnnnnNfnNfnnnsus, wherein vpN=vinyl phosphonate VpUq, lower case (n)=2'-O-Me modified, Nf=2'-F modified, and s=phosphorothioate backbone modification. In some embodiments, the polynucleic acid molecule comprises a sense strand and an antisense strand, and the antisense strand comprises a nucleic acid sequence that is at least 80%, at least 85%, at least 90%, at least 95%, or 100% identical to a sequence selected from SEQ ID NOs: 412-420 or 430-438. In some embodiments, the polynucleic acid molecule comprises a sense strand and an antisense strand, and the sense strand comprises a nucleic acid sequence that is at least 80%, at least 85%, at least 90%, at least 95%, or 100% identical to a sequence selected from SEQ ID NOs: 2, 6, 56, or 61-66, wherein the sense strand comprises at least 2 or at least 3 consecutive 2'-F modified nucleotides. In some embodiments, the polynucleic acid molecule comprises a sense strand and an antisense strand, and the sense strand comprises a nucleic acid sequence that is at least 80%, at least 85%, at least 90%, at least 95%, or 100% identical to a sequence selected from SEQ ID NOs: 2, 6, 56, or 61-66. In some embodiments, the polynucleic acid molecule comprises a phosphorothioate linkage or a phosphorodithioate linkage. In some embodiments, the polynucleic acid molecule comprises six or more 2' modified nucleotides selected from 2'-O-methyl and 2'-deoxy-2'-fluoro. In some embodiments, the polynucleic acid molecule comprises a 5'-terminal vinylphosphonate modified nucleotide. In some embodiments, the 5'-terminal vinylphosphonate modified nucleotide is selected from:

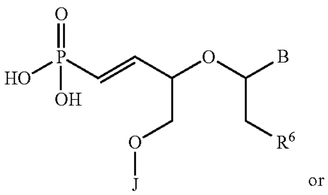

or

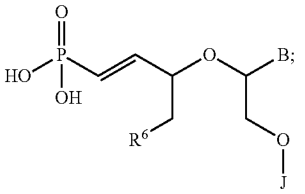

where B is a heterocyclic base moiety; R6 is selected from hydrogen, halogen, alkyl or alkoxy; and J is an internucleotide linking group linking to the adjacent nucleotide of the polynucleic acid molecule. In some embodiments, the sense strand and antisense strand comprises at least two, three, or four consecutive 2'-O-methyl modified nucleotides at the 5'-end or 3'-end. In some embodiments, the polynucleic acid molecule conjugate comprises a linker connecting the antibody or antigen binding fragment thereof to the polynucleic acid molecule via a cysteine residue or a lysine residue on the antibody or antigen binding fragment thereof. In some embodiments, the linker is a $C_1$-$C_6$ alkyl linker. In some embodiments, the linker is a homobifunctional linker or heterobifunctional linker, and comprises a maleimide group, a dipeptide moiety, a benzoic acid group, or its derivative thereof. In some embodiments, the linker is a cleavable or non-cleavable linker. In some embodiments, the polynucleic acid molecule conjugate comprises a ratio between the polynucleic acid molecule and the antibody or antigen binding fragment thereof is about 1:1, 2:1, 3:1, or 4:1.

Described herein, in some aspects, is a method for treating muscular dystrophy in a subject in need thereof, comprising: providing a polynucleic acid conjugate as described herein; and administering the polynucleic acid conjugate to the subject in need thereof to treat the muscular dystrophy, wherein the polynucleic acid conjugate reduces a quantity of the mRNA transcript of human DUX4. In some embodiments, the polynucleic acid conjugate mediates RNA interference against the human DUX4 and modulates muscle dystrophy in the subject. In some embodiments, the RNA interference comprises reducing expression of the mRNA transcript of DUX4 gene by at least 50%, at least 60%, or at least 70% or more compared to a quantity of the mRNA transcript of DUX4 gene in an untreated cell. In some embodiments, the RNA interference comprises affecting expression of a marker gene selected from a group consisting of MBD3L2, TRIM43, PRAMEF1, ZSCAN4, KHDCIL, LEUTX, WFDC3, ILVBL, SLC15A2, and SORD in a cell affected by the muscle dystrophy. In some embodiments, the affecting expression comprises reducing expression of the marker gene by at least 20%, at least 30%, at least 40%, at least 50%, at least 60% or more in the cell. In some embodiments, the muscular dystrophy is Facioscapulohumeral muscular dystrophy (FSHD).

Described herein, in some aspects, is a double-stranded polynucleic acid molecule that mediates RNA interference against DUX4, wherein the double-stranded polynucleic acid molecule comprises a sense strand and an antisense strand, wherein the antisense strand comprises a nucleic acid sequence that is at least 80%, at least 85%, at least 90%, at least 95%, or 100% identical to a sequence selected from SEQ ID NOs: 412-420 or 430-438; and the sense strand comprises a nucleic acid sequence that is at least 80%, at least 85%, at least 90%, at least 95%, or 100% identical to a sequence selected from SEQ ID NOs: 142, 146, 196, or 201-206.

Described herein, in some aspects, is a double-stranded polynucleic acid molecule that mediates RNA interference against DUX4, wherein the double-stranded polynucleic acid molecule comprises a sense strand and an antisense strand, wherein the antisense strand comprises a nucleic acid sequence comprising at least 15 contiguous nucleotides differing by no more than 1, 2, 3 nucleotides from a sequence selected from SEQ ID NOs: 412-420 or 430-438; and the sense strand comprises at least 15 contiguous nucleotides differing by no more than 1, 2, 3 nucleotides from a sequence selected from SEQ ID NOs: 142, 146, 196, or 201-206.

Disclosed herein, in certain aspects, are polynucleic acid molecules and pharmaceutical compositions for modulating a gene associated with muscle atrophy, especially Facioscapulohumeral muscular dystrophy (FSHD). In some aspects, also described herein are methods of treating muscle atrophy, especially FSHD, with a polynucleic acid molecule or a polynucleic acid molecule conjugate disclosed herein.

Disclosed herein, in certain aspects, is a polynucleic acid molecule conjugate comprising an antibody or antigen binding fragment thereof conjugated to a polynucleic acid molecule that hybridizes to a target sequence of DUX4, and the polynucleic acid molecule conjugate mediates RNA interference against the DUX4. In certain aspects, the antibody or antigen binding fragment thereof comprises a non-human antibody or binding fragment thereof, a human antibody or antigen binding fragment thereof, a humanized antibody or antigen binding fragment thereof, chimeric antibody or antigen binding fragment thereof, monoclonal antibody or antigen binding fragment thereof, monovalent Fab', divalent Fab2, single-chain variable fragment (scFv), diabody, minibody, nanobody, single-domain antibody (sdAb), or camelid antibody or antigen binding fragment thereof. In certain aspects, the antibody or antigen binding fragment thereof is an anti-transferrin receptor antibody or antigen binding fragment thereof.

In certain aspects, the polynucleic acid molecule comprises a sense strand and/or an antisense strand, and wherein the sense strand and/or the antisense strand each independently comprises at least one 2' modified nucleotide, at least one modified internucleotide linkage, or at least one inverted abasic moiety. In certain aspects, the polynucleotide hybridizes to at least 8 contiguous bases of the target sequence of DUX4. In certain aspects, the polynucleotide is from about 8 to about 50 nucleotides in length or from about 10 to about 30 nucleotides in length. In certain aspects, the polynucleic acid molecule comprises a sense strand and/or an antisense strand, and the sense strand comprises at least 80%, at least 85%, at least 90%, at least 95%, at least 96%, at least 97%, at least 98%, at least 99% identical to a sequence selected from SEQ ID NOs: 1-70 or SEQ ID NOs: 141-210. Alternatively and/or additionally, the polynucleic acid molecule comprises a sense strand and/or an antisense strand, and the antisense strand comprises at least 80%, at least 85%, at least 90%, at least 95%, at least 96%, at least 97%, at least 98%, at least 99% identical to a sequence selected from SEQ ID NOs: 71-140 or SEQ ID NOs: 211-280. Alternatively and/or additionally, the polynucleic acid molecule comprises a sense strand and/or an antisense strand, and the antisense strand comprises at least 80%, at least 85%, at least 90%, at least 95%, at least 96%, at least 97%, at least 98%, at least 99% identical to a sequence selected from SEQ ID NOs: 142, 146, 196, 201-206, 412-420, or 430-438. In some embodiments, the polynucleic acid molecule comprises a sense strand and/or an antisense strand, and the antisense strand comprises at least 80%, at least 85%, at least 90%, at least 95%, at least 96%, at least 97%, at least 98%, at least 99% identical to a sequence selected from SEQ ID NOs: 412-420 or 430-438. In some embodiments, the polynucleic acid molecule comprises a sense strand and/or an antisense strand, and the antisense is identical to a sequence selected from SEQ ID NOs: 412-420 or 430-438. In some embodiments, the polynucleic acid molecule comprises a sense strand and/or an antisense strand, and the sense strand comprises at least 80%, at least 85%, at least 90%, at least 95%, at least 96%, at least 97%, at least 98%, at least 99% identical to a sequence selected from SEQ ID NOs: 142, 146, 196, or 201-206. In some embodiments, the polynucleic acid molecule comprises a sense strand and/or an antisense strand, and the sense strand is identical to a sequence selected from SEQ ID NOs: 142, 146, 196, or 201-206.

In certain aspects, the polynucleotide comprises at least one 2' modified nucleotide, and further the 2' modified nucleotide comprises 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified nucleotide, or comprises locked nucleic acid (LNA) or ethylene nucleic acid (ENA), or comprises a combination thereof. In certain aspects, the at least one modified internucleotide linkage comprises a phosphorothioate linkage or a phosphorodithioate linkage. In certain aspects, the polynucleic acid molecule comprises three or more 2' modified nucleotides selected from 2'-O-methyl and 2'-deoxy-2'-fluoro. In certain aspects, the polynucleic acid molecule comprises a 5'-terminal vinylphosphonate modified nucleotide.

Another embodiment provides the polynucleic acid molecule of the polynucleic acid molecule conjugate, wherein the at least one S'-vinylphosphonate modified non-natural nucleotide is selected from:

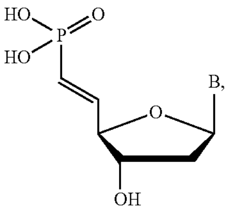

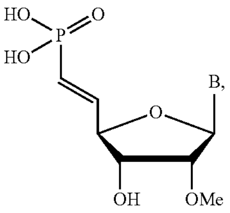

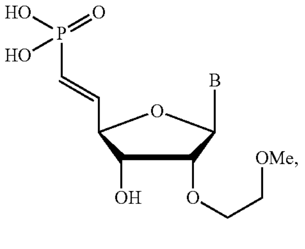

-continued

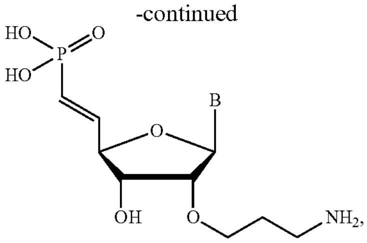

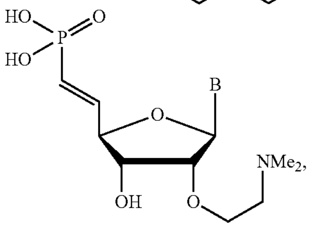

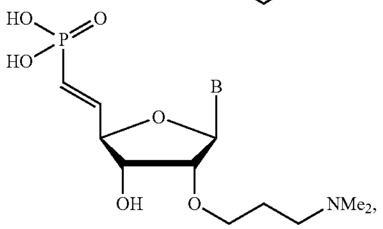

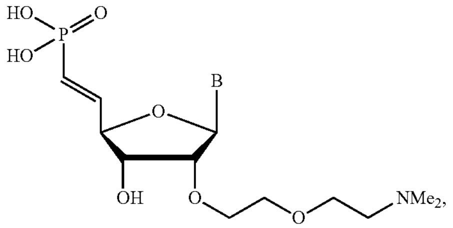

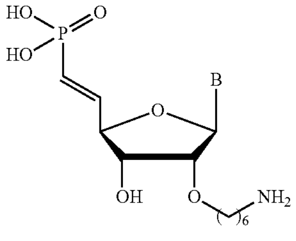

or

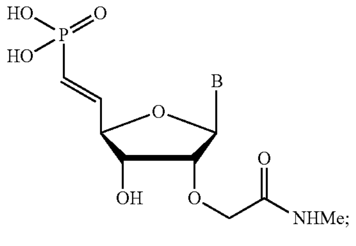

where B is a heterocyclic base moiety.

Another embodiment provides the polynucleic acid molecule of the polynucleic acid molecule conjugate, wherein the at least one S'-vinylphosphonate modified non-natural nucleotide is selected from:

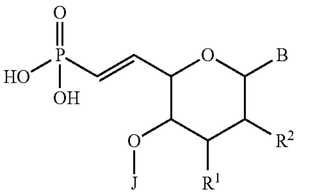

or

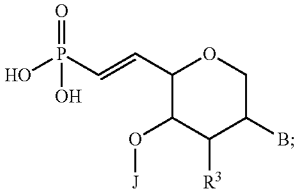

where B is a heterocyclic base moiety; R1, R2, and R3 are independently selected from hydrogen, halogen, alkyl or alkoxy; and J is an internucleotide linking group linking to the adjacent nucleotide of the polynucleotide.

Another embodiment provides the polynucleic acid molecule of the polynucleic acid molecule conjugate, wherein the at least one 5'-vinylphosphonate modified non-natural nucleotide is selected from:

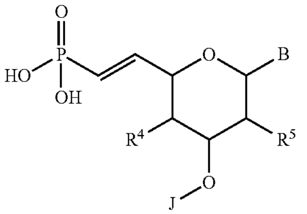

or

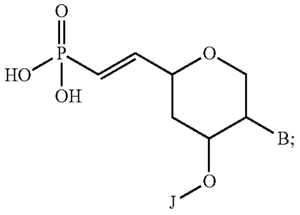

where B is a heterocyclic base moiety; R4, and R5 are independently selected from hydrogen, halogen, alkyl or alkoxy; and J is an internucleotide linking group linking to the adjacent nucleotide of the polynucleotide.

Another embodiment provides the polynucleic acid molecule of the polynucleic acid molecule conjugate, wherein the at least one S'-vinylphosphonate modified non-natural nucleotide is selected from:

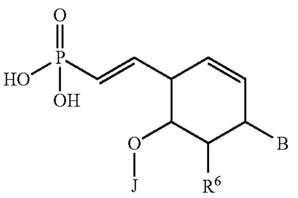

or

-continued

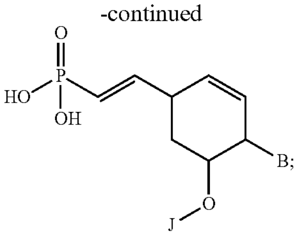

where B is a heterocyclic base moiety; R6 is selected from hydrogen, halogen, alkyl or alkoxy; and J is an internucleotide linking group linking to the adjacent nucleotide of the polynucleotide.

Another embodiment provides the polynucleic acid molecule of the polynucleic acid molecule conjugate, wherein the at least one S'~vinylphosphonate modified non-natural nucleotide is selected from locked nucleic acid (LNA) or ethylene nucleic acid (ENA).

Another embodiment provides the polynucleic acid molecule of the polynucleic acid molecule conjugate, wherein the at least one S'-vinylphosphonate modified non-natural nucleotide is selected from:

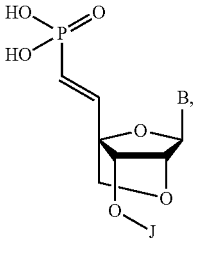

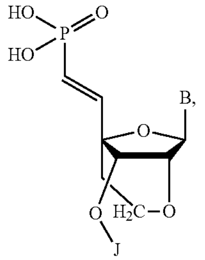

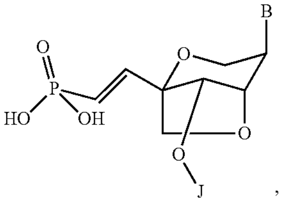

,

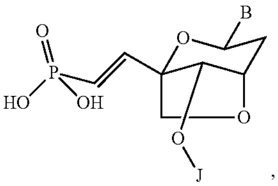

,

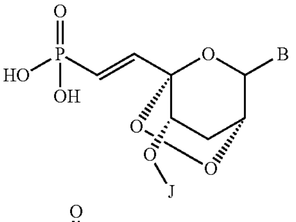

or

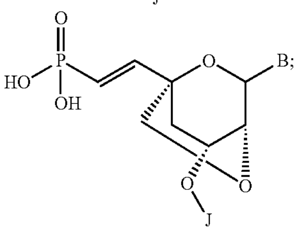

where B is a heterocyclic base moiety; and J is an internucleotide linking group linking to the adjacent nucleotide of the polynucleotide Another embodiment provides the polynucleic acid molecule of the polynucleic acid molecule conjugate, wherein the at least one S'-vinylphosphonate modified non-natural nucleotide is selected from:

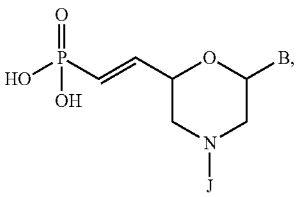

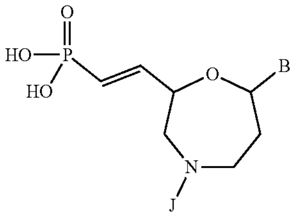

or

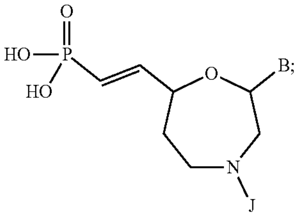

where B is a heterocyclic base moiety; and J is an internucleotide linking group linking to the adjacent nucleotide of the polynucleotide.

Another embodiment provides the polynucleic acid molecule of the polynucleic acid molecule conjugate, wherein the at least one 5'-vinylphosphonate modified non-natural nucleotide is selected from:

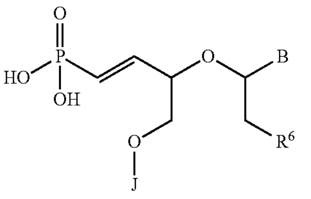

or

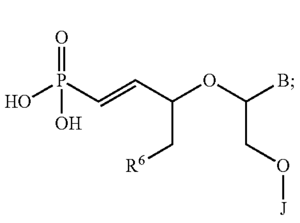

where B is a heterocyclic base moiety; R6 is selected from hydrogen, halogen, alkyl or alkoxy; and J is an internucleotide linking group linking to the adjacent nucleotide of the polynucleotide.

Another embodiment provides the polynucleic acid molecule of the polynucleic acid molecule conjugate, wherein the at least one S'-vinylphosphonate modified non-natural nucleotide is:

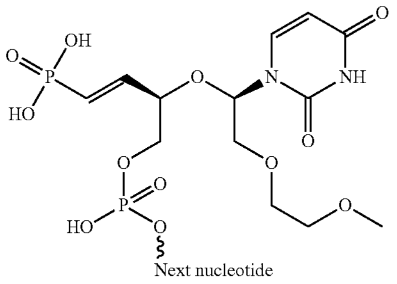

vpUq

In certain aspects, the 2' modified nucleotide is 2'-O-methyl modified nucleotide, and 2'-O-methyl modified nucleotide is at the 5'-end of the sense strand and/or the antisense strand. In some aspects, the 2'-O-methyl modified nucleotide is a purine nucleotide, or the 2'-O-methyl modified nucleotide is a pyridine nucleotide. In certain aspects, the sense and/or antisense strands comprise at least two, three, four consecutive the 2'-O-methyl modified nucleotides at the 5'-end.

In certain aspects, the polynucleic acid molecule conjugate comprises a linker connecting the target cell binding moiety to the polynucleic acid moiety. In such aspects, the linker is $C_1$-$C_6$ alkyl linker, or the linker is a homobifunctional linker or heterobifunctional linker, and comprises a maleimide group, a dipeptide moiety, a benzoic acid group, or its derivative thereof. Alternatively and/or additionally, the linker is a cleavable or non-cleavable linker. In certain aspects, a ratio between the polynucleic acid moiety and the target cell binding moiety is about 1:1, 2:1, 3:1, or 4:1.

In certain aspects, the polynucleic acid moiety mediates RNA interference against the human DUX4 and modulates symptoms of muscle dystrophy or atrophy in a subject. In some aspects, the RNA interference comprises reducing expression of the mRNA transcript of DUX4 gene at least 50%, at least 60%, or at least 70% or more compared to a quantity of the mRNA transcript of DUX4 gene in an untreated cell. Alternatively and/or additionally, the RNA interference comprises affecting expression of a marker gene selected from a group comprising or consisting of MBD3L2, TRIM43, PRAMEF1, ZSCAN4, KHDCIL, and LEUTX in a cell. In some aspects, the affecting expression of the marker gene is reducing expression of the marker gene at least 20%, at least 30%, at least 40%, at least 50%, at least 60% or more. In some aspects, the muscle dystrophy is Facioscapulohumeral muscular dystrophy (FSHD).

Alternatively and/or additionally, the RNA interference comprises affecting expression of a marker gene selected from a group comprising or consisting of WFDC3, ILVBL, SLC15A2, and SORD in a cell. In some aspects, the affecting expression of the marker gene is reducing expression of the marker gene at least 20%, at least 30%, at least 40%, at least 50%, at least 60% or more. In some aspects, the muscle dystrophy is Facioscapulohumeral muscular dystrophy (FSHD).

In certain aspects, polynucleic acid molecule conjugate comprises a molecule of Formula (I): A-X-B, where A is the antibody or antigen binding fragment thereof, B is the polynucleic acid molecule that hybridizes to a target sequence of DUX4, X is a bond or a non-polymeric linker, which is conjugated to a cysteine residue of A.

Disclosed herein, in certain aspects, is a pharmaceutical composition comprising a polynucleic acid molecule conjugate as described herein, and a pharmaceutically acceptable excipient. In some aspects, the pharmaceutical composition is formulated as a nanoparticle formulation. In some aspects, the pharmaceutical composition is formulated for parenteral, oral, intranasal, buccal, rectal, transdermal, or intravenous, subcutaneous, or intrathecal administration.

The symptoms of FSHD include effects on skeletal muscles. The skeletal muscles affected by FSHD include muscles around the eyes and mouth, muscle of the shoulders, muscle of the upper arms, muscle of the lower legs, abdominal muscles and hip muscles. In some instances, the symptoms of FSHD also affects vision and hearing. In some instances, the symptoms of FSHD also affect the function of the heart or lungs. In some instances, the symptoms of FSHD include muscle weakness, muscle atrophy, muscle dystrophy, pain inflammation, contractures, scoliosis, lordosis, hypoventilation, abnormalities of the retina, exposure to keratitis, mild hearing loss, and EMG abnormality. The term muscle atrophy as used herein refers to a wide range of muscle related effects of FSHD.

Disclosed herein, in certain aspects, is a method for treating muscular dystrophy in a subject in need thereof by providing a polynucleic acid conjugate as described herein, and administering the polynucleic acid conjugate to the subject in need thereof to treat the muscular dystrophy. The polynucleic acid conjugate reduces a quantity of the mRNA transcript of human DUX4. In some aspects, the polynucleic acid moiety mediates RNA interference against the human DUX4 modulates muscle atrophy in a subject. In certain aspects, the RNA interference comprises affecting expression of a marker gene for DUX4 selected from a group comprising or consisting of MBD3L2, TRIM43, PRAMEF1, ZSCAN4, KHDCIL, and LEUTX in a cell affected by a muscle dystrophy. In certain aspects, the RNA interference comprises affecting expression of a marker gene for DUX4 selected from a group comprising or consisting of WFDC3, ILVBL, SLC15A2, and SORD in a cell affected by a muscle dystrophy.

Preferably, the muscular dystrophy is Facioscapulohumeral muscular dystrophy (FSHD).

Disclosed herein, in certain aspects, is a use of the polynucleic acid molecule conjugate or a pharmaceutical composition as described herein for treating in a subject diagnosed with or suspected to have Facioscapulohumeral muscular dystrophy (FSHD). Also disclosed herein, in certain aspects, is a use of the polynucleic acid molecule conjugate or the pharmaceutical composition as described herein for manufacturing a medicament for treating in a subject diagnosed with or suspected to have Facioscapulohumeral muscular dystrophy (FSHD).

Disclosed herein, in certain aspects, is a kit comprising the polynucleic acid molecule conjugate or the pharmaceutical composition as described herein.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative aspects, in which the principles of the disclosure are utilized, and the accompanying drawings below.

DETAILED DESCRIPTION OF THE DISCLOSURE

FSHD is caused by aberrant expression of a gene, DUX4, in skeletal muscle resulting in the inappropriate presence of DUX4 protein. DUX4 itself is a transcription factor that induces the expression of other genes and it is these inappropriately expressed downstream genes that result in the muscle pathology. Normally DUX4-driven gene expression is limited to germline and early stem cell development. In patients with FSHD, the DUX4 protein in skeletal muscle regulates other gene products, some of which are toxic to the muscle. Evidence of aberrant DUX4-driven gene expression is the major molecular signature that distinguishes muscle tissue affected by FSHD from healthy muscle. The result of aberrant DUX4 expression in FSHD is death of muscle and its replacement by fat, resulting in skeletal muscle weakness and progressive disability. Data suggest that reducing expression of the DUX4 gene and its downstream transcriptional program could provide a disease-modifying therapeutic approach for the treatment of FSHD at its root cause.

Figure 1:
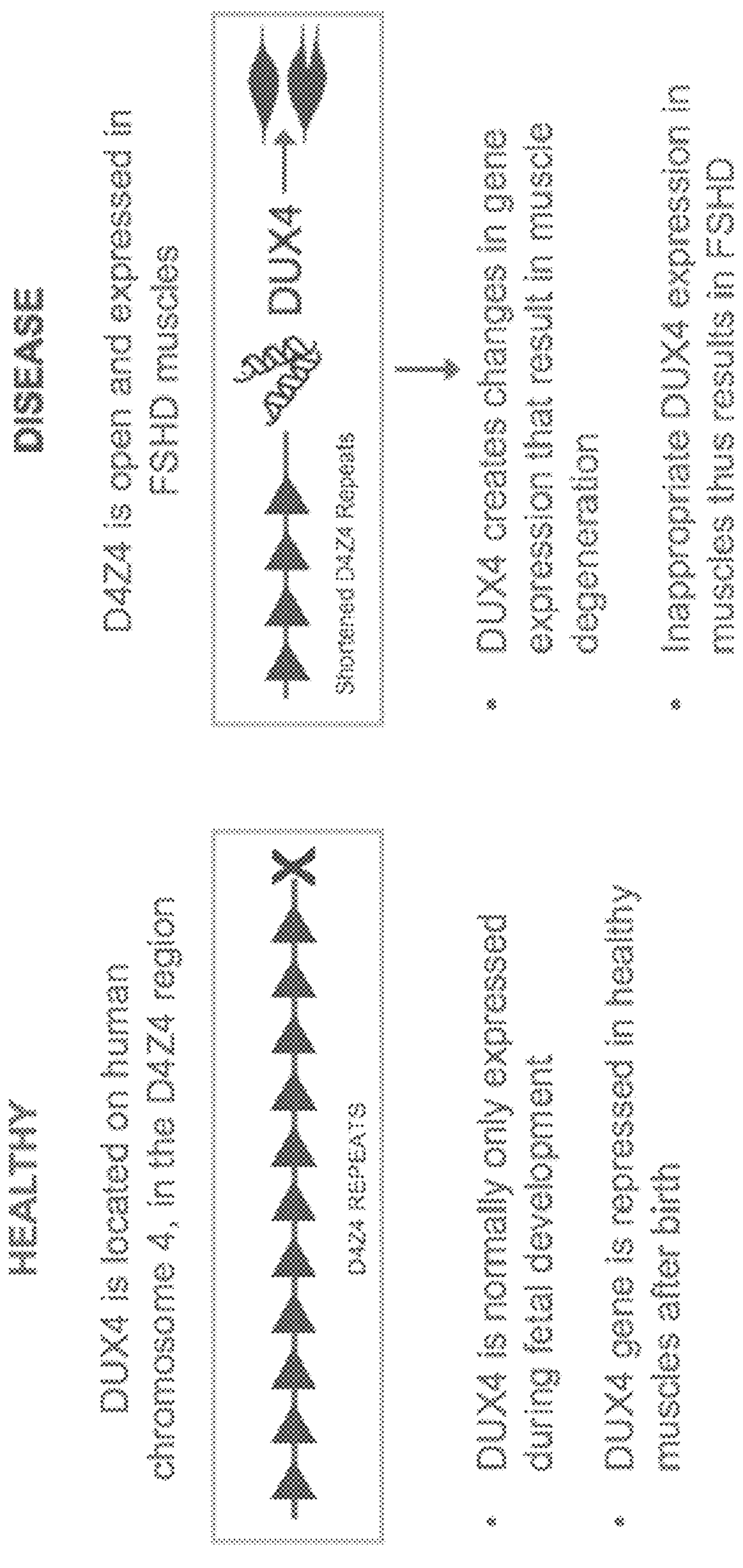
FIG. 1 illustrates a diagram of FSHD pathology.

There are two ways the DUX4 gene can be unsilenced, or de-repressed. In FSHD1, which comprises approximately 95% of FSHD patients, there are mutations that lead to the shortening of an array of DNA in a region near the end of the long arm of chromosome 4, known as D4Z4, which has repeats in the subtelomeric region of the chromosome. The D4Z4 region is abnormally shortened and contains between 1-10 repeats instead of the normal 11 to 100 repeats. This contraction causes hypomethylation of the D4Z4 region and de-repression of DUX4. Patients with FSHD2 do not have a meaningful D4Z4 repeat contraction, but have mutations in a regulatory gene, known as the SMCHD1 gene, that normally contributes to the repression of the DUX4 gene via DNA methylation. When that repression is lost due to the mutations of the SMCHD1 gene leading to the hypomethylation of the D4Z4 region, DUX4 is inappropriately expressed, inducing the disease state. FIG. 1 shows an illustrative diagram of FSHD pathology.

Nucleic acid (e.g., RNAi) therapy is a targeted therapy with high selectivity and specificity. However, in some instances, nucleic acid therapy is also hindered by poor intracellular uptake, limited blood stability and non-specific immune stimulation. To address these issues, various modifications of the nucleic acid composition are explored, such as for example, novel linkers for better stabilizing and/or lower toxicity, optimization of binding moiety for increased target specificity and/or target delivery, and nucleic acid polymer modifications for increased stability and/or reduced off-target effect.

In some aspects, the arrangement or order of the different components that make-up the nucleic acid composition further effects intracellular uptake, stability, toxicity, efficacy, and/or non-specific immune stimulation. For example, if the nucleic acid component includes a binding moiety, a polymer, and a polynucleic acid molecule (or polynucleotide), the order or arrangement of the binding moiety, the polymer, and/or the polynucleic acid molecule (or polynucleotide) (e.g., binding moiety-polynucleic acid molecule-polymer, binding moiety-polymer-polynucleic acid molecule, or polymer-binding moiety-polynucleic acid molecule) further effects intracellular uptake, stability, toxicity, efficacy, and/or non-specific immune stimulation.

In some aspects, described herein include polynucleic acid molecules and polynucleic acid molecule conjugates for the treatment of Facioscapulohumeral Muscular Dystrophy (FSHD) especially muscle dystrophy and/or muscle atrophy associated therewith. In some instances, the polynucleic acid molecule conjugates described herein enhance intracellular uptake, stability, and/or efficacy. In some cases, the polynucleic acid molecule conjugates comprise an antibody or antigen binding fragment thereof conjugated to a polynucleic acid molecule. In some cases, the polynucleic acid molecules that hybridize to target sequences of DUX4, preferably human DUX4. In some cases, the nucleic acid molecules that hybridize to target sequences of human DUX4 having the accession number NM_001306068. In some cases, the nucleic acid molecules that hybridize to target sequences of human DUX4 having the SEQ ID NO: 439.

Additional aspects described herein include methods of treating FSHD, comprising administering to a subject a polynucleic acid molecule or a polynucleic acid molecule conjugate described herein.

Polynucleic Acid Molecules

In certain aspects, a polynucleic acid molecule hybridizes to a target sequence of Double homeobox 4 (DUX4) gene. In some instances, a polynucleic acid molecule described herein hybridizes to a target sequence of human DUX4 gene (DUX4) and reduces DUX4 mRNA in muscle cells.

In some aspects, the polynucleic acid molecule comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 1-70. In some aspects, the polynucleic acid molecule comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 141-210. In some aspects, the polynucleic acid molecule comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 71-140. In some aspects, the polynucleic acid molecule comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 211-280.

In some aspects, the polynucleic acid molecule comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 142, 146, 196, 201-206, 412-420, or 430-438.

In some aspects, the polynucleic acid molecule comprises a first polynucleotide and a second polynucleotide. In some instances, the first polynucleotide comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 1-70. In some cases, the second polynucleotide comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 71-140. In some cases, the polynucleic acid molecule comprises a first polynucleotide and a second polynucleotide. In some instances, the first polynucleotide comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 141-210. In some cases, the second polynucleotide comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 211-280.

In some instances, the first polynucleotide comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 142, 146, 196, or 201-206. In some cases, the second polynucleotide comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 412-420 or 430-438.

In some aspects, the polynucleic acid molecule comprises a sense strand (e.g., a passenger strand) and an antisense strand (e.g., a guide strand). In some instances, the sense strand (e.g., the passenger strand) comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 1-70. In some instances, the antisense strand (e.g., the guide strand) comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 71-140. In some aspects, the polynucleic acid molecule comprises a sense strand (e.g., a passenger strand) and an antisense strand (e.g., a guide strand). In some instances, the sense strand (e.g., the passenger strand) comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 141-210. In some instances, the antisense strand (e.g., the guide strand) comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 211-280. In some instances, the sense strand (e.g., the passenger strand) comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 142, 146, 196, or 201-206. In some instances, the antisense strand (e.g., the guide strand) comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 412-420 or 430-438.

In some instances, the sense strand comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 1, 2, 3, 6, 14, 36, 52, 56, 61, 62, 63, 65, or 66. In some instances, the antisense strand comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 71, 72, 73, 76, 84, 106, 122, 127, 131, 132, 133, 135, or 136. In some instances, the siRNA comprises sense strand and antisense strand as presented in Table 11.

In some instances, the sense strand comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 141, 142, 143, 146, 176, 192, 196, 201, 202, 203, 205, or 206. In some instances, the antisense strand comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 211, 212, 213, 216, 246, 262, 266, 271, 272, 273, 275, or 276. In some instances, the siRNA comprises sense strand and antisense strand as presented in Table 12.

In some instances, the sense strand comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 142, 146, 196, or 201-206 in Table 14 and Table 15.

In some instances, the antisense strand comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 412-420 or 430-438 in Table 14 and Table 15.

In some embodiments, the polynucleic acid molecule comprises a sense strand and/or an antisense strand, and the antisense strand comprises at least 80%, at least 85%, at least 90%, at least 95%, at least 96%, at least 97%, at least 98%, at least 99% identical to a sequence selected from SEQ ID NOs: 412-420 or 430-438. In some embodiments, the polynucleic acid molecule comprises a sense strand and/or an antisense strand, and the antisense is identical to a sequence selected from SEQ ID NOs: 412-420 or 430-438. In some embodiments, the polynucleic acid molecule comprises a sense strand and/or an antisense strand, and the sense strand comprises at least 80%, at least 85%, at least 90%, at least 95%, at least 96%, at least 97%, at least 98%, at least 99% identical to a sequence selected from SEQ ID NOs: 142, 146, 196, or 201-206. In some embodiments, the polynucleic acid molecule comprises a sense strand and/or an antisense strand, and the sense strand is identical to a sequence selected from SEQ ID NOs: 142, 146, 196, or 201-206.

In some aspects, the sequence polynucleic acid molecule has at least 14, 15, 16, 17, 18, or 19 contiguous nucleotides differing by no more than 3 nucleotides, no more than 2 nucleotides, or no more than 1 nucleotide from any one of SEQ ID NOs: 142, 146, 196, or 201-206, or SEQ ID NOs: 412-420 or 430-438. In some aspects, the polynucleic acid molecule is single-stranded. In some aspects, the polynucleic acid molecule is double-stranded.

In some aspects, the polynucleic acid molecule described herein comprises RNA or DNA. In some cases, the polynucleic acid molecule comprises RNA. In some instances, RNA comprises short interfering RNA (siRNA), short hairpin RNA (shRNA), microRNA (miRNA), double-stranded RNA (dsRNA), transfer RNA (IRNA), ribosomal RNA (rRNA), or heterogeneous nuclear RNA (hnRNA). In some instances, RNA comprises shRNA. In some instances, RNA comprises miRNA. In some instances, RNA comprises dsRNA. In some instances, RNA comprises tRNA. In some instances, RNA comprises rRNA. In some instances, RNA comprises hnRNA. In some instances, the oligonucleotide is a phosphorodiamidate morpholino oligomers (PMO), which are short single-stranded oligonucleotide analogs that are built upon a backbone of morpholine rings connected by phosphorodiamidate linkages. In some instances, the RNA comprises siRNA. In some instances, the polynucleic acid molecule comprises siRNA.

In some aspects, the polynucleic acid molecule is from about 8 to about 50 nucleotides in length. In some aspects, the polynucleic acid molecule is from about 10 to about 50 nucleotides in length. In some instances, the polynucleic acid molecule is from about 10 to about 30, from about 15 to about 30, from about 18 to about 25, form about 18 to about 24, from about 19 to about 23, or from about 20 to about 22 nucleotides in length.

In some aspects, the polynucleic acid molecule is about 50 nucleotides in length. In some instances, the polynucleic acid molecule is about 45 nucleotides in length. In some instances, the polynucleic acid molecule is about 40 nucleotides in length. In some instances, the polynucleic acid molecule is about 35 nucleotides in length. In some instances, the polynucleic acid molecule is about 30 nucleotides in length. In some instances, the polynucleic acid molecule is about 25 nucleotides in length. In some instances, the polynucleic acid molecule is about 20 nucleotides in length. In some instances, the polynucleic acid molecule is about 19 nucleotides in length. In some instances, the polynucleic acid molecule is about 18 nucleotides in length. In some instances, the polynucleic acid molecule is about 17 nucleotides in length. In some instances, the polynucleic acid molecule is about 16 nucleotides in length. In some instances, the polynucleic acid molecule is about 15 nucleotides in length. In some instances, the polynucleic acid molecule is about 14 nucleotides in length. In some instances, the polynucleic acid molecule is about 13 nucleotides in length. In some instances, the polynucleic acid molecule is about 12 nucleotides in length. In some instances, the polynucleic acid molecule is about 11 nucleotides in length. In some instances, the polynucleic acid molecule is about 10 nucleotides in length. In some instances, the polynucleic acid molecule is about 8 nucleotides in length. In some instances, the polynucleic acid molecule is between about 8 and about 50 nucleotides in length. In some instances, the polynucleic acid molecule is between about 10 and about 50 nucleotides in length. In some instances, the polynucleic acid molecule is between about 10 and about 45 nucleotides in length. In some instances, the polynucleic acid molecule is between about 10 and about 40 nucleotides in length. In some instances, the polynucleic acid molecule is between about 10 and about 35 nucleotides in length. In some instances, the polynucleic acid molecule is between about 10 and about 30 nucleotides in length. In some instances, the polynucleic acid molecule is between about 10 and about 25 nucleotides in length. In some instances, the polynucleic acid molecule is between about 10 and about 20 nucleotides in length. In some instances, the polynucleic acid molecule is between about 15 and about 25 nucleotides in length. In some instances, the polynucleic acid molecule is between about 15 and about 30 nucleotides in length. In some instances, the polynucleic acid molecule is between about 12 and about 30 nucleotides in length.

In some aspects, the polynucleic acid molecule comprises a first polynucleotide. In some instances, the polynucleic acid molecule comprises a second polynucleotide. In some instances, the polynucleic acid molecule comprises a first polynucleotide and a second polynucleotide. In some instances, the first polynucleotide is a sense strand or passenger strand. In some instances, the second polynucleotide is an antisense strand or guide strand.

In some aspects, the polynucleic acid molecule is a first polynucleotide. In some aspects, the first polynucleotide is from about 8 to about 50 nucleotides in length. In some aspects, the first polynucleotide is from about 10 to about 50 nucleotides in length. In some instances, the first polynucleotide is from about 10 to about 30, from about 15 to about 30, from about 18 to about 25, form about 18 to about 24, from about 19 to about 23, or from about 20 to about 22 nucleotides in length.

In some instances, the first polynucleotide is about 50 nucleotides in length. In some instances, the first polynucleotide is about 45 nucleotides in length. In some instances, the first polynucleotide is about 40 nucleotides in length. In some instances, the first polynucleotide is about 35 nucleotides in length. In some instances, the first polynucleotide is about 30 nucleotides in length. In some instances, the first polynucleotide is about 25 nucleotides in length. In some instances, the first polynucleotide is about 20 nucleotides in length. In some instances, the first polynucleotide is about 19 nucleotides in length. In some instances, the first polynucleotide is about 18 nucleotides in length. In some instances, the first polynucleotide is about 17 nucleotides in length. In some instances, the first polynucleotide is about 16 nucleotides in length. In some instances, the first polynucleotide is about 15 nucleotides in length. In some instances, the first polynucleotide is about 14 nucleotides in length. In some instances, the first polynucleotide is about 13 nucleotides in length. In some instances, the first polynucleotide is about 12 nucleotides in length. In some instances, the first polynucleotide is about 11 nucleotides in length. In some instances, the first polynucleotide is about 10 nucleotides in length. In some instances, the first polynucleotide is about 8 nucleotides in length. In some instances, the first polynucleotide is between about 8 and about 50 nucleotides in length. In some instances, the first polynucleotide is between about 10 and about 50 nucleotides in length. In some instances, the first polynucleotide is between about 10 and about 45 nucleotides in length. In some instances, the first polynucleotide is between about 10 and about 40 nucleotides in length. In some instances, the first polynucleotide is between about 10 and about 35 nucleotides in length. In some instances, the first polynucleotide is between about 10 and about 30 nucleotides in length. In some instances, the first polynucleotide is between about 10 and about 25 nucleotides in length. In some instances, the first polynucleotide is between about 10 and about 20 nucleotides in length. In some instances, the first polynucleotide is between about 15 and about 25 nucleotides in length. In some instances, the first polynucleotide is between about 15 and about 30 nucleotides in length. In some instances, the first polynucleotide is between about 12 and about 30 nucleotides in length.

In some aspects, the polynucleic acid molecule is a second polynucleotide. In some aspects, the second polynucleotide is from about 8 to about 50 nucleotides in length. In some aspects, the second polynucleotide is from about 10 to about 50 nucleotides in length. In some instances, the second polynucleotide is from about 10 to about 30, from about 15 to about 30, from about 18 to about 25, form about 18 to about 24, from about 19 to about 23, or from about 20 to about 22 nucleotides in length.

In some instances, the second polynucleotide is about 50 nucleotides in length. In some instances, the second polynucleotide is about 45 nucleotides in length. In some instances, the second polynucleotide is about 40 nucleotides in length. In some instances, the second polynucleotide is about 35 nucleotides in length. In some instances, the second polynucleotide is about 30 nucleotides in length. In some instances, the second polynucleotide is about 25 nucleotides in length. In some instances, the second polynucleotide is about 20 nucleotides in length. In some instances, the second polynucleotide is about 19 nucleotides in length. In some instances, the second polynucleotide is about 18 nucleotides in length. In some instances, the second polynucleotide is about 17 nucleotides in length. In some instances, the second polynucleotide is about 16 nucleotides in length. In some instances, the second polynucleotide is about 15 nucleotides in length. In some instances, the second polynucleotide is about 14 nucleotides in length. In some instances, the second polynucleotide is about 13 nucleotides in length. In some instances, the second polynucleotide is about 12 nucleotides in length. In some instances, the second polynucleotide is about 11 nucleotides in length. In some instances, the second polynucleotide is about 10 nucleotides in length. In some instances, the second polynucleotide is about 8 nucleotides in length. In some instances, the second polynucleotide is between about 8 and about 50 nucleotides in length. In some instances, the second polynucleotide is between about 10 and about 50 nucleotides in length. In some instances, the second polynucleotide is between about 10 and about 45 nucleotides in length. In some instances, the second polynucleotide is between about 10 and about 40 nucleotides in length. In some instances, the second polynucleotide is between about 10 and about 35 nucleotides in length. In some instances, the second polynucleotide is between about 10 and about 30 nucleotides in length. In some instances, the second polynucleotide is between about 10 and about 25 nucleotides in length. In some instances, the second polynucleotide is between about 10 and about 20 nucleotides in length. In some instances, the second polynucleotide is between about 15 and about 25 nucleotides in length. In some instances, the second polynucleotide is between about 15 and about 30 nucleotides in length. In some instances, the second polynucleotide is between about 12 and about 30 nucleotides in length.

In some aspects, the polynucleic acid molecule comprises a first polynucleotide and a second polynucleotide. In some instances, the polynucleic acid molecule further comprises a blunt terminus, an overhang, or a combination thereof. In some instances, the blunt terminus is a 5' blunt terminus, a 3' blunt terminus, or both. In some cases, the overhang is a S' overhang, 3' overhang, or both. In some cases, the overhang comprises 1, 2, 3, 4, 5, 6, 7, 8, 9, or 10 non-base pairing nucleotides. In some cases, the overhang comprises 1, 2, 3, 4, 5, or 6 non-base pairing nucleotides. In some cases, the overhang comprises 1, 2, 3, or 4 non-base pairing nucleotides. In some cases, the overhang comprises 1 non-base pairing nucleotide. In some cases, the overhang comprises 2 non-base pairing nucleotides. In some cases, the overhang comprises 3 non-base pairing nucleotides. In some cases, the overhang comprises 4 non-base pairing nucleotides. In some aspects, the polynucleic acid molecule comprises a sense strand and an antisense strand, and the antisense strand includes two non-base pairing nucleotides as an overhang at the 3'-end while the sense strand has no overhang. Optionally, in such aspects, the non-base pairing nucleotides have a sequence of TT, dTdT, or UU. In some aspects, the polynucleic acid molecule comprises a sense strand and an antisense strand, and the sense strand has one or more nucleotides at the 5'-end that are complementary to the antisense sequence.

In some aspects, the sequence of the polynucleic acid molecule is at least 40%, 50%, 55%, 60%, 65%, 70%, 75%, 80%, 85%, 90%, 95%, 98%, 99%, or 99.5% complementary to a target sequence of DUX4. In some aspects, the target sequence of DUX4 is a nucleic acid sequence of about 10-50 base pair length, about 15-50 base pair length, 15-40 base pair length, 15-30 base pair length, or 15-25 base pair length sequences in DUX4, in which the first nucleotide of the target sequence starts at any nucleotide in DUX4 mRNA transcript in the coding region, or in the 5' or 3'-untranslated region (UTR). For example, the first nucleotide of the target sequence can be selected so that it starts at the nucleic acid location (nal, number starting from the 5'-end of the full length of DUX mRNA, e.g., the S'-end first nucleotide is nal. 1) 1, nal 2, nal 3, nal 4, nal 5, nal 6, nal 7, nal 8, nal 9, nal 10, nal 11, nal 12, nal 13, nal 14, nal 15, nal 15, nal 16, nal 17, or any other nucleic acid location in the coding or noncoding regions (5' or 3'-untraslated region) of DUX mRNA. In some aspects, the first nucleotide of the target sequence can be selected so that it starts at a location within, or between, nal 10-nal 15, nal 10-nal 20, nal 50-nal 60, nal 55-nal 65, nal 75-nal 85, nal 95-nal 105, nal 135-nal 145, nal 155-nal 165, nal 225-nal 235, nal 265-nal 275, nal 275-nal 285, nal 285-nal 295, nal 325-nal 335, nal 335-nal 345, nal 385-nal 395, nal 515-nal 525, nal 665-nal 675, nal 675-nal 685, nal 695-nal 705, nal 705-nal 715, nal 875-nal 885, nal 885-nal 895, nal 895-nal 905, nal 1035-nal 1045, nal 1045-nal 1055, nal 1125-nal 1135, nal 1135-nal 1145, nal 1145-nal 1155, nal 1155-nal 1165, nal 1125-nal 1135, nal 1155-nal 1165, nal 1225-nal 1235, nal 1235-nal 1245, nal 1275-nal 1285, nal 1285-nal 1295, nal 1305-nal 1315, nal 1125-nal 1135, nal 1155-pal 1165, nal 1225-nal 1235, nal 1235-nal 1245, nal 1275-nal 1285, nal 1285-nal 1295, nal 1305-nal 1315, nal 1315-nal 1325, nal 1335-nal 1345, nal 1345-nal 1355, nal 1525-nal 1535, nal 1535-nal 1545, nal 1605-nal 1615, nal 1615-c.1625, nal 1625-nal 1635.

In some aspects, the sequence of the polynucleic acid molecule is at least 50% complementary to a target sequence described herein. In some aspects, the sequence of the polynucleic acid molecule is at least 60% complementary to a target sequence described herein. In some aspects, the sequence of the polynucleic acid molecule is at least 70% complementary to a target sequence described herein. In some aspects, the sequence of the polynucleic acid molecule is at least 80% complementary to a target sequence described herein. In some aspects, the sequence of the polynucleic acid molecule is at least 90% complementary to a target sequence described herein. In some aspects, the sequence of the polynucleic acid molecule is at least 95% complementary to a target sequence described herein. In some aspects, the sequence of the polynucleic acid molecule is at least 99% complementary to a target sequence described herein. In some instances, the sequence of the polynucleic acid molecule is 100% complementary to a target sequence described herein.

In some aspects, the sequence of the polynucleic acid molecule has five or fewer mismatches to a target sequence described herein. In some aspects, the sequence of the polynucleic acid molecule has four or fewer mismatches to a target sequence described herein. In some instances, the sequence of the polynucleic acid molecule has three or fewer mismatches to a target sequence described herein. In some cases, the sequence of the polynucleic acid molecule has two or fewer mismatches to a target sequence described herein. In some cases, the sequence of the polynucleic acid molecule has one or fewer mismatches to a target sequence described herein.

In some aspects, a group of polynucleic acid molecules among all the polynucleic acid molecules potentially binds to the target sequence of DUX4 are selected to generate a polynucleic acid molecule library. In certain aspects, such selection process is conducted in silico via one or more steps of eliminating less desirable polynucleic acid molecules from candidates. For example, in some aspects, the selection process comprises an elimination step of one or more polynucleic acid molecule that has single nucleotide polymorphism (SNP) and/or MEF <−5. Alternatively and/or additionally, in some aspects, the selection process comprises an elimination step of one or more polynucleic acid molecule with 0 and 1 mismatch (MM) in the human transcriptome (such that only hits allowed are DUX, DUX5, and DBET). Alternatively and/or additionally, in some aspects, the selection process comprises an elimination step of one or more polynucleic acid molecule with 0 MM in the human intragenic regions (such that only hits allowed are DUX1, DUX5 and DBET pseudogenes). Alternatively and/or additionally, in some aspects, the selection process comprises an elimination step of one or more polynucleic acid molecule with a MM to DUX4 human sequence used in FLEXDUX4 FSHD mouse model. Alternatively and/or additionally, in some aspects, the selection process comprises an elimination step of one or more polynucleic acid molecule predicted viability <60. Alternatively and/or additionally, such selection process comprises carrying forward one or more polynucleic acid molecule predicted viability >60. Alternatively and/or additionally, in some aspects, the selection process comprises an elimination step of one or more polynucleic acid molecule with a match to a seed region of known miRNAs 1-1000. Alternatively and/or additionally, in some aspects, the selection process comprises an elimination step of one or more polynucleic acid molecule with % GC content 75 and above. Alternatively and/or additionally, in some aspects, the selection process comprises a selection step of eight or fewer predicted off-target hits with 2 MM. In some aspects, for the region 295-1132 (nal 295-1132), 12 or fewer predicted off-target hits with 2 MM is allowed.

In some aspects, selection process is conducted in silico via one or more consecutive steps of eliminating less desirable polynucleic acid molecules from candidates. For example, in some aspects, selection process begins with collecting candidate polynucleic acid molecules to generate a library. From the library, the first eliminating step comprises eliminating one or more polynucleic acid molecule that has single nucleotide polymorphism (SNP) and/or MEF <−5. Then, the second eliminating step comprises eliminating one or more polynucleic acid molecule with 0 and 1 MM in the human transcriptome (such that only hits allowed are DUX, DUX5, and DBET). Then, the third eliminating step comprises eliminating one or more polynucleic acid molecule with 0 MM in the human intragenic regions (such that only hits allowed are DUX1, DUX5 and DBET pseudogenes). Then, the next eliminating step comprises eliminating one or more polynucleic acid molecule with a MM to DUX4 human sequence used in FLExDUX4 FSHD mouse model. Then, the next step is carrying forward only or one or more polynucleic acid molecule with predicted viability ≥60. Next, the eliminating step comprises eliminating one or more polynucleic acid molecule with a match to a seed region of known miRNAs 1-1000. Then, the eliminating step continues with eliminating one or more polynucleic acid molecule with % GC content 75 and above. Then, the final selection process comprises with eight or fewer predicted off-target hits with 2 MM, except for the region 295-1132, for which up to 12 hits are allowed.

In some aspects, the specificity of the polynucleic acid molecule that hybridizes to a target sequence described herein is a 95%, 98%, 99%, 99.5%, or 100% sequence complementarity of the polynucleic acid molecule to a target sequence. In some instances, the hybridization is a high stringent hybridization condition.

In some aspects, the polynucleic acid molecule has reduced off-target effect. In some instances, "off-target" or "off-target effects" refer to any instance in which a polynucleic acid polymer directed against a given target causes an unintended effect by interacting either directly or indirectly with another mRNA sequence, a DNA sequence or a cellular protein or other moiety. In some instances, an "off-target effect" occurs when there is a simultaneous degradation of other transcripts due to partial homology or complementarity between that other transcript and the sense and/or antisense strand of the polynucleic acid molecule.

In some aspects, the polynucleic acid molecule comprises natural or synthetic or artificial nucleotide analogues or bases. In some cases, the polynucleic acid molecule comprises combinations of DNA, RNA and/or nucleotide analogues. In some instances, the synthetic or artificial nucleotide analogues or bases comprise modifications at one or more of ribose moiety, phosphate moiety, nucleoside moiety, or a combination thereof.

In some aspects, nucleotide analogues or artificial nucleotide base comprise a nucleic acid with a modification at a 2' hydroxyl group of the ribose moiety. In some instances, the modification includes an H, OR, R, halo, SH, SR, $NH_2$, NHR, NR2, or CN, wherein R is an alkyl moiety. Exemplary alkyl moiety includes, but is not limited to, halogens, sulfurs, thiols, thioethers, thioesters, amines (primary, secondary, or tertiary), amides, ethers, esters, alcohols and oxygen. In some instances, the alkyl moiety further comprises a modification. In some instances, the modification comprises an azo group, a keto group, an aldehyde group, a carboxyl group, a nitro group, a nitroso, group, a nitrile group, a heterocycle (e.g., imidazole, hydrazino or hydroxylamino) group, an isocyanate or cyanate group, or a sulfur containing group (e.g., sulfoxide, sulfone, sulfide, and disulfide). In some instances, the alkyl moiety further comprises a hetero substitution. In some instances, the carbon of the heterocyclic group is substituted by a nitrogen, oxygen or sulfur. In some instances, the heterocyclic substitution includes but is not limited to, morpholino, imidazole, and pyrrolidino.

In some instances, the modification at the 2' hydroxyl group is a 2'-O-methyl modification or a 2'-O-methoxyethyl (2'-O-MOE) modification. In some cases, the 2'-O-methyl modification adds a methyl group to the 2' hydroxyl group of the ribose moiety whereas the 2'-O-methoxyethyl modification adds a methoxyethyl group to the 2' hydroxyl group of the ribose moiety. Exemplary chemical structures of a 2'-O-methyl modification of an adenosine molecule and 2'-O-methoxyethyl modification of an uridine are illustrated below.

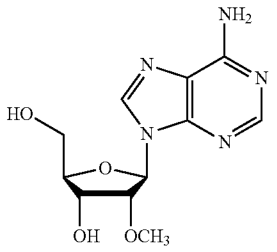

2'-O-methyl-adenosine

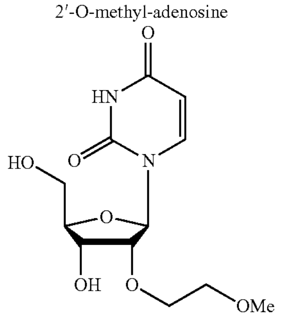

2'-O-methoxyethyl uridine

In some instances, the modification at the 2' hydroxyl group is a 2'-O-aminopropyl modification in which an extended amine group comprising a propyl linker binds the amine group to the 2' oxygen. In some instances, this modification neutralizes the phosphate derived overall negative charge of the oligonucleotide molecule by introducing one positive charge from the amine group per sugar and thereby improves cellular uptake properties due to its zwitterionic properties. An exemplary chemical structure of a 2'-O-aminopropyl nucleoside phosphoramidite is illustrated below.

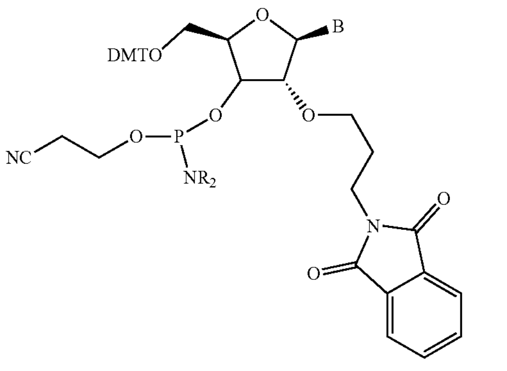

2'-O-aminopropyl nucleoside phosphoramidite

In some instances, the modification at the 2' hydroxyl group is a locked or bridged ribose modification (e.g., locked nucleic acid or LNA) in which the oxygen molecule bound at the 2' carbon is linked to the 4' carbon by a methylene group, thus forming a 2'-C,4'-C-oxy-methylene-linked bicyclic ribonucleotide monomer. Exemplary representations of the chemical structure of LNA are illustrated below. The representation shown to the left highlights the chemical connectivities of an LNA monomer. The representation shown to the right highlights the locked 3'-endo (E) conformation of the furanose ring of an LNA monomer.

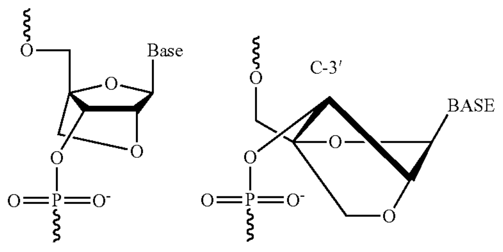

LNA (Locked Nucleic Acids)

In some instances, the modification at the 2' hydroxyl group comprises ethylene nucleic acids (ENA) such as for example 2'-4'-ethylene-bridged nucleic acid, which locks the sugar conformation into a $C_3$'-endo sugar puckering conformation. ENA are part of the bridged nucleic acids class of modified nucleic acids that also comprises LNA. Exemplary chemical structures of the ENA and bridged nucleic acids are illustrated below.

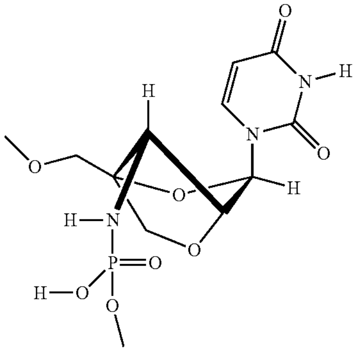

3'-amino-2',4'-BNA

-continued

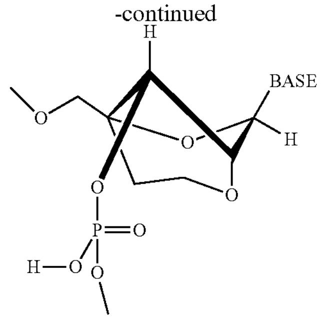

2',4'-ENA

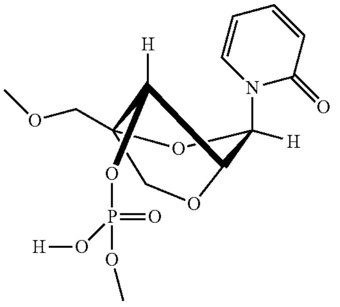

2',4'-BNA-2-pyridone

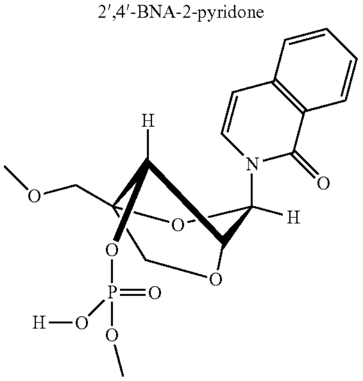

2',4'-BNA-1-isoquinolone

In some aspects, additional modifications at the 2' hydroxyl group include 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O)-DMAP), 2'-O-dimethylaminoethyloxyethyl (2'-O-DMAEOE), or 2'-O—N-methylacetamido (2'-O-NMA).

In some aspects, nucleotide analogues comprise modified bases such as, but not limited to, 5-propynyluridine, 5-propynylcytidine, 6-methyladenine, 6-methylguanine, N, N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2, 2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2, 4, 6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties, in some cases are or be based on, mannoses, arabinoses, glucopyranoses, galactopyranoses, 4'-thioribose, and other sugars, heterocycles, or carbocycles. The term nucleotide also includes what are known in the art as universal bases. By way of example, universal bases include but are not limited to 3-nitropyrrole, 5-nitroindole, or nebularine.

In some aspects, nucleotide analogues further comprise morpholinos, peptide nucleic acids (PNAs), methylphosphonate nucleotides, thiolphosphonate nucleotides, 2'-fluoro N3-P5'-phosphoramidites, 1', 5'-anhydrohexitol nucleic acids (HNAs), or a combination thereof. Morpholino or phosphorodiamidate morpholino oligo (PMO) comprises synthetic molecules whose structure mimics natural nucleic acid structure by deviates from the normal sugar and phosphate structures. In some instances, the five member ribose ring is substituted with a six member morpholino ring containing four carbons, one nitrogen and one oxygen. In some cases, the ribose monomers are linked by a phosphordiamidate group instead of a phosphate group. In such cases, the backbone alterations remove all positive and negative charges making morpholinos neutral molecules capable of crossing cellular membranes without the aid of cellular delivery agents such as those used by charged oligonucleotides.

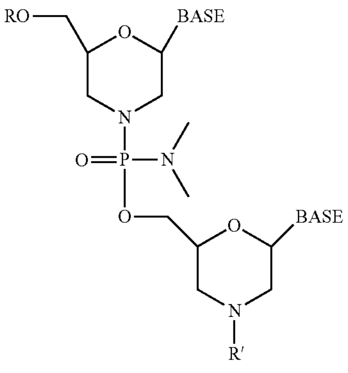

Morpholino

In some aspects, peptide nucleic acid (PNA) does not contain sugar ring or phosphate linkage and the bases are attached and appropriately spaced by oligoglycine-like molecules, therefore, eliminating a backbone charge.

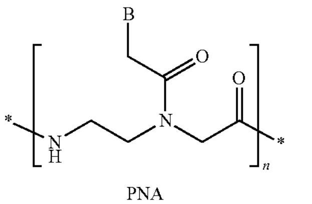

PNA

In some aspects, one or more modifications optionally occur at the internucleotide linkage. In some instances, modified internucleotide linkage include, but is not limited to, phosphorothioates, phosphorodithioates, methylphosphonates, 5'-alkylenephosphonates, 5'-methylphosphonate, 3'-alkylene phosphonates, borontrifluoridates, borano phosphate esters and selenophosphates of 3'-S' linkage or 2'-5' linkage, phosphotriesters, thionoalkylphosphotriesters, hydrogen phosphonate linkages, alkyl phosphonates, alkylphosphonothioates, arylphosphonothioates, phosphoroselenoates, phosphorodiselenoates, phosphinates, phosphoramidates, 3'-alkylphosphoramidates, aminoalkylphosphoramidates, thionophosphoramidates, phosphoropiperazidates, phosphoroanilothioates, phosphoroanilidates, ketones, sulfones, sulfonamides, carbonates, carbamates, methylenehydrazos, methylenedimethylhydrazos, formacetals, thioformacetals, oximes, methyleneiminos, methylenemethyliminos, thioamidates, linkages with riboacetyl groups, aminoethyl glycine, silyl or siloxane linkages, alkyl or cycloalkyl linkages with or without heteroatoms of, for example, 1 to 10 carbons that are saturated or unsaturated and/or substituted and/or contain heteroatoms, linkages with morpholino structures, amides, polyamides wherein the bases are attached to the aza nitrogens of the backbone directly or indirectly, and combinations thereof. Phosphorothioate antisense oligonucleotides (PS ASO) are antisense oligonucleotides comprising a phosphorothioate linkage. An exemplary PS ASO is illustrated below.

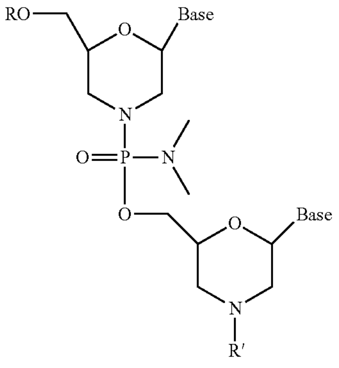

Morpholino

In some instances, the modification is a methyl or thiol modification such as methylphosphonate or thiolphosphonate modification. Exemplary thiolphosphonate nucleotide (left) and methylphosphonate nucleotide (right) are illustrated below.

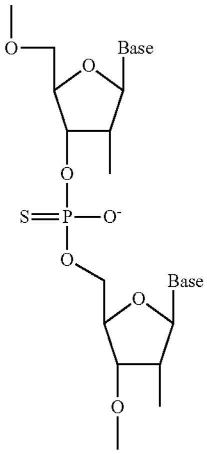
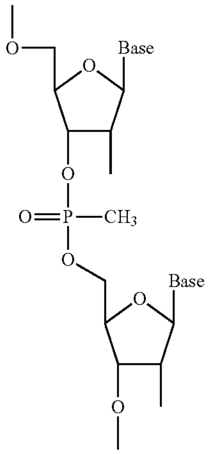

In some instances, a modified nucleotide includes, but is not limited to, 2'-fluoro N3-P5'-phosphoramidites illustrated as:

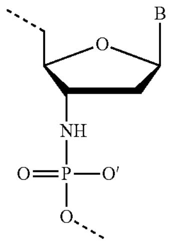

N3′-P5′
Phosphoroamidate

In some instances, a modified nucleotide includes, but is not limited to a 5'-vinylphosphonate modified non-natural nucleotide selected from:

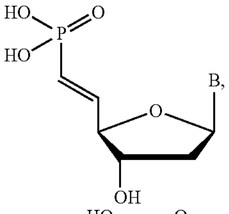
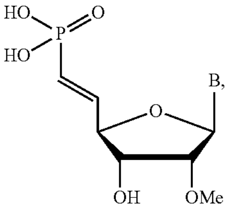
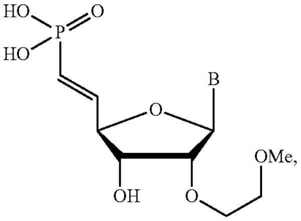
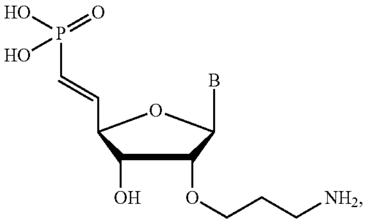

-continued

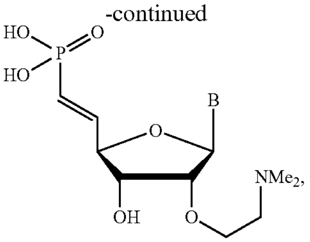
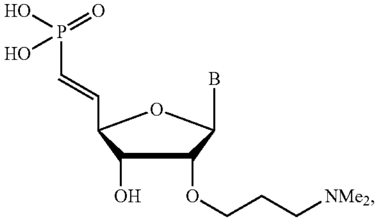
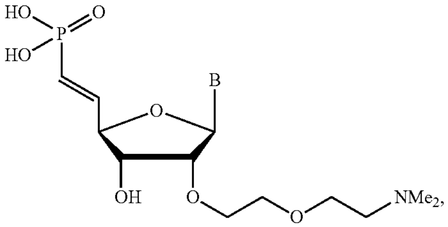
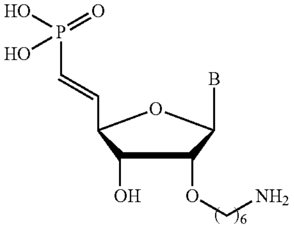

or

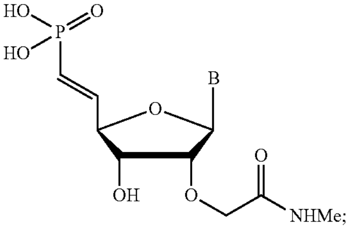

where B is a heterocyclic base moiety.

In some instances, a modified nucleotide includes, but is not limited to one 5'-vinylphosphonate modified non-natural nucleotide selected from:

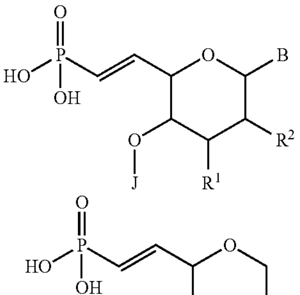

or

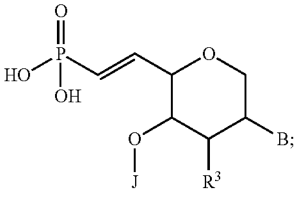

where B is a heterocyclic base moiety; R1, R2, and R3 are independently selected from hydrogen, halogen, alkyl or alkoxy; and J is an internucleotide linking group linking to the adjacent nucleotide of the polynucleotide.

In some instances, a modified nucleotide includes, but is not limited to one 5'-vinylphosphonate modified non-natural nucleotide selected from:

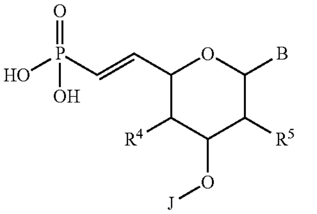

or

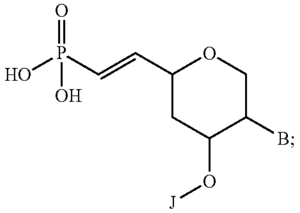

where B is a heterocyclic base moiety; R4, and R5 are independently selected from hydrogen, halogen, alkyl or alkoxy; and J is an internucleotide linking group linking to the adjacent nucleotide of the polynucleotide.

In some instances, a modified nucleotide includes, but is not limited to one 5 vinylphosphonate modified non-natural nucleotide selected from:

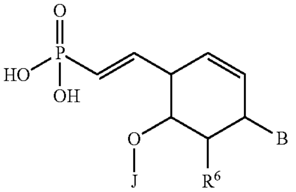

or

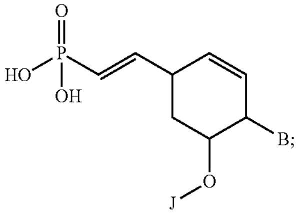

where B is a heterocyclic base moiety; R6 is selected from hydrogen, halogen, alkyl or alkoxy; and J is an internucleotide linking group linking to the adjacent nucleotide of the polynucleotide.

In some instances, a modified nucleotide includes, but is not limited to one 5'-vinylphosphonate modified non-natural nucleotide selected from locked nucleic acid (LNA) or ethylene nucleic acid (ENA).

In some instances, a modified nucleotide includes, but is not limited to one 5'-vinylphosphonate modified non-natural nucleotide selected from:

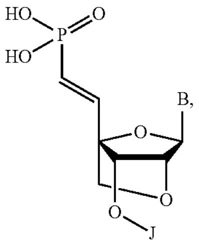

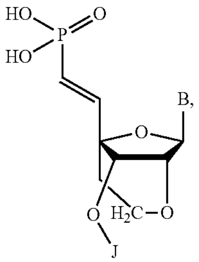

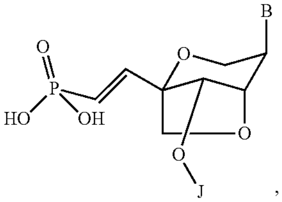

,

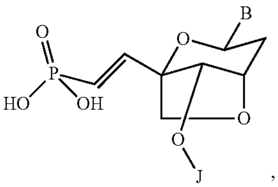

,

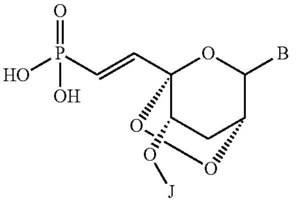

or

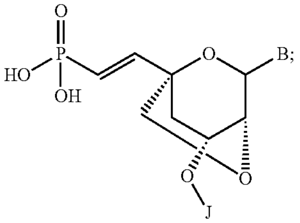

where B is a heterocyclic base moiety; and J is an internucleotide linking group linking to the adjacent nucleotide of the polynucleotide.

In some instances, a modified nucleotide includes, but is not limited to one 5'-vinylphosphonate modified non-natural nucleotide selected from:

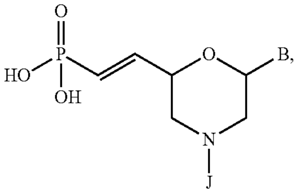

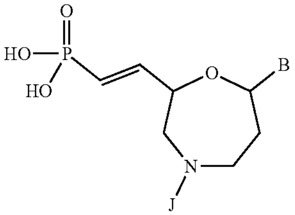

or

-continued

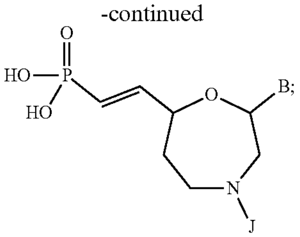

where B is a heterocyclic base moiety; and J is an internucleotide linking group linking to the adjacent nucleotide of the polynucleotide.

In some instances, a modified nucleotide includes, but is not limited to one 5'-vinylphosphonate modified non-natural nucleotide selected from:

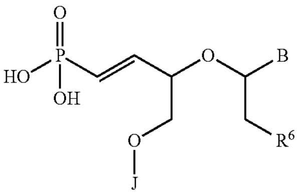

or

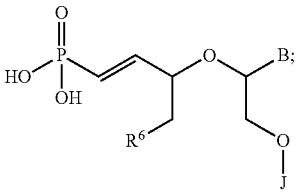

where B is a heterocyclic base moiety; R6 is selected from hydrogen, halogen, alkyl or alkoxy; and J is an internucleotide linking group linking to the adjacent nucleotide of the polynucleotide.

In some instances, a modified nucleotide includes, but is not limited to one S'-vinylphosphonate modified non-natural nucleotide is:

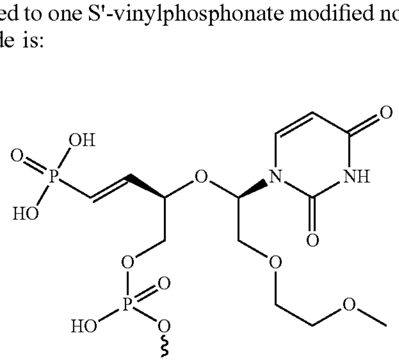

Next nucleotide vpUq

In some instances, a modified nucleotide includes, but is not limited to, hexitol nucleic acid (or 1', 5'-anhydrohexitol nucleic acids (HNA)) illustrated as:

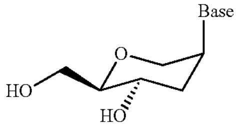

HNA

In some aspects, one or more modifications further optionally include modifications of the ribose moiety, phosphate backbone and the nucleoside, or modifications of the nucleotide analogues at the 3' or the 5' terminus. For example, the 3' terminus optionally include a 3' cationic group, or by inverting the nucleoside at the 3'-terminus with a 3'-3' linkage. In another alternative, the 3'-terminus is optionally conjugated with an aminoalkyl group, e.g., a 3' $C_5$-aminoalkyl dT. In an additional alternative, the 3'-terminus is optionally conjugated with an abasic site, e.g., with an apurinic or apyrimidinic site. In some instances, the 5'-terminus is conjugated with an aminoalkyl group, e.g., a 5'-O-alkylamino substituent. In some cases, the 5'-terminus is conjugated with an abasic site, e.g., with an apurinic or apyrimidinic site.

In some aspects, the polynucleic acid molecule comprises one or more of the artificial nucleotide analogues described herein. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues described herein. In some aspects, the artificial nucleotide analogues include 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues selected from 2'-O-methyl, 2'-O-methoxyethyl (2'-O-MOB), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methyl modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methoxyethyl (2'-O-MOE) modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of thiolphosphonate nucleotides.

In some instances, the polynucleic acid molecule comprises at least one of: from about 5% to about 100% modification, from about 10% to about 100% modification, from about 20% to about 100% modification, from about 30% to about 100% modification, from about 40% to about 100% modification, from about 50% to about 100% modification, from about 60% to about 100% modification, from about 70% to about 100% modification, from about 80% to about 100% modification, and from about 90% to about 100% modification.

In some cases, the polynucleic acid molecule comprises at least one of: from about 10% to about 90% modification, from about 20% to about 90% modification, from about 30% to about 90% modification, from about 40% to about 90% modification, from about 50% to about 90% modification, from about 60% to about 90% modification, from about 70% to about 90% modification, and from about 80% to about 100% modification.

In some cases, the polynucleic acid molecule comprises at least one of: from about 10% to about 80% modification, from about 20% to about 80% modification, from about 30% to about 80% modification, from about 40% to about 80% modification, from about 50% to about 80% modification, from about 60% to about 80% modification, and from about 70% to about 80% modification.

In some instances, the polynucleic acid molecule comprises at least one of: from about 10% to about 70% modification, from about 20% to about 70% modification, from about 30% to about 70% modification, from about 40% to about 70% modification, from about 50% to about 70% modification, and from about 60% to about 70% modification.

In some instances, the polynucleic acid molecule comprises at least one of; from about 10% to about 60% modification, from about 20% to about 60% modification, from about 30% to about 60% modification, from about 40% to about 60% modification, and from about 50% to about 60% modification.

In some cases, the polynucleic acid molecule comprises at least one of: from about 10% to about 50% modification, from about 20% to about 50% modification, from about 30% to about 50% modification, and from about 40% to about 50% modification.

In some cases, the polynucleic acid molecule comprises at least one of: from about 10% to about 40% modification, from about 20% to about 40% modification, and from about 30% to about 40% modification.

In some cases, the polynucleic acid molecule comprises at least one of: from about 10% to about 30% modification, and from about 20% to about 30% modification.

In some cases, the polynucleic acid molecule comprises from about 10% to about 20% modification.

In some cases, the polynucleic acid molecule comprises from about 15% to about 90%, from about 20% to about 80%, from about 30% to about 70%, or from about 40% to about 60% modifications.

In additional cases, the polynucleic acid molecule comprises at least about 15%, 20%, 30%, 40%, 50%, 60%, 70%, 80%, 90%, 95%, or 99% modification.

In some aspects, the polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22 or more modifications.

In some instances, the polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22 or more modified nucleotides.

In some instances, from about 5 to about 100% of the polynucleic acid molecule comprise the artificial nucleotide analogues described herein. In some instances, about 5%, 10%, 15%, 20%, 25%, 30%, 35%, 40%, 45%, 50%, 55%, 60%, 65%, 70%, 75%, 80%, 85%, 90%, 95% or 100% of the polynucleic acid molecule comprise the artificial nucleotide analogues described herein. In some instances, about 5% of the polynucleic acid molecule comprises the artificial nucleotide analogues described herein. In some instances, about 10% of the polynucleic acid molecule comprises the artificial nucleotide analogues described herein. In some instances, about 15% of the polynucleic acid molecule comprises the artificial nucleotide analogues described herein. In some instances, about 20% of the polynucleic acid molecule comprises the artificial nucleotide analogues described herein. In some instances, about 25% of the polynucleic acid molecule comprises the artificial nucleotide analogues described herein. In some instances, about 30% of the polynucleic acid molecule comprises the artificial nucleotide analogues described herein. In some instances, about 35% of the polynucleic acid molecule comprises the artificial nucleotide analogues described herein. In some instances, about 40% of the polynucleic acid molecule comprises the artificial nucleotide analogues described herein. In some instances, about 45% of the polynucleic acid molecule comprises the artificial nucleotide analogues described herein. In some instances, about 50% of the polynucleic acid molecule comprises the artificial nucleotide analogues described herein. In some instances, about 55% of the polynucleic acid molecule comprises the artificial nucleotide analogues described herein. In some instances, about 60% of the polynucleic acid molecule comprises the artificial nucleotide analogues described herein. In some instances, about 65% of the polynucleic acid molecule comprises the artificial nucleotide analogues described herein. In some instances, about 70% of the polynucleic acid molecule comprises the artificial nucleotide analogues described herein. In some instances, about 75% of the polynucleic acid molecule comprises the artificial nucleotide analogues described herein. In some instances, about 80% of the polynucleic acid molecule comprises the artificial nucleotide analogues described herein. In some instances, about 85% of the polynucleic acid molecule comprises the artificial nucleotide analogues described herein. In some instances, about 90% of the polynucleic acid molecule comprises the artificial nucleotide analogues described herein. In some instances, about 95% of the polynucleic acid molecule comprises the artificial nucleotide analogues described herein. In some instances, about 96% of the polynucleic acid molecule comprises the artificial nucleotide analogues described herein. In some instances, about 97% of the polynucleic acid molecule comprises the artificial nucleotide analogues described herein. In some instances, about 98% of the polynucleic acid molecule comprises the artificial nucleotide analogues described herein. In some instances, about 99% of the polynucleic acid molecule comprises the artificial nucleotide analogues described herein. In some instances, about 100% of the polynucleic acid molecule comprises the artificial nucleotide analogues described herein. In some aspects, the artificial nucleotide analogues include 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof.

In some aspects, the polynucleic acid molecule comprises from about one to about 25 modifications in which the modification comprises an artificial nucleotide analogues described herein. In some aspects, the polynucleic acid molecule comprises about one modification in which the modification comprises an artificial nucleotide analogue described herein. In some aspects, the polynucleic acid molecule comprises about two modifications in which the modifications comprise an artificial nucleotide analogue described herein. In some aspects, the polynucleic acid molecule comprises about three modifications in which the modifications comprise an artificial nucleotide analogue described herein. In some aspects, the polynucleic acid molecule comprises about four modifications in which the modifications comprise an artificial nucleotide analogue described herein. In some aspects, the polynucleic acid molecule comprises about five modifications in which the modifications comprise an artificial nucleotide analogue described herein. In some aspects, the polynucleic acid molecule comprises about six modifications in which the modifications comprise an artificial nucleotide analogue described herein. In some aspects, the polynucleic acid molecule comprises about seven modifications in which the modifications comprise an artificial nucleotide analogue described herein. In some aspects, the polynucleic acid molecule comprises about eight modifications in which the modifications comprise an artificial nucleotide analogue described herein. In some aspects, the polynucleic acid molecule comprises about nine modifications in which the modifications comprise an artificial nucleotide analogue described herein. In some aspects, the polynucleic acid molecule comprises about 10 modifications in which the modifications comprise an artificial nucleotide analogue described herein. In some aspects, the polynucleic acid molecule comprises about 11 modifications in which the modifications comprise an artificial nucleotide analogue described herein. In some aspects, the polynucleic acid molecule comprises about 12 modifications in which the modifications comprise an artificial nucleotide analogue described herein. In some aspects, the polynucleic acid molecule comprises about 13 modifications in which the modifications comprise an artificial nucleotide analogue described herein. In some aspects, the polynucleic acid molecule comprises about 14 modifications in which the modifications comprise an artificial nucleotide analogue described herein. In some aspects, the polynucleic acid molecule comprises about 15 modifications in which the modifications comprise an artificial nucleotide analogue described herein. In some aspects, the polynucleic acid molecule comprises about 16 modifications in which the modifications comprise an artificial nucleotide analogue described herein. In some aspects, the polynucleic acid molecule comprises about 17 modifications in which the modifications comprise an artificial nucleotide analogue described herein. In some aspects, the polynucleic acid molecule comprises about 18 modifications in which the modifications comprise an artificial nucleotide analogue described herein. In some aspects, the polynucleic acid molecule comprises about 19 modifications in which the modifications comprise an artificial nucleotide analogue described herein. In some aspects, the polynucleic acid molecule comprises about 20 modifications in which the modifications comprise an artificial nucleotide analogue described herein. In some aspects, the polynucleic acid molecule comprises about 21 modifications in which the modifications comprise an artificial nucleotide analogue described herein. In some aspects, the polynucleic acid molecule comprises about 22 modifications in which the modifications comprise an artificial nucleotide analogue described herein. In some aspects, the polynucleic acid molecule comprises about 23 modifications in which the modifications comprise an artificial nucleotide analogue described herein. In some aspects, the polynucleic acid molecule comprises about 24 modifications in which the modifications comprise an artificial nucleotide analogue described herein. In some aspects, the polynucleic acid molecule comprises about 25 modifications in which the modifications comprise an artificial nucleotide analogue described herein.

In some aspects, a polynucleic acid molecule is assembled from two separate polynucleotides wherein one polynucleotide comprises the sense strand and the second polynucleotide comprises the antisense strand of the polynucleic acid molecule. In other aspects, the sense strand is connected to the antisense strand via a linker molecule, which in some instances is a polynucleotide linker or a non-nucleotide linker.

In some aspects, a polynucleic acid molecule comprises a sense strand and an antisense strand, wherein pyrimidine nucleotides in the sense strand comprises 2'-O-methylpyrimidine nucleotides and purine nucleotides in the sense strand comprise 2'-deoxy purine nucleotides. In some aspects, a polynucleic acid molecule comprises a sense strand and an antisense strand, wherein pyrimidine nucleotides present in the sense strand comprise 2'-deoxy-2'-fluoro pyrimidine nucleotides and wherein purine nucleotides present in the sense strand comprise 2'-deoxy purine nucleotides.

In some aspects, a polynucleic acid molecule comprises a sense strand and an antisense strand, wherein the pyrimidine nucleotides when present in said antisense strand are 2'-deoxy-2'-fluoro pyrimidine nucleotides and the purine nucleotides when present in said antisense strand are 2'-O-methyl purine nucleotides.

In some aspects, a polynucleic acid molecule comprises a sense strand and an antisense strand, wherein the pyrimidine nucleotides when present in said antisense strand are 2'-deoxy-2'-fluoro pyrimidine nucleotides and wherein the purine nucleotides when present in said antisense strand comprise 2'-deoxy-purine nucleotides.

In some aspects, a polynucleic acid molecule comprises a sense strand and an antisense strand, and at least one of sense strand and an antisense strand has a plurality of (e.g., two or more, three or more, four or more, five or more, six or more, seven or more, eight or more, etc.) 2'-O-methyl or 2'-deoxy-2'-fluoro modified nucleotides. In some aspects, where at least two out of the a plurality of 2'-O-methyl or 2'-deoxy-2'-fluoro modified nucleotides are consecutive nucleotides. In some aspects, where consecutive 2'-O-methyl or 2'-deoxy-2'-fluoro modified nucleotides are located at the 5'-end of the sense strand and/or the antisense strand. In some aspects, where consecutive 2'-O-methyl or 2'-deoxy-2'-fluoro modified nucleotides are located at the 3'-end of the sense strand and/or the antisense strand. In some aspects, the sense strand of polynucleic acid molecule includes at least four, at least five, at least six consecutive 2'-O-methyl modified nucleotides at its 5' end and/or 3' end, or both. Optionally, in such aspects, the sense strand of polynucleic acid molecule includes at least one, at least two, at least three, at least four 2'-deoxy-2'-fluoro modified nucleotides at the 3' end of the at least four, at least five, at least six consecutive 2'-O-methyl modified nucleotides at the polynucleotides' 5' end, or at the 5' end of the at least four, at least five, at least six consecutive 2'-O-methyl modified nucleotides at polynucleotides' 3' end. Also optionally, such at least two, at least three, at least four 2'-deoxy-2'-fluoro modified nucleotides are consecutive nucleotides.

In some aspects, a polynucleic acid molecule comprises a sense strand and an antisense strand, and at least one of sense strand and antisense strands has 2'-O-methyl modified nucleotide located at the S'-end of the sense strand and/or the antisense strand. In some aspects, at least one of sense strand and antisense strands has 2'-O-methyl modified nucleotide located at the 3'-end of the sense strand and/or the antisense strand. In some aspects, the 2'-O-methyl modified nucleotide located at the S'-end of the sense strand and/or the antisense strand is a purine nucleotide. In some aspects, the 2'-O-methyl modified nucleotide located at the 5'-end of the sense strand and/or the antisense strand is a pyridine nucleotide.

In some aspects, a polynucleic acid molecule comprises a sense strand and an antisense strand, and the antisense strand has two or more consecutive 2'-deoxy-2'-fluoro modified nucleotides at 5'-end. In some aspects, a polynucleic acid molecule comprises a sense strand and an antisense strand, and the antisense strand has two or more consecutive 2'-O-methyl modified nucleotides at 3'-end. In some aspects, a polynucleic acid molecule comprises a sense strand and an antisense strand, and the antisense strand has at least 2, 3, 4, 5, 6, or 7 consecutive 2'-O-methyl modified nucleotides.

In some aspects, a polynucleic acid molecule comprises a sense strand and an antisense strand, and the sense strand comprises a nucleic acid of 5'-nsnsnnnnNfNfNfnnnnnnnnnsnsa-3' (lower case (n)=2'-O-Me (methyl), Nf=2'-F (fluoro); s=phosphorothioate backbone modification). In some aspects, a polynucleic acid molecule comprises a sense strand and an antisense strand, and the antisense strand comprises a nucleic acid of 5'-UfsNfsnnnNfnnnnnnnNfnNfnnnsusu-3' (lower case (n)=2'-O-Me (methyl), Nf=2'-F (fluoro); s=phosphorothioate backbone modification). In some aspects, a polynucleic acid molecule comprises a sense strand and an antisense strand, and the sense strand comprises a nucleic acid of 5'-nsnsnnnnNfNfNfnnnnnnnnnsnsa-3' (lower case (n)=2'-O-Me (methyl), Nf=2'-F (fluoro); s=phosphorothioate backbone modification) and the antisense strand comprises a nucleic acid of S'-UfsNfsnnnNfnnnnnnnNfhNfinnsusu-3' (lower case (n)=2'-O-Me (methyl), Nf=2'-F (fluoro); s=phosphorothioate backbone modification).

In some aspects, a polynucleic acid molecule comprises a sense strand and an antisense strand, wherein the sense strand includes a terminal cap moiety at the 5'-end, the 3'-end, or both of the S' and 3' ends of the sense strand. In other aspects, the terminal cap moiety is an inverted deoxy abasic moiety.

In some aspects, a polynucleic acid molecule comprises a sense strand and an antisense strand, wherein the antisense strand comprises a glyceryl modification at the 3' end of the antisense strand.

In some aspects, a polynucleic acid molecule comprises a sense strand and an antisense strand, in which the sense strand comprises one or more, for example, about 1, 2, 3, 4, 5, 6, 7, 8, 9, 10, 11, 12, 13, 14, 15, 16, 17, 18, 19, 20, or more phosphorothioate intemucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or about one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and in which the antisense strand comprises about 1 to about 10 or more, specifically about 1, 2, 3, 4, 5, 6, 7, 8, 9, 10, 11, 12, 13, 14, 15, 16, 17, 18, 19, 20, or more phosphorothioate intemnucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other aspects, one or more, for example about 1, 2, 3, 4, 5, 6, 7, 8, 9, 10, or more, pyrimidine nucleotides of the sense and/or antisense strand are chemically-modified with 2'-deoxy, 2'-O-methyl and/or 2'-deoxy-2'-fluoro nucleotides, with or without one or more, for example about 1, 2, 3, 4, 5, 6, 7, 8, 9, 10, or more, phosphorothioate internucleotide linkages and/or a terminal cap molecule at the 3'-end, the 5'-end, or both of the 3'- and 5'-ends, being present in the same or different strand.

In some aspects, a polynucleic acid molecule comprises a sense strand and an antisense strand, in which the sense strand comprises about 1 to about 25, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10, or more) 2'-deoxy, 2'-O-methyl, 2'-deoxy-2'-fluoro, and/or one or more (e.g., about 1, 2, 3, 4, 5, 6, 7, 8, 9, 10, or more) universal base modified nucleotides, and optionally a terminal cap molecule at the 3'-end, the 5'-end, or both of the 3'- and 5'-ends of the sense strand; and in which the antisense strand comprises about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'~fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and S'-ends of the antisense strand. In other aspects, one or more, for example about 1, 2, 3, 4, 5, 6, 7, 8, 9, 10, or more, pyrimidine nucleotides of the sense and/or antisense strand are chemically-modified with 2'-deoxy, 2'-O-methyl and/or 2'-deoxy-2'-fluoro nucleotides, with or without about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages and/or a terminal cap molecule at the 3'-end, the 5'-end, or both of the 3'- and 5'-ends, being present in the same or different strand.

In some aspects, a polynucleic acid molecule comprises a sense strand and an antisense strand, in which the antisense strand comprises one or more, for example, about 1, 2, 3, 4, 5, 6, 7, 8, 9, 10, 11, 12, 13, 14, 15, 16, 17, 18, 19, 20, or more phosphorothioate internucleotide linkages, and/or about one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides at the 3'-end, the 5'-end, or both of the 3'- and 5'-ends of the sense strand and/or antisense strand, and optionally a terminal cap molecule at the 3'-end, the S'-end, or both of the 3'- and 5'-ends of the sense strand. In some aspects, the antisense strand comprises about 1 to about 10 or more, specifically about 1, 2, 3, 4, 5, 6, 7, 8, 9, 10 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other aspects, one or more, for example about 1, 2, 3, 4, 5, 6, 7, 8, 9, 10, 11, 12, 13, 14, 15, 16, 17, 18, 19, 20, or more pyrimidine nucleotides of the sense and/or antisense strand are chemically-modified with 2'-deoxy, 2'-O-methyl and/or 2'-deoxy-2'-fluoro nucleotides, with or without one or more, for example, about 1, 2, 3, 4, 5, 6, 7, 8, 9, 10 or more phosphorothioate internucleotide linkages and/or a terminal cap molecule at the 3'-end, the 5'-end, or both of the 3' and 5'-ends, being present in the same or different strand.

In some aspects, a polynucleic acid molecule comprises a sense strand and an antisense strand, in which the antisense strand comprises about 1 to about 25 or more, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and the antisense strand comprises about 1 to about 25 or more, for example about 1, 2, 3, 4, 5, 6, 7, 8, 9, 10, 11, 12, 13, 14, 15, 16, 17, 18, 19, 20, or more phosphorothioate intemnucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other aspects, one or more, for example about 1, 2, 3, 4, 5, 6, 7, 8, 9, 10 or more pyrimidine nucleotides of the sense and/or antisense strand are chemically-modified with 2'-deoxy, 2'-O-methyl and/or 2'-deoxy-2'-fluoro nucleotides, with or without about 1 to about 5, for example about 1, 2, 3, 4, 5 or more phosphorothioate internucleotide linkages and/or a terminal cap molecule at the 3'-end, the 5'-end, or both of the 3'- and 5'-ends, being present in the same or different strand.

In some aspects, a polynucleic acid molecule described herein is a chemically-modified short interfering nucleic acid molecule having about 1 to about 25, for example, about 1, 2, 3, 4, 5, 6, 7, 8, 9, 10, 11, 12, 13, 14, 15, 16, 17, 18, 19, 20 or more phosphorothioate internucleotide linkages in each strand of the polynucleic acid molecule. In some aspects, a polynucleic acid molecule comprises a sense strand and an antisense strand, and the antisense strand comprises a phosphate backbone modification at the 3' end of the antisense strand. Alternatively and/or additionally, a polynucleic acid molecule comprises a sense strand and an antisense strand, and the sense strand comprises a phosphate backbone modification at the 5' end of the antisense strand. In some instances, the phosphate backbone modification is a phosphorothioate. In some aspects, the sense or antisense strand has three consecutive nucleosides that are coupled via two phosphorothioate backbone.

In another embodiment, a polynucleic acid molecule described herein comprises 2'-5' internucleotide linkages. In some instances, the 2'-5' internucleotide linkage(s) is at the 3'-end, the 5'-end, or both of the 3'- and 5'-ends of one or both sequence strands. In addition instances, the 2'-5' internucleotide linkage(s) is present at various other positions within one or both sequence strands, for example, about 1, 2, 3, 4, 5, 6, 7, 8, 9, 10, or more including every internucleotide linkage of a pyrimidine nucleotide in one or both strands of the polynucleic acid molecule comprise a 2'-5' internucleotide linkage, or about 1, 2, 3, 4, 5, 6, 7, 8, 9, 10, or more including every internucleotide linkage of a purine nucleotide in one or both strands of the polynucleic acid molecule comprise a 2'-5' internucleotide linkage.

In some aspects, a polynucleic acid molecule is a single stranded polynucleic acid molecule that mediates RNAi activity in a cell or reconstituted in vitro system, wherein the polynucleic acid molecule comprises a single stranded polynucleotide having complementarity to a target nucleic acid sequence, and wherein one or more pyrimidine nucleotides present in the polynucleic acid are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the polynucleic acid are 2'-deoxy purine nucleotides (e.g., wherein all purine nucleotides are 2'-deoxy purine nucleotides or alternately a plurality of purine nucleotides are 2'-deoxy purine nucleotides), and a terminal cap modification, that is optionally present at the 3'-end, the 5'-end, or both of the 3' and 5'-ends of the antisense sequence, the polynucleic acid molecule optionally further comprising about 1 to about 4 (e.g., about 1, 2, 3, or 4) terminal 2'-deoxynucleotides at the 3'-end of the polynucleic acid molecule, wherein the terminal nucleotides further comprise one or more (e.g., 1, 2, 3, or 4)phosphorothioate internucleotide linkages, and wherein the polynucleic acid molecule optionally further comprises a terminal phosphate group, such as a 5'-terminal phosphate group.

In some cases, one or more of the artificial nucleotide analogues described herein are resistant toward nucleases such as for example ribonuclease such as RNase H, deoxyribonuclease such as DNase, or exonuclease such as 5'-3' exonuclease and 3'-5' exonuclease when compared to natural polynucleic acid molecules. In some instances, artificial nucleotide analogues comprising 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or combinations thereof are resistant toward nucleases such as for example ribonuclease such as RNase H, deoxyribonuclease such as DNase, or exonuclease such as 5'-3' exonuclease and 3'-5' exonuclease. In some instances, 2'-O-methyl modified polynucleic acid molecule is nuclease resistance (e.g., RNase H, DNase, 5'-3' exonuclease or 3'-5' exonuclease resistance). In some instances, 2'-O-methoxyethyl (2'-O-MOE) modified polynucleic acid molecule is nuclease resistance (e.g., RNase H, DNase, 5'-3' exonuclease or 3'-5' exonuclease resistance). In some instances, 2'-O-aminopropyl modified polynucleic acid molecule is nuclease resistance (e.g., RNase H, DNase, 5'-3' exonuclease or 3'-5' exonuclease resistance). In some instances, 2'-deoxy modified polynucleic acid molecule is nuclease resistance (e.g., RNase H, DNase, 5'-3' exonuclease or 3'-5' exonuclease resistance). In some instances, 2'-deoxy-2'-fluoro modified polynucleic acid molecule is nuclease resistance (e.g., RNase H, DNase, 5'-3' exonuclease or 3'-5' exonuclease resistance). In some instances, 2'-O-aminopropyl (2'-O-AP) modified polynucleic acid molecule is nuclease resistance (e.g., RNase H, DNase, 5'-3' exonuclease or 3'-5' exonuclease resistance). In some instances, 2'-O-dimethylaminoethyl (2'-O-DMAOE) modified polynucleic acid molecule is nuclease resistance (e.g., RNase H, DNase, 5'-3' exonuclease or 3'-5' exonuclease resistance). In some instances, 2'-O-dimethylaminopropyl (2'-O-DMAP) modified polynucleic acid molecule is nuclease resistance (e.g., RNase H, DNase, 5'-3' exonuclease or 3'-5' exonuclease resistance). In some instances, 2'-O-dimethylaminoethyloxyethyl (2'-O-DMAEOE) modified polynucleic acid molecule is nuclease resistance (e.g., RNase H, DNase, 5'-3' exonuclease or 3'-5' exonuclease resistance). In some instances, 2'-O—N-methylacetamido (2'-O-NMA) modified polynucleic acid molecule is nuclease resistance (e.g., RNase H, DNase, S'-3' exonuclease or 3'-5' exonuclease resistance). In some instances, LNA modified polynucleic acid molecule is nuclease resistance (e.g., RNase H, DNase, 5'-3' exonuclease or 3'-5' exonuclease resistance). In some instances, ENA modified polynucleic acid molecule is nuclease resistance (e.g., RNase H, DNase, 5'-3' exonuclease or 3'-5' exonuclease resistance). In some instances, HNA modified polynucleic acid molecule is nuclease resistance (e.g., RNase H, DNase, 5'-3' exonuclease or 3'-5' exonuclease resistance). In some instances, morpholinos is nuclease resistance (e.g., RNase H, DNase, 5'-3' exonuclease or 3'-5' exonuclease resistance). In some instances, PNA modified polynucleic acid molecule is resistant to nucleases (e.g., RNase H, DNase, 5'-3' exonuclease or 3'-5' exonuclease resistance). In some instances, methylphosphonate nucleotides modified polynucleic acid molecule is nuclease resistance (e.g., RNase H, DNase, 5'-3' exonuclease or 3'-5' exonuclease resistance). In some instances, thiolphosphonate nucleotides modified polynucleic acid molecule is nuclease resistance (e.g., RNase H, DNase, 5'-3' exonuclease or 3'-5' exonuclease resistance). In some instances, polynucleic acid molecule comprising 2'-fluoro N3-P5'-phosphoramidites is nuclease resistance (e.g., RNase H, DNase, 5'-3' exonuclease or 3'-S' exonuclease resistance). In some instances, the S' conjugates described herein inhibit S'-3' exonucleolytic cleavage. In some instances, the 3' conjugates described herein inhibit 3'-5' exonucleolytic cleavage.

In some aspects, one or more of the artificial nucleotide analogues described herein have increased binding affinity toward their mRNA target relative to an equivalent natural polynucleic acid molecule. The one or more of the artificial nucleotide analogues comprising 2'-O-methyl, 2'-O-methoxyethyl (2'-O)-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, or 2'-fluoro N3-PS'-phosphoramidites have increased binding affinity toward their mRNA target relative to an equivalent natural polynucleic acid molecule. In some instances, 2'-O-methyl modified polynucleic acid molecule has increased binding affinity toward their mRNA target relative to an equivalent natural polynucleic acid molecule. In some instances, 2'-O-methoxyethyl (2'-O-MOB) modified polynucleic acid molecule has increased binding affinity toward their mRNA target relative to an equivalent natural polynucleic acid molecule. In some instances, 2'-O-aminopropyl modified polynucleic acid molecule has increased binding affinity toward their mRNA target relative to an equivalent natural polynucleic acid molecule. In some instances, 2'-deoxy modified polynucleic acid molecule has increased binding affinity toward their mRNA target relative to an equivalent natural polynucleic acid molecule. In some instances, 2'-deoxy-2'-fluoro modified polynucleic acid molecule has increased binding affinity toward their mRNA target relative to an equivalent natural polynucleic acid molecule. In some instances, 2'-O-aminopropyl (2'-O-AP) modified polynucleic acid molecule has increased binding affinity toward their mRNA target relative to an equivalent natural polynucleic acid molecule. In some instances, 2'-O-dimethylaminoethyl (2'-O-DMAOE) modified polynucleic acid molecule has increased binding affinity toward their mRNA target relative to an equivalent natural polynucleic acid molecule. In some instances, 2'-O-dimethylaminopropyl (2'-O-DMAP) modified polynucleic acid molecule has increased binding affinity toward their mRNA target relative to an equivalent natural polynucleic acid molecule. In some instances, 2'-0~ dimethylaminoethyloxyethyl (2'-O-DMAEOE) modified polynucleic acid molecule has increased binding affinity toward their mRNA target relative to an equivalent natural polynucleic acid molecule. In some instances, 2'-O—N-methylacetamido (2'-O-NMA) modified polynucleic acid molecule has increased binding affinity toward their mRNA target relative to an equivalent natural polynucleic acid molecule. In some instances, LNA modified polynucleic acid molecule has increased binding affinity toward their mRNA target relative to an equivalent natural polynucleic acid molecule. In some instances, ENA modified polynucleic acid molecule has increased binding affinity toward their mRNA target relative to an equivalent natural polynucleic acid molecule. In some instances, PNA modified polynucleic acid molecule has increased binding affinity toward their mRNA target relative to an equivalent natural polynucleic acid molecule. In some instances, HNA modified polynucleic acid molecule has increased binding affinity toward their mRNA target relative to an equivalent natural polynucleic acid molecule. In some instances, morpholino modified polynucleic acid molecule has increased binding affinity toward their mRNA target relative to an equivalent natural polynucleic acid molecule. In some instances, methylphosphonate nucleotides modified polynucleic acid molecule has increased binding affinity toward their mRNA target relative to an equivalent natural polynucleic acid molecule. In some instances, thiolphosphonate nucleotides modified polynucleic acid molecule has increased binding affinity toward their mRNA target relative to an equivalent natural polynucleic acid molecule. In some instances, polynucleic acid molecule comprising 2'-fluoro N3-P5'-phosphoramidites has increased binding affinity toward their mRNA target relative to an equivalent natural polynucleic acid molecule. In some cases, the increased affinity is illustrated with a lower Kd, a higher melt temperature (Tm), or a combination thereof.

In some aspects, a polynucleic acid molecule described herein is a chirally pure (or stereo pure) polynucleic acid molecule, or a polynucleic acid molecule comprising a single enantiomer. In some instances, the polynucleic acid molecule comprises L-nucleotide. In some instances, the polynucleic acid molecule comprises D-nucleotides. In some instance, a polynucleic acid molecule composition comprises less than 30%, 25%, 20%, 15%, 10%, 5%, 4%, 3%, 2%, 1%, or less of its mirror enantiomer. In some cases, a polynucleic acid molecule composition comprises less than 30%, 25%, 20%, 15%, 10%, 5%, 4%, 3%, 2%, 1%, or less of a racemic mixture. In some instances, the polynucleic acid molecule is a polynucleic acid molecule described in: U.S. Patent Publication Nos: 2014/194610 and 2015/211006; and PCT Publication No: WO2015107425.

In some aspects, a polynucleic acid molecule described herein is further modified to include an aptamer conjugating moiety. In some instances, the aptamer conjugating moiety is a DNA aptamer conjugating moiety. In some instances, the aptamer conjugating moiety is Alphamer (Centauri Therapeutics), which comprises an aptamer portion that recognizes a specific cell-surface target and a portion that presents a specific epitopes for attaching to circulating antibodies. In some instance, a polynucleic acid molecule described herein is further modified to include an aptamer conjugating moiety as described in: U.S. Pat. Nos. 8,604,184, 8,591,910, and 7,850,975.

In additional aspects, a polynucleic acid molecule described herein is modified to increase its stability. In some embodiment, the polynucleic acid molecule is RNA (e.g., siRNA). In some instances, the polynucleic acid molecule is modified by one or more of the modifications described above to increase its stability. In some cases, the polynucleic acid molecule is modified at the 2' hydroxyl position, such as by 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modification or by a locked or bridged ribose conformation (e.g., LNA or ENA). In some cases, the polynucleic acid molecule is modified by 2'-O-methyl and/or 2'-O-methoxyethyl ribose. In some cases, the polynucleic acid molecule also includes morpholinos, PNAs, HNA, methylphosphonate nucleotides, thiolphosphonate nucleotides, and/or 2'-fluoro N3-P5'-phosphoramidites to increase its stability. In some instances, the polynucleic acid molecule is a chirally pure (or stereo pure) polynucleic acid molecule. In some instances, the chirally pure (or stereo pure) polynucleic acid molecule is modified to increase its stability. Suitable modifications to the RNA to increase stability for delivery will be apparent to the skilled person.

In some instances, the polynucleic acid molecule is a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. In some instances, the polynucleic acid molecule is assembled from two separate polynucleotides, where one strand is the sense strand and the other is the antisense strand, wherein the antisense and sense strands are self-complementary (e.g., each strand comprises nucleotide sequence that is complementary to nucleotide sequence in the other strand; such as where the antisense strand and sense strand form a duplex or double stranded structure, for example wherein the double stranded region is about 19, 20, 21, 22, 23, or more base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the polynucleic acid molecule is assembled from a single oligonucleotide, where the self-complementary sense and antisense regions of the polynucleic acid molecule are linked by means of a nucleic acid based or non-nucleic acid-based linker(s).

In some cases, the polynucleic acid molecule is a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. In other cases, the polynucleic acid molecule is a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide is processed either in vivo or in vitro to generate an active polynucleic acid molecule capable of mediating RNAi. In additional cases, the polynucleic acid molecule also comprises a single-stranded polynucleotide having nucleotide sequence complementary to nucleotide sequence in a target nucleic acid molecule or a portion thereof (for example, where such polynucleic acid molecule does not require the presence within the polynucleic acid molecule of nucleotide sequence corresponding to the target nucleic acid sequence or a portion thereof), wherein the single stranded polynucleotide further comprises a terminal phosphate group, such as a S'-phosphate, or S', 3'-diphosphate.

In some instances, an asymmetric hairpin is a linear polynucleic acid molecule comprising an antisense region, a loop portion that comprises nucleotides or non-nucleotides, and a sense region that comprises fewer nucleotides than the antisense region to the extent that the sense region has enough complimentary nucleotides to base pair with the antisense region and form a duplex with loop. For example, an asymmetric hairpin polynucleic acid molecule comprises an antisense region having length sufficient to mediate RNAi in a cell or in vitro system (e.g. about 19 to about 22 nucleotides) and a loop region comprising about 4 to about 8 nucleotides, and a sense region having about 3 to about 18 nucleotides that are complementary to the antisense region. In some cases, the asymmetric hairpin polynucleic acid molecule also comprises a 5'-terminal phosphate group that is chemically modified. In additional cases, the loop portion of the asymmetric hairpin polynucleic acid molecule comprises nucleotides, non-nucleotides, linker molecules, or conjugate molecules.

In some aspects, an asymmetric duplex is a polynucleic acid molecule having two separate strands comprising a sense region and an antisense region, wherein the sense region comprises fewer nucleotides than the antisense region to the extent that the sense region has enough complimentary nucleotides to base pair with the antisense region and form a duplex. For example, an asymmetric duplex polynucleic acid molecule comprises an antisense region having length sufficient to mediate RNAi in a cell or in vitro system (e.g., about 19 to about 22 nucleotides) and a sense region having about 3 to about 18 nucleotides that are complementary to the antisense region.

In some cases, a universal base refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art.

Polynucleic Acid Molecule Synthesis

In some aspects, a polynucleic acid molecule described herein is constructed using chemical synthesis and/or enzymatic ligation reactions using procedures known in the art. For example, a polynucleic acid molecule is chemically synthesized using naturally occurring nucleotides or variously modified nucleotides designed to increase the biological stability of the molecules or to increase the physical stability of the duplex formed between the polynucleic acid molecule and target nucleic acids. Exemplary methods include those described in: U.S. Pat. Nos. 5,142,047; 5,185,444; 5,889,136; 6,008,400; and 6,111,086; PCT Publication No. WO2009099942; or European Publication NO. 1579015. Additional exemplary methods include those described in: Griffey et al., "2'-O-aminopropyl ribonucleotides: a zwitterionic modification that enhances the exonuclease resistance and biological activity of antisense oligonucleotides," *J. Med. Chem.* 39 (26): 5100-5109 (1997)); Obika, et al. "Synthesis of 2'-0,4'-C-methyleneuridine and -cytidine. Novel bicyclic nucleosides having a fixed $C_3$,-endo sugar puckering". *Tetrahedron Letters* 38 (50): 8735 (1997); Koizumi, M. "ENA oligonucleotides as therapeutics". *Current opinion in molecular therapeutics* 8 (2): 144-149 (2006); and Abramova et al., "Novel oligonucleotide analogues based on morpholino nucleoside subunits-antisense technologies: new chemical possibilities," *Indian Journal of Chemistry* 48B: 1721-1726 (2009). Alternatively, the polynucleic acid molecule is produced biologically using an expression vector into which a polynucleic acid molecule has been subcloned in an antisense orientation (i.e., RNA transcribed from the inserted polynucleic acid molecule will be of an antisense orientation to a target polynucleic acid molecule of interest).

In some aspects, a polynucleic acid molecule is synthesized via a tandem synthesis methodology, wherein both strands are synthesized as a single contiguous oligonucleotide fragment or strand separated by a cleavable linker which is subsequently cleaved to provide separate fragments or strands that hybridize and permit purification of the duplex.

In some instances, a polynucleic acid molecule is also assembled from two distinct nucleic acid strands or fragments wherein one fragment includes the sense region and the second fragment includes the antisense region of the molecule.

Additional modification methods for incorporating, for example, sugar, base and phosphate modifications include: Eckstein et al., International Publication PCT No. WO 92/07065; Perrault et al. *Nature,* 1990, 344, 565-568; Pieken et al. *Science,* 1991, 253, 314-317; Usman and Cedergren, *Trends in Biochem. Sci.,* 1992, 17, 334-339; Usman et al. International Publication PCT No. WO 93/15187; Sproat, U.S. Pat. No. 5,334,711 and Beigelman et al., 1995, *J. Biol. Chem.,* 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, *Tetrahedron Lett.,* 39, 1131; Earnshaw and Gait, 1998, Biopolymers (Nucleic Acid Sciences), 48, 39-55; Verma and Eckstein, 1998, *Annu. Rev. Biochem.,* 67, 99-134; and Burlina et al., 1997, *Bioorg. Med. Chem.,* 5, 1999-2010. Such publications describe general methods and strategies to determine the location of incorporation of sugar, base and/or phosphate modifications and the like into nucleic acid molecules without modulating catalysis.

In some instances, while chemical modification of the polynucleic acid molecule internucleotide linkages with phosphorothioate, phosphorodithioate, and/or 5'-methylphosphonate linkages improves stability, excessive modifications sometimes cause toxicity or decreased activity. Therefore, when designing nucleic acid molecules, the amount of these internucleotide linkages in some cases is minimized. In such cases, the reduction in the concentration of these linkages lowers toxicity, increases efficacy and higher specificity of these molecules.

Polynucleic Acid Molecule Conjugates

In some aspects, a polynucleic acid molecule (B) is further conjugated to a polypeptide (A) for delivery to a site of interest. In some instances, at least one polypeptide A is conjugated to at least one B. In some instances, the at least one polypeptide A is conjugated to the at least one B to form an A-B conjugate. In some aspects, at least one A is conjugated to the 5' terminus of B, the 3' terminus of B, an internal site on B, or in any combinations thereof. In some instances, the at least one polypeptide A is conjugated to at least two B. In some instances, the at least one polypeptide A is conjugated to at least 2, 3, 4, 5, 6, 7, 8, or more B.

In some cases, a polynucleic acid molecule is conjugated to a polypeptide (A) and optionally a polymeric moiety (C). In some aspects, at least one polypeptide A is conjugated at one terminus of at least one B while at least one C is conjugated at the opposite terminus of the at least one B to form an A-B-C conjugate. In some instances, at least one polypeptide A is conjugated at one terminus of the at least one B while at least one of C is conjugated at an internal site on the at least one B. In some instances, at least one polypeptide A is conjugated directly to the at least one C. In some instances, the at least one B is conjugated indirectly to the at least one polypeptide A via the at least one C to form an A-C-B conjugate.

In some instances, at least one B and/or at least one C, and optionally at least one D are conjugated to at least one polypeptide A. In some instances, the at least one B is conjugated at a terminus (e.g., a 5' terminus or a 3' terminus) to the at least one polypeptide A or are conjugated via an internal site to the at least one polypeptide A. In some cases, the at least one C is conjugated either directly to the at least one polypeptide A or indirectly via the at least one B. If indirectly via the at least one B, the at least one C is conjugated either at the same terminus as the at least one polypeptide A on B, at opposing terminus from the at least one polypeptide A, or independently at an internal site. In some instances, at least one additional polypeptide A is further conjugated to the at least one polypeptide A, to B, or to C. In additional instances, the at least one D is optionally conjugated either directly or indirectly to the at least one polypeptide A, to the at least one B, or to the at least one C. If directly to the at least one polypeptide A, the at least one D is also optionally conjugated to the at least one B to form an A-D-B conjugate or is optionally conjugated to the at least one B and the at least one C to form an A-D-B-C conjugate. In some instances, the at least one D is directly conjugated to the at least one polypeptide A and indirectly to the at least one B and the at least one C to form a D-A-B-C conjugate. If indirectly to the at least one polypeptide A, the at least one D is also optionally conjugated to the at least one B to form an A-B-D conjugate or is optionally conjugated to the at least one B and the at least one C to form an A-B-D-C conjugate. In some instances, at least one additional D is further conjugated to the at least one polypeptide A, to B, or to C.

Binding Moiety

In some aspects, the binding moiety A is a polypeptide. In some instances, the polypeptide is an antibody or its fragment thereof. In some cases, the fragment is an antigen binding fragment. In some instances, the antibody or antigen binding fragment thereof comprises a humanized antibody or antigen binding fragment thereof, murine antibody or antigen binding fragment thereof, chimeric antibody or antigen binding fragment thereof, monoclonal antibody or antigen binding fragment thereof, a binding fragment having a light chain domain and a heavy chain domain, a binding fragment having two light chain domains and two heavy chain domains, a binding fragment having two or more light chain domains and heavy chain domains, monovalent Fab', divalent Fab2, F (ab)'3 fragments, single-chain variable fragment (scFv), bis-scFv, (scFv) 2, diabody, minibody, nanobody, triabody, tetrabody, disulfide stabilized Fv protein (dsFv), single-domain antibody (sdAb), Ig NAR, camelid antibody or antigen binding fragment thereof, bispecific antibody or biding fragment thereof, or a chemically modified derivative thereof.

In some aspects, the binding moiety A is a bispecific antibody or antigen binding fragment thereof. In some instances, the bispecific antibody is a trifunctional antibody or a bispecific mini-antibody. In some cases, the bispecific antibody is a trifunctional antibody. In some instances, the trifunctional antibody is a full length monoclonal antibody comprising binding sites for two different antigens.

In some cases, the bispecific antibody is a bispecific mini-antibody. In some instances, the bispecific mini-antibody comprises divalent Fab2, F (ab)'3 fragments, bis-scFv, (scFv) 2, diabody, minibody, triabody, tetrabody or a bispecific T-cell engager (BiTE). In some aspects, the bispecific T-cell engager is a fusion protein that contains two single-chain variable fragments (scFvs) in which the two scFvs target epitopes of two different antigens.

In some aspects, the binding moiety A is a bispecific mini-antibody. In some instances, A is a bispecific Fab2. In some instances, A is a bispecific F (ab)'3 fragment. In some cases, A is a bispecific bis-scFv. In some cases, A is a bispecific (scFv) 2. In some aspects, A is a bispecific diabody. In some aspects, A is a bispecific minibody. In some aspects, A is a bispecific triabody. In other aspects, A is a bispecific tetrabody. In other aspects, A is a bi-specific T-cell engager (BiTE).

In some aspects, the binding moiety A is a trispecific antibody. In some instances, the trispecific antibody comprises F (ab)'3 fragments or a triabody. In some instances, A is a trispecific F (ab)'3 fragment. In some cases, A is a triabody. In some aspects, A is a trispecific antibody as described in Dimas, et al., "Development of a trispecific antibody designed to simultaneously and efficiently target three different antigens on tumor cells," *Mol. Pharmaceutics,* 12 (9): 3490-3501 (2015).

In some aspects, the binding moiety A is an antibody or antigen binding fragment thereof that recognizes a cell surface protein. In some instances, the binding moiety A is an antibody or antigen binding fragment thereof that recognizes a cell surface protein on a muscle cell. In some cases, the binding moiety A is an antibody or antigen binding fragment thereof that recognizes a cell surface protein on a skeletal muscle cell.

In some aspects, exemplary antibodies include, but are not limited to, an anti-myosin antibody, an anti-transferrin receptor antibody, and an antibody that recognizes Muscle-Specific kinase (MuSK). In some instances, the antibody is an anti-transferrin receptor (anti-CD71) antibody.

In some aspects, where the antibody is an anti-transferrin receptor (anti-CD71) antibody, the anti-transferrin antibody specifically binds to a transferrin receptor (TIR), preferably, specifically binds to transferrin receptor 1 (TfR1), or more preferably, specifically binds to human transferrin receptor 1 (TIRI) (or human CD71).

In some instances, the anti-transferrin receptor antibody comprises a variable heavy chain (VH) region and a variable light chain (VL) region, wherein the VH region comprises HCDR1 sequence comprising SEQ ID NO: 281; HCDR2 sequence EINPIX GRSNYAX2KFQG (SEQ ID NO: 406), wherein $X_1$ is selected from N or Q and $X_2$ is selected from Q or E; and HCDR3 sequence comprising SEQ ID NO: 283.

In some aspects, the VH region of the anti-transferrin receptor antibody comprises HCDR1, HCDR2, and HCDR3 sequences selected from Table 1.

TABLE 1

| Name | HCDR1 | SEQ ID NO: | HCDR2 | SEQ ID NO: | HCDR3 | SEQ ID NO: |
|---|---|---|---|---|---|---|
| 13E4_VH1 | YTFTNYWMH | 281 | EINPINGRSNYAQKFQG | 282 | GTRAMHY | 283 |
| 13E4_VH2* | YTFTNYWMH | 281 | EINPINGRSNYAEKFQG | 284 | GTRAMHY | 283 |
| 13E4_VH3 | YTFTNYWMH | 281 | EINPIQGRSNYAEKFQG | 285 | GTRAMHY | 283 |

*13E4_VH2 shares the same HCDR1, HCDR2, and HCDR3 sequences with anti-transferrin receptor antibody 13E4_VH4

In some aspects, the VH region comprises HCDR1 sequence comprising SEQ ID NO: 281; HCDR2 sequence comprising SEQ ID NO: 282, 284, or 285; and HCDR3 sequence comprising SEQ ID NO: 283. In some instances, the VH region comprises HCDR1 sequence comprising SEQ ID NO: 281, HCDR2 sequence comprising SEQ ID NO: 282, and HCDR3 sequence comprising SEQ ID NO: 283. In some instances, the VH region comprises HCDR1 sequence comprising SEQ ID NO: 281, HCDR2 sequence comprising SEQ ID NO: 284, and HCDR3 sequence comprising SEQ ID NO: 283. In some instances, the VH region comprises HCDR1 sequence comprising SEQ ID NO: 281, HCDR2 sequence comprising SEQ ID NO: 285, and HCDR3 sequence comprising SEQ ID NO: 283.

In some aspects, the VL region of the anti-transferrin receptor antibody comprises LCDR1 sequence RTSENIY$X_3$NLA (SEQ ID NO: 407), LCDR2 sequence A$X_4$TNLA$X_5$ (SEQ ID NO: 408), and LCDR3 sequence QHFWGTPLT$X_6$ (SEQ ID NO: 409), wherein $X_3$ is selected from N or S, $X_4$ is selected from A or G, $X_5$ is selected from D or E, and $X_6$ is present or absence, and if present, is F.

In some aspects, the VL region of the anti-transferrin receptor antibody comprises LCDR1, LCDR2, and LCDR3 sequences selected from Table 2.

TABLE 2

| Name | LCDR1 | SEQ ID NO: | LCDR2 | SEQ ID NO: | LCDR3 | SEQ ID NO: |
|---|---|---|---|---|---|---|
| 13E4_VL1* | RTSENIYNNLA | 286 | AATNLAD | 287 | QHFWGTPLT | 288 |
| 13E4_VL3 | RTSENIYNNLA | 286 | AATNLAE | 289 | QHFWGTPLTF | 290 |
| 13E4_VL4 | RTSENIYSNLA | 291 | AGTNLAD | 292 | QHFWGTPLTF | 290 |

*13E4_VL1 shares the same LCDR1, LCDR2, and LCDR3 sequences with anti-transferrin receptor antibody 13E4_VL2

In some instances, the VL region comprises LCDR1 sequence RTSENIYXANLA (SEQ ID NO: 407), LCDR2 sequence comprising SEQ ID NO: 287, 289, or 292, and LCDR3 sequence comprising SEQ ID NO: 288 or 290, wherein $X_3$ is selected from N or S.

In some instances, the VL region comprises LCDR1 sequence comprising SEQ ID NO: 286 or 291, LCDR2 sequence AX4TNLA$X_5$ (SEQ ID NO: 408), and LCDR3 sequence comprising SEQ ID NO: 288 or 290, wherein $X_4$ is selected from A or G, and $X_5$ is selected from D or E.

In some instances, the VL region comprises LCDR1 sequence comprising SEQ ID NO: 286 or 291, LCDR2 sequence SEQ ID NO: 287, 289, or 292, and LCDR3 sequence QHFWGTPLT$X_6$ (SEQ ID NO: 409), wherein $X_6$ is present or absence, and if present, is F.

In some instances, the VL region comprises LCDR1 sequence comprising SEQ ID NO: 286, LCDR2 sequence AATNLA$X_5$ (SEQ ID NO: 410), and LCDR3 sequence QHFWGTPLT$X_6$ (SEQ ID NO: 409), wherein $X_5$ is selected from D or E and Xe is present or absence, and if present, is F.

In some instances, the VL region comprises LCDR1 sequence comprising SEQ ID NO; 286, LCDR2 sequence comprising SEQ ID NO: 287, and LCDR3 sequence comprising SEQ ID NO: 288.

In some instances, the VL region comprises LCDR1 sequence comprising SEQ ID NO: 286, LCDR2 sequence comprising SEQ ID NO: 289, and LCDR3 sequence comprising SEQ ID NO: 290.

In some instances, the VL region comprises LCDR1 sequence comprising SEQ ID NO: 291, LCDR2 sequence comprising SEQ ID NO: 292, and LCDR3 sequence comprising SEQ ID NO: 290.

In some aspects, the anti-transferrin receptor antibody comprises a VH region and a VL region, wherein the VH region comprises HCDR1 sequence comprising SEQ ID NO: 281; HCDR2 sequence EINPIX: GRSNYAX2KFQG (SEQ ID NO: 406), wherein $X_1$ is selected from Nor Q and $X_2$ is selected from Q or E; and HCDR3 sequence comprising SEQ ID NO: 283; and the VL region comprises LCDR1 sequence RTSENIY$X_3$NLA (SEQ ID NO: 407), LCDR2 sequence AX4TNLA$X_5$ (SEQ ID NO: 408), and LCDR3 sequence QHFWGTPLT$X_6$ (SEQ ID NO: 409), wherein $X_3$ is selected from N or S, $X_4$ is selected from A or G, $X_5$ is selected from D or E, and $X_6$ is present or absence, and if present, is F.

In some instances, the anti-transferrin receptor antibody comprises a VH region and a VL region, wherein the VH region comprises HCDR1 sequence comprising SEQ ID NO: 281; HCDR2 sequence EINPIX: GRSNYAX2KFQG (SEQ ID NO: 406), wherein $X_1$ is selected from Nor Q and $X_2$ is selected from Q or E; and HCDR3 sequence comprising SEQ ID NO: 283; and the VL region comprises LCDR1 sequence RTSENIY$X_3$NLA (SEQ ID NO: 407), LCDR2 sequence comprising SEQ ID NO: 287, 289, or 292, and LCDR3 sequence comprising SEQ ID NO: 288 or 290, wherein $X_3$ is selected from N or S.

In some instances, the anti-transferrin receptor antibody comprises a VH region and a VL region, wherein the VH region comprises HCDR1 sequence comprising SEQ ID NO: 281; HCDR2 sequence EINPIX: GRSNYAX2KFQG (SEQ ID NO: 406), wherein $X_1$ is selected from Nor Q and $X_2$ is selected from Q or E; and HCDR3 sequence comprising SEQ ID NO: 283; and the VL region comprises LCDR1 sequence comprising SEQ ID NO: 286 or 291, LCDR2 sequence AXATNLA$X_5$ (SEQ ID NO: 408), and LCDR3 sequence comprising SEQ ID NO: 288 or 290, wherein $X_4$ is selected from A or G, and $X_5$ is selected from D or E.

In some instances, the anti-transferrin receptor antibody comprises a VH region and a VL region, wherein the VH region comprises HCDR1 sequence comprising SEQ ID NO: 281; HCDR2 sequence EINPIX: GRSNYAX2KFQG (SEQ ID NO: 406), wherein $X_1$ is selected from Nor Q and $X_2$ is selected from Q or E; and HCDR3 sequence comprising SEQ ID NO: 283; and the VL region comprises LCDR1 sequence comprising SEQ ID NO: 286 or 291, LCDR2 sequence SEQ ID NO: 287, 289, or 292, and LCDR3 sequence QHFWGTPLT$X_6$ (SEQ ID NO: 409), wherein $X_6$ is present or absence, and if present, is F.

In some instances, the anti-transferrin receptor antibody comprises a VH region and a VL region, wherein the VH region comprises HCDR1 sequence comprising SEQ ID NO: 281; HCDR2 sequence EINPIX: GRSNYAX2KFQG (SEQ ID NO: 406), wherein $X_1$ is selected from N or Q and $X_2$ is selected from Q or E; and HCDR3 sequence comprising SEQ ID NO: 283; and the VL region comprises LCDR1 sequence comprising SEQ ID NO: 286, LCDR2 sequence AATNLA$X_5$ (SEQ ID NO: 410), and LCDR3 sequence QHFWGTPLT$X_6$ (SEQ ID NO: 409), wherein $X_5$ is selected from D or E and Xe is present or absence, and if present, is F.

In some instances, the anti-transferrin receptor antibody comprises a VH region and a VL region, wherein the VH region comprises HCDR1 sequence comprising SEQ ID NO: 281; HCDR2 sequence EINPIX: GRSNYAX2KFQG (SEQ ID NO: 406), wherein $X_1$ is selected from N or Q and $X_2$ is selected from Q or E; and HCDR3 sequence comprising SEQ ID NO: 283; and the VL region comprises LCDR1 sequence comprising SEQ ID NO: 286, LCDR2 sequence comprising SEQ ID NO: 287, and LCDR3 sequence comprising SEQ ID NO: 288.

In some instances, the anti-transferrin receptor antibody comprises a VH region and a VL region, wherein the VH region comprises HCDR1 sequence comprising SEQ ID NO: 281; HCDR2 sequence EINPIX: GRSNYAX2KFQG (SEQ ID NO: 406), wherein X; is selected from Nor Q and $X_2$ is selected from Q or E; and HCDR3 sequence comprising SEQ ID NO: 283; and the VL region comprises LCDR1 sequence comprising SEQ ID NO: 286, LCDR2 sequence comprising SEQ ID NO: 289, and LCDR3 sequence comprising SEQ ID NO: 290.

In some instances, the anti-transferrin receptor antibody comprises a VH region and a VL region, wherein the VH region comprises HCDR1 sequence comprising SEQ ID NO: 281; HCDR2 sequence EINPIX: GRSNYAX2KFQG (SEQ ID NO: 406), wherein $X_1$ is selected from Nor Q and $X_2$ is selected from Q or E; and HCDR3 sequence comprising SEQ ID NO: 283; and the VL region comprises LCDR1 sequence comprising SEQ ID NO: 291, LCDR2 sequence comprising SEQ ID NO: 292, and LCDR3 sequence comprising SEQ ID NO: 290.

In some instances, the anti-transferrin receptor antibody comprises a VH region and a VL region, in which the VH region comprises HCDR1 sequence comprising SEQ ID NO: 281, HCDR2 sequence comprising SEQ ID NO: 282, and HCDR3 sequence comprising SEQ ID NO: 283; and the VL region comprises LCDR1 sequence RTSENIYX,NLA (SEQ ID NO: 407), LCDR2 sequence comprising SEQ ID NO: 287, 289, or 292, and LCDR3 sequence comprising SEQ ID NO: 288 or 290, wherein $X_3$ is selected from N or S.

In some instances, the anti-transferrin receptor antibody comprises a VH region and a VL region, in which the VH region comprises HCDR1 sequence comprising SEQ ID NO: 281, HCDR2 sequence comprising SEQ ID NO: 282, and HCDR3 sequence comprising SEQ ID NO: 283; and the VL region comprises LCDR1 sequence comprising SEQ ID NO: 286 or 291, LCDR2 sequence AX4TNLAX$_5$ (SEQ ID NO: 408), and LCDR3 sequence comprising SEQ ID NO: 288 or 290, wherein $X_4$ is selected from A or G, and $X_5$ is selected from D or E.

In some instances, the anti-transferrin receptor antibody comprises a VH region and a VL region, in which the VH region comprises HCDR1 sequence comprising SEQ ID NO: 281, HCDR2 sequence comprising SEQ ID NO: 2, and HCDR3 sequence comprising SEQ ID NO: 283; and the VL region comprises LCDR1 sequence comprising SEQ ID NO: 286 or 291, LCDR2 sequence SEQ ID NO: 287, 289, or 292, and LCDR3 sequence QHFWGTPLTX$_6$ (SEQ ID NO: 409), wherein $X_6$ is present or absence, and if present, is F.

In some instances, the anti-transferrin receptor antibody comprises a VH region and a VL region, in which the VH region comprises HCDR1 sequence comprising SEQ ID NO: 281, HCDR2 sequence comprising SEQ ID NO: 282, and HCDR3 sequence comprising SEQ ID NO: 283; and the VL region comprises LCDR1 sequence comprising SEQ ID NO: 286, LCDR2 sequence AATNLAX$_5$ (SEQ ID NO: 410), and LCDR3 sequence QHFWGTPLTX$_6$ (SEQ ID NO: 409), wherein $X_5$ is selected from D or E and $X_6$ is present or absence, and if present, is F.

In some instances, the anti-transferrin receptor antibody comprises a VH region and a VL region, in which the VH region comprises HCDR1 sequence comprising SEQ ID NO: 281, HCDR2 sequence comprising SEQ ID NO: 282, and HCDR3 sequence comprising SEQ ID NO: 283; and the VL region comprises LCDR1 sequence comprising SEQ ID NO: 286, LCDR2 sequence comprising SEQ ID NO: 287, and LCDR3 sequence comprising SEQ ID NO: 288.

In some instances, the anti-transferrin receptor antibody comprises a VH region and a VL region, in which the VH region comprises HCDR1 sequence comprising SEQ ID NO: 281, HCDR2 sequence comprising SEQ ID NO: 282, and HCDR3 sequence comprising SEQ ID NO: 283; and the VL region comprises LCDR1 sequence comprising SEQ ID NO: 286, LCDR2 sequence comprising SEQ ID NO: 289, and LCDR3 sequence comprising SEQ ID NO: 290.

In some instances, the anti-transferrin receptor antibody comprises a VH region and a VL region, in which the VH region comprises HCDR1 sequence comprising SEQ ID NO: 281, HCDR2 sequence comprising SEQ ID NO: 282, and HCDR3 sequence comprising SEQ ID NO: 283; and the VL region comprises LCDR1 sequence comprising SEQ ID NO: 291, LCDR2 sequence comprising SEQ ID NO: 292, and LCDR3 sequence comprising SEQ ID NO: 290.

In some instances, the anti-transferrin receptor antibody comprises a VH region and a VL region, in which the VH region comprises HCDR1 sequence comprising SEQ ID NO: 281, HCDR2 sequence comprising SEQ ID NO: 284, and HCDR3 sequence comprising SEQ ID NO: 283; and the VL region comprises LCDR1 sequence RTSENIYX$_3$NLA (SEQ ID NO: 407), LCDR2 sequence comprising SEQ ID NO: 287, 289, or 292, and LCDR3 sequence comprising SEQ ID NO: 288 or 290, wherein $X_3$ is selected from N or S.

In some instances, the anti-transferrin receptor antibody comprises a VH region and a VL region, in which the VH region comprises HCDR1 sequence comprising SEQ ID NO: 281, HCDR2 sequence comprising SEQ ID NO: 284, and HCDR3 sequence comprising SEQ ID NO: 283; and the VL region comprises LCDR1 sequence comprising SEQ ID NO: 286 or 291, LCDR2 sequence AX4TNLAX$_5$ (SEQ ID NO: 408), and LCDR3 sequence comprising SEQ ID NO: 288 or 290, wherein $X_4$ is selected from A or G, and $X_5$ is selected from D or E.

In some instances, the anti-transferrin receptor antibody comprises a VH region and a VL region, in which the VH region comprises HCDR1 sequence comprising SEQ ID NO: 281, HCDR2 sequence comprising SEQ ID NO: 284, and HCDR3 sequence comprising SEQ ID NO: 283; and the VL region comprises LCDR1 sequence comprising SEQ ID NO: 286 or 291, LCDR2 sequence SEQ ID NO: 287, 289, or 292, and LCDR3 sequence QHFWGTPLTX$_6$ (SEQ ID NO: 409), wherein $X_6$ is present or absence, and if present, is F.

In some instances, the anti-transferrin receptor antibody comprises a VH region and a VL region, in which the VH region comprises HCDR1 sequence comprising SEQ ID NO: 281, HCDR2 sequence comprising SEQ ID NO: 284, and HCDR3 sequence comprising SEQ ID NO: 283; and the VL region comprises LCDR1 sequence comprising SEQ ID NO: 286, LCDR2 sequence AATNLAX5 (SEQ ID NO: 410), and LCDR3 sequence QHFWGTPLTX$_6$ (SEQ ID NO: 409), wherein $X_5$ is selected from D or E and $X_6$ is present or absence, and if present, is F.

In some instances, the anti-transferrin receptor antibody comprises a VH region and a VL region, in which the VH region comprises HCDR1 sequence comprising SEQ ID NO: 281, HCDR2 sequence comprising SEQ ID NO: 284, and HCDR3 sequence comprising SEQ ID NO: 283; and the VL region comprises LCDR1 sequence comprising SEQ ID NO: 286, LCDR2 sequence comprising SEQ ID NO: 287, and LCDR3 sequence comprising SEQ ID NO: 288.

In some instances, the anti-transferrin receptor antibody comprises a VH region and a VL region, in which the VH region comprises HCDR1 sequence comprising SEQ ID NO: 281, HCDR2 sequence comprising SEQ ID NO: 284, and HCDR3 sequence comprising SEQ ID NO: 283; and the VL region comprises LCDR1 sequence comprising SEQ ID NO: 286, LCDR2 sequence comprising SEQ ID NO: 289, and LCDR3 sequence comprising SEQ ID NO:290.

In some instances, the anti-transferrin receptor antibody comprises a VH region and a VL region, in which the VH region comprises HCDR1 sequence comprising SEQ ID NO: 281, HCDR2 sequence comprising SEQ ID NO: 284, and HCDR3 sequence comprising SEQ ID NO: 283; and the VL region comprises LCDR1 sequence comprising SEQ ID NO: 291, LCDR2 sequence comprising SEQ ID NO: 292, and LCDR3 sequence comprising SEQ ID NO: 290.

In some instances, the anti-transferrin receptor antibody comprises a VH region and a VL region, in which the VH region comprises HCDR1 sequence comprising SEQ ID NO: 281, HCDR2 sequence comprising SEQ ID NO: 285, and HCDR3 sequence comprising SEQ ID NO: 283; and the VL region comprises LCDR1 sequence RTSENIYX$_3$NLA (SEQ ID NO: 407), LCDR2 sequence comprising SEQ ID NO: 287, 289, or 292, and LCDR3 sequence comprising SEQ ID NO: 288 or 290, wherein X$_3$ is selected from N or S.

In some instances, the anti-transferrin receptor antibody comprises a VH region and a VL region, in which the VH region comprises HCDR1 sequence comprising SEQ ID NO: 281, HCDR2 sequence comprising SEQ ID NO: 285, and HCDR3 sequence comprising SEQ ID NO: 283; and the VL region comprises LCDR1 sequence comprising SEQ ID NO: 286 or 291, LCDR2 sequence AX4TNLAX$_5$ (SEQ ID NO: 408), and LCDR3 sequence comprising SEQ ID NO: 288 or 290, wherein X$_4$ is selected from A or G, and X$_5$ is selected from D or E.

In some instances, the anti-transferrin receptor antibody comprises a VH region and a VL region, in which the VH region comprises HCDR1 sequence comprising SEQ ID NO: 281, HCDR2 sequence comprising SEQ ID NO: 285, and HCDR3 sequence comprising SEQ ID NO: 283; and the VL region comprises LCDR1 sequence comprising SEQ ID NO: 286 or 291, LCDR2 sequence SEQ ID NO: 287, 289, or 292, and LCDR3 sequence QHFWGTPLTX$_6$ (SEQ ID NO: 409), wherein X$_6$ is present or absence, and if present, is F.

In some instances, the anti-transferrin receptor antibody comprises a VH region and a VL region, in which the VH region comprises HCDR1 sequence comprising SEQ ID NO: 281, HCDR2 sequence comprising SEQ ID NO: 285, and HCDR3 sequence comprising SEQ ID NO: 283 and the VL region comprises LCDR1 sequence comprising SEQ ID NO: 286, LCDR2 sequence AATNLAX$_5$ (SEQ ID NO: 410), and LCDR3 sequence QHFWGTPLTX$_6$ (SEQ ID NO: 409), wherein X$_5$ is selected from D or E and X$_6$ is present or absence, and if present, is F.

In some instances, the anti-transferrin receptor antibody comprises a VH region and a VL region, in which the VH region comprises HCDR1 sequence comprising SEQ ID NO: 281, HCDR2 sequence comprising SEQ ID NO: 285, and HCDR3 sequence comprising SEQ ID NO: 283; and the VL region comprises LCDR1 sequence comprising SEQ ID NO: 286, LCDR2 sequence comprising SEQ ID NO: 287, and LCDR3 sequence comprising SEQ ID NO: 288.

In some instances, the anti-transferrin receptor antibody comprises a VH region and a VL region, in which the VH region comprises HCDR1 sequence comprising SEQ ID NO: 281, HCDR2 sequence comprising SEQ ID NO: 285, and HCDR3 sequence comprising SEQ ID NO: 283; and the VL region comprises LCDR1 sequence comprising SEQ ID NO: 286, LCDR2 sequence comprising SEQ ID NO: 289, and LCDR3 sequence comprising SEQ ID NO: 290.

In some instances, the anti-transferrin receptor antibody comprises a VH region and a VL region, in which the VH region comprises HCDR1 sequence comprising SEQ ID NO: 281, HCDR2 sequence comprising SEQ ID NO: 285, and HCDR3 sequence comprising SEQ ID NO: 283; and the VL region comprises LCDR1 sequence comprising SEQ ID NO: 291, LCDR2 sequence comprising SEQ ID NO: 292, and LCDR3 sequence comprising SEQ ID NO: 290.

In some aspects, the anti-transferrin receptor antibody comprises a VH region and a VL region in which the sequence of the VH region comprises about 80%, 85%, 90%, 95%, 96% 97%, 98%, 99%, or 100% sequence identity to SEQ ID NOs: 293-296 and the sequence of the VL region comprises about 80%, 85%, 90%, 95%, 96% 97%, 98%, 99%, or 100% sequence identity to SEQ ID NOs: 298-301.

In some aspects, the VH region comprises a sequence selected from SEQ ID NOs: 293-296 (Table 3) and the VL region comprises a sequence selected from SEQ ID NOs: 298-301 (Table 4). The underlined regions in Table 3 and Table 4 denote the respective CDR1, CDR2, or CDR3 sequence.

TABLE 3

| NAME | VH SEQUENCE | SEQ ID NO: |
|---|---|---|
| 13E4_VH1 | QVQLVQSGAEVKKPGASVKVSCKASGYTFTNYWMHWVRQAPGQ GLEWMGEINPINGRSNYAQKFQGRVTLTVDTSISTAYMELSRLRSD DTAVYYCARGTRAMHYWGQGTLVTVSS | 293 |
| 13E4_VH2 | QVQLVQSGAEVKKPGASVKVSCKASGYTFTNYWMHWVRQAPGQ GLEWIGEINPINGRSNYAEKFQGRVTLTVDTSSSTAYMELSRLRSD DTAVYYCARGTRAMHYWGQGTLVTVSS | 294 |
| 13E4_VH3 | QVQLVQSGAEVKKPGASVKVSCKASGYTFTNYWMHWVRQAPGQ GLEWMGEINPIQGRSNYAEKFQGRVTLTVDTSSSTAYMELSSLRSE DTATYYCARGTRAMHYWGQGTLVTVSS | 295 |
| 13E4_VH4 | QVQLVQSGAEVKKPGASVKVSCKASGYTFTNYWMHWVRQAPGQ GLEWMGEINPINGRSNYAEKFQGRVTLTVDTSSSTAYMELSSLRSE DTATYYCARGTRAMHYWGQGTLVTVSS | 296 |
| 13E4_VH | QVQLQQPGAELVKPGASVKLSCKASGYTFTNYWMHWVKQRPGQ GLEWIGEINPINGRSNYGERFKTKATLTVDKSSSTAYMQLSSLTSED SAVYYCARGTRAMHYWGQGTSVTVSS | 297 |

TABLE 4

| NAME | VL SEQUENCE | SEQ ID NO: |
|---|---|---|
| 13E4_VL1 | DIQMTQSPSSLSASVGDRVTITCRTSENIYNNLAWYQQKPGKSPKL LIYAATNLADGVPSRFSGSGSGTDYTLTISSLQPEDFATYYCQHFW GTPLTFGGGTKVEIK | 298 |
| 13E4_VL2 | DIQMTQSPSSLSASVGDRVTITCRTSENIYNNLAWYQQKPGKAPKL LIYAATNLADGVPSRFSGSGSGTDYTLTISSLQPEDFATYYCQHFW GTPLTFGGGTKVEIK | 299 |
| 13E4_VL3 | DIQMTQSPSSLSASVGDRVTITCRTSENIYNNLAWYQQKPGKAPKL LIYAATNLAEGVPSRFSGSGSGTDYTLTISSLQPEDFATYYCQHFWG TPLTGGGTKVEIK | 300 |
| 13E4_VL4 | DIQMTQSPSSLSASVGDRVTITCRTSENIYSNLAWYQQKPGKAPKL LIYAGTNLADGVPSRFSGSGSGTDYTLTISSLQPEDFANYYCQHFW GTPLTFGGGTKVEIK | 301 |
| 13E4_VL | DIQMTQSPASLSVSVGETVTITCRTSENIYNNLAWYQQKQGKSPQL LVYAATNLADGVPSRFSGSGSGTQYSLKINSLQSEDFGNYYCQHF WGTPLTFGAGTKLELK | 302 |

In some aspects, the anti-transferrin receptor antibody comprises a VH region and a VL region as illustrated in Table 5.

TABLE 5

| | 13E4_VH1 (SEQ ID NO: 293) | 13E4_VH2 (SEQ ID NO: 294) | 13E4_VH3 (SEQ ID NO: 295) | 13E4_VH4 (SEQ ID NO: 296) |
|---|---|---|---|---|
| 13E4_VL1 (SEQ ID NO: 298) | SEQ ID NO: 293 + SEQ ID NO: 298 | SEQ ID NO: 294 + SEQ ID NO: 298 | SEQ ID NO: 295 + SEQ ID NO: 298 | SEQ ID NO: 296 + SEQ ID NO: 298 |
| 13E4_VL2 (SEQ ID NO: 299) | SEQ ID NO: 293 SEQ ID NO: 299 | SEQ ID NO: 294 + SEQ ID NO: 299 | SEQ ID NO: 295 + SEQ ID NO: 299 | SEQ ID NO: 296 + SEQ ID NO: 299 |
| 13E4_VL3 (SEQ ID NO: 300) | SEQ ID NO: 293 + SEQ ID NO: 300 | SEQ ID NO: 294 + SEQ ID NO: 300 | SEQ ID NO: 295 + SEQ ID NO: 300 | SEQ ID NO: 296 + SEQ ID NO: 300 |
| 13E4_VL4 (SEQ ID NO: 301) | SEQ ID NO: 293 + SEQ ID NO: 301 | SEQ ID NO: 294 + SEQ ID NO: 301 | SEQ ID NO: 295 + SEQ ID NO: 301 | SEQ ID NO: 296 + SEQ ID NO: 301 |

In some aspects, an anti-transferrin receptor antibody described herein comprises an IgG framework, an IgA framework, an IgE framework, or an IgM framework. In some instances, the anti-transferrin receptor antibody comprises an IgG framework (e.g., IgG1, IgG2, IgG3, or IgG4). In some cases, the anti-transferrin receptor antibody comprises an IgG1 framework. In some cases, the anti-transferrin receptor antibody comprises an IgG2 (e.g., an IgG2a or IgG2b) framework. In some cases, the anti-transferrin receptor antibody comprises an IgG2a framework. In some cases, the anti-transferrin receptor antibody comprises an IgG2b framework. In some cases, the anti-transferrin receptor antibody comprises an IgG3 framework. In some cases, the anti-transferrin receptor antibody comprises an IgG4 framework.

In some cases, an anti-transferrin receptor antibody comprises one or more mutations in a framework region, e.g., in the CH1 domain, CH2 domain, CH3 domain, hinge region, or a combination thereof. In some instances, the one or more mutations are to stabilize the antibody and/or to increase half-life. In some instances, the one or more mutations are to modulate Fc receptor interactions, to reduce or eliminate Fc effector functions such as FcγR, antibody-dependent cell-mediated cytotoxicity (ADCC), or complement-dependent cytotoxicity (CDC). In additional instances, the one or more mutations are to modulate glycosylation.

In some aspects, the one or more mutations are located in the Fc region. In some instances, the Fc region comprises a mutation at residue position L234, L235, or a combination thereof. In some instances, the mutations comprise L234 and L235. In some instances, the mutations comprise L234A and L235A. In some cases, the residue positions are in reference to IgG1.

In some instances, the Fc region comprises a mutation at residue position L234, L235, D265, N297, K322, L328, or P329, or a combination thereof. In some instances, the mutations comprise L234 and L235 in combination with a mutation at residue position K322, L328, or P329. In some cases, the Fc region comprises mutations at L234, L235, and K322. In some cases, the Fc region comprises mutations at L234, L235, and L328. In some cases, the Fc region comprises mutations at L234, L235, and P329. In some cases, the Fc region comprises mutations at D265 and N297. In some cases, the residue position is in reference to IgG1.

In some instances, the Fc region comprises L234A, L235A, D265A, N297G, K322G, L328R, or P329G, or a combination thereof. In some instances, the Fc region comprises L234A and L235A in combination with K322G, L328R, or P329G. In some cases, the Fc region comprises L234A, L235A, and K322G. In some cases, the Fc region comprises L234A, L235A, and L328R. In some cases, the Fc region comprises L234A, L235A, and P329G. In some cases, the Fc region comprises D265A and N297G. In some cases, the residue position is in reference to IgG1.

In some instances, the Fc region comprises a mutation at residue position L235, L236, D265, N297, K322, L328, or P329, or a combination of the mutations. In some instances, the Fc region comprises mutations at L235 and L236. In some instances, the Fc region comprises mutations at L235 and L236 in combination with a mutation at residue position K322, L328, or P329. In some cases, the Fc region comprises mutations at L235, L236, and K322. In some cases, the Fc region comprises mutations at L235, L236, and L328. In some cases, the Fc region comprises mutations at L235, L236, and P329. In some cases, the Fc region comprises mutations at D265 and N297. In some cases, the residue position is in reference to IgG2b.

In some aspects, the Fc region comprises L235A, L236A, D265A, N297G, K322G, L328R, or P329G, or a combination thereof. In some instances, the Fc region comprises L235A and L236A. In some instances, the Fc region comprises L235A and L236A in combination with K322G, L328R, or P329G. In some cases, the Fc region comprises L235A, L236A, and K322G. In some cases, the Fc region comprises L235A, L236A, and L328R. In some cases, the Fc region comprises L235A, L236A, and P329G. In some cases, the Fc region comprises D265A and N297G. In some cases, the residue position is in reference to IgG2b.

In some aspects, the Fc region comprises a mutation at residue position L233, L234, D264, N296, K321, L327, or P328, wherein the residues correspond to positions 233, 234, 264, 296, 321, 327, and 328 of SEQ ID NO: 303. In some instances, the Fc region comprises mutations at L233 and L234. In some instances, the Fc region comprises mutations at L233 and L234 in combination with a mutation at residue position K321, L327, or P328. In some cases, the Fc region comprises mutations at L233, L234, and K321. In some cases, the Fc region comprises mutations at L233, L234, and L327. In some cases, the Fc region comprises mutations at L233, L234, and K321. In some cases, the Fc region comprises mutations at L233, L234, and P328. In some instances, the Fc region comprises mutations at D264 and N296. In some cases, equivalent positions to residue L233, L234, D264, N296, K321, L327, or P328 in an IgG1, IgG2, IgG3, or IgG4 framework are contemplated. In some cases, mutations to a residue that corresponds to residue L233, L234, D264, N296, K321, L327, or P328 of SEQ ID NO: 23 in an IgG1, IgG2, or lgG4 framework are also contemplated.

In some aspects, the Fe region comprises L233A, L234A, D264A, N296G, K321G, L327R, or P328G, wherein the residues correspond to positions 233, 234, 264, 296, 321, 327, and 328 of SEQ ID NO: 303. In some instances, the Fc region comprises L233A and L234A. In some instances, the Fc region comprises L233A and L234A in combination with K321G, L327R, or P328G. In some cases, the Fc region comprises L233A, L234A, and K321G. In some cases, the Fc region comprises L233A, L234A, and L327R. In some cases, the Fc region comprises L233A, L234A, and K321G. In some cases, the Fc region comprises L233A, L234A, and P328G. In some instances, the Fc region comprises D264A and N296G.

In some aspects, the human IgG constant region is modified to alter antibody-dependent cellular cytotoxicity (ADCC) and/or complement-dependent cytotoxicity (CDC), e.g., with an amino acid modification described in Natsume et al., 2008 *Cancer Res,* 68 (10): 3863-72; Idusogie et al., 2001 *J Immunol,* 166 (4): 2571-5; Moore et al., 2010 mAbs, 2 (2): 181-189; Lazar et al., 2006 *PNAS,* 103 (11): 4005-4010, Shields et al., 2001 JBC, 276 (9): 6591-6604; Stavenhagen et al., 2007 *Cancer Res,* 67 (18): 8882-8890; Stavenhagen et al., 2008 Advan. Enzyme Regul., 48:152-164; Alegre et al, 1992 *J Immunol,* 148:3461-3468; Reviewed in Kaneko and Niwa, 2011 Biodrugs, 25 (1): 1-11.

In some aspects, an anti-transferrin receptor antibody described herein is a full-length antibody, comprising a heavy chain (HC) and a light chain (LC). In some cases, the heavy chain (HC) comprises a sequence selected from Table 6. In some cases, the light chain (LC) comprises a sequence selected from Table 7. The underlined region denotes the respective CDRs.

TABLE 6

| NAME | HC SEQUENCE | SEQ ID NO: |
|---|---|---|
| 13E4_VH1 | QVQLVQSGAEVKKPGASVKVSCKASGYTFINYWMHWVRQAPGQ<br>GLEWMGEINPINGRSNYAQKFQGRVTLTVDTSISTAYMELSRLRSD<br>DTAVYYCARGTRAMHYWGQGTLVTVSSASTKGPSVFPLAPSSKST<br>SGGTAALGCLVKDYFPEPVTVSWNSGALTSGVHTFPAVLQSSGLY<br>SLSSVVTVPSSSLGTQTYICNVNHKPSNTKVDKRVEPKSCDKTHTC<br>PPCPAPELLGGPSVFLFPPKPKDTLMISRTPEVTCVVVDVSHEDPEV<br>KFNWYVDGVEVHNAKTKPREEQYNSTYRVVSVLTVLHQDWLNG<br>KEYKCKVSNKALPAPIEKTISKAKGQPREPQVYTLPPSREEMTKNQ<br>VSLTCLVKGFYPSDIAVEWESNGQPENNYKTTPPVLDSDGSFFLYS<br>KLTVDKSRWQQGNVFSCSVMHEALHNHYTQKSLSLSPG | 303 |
| 13E4_VH1_a | QVQLVQSGAEVKKPGASVKVSCKASGYTFTNYWMHWVRQAPGQ<br>GLEWMGEINPINGRSNYAQKFQGRVTLTVDTSISTAYMELSRLRSD<br>DTAVYYCARGTRAMHYWGQGTLVTVSSASTKQPSVFPLAPSSKST<br>SGGTAALGCLVKDYFPEPVTVSWNSGALTSGVHTFPAVLQSSGLY<br>SLSSVVTVPSSSLGTQTYICNVNHKPSNTKVDKRVEPKSCDKTHTC<br>PPCPAPEAAGGPSVFLFPPKPKDTLMISRTPEVTCVVVDVSHEDPEV<br>KFNWYVDGVEVHNAKTKPREEQYNSTYRVVSVLTVLHQDWLNG | 304 |

TABLE 6-continued

| NAME | HC SEQUENCE | SEQ ID NO: |
|---|---|---|
| | KEYKCKVSNKALPAPIEKTISKAKGQPREPQVYTLPPSREEMTKNQ<br>VSLTCLVKGFYPSDIAVEWESNGQPENNYKTTPPVLDSDGSFFLYS<br>KLTVDKSRWQQGNVFSCSVMHEALHNHYTQKSLSLSPG | |
| 13E4_VH1_b | QVQLVQSGAEVKKPGASVKVSCKASGYTFINYWMHWVRQAPGQ<br>GLEWMGEINPINGRSNYAQKFQGRVTLTVDTSISTAYMELSRLRSD<br>DTAVYYCARGTRAMHYWGQGTLVTVSSASTKGPSVFPLAPSSKST<br>SGGTAALQCLVKDYFPEPVTVSWNSGALTSQVHTFPAVIQSSQLY<br>SLSSVVTVPSSSLGTQTYICNVNHKPSNTKVDKRVEPKSCDKTHTC<br>PPCPAPEAAGGPSVFLFPPKPKDTLMISRTPEVTCVVVDVSHEDPEV<br>KENWYVDGVEVHNAKTKPREEQYNSTYRVVSVLTVLHQDWLNG<br>KEYKCGVSNKALPAPIEKTISKAKGQPREPQVYTLPPSREEMTKNQ<br>VSLTCLVKGFYPSDIAVEWESNGQPENNYKTTPPVLDSDGSFFLYS<br>KLTVDKSRWQQGNVFSCSVMHEALHNHYTQKSLSLSPG | 305 |
| 13E4_VH1_c | QVQLVQSGAEVKKPGASVKVSCKASGYTFTNYWMHWVRQAPGQ<br>GLEWMGEINPINGRSNYAQKFQGRVTLTVDTSTSTAYMELSRLRSD<br>DTAVYYCARGTRAMHYWGQGTLVTVSSASTKGPSVFPLAPSSKST<br>SGGTAALGCLVKDYFPEPVTVSWNSGALTSGVHTFPAVLQSSGLY<br>SLSSVVTVPSSSLGTQTYICNVNHKPSNTKVDKRVEPKSCDKTHTC<br>PPCPAPEAAGGPSVFLFPPKPKDTLMISRTPEVTCVVVDVSHEDPEV<br>KFNWYVDGVEVHNAKTKPREEQYNSTYRVVSVLTVLHQDWLNG<br>KEYKCKVSNKARPAPIEKTISKAKGQPREPQVYTLPPSREEMTKNQ<br>VSLTCLVKGFYPSDIAVEWESNGQPENNYKTTPPVLDSDGSFFLYS<br>KLTVDKSRWQQGNVFSCSVMHEALHNHYTQKSLSLSPG | 306 |
| 13E4_VH1_d | QVQLVQSGAEVKKPGASVKVSCKASGYTFINYWMHWVRQAPGQ<br>GLEWMGEINPINGRSNYAQKFQGRVTLTVDTSISTAYMELSRLRSD<br>DTAVYYCARGTRAMHYWGQGTLVTVSSASTKGPSVFPLAPSSKST<br>SGGTAALGCLVKDYFPEPVTVSWNSGALTSGVHTFPAVLQSSGLY<br>SLSSVVTVPSSSLGTQTYICNVNHKPSNTKVDKRVEPKSCDKTHTC<br>PPCPAPEAAGGPSVFLFPPKPKDTLMISRTPEVTCVVVDVSHEDPEV<br>KFNWYVDGVEVHNAKTKPREEQYNSTYRVVSVLTVLHQDWLNG<br>KEYKCKVSNKALGAPIEKTISKAKGQPREPQVYTLPPSREEMTKNQ<br>VSLTCLVKGFYPSDIAVEWESNGQPENNYKTTPPVLDSDGSFFLYS<br>KLTVDKSRWQQGNVFSCSVMHEALHNHYTQKSLSLSPG | 307 |
| 13E4_VH1_e | QVQLVQSGAEVKKPGASVKVSCKASGYTFTNYWMHWVRQAPGQ<br>GLEWMGEINPINGRSNYAQKFQGRVTLTVDTSISTAYMELSRLRSD<br>DTAVYYCARGTRAMHYWGQGTLVTVSSASTKGPSVFPLAPSSKST<br>SGGTAALQCLVKDYFPEPVTVSWNSGALTSQVHTFPAVIQSSQLY<br>SLSSVVTVPSSSLGTQTYICNVNHKPSNTKVDKRVEPKSCDKTHTC<br>PPCPAPELLGGPSVFLFPPKPKDTLMISRTPEVTCVVVAVSHEDPEV<br>KFNWYVDGVEVHNAKTKPREEQYGSTYRVVSVLTVLHQDWLNG<br>KEYKCKVSNKALPAPIEKTISKAKGQPREPQVYTLPPSREEMTKNQ<br>VSLTCLVKGFYPSDIAVEWESNGQPENNYKTTPPVLDSDQSFFLYS<br>KLTVDKSRWQQGNVFSCSVMHEALHNHYTQKSLSLSPG | 308 |
| 13E4_VH2 | QVQLVQSGAEVKKPGASVKVSCKASGYTFTNYWMHWVRQAPGQ<br>GLEWIGEINPINGRSNYAEKFQGRVTLTVDTSSSTAYMELSRLRSD<br>DTAVYYCARGTRAMHYWGQGTLVTVSSASTKGPSVFPLAPSSKST<br>SGGTAALGCLVKDYFPEPVTVSWNSGALTSGVHTFPAVLQSSGLY<br>SLSSVVTVPSSSLGTQTYTCNVNHKPSNTKVDKRVEPKSCDKTHTC<br>PPCPAPELLGGPSVFLFPPKPKDTLMISRTPEVTCVVVDVSHEDPEV<br>KFNWYVDGVEVHNAKTKPREEQYNSTYRVVSVLTVLHQDWLNG<br>KEYKCKVSNKALPAPIEKTISKAKGQPREPQVYTLPPSREEMTKNQ<br>VSLTCLVKGFYPSDIAVEWESNGQPENNYKTTPPVLDSDGSFFLYS<br>KLTVDKSRWQQGNVFSCSVMHEALHNHYTQKSLSLSPG | 309 |
| 13E4_VH2_a | QVQLVQSGAEVKKPGASVKVSCKASGYTFINYWMHWVRQAPGQ<br>GLEWIGEINPINGRSNYAEKFQGRVTLTVDTSSSTAYMELSRLRSD<br>DTAVYYCARGTRAMHYWGQGTLVTVSSASTKGPSVFPLAPSSKST<br>SGGTAALGCLVKDYFPEPVTVSWNSGALTSGVHTFPAVLQSSGLY<br>SLSSVVTVPSSSLGTQTYICNVNHKPSNTKVDKRVEPKSCDKTHTC<br>PPCPAPEAAGGPSVFLFPPKPKDTLMISRTPEVTCVVVDVSHEDPEV<br>KFNWYVDGVEVIINAKTKPREEQYNSTYRVVSVLTVLHQDWLNG<br>KEYKCKVSNKALPAPIEKTISKAKGQPREPQVYTLPPSREEMTKNQ<br>VSLTCLVKGFYPSDIAVEWESNGQPENNYKTTPPVLDSDGSFFLYS<br>KLTVDKSRWQQGNVFSCSVMHEALHNHYTQKSLSLSPG | 310 |
| 13E4_VH2_b | QVQLVQSGAEVKKPGASVKVSCKASGYTFTNYWMHWVRQAPGQ<br>GLEWIGEINPINGRSNYAEKFQGRVTLTVDTSSSTAYMELSRLRSD<br>DTAVYYCARGTRAMHYWGQGTLVTVSSASTKQPSVFPLAPSSKST<br>SGGTAALGCLVKDYFPEPVTVSWNSGALTSGVHTFPAVLQSSGLY<br>SLSSVVTVPSSSLGTQTYICNVNHKPSNTKVDKRVEPKSCDKTHTC<br>PPCPAPEAAGGPSVFLFPPKPKDTLMISRTPEVTCVVVDVSHEDPEV<br>KFNWYVDGVEVHNAKTKPREEQYNSTYRVVSVLTVLHQDWLNG | 311 |

TABLE 6-continued

| NAME | HC SEQUENCE | SEQ ID NO: |
|---|---|---|
| | KEYKCGVSNKALPAPIEKTISKAKGQPREPQVYTLPPSREEMTKNQ VSLTCLVKGFYPSDIAVEWESNGQPENNYKTTPPVLDSDGSFFLYS KLTVDKSRWQQGNVFSCSVMHEALHNHYTQKSLSLSPG | |
| 13E4_VH2_c | QVQLVQSGAEVKKPGASVKVSCKASGYTFTNYWMHWVRQAPGQ GLEWIGEINPINGRSNYAEKFQGRVTLTVDTSSSTAYMELSRLRSD DTAVYYCARGTRAMHYWGQGTLVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHTC PPCPAPEAAGGPSVFLFPPKPKDTLMISRTPEVTCVVVDVSHEDPEV KFNWYVDGVEVHNAKTKPREEQYNSTYRVVSVLTVLHQDWLNG KEYKCKVSNKARPAPIEKTISKAKGQPREPQVYTLPPSREEMTKNQ VSLTCLVKGFYPSDIAVEWESNGQPENNYKTTPPVLDSDGSFFLYS KLTVDKSRWQQGNVFSCSVMHEALHNHYTQKSLSLSPG | 312 |
| 13E4_VH2_d | QVQLVQSGAEVKKPGASVKVSCKASGYTFTNYWMHWVRQAPGQ GLEWIGEINPINGRSNYAEKFQGRVTLTVDTSSSTAYMELSRLRSD DTAVYYCARGTRAMHYWGQGTLVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHTC PPCPAPEAAGGPSVFLFPPKPKDTLMISRTPEVTCVVVDVSHEDPEV KFNWYVDGVEVHNAKTKPREEQYNSTYRVVSVLTVLHQDWLNG KEYKCKVSNKALGAPIEKTISKAKGQPREPQVYTLPPSREEMTKNQ VSLTCLVKGFYPSDIAVEWESNGQPENNYKTTPPVLDSDGSFFLYS KLTVDKSRWQQGNVFSCSVMHEALHNHYTQKSLSLSPG | 313 |
| 13E4_VH2_e | QVQLVQSGAEVKKPGASVKVSCKASGYTFTNYWMHWVRQAPGQ GLEWIGEINPINGRSNYAEKFQGRVTLTVDTSSSTAYMELSRLRSD DTAVYYCARGTRAMHYWGQGTLVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHTC PPCPAPELLGGPSVFLFPPKPKDTLMISRTPEVTCVVVAVSHEDPEV KFNWYVDGVEVHNAKTKPREEQYQSTYRVVSVLTVLHQDWLNG KEYKCKVSNKALPAPIEKTISKAKGQPREPQVYTLPPSREEMTKNQ VSLTCLVKGFYPSDIAVEWESNGQPENNYKTTPPVLDSDGSFFLYS KLTVDKSRWQQGNVFSCSVMHEALHNHYTQKSLSLSPG | 314 |
| 13E4_VH3 | QVQLVQSGAEVKKPGASVKVSCKASGYTFTNYWMHWVRQAPGQ GLEWMGEINPIQGRSNYAEKFQGRVTLTVDTSSSTAYMELSSLRSE DTATYYCARGTRAMHYWGQGTLVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHTC PPCPAPELLGGPSVFLFPPKPKDTLMISRTPEVTCVVVDVSHEDPEV KFNWYVDGVEVHNAKTKPREEQYNSTYRVVSVLTVLHQDWLNG KEYKCKVSNKALPAPIEKTISKAKGQPREPQVYTLPPSREEMTKNQ VSLTCLVKGFYPSDIAVEWESNGQPENNYKTTPPVLDSDGSFFLYS KLTVDKSRWQQGNVFSCSVMHEALHNHYTQKSLSLSPG | 315 |
| 13E4_VH3_a | QVQLVQSGAEVKKPGASVKVSCKASGYTFTNYWMHWVRQAPGQ GLEWMGEINPIQGRSNYAEKFQGRVTLTVDTSSSTAYMELSSLRSE DTATYYCARGTRAMHYWGQGTLVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHTC PPCPAPEAAGGPSVFLFPPKPKDTLMISRTPEVTCVVVDVSHEDPEV KFNWYVDGVEVHNAKTKPREEQYNSTYRVVSVLTVLHQDWLNG KEYKCKVSNKALPAPIEKTISKAKGQPREPQVYTLPPSREEMTKNQ VSLTCLVKGFYPSDIAVEWESNGQPENNYKTTPPVLDSDGSFFLYS KLTVDKSRWQQGNVFSCSVMHEALHNHYTQKSLSLSPG | 316 |
| 13E4_VH3_b | QVQLVQSGAEVKKPGASVKVSCKASGYTFTNYWMHWVRQAPGQ GLEWMGEINPIQGRSNYAEKFQGRVTLTVDTSSSTAYMELSSLRSE DTATYYCARGTRAMHYWGQGTLVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHTC PPCPAPEAAGGPSVFLFPPKPKDTLMISRTPEVTCVVVDVSHEDPEV KFNWYVDGVEVHNAKTKPREEQYNSTYRVVSVLTVLHQDWLNG KEYKCGVSNKALPAPIEKTISKAKGQPREPQVYTLPPSREEMTKNQ VSLTCLVKGFYPSDIAVEWESNGQPENNYKTTPPVLDSDGSFFLYS KLTVDKSRWQQGNVFSCSVMHEALHNHYTQKSLSLSPG | 317 |
| 13E4_VH3_c | QVQLVQSGAEVKKPGASVKVSCKASGYTFTNYWMHWVRQAPGQ GLEWMGEINPIQGRSNYAEKFQGRVTLTVDTSSSTAYMELSSLRSE DTATYYCARGTRAMHYWGQGTLVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHTC PPCPAPEAAGGPSVFLFPPKPKDTLMISRTPEVTCVVVDVSHEDPEV KFNWYVDGVEVHNAKTKPREEQYNSTYRVVSVLTVLHQDWLNG | 318 |

TABLE 6-continued

| NAME | HC SEQUENCE | SEQ ID NO: |
|---|---|---|
| | KEYKCKVSNKARPAPIEKTISKAKGQPREPQVYTLPPSREEMTKNQ VSLTCLVKGFYPSDIAVEWESNGQPENNYKTTPPVLDSDGSFFLYS KLTVDKSRWQQGNVFSCSVMHEALHNHYTQKSLSLSPG | |
| 13E4_VH3_d | QVQLVQSGAEVKKPGASVKVSCKASGYTFTNYWMHWVRQAPGQ GLEWMGEINPIQGRSNYAEKFQGRVTLTVDTSSSTAYMELSSLRSE DTATYYCARGTRAMHYWGQGTLVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHTC PPCPAPEAAGGPSVFLFPPKPKDTLMISRTPEVTCVVVDVSHEDPEV KFNWYVDGVEVIINAKTKPREEQYNSTYRVVSVLTVLHQDWLNG KEYKCKVSNKALGAP1EKTISKAKGQPREPQVYTLPPSREEMTKNQ VSLTCLVKGFYPSDIAVEWESNGQPENNYKTTPPVLDSDGSFFLYS KLTVDKSRWQQGNVFSCSVMHEALHNHYTQKSLSLSPG | 319 |
| 13E4_VH3_e | QVQLVQSGAEVKKPGASVKVSCKASGYTFTNYWMHWVRQAPGQ GLEWMGEINPIQGRSNYAEKFQGRVTLTVDTSSSTAYMELSSLRSE DTATYYCARGTRAMHYWGQGTLVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHTC PPCPAPELLGGPSVFLFPPKPKDTLMISRTPEVTCVVVAVSHEDPEV KFNWYVDGVEVHNAKTKPREEQYGSTYRVVSVLTVLHQDWLNG KEYKCKVSNKALPAPIEKTISKAKGQPREPQVYTLPPSREEMTKNQ VSLTCLVKGFYPSDIAVEWESNGQPENNYKTTPPVLDSDGSFFLYS KLTVDKSRWQQGNVFSCSVMHEALHNHYTQKSLSLSPG | 320 |
| 13E4_VH4 | QVQLVQSGAEVKKPGASVKVSCKASGYTFTNYWMHWVRQAPGQ GLEWMGEINPINGRSNYAEKFQGRVTLTVDTSSSTAYMELSSLRSE DTATYYCARGTRAMHYWGQGTLVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHTC PPCPAPELLGGPSVTLFPPKPKDTLMISRTPEVTCVWDVSHEDPEV KFNWYVDGVEVHNAKTKPREEQYNSTYRVVSVLTVLHQDWLNG KEYKCKVSNKALPAPIEKTISKAKGQPREPQVYTLPPSREEMTKNQ VSLTCLVKGFYPSDIAVEWESNGQPENNYKTTPPVLDSDGSFFLYS KLTVDKSRWQQGNVFSCSVMHEALHNFIYTQKSLSLSPG | 321 |
| 13E4_VH4_a | QVQLVQSGAEVKKPGASVKVSCKASGYTFTNYWMHWVRQAPGQ GLEWMGEINPINGRSNYAEKFQGRVTLTVDTSSSTAYMELSSLRSE DTATYYCARGTRAMHYWGQGTLVTVSSASTKGPSVFPLAPSSKST SGGTAALQCLVKDYFPEPVTVSWNSGALTSQVHTFPAVLQSSQLY SLSSVVTVPSSSLGTQTYICNVNHKPSNTKVDKRVEPKSCDKTHTC PPCPAPEAAGGPSVFLFPPKPKDTLMISRTPEVTCVVVDVSHEDPEV KFNWYVDGVEVHNAKTKPREEQYNSTYRVVSVLTVLHQDWENG KEYKCKVSNKALPAPIEKTISKAKGQPREPQVYTLPPSREEMTKNQ VSLTCLVKQFYPSDIAVEWESNGQPENNYKTTPPVLDSDQSFFLYS KLTVDKSRWQQGNVFSCSVMHEALHNHYTQKSLSLSPG | 322 |
| 13E4_VH4_b | QVQLVQSGAEVKKPGASVKVSCKASGYTFTNYWMHWVRQAPGQ GLEWMGEINPINGRSNYAEKFQGRVTLTVDTSSSTAYMELSSLRSE DTATYYCARGTRAMHYWGQGTLVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHTC PPCPAPEAAGGPSVFLFPPKPKDTLMISRTPEVTCVVVDVSHEDPEV KFNWYVDGVEVHNAKTKPREEQYNSTYRVVSVLTVLHQDWLNG KEYKCGVSNKALPAPIEKTISKAKGQPREPQVYTLPPSREEMTKNQ VSLTCLVKGFYPSDIAVEWESNGQPENNYKTTPPVLDSDGSFFLYS KLTVDKSRWQQGNVFSCSVMHEALHNHYTQKSLSLSPG | 323 |
| 13E4_VH4_c | QVQLVQSGAEVKKPGASVKVSCKASGYTFINYWMHWVRQAPGQ GLEWMGEINPINGRSNYAEKFQGRVTLTVDTSSSTAYMELSSLRSE DTATYYCARGTRAMHYWGQGTLVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHTC PPCPAPEAAGGPSVFLFPPKPKDTLMISRTPEVTCVVVDVSHEDPEV KFNWYVDGVEVHNAKTKPREEQYNSTYRVVSVLTVLHQDWLNG KEYKCKVSNKARPAPIEKTISKAKGQPREPQVYTLPPSREEMTKNQ VSLTCLVKGFYPSDIAVEWESNGQPENNYKTTPPVLDSDGSFFLYS KLTVDKSRWQQGNVFSCSVMHEALHNHYTQKSLSLSPG | 324 |
| 13E4_VH4_d | QVQLVQSGAEVKKPGASVKVSCKASGYTFTNYWMHWVRQAPGQ GLEWMGEINPINGRSNYAEKFQGRVTLTVDTSSSTAYMELSSLRSE DTATYYCARGTRAMHYWGQGTLVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHTC PPCPAPEAAGGPSVFLFPPKPKDTLMISRTPEVTCVVVDVSHEDPEV KFNWYVDGVEVHNAKTKPREEQYNSTYRVVSVLTVLHQDWLNG | 325 |

TABLE 6-continued

| NAME | HC SEQUENCE | SEQ ID NO: |
|---|---|---|
| | KEYKCKVSNKALGAPIEKTISKAKGQPREPQVYTLPPSREEMTKNQ<br>VSLTCLVKGFYPSDIAVEWESNGQPENNYKTTPPVLDSDGSFFLYS<br>KLTVDKSRWQQGNVFSCSVMHEALHNHYTQKSLSLSPG | |
| 13E4_VH4_e | QVQLVQSGAEVKKPGASVKVSCKASGYTFTNYWMHWVRQAPGQ<br>GLEWMGEINPINGRSNYAEKFQGRVTLTVDTSSSTAYMELSSLRSE<br>DTATYYCARGTRAMHYWGQGTLVTVSSASTKGPSVFPLAPSSKST<br>SGGTAALGCLVKDYFPEPVTVSWNSGALTSQVHTFPAVLQSSQLY<br>SLSSVVTVPSSSLGTQTYICNVNHKPSNTKVDKRVEPKSCDKTHTC<br>PPCPAPELLGGPSVFLFPPKPKDTLMISRTPEVTCVVVAVSHEDPEV<br>KFNWYVDGVEVHNAKTKPREEQYGSTYRVVSVLTVLHQDWLNG<br>KEYKCKVSNKALPAPIEKTISKAKGQPREPQVYTLPPSREEMTKNQ<br>VSLTCLVKQFYPSDIAVEWESNGQPENNYKTTPPVLDSDQSFFLYS<br>KLTVDKSRWQQGNVFSCSVMHEALHNHYTQKSLSLSPG | 326 |

TABLE 7

| NAME | LC SEQUENCE | SEQ ID NO: |
|---|---|---|
| 13E4_VL1 | DIQMTQSPSSLSASVGDRVTITCRTSENIYNNLAWYQQKPGKSPKL<br>LIYAATNLADGVPSRFSGSGSGTDYTLTISSLQPEDFATYYCQHFW<br>GTPLTFGGGTKVEIKRTVAAPSVFIFPPSDEQLKSGTASVVCLLNNF<br>YPREAKVQWKVDNALQSGNSQESVTEQDSKDSTYSLSSTLTLSKA<br>DYEKHKVYACEVTHQGLSSPVTKSFNRGEC | 327 |
| 13E4_VL2 | DIQMTQSPSSLSASVGDRVTITCRTSENIYNNLAWYQQKPGKAPKL<br>LIYAATNLADGVPSRFSGSGSGTDYTLTISSLQPEDFATYYCQHFW<br>GTPLTFGGGTKVEIKRTVAAPSVFIFPPSDEQLKSGTASVVCLLNNF<br>YPREAKVQWKVDNALQSGNSQESVTEQDSKDSTYSLSSTLTLSKA<br>DYEKHKVYACEVTHQGLSSPVTKSFNRGEC | 328 |
| 13E4_VL3 | DIQMTQSPSSLSASVGDRVTITCRTSENIYNNLAWYQQKPGKAPKL<br>LIYAATNLAEGVPSRFSGSQSGTDYTLTISSLQPEDFATYYCQHFW<br>GTPLTFGGGTKVEIKRTVAAPSVFIFPPSDEQLKSGTASVVCLLNNF<br>YPREAKVQWKVDNALQSGNSQESVTEQDSKDSTYSLSSTLTLSKA<br>DYEKHKVYACEVTHQGLSSPVTKSFNRGEC | 329 |
| 13E4_VL4 | DIQMTQSPSSLSASVGDRVTITCRTSENIYSNLAWYQQKPGKAPKL<br>LIYAGTNLADGVPSRFSGSGSGTDYTLTISSLQPEDFANYYCQHFW<br>GTPLTFGGGTKVEIKRTVAAPSVFIFPPSDEQLKSGTASVVCLLNNF<br>YPREAKVQWKVDNALQSGNSQESVTEQDSKDSTYSLSSTLTLSKA<br>DYEKHKVYACEVTHQGLSSPVTKSFNRGEC | 330 |

In some aspects, an anti-transferrin receptor antibody described herein has an improved serum half-life compared to a reference anti-transferrin receptor antibody. In some instances, the improved serum half-life is at least 30 minutes, 1 hour, 1.5 hour, 2 hours, 3 hours, 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, 14 days, 30 days, or longer than reference anti-transferrin receptor antibody.

In some aspects, the binding moiety A is conjugated to a polynucleic acid molecule (B) non-specifically. In some instances, the binding moiety A is conjugated to a polynucleic acid molecule (B) via a lysine residue or a cysteine residue, in a non-site specific manner. In some instances, the binding moiety A is conjugated to a polynucleic acid molecule (B) via a lysine residue (e.g., lysine residue present in the binding moiety A) in a non-site specific manner. In some cases, the binding moiety A is conjugated to a polynucleic acid molecule (B) via a cysteine residue (e.g., cysteine residue present in the binding moiety A) in a non-site specific manner.

In some aspects, the binding moiety A is conjugated to a polynucleic acid molecule (B) in a site-specific manner. In some instances, the binding moiety A is conjugated to a polynucleic acid molecule (B) through a lysine residue, a cysteine residue, at the 5'-terminus, at the 3'-terminus, an unnatural amino acid, or an enzyme-modified or enzyme-catalyzed residue, via a site-specific manner. In some instances, the binding moiety A is conjugated to a polynucleic acid molecule (B) through a lysine residue (e.g., lysine residue present in the binding moiety A) via a site-specific manner. In some instances, the binding moiety A is conjugated to a polynucleic acid molecule (B) through a cysteine residue (e.g., cysteine residue present in the binding moiety A) via a site-specific manner. In some instances, the binding moiety A is conjugated to a polynucleic acid molecule (B) at the 5'-terminus via a site-specific manner. In some instances, the binding moiety A is conjugated to a polynucleic acid molecule (B) at the 3'-terminus via a site-specific manner. In some instances, the binding moiety A is conjugated to a polynucleic acid molecule (B) through an unnatural amino acid via a site-specific manner. In some instances, the binding moiety A is conjugated to a polynucleic acid molecule (B) through an enzyme-modified or enzyme-catalyzed residue via a site-specific manner.

In some aspects, one or more polynucleic acid molecule (B) is conjugated to a binding moiety A. In some instances, about 1, 2, 3, 4, 5, 6, 7, 8, 9, 10, 11, 12, 13, 14, 15, 16, or more polynucleic acid molecules are conjugated to one binding moiety A. In some instances, about 1 polynucleic acid molecule is conjugated to one binding moiety A. In some instances, about 2 polynucleic acid molecules are conjugated to one binding moiety A. In some instances, about 3 polynucleic acid molecules are conjugated to one binding moiety A. In some instances, about 4 polynucleic acid molecules are conjugated to one binding moiety A. In some instances, about 5 polynucleic acid molecules are conjugated to one binding moiety A. In some instances, about 6 polynucleic acid molecules are conjugated to one binding moiety A. In some instances, about 7 polynucleic acid molecules are conjugated to one binding moiety A. In some instances, about 8 polynucleic acid molecules are conjugated to one binding moiety A. In some instances, about 9 polynucleic acid molecules are conjugated to one binding moiety A. In some instances, about 10 polynucleic acid molecules are conjugated to one binding moiety A. In some instances, about 11 polynucleic acid molecules are conjugated to one binding moiety A. In some instances, about 12 polynucleic acid molecules are conjugated to one binding moiety A. In some instances, about 13 polynucleic acid molecules are conjugated to one binding moiety A. In some instances, about 14 polynucleic acid molecules are conjugated to one binding moiety A. In some instances, about 15 polynucleic acid molecules are conjugated to one binding moiety A. In some instances, about 16 polynucleic acid molecules are conjugated to one binding moiety A. In some cases, the one or more polynucleic acid molecules are the same. In other cases, the one or more polynucleic acid molecules are different.

In some aspects, the number of polynucleic acid molecule (B) conjugated to a binding moiety A forms a ratio. In some instances, the ratio is referred to as a DAR (drug-to-antibody) ratio, in which the drug as referred to herein is the polynucleic acid molecule (B). In some instances, the DAR ratio of the polynucleic acid molecule (B) to binding moiety A is about 1, 2, 3, 4, 5, 6, 7, 8, 9, 10, 11, 12, 13, 14, 15, 16, or greater. In some instances, the DAR ratio of the polynucleic acid molecule (B) to binding moiety A is about 1 or greater. In some instances, the DAR ratio of the polynucleic acid molecule (B) to binding moiety A is about 2 or greater. In some instances, the DAR ratio of the polynucleic acid molecule (B) to binding moiety A is about 3 or greater. In some instances, the DAR ratio of the polynucleic acid molecule (B) to binding moiety A is about 4 or greater. In some instances, the DAR ratio of the polynucleic acid molecule (B) to binding moiety A is about 5 or greater. In some instances, the DAR ratio of the polynucleic acid molecule (B) to binding moiety A is about 6 or greater. In some instances, the DAR ratio of the polynucleic acid molecule (B) to binding moiety A is about 7 or greater. In some instances, the DAR ratio of the polynucleic acid molecule (B) to binding moiety A is about 8 or greater. In some instances, the DAR ratio of the polynucleic acid molecule (B) to binding moiety A is about 9 or greater. In some instances, the DAR ratio of the polynucleic acid molecule (B) to binding moiety A is about 10 or greater. In some instances, the DAR ratio of the polynucleic acid molecule (B) to binding moiety A is about 11 or greater. In some instances, the DAR ratio of the polynucleic acid molecule (B) to binding moiety A is about 12 or greater.

In some instances, the DAR ratio of the polynucleic acid molecule (B) to binding moiety A is about 1, 2, 3, 4, 5, 6, 7, 8, 9, 10, 11, 12, 13, 14, 15, or 16. In some instances, the DAR ratio of the polynucleic acid molecule (B) to binding moiety A is about 1. In some instances, the DAR ratio of the polynucleic acid molecule (B) to binding moiety A is about 2. In some instances, the DAR ratio of the polynucleic acid molecule (B) to binding moiety A is about 3. In some instances, the DAR ratio of the polynucleic acid molecule (B) to binding moiety A is about 4. In some instances, the DAR ratio of the polynucleic acid molecule (B) to binding moiety A is about 5. In some instances, the DAR ratio of the polynucleic acid molecule (B) to binding moiety A is about 6. In some instances, the DAR ratio of the polynucleic acid molecule (B) to binding moiety A is about 7. In some instances, the DAR ratio of the polynucleic acid molecule (B) to binding moiety A is about 8. In some instances, the DAR ratio of the polynucleic acid molecule (B) to binding moiety A is about 9. In some instances, the DAR ratio of the polynucleic acid molecule (B) to binding moiety A is about 10. In some instances, the DAR ratio of the polynucleic acid molecule (B) to binding moiety A is about 11. In some instances, the DAR ratio of the polynucleic acid molecule (B) to binding moiety A is about 12. In some instances, the DAR ratio of the polynucleic acid molecule (B) to binding moiety A is about 13. In some instances, the DAR ratio of the polynucleic acid molecule (B) to binding moiety A is about 14. In some instances, the DAR ratio of the polynucleic acid molecule (B) to binding moiety A is about 15. In some instances, the DAR ratio of the polynucleic acid molecule (B) to binding moiety A is about 16.

In some instances, the DAR ratio of the polynucleic acid molecule (B) to binding moiety Ais 1, 2, 3, 4, 5, 6, 7, 8, 9, 10, 11, 12, 13, 14, 15, or 16. In some instances, the DAR ratio of the polynucleic acid molecule (B) to binding moiety A is 1. In some instances, the DAR ratio of the polynucleic acid molecule (B) to binding moiety A is 2. In some instances, the DAR ratio of the polynucleic acid molecule (B) to binding moiety A is 4. In some instances, the DAR ratio of the polynucleic acid molecule (B) to binding moiety A is 6. In some instances, the DAR ratio of the polynucleic acid molecule (B) to binding moiety A is 8. In some instances, the DAR ratio of the polynucleic acid molecule (B) to binding moiety A is 12.

In some instances, a conjugate comprising polynucleic acid molecule (B) and binding moiety A has improved activity as compared to a conjugate comprising polynucleic acid molecule (B) without a binding moiety A. In some instances, improved activity results in enhanced biologically relevant functions, e.g., improved stability, affinity, binding, functional activity, and efficacy in treatment or prevention of a disease state. In some instances, the disease state is a result of one or more mutated exons of a gene. In some instances, the conjugate comprising polynucleic acid molecule (B) and binding moiety A results in increased exon skipping of the one or more mutated exons as compared to the conjugate comprising polynucleic acid molecule (B) without a binding moiety A. In some instances, exon skipping is increased by at least or about 5%, 10%, 20%, 25%, 30%, 40%, 50%, 60%, 70%, 80%, 90%, 95%, or more than 95% in the conjugate comprising polynucleic acid molecule (B) and binding moiety A as compared to the conjugate comprising polynucleic acid molecule (B) without a binding moiety A.

In some aspects, an antibody or antigen binding fragment is further modified using conventional techniques known in the art, for example, by using amino acid deletion, insertion, substitution, addition, and/or by recombination and/or any other modification (e.g., posttranslational and chemical modifications, such as glycosylation and phosphorylation)

known in the art either alone or in combination. In some instances, the modification further comprises a modification for modulating interaction with Fc receptors. In some instances, the one or more modifications include those described in, for example, International Publication No. WO97/34631, which discloses amino acid residues involved in the interaction between the Fc domain and the FcRn receptor. Methods for introducing such modifications in the nucleic acid sequence underlying the amino acid sequence of an antibody or antigen binding fragment is well known to the person skilled in the art.

In some instances, an antigen binding fragment further encompasses its derivatives and includes polypeptide sequences containing at least one CDR.

In some instances, the term “single-chain” as used herein means that the first and second domains of a bi-specific single chain construct are covalently linked, preferably in the form of a co-linear amino acid sequence encodable by a single nucleic acid molecule.

In some instances, a bispecific single chain antibody construct relates to a construct comprising two antibody derived binding domains. In such aspects, bi-specific single chain antibody construct is tandem bi-scFv or diabody. In some instances, a scFv contains a VH and VL domain connected by a linker peptide. In some instances, linkers are of a length and sequence sufficient to ensure that each of the first and second domains can, independently from one another, retain their differential binding specificities.

In some aspects, binding to or interacting with as used herein defines a binding/interaction of at least two antigen-interaction-sites with each other. In some instances, antigen-interaction-site defines a motif of a polypeptide that shows the capacity of specific interaction with a specific antigen or a specific group of antigens. In some cases, the binding/interaction is also understood to define a specific recognition. In such cases, specific recognition refers to that the antibody or its antigen binding fragment is capable of specifically interacting with and/or binding to at least two amino acids of each of a target molecule. For example, specific recognition relates to the specificity of the antibody molecule, or to its ability to discriminate between the specific regions of a target molecule. In additional instances, the specific interaction of the antigen-interaction-site with its specific antigen results in an initiation of a signal, e.g. due to the induction of a change of the conformation of the antigen, an oligomerization of the antigen, etc. In further aspects, the binding is exemplified by the specificity of a “key-lock-principle”. Thus in some instances, specific motifs in the amino acid sequence of the antigen-interaction-site and the antigen bind to each other as a result of their primary, secondary or tertiary structure as well as the result of secondary modifications of said structure. In such cases, the specific interaction of the antigen-interaction-site with its specific antigen results as well in a simple binding of the site to the antigen.

In some instances, specific interaction further refers to a reduced cross-reactivity of the antibody or antigen binding fragment or a reduced off-target effect. For example, the antibody or antigen binding fragment that bind to the polypeptide/protein of interest but do not or do not essentially bind to any of the other polypeptides are considered as specific for the polypeptide/protein of interest. Examples for the specific interaction of an antigen-interaction-site with a specific antigen comprise the specificity of a ligand for its receptor, for example, the interaction of an antigenic determinant (epitope) with the antigenic binding site of an antibody.

Additional Binding Moieties

In some aspects, the binding moiety is a plasma protein. In some instances, the plasma protein comprises albumin. In some instances, the binding moiety A is albumin. In some instances, albumin is conjugated by one or more of a conjugation chemistry described herein to a polynucleic acid molecule. In some instances, albumin is conjugated by native ligation chemistry to a polynucleic acid molecule. In some instances, albumin is conjugated by lysine conjugation to a polynucleic acid molecule.

In some instances, the binding moiety is a steroid. Exemplary steroids include cholesterol, phospholipids, di- and triacylglycerols, fatty acids, hydrocarbons that are saturated, unsaturated, comprise substitutions, or combinations thereof. In some instances, the steroid is cholesterol. In some instances, the binding moiety is cholesterol. In some instances, cholesterol is conjugated by one or more of a conjugation chemistry described herein to a polynucleic acid molecule. In some instances, cholesterol is conjugated by native ligation chemistry to a polynucleic acid molecule. In some instances, cholesterol is conjugated by lysine conjugation to a polynucleic acid molecule.

In some instances, the binding moiety is a polymer, including but not limited to polynucleic acid molecule aptamers that bind to specific surface markers on cells. In this instance the binding moiety is a polynucleic acid that does not hybridize to a target gene or mRNA, but instead is capable of selectively binding to a cell surface marker similarly to an antibody binding to its specific epitope of a cell surface marker.

In some cases, the binding moiety is a peptide. In some cases, the peptide comprises between about 1 and about 3 kDa. In some cases, the peptide comprises between about 1.2 and about 2.8 kDa, about 1.5 and about 2.5 kDa, or about 1.5 and about 2 kDa. In some instances, the peptide is a bicyclic peptide. In some cases, the bicyclic peptide is a constrained bicyclic peptide. In some instances, the binding moiety is a bicyclic peptide (e.g., bicycles from Bicycle Therapeutics).

In additional cases, the binding moiety is a small molecule. In some instances, the small molecule is an antibody-recruiting small molecule. In some cases, the antibody-recruiting small molecule comprises a target-binding terminus and an antibody-binding terminus, in which the target-binding terminus is capable of recognizing and interacting with a cell surface receptor. For example, in some instances, the target-binding terminus comprising a glutamate urea compound enables interaction with PSMA, thereby, enhances an antibody interaction with a cell that expresses PSMA. In some instances, a binding moiety is a small molecule described in Zhang et al., “A remote arene-binding site on prostate specific membrane antigen revealed by antibody-recruiting small molecules,” *J Am Chem Soc.* 132 (36): 12711-12716 (2010); or McEnaney, et al., “Antibody-recruiting molecules: an emerging paradigm for engaging immune function in treating human disease,” *ACS Chem Biol.* 7 (7): 1139-1151 (2012).

Production of Antibodies or Antigen Binding Fragment Thereof

In some aspects, polypeptides described herein (e.g., antibodies and antigen binding fragments) are produced using any method known in the art to be useful for the synthesis of polypeptides (e.g., antibodies), in particular, by chemical synthesis or by recombinant expression, and are preferably produced by recombinant expression techniques.

In some instances, an antibody or antigen binding fragment thereof is expressed recombinantly, and the nucleic acid encoding the antibody or antigen binding fragment is assembled from chemically synthesized oligonucleotides (e.g., as described in Kutmeier et al., 1994, *BioTechniques* 17:242), which involves the synthesis of overlapping oligonucleotides containing portions of the sequence encoding the antibody, annealing and ligation of those oligonucleotides, and then amplification of the ligated oligonucleotides by PCR, Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or its antigen binding is optionally generated by immunizing an animal, such as a rabbit, to generate polyclonal antibodies or, more preferably, by generating monoclonal antibodies, e.g., as described by Kohler and Milstein (1975, *Nature* 256:495-497) or, as described by Kozbor et al. (1983, *Immunology Today* 4:72) or Cole et al. (1985 in *Monoclonal Antibodies and Cancer Therapy*, Alan R. Liss, Inc., pp. 77-96). Alternatively, a clone encoding at least the Fab portion of the antibody is optionally obtained by screening Fab expression libraries (e.g., as described in Huse et al., 1989, *Science* 246:1275-1281) for clones of Fab fragments that bind the specific antigen or by screening antibody libraries (See, e.g., Clackson et al., 1991, *Nature* 352:624; Hane et al., 1997 *Proc. Natl. Acad. Sci. USA* 94:4937).

In some aspects, techniques developed for the production of "chimeric antibodies" (Morrison et al., 1984, *Proc. Natl. Acad. Sci.* 81:851-855; Neuberger et al., 1984, *Nature* 312:604-608; Takeda et al., 1985, *Nature* 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region, e.g., humanized antibodies.

In some aspects, techniques described for the production of single chain antibodies (U.S. Pat. No. 4,694,778; Bird, 1988, *Science* 242:423-42; Huston et al., 1988, *Proc. Natl. Acad. Sci. USA* 85:5879-5883; and Ward et al., 1989, *Nature* 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* are also optionally used (Skerra et al., 1988, *Science* 242:1038-1041).

In some aspects, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific aspects, the expression of the antibody is regulated by a constitutive, an inducible or a tissue, specific promoter.

In some aspects, a variety of host-expression vector systems is utilized to express an antibody or its antigen binding fragment described herein. Such host-expression systems represent vehicles by which the coding sequences of the antibody is produced and subsequently purified, but also represent cells that are, when transformed or transfected with the appropriate nucleotide coding sequences, express an antibody or its antigen binding fragment in situ. These include, but are not limited to, microorganisms such as bacteria (e.g., *E. coli* and *B. subtilis*) transformed with recombinant bacteriophage DNA, plasmid DNA or cosmid DNA expression vectors containing an antibody or its antigen binding fragment coding sequences; yeast (e.g., *Saccharomyces Pichia*) transformed with recombinant yeast expression vectors containing an antibody or its antigen binding fragment coding sequences; insect cell systems infected with recombinant virus expression vectors (e.g., baculovirus) containing an antibody or its antigen binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its antigen binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its antigen binding fragments.

In some instances, a number of selection systems are used, including but not limited to the herpes simplex virus thymidine kinase (Wigler et al., 1977, *Cell* 11:223), hypoxanthine-guanine phosphoribosyltransferase (Szybalska & Szybalski, 192, *Proc. Natl. Acad. Sci. USA* 48:202), and adenine phosphoribosyltransferase (Lowy et al., 1980, *Cell* 22:817) genes are employed in tk-, bgprt- or aprt-cells, respectively. Also, antimetabolite resistance are used as the basis of selection for the following genes: DHFR, which confers resistance to methotrexate (Wigler et al., 1980, *Proc. Natl. Acad. Sci. USA* 77:357; O'Hare et al., 1981, *Proc. Natl. Acad. Sci. USA* 78:1527); GPT, which confers resistance to mycophenolic acid (Mulligan & Berg, 1981, *Proc. Natl. Acad. Sci. USA* 78:2072); neo, which confers resistance to the aminoglycoside G-418 (Clinical Pharmacy 12:488-505; Wu and Wu, 1991, *Biotherapy* 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May 1993, *TIB TECH* 11(5):155-215) and hygro, which confers resistance to hygromycin (Santerre et al., 1984, *Gene* 30:147). Methods commonly known in the art of recombinant DNA technology which can be used are described in Ausubel et al. (eds., 1993, *Current Protocols in Molecular Biology*, John Wiley & Sons, NY; Kriegler, 1990, Gene Transfer and Expression,

*A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al., 1981, *J. Mol. Biol.* 150:1).

In some instances, the expression levels of an antibody are increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell Biol.* 3:257).

In some instances, any method known in the art for purification or analysis of an antibody or antibody conjugates is used, for example, by chromatography (e.g., ion exchange, affinity, particularly by affinity for the specific antigen after Protein A, and sizing column chromatography), centrifugation, differential solubility, or by any other standard technique for the purification of proteins. Exemplary chromatography methods included, but are not limited to, strong anion exchange chromatography, hydrophobic interaction chromatography, size exclusion chromatography, and fast protein liquid chromatography.

Conjugation Chemistry

In some aspects, a polynucleic acid molecule B is conjugated to a binding moiety. In some aspects, a polynucleic acid molecule B is conjugated to a binding moiety in a formula A-X-B (X is a linker conjugating A and B). In some instances, the binding moiety comprises amino acids, peptides, polypeptides, proteins, antibodies, antigens, toxins, hormones, lipids, nucleotides, nucleosides, sugars, carbohydrates, polymers such as polyethylene glycol and polypropylene glycol, as well as analogs or derivatives of all of these classes of substances. Additional examples of binding moiety also include steroids, such as cholesterol, phospholipids, di- and triacylglycerols, fatty acids, hydrocarbons (e.g., saturated, unsaturated, or contains substitutions), enzyme substrates, biotin, digoxigenin, and polysaccharides. In some instances, the binding moiety is an antibody or antigen binding fragment thereof. In some instances, the polynucleic acid molecule is further conjugated to a polymer, and optionally an endosomolytic moiety.

In some aspects, the polynucleic acid molecule is conjugated to the binding moiety by a chemical ligation process. In some instances, the polynucleic acid molecule is conjugated to the binding moiety by a native ligation. In some instances, the conjugation is as described in: Dawson, et al. "Synthesis of proteins by native chemical ligation," *Science* 1994, 266, 776-779; Dawson, et al. "Modulation of Reactivity in Native Chemical Ligation through the Use of Thiol Additives," *J. Am. Chem. Soc.* 1997, 119, 4325-4329; Hackeng, et al. "Protein synthesis by native chemical ligation: Expanded scope by using straightforward methodology.," *Proc. Natl. Acad. Sci. USA* 1999, 96, 10068-10073; or Wu, et al. "Building complex glycopeptides: Development of a cysteine-free native chemical ligation protocol," *Angew. Chem. Int. Ed.* 2006, 45, 4116-4125. In some instances, the conjugation is as described in U.S. Pat. No. 8,936,910. In some aspects, the polynucleic acid molecule is conjugated to the binding moiety either site-specifically or non-specifically via native ligation chemistry.

In some instances, the polynucleic acid molecule is conjugated to the binding moiety by a site-directed method utilizing a "traceless" coupling technology (Philochem). In some instances, the "traceless" coupling technology utilizes an N-terminal 1,2-aminothiol group on the binding moiety which is then conjugate with a polynucleic acid molecule containing an aldehyde group. (see Casi et al., "Site-specific traceless coupling of potent cytotoxic drugs to recombinant antibodies for pharmacodelivery," *JACS* 134 (13): 5887-5892 (2012))

In some instances, the polynucleic acid molecule is conjugated to the binding moiety by a site-directed method utilizing an unnatural amino acid incorporated into the binding moiety. In some instances, the unnatural amino acid comprises p-acetylphenylalanine (pAcPhe). In some instances, the keto group of pAcPhe is selectively coupled to an alkoxy-amine derivatived conjugating moiety to form an oxime bond. (see Axup et al., "Synthesis of site-specific antibody-drug conjugates using unnatural amino acids," *PNAS* 109 (40): 16101-16106 (2012)).

In some instances, the polynucleic acid molecule is conjugated to the binding moiety by a site-directed method utilizing an enzyme-catalyzed process. In some instances, the site-directed method utilizes SMARTag™ technology (Catalent, Inc.). In some instances, the SMARTag™ technology comprises generation of a formylglycine (FGly) residue from cysteine by formylglycine-generating enzyme (FGE) through an oxidation process under the presence of an aldehyde tag and the subsequent conjugation of FGly to an alkylhydraine-functionalized polynucleic acid molecule via hydrazino-Pictet-Spengler (HIPS) ligation. (see Wu et al., "Site-specific chemical modification of recombinant proteins produced in mammalian cells by using the genetically encoded aldehyde tag," *PNAS* 106 (9): 3000-3005 (2009); Agarwal, et al., "A Pictet-Spengler ligation for protein chemical modification," *PNAS* 110 (1): 46-51 (2013))

In some instances, the enzyme-catalyzed process comprises microbial transglutaminase (mTG). In some cases, the polynucleic acid molecule is conjugated to the binding moiety utilizing a microbial transglutaminase-catalyzed process. In some instances, mTG catalyzes the formation of a covalent bond between the amide side chain of a glutamine within the recognition sequence and a primary amine of a functionalized polynucleic acid molecule. In some instances, mTG is produced from *Streptomyces* mobarensis. (see Strop et al., "Location matters: site of conjugation modulates stability and pharmacokinetics of antibody drug conjugates," *Chemistry and Biology* 20 (2) 161-167 (2013))

In some instances, the polynucleic acid molecule is conjugated to the binding moiety by a method as described in PCT Publication No. WO2014/140317, which utilizes a sequence-specific transpeptidase.

In some instances, the polynucleic acid molecule is conjugated to the binding moiety by a method as described in U.S. Patent Publication Nos. 2015/0105539 and 2015/0105540.

Polymer Conjugating Moiety

In some aspects, a polymer moiety C is further conjugated to a polynucleic acid molecule described herein, a binding moiety described herein, or in combinations thereof. In some instances, a polymer moiety C is conjugated a polynucleic acid molecule in a formula A-$X_1$-B-$X_2$-C($X_1$, $X_2$ as two linkers conjugating A and B, B and C, respectively). In some cases, a polymer moiety C is conjugated to a binding moiety. In other cases, a polymer moiety C is conjugated to a polynucleic acid molecule-binding moiety molecule. In additional cases, a polymer moiety C is conjugated, as illustrated supra.

In some instances, the polymer moiety C is a natural or synthetic polymer, consisting of long chains of branched or unbranched monomers, and/or cross-linked network of monomers in two or three dimensions. In some instances, the polymer moiety C includes a polysaccharide, lignin, rubber, or polyalkylen oxide (e.g., polyethylene glycol). In some instances, the at least one polymer moiety C includes, but is not limited to, alpha-, omega-dihydroxylpolyethyleneglycol, biodegradable lactone-based polymer, e.g. polyacrylic acid, polylactide acid (PLA), poly (glycolic acid) (PGA), polypropylene, polystyrene, polyolefin, polyamide, polycyanoacrylate, polyimide, polyethylene terephthalate (also known as poly (ethylene terephthalate), PET, PETG, or PETE), polytetramethylene glycol (PTG), or polyurethane as well as mixtures thereof. As used herein, a mixture refers to the use of different polymers within the same compound as well as in reference to block copolymers. In some cases, block copolymers are polymers wherein at least one section of a polymer is build up from monomers of another polymer. In some instances, the polymer moiety C comprises polyalkylene oxide. In some instances, the polymer moiety C comprises PEG. In some instances, the polymer moiety C comprises polyethylene imide (PEI) or hydroxy ethyl starch (HES).

In some instances, C is a PEG moiety. In some instances, the PEG moiety is conjugated at the 5' terminus of the polynucleic acid molecule while the binding moiety is conjugated at the 3' terminus of the polynucleic acid molecule. In some instances, the PEG moiety is conjugated at the 3' terminus of the polynucleic acid molecule while the binding moiety is conjugated at the 5' terminus of the polynucleic acid molecule. In some instances, the PEG moiety is conjugated to an internal site of the polynucleic acid molecule. In some instances, the PEG moiety, the binding moiety, or a combination thereof, are conjugated to an internal site of the polynucleic acid molecule. In some instances, the conjugation is a direct conjugation. In some instances, the conjugation is via native ligation.

In some aspects, the polyalkylene oxide (e.g., PEG) is a polydisperse or monodisperse compound. In some instances, poly disperse material comprises disperse distribution of different molecular weight of the material, characterized by mean weight (weight average) size and dispersity. In some instances, the monodisperse PEG comprises one size of molecules. In some aspects, C is poly- or monodispersed polyalkylene oxide (e.g., PEG) and the indicated molecular weight represents an average of the molecular weight of the polyalkylene oxide, e.g., PEG, molecules.

In some aspects, the molecular weight of the polyalkylene oxide (e.g., PEG) is about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da.

In some aspects, C is polyalkylene oxide (e.g., PEG) and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some aspects, C is PEG and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some instances, the molecular weight of C is about 200 Da. In some instances, the molecular weight of C is about 300 Da. In some instances, the molecular weight of C is about 400 Da. In some instances, the molecular weight of C is about 500 Da. In some instances, the molecular weight of C is about 600 Da. In some instances, the molecular weight of C is about 700 Da. In some instances, the molecular weight of C is about 800 Da. In some instances, the molecular weight of C is about 900 Da. In some instances, the molecular weight of C is about 1000 Da. In some instances, the molecular weight of C is about 1100 Da. In some instances, the molecular weight of C is about 1200 Da. In some instances, the molecular weight of C is about 1300 Da. In some instances, the molecular weight of C is about 1400 Da. In some instances, the molecular weight of C is about 1450 Da. In some instances, the molecular weight of C is about 1500 Da. In some instances, the molecular weight of C is about 1600 Da. In some instances, the molecular weight of C is about 1700 Da. In some instances, the molecular weight of C is about 1800 Da. In some instances, the molecular weight of C is about 1900 Da. In some instances, the molecular weight of C is about 2000 Da. In some instances, the molecular weight of C is about 2100 Da. In some instances, the molecular weight of C is about 2200 Da. In some instances, the molecular weight of C is about 2300 Da. In some instances, the molecular weight of C is about 2400 Da. In some instances, the molecular weight of C is about 2500 Da. In some instances, the molecular weight of C is about 2600 Da. In some instances, the molecular weight of C is about 2700 Da. In some instances, the molecular weight of C is about 2800 Da. In some instances, the molecular weight of C is about 2900 Da. In some instances, the molecular weight of C is about 3000 Da. In some instances, the molecular weight of C is about 3250 Da. In some instances, the molecular weight of C is about 3350 Da. In some instances, the molecular weight of C is about 3500 Da. In some instances, the molecular weight of C is about 3750 Da. In some instances, the molecular weight of C is about 4000 Da. In some instances, the molecular weight of C is about 4250 Da. In some instances, the molecular weight of C is about 4500 Da. In some instances, the molecular weight of C is about 4600 Da. In some instances, the molecular weight of C is about 4750 Da. In some instances, the molecular weight of C is about 5000 Da. In some instances, the molecular weight of C is about 5500 Da. In some instances, the molecular weight of C is about 6000 Da. In some instances, the molecular weight of C is about 6500 Da. In some instances, the molecular weight of C is about 7000 Da. In some instances, the molecular weight of C is about 7500 Da. In some instances, the molecular weight of C is about 8000 Da. In some instances, the molecular weight of C is about 10,000 Da. In some instances, the molecular weight of C is about 12,000 Da. In some instances, the molecular weight of C is about 20,000 Da. In some instances, the molecular weight of C is about 35,000 Da. In some instances, the molecular weight of C is about 40,000 Da. In some instances, the molecular weight of C is about 50,000 Da. In some instances, the molecular weight of C is about 60,000 Da. In some instances, the molecular weight of C is about 100,000 Da.

In some aspects, the polyalkylene oxide (e.g., PEG) comprises discrete ethylene oxide units (e.g., four to about 48 ethylene oxide units). In some instances, the polyalkylene oxide comprising the discrete ethylene oxide units is a linear chain. In other cases, the polyalkylene oxide comprising the discrete ethylene oxide units is a branched chain.

In some instances, the polymer moiety C is a polyalkylene oxide (e.g., PEG) comprising discrete ethylene oxide units. In some cases, the polymer moiety C comprises between about 4 and about 48 ethylene oxide units. In some cases, the polymer moiety C comprises about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, or about 48 ethylene oxide units.

In some instances, the polymer moiety C is a discrete PEG comprising, e.g., between about 4 and about 48 ethylene oxide units. In some cases, the polymer moiety C is a discrete PEG comprising, e.g., about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, or about 48 ethylene oxide units. In some cases, the polymer moiety C is a discrete PEG comprising, e.g., about 4 ethylene oxide units. In some cases, the polymer moiety C is a discrete PEG comprising, e.g., about 5 ethylene oxide units. In some cases, the polymer moiety C is a discrete PEG comprising, e.g., about 6 ethylene oxide units. In some cases, the polymer moiety C is a discrete PEG comprising, e.g., about 7 ethylene oxide units. In some cases, the polymer moiety C is a discrete PEG comprising, e.g., about 8 ethylene oxide units. In some cases, the polymer moiety C is a discrete PEG comprising, e.g., about 9 ethylene oxide units. In some cases, the polymer moiety C is a discrete PEG comprising, e.g., about 10 ethylene oxide units. In some cases, the polymer moiety C is a discrete PEG comprising, e.g., about 11 ethylene oxide units. In some cases, the polymer moiety C is a discrete PEG comprising, e.g., about 12 ethylene oxide units. In some cases, the polymer moiety C is a discrete PEG comprising, e.g., about 13 ethylene oxide units. In some cases, the polymer moiety C is a discrete PEG comprising, e.g., about 14 ethylene oxide units. In some cases, the polymer moiety C is a discrete PEG comprising, e.g., about 15 ethylene oxide units. In some cases, the polymer moiety C is a discrete PEG comprising, e.g., about 16 ethylene oxide units. In some cases, the polymer moiety C is a discrete PEG comprising, e.g., about 17 ethylene oxide units. In some cases, the polymer moiety C is a discrete PEG comprising, e.g., about 18 ethylene oxide units. In some cases, the polymer moiety C is a discrete PEG comprising, e.g., about 19 ethylene oxide units. In some cases, the polymer moiety C is a discrete PEG comprising, e.g., about 20 ethylene oxide units. In some cases, the polymer moiety C is a discrete PEG comprising, e.g., about 21 ethylene oxide units. In some cases, the polymer moiety C is a discrete PEG comprising, e.g., about 22 ethylene oxide units. In some cases, the polymer moiety C is a discrete PEG comprising, e.g., about 23 ethylene oxide units. In some cases, the polymer moiety C is a discrete PEG comprising, e.g., about 24 ethylene oxide units. In some cases, the polymer moiety C is a discrete PEG comprising, e.g., about 25 ethylene oxide units. In some cases, the polymer moiety C is a discrete PEG comprising, e.g., about 26 ethylene oxide units. In some cases, the polymer moiety C is a discrete PEG comprising, e.g., about 27 ethylene oxide units. In some cases, the polymer moiety C is a discrete PEG comprising, e.g., about 28 ethylene oxide units. In some cases, the polymer moiety C is a discrete PEG comprising, e.g., about 29 ethylene oxide units. In some cases, the polymer moiety C is a discrete PEG comprising, e.g., about 30 ethylene oxide units. In some cases, the polymer moiety C is a discrete PEG comprising, e.g., about 31 ethylene oxide units. In some cases, the polymer moiety C is a discrete PEG comprising, e.g., about 32 ethylene oxide units. In some cases, the polymer moiety C is a discrete PEG comprising, e.g., about 33 ethylene oxide units. In some cases, the polymer moiety C is a discrete PEG comprising, e.g., about 34 ethylene oxide units. In some cases, the polymer moiety C is a discrete PEG comprising, e.g., about 35 ethylene oxide units. In some cases, the polymer moiety C is a discrete PEG comprising, e.g., about 36 ethylene oxide units. In some cases, the polymer moiety C is a discrete PEG comprising, e.g., about 37 ethylene oxide units. In some cases, the polymer moiety C is a discrete PEG comprising, e.g., about 38 ethylene oxide units. In some cases, the polymer moiety C is a discrete PEG comprising, e.g., about 39 ethylene oxide units. In some cases, the polymer moiety C is a discrete PEG comprising, e.g., about 40 ethylene oxide units. In some cases, the polymer moiety C is a discrete PEG comprising, e.g., about 41 ethylene oxide units. In some cases, the polymer moiety C is a discrete PEG comprising, e.g., about 42 ethylene oxide units. In some cases, the polymer moiety C is a discrete PEG comprising, e.g., about 43 ethylene oxide units. In some cases, the polymer moiety C is a discrete PEG comprising, e.g., about 44 ethylene oxide units. In some cases, the polymer moiety C is a discrete PEG comprising, e.g., about 45 ethylene oxide units. In some cases, the polymer moiety C is a discrete PEG comprising, e.g., about 46 ethylene oxide units. In some cases, the polymer moiety C is a discrete PEG comprising, e.g., about 47 ethylene oxide units. In some cases, the polymer moiety C is a discrete PEG comprising, e.g., about 48 ethylene oxide units.

In some cases, the polymer moiety C is dPEG® (Quanta Biodesign Ltd).

In some aspects, the polymer moiety C comprises a cationic mucic acid-based polymer (cMAP). In some instances, cMAP comprises one or more subunit of at least one repeating subunit, and the subunit structure is represented as Formula (V):

Formula V

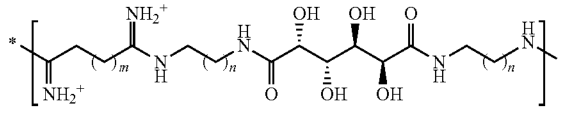

wherein m is independently at each occurrence 1, 2, 3, 4, 5, 6, 7, 8, 9, or 10, preferably 4-6 or 5; and n is independently at each occurrence 1, 2, 3, 4, or 5. In some aspects, m and n are, for example, about 10.

In some instances, cMAP is further conjugated to a PEG moiety, generating a cMAP-PEG copolymer, an mPEG-cMAP-PEGm triblock polymer, or a cMAP-PEG-cMAP triblock polymer. In some instances, the PEG moiety is in a range of from about 500 Da to about 50,000 Da. In some instances, the PEG moiety is in a range of from about 500 Da to about 1000 Da, greater than 1000 Da to about 5000 Da, greater than 5000 Da to about 10,000 Da, greater than 10,000 to about 25,000 Da, greater than 25,000 Da to about 50,000 Da, or any combination of two or more of these ranges.

In some instances, the polymer moiety C is cMAP-PEG copolymer, an mPEG-cMAP-PEGm triblock polymer, or a cMAP-PEG-cMAP triblock polymer. In some cases, the polymer moiety C is cMAP-PEG copolymer. In other cases, the polymer moiety C is an mPEG-cMAP-PEGm triblock polymer. In additional cases, the polymer moiety C is a cMAP-PEG-cMAP triblock polymer.

In some aspects, the polymer moiety C is conjugated to the polynucleic acid molecule, the binding moiety, and optionally to the endosomolytic moiety as illustrated supra.

Endosomolytic or Cell Membrane Penetration Moiety

In some aspects, a molecule of Formula (I): A-$X_1$-B-$X_2$-C, further comprises an additional conjugating moiety. In some instances, the additional conjugating moiety is an endosomolytic moiety and/or a cell membrane penetration moiety. In some cases, the endosomolytic moiety is a cellular compartmental release component, such as a compound capable of releasing from any of the cellular compartments known in the art, such as the endosome, lysosome, endoplasmic reticulum (ER), Golgi apparatus, microtubule, peroxisome, or other vesicular bodies with the cell. In some cases, the endosomolytic moiety comprises an endosomolytic polypeptide, an endosomolytic polymer, an endosomolytic lipid, or an endosomolytic small molecule. In some cases, the endosomolytic moiety comprises an endosomolytic polypeptide. In other cases, the endosomolytic moiety comprises an endosomolytic polymer. In some cases, the cell membrane penetration moiety comprises a cell penetrating peptide (CPP). In other cases, the cell membrane penetration moiety comprises a cell penetrating lipid. In other cases, the cell membrane penetration moiety comprises a cell penetrating small molecule.

Endosomolytic and Cell Membrane Penetration Polypeptides

In some aspects, a molecule of Formula (I): A-$X_1$-B-$X_2$-C, is further conjugated with an endosomolytic polypeptide. In some cases, the endosomolytic polypeptide is a pH-dependent membrane active peptide. In some cases, the endosomolytic polypeptide is an amphipathic polypeptide. In additional cases, the endosomolytic polypeptide is a peptidomimetic. In some instances, the endosomolytic polypeptide comprises INF, melittin, meucin, or their respective derivatives thereof. In some instances, the endosomolytic polypeptide comprises INF or its derivatives thereof. In other cases, the endosomolytic polypeptide comprises melittin or its derivatives thereof. In additional cases, the endosomolytic polypeptide comprises meucin or its derivatives thereof.

In some instances, INF7 is a 24 residue polypeptide those sequence comprises CGIFGEIEELIEEGLENLIDWGNA (SEQ ID NO: 331), or GLFEAIEGFIENGWEGMIDGWYGC (SEQ ID NO: 332). In some instances, INF7 or its derivatives comprise a sequence of: GLFEAIEGFIENGWEGMIWDYGSGSCG (SEQ ID NO: 333), GLFEAIEGFIENGWEGMIDG WYG-(PEG) 6—$NH_2$ (SEQ ID NO: 334), or GLFEAIEGFIENGWEGMIWDYG-SGSC-K (GalNAc) 2 (SEQ ID NO: 335).

In some cases, melittin is a 26 residue polypeptide those sequence comprises CLIGAILKVLATGLPTLISWIKNKRKQ (SEQ ID NO: 336), or GIGAVLKVLTTGLPALISWIKRKRQQ (SEQ ID NO: 337). In some instances, melittin comprises a polypeptide sequence as described in U.S. Pat. No. 8,501,930.

In some instances, meucin is an antimicrobial peptide (AMP) derived from the venom gland of the scorpion Mesobuthus eupeus. In some instances, meucin comprises of meucin-13 those sequence comprises IFGAIAGLLKNIF-$NH_2$ (SEQ ID NO: 338) and meucin-18 those sequence comprises FFGHLFKLATKIIPSLFQ (SEQ ID NO: 339).

In some instances, the endosomolytic polypeptide comprises a polypeptide in which its sequence is at least 50%, 60%, 70%, 80%, 90%, 95%, or 99% sequence identity to INF7 or its derivatives thereof, melittin or its derivatives thereof, or meucin or its derivatives thereof. In some instances, the endosomolytic moiety comprises INF7 or its derivatives thereof, melittin or its derivatives thereof, or meucin or its derivatives thereof.

In some instances, the endosomolytic moiety is INF7 or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 331-335. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 331. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 332-335. In some cases, the endosomolytic moiety comprises SEQ ID NO: 331. In some cases, the endosomolytic moiety comprises SEQ ID NOs: 332-335. In some cases, the endosomolytic moiety consists of SEQ ID NO: 331. In some cases, the endosomolytic moiety consists of SEQ ID NOs: 332-335

In some instances, the endosomolytic moiety is melittin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 336 or 337. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 336. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 337. In some cases, the endosomolytic moiety comprises SEQ ID NO: 286. In some cases, the endosomolytic moiety comprises SEQ ID NO: 337. In some cases, the endosomolytic moiety consists of SEQ ID NO: 336. In some cases, the endosomolytic moiety consists of SEQ ID NO: 337.

In some instances, the endosomolytic moiety is meucin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 338 or 339. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 338. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 339. In some cases, the endosomolytic moiety comprises SEQ ID NO: 338. In some cases, the endosomolytic moiety comprises SEQ ID NO: 339. In some cases, the endosomolytic moiety consists of SEQ ID NO: 338. In some cases, the endosomolytic moiety consists of SEQ ID NO: 339. In some instances, the endosomolytic moiety comprises a sequence as illustrated in Table 8.

TABLE 8

| NAME | ORIGIN | AMINO ACID SEQUENCE | SEQ ID NO: | TYPE |
|---|---|---|---|---|
| Pep-1 | NLS from Simian Virus 40 large antigen and Reverse transcriptase of HIV | KETWWETWWTEWSQPKKK RKV | 340 | Primary amphipathic |
| pVEC | VE-cadherin | LLIILRRRRIRKQAHAHSK | 341 | Primary amphipathic |
| VT5 | Synthetic peptide | DPKGDPKGVTVTVTVTVTG KGDPKPD | 342 | β-sheet amphipathic |
| C105Y | 1-antitrypsin | CSIPPEVKFNKPFVYLI | 343 | — |
| Transportan | Galanin and mastoparan | GWTLNSAGYLLGKINLKAL AALAKKIL | 344 | Primary amphipathic |
| TP10 | Galanin and mastoparan | AGYLLGKINLKALAALAKKI L | 345 | Primary amphipathic |
| MPG | A hydrophobic domain from the fusion sequence of HIV gp41 and NLS of SV40 T antigen | GALFLGFLGAAGSTMGA | 346 | β-sheet amphipathic |
| gH625 | Glycoprotein gH of HSV type 1 | HGLASTLTRWAHYNALIRA F | 347 | Second ary amphipathic α-helical |
| CADY | PPTG1 peptide | GLWRALWRLLRSLWRLLW RA | 348 | Secondary amphipathic α-helical |
| GALA | Synthetic peptide | WEAALAEALAEALAEHLAE ALAEALEALAA | 349 | Secondary amphipathic α-helical |
| INF | Influenza HA2 fusion peptide | GLFEAIEGFIENGWEGMIDG WYGC | 350 | Secondary amphipathic α-helical/ pH-dependent membrane active peptide |
| HA2E5-TAT | Influenza HA2 subunit of influenza virus X31 strain fusion peptide | GLFGAIAGFTENGWEGMIDG WYG | 351 | Secondary amphipathic α-helical/ pH-dependent membrane active peptide |
| HA2-penetratin | Influenza HA2 subunit of influenza virus X31 strain fusion peptide | GLFGAIAGFTENGWEGMIDG RQIKIWFQNRRMKW KK-amide | 352 | pH-dependent membrane active peptide |
| HA-K4 | Influenza HA2 subunit of influenza virus X31 strain fusion peptide | GLFGAIAGFTENGWEGMIDG -SSKKKK | 353 | pH-dependent membrane active peptide |
| HA2E4 | Influenza HA2 subunit of influenza virus X31 strain fusion peptide | GLFEAIAGFIENGWEGMIDG GGYC | 354 | pH-dependent membrane active peptide |
| H5WYG | HA2 analogue | GLFHAIAHFIHGGWH GLIHGWYG | 355 | pH-dependent membrane active peptide |
| GALA-INF3-(PEG)6-NH | INF3 fusion peptide | GLFEAIEGFIENGWEGLAEA LAEALEALAA-(PEG)6-NH2 | 356 | pH-dependent membrane active peptide |
| CM18-TAT11 | Cecropin-A-Melittin$_{2-12}$ ($CM_{18}$) fusion peptide | KWKLFKKIGAVLKVLTTG-YGRKKRRQRRR | 357 | pH-dependent membrane active peptide |

In some cases, the endosomolytic moiety comprises a Bak BH3 polypeptide which induces apoptosis through antagonization of suppressor targets such as Bcl-2 and/or Bcl-XL. In some instances, the endosomolytic moiety comprises a Bak BH3 polypeptide described in Albarran, et al., "Efficient intracellular delivery of a pro-apoptotic peptide with a pH-responsive carrier," *Reactive & Functional Polymers* 71:261-265 (2011).

In some instances, the endosomolytic moiety comprises a polypeptide (e.g., a cell-penetrating polypeptide) as described in PCT Publication Nos. WO2013/166155 or WO2015/069587.

Endosomolytic Lipids

In some aspects, the endosomolytic moiety is a lipid (e.g., a fusogenic lipid). In some aspects, a molecule of Formula (I): A-$X_1$-B-$X_2$-C, is further conjugated with an endosomolytic lipid (e.g., fusogenic lipid). Exemplary fusogenic lipids include 1,2-dileoyl-sn-3-phosphoethanolamine (DOPE), phosphatidylethanolamine (POPE), palmitoyloleoylphosphatidylcholine (POPC), (6Z,9Z,28Z,31Z)-heptatriaconta-6,9,28,31-tetraen-19-ol (Di-Lin), N-methyl (2,2-di((9Z,12Z)-octadeca-9,12-dienyl)-1,3-dioxolan-4-y1) methanamine (DLin-k-DMA) and N-methyl-2-(2,2-di((9Z,12Z)-octadeca-9,12-dienyl)-1,3-dioxolan-4-yl) ethanamine (XTC).

In some instances, an endosomolytic moiety is a lipid (e.g., a fusogenic lipid) described in PCT Publication No. WO09/126,933.

Endosomolytic Small Molecules

In some aspects, the endosomolytic moiety is a small molecule. In some aspects, a molecule of Formula (I): A-$X_1$-B-$X_2$-C, is further conjugated with an endosomolytic small molecule. Exemplary small molecules suitable as endosomolytic moieties include, but are not limited to, quinine, chloroquine, hydroxychloroquines, amodiaquins (carnoquines), amopyroquines, primaquines, mefloquines, nivaquines, halofantrines, quinone imines, or a combination thereof. In some instances, quinoline endosomolytic moieties include, but are not limited to, 7-chloro-4-(4-diethylamino-1-methylbutyl-amino) quinoline (chloroquine); 7-chloro-4-(4-ethyl-(2-hydroxyethyl)-amino-1-methylbutyl-amino) quinoline (hydroxychloroquine); 7-fluoro-4-(4-diethylamino-1-methylbutyl-amino) quinoline; 4-(4-diethylamino-1-methylbutylamino) quinoline; 7-hydroxy-4-(4-diethyl-amino-1-methylbutylamino) quinoline; 7-chloro-4-(4-diethylamino-1-butylamino) quinoline (desmethylchloroquine); 7-fluoro-4-(4-diethylamino-1-butylamino) quinoline); 4-(4-diethyl-amino-1-butylamino) quinoline; 7-hydroxy-4-(4-diethylamino-1-butylamino) quinoline; 7-chloro-4-(1-carboxy-4-diethylamino-1-butylamino) quinoline; 7-fluoro-4-(1-carboxy-4-diethyl-amino-1-butylamino) quinoline; 4-(1-carboxy-4-diethylamino-1-butylamino) quinoline; 7-hydroxy-4-(1-carboxy-4-diethylamino-1-butylamino) quinoline; 7-chloro-4-(1-carboxy-4-diethylamino-1-methylbutylamino) quinoline; 7-fluoro-4-(1-carboxy-4-diethyl-amino-1-methylbutylamino) quinoline; 4-(1-carboxy-4-diethylamino-1-methylbutylamino) quinoline; 7-hydroxy-4-(1-carboxy-4-diethylamino-1-methylbutylamino) quinoline; 7-fluoro-4-(4-ethyl-(2-hydroxyethyl)-amino-1-methylbutylamino) quinoline; 4-(4-ethyl-(2-hydroxy-ethyl)-amino-1-methylbutylamino-) quinoline; 7-hydroxy-4-(4-ethyl-(2-hydroxyethyl)-amino-1-methylbutylamino) quinoline; hydroxychloroquine phosphate; 7-chloro-4-(4-ethyl-(2-hydroxyethyl-1)-amino-1-butylamino) quinoline (desmethylhydroxychloroquine); 7-fluoro-4-(4-ethyl-(2-hydroxyetbyl)-amino-1-butylamino) quinoline; 4-(4-ethyl-(2-hydroxyethyl)-amino-1-butylamino) quinoline; 7-hydroxy-4-(4-ethyl-(2-hydroxyethyl)-amino-1-butylamino) quinoline; 7-chloro-4-(1-carboxy-4-ethyl-(2-hydroxyethyl)-amino-1-butylamino) quinoline; 7-fluoro-4-(1-carboxy-4-ethyl-(2-hydroxyethyl)-amino-1-butylamino) quinoline; 4-(1-carboxy-4-ethyl-(2-hydroxyethyl)-amino-1-butylamino) quinoline; 7-hydroxy-4-(1-carboxy-4-ethyl-(2-hydroxyethyl)-amino-1-butylamino) quinoline; 7-chloro-4-(1-carboxy-4-ethyl-(2-hydroxyethyl)-amino-1-methylbutylamino) quinoline; 7-fluoro-4-(1-carboxy-4-ethyl-(2-hydroxyethyl)-amino-1-methylbutylamino) quinoline; 4-(1-carboxy-4-ethyl-(2-hydroxyethyl)-amino-1-methylbutylamino) quinoline; 7-hydroxy-4-(1-carboxy-4-ethyl-(2-hydroxyethyl)-amino-1-methylbutylamino) quinoline; 8-[(4-aminopentyl)amino-6-methoxy dihydrochloride quinoline; 1-acetyl-1,2,3,4-tetrahydroquinoline; 8-[(4-aminopentyl)amino]-6-methoxyquinoline dihydrochloride; 1-butyryl-1,2,3,4-tetrahydroquinoline; 3-chloro-4-(4-hydroxy-alpha,alpha'-bis(2-methyl-1-pyrrolidinyl)-2,5-xylidinoquinoline, 4-[(4-diethyl-amino)-1-methylbutyl-amino]-6-methoxyquinoline; 3-fluoro-4-(4-hydroxy-alpha, alpha'-bis(2-methyl-1-pyrrolidinyl)-2,5-xylidinoquinoline, 4-[(4-diethylamino)-1-methylbutyl-amino]-6-methoxyquinoline; 4-(4-hydroxy-alpha, alpha'-bis(2-methyl-1-pyrrolidinyl)-2,5-xylidinoquinoline; 4-[(4-diethylamino)-1-methylbutyl-amino]-6-methoxyquinoline; 3,4-dihydro-1-(2H)-quinolinecarboxyaldehyde; 1,1'-pentamethylene diquinoleinium diiodide; 8-quinolinol sulfate and amino, aldehyde, carboxylic, hydroxyl, halogen, keto, sulfhydryl and vinyl derivatives or analogs thereof. In some instances, an endosomolytic moiety is a small molecule described in Naisbitt et al (1997, *J Pharmacol Exp Therapy* 280:884-893) and in U.S. Pat. No. 5,736,557.

Cell Penetrating Polypeptide (CPP)

In some aspects, cell penetrating polypeptide comprises positively charged short peptides with 5-30 amino acids. In some aspects, cell penetrating polypeptide comprises arginine or lysine rich amino acid sequences. In some aspects, cell penetrating polypeptide includes any polypeptide or combination thereof listed in Table 9.

TABLE 9

| PEPTIDE | SEQUENCE | SEQ ID NO |
|---|---|---|
| Antennapedia Penetratin (43-58) | RQIKIWFQNRRMKWKK | 358 |
| HIV-1 TAT protein (48-60) | GRKKRRQRRRPPQ | 359 |
| pVEC Cadherin (615-632) | LLIILRRRIRKQAHAHSK | 360 |
| Transportan Galanine/Mastoparan | GWTLNSAGYLLGKINLKALAALAKKIL | 361 |
| MPG HIV-gp41/SV40 T-antigen | GALFLGFLGAAGSTMGAWSQPKKKRKV | 362 |

TABLE 9-continued

| PEPTIDE | SEQUENCE | SEQ ID NO |
|---|---|---|
| Pep-1 HIV-reverse transcriptase/SV40 T-antigen | KETWWETWWTEWSQPKKKRKV | 363 |
| Polyarginines | R(n); 6 < n < 12 | 364 |
| MAP | KLALKLALKALKAALKLA | 365 |
| R6W3 | RRWWRRWRR | 366 |
| NLS | CGYGPKKKRKVGG | 367 |
| 8-lysines | KKKKKKKK | 368 |
| ARF (1-22) | MVRRFLVTLRIRRACGPPRVRV | 369 |
| Azurin-p28 | LSTAADMQGVVTDGMASGLDKDYLKPDD | 370 |

Linkers

In some aspects, a linker described herein is a cleavable linker or a non-cleavable linker. In some instances, the linker is a cleavable linker. In other instances, the linker is a non-cleavable linker.

In some cases, the linker is a non-polymeric linker. A non-polymeric linker refers to a linker that does not contain a repeating unit of monomers generated by a polymerization process. Exemplary non-polymeric linkers include, but are not limited to, $C_1$-$C_6$ alkyl group (e.g., a $C_5$, $C_4$, $C_3$, $C_2$, or $C_1$ alkyl group), homobifunctional cross linkers, heterobifunctional cross linkers, peptide linkers, traceless linkers, self-immolative linkers, maleimide-based linkers, or combinations thereof. In some cases, the non-polymeric linker comprises a $C_1$-$C_6$ alkyl group (e.g., a $C_5$, $C_4$, $C_3$, $C_2$, or $C_1$ alkyl group), a homobifunctional cross linker, a heterobifunctional cross linker, a peptide linker, a traceless linker, a self-immolative linker, a maleimide-based linker, or a combination thereof. In additional cases, the non-polymeric linker does not comprise more than two of the same type of linkers, e.g., more than two homobifunctional cross linkers, or more than two peptide linkers. In further cases, the non-polymeric linker optionally comprises one or more reactive functional groups.

In some instances, the non-polymeric linker does not encompass a polymer that is described above. In some instances, the non-polymeric linker does not encompass a polymer encompassed by the polymer moiety C. In some cases, the non-polymeric linker does not encompass a polyalkylene oxide (e.g., PEG). In some cases, the non-polymeric linker does not encompass a PEG.

In some instances, the linker comprises a homobifunctional linker. Exemplary homobifunctional linkers include, but are not limited to, Lomant's reagent dithiobis (succinimidylpropionate) DSP, 3'3'-dithiobis (sulfosuccinimidyl proprionate (DTSSP), disuccinimidyl suberate (DSS), bis (sulfosuccinimidyl) suberate (BS), disuccinimidyl tartrate (DST), disulfosuccinimidyl tartrate (sulfo DST), ethylene glycobis (succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio) propionamido) butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[B-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis (iodoacetamide), or N,N'-hexamethylene-bis (iodoacetamide).

In some aspects, the linker comprises a heterobifunctional linker. Exemplary heterobifunctional linker include, but are not limited to, amine-reactive and sulfhydryl cross-linkers such as N-succinimidyl 3-(2-pyridyldithio) propionate (sPDP), long-chain N-succinimidyl 3-(2-pyridyldithio) propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio) toluene (SMPT), sulfosuccinimidyl-6-[α-methyl-α-(2-pyridyldithio) toluamidoJhexanoate (sulfo-LC-sMPT), succinimidy]-4-(N-maleimidomethyl) cyclohexane-1-carboxylate (sMCC), sulfosuccinimidyl-4-(N-maleimidomethyl) cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl (4-jodoacteyl)aminobenzoate (sIAB), sulfosuccinimidyl (4-iodoacteyl)aminobenzoate (sulfo-sIAB), succinimidyl-4-(p-maleimidophenyl) butyrate (sMPB), sulfosuccinimidyl-4-(p-maleimidophenyl) butyrate (sulfo-sMPB), N-(Y-maleimidobutyryloxy) succinimide ester (GMBs), N-(y-maleimidobutyryloxy) sulfosuccinimide ester (sulfo-GMBs), succinimidyl 6-((iodoacetyl)amino) hexanoate (sIAX), succinimidyl 6~ [6-(((iodoacetyl)amino) hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 ($M2C_2H$), 3-(2-pyridyldithio) propionyl hydrazide (PDPH), amine-reactive and photoreactive cross-linkers such as N-hydroxysuccinimidyl-4-azidosalicylic acid (NHS-AsA), N-hydroxysulfosuccinimidyl-4-azidosalicylic acid (sulfo-NHs-AsA), sulfosuccinimidyl-(4-azidosalicylamido) hexanoate (sulfo-NHs-LC-AsA), sulfosuccinimidyl-2-(p-azidosalicylamido) ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido- 2'-nitrophenylamino) hexanoate (sANPAH), sulfosuccinimidyl-6-(4'-azido-2'-nitrophenylamino) hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4 (4-azidophenyl) 1,3'-dithiopropionate (sADP), N-sulfosuccinimidyl (4-azidophenyl)-1,3'-dithiopropionate (sulfo-sADP), sulfosuccinimidyl 4-(p-azidophenyl) butyrate (sulfo-sAPB), sulfosuccinimidyl 2-(7-azido-4-methylcoumarin-3-acetamide)ethyl-1,3'-dithiopropionate (SAED), sulfosuccinimidyl 7-azido-4-methylcoumain-3-acetate (sulfo-sAMCA), p-nitrophenyl diazopyruvate (pNPDP), p-nitrophenyl-2-diazo-3,3,3-trifluoropropionate (PNP-DTP), sulfhydryl-reactive and photoreactive cross-linkers such as1-(p-Azidosalicylamido)-4-(iodoacetamido) butane (AsIB), N-[4-(p-azidosalicylamido)butyl]-3'-(2'-pyridyldithio) propionamide (APDP), benzophenone-4-iodoacetamide, benzophenone-4-maleimide carbonyl-reactive and photoreactive cross-linkers such as p-azidobenzoyl hydrazide (ABH), carboxylate-reactive and photoreactive cross-linkers such as 4-(p-azidosalicylamido) butylamine (AsBA), and arginine-reactive and photoreactive cross-linkers such as p-azidophenyl glyoxal (APG).

In some instances, the linker comprises a reactive functional group. In some cases, the reactive functional group comprises a nucleophilic group that is reactive to an electrophilic group present on a binding moiety. Exemplary electrophilic groups include carbonyl groups—such as aldehyde, ketone, carboxylic acid, ester, amide, enone, acyl halide or acid anhydride. In some aspects, the reactive functional group is aldehyde. Exemplary nucleophilic groups include hydrazide, oxime, amino, hydrazine, thiosemicarbazone, hydrazine carboxylate, and arylhydrazide.

In some aspects, the linker comprises a maleimide group. In some instances, the malcimide group is also referred to as a maleimide spacer. In some instances, the maleimide group further encompasses a caproic acid, forming maleimidocaproyl (mc). In some cases, the linker comprises maleimidocaproyl (mc). In some cases, the linker is maleimidocaproyl (mc). In other instances, the maleimide group comprises a maleimidomethyl group, such as succinimidyl-4~ (N-maleimidomethyl)cyclohexane-1-carboxylate (sMCC) or sulfosuccinimidyl-4-(N-maleimidomethyl) cyclohexane-1-carboxylate (sulfo-sMCC) described above.

In some aspects, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon et al., "Self-hydrolyzing maleimides improve the stability and pharmacological properties of antibody-drug conjugates," *Nat. Biotechnol.* 32 (10): 1059-1062 (2014). In some instances, the linker comprises a self-stabilizing maleimide. In some instances, the linker is a self-stabilizing maleimide.

In some aspects, the linker comprises a peptide moiety. In some instances, the peptide moiety comprises at least 2, 3, 4, 5, or 6 more amino acid residues. In some instances, the peptide moiety comprises at most 2, 3, 4, 5, 6, 7, or 8 amino acid residues. In some instances, the peptide moiety comprises about 2, about 3, about 4, about 5, or about 6 amino acid residues. In some instances, the peptide moiety is a cleavable peptide moiety (e.g., either enzymatically or chemically). In some instances, the peptide moiety is a non-cleavable peptide moiety. In some instances, the peptide moiety comprises Val-Cit (valine-citrulline), Gly-Gly-Phe-Gly (SEQ ID NO: 403), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 404), or Gly-Phe-Leu-Gly (SEQ ID NO: 405). In some instances, the linker comprises a peptide moiety such as: Val-Cit (valine-citrulline), Gly-Gly-Phe-Gly (SEQ ID NO: 403), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 404), or Gly-Phe-Leu-Gly (SEQ ID NO: 405). In some cases, the linker comprises Val-Cit. In some cases, the linker is Val-Cit.

In some aspects, the linker comprises a benzoic acid group, or its derivatives thereof. In some instances, the benzoic acid group or its derivatives thereof comprise paraaminobenzoic acid (PABA). In some instances, the benzoic acid group or its derivatives thereof comprise gamma-aminobutyric acid (GABA).

In some aspects, the linker comprises one or more of a maleimide group, a peptide moiety, and/or a benzoic acid group, in any combination. In some aspects, the linker comprises a combination of a maleimide group, a peptide moiety, and/or a benzoic acid group. In some instances, the maleimide group is maleimidocaproyl (mc). In some instances, the peptide group is val-cit. In some instances, the benzoic acid group is PABA. In some instances, the linker comprises a mc-val-cit group. In some cases, the linker comprises a val-cit-PABA group. In additional cases, the linker comprises a mc-val-cit-PABA group.

In some aspects, the linker is a self-immolative linker or a self-elimination linker. In some cases, the linker is a self-immolative linker. In other cases, the linker is a self-elimination linker (e.g., a cyclization self-elimination linker). In some instances, the linker comprises a linker described in U.S. Pat. No. 9,089,614 or PCT Publication NO. WO2015038426.

In some aspects, the linker is a dendritic type linker. In some instances, the dendritic type linker comprises a branching, multifunctional linker moiety. In some instances, the dendritic type linker is used to increase the molar ratio of polynucleotide B to the binding moiety A. In some instances, the dendritic type linker comprises PAMAM dendrimers.

In some aspects, the linker is a traceless linker or a linker in which after cleavage does not leave behind a linker moiety (e.g., an atom or a linker group) to a binding moiety A, a polynucleotide B, a polymer C, or an endosomolytic moiety D. Exemplary traceless linkers include, but are not limited to, germanium linkers, silicium linkers, sulfur linkers, selenium linkers, nitrogen linkers, phosphorus linkers, boron linkers, chromium linkers, or phenylhydrazide linker. In some cases, the linker is a traceless aryl-triazene linker as described in Hejesen, et al., "A traceless aryl-triazene linker for DNA-directed chemistry," *Org Biomol Chem* 11 (15): 2493-2497 (2013). In some instances, the linker is a traceless linker described in Blaney, et al., "Traceless solid-phase organic synthesis," *Chem. Rev.* 102:2607-2024 (2002). In some instances, a linker is a traceless linker as described in U.S. Pat. No. 6,821,783.

In some instances, the linker is a linker described in U.S. Pat. Nos. 6,884,869; 7,498,298; 8,288,352; 8,609,105; or 8,697,688; U.S. Patent Publication NOs. 2014/0127239; 2013/028919; 2014/286970; 2013/0309256; 2015/037360; or 2014/0294851; or PCT Publication NOs. WO2015057699; WO2014080251; WO2014197854; WO2014145090; or WO2014177042.

In some aspects, $X_1$ and $X_2$ are each independently a bond or a non-polymeric linker. In some instances, $X_1$ and $X_2$ are each independently a bond. In some cases, $X_1$ and $X_2$ are each independently a non-polymeric linker.

In some instances, $X_1$ is a bond or a non-polymeric linker. In some instances, $X_1$ is a bond. In some instances, $X_1$ is a non-polymeric linker. In some instances, the linker is a $C_1$-$C_6$ alkyl group. In some cases, $X_1$ is a $C_1$-$C_6$ alkyl group, such as for example, a $C_5$, $C_4$, $C_3$, $C_2$, or $C_1$ alkyl group. In some cases, the $C_1$-$C_6$ alkyl group is an unsubstituted $C_1$-$C_6$ alkyl group. As used in the context of a linker, and in particular in the context of $X_1$, alkyl means a saturated straight or branched hydrocarbon radical containing up to six carbon atoms. In some instances, $X_1$ includes a homobifunctional linker or a heterobifunctional linker described supra. In some cases, X; includes a heterobifunctional linker. In some cases, $X_1$ includes sMCC. In other instances, $X_1$ includes a heterobifunctional linker optionally conjugated to a $C_1$-$C_6$ alkyl group. In other instances, $X_1$ includes sMCC optionally conjugated to a $C_1$-$C_6$ alkyl group. In additional instances, $X_1$ does not include a homobifunctional linker or a heterobifunctional linker described supra.

In some instances, $X_2$ is a bond or a linker. In some instances, $X_2$ is a bond. In other cases, $X_2$ is a linker. In additional cases, $X_2$ is a non-polymeric linker. In some aspects, $X_2$ is a $C_1$-$C_6$ alkyl group. In some instances, $X_2$ is a homobifunctional linker or a heterobifunctional linker described supra. In some instances, $X_2$ is a homobifunctional linker described supra. In some instances, $X_2$ is a heterobifunctional linker described supra. In some instances, $X_2$ comprises a maleimide group, such as maleimidocaproyl (mc) or a self-stabilizing maleimide group described above. In some instances, $X_2$ comprises a peptide moiety, such as Val-Cit. In some instances, $X_2$ comprises a benzoic acid group, such as PABA. In additional instances, $X_2$ comprises a combination of a maleimide group, a peptide moiety, and/or a benzoic acid group. In additional instances, $X_2$ comprises a me group. In additional instances, $X_2$ comprises a mc-val-cit group. In additional instances, $X_2$ comprises a val-cit-PABA group. In additional instances, $X_2$ comprises a mc-val-cit-PABA group.

Methods of Use

Muscle atrophy refers to a loss of muscle mass and/or to a progressive weakening and degeneration of muscles. In some cases, the loss of muscle mass and/or the progressive weakening and degeneration of muscles occurs due to a high rate of protein degradation, a low rate of protein synthesis, or a combination of both. In some cases, a high rate of muscle protein degradation is due to muscle protein catabolism (i.e., the breakdown of muscle protein in order to use amino acids as substrates for gluconeogenesis).

In one embodiment, muscle atrophy refers to a significant loss in muscle strength. By significant loss in muscle strength is meant a reduction of strength in diseased, injured, or unused muscle tissue in a subject relative to the same muscle tissue in a control subject. In an embodiment, a significant loss in muscle strength is a reduction in strength of at least 10%, at least 15%, at least 20%, at least 25%, at least 30%, at least 35%, at least 40%, at least 45%, at least 50%, or more relative to the same muscle tissue in a control subject. In another embodiment, by significant loss in muscle strength is meant a reduction of strength in unused muscle tissue relative to the muscle strength of the same muscle tissue in the same subject prior to a period of nonuse. In an embodiment, a significant loss in muscle strength is a reduction of at least 10%, at least 15%, at least 20%, at least 25%, at least 30%, at least 35%, at least 40%, at least 45%, at least 50%, or more relative to the muscle strength of the same muscle tissue in the same subject prior to a period of nonuse.

In another embodiment, muscle atrophy refers to a significant loss in muscle mass. By significant loss in muscle mass is meant a reduction of muscle volume in diseased, injured, or unused muscle tissue in a subject relative to the same muscle tissue in a control subject. In an embodiment, a significant loss of muscle volume is at least 10%, at least 15%, at least 20%, at least 25%, at least 30%, at least 35%, at least 40%, at least 45%, at least 50%, or more relative to the same muscle tissue in a control subject. In another embodiment, by significant loss in muscle mass is meant a reduction of muscle volume in unused muscle tissue relative to the muscle volume of the same muscle tissue in the same subject prior to a period of nonuse. In an embodiment, a significant loss in muscle tissue is at least 10%, at least 15%, at least 20%, at least 25%, at least 30%, at least 35%, at least 40%, at least 45%, at least 50%, or more relative to the muscle volume of the same muscle tissue in the same subject prior to a period of nonuse. Muscle volume is optionally measured by evaluating the cross-section area of a muscle such as by Magnetic Resonance Imaging (e.g., by a muscle volume/cross-section area (CSA) MRI method).

In some aspects, described herein is a method of treating muscle atrophy in a subject, which comprises providing polynucleic acid molecule described herein and administering to the subject a therapeutically effective amount of a polynucleic acid molecule described herein or a polynucleic acid molecule conjugate described herein to reduces a quantity of the mRNA transcript of human DUX4. In some embodiments, the polynucleic acid molecule comprises a sense strand and/or an antisense strand, and the antisense strand comprises at least 80%, at least 85%, at least 90%, at least 95%, at least 96%, at least 97%, at least 98%, at least 99% identical to a sequence selected from SEQ ID NOs: 412-420 or 430-438. In some embodiments, the polynucleic acid molecule comprises a sense strand and/or an antisense strand, and the antisense is identical to a sequence selected from SEQ ID NOs: 412-420 or 430-438. In some embodiments, the polynucleic acid molecule comprises a sense strand and/or an antisense strand, and the sense strand comprises at least 80%, at least 85%, at least 90%, at least 95%, at least 96%, at least 97%, at least 98%, at least 99% identical to a sequence selected from SEQ ID NOs: 142, 146, 196, or 201-206. In some embodiments, the polynucleic acid molecule comprises a sense strand and/or an antisense strand, and the sense strand is identical to a sequence selected from SEQ ID NOs: 142, 146, 196, or 201-206.

In some instances, the muscle atrophy is associated with Facioscapulohumeral muscular dystrophy (FSHD). The polynucleic acid moiety mediates RNA interference against the human DUX4 as to modulating muscle atrophy in a subject. In some aspects, expression of one or more marker genes that are affected by DUX4 expression is also altered or modulated (e.g., decreased) by the decreased expression of human DUX4. The marker genes includes, but not limited to, MBD3L2, TRIM43, PRAMEF1, ZSCAN4, KHDCIL, LEUTX, WFDC3, ILVBL, SLC15A2, and SORD. In some aspects, the expression of one or more marker genes is decreased at least 10%, 15%, 20%, 25%, 30%, 35%, 40%, 45%, or 50% compared to untreated cells. In some aspects, the expression of one or more marker genes, as a group or a composite, is decreased at least 10%, 15%, 20%, 25%, 30%, 35%, 40%, 45%, or 50% compared to untreated cells.

In some aspects, described herein is a method of treating muscle atrophy in a subject, which comprises providing an siRNA-antibody conjugate described herein and administering to the subject a therapeutically effective amount of the siRNA-antibody conjugate described herein and reducing the levels of mRNA transcript of human DUX4 in said subject. In some instances, the muscle atrophy is associated with FSHD. The siRNA-antibody conjugate mediates RNA interference against the human DUX4 mRNA as to treat muscle atrophy in the subject, which comprises administering to the subject a therapeutically effective amount of the siRNA-antibody conjugate described herein and reducing the levels of mRNA transcript of human DUX4 in said subject.

In some aspects, described herein is a method of treating muscle atrophy in a subject, which comprises providing a DUX4 siRNA-antibody conjugate (DUX4 siRNA-conjugate or DUX4-AOC) described herein and administering to the subject a therapeutically effective amount of the DUX4 siRNA-antibody conjugate described herein and reducing the levels of mRNA transcript of human DUX4 in said subject. In some instances, the muscle atrophy is associated with FSHD. The DUX4 siRNA-antibody conjugate mediates RNA interference against the human DUX4 mRNA as to treat muscle atrophy in the subject, which comprises administering to the subject a therapeutically effective amount of the DUX4 siRNA-antibody conjugate described herein and reducing the levels of mRNA transcript of human DUX4 in said subject.

In some aspects, described herein is a method of treating FSHD in a subject, which comprises providing a DUX4 siRNA-antibody conjugate (DUX4 siRNA conjugate or DUX4-AOC) described herein and administering to the subject a therapeutically effective amount of the DUX4 siRNA-antibody conjugate described herein and reducing the levels of mRNA transcript of human DUX4 in said subject. In some instances, the FSHD is FSHD type 1 (FSHD1). In some instances, the FSHD is FSHD type 2 (FSHD2). The DUX4 siRNA-antibody conjugate mediates RNA interference against the human DUX4 mRNA as to treat FSHD in the subject, which comprises administering to the subject a therapeutically effective amount of the DUX4 siRNA-conjugate described herein and reducing the levels of mRNA transcript of human DUX4 in said subject. In some aspects, expression levels of one or more marker genes that are affected by DUX4 expression are also altered or modulated by the decreased expression levels of human DUX4. The DUX4 biomarker genes include but are not limited to MBD3L2, TRIM43, PRAMEF1, ZSCAN4, KHDCIL, LEUTX, WFDC3, IL VBL, SLC15A2, and SORD.

In some aspects, described herein is a method of alleviating symptoms in a subject with FSHD, which comprises providing a DUX4 siRNA-antibody conjugate (DUX4-siRNA conjugate or DUX4-AOC) described herein and administering to the subject a therapeutically effective amount of the siRNA conjugate described herein by reducing the levels of mRNA transcript of human DUX4. In some instances, the FSHD is FSHD type 1 (FSHD1). In some instances, the FSHD is FSHD type 2 (FSHD2). In another aspects, described herein is a method of alleviating symptoms in a FSHD patient, which comprises providing an siRNA conjugate described herein and administering to the FSHD patient a therapeutically effective amount of the siRNA conjugate describes herein by reducing the levels of mRNA transcript of human DUX4 or reducing the levels of DUX4 protein.

In some instances, the symptoms of FSHD affect skeletal muscles. The skeletal muscles affected by FSHD include muscles around the eyes and mouth, muscle of the shoulders, muscle of the upper arms, muscle of the lower legs, abdominal muscles and hip muscles. In some instances, the symptoms of FSHD also affects vision and hearing. In some instances, the symptoms of FSHD also affect the function of the heart or lungs. In some instances, the symptoms of FSHD include muscle weakness, muscle atrophy, muscle dystrophy, pain inflammation, contractures, scoliosis, lordosis, hypoventilation, abnormalities of the retina, exposure to keratitis, mild hearing loss, and EMG abnormality.

In some aspects, described herein is a method of improving skeletal muscle functions in a FSHD patient comprising the step of administering to the FSHD patient a therapeutically effective amount of the siRNA conjugate described herein by reducing the levels of mRNA transcript of human DUX4 or reducing the levels of DUX4 protein. In some instances, FSHD is FSHD type 1 (FSHD1). In some instances, FSHD is FSHD type 2. In some aspects, described herein is a method of improving skeletal muscle functions, vision, hearing, heart functions or lung functions in a patient suffering from FSHD comprising the step of administering to the FSHD patient a therapeutically effective amount of the siRNA conjugate described herein by reducing the levels of mRNA transcript of human DUX4 or reducing the levels of DUX4 protein.

In some aspects, described herein is a method of treating FSHD in a subject, which comprises providing an antisense oligonucleotide (ASO) antibody conjugate (ASO conjugate) described herein and administering to the subject a therapeutically effective amount of the ASO-antibody conjugate described herein and reducing the levels of mRNA transcript of human DUX4 in said subject. In some instances, FSHD is FSHD type 1 (FSHD1). In some instances, FSHD is FSHD type 2. The ASO-antibody conjugate mediates RNA interference against the human DUX4 mRNA as to treat FSHD in the subject, which comprises administering to the subject a therapeutically effective amount of the ASO-antibody conjugate described herein and reducing the levels of mRNA transcript of human DUX4 in said subject. In some aspects, expression levels of one or more marker genes that are affected by DUX4 expression is also altered or modulated by the decreased expression levels of human DUX4. The DUX4 biomarker genes include but are not limited to MBD3L2, TRIM43, PRAMEF1, ZSCAN4, KHDCIL, LEUTX, WFDC3, ILVBL, SLC15A2, and SORD.

In some aspects, described herein is a method of treating FSHD in a subject. In some instances, the FSHD subject suffers from FSHD1. In other instances, the FSHD subject suffers from FSHD2. In another embodiment, the FSHD subject has muscle cells abnormally expressing DUX4 protein caused by the genetic and epigenetic molecular changes in the D4Z4 region of the long arm of chromosome 4. The genetic molecular changes in the muscle cells are mutations leading to the contraction of the D4Z4 region containing 1-10 repeats instead of the normal 11 to 100 repeats of chromosome 4 of the FSHD subject. The epigenetic molecular changes in the muscle cells are changes leading to the hypomethylation of the D4Z4 region of chromosome 4 of the FSHD subject. In some instances, the muscle cells are skeletal muscle cells.

Pharmaceutical Formulation

In some aspects, the pharmaceutical formulations described herein are administered to a subject by multiple administration routes, including but not limited to, parenteral (e.g., intravenous, subcutaneous, intramuscular), oral, intranasal, buccal, rectal, or transdermal administration routes. In some instances, the pharmaceutical composition describe herein is formulated for parenteral (e.g., intravenous, subcutaneous, intramuscular, intra-arterial, intraperitoneal, intrathecal, intracerebral, intracerebroventricular, or intracranial) administration. In other instances, the pharmaceutical composition describe herein is formulated for oral administration. In still other instances, the pharmaceutical composition describe herein is formulated for intranasal administration.

In some aspects, the pharmaceutical formulations include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some instances, the pharmaceutical formulation includes multiparticulate formulations. In some instances, the pharmaceutical formulation includes nanoparticle formulations. In some instances, nanoparticles comprise cMAP, cyclodextrin, or lipids. In some cases, nanoparticles comprise solid lipid nanoparticles, polymeric nanoparticles, self-emulsifying nanoparticles, liposomes, microemulsions, or micellar solutions. Additional exemplary nanoparticles include, but are not limited to, paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. In some instances, a nanoparticle is a metal nanoparticle, e.g., a nanoparticle of scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations, alloys or oxides thereof.

In some instances, a nanoparticle includes a core or a core and a shell, as in a core-shell nanoparticle.

In some instances, a nanoparticle is further coated with molecules for attachment of functional elements (e.g., with one or more of a polynucleic acid molecule or binding moiety described herein). In some instances, a coating comprises chondroitin sulfate, dextran sulfate, carboxymethyl dextran, alginic acid, pectin, carragheenan, fucoidan, agaropectin, porphyran, karaya gum, gellan gum, xanthan gum, hyaluronic acids, glucosamine, galactosamine, chitin (or chitosan), polyglutamic acid, polyaspartic acid, lysozyme, cytochrome C, ribonuclease, trypsinogen, chymotrypsinogen, α-chymotrypsin, polylysine, polyarginine, histone, protamine, ovalbumin or dextrin or cyclodextrin. In some instances, a nanoparticle comprises a graphene-coated nanoparticle.

In some cases, a nanoparticle has at least one dimension of less than about 500 nm, 400 nm, 300 nm, 200 nm, or 100 nm.

In some instances, the nanoparticle formulation comprises paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes or quantum dots. In some instances, a polynucleic acid molecule or a binding moiety described herein is conjugated either directly or indirectly to the nanoparticle. In some instances, at least 1, 5, 10, 15, 20, 30, 40, 50, 60, 70, 80, 90, 100 or more polynucleic acid molecules or binding moieties described herein are conjugated either directly or indirectly to a nanoparticle.

In some aspects, the pharmaceutical formulation comprises a delivery vector, e.g., a recombinant vector, the delivery of the polynucleic acid molecule into cells. In some instances, the recombinant vector is DNA plasmid. In other instances, the recombinant vector is a viral vector. Exemplary viral vectors include vectors derived from adeno-associated virus, retrovirus, adenovirus, or alphavirus. In some instances, the recombinant vectors capable of expressing the polynucleic acid molecules provide stable expression in target cells. In additional instances, viral vectors are used that provide for transient expression of polynucleic acid molecules.

In some aspects, the pharmaceutical formulation includes a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington. The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., Pharmaceutical Dosage Forms, *Marcel Decker*, New York, N.Y., 1980; and Pharmaceutical Dosage Forms and Drug Delivery Systems, Seventh Ed. (Lippincott Williams & Wilkins 1999).

In some instances, the pharmaceutical formulation further includes pH adjusting agents or buffering agents which include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some instances, the pharmaceutical formulation further includes diluent which are used to stabilize compounds because they provide a more stable environment. Salts dissolved in buffered solutions (which also provide pHI control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

In some cases, the pharmaceutical formulation includes disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming TiaR, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulation includes filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol has a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. Sometimes, surfactants is included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Therapeutic Regimens

In some aspects, the pharmaceutical compositions described herein are administered for therapeutic applications. In some aspects, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, once in two months, once in three months, once in four months, once in five months, once in six months or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In some aspects, one or more pharmaceutical compositions are administered simultaneously, sequentially, or at an interval period of time. In some aspects, one or more pharmaceutical compositions are administered simultaneously. In some cases, one or more pharmaceutical compositions are administered sequentially. In additional cases, one or more pharmaceutical compositions are administered at an interval period of time (e.g., the first administration of a first pharmaceutical composition is on day one followed by an interval of at least 1, 2, 3, 4, 5, or more days prior to the administration of at least a second pharmaceutical composition).

In some aspects, two or more different pharmaceutical compositions are co-administered. In some instances, the two or more different pharmaceutical compositions are co-administered simultaneously. In some cases, the two or more different pharmaceutical compositions are co-administered sequentially without a gap of time between administrations. In other cases, the two or more different pharmaceutical compositions are co-administered sequentially with a gap of about 0.5 hour, 1 hour, 2 hour, 3 hour, 12 hours, 1 day, 2 days, or more between administrations.

In the case wherein the patient's status does improve, upon the doctor's discretion the administration of the composition is given continuously; alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some aspects, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages is altered depending on a number of variables, not limited to the activity of the compound used, the disease or condition to be treated, the mode of administration, the requirements of the individual subject, the severity of the disease or condition being treated, and the judgment of the practitioner.

In some aspects, toxicity and therapeutic efficacy of such therapeutic regimens are determined by standard pharmaceutical procedures in cell cultures or experimental animals, including, but not limited to, the determination of the LDS0 (the dose lethal to 50% of the population) and the ED50 (the dose therapeutically effective in 50% of the population). The dose ratio between the toxic and therapeutic effects is the therapeutic index and it is expressed as the ratio between LDS0 and EDSO. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain aspects, are kits and articles of manufacture for use with one or more of the compositions and methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include target nucleic acid molecule described herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain aspects, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the terms "individual(s)", "subject(s)" and "patient(s)" mean any mammal. In some aspects, the mammal is a human. In some aspects, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

The term "therapeutically effective amount" relates to an amount of a polynucleic acid molecule conjugate that is sufficient to provide a desired therapeutic effect in a mammalian subject. In some cases, the amount is single or multiple dose administration to a patient (such as a human) for treating, preventing, preventing the onset of, curing, delaying, reducing the severity of, ameliorating at least one symptom of a disorder or recurring disorder, or prolonging the survival of the patient beyond that expected in the absence of such treatment. Naturally, dosage levels of the particular polynucleic acid molecule conjugate employed to provide a therapeutically effective amount vary in dependence of the type of injury, the age, the weight, the gender, the medical condition of the subject, the severity of the condition, the route of administration, and the particular inhibitor employed. In some instances, therapeutically effective amounts of polynucleic acid molecule conjugate, as described herein, is estimated initially from cell culture and animal models. For example, $IC_{50}$ values determined in cell culture methods optionally serve as a starting point in animal models, while $IC_{50}$ values determined in animal models are optionally used to find a therapeutically effective dose in humans.

Skeletal muscle, or voluntary muscle, is generally anchored by tendons to bone and is generally used to effect skeletal movement such as locomotion or in maintaining posture. Although some control of skeletal muscle is generally maintained as an unconscious reflex (e.g., postural muscles or the diaphragm), skeletal muscles react to conscious control. Smooth muscle, or involuntary muscle, is found within the walls of organs and structures such as the esophagus, stomach, intestines, uterus, urethra, and blood vessels.

Skeletal muscle is further divided into two broad types: Type I (or "slow twitch") and Type II (or "fast twitch"). Type I muscle fibers are dense with capillaries and are rich in mitochondria and myoglobin, which gives Type I muscle tissue a characteristic red color. In some cases, Type I muscle fibers carries more oxygen and sustain aerobic activity using fats or carbohydrates for fuel. Type I muscle fibers contract for long periods of time but with little force. Type II muscle fibers are further subdivided into three major subtypes (IIa, IIx, and IIb) that vary in both contractile speed and force generated. Type II muscle fibers contract quickly and powerfully but fatigue very rapidly, and therefore produce only short, anaerobic bursts of activity before muscle contraction becomes painful.

Unlike skeletal muscle, smooth muscle is not under conscious control.

Cardiac muscle is also an involuntary muscle but more closely resembles skeletal muscle in structure and is found only in the heart. Cardiac and skeletal muscles are striated in that they contain sarcomeres that are packed into highly regular arrangements of bundles. By contrast, the myofibrils of smooth muscle cells are not arranged in sarcomeres and therefore are not striated.

Muscle cells encompass any cells that contribute to muscle tissue. Exemplary muscle cells include myoblasts, satellite cells, myotubes, and myofibril tissues.

As used here, muscle force is proportional to the cross-sectional area (CSA), and muscle velocity is proportional to muscle fiber length. Thus, comparing the cross-sectional areas and muscle fibers between various kinds of muscles is capable of providing an indication of muscle atrophy. Various methods are known in the art to measure muscle strength and muscle weight, see, for example, "Musculoskeletal assessment: Joint range of motion and manual muscle strength" by Hazel M. Clarkson, published by Lippincott *Williams & Wilkins,* 2000. The production of tomographic images from selected muscle tissues by computed axial tomography and sonographic evaluation are additional methods of measuring muscle mass.

The term antibody oligonucleotide conjugate (AOC) refers to an antibody conjugated to a nucleotide.

The term "siRNA conjugate" or "siRNA-antibody conjugate" refers to an antibody conjugated to an siRNA.

The term "DUX4 siRNA-conjugate" or "DUX4 siRNA-antibody conjugate" refers to an antibody conjugated to an siRNA hybridizing to a target sequence of the human DUX4 mRNA.

The term "DUX4-AOC" refers to an antibody conjugated to an siRNA hybridizing to a target sequence of the human DUX4 mRNA.

Embodiments

Embodiment 1. A polynucleic acid molecule conjugate comprising: an antibody or antigen binding fragment thereof conjugated to a polynucleic acid molecule that hybridizes to a target sequence of DUX4; and wherein the polynucleic acid molecule conjugate mediates RNA interference against the DUX4.

Embodiment 2. The polynucleic acid molecule conjugate of Embodiment 1, wherein the antibody or antigen binding fragment thereof comprises a non-human antibody or antigen binding fragment thereof, a human antibody or antigen binding fragment thereof, a humanized antibody or antigen binding fragment thereof, chimeric antibody or antigen binding fragment thereof, monoclonal antibody or antigen binding fragment thereof, monovalent Fab', divalent Fab2, single-chain variable fragment (scFv), diabody, minibody, nanobody, single-domain antibody (sdAb), or camelid antibody or antigen binding fragment thereof.

Embodiment 3. The polynucleic acid molecule conjugate of Embodiment 1 or 2, wherein the antibody or antigen binding fragment thereof is an anti-transferrin receptor antibody or antigen binding fragment thereof.

Embodiment 4. The polynucleic acid molecule conjugate of any one of Embodiments 1~ 3, wherein the polynucleic acid molecule comprises a sense strand and/or an antisense strand, and wherein the sense strand and/or the antisense strand each independently comprises at least one 2' modified nucleotide, at least one modified intemnucleotide linkage, or at least one inverted abasic moiety.

Embodiment 5. The polynucleic acid molecule conjugate of any one of Embodiments 1-4, wherein the polynucleotide hybridizes to at least 8 contiguous bases of the target sequence of DUX4.

Embodiment 6. The polynucleic acid molecule conjugate of any one of Embodiments 1-5, wherein the polynucleotide is from about 8 to about 50 nucleotides in length or from about 10 to about 30 nucleotides in length.

Embodiment 7. The polynucleic acid molecule conjugate of any one of Embodiments 1-6, wherein the polynucleic acid molecule comprises a sense strand and/or an antisense strand, and the sense strand comprises at least 80%, at least 85%, at least 90%, at least 95%, at least 96%, at least 97%, at least 98%, at least 99% identical to a sequence selected from SEQ ID NOS: 1-70 or SEQ ID NOs: 141-210.

Embodiment 8. The polynucleic acid molecule conjugate of any one of Embodiments 1-7, wherein the polynucleic acid molecule comprises a sense strand and/or an antisense strand, and the sense strand comprises at least 80%, at least 85%, at least 90%, at least 95%, at least 96%, at least 97%, at least 98%, at least 99% identical to a sequence selected from SEQ ID NOs: 142, 146, 196, 201-206.

Embodiment 9. The polynucleic acid molecule conjugate of any one of Embodiments 1-8, wherein the polynucleic acid molecule comprises a sense strand and/or an antisense strand, and the antisense strand comprises at least 80%, at least 85%, at least 90%, at least 95%, at least 96%, at least 97%, at least 98%, at least 99% identical to a sequence selected from SEQ ID NOs: 71-140 or SEQ ID NOs: 211-280.

Embodiment 10. The polynucleic acid molecule conjugate of any one of Embodiments 1-9, wherein the polynucleic acid molecule comprises a sense strand and/or an antisense strand, and the antisense strand comprises at least 80%, at least 85%, at least 90%, at least 95%, at least 96%, at least 97%, at least 98%, at least 99% identical to a sequence selected from SEQ ID NOs: 412-420 and 430-438.

Embodiment 11. The polynucleic acid molecule conjugate of any one of Embodiments 1-10, wherein the polynucleotide comprises at least one 2' modified nucleotide, and further wherein the 2' modified nucleotide: comprises 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMABOE), or 2'-O—N-methylacetamido (2'-O-NMA) modified nucleotide; comprises locked nucleic acid (LNA) or ethylene nucleic acid (ENA); or comprises a combination thereof.

Embodiment 12. The polynucleic acid molecule conjugate of any one of Embodiments 1-11, wherein the at least one modified internucleotide linkage comprises a phosphorothioate linkage or a phosphorodithioate linkage.

Embodiment 13. The polynucleic acid molecule conjugate of any one of Embodiments 1-12, wherein the polynucleic acid molecule comprises 3 or more 2' modified nucleotides selected from 2'-O-methyl and 2'-deoxy-2'-fluoro.

Embodiment 14. The polynucleic acid molecule conjugate of any one of Embodiments 1-13, wherein the polynucleic acid molecule comprises a S'-terminal vinylphosphonate modified nucleotide.

Embodiment 15. The polynucleic acid molecule conjugate of any one of Embodiments 1~ 14, wherein the 5'-terminal vinylphosphonate modified nucleotide is selected from:

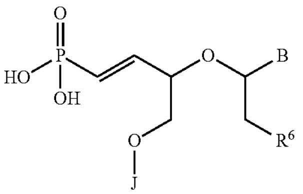

or

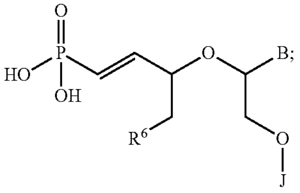

wherein B is a heterocyclic base moiety;

R6 is selected from hydrogen, halogen, alkyl or alkoxy; and

J is an internucleotide linking group linking to the adjacent nucleotide of the polynucleotide.

Embodiment 16. The polynucleic acid molecule conjugate of any one of Embodiments 1-15, wherein the 2' modified nucleotide is 2'-O-methyl modified nucleotide, and 2'-O-methyl modified nucleotide is at the S'-end of the sense strand and/or the antisense strand.

Embodiment 17. The polynucleic acid molecule conjugate of Embodiment 16, wherein the 2'-O-methyl modified nucleotide is a purine nucleotide.

Embodiment 18. The polynucleic acid molecule conjugate of Embodiment 16, wherein the 2'-O-methyl modified nucleotide is a pyridine nucleotide.

Embodiment 19. The polynucleic acid molecule conjugate of any one of Embodiments 16-18, wherein the sense and/or antisense strands comprise at least two, three, four consecutive the 2'-O-methyl modified nucleotides at the 5'-end.

Embodiment 20. The polynucleic acid molecule conjugate of any one of Embodiments I-19, wherein the polynucleic acid molecule conjugate comprises a linker connecting the antibody or antigen binding fragment thereof to the polynucleic acid molecule.

Embodiment 21. The polynucleic acid molecule conjugate of Embodiment 20, wherein the linker is $C_1$-$C_6$ alkyl linker.

Embodiment 22. The polynucleic acid molecule conjugate of Embodiment 20, wherein the linker is a homobifunctional linker or heterobifunctional linker, and comprises a maleimide group, a dipeptide moiety, a benzoic acid group, or its derivative thereof.

Embodiment 23. The polynucleic acid molecule conjugate of Embodiment 20, wherein the linker is a cleavable or non-cleavable linker.

Embodiment 24. The polynucleic acid molecule conjugate of any one of Embodiments 1-23, wherein a ratio between the polynucleic acid molecule and the antibody or antigen binding fragment thereof is about 1:1, 2:1, 3:1, or 4:1.

Embodiment 25. The polynucleic acid molecule conjugate of any one of Embodiments 1-24, wherein the polynucleic acid molecule mediates RNA interference against the human DUX4 and modulates muscle atrophy in a subject.

Embodiment 26. The polynucleic acid molecule conjugate of Embodiment 25, wherein the RNA interference comprises reducing expression of the mRNA transcript of DUX4 gene at least 50%, at least 60%, or at least 70% or more compared to a quantity of the mRNA transcript of DUX4 gene in an untreated cell.

Embodiment 27. The polynucleic acid molecule conjugate of any one of Embodiments 25-26, wherein the RNA interference comprises affecting expression of a marker gene selected from a group consisting of MBD3L2, TRIM43, PRAMEF1, ZSCAN4, KHDCIL, and LEUTX in a cell.

Embodiment 28. The polynucleic acid molecule conjugate of any one of Embodiments 25-26, wherein the RNA interference comprises affecting expression of a marker gene selected from a group consisting of WFDC3, ILVBL, SLC15A2, and SORD in a cell Embodiment 29. The polynucleic acid molecule conjugate of Embodiment 28, wherein the affecting expression of the marker gene is reducing expression of the marker gene at least 20%, at least 30%, at least 40%, at least 50%, at least 60% or more.

Embodiment 30. The polynucleic acid molecule conjugate of any one of Embodiments 25-29, wherein the muscle dystrophy is Facioscapulohumeral muscular dystrophy (FSHD).

Embodiment 31. The polynucleic acid molecule conjugate of any one of Embodiments 1-30, wherein the polynucleic acid molecule conjugate comprises a molecule of Formula (I):

$$A—X—B \quad \text{(Formula I)}$$

wherein,

A is the antibody or antigen binding fragment thereof;

B is the polynucleic acid molecule that hybridizes to a target sequence of DUX4;

X is a bond or a non-polymeric linker; and wherein X is conjugated to a cysteine residue of A.

Embodiment 32. A pharmaceutical composition comprising:

a polynucleic acid molecule conjugate of Embodiments 1-31; and a pharmaceutically acceptable excipient.

Embodiment 33. The pharmaceutical composition of Embodiment 32, wherein the pharmaceutical composition is formulated as a nanoparticle formulation.

Embodiment 34. The pharmaceutical composition of any one of Embodiments 32-33, wherein the pharmaceutical composition is formulated for parenteral, oral, intranasal, buccal, rectal, transdermal, intravenous, subcutaneous, or intrathecal administration.

Embodiment 35. A method for treating muscular dystrophy in a subject in need thereof, comprising:

providing a polynucleic acid conjugate of any one of Embodiments 1-34; and administering the polynucleic acid conjugate to the subject in need thereof to treat the muscular dystrophy, wherein the polynucleic acid conjugate reduces a quantity of the mRNA transcript of human DUX4.

Embodiment 36. The method of Embodiment 35, wherein the polynucleic acid moiety mediates RNA interference against the human DUX4 and modulates muscle atrophy in a subject.

Embodiment 37. The method of Embodiment 36, wherein the RNA interference comprises affecting expression of a marker gene selected from a group consisting of MBD3L2, TRIM43, PRAMEF1, ZSCAN4, KHDCIL, LEUTX, WFDC3, ILVBL, SLC15A2, and SORD in a cell affected by a muscle dystrophy.

Embodiment 38. The method of any one of Embodiments 35-38, wherein the muscular dystrophy is Facioscapulohumeral muscular dystrophy (FSHD).

Embodiment 39. Use of the polynucleic acid molecule conjugate of any one of Embodiments 1-30 or the pharmaceutical composition of any one of Embodiments 32-34 for treating in a subject diagnosed with or suspected to have Facioscapulohumeral muscular dystrophy (FSHD).

Embodiment 40. Use of the polynucleic acid molecule conjugate of any one of Embodiments 1-30 or the pharmaceutical composition of any one of Embodiments 32-34 for manufacturing a medicament for treating in a subject diagnosed with or suspected to have Facioscapulohumeral muscular dystrophy (FSHD).

Embodiment 41. A kit comprising a polynucleic acid molecule conjugate of Embodiments 1-31 or the pharmaceutical composition of any one of Embodiments 32-34.

EXAMPLES

These examples are provided for illustrative purposes only and not to limit the scope of the claims provided herein.

Figure 2:
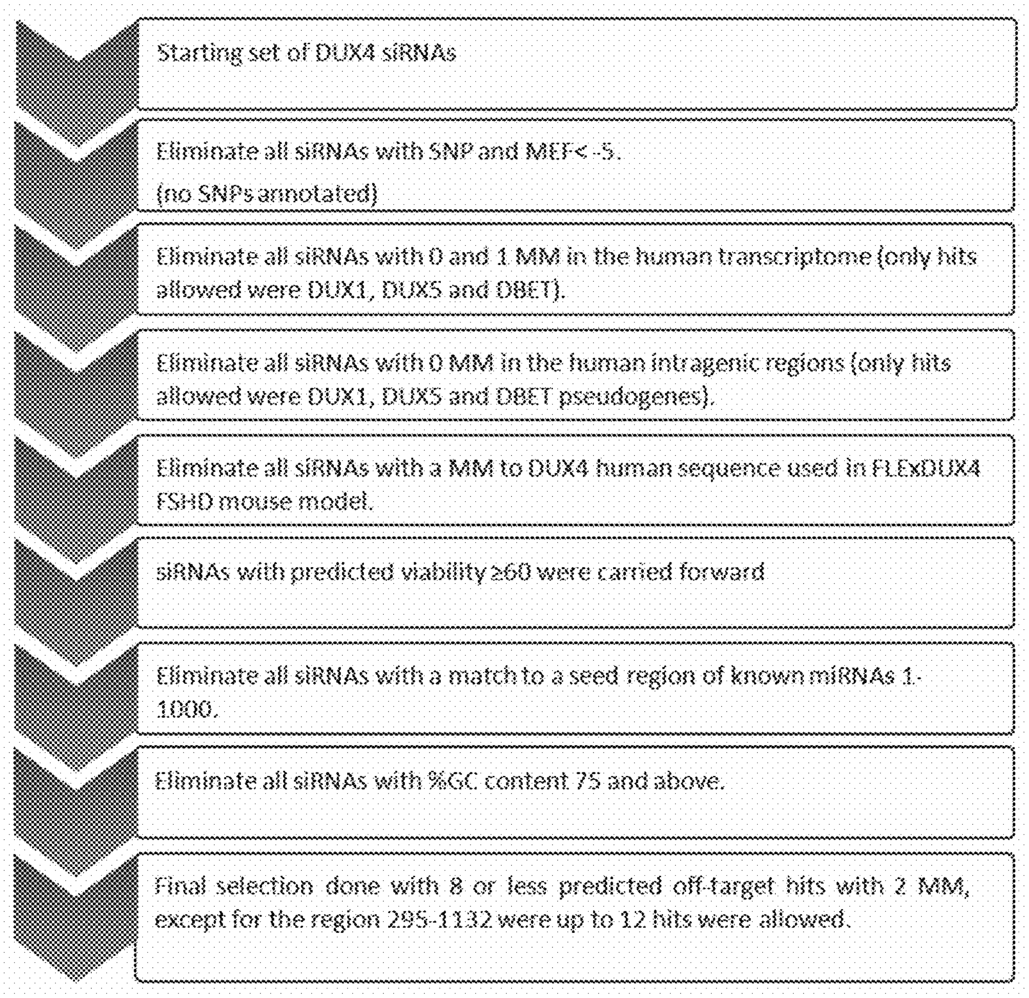
FIG. 2 shows a flowchart diagram of in silico selection of DUX4 siRNA.
Figure 3:
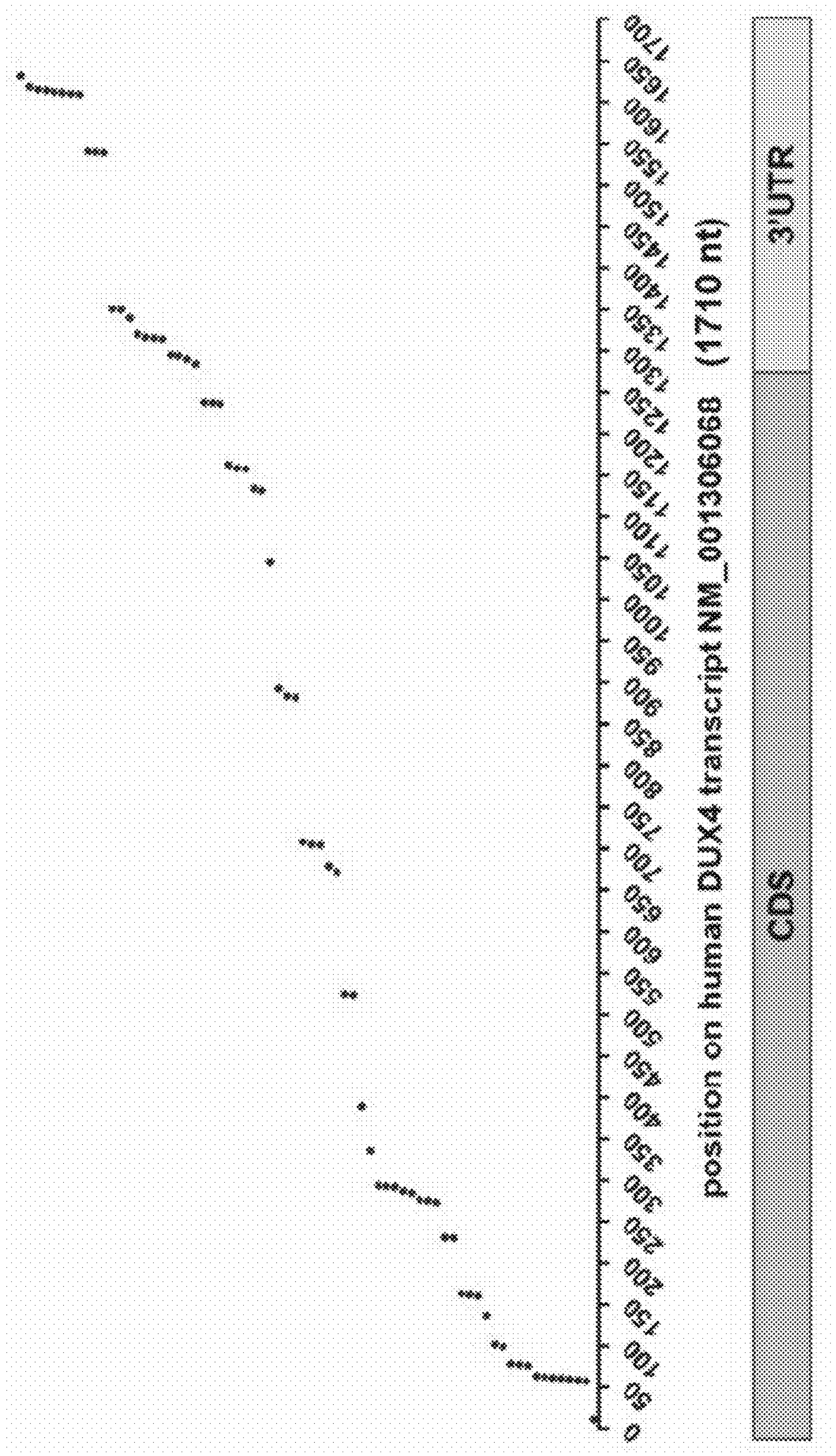
FIG. 3 illustrates the location and numbers of selected DUX4 siRNA in the DUX4 mRNA transcript.

Example 1. Bioinformatic siRNA Library Design Against Human Full Length DUX4 Transcript FIG. 2 shows a flowchart of in silico selection process of DUX4 siRNA. Sequences of all siRNAs that can binds to DUX4, or a pre-determined region of the DUX4 are collected to generate a starting set of DUX4 siRNA. From the starting set of DUX siRNAs, the first eliminating step comprises eliminating one or more DUX siRNAs that has single nucleotide polymorphism (SNP) and/or MEF <−5. Then, the second eliminating step comprises eliminating DUX siRNAs with 0 and 1 MM in the human transcriptome (such that only hits allowed are DUX, DUX5, and DBET). Then, the third eliminating step comprises eliminating DUX siRNAs with 0 mismatch (MM) in the human intragenic regions (such that only hits allowed are DUX1, DUX5 and DBET pseudogenes). Then, the next eliminating step comprises eliminating DUX siRNAs with a MM to DUX4 human sequence used in FLExDUX4 FSHD mouse model. Then, the next step is carrying forward only or one or more DUX siRNAs with predicted viability ≥60. Next, the eliminating step comprises eliminating one or more DUX siRNAs with a match to a seed region of known miRNAs 1-1000. Then, the eliminating step continues with eliminating DUX siRNAs molecule with % GC content 75 and above. Then, the final selection process comprises with eight or fewer predicted off-target hits with 2 MM, except for the region 295-1132, for which up to 12 hits are allowed. Using such series of selection steps, final 70 candidate DUX siRNAs could be selected from a starting set of 1694 DUX siRNAs. FIG. 3 shows the location and numbers of such selected DUX4 siRNA in the DUX4 mRNA transcript (NM_001306068).

Identified siRNA candidates share common characteristics in their sequences as shown below in Table 10 The identified siRNAs have mostly 2'-O-Me modifications, with 2'-F modifications only located on sense strand at positions 7, 8, 9 for all 3 DUX4 templates. The 2'-O-Me modifications, with 2'-F modifications, are located on antisense strand at positions 1, 2, 6, 14, 16 for the DUX4 template 1 and at positions 2, 6, 14, 16 for the DUX4 templates 1 and 2. Also, the identified siRNAs comprises 4 phosphorothioate modifications on each strand, located at the final 2 linkages of each 5' and 3' terminus. The identified siRNAs further comprises "Uf" at the first position of 5' end of the antisense strand for the DUX4 template 1, regardless of the actual target mRNA sequence (coupled with "a" at the last position at the 3' end of the sense strand) and comprises "vpN" at the first position of the 5' end of the antisense strand for the DUX4 template 3. The identified siRNAs further comprises "uu" overhang at the 3' end of the antisense strand only, with no overhang at the 3' end of the sense strand. The optimization of the identified siRNAs may comprise a vinyl phosphonate nucleotide, an inverted abasic moiety, or an amine linker to the passenger strand or the guide strand.

TABLE 10

| Duplex Name | Sense Strand Sequence (5'-3') (passenger strand) | Antisense Strand Sequence (5'-3') (guide strand) |
|---|---|---|
| DUX4 template 1 | nsnsnnnnNfNfNfnnnnnnnsnsa | UfsNfsnnnNfnnnnnnnNfnNfnnnsusu |
| DUX4 template 2 | nsnsnnnnNfNfNfnnnnnnnsnsa | usNfsnnnNfnnnnnnnNfnNfnnnsusu |
| DUX4 template 3 | nsnsnnnnNfNfNfnnnnnnnsnsa | vpNsNfsnnnNfnnnnnnnNfnNfnnnsusu |

vpN = vinyl phosphonate VpUq; upper case (N) = 2'-OH (ribo); lower case (n) = 2'-O-Me(methyl) dN = 2'-H (deoxy); Nf = 2'F (fluoro); s = phosphorothioate backbone modification; iB = inverted abasic Tables 11, 12, 13, 14, and 15 illustrate identified siRNA candidates for the regulation of human DUX4.

TABLE 11

| Name | 19 mer start site | SEQ ID NO | sense/passenger_seq (5'-3') | SEQ ID NO | antisense/guide_seq (5'-3') |
|---|---|---|---|---|---|
| NM_001306068_11_29 | 11 | 1 | cgacaccctcggacagcac | 71 | gtgctgtccgagggtgtcg |
| NM_001306068_57_75 | 57 | 2 | acggcgacggagactcgtt | 72 | aacgagtctccgtcgccgt |
| NM_001306068_58_76 | 58 | 3 | cggcgacggagactcgttt | 73 | aaacgagtctccgtcgccg |
| NM_001306068_59_77 | 59 | 4 | ggcgacggagactcgtttg | 74 | caaacgagtctccgtcgcc |
| NM_001306068_60_78 | 60 | 5 | gcgacggagactcgtttgg | 75 | ccaaacgagtctccgtcgc |
| NM_001306068_61_79 | 61 | 6 | cgacggagactcgtttgga | 76 | tccaaacgagtctccgtcg |
| NM_001306068_62_80 | 62 | 7 | gacggaaactcgtttggac | 77 | gtccaaacgagtctccgtc |
| NM_001306068_63_81 | 63 | 8 | acggagactcgtttggacc | 78 | ggtccaaacgagtctccgt |
| NM_001306068_77_95 | 77 | 9 | ggaccccgagccaaagcga | 79 | tcgctttggctcggggtcc |
| NM_001306068_78_96 | 78 | 10 | gaccccgagccaaagcgag | 80 | ctcgctttggctcggggtc |
| NM_001306068_79_97 | 79 | 11 | accccgagccaaagcgagg | 81 | cctcgctttggctcggggt |
| NM_001306068_99_117 | 99 | 12 | cctgcgagcctgctttgag | 82 | ctcaaagcaggctcgcagg |
| NM_001306068_102_120 | 102 | 13 | gcgagcctgctttgagcgg | 83 | ccgctcaaagcaggctcgc |
| NM_001306068_137_155 | 137 | 14 | tcgccaccagagaacggct | 84 | agccgttctctggtggcga |
| NM_001306068_160_178 | 160 | 15 | caggccatcggcattccgg | 85 | ccggaatgccgatggcctg |
| NM_001306068_162_180 | 162 | 16 | ggccatcggcattccggag | 86 | ctccggaatgccgatggcc |
| NM_001306068_163_181 | 163 | 17 | gccatcggcattccggagc | 87 | gctccggaatgccgatggc |

TABLE 11-continued

| Name | 19 mer start site | SEQ ID NO | sense/passenger_seq (5'-3') | SEQ ID NO | antisense/guide_seq (5'-3') |
|---|---|---|---|---|---|
| NM_001306068_231_249 | 231 | 18 | gcaccggcgggaatctcgg | 88 | ccgagattcccgccggtgc |
| NM_001306068_232_250 | 232 | 19 | caccggcgggaatctcggc | 89 | gccgagattcccgccggtg |
| NM_001306068_274_292 | 274 | 20 | ccagaaggccggcgaaagc | 90 | gctttcgccggccttctgg |
| NM_001306068_276_294 | 276 | 21 | agaaggccggcgaaagcgg | 91 | ccgctttcgccggccttct |
| NM_001306068_277_295 | 277 | 22 | gaaggccggcgaaagcgga | 92 | tccgctttcgccggccttc |
| NM_001306068_285_303 | 285 | 23 | gcgaaagcggaccgccgtc | 93 | gacggcggtccgctttcgc |
| NM_001306068_287_305 | 287 | 24 | gaaagcggaccgccgtcac | 94 | gtgacggcggtccgctttc |
| NM_001306068_292_310 | 292 | 25 | cggaccgccgtcaccggat | 95 | atccggtgacggcggtccg |
| NM_001306068_293_311 | 293 | 26 | ggaccgccgtcaccggatc | 96 | gatccggtgacggcggtcc |
| NM_001306068_294_312 | 294 | 27 | gaccgccgtcaccggatcc | 97 | ggatccggtgacggcggtc |
| NM_001306068_389_407 | 389 | 28 | agacgggcctcccggagtc | 98 | gactccgggaggcccgtct |
| NM_001306068_524_542 | 524 | 29 | cctcgtgggtcgccttcgc | 99 | gcgaaggcgacccacgagg |
| NM_001306068_525_543 | 525 | 30 | ctcgtgggtcgccttcgcc | 100 | ggcgaaggcgacccacgag |
| NM_001306068_679_697 | 679 | 31 | gaggggatctcccaacctg | 101 | caggttgggagatcccctc |
| NM_001306068_704_722 | 704 | 32 | cgcgcggggatttcgccla | 102 | taggcgaaatccccgcgcg |
| NM_001306068_705_723 | 705 | 33 | gcgcggggatttcgcctac | 103 | gtaggcgaaatccccgcgc |
| NM_001306068_708_726 | 708 | 34 | cggggatttcgcctacgcc | 104 | ggcglaggcgaaatccccg |
| NM_001306068_893_911 | 893 | 35 | tgcttgcgccacccacgtc | 105 | gacgtgggtggcgcaagca |
| NM_001306068_1132_1150 | 1132 | 36 | ctggcgagcccggagtttc | 106 | gaaactccgggctcgccag |
| NM_001306068_1134_1152 | 1134 | 37 | ggcgagcccggagtttctg | 107 | cagaaactccgggctcgcc |
| NM_001306068_1158_1176 | 1158 | 38 | ggcgcaacctctcctagaa | 108 | ttctaggagaggttgcgcc |
| NM_001306068_1159_1177 | 1159 | 39 | gcgcaacctctcctagaaa | 109 | tttctaggagaggttgcgc |
| NM_001306068_1163_1181 | 1163 | 40 | aacctctcctagaaacgga | 110 | tccgtttctaggagaggtt |
| NM_001306068_1236_1254 | 1236 | 41 | cagcgaggaagaataccgg | 111 | ccggtattcttcctcgctg |
| NM_001306068_1237_1255 | 1237 | 42 | agcgaggaagaataccggg | 112 | cccggtattcttcctcgct |
| NM_001306068_1238_1256 | 1238 | 43 | gcgaggaagaataccgggc | 113 | gcccggtattcttcctcgc |
| NM_001306068_1284_1302 | 1284 | 44 | gttgggacggggtcgggtg | 114 | cacccgaccccgtcccaac |
| NM_001306068_1290_1308 | 1290 | 45 | acggggtcgggtggttcgg | 115 | ccgaaccacccgaccccgt |
| NM_001306068_1294_1312 | 1294 | 46 | ggtcgggtggttcggggca | 116 | tgccccgaaccacccgacc |
| NM_001306068_1295_1313 | 1295 | 47 | gtcgggtggttcggggcag | 117 | ctgccccgaaccacccgac |
| NM_001306068_1315_1333 | 1315 | 48 | gcggtggcctctctttcgc | 118 | gcgaaagagaggccaccgc |
| NM_001306068_1316_1334 | 1316 | 49 | cggtggcctctctttcgcg | 119 | cgcgaaagagaggccaccg |
| NM_001306068_1317_1335 | 1317 | 50 | ggtggcctctctttcgcgg | 120 | ccgcgaaagagaggccacc |
| NM_001306068_1321_1339 | 1321 | 51 | gcctctctttcgcggggaa | 121 | ttccccgcgaaagagaggc |
| NM_001306068_1340_1358 | 1340 | 52 | cacctggctggctacggag | 122 | ctccgtagccagccaggtg |
| NM_001306068_1350_1368 | 1350 | 53 | gctacggaggggcgtgtct | 123 | agacacgcccctccgtagc |
| NM_001306068_1351_1369 | 1351 | 54 | ctacggaggggcgtgtctc | 124 | gagacacgcccctccgtag |
| NM_001306068_1539_1557 | 1539 | 55 | acgtgcaagggagctcgct | 125 | agcgagctcccttgcacgt |

TABLE 11-continued

| Name | 19 mer start site | SEQ ID NO | sense/passenger_seq (5'-3') | SEQ ID NO | antisense/guide_seq (5'-3') |
|---|---|---|---|---|---|
| NM_001306068_1540_1558 | 1540 | 56 | cgtgcaagggagctcgctg | 126 | cagcgagctcccttgcacg |
| NM_001306068_1541_1559 | 1541 | 57 | gtgcaagggagctcgctgg | 127 | ccagcgagctcccttgcac |
| NM_001306068_1610_1628 | 1610 | 58 | caccttccgacgclgtcta | 128 | tagacagcgtcggaaggtg |
| NM_001306068_1611_1629 | 1611 | 59 | accttccgacgctgtctag | 129 | ctagacagcgtcggaaggt |
| NM_001306068_1612_1630 | 1612 | 60 | ccttccgacgctgtctagg | 130 | cctagacagcgtcggaagg |
| NM_001306068_1613_1631 | 1613 | 61 | cttccgacgctgtctaggc | 131 | gcctagacagcgtcggaag |
| NM_001306068_1615_1633 | 1615 | 62 | tccgacgctgtctaggcaa | 132 | ttgcctagacagcgtcgga |
| NM_001306068_1616_1634 | 1616 | 63 | ccgacgctgtctaggcaaa | 133 | tttgcctagacagcgtcgg |
| NM_001306068_1619_1637 | 1619 | 64 | acgctgtctaggcaaacct | 134 | aggtttgcctagacagcgt |
| NM_001306068_1632_1650 | 1632 | 65 | aaacctggattagagttac | 135 | gtaactctaatccaggttt |
| NM_001306068_336_354 | 336 | 66 | ctttgagaaggatcgcttt | 136 | aaagcgatccttctcaaaa |
| NM_001306068_672_690 | 672 | 67 | gccggcagaggggatctcc | 137 | ggagatcccctctgccggc |
| NM_001306068_882_900 | 882 | 68 | gggccaaggggtgcttgcg | 138 | cgcaagcaccccttggccc |
| NM_001306068_884_902 | 884 | 69 | gccaaggggtgcttgcgcc | 139 | ggcgcaagcaccccttggc |
| NM_001306068_1045_1063 | 1045 | 70 | atgcaaggcatcccggcgc | 140 | gcgccgggatgccttgcat |

TABLE 12

| Name | 19 mer start site | SEQ ID NO | sense/passenger_seq (5'-3') | SEQ ID NO | antisense/guide_seq (5'-3') |
|---|---|---|---|---|---|
| NM_001306068_11_29 | 11 | 141 | csgsacacCfCfUfcg gacagcsasa | 211 | UfsUfsgcuGfuccgagg GfuGfucgsusu |
| NM_001306068_57_75 | 57 | 142 | ascsggcgAfCfGfg agacucgsusa | 212 | UfsAfscgaGfucuccgu CfgCfcgsusu |
| NM_001306068_58_76 | 58 | 143 | csgsgcgaCfGfGfa gacucgsusa | 213 | UfsAfsacgAfgucuccg UfcGfccgsusu |
| NM_001306068_59_77 | 59 | 144 | gsgscgacGfGfAfg acucguusua | 214 | UfsAfsaacGfagucucc GfuCfgccsusu |
| NM_001306068_60_78 | 60 | 145 | gscsgacgGfAfGfa cucgauusgsa | 215 | UfsCfsaaaCfgagucucC fgUfcgcsusu |
| NM_001306068_61_79 | 61 | 146 | csgsacggAfGfAf ucguuugsgsa | 216 | UfsCfscaaAfgagucuC fcGfucgsusu |
| NM_001306068_62_80 | 62 | 147 | gsascggaGfAfCfa cguuuggsasa | 217 | UfsUfsccaAfacgaguc UfcCfgucsusu |
| NM_001306068_63_81 | 63 | 148 | ascsggagAfCfUfc guuuggascsa | 218 | UfsGfsuccAfaacgagu CfuCfcgusus u |
| NM_001306068_77_95 | 77 | 149 | gsgsacccCfGfAfgc caaagcsgsa | 219 | UfsCfsgcuUfuggcucg GfgGfuccsusu |
| NM_001306068_78_96 | 78 | 150 | gsascccCfGfAfGfcc aaagcgsasa | 220 | UfsUfscgcUfuuggcuc GfgGfgucsusu |
| NM_001306068_79_97 | 79 | 151 | ascsccgAfGfCfca aagcgasgsa | 221 | UfsCfsucgCfuuuggcu CfgGfcgusus u |
| NM_001306068_99_117 | 99 | 152 | cscsugcgAfGfCfc ugcauugsasa | 222 | UfsUfscaaAfgcaggcu CfgCfaggsusu |

TABLE 12-continued

| Name | 19 mer start site | SEQ ID NO | sense/passenger_seq (5'-3') | SEQ ID NO | antisense/guide_seq (5'-3') |
|---|---|---|---|---|---|
| NM_001306068_102_120 | 102 | 153 | gscsgagcCfUfGf uuugagcsgsa | 223 | UfsCfsgcuCfaaagcagG fcUfcgcsusu |
| NM_001306068_137_155 | 137 | 154 | uscsgccaCCfAfga gaacggscsa | 224 | UfsGfsccgUfucucugg UfgGfcgasusu |
| NM_001306068_160_178 | 160 | 155 | csasggccAfUfCfg gcauuccsgsa | 225 | UfsCfsggaAfugccgau GfgCfcugsusu |
| NM_001306068_162_180 | 162 | 156 | gsgsccauCfGfGfca uuccggsasa | 226 | UfsUfsccgGfaaugccg AfuGfgccsusu |
| NM_001306068_163_181 | 163 | 157 | gscscaucGfGfCfau uccggasgsa | 227 | UfsCfsuccGfgaaugcc GfaUfggcsusu |
| NM_001306068_231_249 | 231 | 158 | gscsaccgCfCfCfg gaaucucsgsa | 228 | UfsCfsgagAfuucccgc CfgGfugcsusu |
| NM_001306068_232_250 | 232 | 159 | csasccggCfGfGfga aucucgsgsa | 229 | UfsCfscgaGfauucccgC fcGfgugsusu |
| NM_001306068_274_292 | 274 | 160 | cscsagaaGfGfCfcg gcgaaasgsa | 230 | UfsCfsuuuCfgccggcc UfuCfuggsusu |
| NM_001306068_276_294 | 276 | 161 | asgsaaggCfCfGfgc gaaagcsgsa | 231 | UfsCfsgcuUfucgccgg CfcUfucusu su |
| NM_001306068_277_295 | 277 | 162 | gsasaggcCfGfGfc gaaagcgsgsa | 232 | UfsCfscgcUfuncgccg GfcCfuucsusu |
| NM_001306068_285_303 | 285 | 163 | gscsgaaaGfCfGfga ccgccgsusa | 233 | UfsAfscggCfgguccgc UfuUfcgcsusu |
| NM_001306068_287_305 | 287 | 164 | gsasaagcGfGfAfcc gccgucsasa | 234 | UfsUfsgacGfgcggucc GfcUfaucsusu |
| NM_001306068_292_310 | 292 | 165 | csgsgaccGfCfCfgu caccggsasa | 235 | UfsUfsccgGfugacggc GfgUfccgsusu |
| NM_001306068_293_311 | 293 | 166 | gsgsaccgCfCfGfuc accggasusa | 236 | UfsAfsuccGfgugacgg CfgGfuccsusu |
| NM_001306068_294_312 | 294 | 167 | gsasccgcCfGfUfca ccggauscsa | 237 | UfsGfsaucCfggugacg GfcGfgucsusu |
| NM_001306068_389_407 | 389 | 168 | asgsacggGfCfCfuc ccggagsusa | 238 | UfsAfscucCfgggaggc CfGfucususu |
| NM_001306068_524_542 | 524 | 169 | cscsucgaGfGfGfu cgccuucsgsa | 239 | UfsCfsgaaGfgcgacccA fcGfaggsusu |
| NM_001306068_525_543 | 525 | 170 | csuscgugGfGfUfc gccuucgscsa | 240 | UfsGfscgaAfggcgacc CfaCfgagsusu |
| NM_001306068_679_697 | 679 | 171 | gsasggggAfUfCfu cccaaccsusa | 241 | UfsAfsgguUfgggagau CfcCfcucsusu |
| NM_001306068_704_722 | 704 | 172 | csgscgcgGfGfGfa uuucgccsusa | 242 | UfsAfsggcGfaaaucccC fgCfgcgsusu |
| NM_001306068_705_723 | 705 | 173 | gscsgcggGfGfAfu uucgccusasa | 243 | UfsUfsaggCfgaaauccC fcGfcgcsusu |
| NM_001306068_708_726 | 708 | 174 | csgsgggaUfUfUfc gccuacgscsa | 244 | UfsGfscguAfggcgaaa UfcCfccgsusu |
| NM_001306068_893_911 | 893 | 175 | usgscuugCfGfCfc acccacgsusa | 245 | UfsAfscguGfgguggcg CfaAfgcasusu |
| NM_001306068_1132_1150 | 1132 | 176 | csusggcgAfGfCfc cggaguusus a | 246 | UfsAfsaacUfccgggcu CfgCfcagsusu |
| NM_001306068_1134_1152 | 1134 | 177 | gsgscgagCfCfCfg gaguuucsusa | 247 | UfsAfsgaaAfcuccggg CfuCfgccsusu |

TABLE 12-continued

| Name | 19 mer start site | SEQ ID NO | sense/passenger_seq (5'-3') | SEQ ID NO | antisense/guide_seq (5'-3') |
|---|---|---|---|---|---|
| NM_001306068_1158_1176 | 1158 | 178 | gsgscgcaAfCfCfuc uccuagsasa | 248 | UfsUfscuaGfgagaggu UfgCfgccsusu |
| NM_001306068_1159_1177 | 1159 | 179 | gscsgcaaCfCfUfcu ccuagasasa | 249 | UfsUfsucuAfggagagg UfuGfcgcsusu |
| NM_001306068_1163_1181 | 1163 | 180 | asasccucUfCfCfua gaaacgsgsa | 250 | UfsCfscguUfucuagga GfaGfguusus u |
| NM_001306068_1236_1254 | 1236 | 181 | csasgcgaGfGfAfa gaauaccsgsa | 251 | UfsCfsgguAfuucuucc UfcGfcugsusu |
| NM_001306068_1237_1255 | 1237 | 182 | asgscgagGfAfAfg aauaccgsgsa | 252 | UfsCfscggUfauucuuc CfuCfgcusus u |
| NM_001306068_1238_1256 | 1238 | 183 | gscsgaggAfAfGfa auaccggsgsa | 253 | UfsCfsccgGfuauucuu CfcUfcgcsusu |
| NM_001306068_1284_1302 | 1284 | 184 | gsusugggAfCfGfg ggucgggsusa | 254 | UfsAfscccGfaccccguC fcCfaacsusu |
| NM_001306068_1290_1308 | 1290 | 185 | ascsggggUfCfGfg gugguucsgsa | 255 | UfsCfsgaaCfcacccgaC fcCfcgusus u |
| NM_001306068_1294_1312 | 1294 | 186 | gsgsucggGfUfGfg uucggggscsa | 256 | UfsGfscccCfgaaccacC fcGfaccsusu |
| NM_001306068_1295_1313 | 1295 | 187 | gsuscgggUfGfGfu ucggggcsasa | 257 | UfsUfsgccCfcgaaccaC fcCfgacsusu |
| NM_001306068_1315_1333 | 1315 | 188 | gscsggugGfCfCfu cucuuucsgsa | 258 | UfsCfsgaaAfgagaggc CfaCfcgcsusu |
| NM_001306068_1316_1334 | 1316 | 189 | csgsguggCfCfUfc ucuuucgscsa | 259 | UfsGfscgaAfagagagg CfAfccgsusu |
| NM_001306068_1317_1335 | 1317 | 190 | gsgsuggcCfUfCfu cuuucgcsgsa | 260 | UfsCfsgcgAfaagagag GfcCfaccsusu |
| NM_001306068_1321_1339 | 1321 | 191 | gscscucuCfUfUfu cgcggggsasa | 261 | UfsUfscccCfgcgaaagA fgAfggcsusu |
| NM_001306068_1340_1358 | 1340 | 192 | csasccugGfCfUfg gcuacggsasa | 262 | UfsUfsccgUfagccagcC faGfgugsusu |
| NM_001306068_1350_1368 | 1350 | 193 | gscsuacgGfAfGfg ggcguguscsa | 263 | UfsGfsacaCfgccccucC fgUfagcsusu |
| NM_001306068_1351_1369 | 1351 | 194 | csusacggAfGfGfg gcgugucsusa | 264 | UfsAfsgacAfcgccccuC fcGfuagsusu |
| NM_001306068_1539_1557 | 1539 | 195 | ascsgugcAfAfGfg gagcucgscsa | 265 | UfsGfscgaGfcuccccuu GfAfcgusus u |
| NM_001306068_1540_1558 | 1540 | 196 | csgsugcaAfGfGfg agcucgcsusa | 266 | UfsAfsgcgAfgcucccu UfgCfacgsusu |
| NM_001306068_1541_1559 | 1541 | 197 | gsusgcaaGfGfGfa gcucgcusgsa | 267 | UfsCfsagcGfagcucccU fuGfcacsusu |
| NM_001306068_1610_1628 | 1610 | 198 | csasccuuCfCfGfac gcugucsusa | 268 | UfsAfsgacAfgcgucgg AfaGfgugsusu |
| NM_001306068_1611_1629 | 1611 | 199 | ascscaucCfGfAfcg cugucusasa | 269 | UfsUfsagaCfagcgucg GfaAfggusus u |
| NM_001306068_1612_1630 | 1612 | 200 | cscsuuccGfAfCfgc ugucuasgsa | 270 | UfsCfsuagAfcagcguc GfgAfaggsusu |
| NM_001306068_1613_1631 | 1613 | 201 | csusuccgAfCfGfc ugucuagsgsa | 271 | UfsCfscuaGfacagcguC fgGfaagsusu |
| NM_001306068_1615_1633 | 1615 | 202 | uscscgacGfCfUfg ucuaggcsasa | 272 | UfsUfsgccUfagacagc GfuCfggasusu |

TABLE 12-continued

| Name | 19 mer start site | SEQ ID NO | sense/passenger_seq (5'-3') | SEQ ID NO | antisense/guide_seq (5'-3') |
|---|---|---|---|---|---|
| NM_001306068_1616_1634 | 1616 | 203 | cscsgacgCfUfGfuc uaggcasasa | 273 | UfsUfsugcCfuagacag CfgUfcggsusu |
| NM_001306068_1619_1637 | 1619 | 204 | ascsgcugUfCfUfa ggcaaacscsa | 274 | UfsGfsguuUfgccuaga CfaGfcgususu |
| NM_001306068_1632_1650 | 1632 | 205 | asasaccuGfGfAfu uagaguusasa | 275 | UfsUfsaacUfcuaauccA fgGfuuususu |
| NM_001306068_336_354 | 336 | 206 | csusuugaGfAfAfg gaucgcususa | 276 | UfsAfsagcGfauccuuc UfcAfaagsusu |
| NM_001306068_672_690 | 672 | 207 | gscscggcAfGfAfg gggaucuscsa | 277 | UfsGfsagaUfccccucu GfcCfggcsusu |
| NM_001306068_882_900 | 882 | 208 | gsgsgccaAfGfGfg gugcuugscsa | 278 | UfsGfscaaGfcaccccuU fgGfcccsusu |
| NM_001306068_884_902 | 884 | 209 | gscscaagGfGfGfu gcuugcgscsa | 279 | UfsGfscgcAfagcacccC fuUfggcsusu |
| NM_001306068_1045_1063 | 1045 | 210 | asusgcaaGfGfCfau cccggcsgsa | 280 | UfsCfsgccGfggaugcc UfuGfcaususu |

vpN = vinyl phosphonate 2'-MOE; upper case (N) = 2'-OH (ribo); lower case (n) = 2'-O-Me(methyl) dN = 2'-H (deoxy); Nf = 2'-F (fluoro); s = phosphorothioate backbone modification; iB = inverted abasic

TABLE 13

| SEQ ID NO | sense/passenger_seq (5'-3') | SEQ ID NO | antisense/guide_seq (5'-3') |
|---|---|---|---|
| 371 | CTGCCTCTCCACCAGCCCA | 372 | TGGGCTGGTGGAGAGGCAG |
| 373 | GCAGAGATGGAGAGAGGAA | 374 | TTCCTCTCTCCATCTCTGC |
| 375 | GCGGTTTCCTCCGGGACAA | 376 | TTGTCCCGGAGGAAACCGC |
| 377 | GGACGACGGAGGCGTGATT | 378 | AATCACGCCTCCGTCGTCC |
| 379 | CGGGCACCCGGAAACTGCAGG GAA | 380 | TTCCCTGCATGTTTCCGGGTGCCC G |
| 381 | CCGGAAACATGCAGGGAAG | 382 | CTTCCCTGCATGTTTCCGG |
| 383 | GAAATGAACGAGAGCCACA | 384 | TGTGGCTCTCGTTCATTTC |
| 385 | TGGCACACTCAAGACTCCCACGG AG | 386 | CTCCGTGGGAGTCTTGAGTGTGC CA |
| 387 | CCACGGAGGTTCAGTTCCA | 388 | TGGAACTGAACCTCCGTGG |
| 389 | ACCACCACCACCACCACCA | 390 | TGGTGGTGGTGGTGGTGGT |
| 391 | CGCCATTCATGAAGGGGTG | 392 | CACCCCTTCATGAATGGCG |
| 393 | CATGAAGGGGTGGAGCCTG | 394 | CAGGCTCCACCCCTTCATG |
| 395 | GAGCCTGCTTTGAGCGGAA | 396 | TTCCGCTCAAGCAGGCTC |
| 397 | CCGAGCCTTTGAGAAGGATCGCT TT | 398 | AAAGCGATCCTTCTCAAAGGCTC GG |
| 399 | GGCAGGGCGCCCGCGCAGG | 400 | CCTGCGCGGGCGCCCTGCC |
| 401 | GATGATTAGTTCAGAGATA | 402 | TATCTCTGAACTAATCATC |

TABLE 14

| Name | 19 mer start site | SEQ ID NO | sense/passenger_seq (5'-3') | SEQ ID NO | antisense/guide_seq (5'-3') |
|---|---|---|---|---|---|
| NM_001306068_57_75 | 57 | 142 | ascsggcgAfCfGfgagacucgsusa | 412 | usAfscgaGfucuccguCfgCfcgususu |
| NM_001306068_61_79 | 61 | 146 | csgsacggAfGfAfcucgauugsgsa | 413 | usCfscaaAfcgagucuCfcGfucgsusu |
| NM_001306068_336_354 | 336 | 206 | csusuugaGfAfAfggaucgcususa | 414 | usAfsagcGfauccuucUfAfaagsusu |
| NM_001306068_1540_1558 | 1540 | 196 | csgsugcaAfGfGfgagcucgcsusa | 415 | usAfsgCgAfgcucccuUfgCfacgsusu |
| NM_001306068_1613_1631 | 1613 | 201 | csusuccgAfCfGfugucuagsgsa | 416 | usCfscuaGfacagcguCfgGfaagsusu |
| NM_001306068_1615_1633 | 1615 | 202 | usCscgacGfCfUfgucuaggcsasa | 417 | usUfsgccUfagacagcGfuCfggasusu |
| NM_001306068_1616_1634 | 1616 | 203 | cscsgacgCfUfGfucuaggcasasa | 418 | asUfsugcCfuagacagCfgUfcggsusu |
| NM_001306068_1619_1637 | 1619 | 204 | ascsgcugUfCfUfaggcaaacscsa | 419 | usGfsguuUfgccuagaCfaGfgususu |
| NM_001306068_1632_1650 | 1632 | 205 | asasaccuGfGfAfuuagaguusasa | 420 | usUfsaacUfcuaauccAfgGfuuususu |

vpN = vinyl phosphonate vpUq; upper case (N) = 2'-OH (ribo); lower case (n) = 2'-O-Me(methyl) dN = 2'-H (deoxy); Nf = 2'F (fluoro); s = phosphorothioate backbone modification; iB = inverted abasic

TABLE 15

| Name | 19 mer start site | SEQ ID NO | sense/passenger_seq (5'-3') | SEQ ID NO | antisense/guide_seq (5'-3') |
|---|---|---|---|---|---|
| NM_001306068_57_75 | 57 | 142 | ascsggcgAfCfGfgagacucgsusa | 430 | vpUsAfscgaGfucaccguCfgCfcgususu |
| NM_001306068_61_79 | 61 | 146 | csgsacggAfGfAfcucguuugsgsa | 431 | vpUsCfscaaAfgagucuCfcGfucgsusu |
| NM_001306068_336_354 | 336 | 206 | csusuugaGfAfAfggaucgcususa | 432 | vpUsAfsagcGfauccuucUfcAfaagsusu |
| NM_001306068_1540_1558 | 1540 | 196 | csgsugcaAfGfGfgagcucgcsusa | 433 | vpUsAfsgcgAfgcucccuUfgCfacgsusu |
| NM_001306068_1613_1631 | 1613 | 201 | csusuccgAfCfGfcugucuagsgsa | 434 | vpUsCfscuaGfacagcguCfgGfaagsusu |
| NM_001306068_1615_1633 | 1615 | 202 | uscscgacGfCfUfgucuaggcsasa | 435 | vpUsUfsgccUfagacagcGfaCfggasasu |
| NM_001306068_1616_1634 | 1616 | 203 | cscsgacgCfUfGfucuaggcasasa | 436 | vpUsUfsugcCfuagacagCfgUfcggsusu |
| NM_001306068_1619_1637 | 1619 | 204 | ascsgcugUfCfUfaggcaaacscsa | 437 | vpUsGfsgauUfgccuagaCfaGfcgususu |
| NM_001306068_16321650 | 1632 | 205 | asasaccuGfGfAfuuagaguusasa | 438 | vpUsUfsaacUfcuaauccAfgGfuuususu |

vpN = vinyl phosphonate vpUq; upper case (N) = 2'-OH (ribo); lower case (n) = 2'-O-Me (methyl) dN = 2'-H (deoxy); Nf = 2'F (fluoro); s = phosphorothioate backbone modification; iB = inverted abasic

Example 2. SiRNA Sequences and Synthesis

Figure 5A:
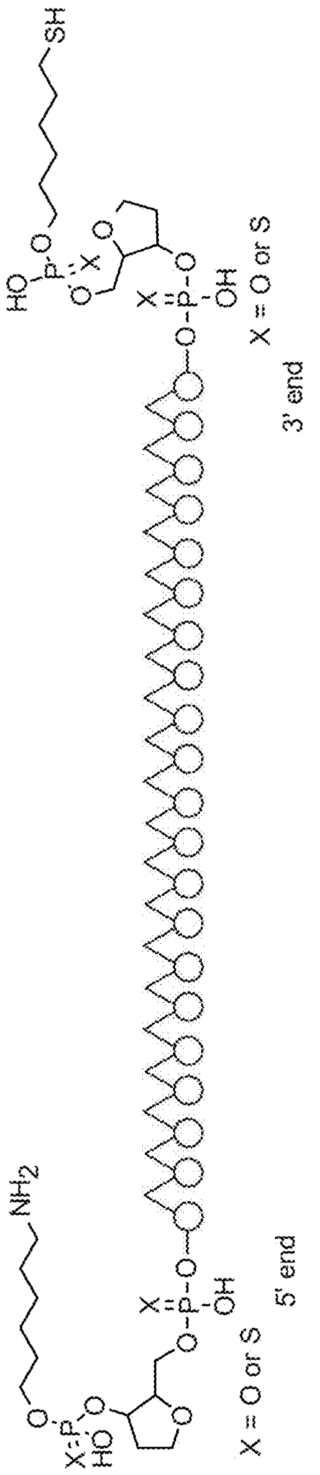
FIG. 5A illustrates a representative structure of siRNA with $C_6$—$NH_2$ conjugation handle at the S' end and Co-SH at 3' end of the passenger strand or guide strand.
Figure 5B:
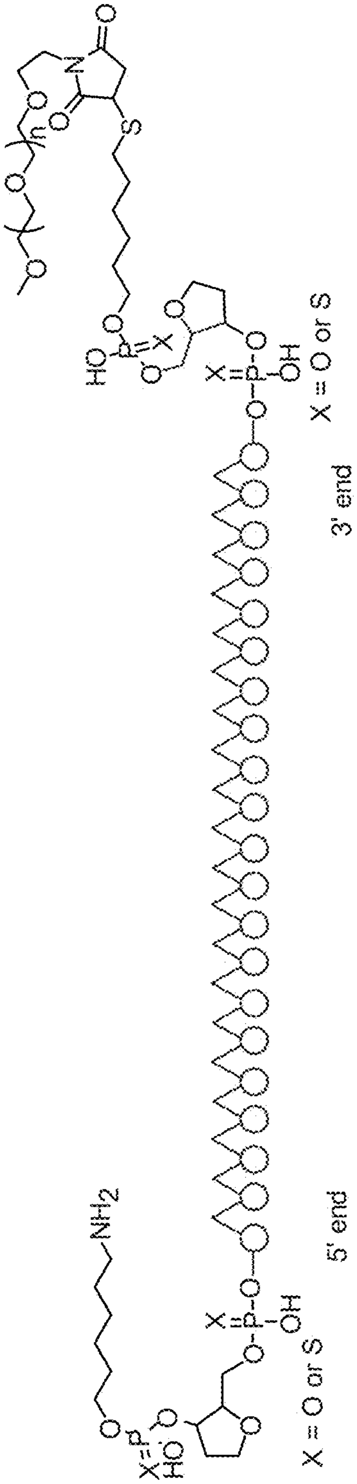
FIG. 5B illustrates a representative structure of siRNA passenger strand or guide strand with $C_6$—$NH_2$ conjugation handle at the 5' end and Co—S-PEG at 3' end.
Figure 5C:
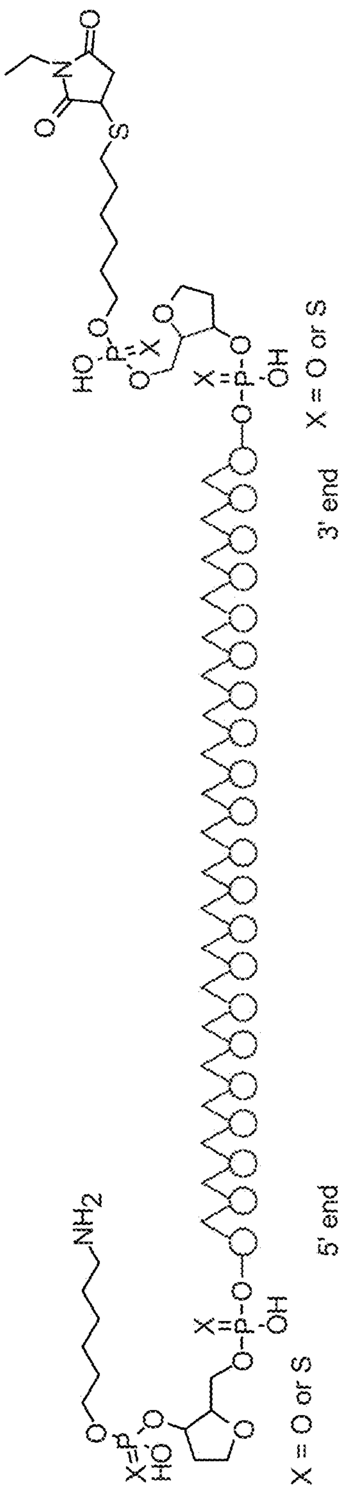
FIG. 5C illustrates a representative structure of siRNA passenger strand or guide strand with $C_6$—$NH_2$ conjugation handle at the S' end and Co—S-NEM at 3' end.
Figure 5D:
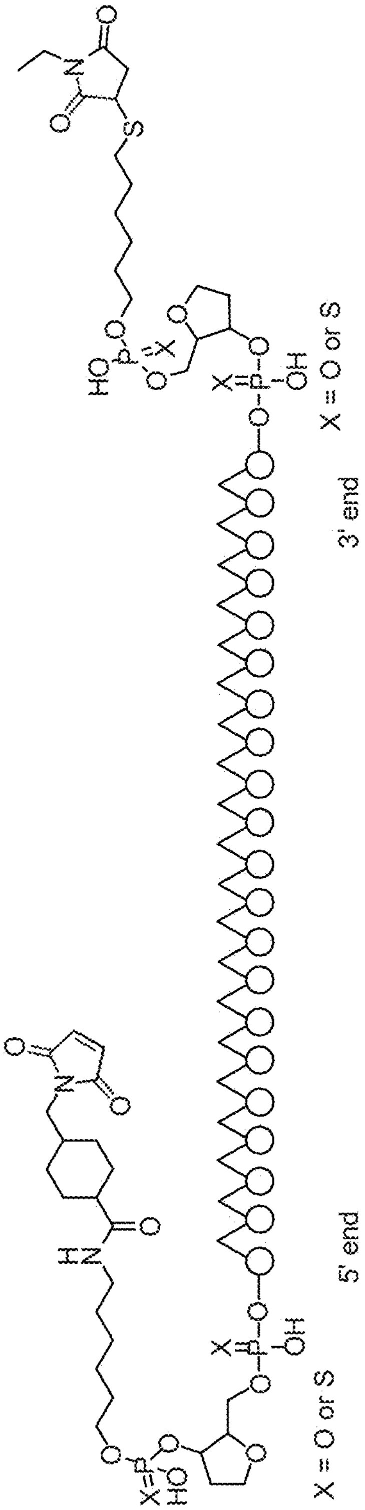
FIG. 5D illustrates a representative structure of siRNA passenger strand with $C_6$-N-SMCC conjugation handle at the 5' end and $C_6$-S-NEM at 3' end.
Figure 5E:
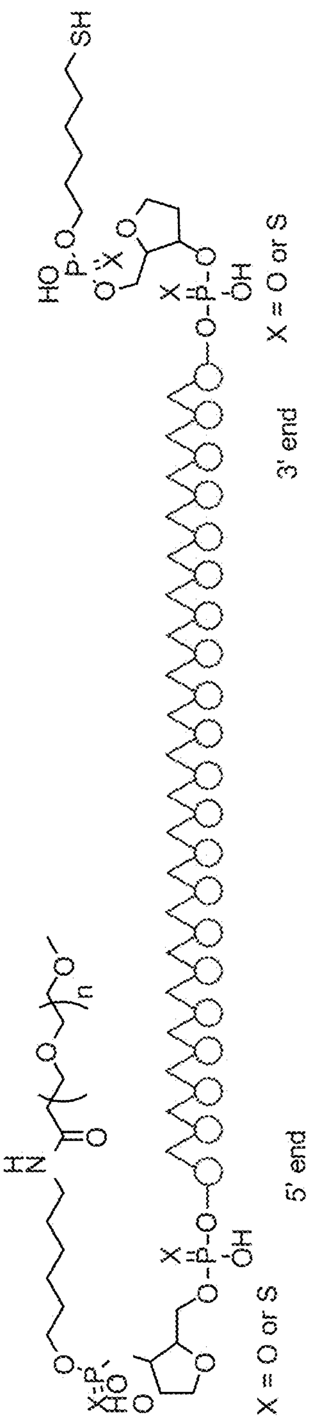
FIG. 5E illustrates a representative structure of siRNA passenger strand or guide strand with PEG at the S' end and Co-SH at 3' end.
Figure 5F:
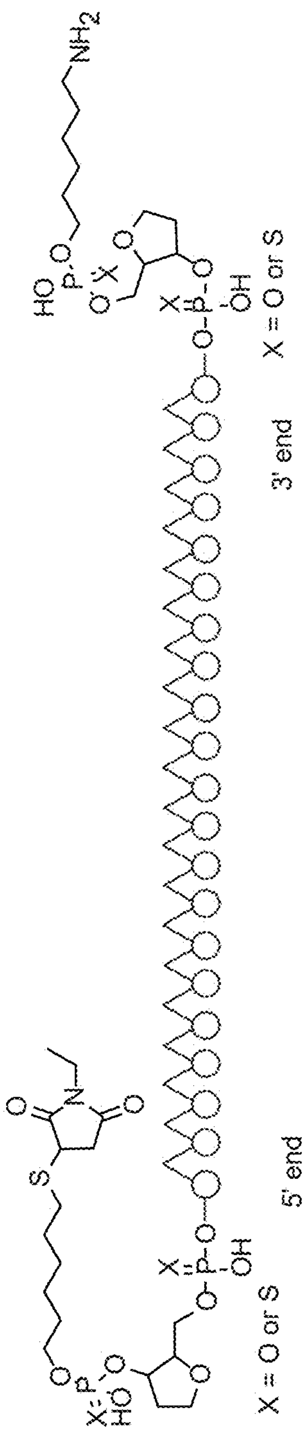
FIG. 5F illustrates a representative structure of siRNA passenger strand or guide strand with Co—S-NEM at the 5' end and $C_6$—$NH_2$ conjugation handle at 3' end.

All siRNA single strands were fully assembled on solid phase using standard phosphoramidite chemistry and purified over HPLC. Purified single strands were duplexed to get the double stranded siRNA. For vinylphosphonate modified guide strand, the guide strand was produced with a vinylphosphonate modified nucleotide structures at the S'end (VpUq). All the siRNA passenger strand contains conjugation handles in different formats, $C_6$—$NH_2$ and/or $C_6$-SH, one at each end of the strand. The conjugation handle or handles were connected to the siRNA passenger strand or siRNA guide strand via inverted abasic phosphodiester or phosphorothioate. FIGS. 5A-5F are representative structures of the formats used in the in vivo experiments. FIG. 5A illustrates a representative structure of siRNA with $C_6$—$NH_2$ conjugation handle at the S' end and $C_6$-SH at 3' end of the passenger strand or guide strand. FIG. 5B illustrates a representative structure of siRNA passenger strand or guide strand with $C_6$—$NH_2$ conjugation handle at the 5' end and Ce—S-PEG at 3' end. FIG. 5C illustrates a representative structure of siRNA passenger strand or guide strand with $C_6$—$NH_2$ conjugation handle at the 5' end and Co—S-NEM at 3' end. FIG. 5D illustrates a representative structure of siRNA passenger strand with $C_6$-N-SMCC conjugation handle at the 5' end and Co—S-NEM at 3' end. FIG. 5E illustrates a representative structure of siRNA passenger strand or guide strand with PEG at the 5' end and Co-SH at 3' end. FIG. 5F illustrates a representative structure of siRNA passenger strand or guide strand with Ce—S-NEM at the S' end and $C_6$—$NH_2$ conjugation handle at 3' end.

Example 3. Conjugate Synthesis

Figure 6A:
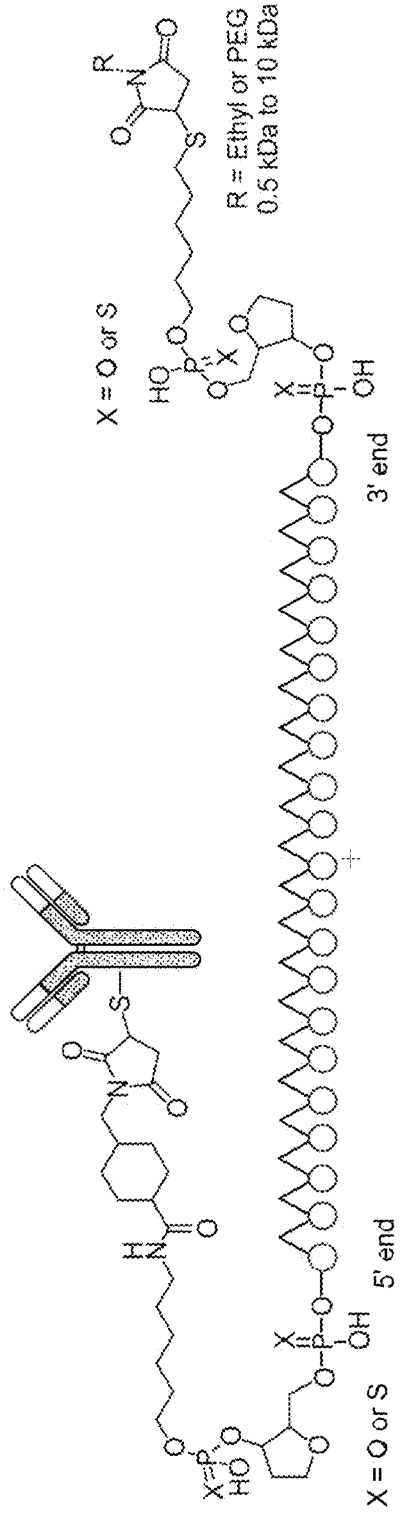
FIG. 6A illustrates an antibody-Cys-SMCC-5'-passenger strand (Architecture-1). This conjugate was generated by antibody inter-chain cysteine conjugation to maleimide (SMCC) at the 5' end of passenger strand.
Figure 6B:
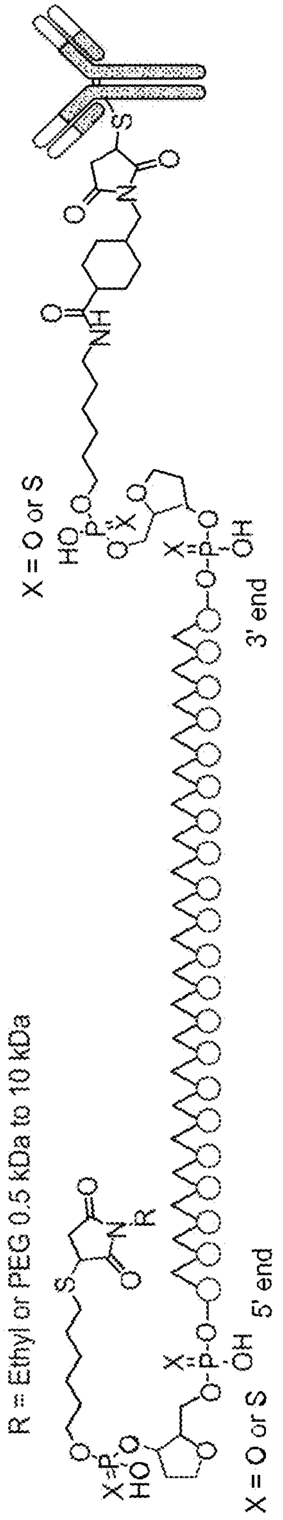
FIG. 6B illustrates an antibody-Cys-SMCC-3'-Passenger strand (Architecture-2). This conjugate was generated by antibody inter-chain cysteine conjugation to maleimide (SMCC) at the 3' end of passenger strand.
Figure 6C:
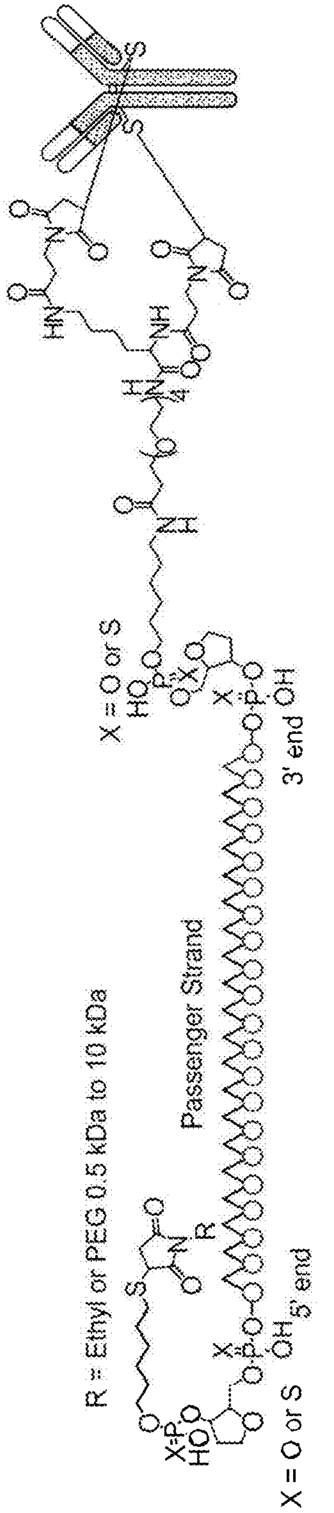
FIG. 6C illustrates an antibody-Cys-bisMal-3'-Passenger strand (ASC Architecture-3). This conjugate was generated by antibody inter-chain cysteine conjugation to bismaleimide (bisMal) linker at the 3' end of passenger strand.
Figure 6D:
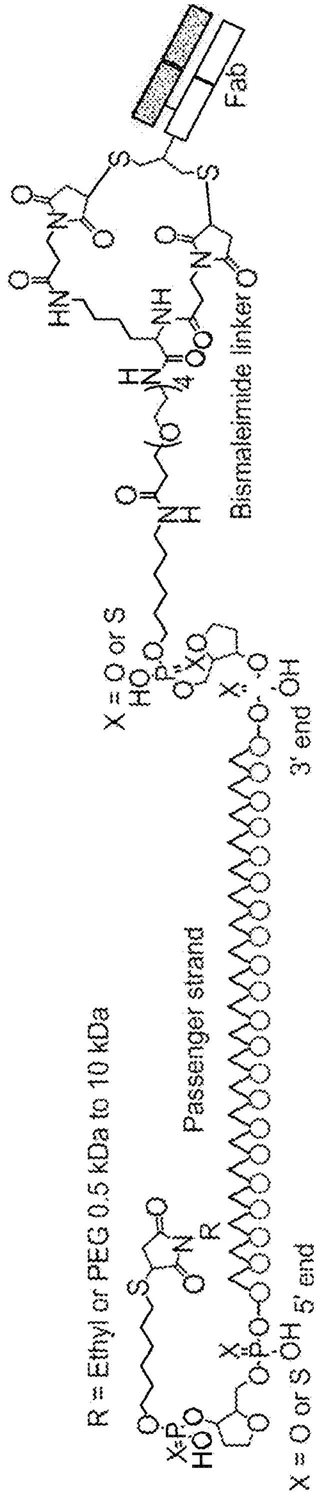
FIG. 6D illustrates a model structure of the Fab-Cys-bisMal-3'-Passenger strand (ASC Architecture-4). This conjugate was generated by Fab inter-chain cysteine conjugation to bismaleimide (bisMal) linker at the 3' end of passenger strand.
Figure 6E:
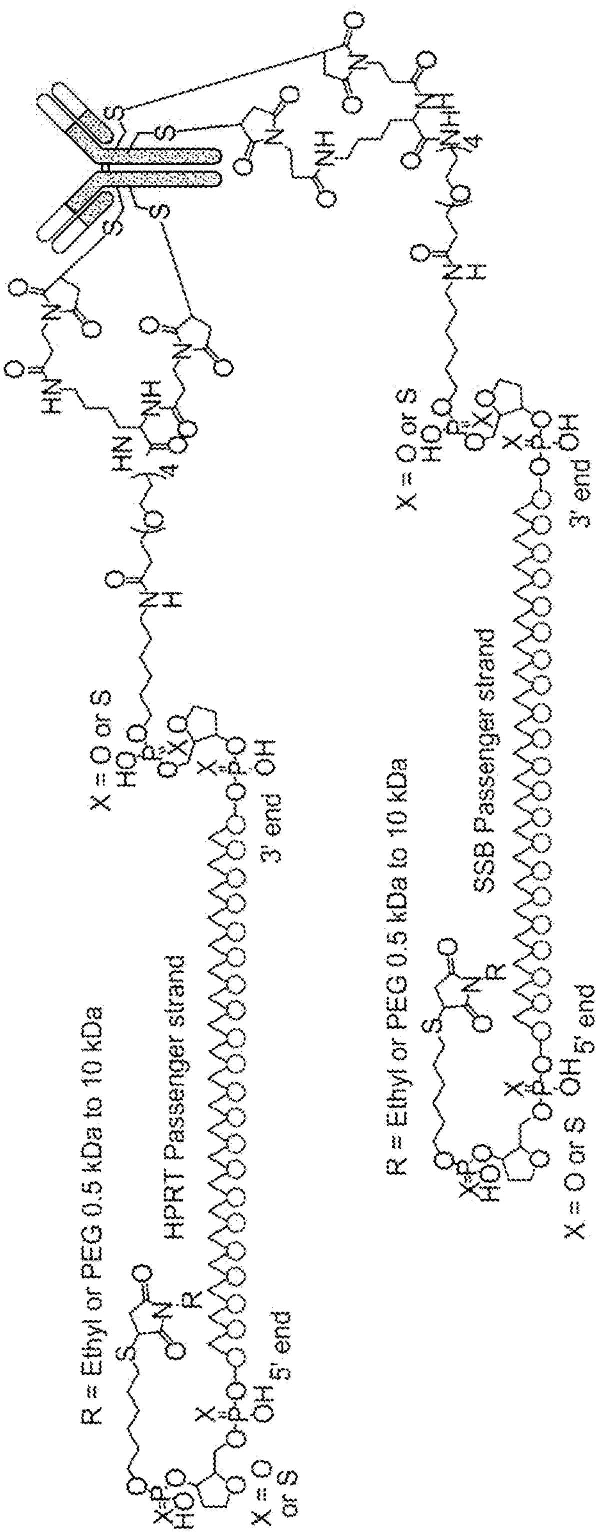
FIG. 6E illustrates a model structure of the antibody siRNA conjugate with two different siRNAs attached to one antibody molecule (ASC Architecture-5). This conjugate was generated by conjugating a mixture of SSB and HPRT siRNAs to the reduced mAb inter-chain cysteines to bismaleimide (bisMal) linker at the 3' end of passenger strand of each siRNA.
Figure 6F:
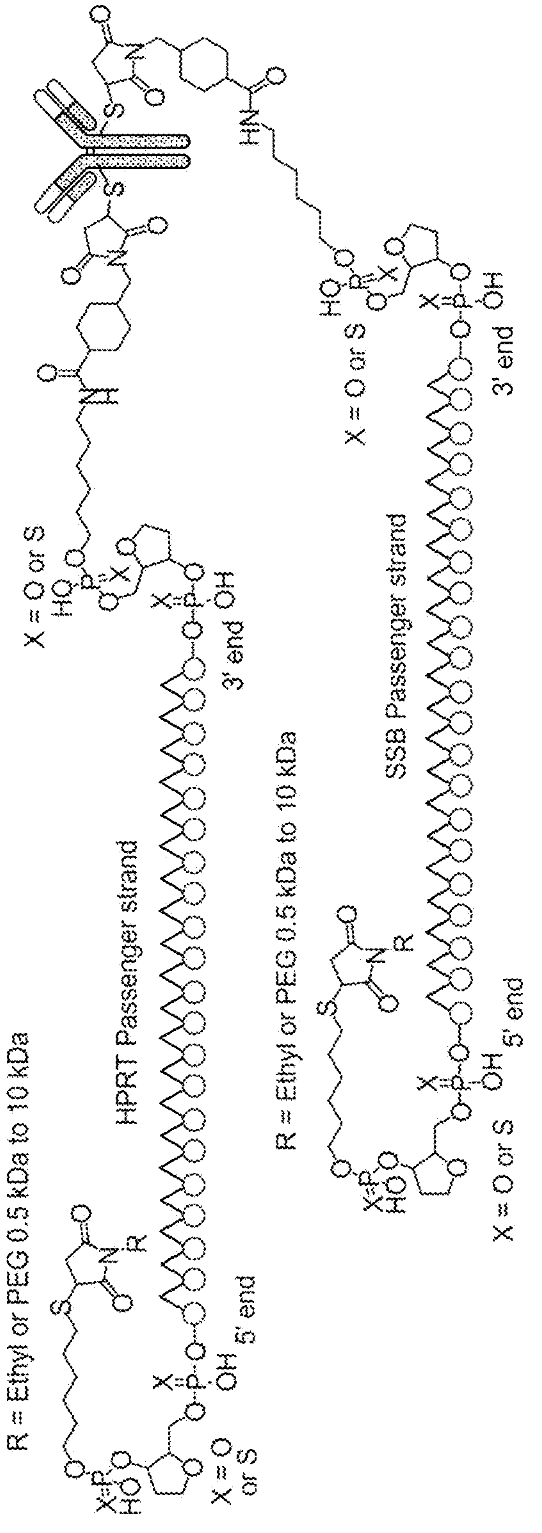
FIG. 6F illustrates a model structure of the antibody siRNA conjugate with two different siRNAs attached (ASC Architecture-6). This conjugate was generated by conjugating a mixture of SSB and HPRT siRNAs to the reduced mAb inter-chain cysteines to maleimide (SMCC) linker at the 3' end of passenger strand of each siRNA.

FIG. 6A-FIG. 6F illustrate exemplary structure of A-$X_1$-B-$X_2$-Y (Formula I) architectures described herein. FIG. 6A illustrates an antibody-Cys-SMCC-5'-passenger strand (Architecture-1). This conjugate was generated by antibody inter-chain cysteine conjugation to maleimide (SMCC) at the 5' end of passenger strand. FIG. 6B illustrates an antibody-Cys-SMCC-3'-Passenger strand (Architecture-2). This conjugate was generated by antibody inter-chain cysteine conjugation to maleimide (SMCC) at the 3' end of passenger strand. FIG. 6C illustrates an antibody-Cys-bis-Mal-3'-Passenger strand (ASC Architecture-3). This conjugate was generated by antibody inter-chain cysteine conjugation to bismaleimide (bisMal) linker at the 3' end of passenger strand. FIG. 6D illustrates a model structure of the Fab-Cys-bisMal-3'-Passenger strand (ASC Architecture-4). This conjugate was generated by Fab inter-chain cysteine conjugation to bismaleimide (bisMal) linker at the 3' end of passenger strand. FIG. 6E illustrates a model structure of the antibody siRNA conjugate with two different siRNAs attached to one antibody molecule (ASC Architecture-5). This conjugate was generated by conjugating a mixture of SSB and HPRT siRNAs to the reduced mAb inter-chain cysteines to bismaleimide (bisMal) linker at the 3' end of passenger strand of each siRNA. FIG. 6F illustrates a model structure of the antibody siRNA conjugate with two different siRNAs attached (ASC Architecture-6). This conjugate was generated by conjugating a mixture of SSB and HPRT siRNAs to the reduced mAb inter-chain cysteines to maleimide (SMCC) linker at the 3' end of passenger strand of each siRNA.

Example 3.1 Antibody siRNA Conjugate Synthesis Using SMCC Linker

Figure 7A:
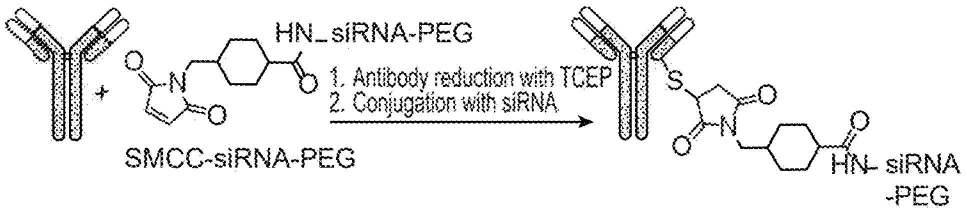
FIG. 7A illustrates an exemplary synthesis scheme (Synthesis scheme-1) for antibody-Cys-SMCC-siRNA-PEG conjugates via antibody cysteine conjugation.

FIG. 7A illustrates an exemplary synthesis scheme (Synthesis scheme-1) for antibody-Cys-SMCC-siRNA-PEG conjugates via antibody cysteine conjugation.

Step 1: Antibody Interchain Disulfide Reduction with TCEP

Antibody was buffer exchanged with borax buffer (pH 8) and made up to 10 mg/ml concentration. To this solution, 2 equivalents of TCEP in water was added and rotated for 2 hours at RT. The resultant reaction mixture was buffer exchanged with pH 7.4 PBS containing 5 mM EDTA and added to a solution of SMCC-$C_6$-siRNA or SMCC-$C_6$-siRNA-$C_6$-NHCO-PEG-XkDa (2 equivalents) (X=0.5 kDa to 10 kDa) in pH 7.4 PBS containing 5 mM EDTA at RT and rotated overnight. Analysis of the reaction mixture by analytical SAX column chromatography showed antibody siRNA conjugate along with unreacted antibody and siRNA.

Step 2: Purification

The crude reaction mixture was purified by AKTA explorer FPLC using anion exchange chromatography method-1 as described in Example 3.4. Fractions containing DAR1 and DAR>2 antibody-siRNA-PEG conjugates were separated, concentrated and buffer exchanged with pH 7.4 PBS.

Step 3: Analysis of the Purified Conjugate

The isolated conjugates were characterized by SEC, SAX chromatography and SDS-PAGE. The purity of the conjugate was assessed by analytical HPLC using either anion exchange chromatography method-2 or anion exchange chromatography method-3. Both methods are described in Example 3.4. Isolated DAR1 conjugates are typically eluted at 9.0+0.3 min on analytical SAX method and are greater than 90% pure. The typical DAR>2 cysteine conjugate contains more than 85% DAR2 and less than 15% DAR3.

Figure 7B:
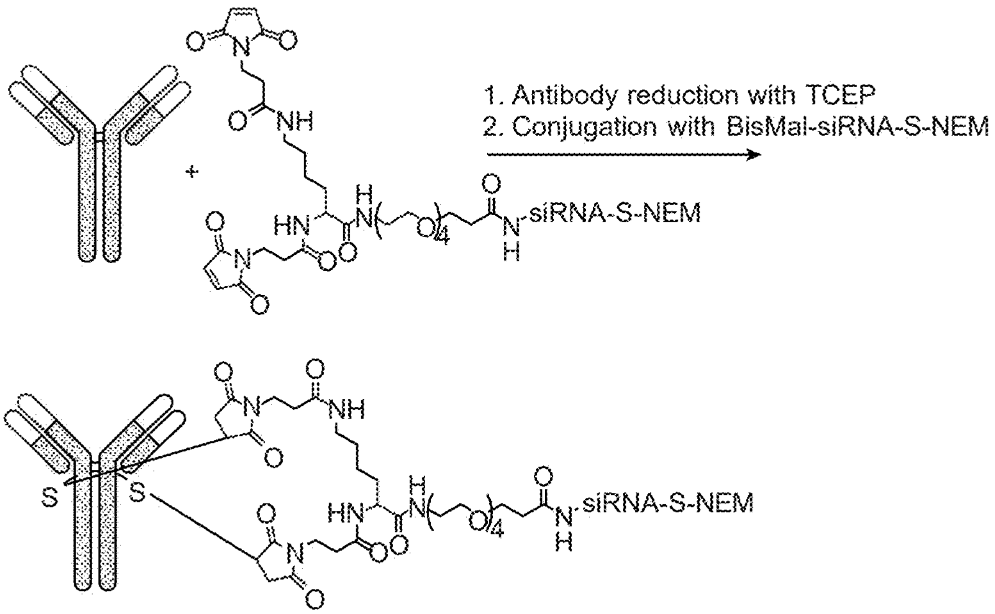
FIG. 7B illustrates an exemplary synthesis scheme (Synthesis scheme-2) for antibody-Cys-BisMal-siRNA-PEG conjugates.

Example 3.2. Antibody siRNA Conjugate Synthesis Using Bis-Maleimide (BisMal) Linker FIG. 7B illustrates an exemplary synthesis scheme (Synthesis scheme-2) for antibody-Cys-BisMal-siRNA-PEG conjugates.

Step 1: Antibody Reduction with TCEP

Antibody was buffer exchanged with borax buffer (pH 8) and made up to 5 mg/ml concentration. To this solution, 2 equivalents of TCEP in water was added and rotated for 2 hours at RT. The resultant reaction mixture was exchanged with pH 7.4 PBS containing 5 mM EDTA and added to a solution of BisMal-$C_6$-siRNA-$C_6$-S-NEM (2 equivalents) in pH 7.4 PBS containing 5 mM EDTA at RT and kept at 4° C. overnight. Analysis of the reaction mixture by analytical SAX column chromatography showed antibody siRNA conjugate along with unreacted antibody and siRNA.

Step 2: Purification

The crude reaction mixture was purified by AKTA explorer FPLC using anion exchange chromatography method-1. Fractions containing DAR1 and DAR2 antibody-siRNA conjugates were separated, concentrated and buffer exchanged with pH 7.4 PBS.

Step-3: Analysis of the Purified Conjugate

The isolated conjugates were characterized by either mass spec or SDS-PAGE. The purity of the conjugate was assessed by analytical HPLC using either anion exchange chromatography method-2 or 3 as well as size exclusion chromatography method-1.

Example 3.3. Fab' Generation from mAb and Conjugation to siRNA

Figure 7C:
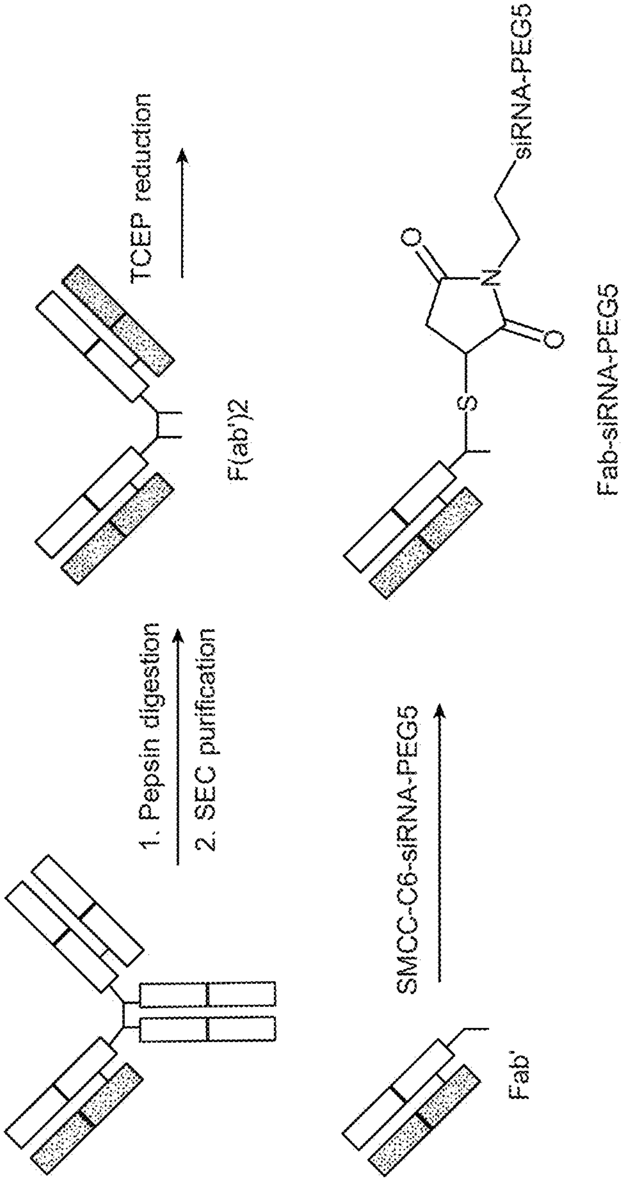
FIG. 7C illustrates an exemplary synthesis scheme (Synthesis scheme-3) for Fab-siRNA conjugate generation.

FIG. 7C illustrates an exemplary synthesis scheme (Synthesis scheme-3) for Fab-siRNA conjugate generation.

Step 1: Antibody Digestion with Pepsin

Antibody was buffer exchanged with pH 4.0, 20 mM sodium acetate/acetic acid buffer and made up to 5 mg/ml concentration. Immobilized pepsin (Thermo Scientific, Prod #20343) was added and incubated for 3 hours at 37° C. The reaction mixture was filtered using 30 kDa MWCO Amicon spin filters and pH 7.4 PBS. The retentate was collected and purified using size exclusion chromatography to isolate F (ab') 2. The collected F (ab') 2 was then reduced by 10 equivalents of TCEP and conjugated with SMCC-Ce-siRNA-PEGS at room temperature in pH 7.4 PBS. Analysis of reaction mixture on SAX chromatography showed Fab-siRNA conjugate along with unreacted Fab and siRNA-PEG.

Step 2: Purification

The crude reaction mixture was purified by AKTA explorer FPLC using anion exchange chromatography method-1. Fractions containing DAR1 and DAR2 Fab-siRNA conjugates were separated, concentrated and buffer exchanged with pH 7.4 PBS.

Step-3: Analysis of the Purified Conjugate

The characterization and purity of the isolated conjugate was assessed by analytical HPLC using anion exchange chromatography method-2 or 3 as well as by SEC method-1.

Example 3.4. Purification and Analytical Methods

Anion Exchange Chromatography Method (SAX)-1

1. Column: Tosoh Bioscience, TSKGel SuperQ-5 PW, 21.5 mm ID×15 cm, 13 μm

2. Solvent A: 20 mM TRIS buffer, pH 8.0; Solvent B: 20 mM TRIS, 1.5 M NaCl, pH 8.0; Flow Rate: 6.0 ml/min

| 3. | Gradient: | | | |
|---|---|---|---|---|
| | a. | % A | % B | Column Volume |
| | b. | 100 | 0 | 1.00 |
| | c. | 60 | 40 | 18.00 |
| | d. | 40 | 60 | 2.00 |
| | e. | 40 | 60 | 5.00 |
| | f. | 0 | 100 | 2.00 |
| | g. | 100 | 0 | 2.00 |

Anion Exchange Chromatography (SAX) Method-2

1. Column: Thermo Scientific, ProPac™ SAX-10, Bio LCIM, 4×250 mm

2. Solvent A: 80% 10 mM TRIS pH 8, 20% ethanol; Solvent B: 80% 10 mM TRIS pH 8, 20% ethanol, 1.5 M NaCl; Flow Rate: 0.75 ml/min

| 3. | Gradient: | | | |
|---|---|---|---|---|
| | a. | Time | % A | % B |
| | b. | 0.0 | 90 | 10 |
| | c. | 3.00 | 90 | 10 |
| | d. | 11.00 | 40 | 60 |
| | e. | 13.00 | 40 | 60 |
| | f. | 15.00 | 90 | 10 |
| | | 20.00 | 90 | 10 |

Anion Exchange Chromatography (SAX) Method-3

1. Column: Thermo Scientific, ProPac™ SAX-10, Bio LC™, 4×250 mm

2. Solvent A: 80% 10 mM TRIS pH 8, 20% ethanol; Solvent B: 80% 10 mM TRIS pH 8, 20% ethanol, 1.5 M NaCl 3. Flow Rate: 0.75 ml/min

| 4. | Gradient: | | | |
|---|---|---|---|---|
| | a. | Time | % A | % B |
| | b. | 0.0 | 90 | 10 |
| | c. | 3.00 | 90 | 10 |
| | d. | 11.00 | 40 | 60 |

-continued

| 4. | Gradient: | | | |
|---|---|---|---|---|
| | a. | Time | % A | % B |
| | e. | 23.00 | 40 | 60 |
| | f. | 25.00 | 90 | 10 |
| | g. | 30.00 | 90 | 10 |

Size exclusion chromatography (SEC) method-1

1. Column: TOSOH Biosciences, TSKgelG3000SW XL, 7.8×300 mm, 5 μM

2. Mobile phase: 150 mM phosphate buffer

3. Flow Rate: 1.0 ml/min for 15 mins

Example 3.5. Antibody siRNA Conjugate Synthesis Using Bis-Maleimide (BisMal) Linker Antibody Reduction with TCEP Antibody was buffer exchanged with 25 mM borate buffer (pH 8) with ImM DTPA and made up to 10 mg/ml concentration. To this solution, 4 equivalents of TCEP in the same borate buffer were added and incubated for 2 hours at 37° C. The resultant reaction mixture was combined with a solution of BisMal-siRNA (1.25 equivalents) in pH 6.0 10 mM acetate buffer at RT and kept at 4° C. overnight. Analysis of the reaction mixture by analytical SAX column chromatography showed antibody siRNA conjugate along with unreacted antibody and siRNA. The reaction mixture was treated with 10 EQ of N-ethylmaleimide (in DMSO at 10 mg/mL) to cap any remaining free cysteine residues.

Step 2: Purification

The crude reaction mixture was purified by AKTA Pure FPLC using anion exchange chromatography (SAX) method-1. Fractions containing DAR1 and DAR2 antibody-siRNA conjugates were isolated, concentrated and buffer exchanged with pH 7.4 PBS.

Anion Exchange Chromatography Method (SAX)-1.

Column: Tosoh Bioscience, TSKGel SuperQ-5 PW, 21.5 mm ID×15 cm, 13 um

Solvent A: 20 mM TRIS buffer, pH 8.0; Solvent B: 20 mM TRIS, 1.5 M NaCl, pH 8.0; Flow Rate: 6.0 ml/min

| Gradient: | | | |
|---|---|---|---|
| a. | % A | % B | Column Volume |
| b. | 100 | 0 | 1 |
| c. | 81 | 19 | 0.5 |
| d. | 50 | 50 | 13 |
| e. | 40 | 60 | 0.5 |
| f. | 0 | 100 | 0.5 |
| g. | 100 | 0 | 2 |

Anion Exchange Chromatography (SAX) Method-2

Column: Thermo Scientific, ProPac™ SAX-10, Bio LC™, 4×250 mm

Solvent A: 80% 10 mM TRIS pH 8, 20% ethanol; Solvent B: 80% 10 mM TRIS pH 8, 20% ethanol, 1.5 M NaCl; Flow Rate: 0.75 ml/min

| Gradient: | | | |
|---|---|---|---|
| a. | Time | % A | % B |
| b. | 0.0 | 90 | 10 |
| c. | 3.00 | 90 | 10 |
| d. | 11.00 | 40 | 60 |

-continued

| Gradient: | | | |
|---|---|---|---|
| a. | Time | % A | % B |
| e. | 14.00 | 40 | 60 |
| f. | 15.00 | 20 | 80 |
| g. | 16.00 | 90 | 10 |
| h. | 20.00 | 90 | 10 |

Example 4. In Vivo Activity of DUX4-Targeted AOCs in the FSHD Mouse Model ACTA1-MCM: FLExDUX4

The DUX4 siRNAs (DUX4.61 non-VP, DUX4.61 vpUq, and DUX4.1613 vpUq) were conjugated to the murine transferrin receptor (Tfrc) antibody to generate mouse-specific DUX4 AOCs. DUX4 AOCs were administered intravenously in the ACTA1-MCM: FLExDUX4 mouse model of FSHD disease that expresses human DUX4 gene: STOCK Tg (ACTA1-cre/Esr1*) 2Kesr/J (Stock #025750) crossed with B6 (Cg)-Gt (ROSA) 26Sortm1.1 (DUX4*) Plj/J (Stock #028710) (Jones T, Jones PL. A cre-inducible DUX4 transgenic mouse model for investigating facioscapulobumeral muscular dystrophy. *PLOS One.* 2018 Feb. 7;13 (2): e0192657). Age of mice at Day 0:8-11 weeks (N=8 or 10 mixed males and females). Skeletal muscles were collected 3 weeks post single IV dose of DUX4 AOCs.

Gene expression was analyzed by RT-qPCR. Muscle tissue was homogenized in Trizol in Lysing Matrix D using homogenizer FastPrep-24 (MPBio) and spun 6,000 RPM for 5 mins at 4° C. RNA was isolated using Zymo-Spin™ I-96 kit according to manufacturer's instructions. cDNA was synthetized using High-Capacity cDNA Reverse Transcription Kit (Applied Biosystems) using SimpliAmp Thermal Cycler (Applied Biosystems). cDNA was analyzed by qPCR using TaqMan Fast Universal Master Mix II (Thermo Fisher) and TaqMan probes (Thermo Fisher) in duplicates, using QuantStudio 6 or 7 Flex Real-Time PCR instruments (Applied Biosystems). Data were analyzed by QuantStudio™ Real-Time PCR Software v1.3 (Applied Biosystems). The expression levels of 4 DUX4-target genes were evaluated: WFDC3, ILVBL, SLC15A2, SORD (Jones TI, Chew GL, Barraza-Flores P, Schreier S, Ramirez M, Wuebbles RD, Burkin DJ, Bradley RK, Jones PL. Transgenic mice expressing tunable levels of DUX4 develop characteristic facioscapulohumeral muscular dystrophy-like pathophysiology ranging in severity. Skelet Muscle. 2020 Apr. 11;10 (1): 8). DUX4-target gene expression was normalized to PPIB reference gene. The level of target mRNA downregulation was determined relative to PBS vehicle treated animals by using the 2-AACt method.

General primer and TaqMan probe designs as well as the methodology for the stem-loop RT-qPCR (SL-RT-qPCR) assay have been described previously (Chen, 2005, Real-time quantification of microRNAs by stem-loop RT-PCR. *Nucleic Acids Res* 33, e179). A specific SL-RT-qPCR assay was designed to quantify the guide strand of the DUX4 siRNAs. Tissue homogenates were diluted into TE Buffer with 0.1% Triton X-100 and then analyzed by SL-RT-qPCR. Standard curves were generated by spiking different concentrations of siRNA into the appropriate matrix for comparison to the samples. Linear regressions of siRNA standard curves were performed in Prism and the slope and y-intercept values were used to interpolate tissue and plasma sample concentrations.

The composite of the DUX4 target genes is the geometric mean of 4 DUX4-target mouse genes (WFDC3, ILVBL, SLC15A2, and SORD) and the data is expressed as mean ~/+SEM % of vehicle (PBS) treated animals, N=8 or 10 mixed males and females.

Figure 4A:
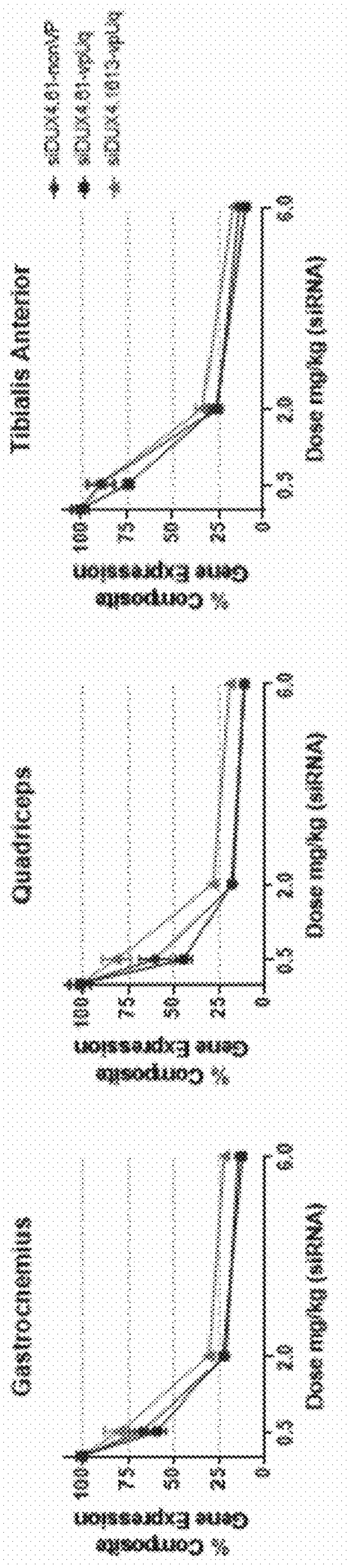
FIG. 4A shows graphs of the in vivo downregulation of DUX4-target genes in skeletal muscles in mouse model of FSHD.
Figure 4B:
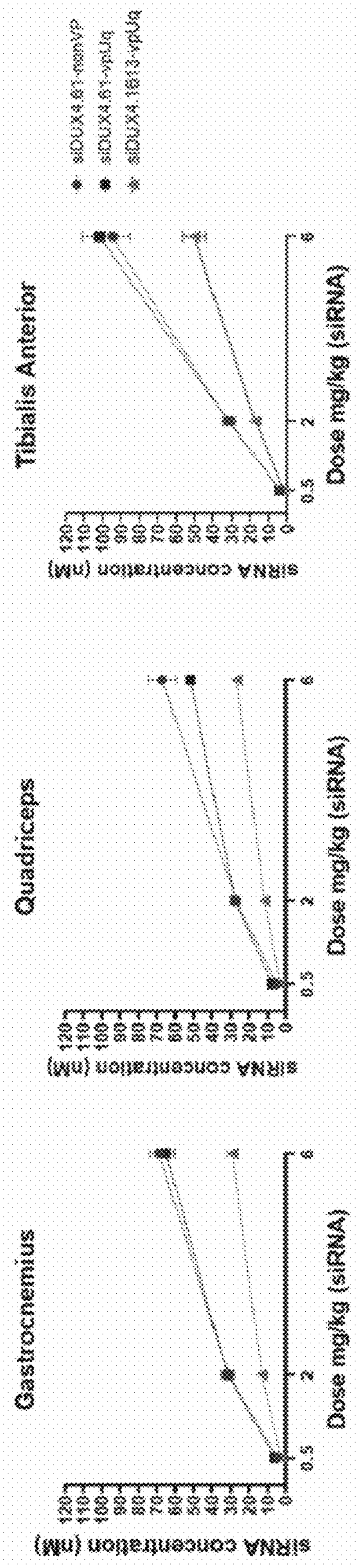
FIG. 4B shows graphs of the in vivo muscle tissue concentration of DUX-4 siRNA.

FIG. 4A and FIG. 4B show the in vivo activity of DUX4-targeted AOCs in the FSHD mouse model ACTA1-MCM;FLExDUX4. FIG. 4A shows DUX4 AOCs demonstrate a dose-dependent downregulation of the composite murine DUX4 target genes (WFDC3, ILVBL, SLC15A2, and SORD) in tibialis anterior, gastrocnemius and quadriceps skeletal muscles 3 weeks after the single AOC dose. In addition, FIG. 4B shows the dose dependent increase concentration for the DUX4 siRNAs in muscle tissue 3 weeks after the single intravenous dose of the DUX4 AOCs.

Overall, these data demonstrate a robust and durable activity of the DUX4 AOCs in vivo, thus demonstrating their potential treatment of FSHD disease.

Example 5. Functional Improvement in Mouse Model of FSHD after Treatment with DUX4-Targeted AOCs Example 5 demonstrates the efficacy of DUX4 siRNAs in suppression of FSHD disease phenotype after the treatment of DUX4-targeted AOCs in mice expressing human DUX4 in skeletal muscles. ACTA1-MCM;FLExDUX4 mice are treated at 6-9 weeks of age. 10 mice per group are treated with a single IP injection of Tamoxifen (TMX) 5 mg/kg either once or twice to induce FSHD phenotype. Within two days after the TMX dosing, mice are dosed by IV injection with test DUX4 AOCs and control AOC articles or with a vehicle. Immediately after the dosing and three times per week afterwards, mice are observed for the following: signs of pain, impaired locomotion, avoidance, hydration. Body weights are measured three times per week. Neuroscoring is performed three times per week.

The following functional measurements are performed to assess the muscle phenotype:

1. in vivo muscle force measurement (Isometric force-frequency curve and relaxation time from tetanus) 13 days post AOC treatment,
2. treadmill exercise at days 7, 10 and 14 post AOC treatment,
3. EMG 15 days post AOC treatment will be performed on all mice.

One or two days after the functional endpoint measurements are completed, mice are sacrificed and the following tissues necropsies are collected for further evaluation:

a. Gastrocnemius
   i. Left leg muscle is flash frozen and stored at −80° C.
   ii. Right leg muscle is fixed in 10% NBF at room temperature.
b. Tibialis Anterior
   i. Left leg muscle is flash frozen and stored at −80° C.
   ii. Right leg muscle is fixed in 10% NBF at room temperature.
c. Quadriceps
   i. Left leg muscle is flash frozen and stored at −80° C.
   ii. Right leg muscle is fixed in 10% NBF at room temperature.
d. Diaphragm cut in half
   i. Left half is flash frozen and stored at −80° C.
   ii. Right half is fixed in 10% NBF at room temperature.

Frozen tissue samples are analyzed for the DUX4-dependent gene expression and DUX4 siRNA concentration in the tissue.

The formaldehyde fixed tissues are trimmed for embedding. Two sections are cut from each tissue.

a. One section is stained with Sirius Red. On Sirius Red stained sections, the extent of fibrosis is measured by semiautomated image analysis.
b. The other section is stained for Reticulin. On Reticulin stained sections, muscle fiber sizes and % central nuclei are measured by automated image analysis.

While preferred aspects of the present disclosure have been shown and described herein, it will be obvious to those skilled in the art that such aspects are provided by way of example only. Numerous variations, changes, and substitutions will now occur to those skilled in the art without departing from the disclosure. It should be understood that various alternatives to the aspects of the disclosure described herein may be employed in practicing the disclosure. It is intended that the following claims define the scope of the disclosure and that methods and structures within the scope of these claims and their equivalents be covered thereby.

What is claimed is:

1. A conjugate comprising (i) an anti-transferrin receptor antibody or antigen binding fragment thereof, (ii) an siRNA, which comprises a guide strand and a passenger strand, and (iii) a linker;

wherein the anti-transferrin receptor antibody or antigen binding fragment thereof comprises a variable heavy chain (VH) region, which comprises an HCDR1 comprising the sequence of SEQ ID NO: 281; an HCDR2 comprising the sequence of SEQ ID NO: 284; and an HCDR3 comprising the sequence of SEQ ID NO: 283;

wherein the anti-transferrin receptor antibody or antigen binding fragment thereof comprises a variable light chain (VL) region, which comprises an LCDR1 comprising the sequence of SEQ ID NO: 286; an LCDR2 comprising the sequence of SEQ ID NO: 287; and an LCDR3 comprising the sequence of SEQ ID NO: 288;

wherein the guide strand of the siRNA comprises the sequence of SEQ ID NO: 413 and the passenger strand of the siRNA comprises the sequence of SEQ ID NO: 146; and wherein the linker comprises a maleimide group that conjugates the anti-transferrin receptor antibody or antigen binding fragment thereof to a terminus of the guide strand or the passenger strand.

2. The conjugate of claim 1, wherein the maleimide group is selected from the group consisting of succinimidyl 4-(N-maleimidomethyl)cyclohexane-1-carboxylate (SMCC) and sulfosuccinimidyl-4-(N-maleimidomethyl)cyclohexane-1-carboxylate (sulfo-sMCC).

3. The conjugate of claim 1, wherein the linker conjugates the anti-transferrin receptor antibody or antigen binding fragment thereof to the 5' terminus of the passenger strand.

4. The conjugate of claim 1, wherein the anti-transferrin receptor antibody or antigen binding fragment thereof is a full-length anti-transferrin receptor antibody.

5. The conjugate of claim 4, wherein the full-length anti-transferrin receptor antibody is a humanized anti-transferrin receptor antibody or a human anti-transferrin receptor antibody.

6. The conjugate of claim 4, wherein the full-length anti-transferrin receptor antibody further comprises a mutation in the heavy chain constant region selected from the group consisting of L233A, L234A, and L327R.

7. The conjugate of claim 4, wherein the full-length anti-transferrin receptor antibody further comprises L233A, L234A and L327R mutations in the heavy chain constant region.

8. The conjugate of claim 1, wherein the anti-transferrin receptor antibody or antigen binding fragment thereof is selected from the group consisting of monovalent Fab', divalent Fab2, and single chain variable fragment (scFv).

9. A conjugate comprising (i) an anti-transferrin receptor antibody or antigen binding fragment thereof, an siRNA, which comprises a guide strand and a passenger strand, and (iii) a linker;

wherein the anti-transferrin receptor antibody or antigen binding fragment thereof comprises the variable heavy chain (VH) sequence of SEQ ID NO: 294 and the variable light chain (VL) sequence of SEQ ID NO: 298;

wherein the guide strand of the siRNA comprises the sequence of SEQ ID NO: 413 and the passenger strand of the siRNA comprises the sequence of SEQ ID NO: 146; and wherein the linker comprises a maleimide group that conjugates the anti-transferrin receptor antibody or antigen binding fragment thereof to a terminus of the guide strand or the passenger strand.

10. The conjugate of claim 9, wherein the maleimide group is selected from the group consisting of succinimidyl 4-(N-maleimidomethyl)cyclohexane-1-carboxylate (SMCC) and sulfosuccinimidyl-4-(N-maleimidomethyl)cyclohexane-1-carboxylate (sulfo-sMCC).

11. The conjugate of claim 9, wherein the linker conjugates the anti-transferrin receptor antibody or antigen binding fragment thereof to the 5' terminus of the passenger strand.

12. The conjugate of claim 9, wherein the anti-transferrin receptor antibody or antigen binding fragment thereof is a full-length anti-transferrin receptor antibody.

13. The conjugate of claim 12, wherein the full-length anti-transferrin receptor antibody is a humanized anti-transferrin receptor antibody or a human anti-transferrin receptor antibody.

14. The conjugate of claim 12, wherein the full-length anti-transferrin receptor antibody further comprises a mutation in the heavy chain constant region selected from the group consisting of L233A, L234A, and L327R.

15. The conjugate of claim 12, wherein the full-length anti-transferrin receptor antibody further comprises L233A, L234A and L327R mutations in the heavy chain constant region.

16. The conjugate of claim 9, wherein the anti-transferrin receptor antibody or antigen binding fragment thereof is selected from the group consisting of monovalent Fab', divalent Fab2, and single chain variable fragment (scFv).

17. A conjugate comprising (i) an anti-transferrin receptor antibody, (ii) an siRNA, which comprises a guide strand and a passenger strand, (iii) and a linker;

wherein the anti-transferrin receptor antibody comprises two heavy chains, each comprising the sequence of SEQ ID NO: 312, and two light chains, each comprising the sequence of SEQ ID NO: 327;

wherein the guide strand of the siRNA comprises the sequence of SEQ ID NO: 413 and the passenger strand of the siRNA comprises the sequence of SEQ ID NO: 146; and wherein the linker comprises a maleimide group that conjugates the anti-transferrin receptor antibody to the S'terminus of the passenger strand.

18. The conjugate of claim 17, wherein the maleimide group is selected from the group consisting of succinimidyl 4-(N-maleimidomethyl)cyclohexane-1-carboxylate (SMCC) and sulfosuccinimidyl-4-(N-maleimidomethyl)cyclohexane-1-carboxylate (sulfo-sMCC).

19. A conjugate comprising (i) an anti-transferrin receptor antibody or antigen binding fragment thereof, (ii) an siRNA, which comprises a guide strand and a passenger strand, and (iii) a linker;

wherein the anti-transferrin receptor antibody or antigen binding fragment thereof comprises a variable heavy chain (VH) region, which comprises an HCDR1 comprising the sequence of SEQ ID NO: 281; an HCDR2 comprising the sequence of SEQ ID NO: 284; and an HCDR3 comprising the sequence of SEQ ID NO: 283;

wherein the anti-transferrin receptor antibody or antigen binding fragment thereof comprises a variable light chain (VL) region, which comprises an LCDR1 comprising the sequence of SEQ ID NO: 286; an LCDR2 comprising the sequence of SEQ ID NO: 287; and an LCDR3 comprising the sequence of SEQ ID NO: 288;

wherein the guide strand of the siRNA comprises the sequence of SEQ ID NO: 416 and the passenger strand of the siRNA comprises the sequence of SEQ ID NO: 201; and wherein the linker comprises a maleimide group that conjugates the anti-transferrin receptor antibody or antigen binding fragment thereof to a terminus of the guide strand or the passenger strand.

* * * * *